United States Patent
Babaoglu et al.

(10) Patent No.: US 9,957,275 B2
(45) Date of Patent: May 1, 2018

(54) PYRAZOLO[1,5-A]PYRIMIDINES FOR ANTIVIRAL TREATMENT

(71) Applicant: Gilead Sciences, Inc., Foster City, CA (US)

(72) Inventors: Kerim Babaoglu, Lansdale, PA (US); Constantine G. Boojamra, San Francisco, CA (US); Eugene J. Eisenberg, San Carlos, CA (US); Hon Chung Hui, San Mateo, CA (US); Richard L. Mackman, Millbrae, CA (US); Jay P. Parrish, El Dorado Hills, CA (US); Michael Sangi, San Mateo, CA (US); Oliver L. Saunders, Clovis, CA (US); Dustin Siegel, Half Moon Bay, CA (US); David Sperandio, Palo Alto, CA (US); Hai Yang, San Mateo, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days. days.

(21) Appl. No.: 15/639,970

(22) Filed: Jun. 30, 2017

(65) Prior Publication Data
US 2017/0362244 A1 Dec. 21, 2017

Related U.S. Application Data

(63) Continuation of application No. 15/347,494, filed on Nov. 9, 2016, now abandoned, which is a continuation of application No. 14/995,486, filed on Jan. 14, 2016, now abandoned, which is a continuation of application No. 13/905,410, filed on May 30, 2013, now Pat. No. 9,238,039, which is a
(Continued)

(51) Int. Cl.
C07D 487/04 (2006.01)
C07D 487/08 (2006.01)
C07D 495/04 (2006.01)
C07D 513/04 (2006.01)
A61K 31/519 (2006.01)
A61K 45/06 (2006.01)
A61K 31/5377 (2006.01)
A61K 31/55 (2006.01)
A61K 31/551 (2006.01)
A61K 31/675 (2006.01)
C07F 9/6561 (2006.01)
C07D 519/00 (2006.01)

(52) U.S. Cl.
CPC .......... C07D 487/04 (2013.01); A61K 31/519 (2013.01); A61K 31/5377 (2013.01); A61K 31/55 (2013.01); A61K 31/551 (2013.01); A61K 31/675 (2013.01); A61K 45/06 (2013.01); C07D 495/04 (2013.01); C07D 513/04 (2013.01); C07D 519/00 (2013.01); C07F 9/65616 (2013.01)

(58) Field of Classification Search
CPC .. C07D 487/04; C07D 487/08; C07D 495/04; C07D 513/04
See application file for complete search history.

(56) References Cited

U.S. PATENT DOCUMENTS 6,342,501 B1  1/2002  Townsend et al.
7,304,068 B2 12/2007  Gudmundsson et al.
(Continued)

FOREIGN PATENT DOCUMENTS

CN   1297447 A   5/2001
DE   10247271 A1  8/2004
(Continued)

OTHER PUBLICATIONS

Asinex Compounds (Nov. 2008-Mar. 2011) Aisnex Ltd., 20 Geroev Panfilovtzev Str. Bldg. 1, Moscow 125480, Russia, 27 pages.
(Continued)

Primary Examiner — Bruck Kifle

(57) ABSTRACT

The invention provides compounds of Formula I or Formula II:

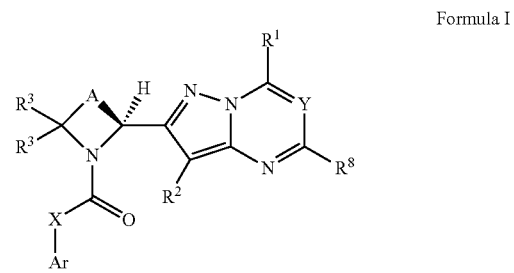

Formula I

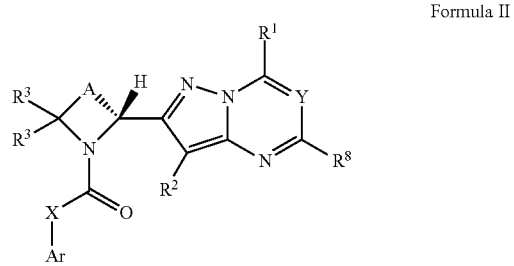

Formula II or a pharmaceutically acceptable salt or ester, thereof, as described herein. The compounds and compositions thereof are useful for treating Pneumovirinae virus infections. The compounds, compositions, and methods provided are particularly useful for the treatment of Human respiratory syncytial virus infections.

17 Claims, No Drawings

232 Related U.S. Application Data continuation of application No. 13/167,618, filed on Jun. 23, 2011, now Pat. No. 8,486,938.

(60) Provisional application No. 61/358,122, filed on Jun. 24, 2010.

(56) References Cited

U.S. PATENT DOCUMENTS

| | | | |
|---|---|---|---|
| 8,486,938 | B2 | 7/2013 | Babaoglu et al. |
| 8,809,330 | B2 | 8/2014 | Babaoglu et al. |
| 9,238,039 | B2 | 1/2016 | Babaoglu et al. |
| 9,278,975 | B2 | 3/2016 | Sangi |
| 9,504,689 | B2 | 11/2016 | Siegel et al. |
| 2004/0038993 | A1 | 2/2004 | Shipps et al. |
| 2007/0287700 | A1 | 12/2007 | Bond et al. |
| 2010/0215616 | A1 | 8/2010 | Romine et al. |
| 2010/0316607 | A1 | 12/2010 | Or et al. |
| 2011/0319412 | A1 | 12/2011 | Sakagami et al. |
| 2013/0164280 | A1 | 6/2013 | Boojamra et al. |
| 2013/0273037 | A1 | 10/2013 | Siegel et al. |
| 2014/0072554 | A1 | 3/2014 | Babaoglu et al. |

FOREIGN PATENT DOCUMENTS

| | | |
|---|---|---|
| WO | WO-199600730 A1 | 1/1996 |
| WO | WO-99/41253 A1 | 8/1999 |
| WO | WO-00/42043 A1 | 7/2000 |
| WO | WO-200042043 A1 | 7/2000 |
| WO | WO-01/46189 A1 | 6/2001 |
| WO | WO-200146189 A1 | 6/2001 |
| WO | WO-03/078435 A1 | 9/2003 |
| WO | WO-2003078435 A1 | 9/2003 |
| WO | WO-03/095455 A2 | 11/2003 |
| WO | WO-2003095455 A2 | 11/2003 |
| WO | WO-2005061513 A1 | 7/2005 |
| WO | WO-2007077186 A1 | 7/2007 |
| WO | WO-2008070447 A2 | 6/2008 |
| WO | WO-2009/076679 A2 | 6/2009 |
| WO | WO-2009079011 A1 | 6/2009 |
| WO | WO-2009106539 A1 | 9/2009 |
| WO | WO-2009126691 A1 | 10/2009 |
| WO | WO-2010033701 A2 | 3/2010 |
| WO | WO-2010/048950 A1 | 5/2010 |
| WO | WO-2010065674 A1 | 6/2010 |
| WO | WO-2010075376 A2 | 7/2010 |
| WO | WO-2010080357 A1 | 7/2010 |
| WO | WO-2010099527 A1 | 9/2010 |
| WO | WO-2010101246 A1 | 9/2010 |
| WO | WO-2010144646 A2 | 12/2010 |
| WO | WO-2010148006 A1 | 12/2010 |
| WO | WO-2011/015658 A1 | 2/2011 |
| WO | WO-2011059887 A1 | 5/2011 |
| WO | WO-2011099832 A2 | 8/2011 |
| WO | WO-2011/149856 A1 | 12/2011 |
| WO | WO-2011/163518 A1 | 12/2011 |
| WO | WO-2012/012776 A1 | 1/2012 |
| WO | WO-2013/096681 A1 | 6/2013 |
| WO | WO-2013/158776 A1 | 10/2013 |

OTHER PUBLICATIONS

Boulatov, Roman et al., "Functional Analogues of the Dioxygen Reduction Site in Cytochrome Oxidase: Mechanistic Aspects and Possible Effects of CuB," J. Am. Chem. Soc. 124(40):11923-11935, 2002.
Chapman, J. et al. (2007) "RSV604, a Novel Inhibitor of Respiratory Syncytial Virus Replication", Antimicrobial Agents and Chemotherapy, vol. 51, No. 9, pp. 3346-3353.
"Chemivate Limited Screening Compounds", Chemivate Limited, Jun. 2007 XP002708502, retrieved from the Internet: URL:http://chemivate.com/chemivate/Downloads/ChemivateJun07.pdf [retrieved on Aug. 1, 2013].
Cihlar, T. et al. (2008) "Design and Profiling of GS-9148, a Novel Nucleotide Analog Active against Nuceloside-Resistant Variants of Human Immunodeficiency Virus Type 1, and Its Orally Bioavailable Phosphonoamidate Prodrug, GS-9131", Antimicrobial Agents and Chemotherapy, vol. 52, No. 2, pp. 655-665.
Cockerill, G. Stuart et al., "The discovery and development of a novel inhibitor of RSV," Division of Medicinal Chemistry Program, 231st Acs National Meeting, Atlanta, GA, 2006.
Communication pursuant to Artcile 94(3), dated Jan. 18, 2017, for EP Patent Application No. 15195216.5.
Communication pursuant to Article 94(3), dated Jul. 14, 2017, for EP Application No. 15195216.5.
Communication pursuant to Rules 161(1) and 162 EPC dated Aug. 7, 2014, for EP Patent Application No. 12814092.8.
Completion of final requirements dated Dec. 23, 2014, for Philipines Application No. 1-2012-502528.
Completion of final requirements dated Mar. 12, 2015, for Philipines Application No. 1-2012-502528.
Dall'Aqua, William F. et al. "Properties of Human IgG1s Engineered for Enhanced Binding to the Neonatal Fc Receptor (FcRn)," The Journal of Biological Chemistry, 281(33):23514-23524, 2006.
Database Chemcats [Online], Accession No. 0056408351, Chemical Abstract Service, Columbus, Ohio, US, XP002658304, 15 pages, 2011.
Dominy, Jr., John E., "Synthesis of Amino Acid Cofactor in Cysteine Dioxygenase Is Regulated by Substrate and Represents a Novel Post-translational Regulation of Activity," Journal of Biological Chemistry, 283(18):12188-12201, 2008. cited byapplicant.
Douglas et al., "Small Molecules VP-14637 and JNJ-2408068 Inhibit Respiratory Syncytial Virus Fusion by Similar Mechanisms," Antimicrobial Agents and Chemotherapy 49(6):2460-2466, Jun. 2005.
Eurasian Office Action for EA Patent Appliation No. 201291172, dated Feb. 3, 2015.
Eurasian Office Action for EA Patent Appliation No. 201591390, dated Sep. 15, 2017.
Eurasian Office Action for EA Patent Application No. 201291172 (with English translation), dated Jan. 10, 2014.
Final Office Action dated Aug. 11, 2016, for U.S. Appl. No. 14/995,486.
Final Rejection, dated Aug. 4, 2014, for U.S. Appl. No. 13/865,069.
First Examination Report dated Feb. 27, 2015 for New Zealand Application No. 704655.
First Examination Report dated Jun. 28, 2016 for New Zealand Application No. 720869.
First Examination Report for NZ Patent Application No. 604345, dated Aug. 9, 2013.
Further Examination Report dated Jun. 28, 2016 for New Zealand Application No. 704655.
Further Examination Report for Nz Patent Application No. 604345, dated Nov. 24, 2014.
Grimes et al., "Copper(II)-Catalyzed Conversion of Aryl/Heteroaryl Boronic Acids, Boronates, and Trifluoroborates into the Corresponding Azides: Substrate Scope and Limitations," Synthesis-(Stuttg) 2010(9):1441-1448.
International Preliminary Report on Patentability for PCT International Application No. PCT/US2011/041688, dated Dec. 28, 2012.
International Preliminary Report on Patentability for PCT International Application No. PCT/US2012/071065, dated Jul. 3, 2014 (9 pages).
International Preliminary Report on Patentability for PCT International Application No. PCT/US2013/037001, dated Oct. 30, 2014 (10 pages).
International Search Report and Written Opinion for International Patent Applicatin No. PCT/US2011/041688, dated Sep. 30, 2011.
International Search Report and Written Opinion for PCT International Application No. PCT/US2013/037001, dated Aug. 29, 2013 (13 pages).
International Search Report for PCT International Application No. PCT/US2012/071065, dated Mar. 11, 2013 (3 pages).
Morrison et al., "Salts of Amines," Organic Chemistry, 6th Edition, p. 823, 1992.

(56) References Cited

OTHER PUBLICATIONS

Notice of Allowability dated Jun. 18, 2013 for U.S. Appl. No. 13/167,618.
Notice of Allowance and Fee(s) Due dated Dec. 13, 2013 for U.S. Appl. No. 14/069,685.
Notice of Allowance and Fee(s) Due dated Sep. 10, 2014 for U.S. Appl. No. 13/722,962.
Notice of Allowance and Fees Due, dated Jan. 21, 2015, for U.S. Appl. No. 13/905,410.
Notice of Allowance and Fees Due, dated Nov. 10, 2014, for U.S. Appl. No. 13/905,410.
Notice of Allowance and Fees Due, dated Oct. 22, 2014, for U.S. Appl. No. 13/865,069.
Notice of Allowance dated Mar. 12, 2013 for U.S. Appl. No. 13/167,618.
Notice of Reasons for Rejection, dated Apr. 15, 2015, for Japanese Application No. 2013-516776.
Notification of Defects in IL Patent Application No. 223253, dated Aug. 11, 2014.
Notification of the First Office Action, dated May 3, 2017, for CN Application No. 2016100043400.
Notification of the First Office Action, dated Mar. 3, 2014, for CN Patent Application No. 201180030620.4 (with English translation).
Notification of the Second Office Action, Nov. 4, 2014, for CN Patent Application No. 201180030620.4 (with English translation).
Notification of the Third Office Action, dated Apr. 9, 2015, for CN Application No. 201180030620.4.
Office Action dated Feb. 9, 2016 for Chilean App. No. 3632-12.
Office Action dated Nov. 28, 2016 for Peruvian Application No. 002481-2012.
Office Action for Columbian Patent Application No. 12-217.437 dated Jan. 3, 2014.
Office Action for MX Patent Application No. MX/a/2012/015292, dated Mar. 31, 2014.
Office Action dated Apr. 11, 2017 for U.S. Appl. No. 15/347,494, 19 pages.
Office Action dated Apr. 20, 2016, for U.S. Appl. No. 14/995,486.
Office Action dated Dec. 4, 2012 for U.S. Appl. No. 13/167,618.
Office Action dated Mar. 12, 2014 for U.S. Appl. No. 13/905,410.
Office Action dated Nov. 23, 2016 for TW Application No. 105109583.
Office Action dated Oct. 16, 2015 for TW Application No. 103145818.
Office Action, dated Jul. 13, 2017, for Candian Patent Application No. 2880834.
Office Action, dated Jul. 28, 2016, for Chilean Application No. 2012-003632.
Office Action, dated Mar. 17, 2014, for U.S. Appl. No. 13/865,069.
Office Action, dated Jul. 7, 2015, for Ukranian Application No. 2012-13827.
Pakistan Examination Report for PK Patent Application No. 469/2011, dated Jul. 26, 2012.
Pandey, Gunjan et al., "Branching of o-nitrobenzoate degradation pathway in Arthrobacter protophormiae Rkji 00: identification of new intermediates," FEMS Microbiology Letters229(2):231-236, 2003.
Patent Examination Report No. 1, dated Mar. 7, 2014, for Australian Patent Application No. 2011270798.
Patent Examination Report No. 1, dated Oct. 28, 2015, for Australian Patent Application No. 2015200638.
Patent Examination Report No. 1, dated Sep. 26, 2017, for Australian Patent Application No. 2016247174.
Patent Examination Report No. 2, dated Aug. 26, 2014, for Australian Patent Application No. 2011270798.
Restriction Requirement, dated Dec. 6, 2013, for U.S. Appl. No. 13/865,069.
Restriction Requirement, dated May 16, 2014, for U.S. Appl. No. 13/722,962.
Roymans et al., "Treatment of Respiratory Synctial Virus Infection: Past Present and Future," http://cdn.intechopen.com/pdfs-wm/24399.pdf, pp. 197-234. (2011).
Sandritter et al., "Part 1: Respiratory syncytial virus-immunoglobulin intravenous (RSV-IGIV) for respiratory syncytial viral infections," J. Pediatric Helath Care, 11:6:284-291, Nov.-Dec. 1997.
Search Report for ARIPO Application No. AP/P/2013/006686, dated Nov. 13, 2014.
Second Notice of Allowance and Fee(s) Due dated Apr. 14, 2014 for U.S. Appl. No. 14/069,685.
Sin et al., "Part 7: Structure-Activity relationships associated with a series of isatin oximes that demonstrate antiviral activity in vivo,"Biooganic & Medicinal Chemistry Letters 19:4857-4862. (2009).
Statement of Bolivian Opposition, dated Jan. 29, 2013, for BO Patent Application No. SP-0188-2011.
Substantive Examination Report for PH Patent Application No. 1/2012/502528, dated Jul. 16, 2014.
Substantive Examination Report Stage I for ID Application No. W-00201205282, dated Oct. 6, 2016.
Substantive Examination Report Stage II for ID Application No. W-00201205282, dated Mar. 1, 2017.
Sun et al., "Respiratory Syncytial Virus Entry Inhibitors Targeting the F Protein," Viruses 5:211-225, 2013.
Taiwan Office Action for TW Patent Application No. 100122237, dated Jun. 13, 2014.
Taiwan Office Action with Search Report (+ English translation) for TW Patent Application No. 100122237, dated Jan. 7, 2014.
The Random House Dictionary of the English Language, Second Edition, Definition of "obligate" (1987).
Vietnam National Office of Intellectual Property (NOIP)'s Opinion dated Jun. 30, 2014, with English translation for Vn Patent Application No. 1-2013-00161.
Written Opinion for PCT International Application No. PCT/US2012/071065, dated Mar. 11, 2013 (7 pages).
Wu, H. et al., In: Current Topics in Microbiology and Immunology, Dessain, S.K. (ed.), Springer-Verlag Berlin Heidelberg, p. 118, 2008.
Technical Report for OM Patent Application No. OM/P/2012/00246, dated Nov. 5, 2017 with English translation.
Office Action dated Dec. 22, 2017 for Taiwanese Application No. 105109583.
Office Action dated Dec. 5, 2017 for Eurasian Application No. 201591390.
Office Action dated Feb. 11, 2018 for IL Application No. 257410.
Office Action dated Feb. 13, 2018 for KR Application No. 10-2013-7001645.

PYRAZOLO[1,5-A]PYRIMIDINES FOR ANTIVIRAL TREATMENT

CROSS REFERENCE TO RELATED APPLICATIONS

This patent application is a continuation of U.S. patent application Ser. No. 15/347,494, filed Nov. 9, 2016; which is a continuation of U.S. patent application Ser. No. 14/995,486, filed Jan. 14, 2016, now abandoned; which is a continuation of U.S. patent application Ser. No. 13/905,410, filed May 30, 2013, now U.S. Pat. No. 9,238,039; which is a continuation of U.S. patent application Ser. No. 13/167,618, filed Jun. 23, 2011, now U.S. Pat. No. 8,486,938; all of which claim the benefit of priority of U.S. Provisional Application No. 61/358,122, filed Jun. 24, 2010. These applications are incorporated herein by reference in their entirety.

FIELD OF THE INVENTION

The invention relates generally to methods and compounds for treating Pneumovirinae virus infections, particularly methods and nucleosides for treating respiratory syncytial virus infections.

BACKGROUND OF THE INVENTION

Pneumovirinae viruses are negative-sense, single-stranded, RNA viruses that are responsible for many prevalent human and animal diseases. The Pneumovirinae subfamily of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumovirinae therapeutics.

Certain racemic phenyl(2-(pyrazolo[1,5-a]pyrimidin-2-yl)piperidin-1-yl)methanone compounds are offered for sale by Asinex Corporation (101 N. Chestnut St., Winston-Salem, N.C. 27101) but the utility of these compounds for treating Pneumovirinae virus infections has not been disclosed.

SUMMARY OF THE INVENTION

Provided are methods and compounds for the treatment of infections caused by the Pneumovirinae virus family.

In one aspect, this invention provides a compound of Formula I or Formula II:

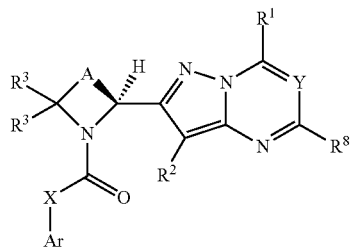

Formula I

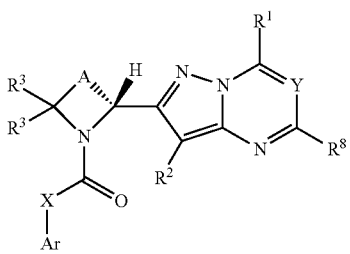

Formula II or a pharmaceutically acceptable salt or ester, thereof; wherein:

A is $-(C(R^4)_2)_n-$ wherein any one $C(R^4)_2$ of said $-(C(R^4)_2)_n-$ may be optionally replaced with $-O-$, $-S-$, $-S(O)_p-$, NH or $NR^a$;

n is 3, 4, 5 or 6;

each p is 1 or 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1 to 5 $R^6$;

X is $-C(R^{13})(R^{14})-$, $-N(CH_2R^{14})-$ or X is absent;

Y is N or $CR^7$;

each $R^1$, $R^2$, $R^3$, $R^4$, $R^5$, $R^6$, $R^7$ or $R^8$ is independently H, oxo, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $S(O)_pR^a$, $NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $NR^{11}C(=NR^{11})NR^{11}R^{12}$, halogen, $C_1$-$C_8$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl;

two $R^4$ on adjacent carbon atoms, when taken together, may form a double bond between the two carbons to which they are attached or may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

four $R^4$ on adjacent carbon atoms, when taken together, may form an optionally substituted $C_6$ aryl ring;

two $R^4$ on the same carbon atom, when taken together, may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

two $R^6$ on adjacent carbon atoms, when taken together, may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

any $R^6$ adjacent to the obligate carbonyl group of said Ar, when taken together with $R^3$, may form a bond or a $-(C(R^5)_2)_m-$ group wherein m is 1 or 2;

any $R^6$ adjacent to the obligate carbonyl group of said Ar, when taken together with $R^2$, may form a bond;

each $R^a$ is independently $(C_1$-$C_8)$alkyl, $(C_1$-$C_8)$haloalkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, ($C_3$-$C_7$)cycloalkyl or ($C_4$-$C_8$)carbocyclylalkyl wherein any ($C_1$-$C_8$)alkyl, ($C_1$-$C_8$)haloalkyl, ($C_2$-$C_8$)alkenyl or ($C_2$-$C_8$)alkynyl of $R^a$ is optionally substituted with one or more (e.g. 1, 2, 3, 4 or 5) OH, $NH_2$, $CO_2H$, $C_2$-$C_{20}$ heterocyclyl, and wherein any aryl($C_1$-$C_8$) alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of $R^a$ is optionally substituted with one or more (e.g. 1, 2, 3, 4 or 5) OH, $NH_2$, $CO_2H$, $C_2$-$C_{20}$ heterocyclyl or ($C_1$-$C_8$)alkyl;

each $R^{11}$ or $R^{12}$ is independently H, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl, ($C_4$-$C_8$)carbocyclylalkyl, —C(=O)$R^a$, —S(O)$_p R^a$, or aryl($C_1$-$C_8$)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S—, —S(O)$_p$—, —NH—, —NR$^a$— or —C(O)—;

$R^{13}$ is H or ($C_1$-$C_8$)alkyl;

$R^{14}$ is H, ($C_1$-$C_8$)alkyl, NR$^{11}$R$^{12}$, NR$^{11}$C(O)R$^{12}$, NR$^{11}$C(O)OR$^{11}$, NR$^{11}$C(O)NR$^{11}$R$^{12}$, NR$^{11}$S(O)$_p R^a$, —NR$^{11}$S(O)$_p$(OR$^{11}$) or NR$^{11}$SO$_p$NR$^{11}$R$^{12}$; and wherein each ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of each $R^1$, $R^2$, $R^3$, $R^4$, $R^5$, $R^6$, $R^7$, $R^8$, $R^{11}$ or $R^{12}$ is, independently, optionally substituted with one or more, (e.g. 1, 2, 3 4 or 5) oxo, halogen, hydroxy, $NH_2$, CN, $N_3$, N($R^a$)$_2$, NHR$^a$, SH, SR$^a$, S(O)$_p R^a$, OR$^a$, ($C_1$-$C_8$)alkyl, ($C_1$-$C_8$)haloalkyl, —C(O)$R^a$, —C(O)H, —C(=O)OR$^a$, —C(=O)OH, —C(=O)N($R^a$)$_2$, —C(=O)NHR$^a$, —C(=O)NH$_2$, NHS(O)$_p R^a$, NR$^a$S(O)$_p R^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N($R^a$)$_2$, NR$^a$C(O)NH$_2$, NHC(O)NHR$^a$, NHC(O)N($R^a$)$_2$, NHC(O)NH$_2$, =NH, =NOH, =NOR$^a$, NR$^a$S(O)$_p$NHR$^a$, NR$^a$S(O)$_p$N($R^a$)$_2$, NR$^a$S(O)$_p$NH$_2$, NHS(O)$_p$NHR$^a$, NHS(O)$_p$N($R^a$)$_2$, NHS(O)$_p$NH$_2$, —OC(=O)R$^a$, —OP(O)(OH)$_2$ or $R^a$.

In another embodiment, provided is a method of treating a Pneumovirinae infection in a mammal in need thereof by administering a therapeutically effective amount of a compound of Formula I or Formula II or a pharmaceutically acceptable salt or ester thereof.

In another embodiment, provided is a method of treating a Pneumovirinae infection in a mammal in need thereof by administering a therapeutically effective amount of a racemate, enantiomer, diastereomer, tautomer, polymorph, pseudopolymorph, amorphous form, hydrate or solvate of a compound of a compound of Formula I or Formula II or a pharmaceutically acceptable salt or ester thereof.

In another embodiment, provided is a method treating a respiratory syncytial virus infection in a mammal in need thereof by administering a therapeutically effective amount of a compound of Formula I or Formula II or a pharmaceutically acceptable salt or ester thereof.

In another embodiment, provided is a method of treating a respiratory syncytial virus infection in a mammal in need thereof by administering a therapeutically effective amount of a racemate, enantiomer, diastereomer, tautomer, polymorph, pseudopolymorph, amorphous form, hydrate or solvate of a compound of a compound of Formula I or Formula II or a pharmaceutically acceptable salt or ester thereof.

In another embodiment, provided is a method of treating a Pneumovirinae infection in a mammal in need thereof by administering a therapeutically effective amount of a compound of Formula I or Formula II or a pharmaceutically acceptable salt or ester thereof, in combination with a pharmaceutically acceptable diluent or carrier.

In another embodiment, provided is a method of treating a Pneumovirinae infection in a mammal in need thereof by administering a therapeutically effective amount of a compound of Formula I or Formula II or a pharmaceutically acceptable salt or ester thereof in combination with at least one additional therapeutic agent.

In another embodiment, provided is a method of treating a Pneumovirinae infection in a mammal in need thereof, by administering a therapeutically effective amount of a combination pharmaceutical agent comprising:

a) a first pharmaceutical composition comprising a compound of Formula I or Formula II; or a pharmaceutically acceptable salt or ester thereof; and b) a second pharmaceutical composition comprising at least one additional therapeutic agent active against infectious Pneumovirinae viruses.

In another embodiment, provided is a method of treating a respiratory syncytial virus infection in a mammal in need thereof, by administering a therapeutically effective amount of a combination pharmaceutical agent comprising:

a) a first pharmaceutical composition comprising a compound of Formula I or Formula II; or a pharmaceutically acceptable salt or ester thereof; and b) a second pharmaceutical composition comprising at least one additional therapeutic agent active against infectious respiratory syncytial viruses.

In another embodiment, provided is the use of a compound of Formula I or Formula II or a pharmaceutically acceptable salt and/or ester thereof to treat a viral infection caused by a Pneumovirinae virus or a respiratory syncytial virus.

In another aspect, the invention also provides processes and novel intermediates disclosed herein which are useful for preparing Formula I or Formula II compounds of the invention.

In other aspects, novel methods for synthesis, analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the full scope of the present invention as described herein.

In one embodiment, provided is a compound of Formula I or Formula II represented by Formula Ia or Formula IIa:

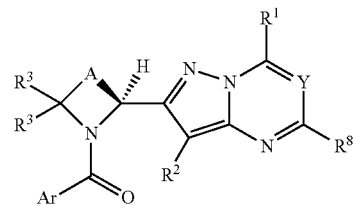

Formula Ia

-continued

Formula IIa

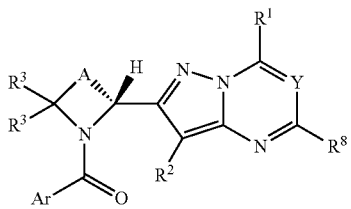

or a pharmaceutically acceptable salt or ester, thereof; wherein:

A is —(C(R$^4$)$_2$)$_n$— wherein any one C(R$^4$)$_2$ of said —(C(R$^4$)$_2$)$_n$— may be optionally replaced with —O—, —S—, or —S(O)$_p$—;

n is 3 or 4;

each p is 1 or 2;

Y is N or CR$^7$;

Ar is a C$_6$-C$_{20}$ aryl group optionally substituted with 1 to 5 R$^6$;

each R$^1$, R$^2$, R$^3$, R$^4$, R$^5$, R$^6$, R$^7$ or R$^8$ is independently H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl;

two R$^4$ on adjacent carbon atoms, when taken together, may form a double bond between the two carbons to which they are attached or may form a (C$_3$-C$_7$)cycloalkyl ring wherein one carbon atom of said (C$_3$-C$_7$)cycloalkyl ring may be optionally replaced by —O—, —S—, —S(O)$_p$—, —NH— or —NR$^a$—;

four R$^4$ on adjacent carbon atoms, when taken together, may form an optionally substituted C$_6$ aryl ring;

two R$^4$ on the same carbon atom, when taken together, may form a (C$_3$-C$_7$)cycloalkyl ring wherein one carbon atom of said (C$_3$-C$_7$)cycloalkyl ring may be optionally replaced by —O—, —S—, —S(O)$_p$—, —NH— or —NR$^a$—;

two R$^6$ on adjacent carbon atoms, when taken together, may form a (C$_3$-C$_7$)cycloalkyl ring wherein one carbon atom of said (C$_3$-C$_7$)cycloalkyl ring may be optionally replaced by —O—, —S—, —S(P)$_p$—, —NH— or —NR$^a$—;

any R$^6$ adjacent to the obligate carbonyl group of said Ar, when taken together with R$^3$, may form a bond or a —(C(R$^5$)$_2$)$_m$— group wherein m is 1 or 2;

any R$^6$ adjacent to the obligate carbonyl group of said Ar, when taken together with R$^2$, may form a bond;

each R$^a$ is independently (C$_1$-C$_8$)alkyl, (C$_1$-C$_8$)haloalkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl;

each R$^{11}$ or R$^{12}$ is independently H, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl, (C$_4$-C$_8$)carbocyclylalkyl, —C(=O)R$^a$, —S(O)$_p$R$^a$, or aryl(C$_1$-C$_8$)alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S—, —S(O)$_p$—, —NH— or —NR$^a$—; and wherein each (C$_1$-C$_8$)alkyl, (C$_1$-C$_8$)haloalkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl of each R$^1$, R$^2$, R$^3$, R$^4$, R$^5$, R$^6$, R$^7$, R$^8$, R$^{11}$ or R$^{12}$ is, independently, optionally substituted with one or more halogen, hydroxy, NH$_2$, CN, N$_3$, N(R$^a$)$_2$, SH, SR$^a$, S(O)$_p$R$^a$ or OR$^a$.

In one embodiment of Formula Ia or IIa, A is —(C(R$^4$)$_2$)$_3$—. In another aspect of this embodiment, A is —(C(R$^4$)$_2$)$_4$—. In another aspect of this embodiment, R$^4$ is H. In another aspect of this embodiment, R$^4$ is optionally substituted (C$_1$-C$_8$)alkyl. In another aspect of this embodiment, R$^1$ is H, optionally substituted (C$_1$-C$_8$)alkyl, or OH. In another aspect of this embodiment, R$^1$ is H or CH$_3$. In another aspect of this embodiment, R$^8$ is optionally substituted (C$_1$-C$_8$)alkyl, optionally substituted (C$_3$-C$_7$)cycloalkyl or optionally substituted (C$_4$-C$_8$)carbocyclylalkyl. In another aspect of this embodiment, R$^8$ is optionally substituted cyclopropyl.

In one embodiment, provided is a compound of Formula I or Formula II represented by Formula III or Formula IV:

Formula III

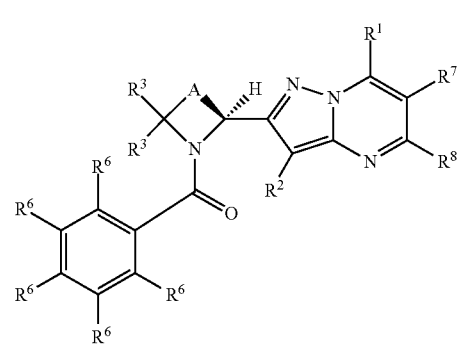

Formula IV

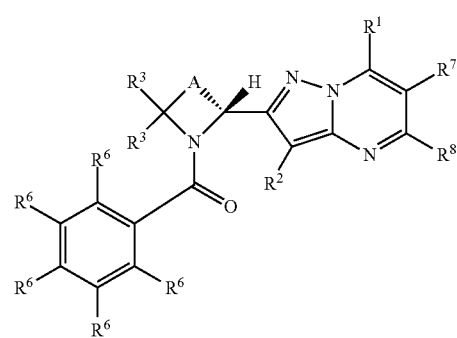

or a pharmaceutically acceptable salt or ester, thereof; wherein:

A is —(C(R$^4$)$_2$)$_n$— wherein any one C(R$^4$)$_2$ of said —(C(R$^4$)$_2$)$_n$— may be optionally replaced with —O—, —S—, or —S(O)$_p$;

n is 3 or 4;

each p is 1 or 2;

each R$^1$, R$^2$, R$^3$, R$^4$, R$^6$, R$^7$ or R$^8$ is independently H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl;

two R$^4$ on adjacent carbon atoms, when taken together, may form a double bond between the two carbons to which they are attached or may form a (C$_3$-C$_7$)cycloalkyl ring wherein one carbon atom of said $(C_3\text{-}C_7)$cycloalkyl ring may be optionally replaced by —O—, —S—, —S(O)$_p$—, —NH— or —NR$^a$—;

four R$^4$ on adjacent carbon atoms, when taken together, may form an optionally substituted $C_6$ aryl ring;

two R$^4$ on the same carbon atom, when taken together, may form a $(C_3\text{-}C_7)$cycloalkyl ring wherein one carbon atom of said $(C_3\text{-}C_7)$cycloalkyl ring may be optionally replaced by —O—, —S—, —S(O)$_p$—, —NH— or —NR$^a$—;

each R$^a$ is independently $(C_1\text{-}C_8)$alkyl, $(C_1\text{-}C_8)$haloalkyl, $(C_2\text{-}C_8)$alkenyl, $(C_2\text{-}C_8)$alkynyl, aryl$(C_1\text{-}C_8)$alkyl, $C_6\text{-}C_{20}$ aryl, $C_2\text{-}C_{20}$ heterocyclyl, $(C_3\text{-}C_7)$cycloalkyl or $(C_4\text{-}C_8)$carbocyclylalkyl;

each R$^{11}$ or R$^{12}$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $C_6\text{-}C_{20}$ aryl, $C_2\text{-}C_{20}$ heterocyclyl, $(C_3\text{-}C_7)$cycloalkyl, $(C_4\text{-}C_8)$carbocyclylalkyl, —C(=O)R$^a$, —S(O)$_p$R$^a$, or aryl$(C_1\text{-}C_8)$alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S—, —S(O)$_p$—, —NH— or —NR$^a$—; and wherein each $(C_1\text{-}C_8)$alkyl, $(C_1\text{-}C_8)$haloalkyl, $(C_2\text{-}C_8)$alkenyl, $(C_2\text{-}C_8)$alkynyl, aryl$(C_1\text{-}C_8)$alkyl, $C_6\text{-}C_{20}$ aryl, $C_2\text{-}C_{20}$ heterocyclyl, $(C_3\text{-}C_7)$cycloalkyl or $(C_4\text{-}C_8)$carbocyclylalkyl of each R$^1$, R$^2$, R$^3$, R$^4$, R$^6$, R$^7$, R$^8$, R$^{11}$ or R$^{12}$ is, independently, optionally substituted with one or more halogen, hydroxy, NH$_2$, CN, N$_3$, N(R$^a$)$_2$, SH, SR$^a$, S(O)$_p$R$^a$ or OR$^a$.

In one embodiment of Formula III or IV, the compound is represented by Formula III. In another aspect of this embodiment, A is —(C(R$^4$)$_2$)$_3$—. In another aspect of this embodiment, A is —(C(R$^4$)$_2$)$_4$—. In another aspect of this embodiment, A is —C(R$^4$)$_2$OC(R$^4$)$_2$—. In another aspect of this embodiment, A is —C(R$^4$)$_2$SC(R$^4$)$_2$—. In another aspect of this embodiment, A is —C(R$^4$)$_2$S(O)$_p$C(R$^4$)$_2$—. In another aspect of this embodiment, each R$^3$ is H. In another aspect of this embodiment, R$^2$ is H. In another aspect of this embodiment, each R$^3$ and R$^2$ is H. In another aspect of this embodiment, R$^8$ is optionally substituted $(C_3\text{-}C_7)$cycloalkyl.

In another embodiment of Formula III or IV, the compound is represented by Formula III wherein A is —(C(R$^4$)$_2$)$_3$—. In another aspect of this embodiment, each R$^4$ is H. In another aspect of this embodiment, at least one R$^4$ is optionally substituted $(C_1\text{-}C_8)$alkyl. In another aspect of this embodiment, at least one R$^4$ is methyl. In another aspect of this embodiment, each R$^3$ is H. In another aspect of this embodiment, R$^2$ is H. In another aspect of this embodiment, each R$^3$ and R$^2$ is H. In another aspect of this embodiment, R$^8$ is optionally substituted $(C_3\text{-}C_7)$cycloalkyl. In another aspect of this embodiment, at least one R$^6$ is —NR$^{11}$S(O)$_p$R$^a$. In another aspect of this embodiment, at least one R$^6$ is NR$^{11}$C(O)R$^{11}$. In another aspect of this embodiment, at least one R$^6$ is NR$^{11}$R$^{12}$. In another aspect of this embodiment, at least one R$^6$ is halogen. In another aspect of this embodiment, R$^1$ is H. In another aspect of this embodiment, R$^1$ is optionally substituted $(C_1\text{-}C_8)$alkyl. In another aspect of this embodiment, R$^1$ is methyl. In another aspect of this embodiment, R$^1$ is OR$^{11}$. In another aspect of this embodiment, each R$^3$ and R$^2$ is H.

In another embodiment of Formula III or IV, the compound is represented by Formula III wherein A is —(C(R$^4$)$_2$)$_3$— and each R$^3$ is H. In another aspect of this embodiment, each R$^4$ is H. In another aspect of this embodiment, at least one R$^4$ is optionally substituted $(C_1\text{-}C_8)$alkyl. In another aspect of this embodiment, at least one R$^4$ is methyl. In another aspect of this embodiment, R$^2$ is H. In another aspect of this embodiment, R$^8$ is optionally substituted $(C_3\text{-}C_7)$cycloalkyl. In another aspect of this embodiment, at least one R$^6$ is —NR$^{11}$S(O)$_p$R$^a$. In another aspect of this embodiment, at least one R$^6$ is NR$^{11}$C(O)R$^{11}$. In another aspect of this embodiment, at least one R$^6$ is NR$^{11}$R$^{12}$. In another aspect of this embodiment, at least one R$^6$ is halogen. In another aspect of this embodiment, R$^1$ is H. In another aspect of this embodiment, R$^1$ is optionally substituted $(C_1\text{-}C_8)$alkyl. In another aspect of this embodiment, R$^1$ is methyl. In another aspect of this embodiment, R$^1$ is OR$^{11}$.

In another embodiment of Formula III or IV, the compound is represented by Formula III wherein A is —(C(R$^4$)$_2$)$_3$— and each R$^2$ is H. In another aspect of this embodiment, each R$^4$ is H. In another aspect of this embodiment, at least one R$^4$ is optionally substituted $(C_1\text{-}C_8)$alkyl. In another aspect of this embodiment, at least one R$^4$ is methyl. In another aspect of this embodiment, each R$^3$ is H. In another aspect of this embodiment, R$^8$ is optionally substituted $(C_3\text{-}C_7)$cycloalkyl. In another aspect of this embodiment, at least one R$^6$ is —NR$^{11}$S(O)$_p$R$^a$. In another aspect of this embodiment, at least one R$^6$ is NR$^{11}$C(O)R$^{11}$. In another aspect of this embodiment, at least one R$^6$ is NR$^{11}$R$^{12}$. In another aspect of this embodiment, at least one R$^6$ is halogen. In another aspect of this embodiment, R$^1$ is H. In another aspect of this embodiment, R$^1$ is optionally substituted $(C_1\text{-}C_8)$alkyl. In another aspect of this embodiment, R$^1$ is methyl. In another aspect of this embodiment, R$^1$ is OR$^{11}$.

In one embodiment of Formula III or IV, the compound is represented by Formula IV. In another aspect of this embodiment, A is —(C(R$^4$)$_2$)$_3$—. In another aspect of this embodiment, A is —(C(R$^4$)$_2$)$_4$—. In another aspect of this embodiment, A is —C(R$^4$)$_2$OC(R$^4$)$_2$—. In another aspect of this embodiment, A is —C(R$^4$)$_2$SC(R$^4$)$_2$—. In another aspect of this embodiment, A is —C(R$^4$)$_2$S(O)$_p$C(R$^4$)$_2$—. In another aspect of this embodiment, each R$^3$ is H. In another aspect of this embodiment, R$^2$ is H. In another aspect of this embodiment, each R$^3$ and R$^2$ is H. In another aspect of this embodiment, each R$^3$ and R$^2$ is H. In another aspect of this embodiment, R$^8$ is optionally substituted $(C_3\text{-}C_7)$cycloalkyl.

In another embodiment of Formula III or IV, the compound is represented by Formula IV wherein A is —(C(R$^4$)$_2$)$_3$—. In another aspect of this embodiment, each R$^4$ is H. In another aspect of this embodiment, at least one R$^4$ is optionally substituted $(C_1\text{-}C_8)$alkyl. In another aspect of this embodiment, at least one R$^4$ is methyl. In another aspect of this embodiment, each R$^3$ is H. In another aspect of this embodiment, R$^2$ is H. In another aspect of this embodiment, each R$^3$ and R$^2$ is H. In another aspect of this embodiment, R$^8$ is optionally substituted $(C_3\text{-}C_7)$cycloalkyl. In another aspect of this embodiment, at least one R$^6$ is —NR$^{11}$S(O)$_p$R$^a$. In another aspect of this embodiment, at least one R$^6$ is NR$^{11}$C(O)R$^{11}$. In another aspect of this embodiment, at least one R$^6$ is NR$^{11}$R$^{12}$. In another aspect of this embodiment, at least one R$^6$ is halogen. In another aspect of this embodiment, R$^1$ is H. In another aspect of this embodiment, R$^1$ is optionally substituted $(C_1\text{-}C_8)$alkyl. In another aspect of this embodiment, R$^1$ is methyl. In another aspect of this embodiment, R$^1$ is OR$^{11}$. In another aspect of this embodiment, each R$^3$ and R$^2$ is H.

In another embodiment of Formula III or IV, the compound is represented by Formula IV wherein A is —(C(R$^4$)$_2$)$_3$— and each R$^3$ is H. In another aspect of this embodiment, each R$^4$ is H. In another aspect of this embodiment, at least one R$^4$ is optionally substituted $(C_1\text{-}C_8)$alkyl. In another aspect of this embodiment, at least one R$^4$ is methyl. In another aspect of this embodiment, R$^2$ is H. In another aspect of this embodiment, R$^8$ is optionally substituted $(C_3-C_7)$cycloalkyl. In another aspect of this embodiment, at least one $R^6$ is $-NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is $OR^{11}$.

In another embodiment of Formula III or IV, the compound is represented by Formula IV wherein A is $-C(R^4)_2)_3-$ and each $R^2$ is H. In another aspect of this embodiment, each $R^4$ is H. In another aspect of this embodiment, at least one $R^4$ is optionally substituted $(C_1-C_8)$alkyl. In another aspect of this embodiment, at least one $R^4$ is methyl. In another aspect of this embodiment, each $R^3$ is H. In another aspect of this embodiment, $R^8$ is optionally substituted $(C_3-C_7)$cycloalkyl. In another aspect of this embodiment, at least one $R^6$ is $-NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is $OR^{11}$.

In another embodiment, provided is a compound of Formula I or Formula II represented by Formula V or Formula VI:

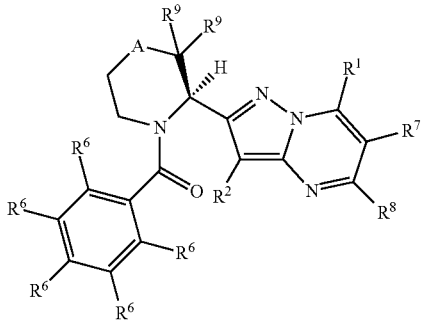

Formula V

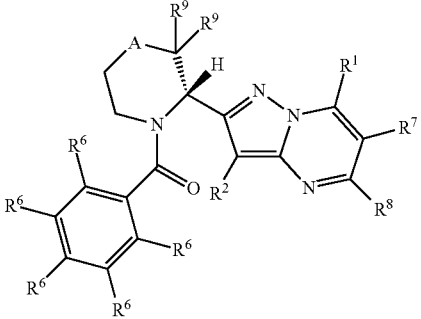

Formula VI or a pharmaceutically acceptable salt or ester, thereof; wherein:

A is $-C(R^4)_2-$, $-(C(R^4)_2)_2-$, $-O-$, $-S-$, or $-S(O)_p-$;

each p is 1 or 2;

each $R^1$, $R^2$, $R^4$, $R^6$, $R^7$ or $R^8$ is independently H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $-C(=O)R^{11}$, $-C(=O)OR^{11}$, $C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, halogen, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl;

each $R^a$ is independently $(C_1-C_8)$alkyl, $(C_1-C_8)$haloalkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl;

each $R^9$ is independently H, $(C_1-C_8)$alkyl, $(C_2-C_8)$alkenyl, $(C_2-C_8)$alkynyl, $(C_3-C_7)$cycloalkyl or $(C_4-C_8)$carbocyclylalkyl;

each $R^{11}$ or $R^{12}$ is independently H, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl, $(C_4-C_8)$carbocyclylalkyl, $-C(=O)R^a$, $-S(P)_pR^a$, or aryl$(C_1-C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S-$, $-S(O)_p-$, $-NH-$ or $-NR^a-$; and wherein each $(C_1-C_8)$alkyl, $(C_1-C_8)$haloalkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl of each $R^1$, $R^2$, $R^4$, $R^6$, $R^7$, $R^8$, $R^9$, $R^{11}$ or $R^{12}$ is, independently, optionally substituted with one or more halogen, hydroxy, $NH_2$, CN, $N_3$, $N(R^a)_2$, SH, $SR^a$, $S(O)_pR^a$ or $OR^a$.

In one embodiment of Formula V or VI, the compound is represented by Formula V. In another aspect of this embodiment, A is $-C(R^4)_2)_2-$. In another aspect of this embodiment, A is $-C(R^4)_2-$. In another aspect of this embodiment, A is $-O-$. In another aspect of this embodiment, A is $-S-$. In another aspect of this embodiment, A is $-S(O)_p-$. In another aspect of this embodiment, $R^2$ is H. In another aspect of this embodiment, $R^8$ is optionally substituted $(C_3-C_7)$cycloalkyl. In another aspect of this embodiment, at least one $R^6$ is $-NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is $OR^{11}$. In another aspect of this embodiment, each $R^3$ and $R^2$ is H.

In another embodiment of Formula V or VI, the compound is represented by Formula V wherein A is $-C(R^4)_2-$. In another aspect of this embodiment, each $R^4$ is H. In another aspect of this embodiment, one $R^4$ is optionally substituted $(C_1-C_8)$alkyl and the remaining $R^4$ is H. In another aspect of this embodiment, one $R^4$ is $CH_3$ and the remaining $R^4$ is H. In another aspect of this embodiment, $R^2$ is H. In another aspect of this embodiment, $R^8$ is optionally substituted $(C_3-C_7)$cycloalkyl. In another aspect of this embodiment, at least one $R^6$ is $-NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is $OR^{11}$. In another aspect of this embodiment, each $R^3$ and $R^2$ is H. In another aspect of this embodiment, each $R^9$ is H. In another aspect of this embodiment, one $R^9$ is H and the other $R^9$ is optionally substituted $(C_1$-$C_8)$alkyl. In another aspect of this embodiment, one $R^9$ is H and the other $R^9$ is methyl.

In another embodiment of Formula V or VI, the compound is represented by Formula V wherein A is —$C(R^4)_2$— and $R^2$ is H. In another aspect of this embodiment, each $R^4$ is H. In another aspect of this embodiment, one $R^4$ is optionally substituted $(C_1$-$C_8)$alkyl and the remaining $R^4$ is H. In another aspect of this embodiment, one $R^4$ is $CH_3$ and the remaining $R^4$ is H. In another aspect of this embodiment, $R^8$ is optionally substituted $(C_3$-$C_7)$cycloalkyl. In another aspect of this embodiment, at least one $R^6$ is —$NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1$-$C_8)$alkyl. In another aspect of this embodiment, $R^1$ is $CH_3$. In another aspect of this embodiment, $R^1$ is $OR^{11}$. In another aspect of this embodiment, at least one $R^6$ is $NHSO_2CH_3$. In another aspect of this embodiment, $R^1$ is $OR^{11}$. In another aspect of this embodiment, $R^1$ is OH. In one aspect of this embodiment, $R^1$ is optionally substituted $(C_1$-$C_8)$alkyl and $R^8$ is optionally substituted $(C_3$-$C_7)$cycloalkyl. In another aspect of this embodiment, $R^1$ is methyl and $R^8$ is cyclopropyl. In another aspect of this embodiment, each $R^3$ and $R^2$ is H. In another aspect of this embodiment, each $R^9$ is H. In another aspect of this embodiment, one $R^9$ is H and the other $R^9$ is optionally substituted $(C_1$-$C_8)$alkyl. In another aspect of this embodiment, one $R^9$ is H and the other $R^9$ is methyl. In another aspect of this embodiment.

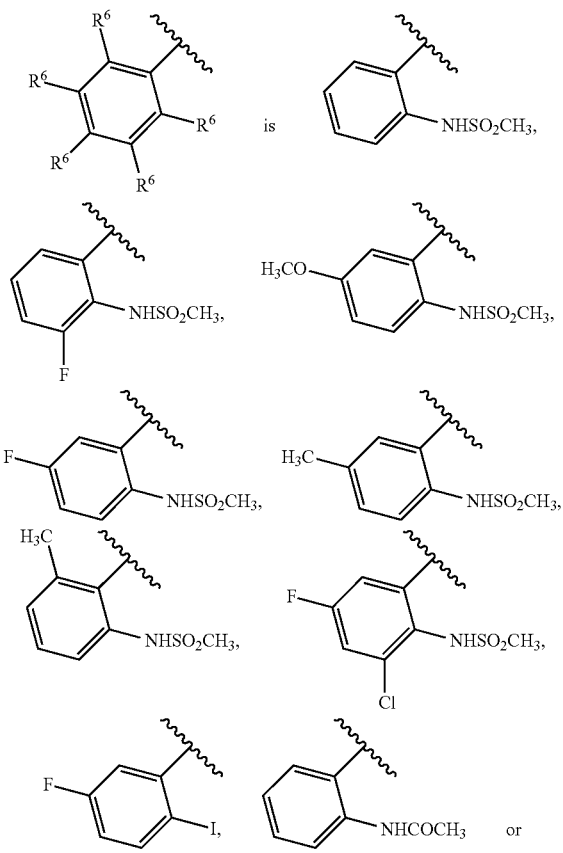

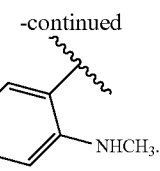

In one embodiment of Formula V or VI, the compound is represented by Formula VI. In another aspect of this embodiment, A is —$(C(R^4)_2)_2$—. In another aspect of this embodiment, A is —$C(R^4)_2$—. In another aspect of this embodiment, A is —O—. In another aspect of this embodiment, A is —S—. In another aspect of this embodiment, A is —$S(O)_p$—. In another aspect of this embodiment, $R^2$ is H. In another aspect of this embodiment, at least one $R^6$ is —$NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1$-$C_8)$alkyl. In another aspect of this embodiment, $R^1$ is methyl. In another aspect of this embodiment, $R^1$ is $OR^{11}$. In another aspect of this embodiment, each $R^3$ and $R^2$ is H. In another aspect of this embodiment, $R^8$ is optionally substituted $(C_3$-$C_7)$cycloalkyl.

In another embodiment of Formula V or VI, the compound is represented by Formula VI wherein A is —$C(R^4)_2$—. In another aspect of this embodiment, each $R^4$ is H. In another aspect of this embodiment, one $R^4$ is optionally substituted $(C_1$-$C_8)$alkyl and the remaining $R^4$ is H. In another aspect of this embodiment, one $R^4$ is $CH_3$ and the remaining $R^4$ is H. In another aspect of this embodiment, $R^2$ is H. In another aspect of this embodiment, $R^8$ is optionally substituted $(C_3$-$C_7)$cycloalkyl. In another aspect of this embodiment, at least one $R^6$ is —$NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1$-$C_8)$alkyl. In another aspect of this embodiment, $R^1$ is methyl. In another aspect of this embodiment, $R^1$ is $OR^{11}$. In another aspect of this embodiment, each $R^3$ and $R^2$ is H. In another aspect of this embodiment, each $R^9$ is H. In another aspect of this embodiment, one $R^9$ is H and the other $R^9$ is optionally substituted $(C_1$-$C_8)$alkyl. In another aspect of this embodiment, one $R^9$ is H and the other $R^9$ is methyl.

In another embodiment of Formula V or VI, the compound is represented by Formula VI wherein A is —$C(R^4)_2$— and $R^2$ is H. In another aspect of this embodiment, each $R^4$ is H. In another aspect of this embodiment, one $R^4$ is optionally substituted $(C_1$-$C_8)$alkyl and the remaining $R^4$ is H. In another aspect of this embodiment, one $R^4$ is $CH_3$ and the remaining $R^4$ is H. In another aspect of this embodiment, $R^8$ is optionally substituted $(C_3$-$C_7)$cycloalkyl. In another aspect of this embodiment, at least one $R^6$ is —$NR^{11}S(O)_pR^a$. In another aspect of this embodiment, at least one $R^6$ is $NR^{11}C(O)R^{11}$. In another aspect of this embodiment, at least one $R^6$ is $NR^{11}R^{12}$. In another aspect of this embodiment, at least one $R^6$ is halogen. In another aspect of this embodiment, $R^1$ is H. In another aspect of this embodiment, $R^1$ is optionally substituted $(C_1$-$C_8)$alkyl. In another aspect of this embodiment, $R^1$ is methyl. In another aspect of this embodiment, $R^1$ is $OR^{11}$. In another aspect of this embodiment, at least one $R^6$ is $NHSO_2CH_3$. In another aspect of this embodiment, $R^1$ is $OR^{11}$. In another aspect of this embodiment, each $R^3$ and $R^2$ is H. In another aspect of this embodiment, each $R^9$ is H. In another aspect of this embodiment, one $R^9$ is H and the other $R^9$ is optionally substituted $(C_1-C_8)$alkyl. In another aspect of this embodiment, one $R^9$ is H and the other $R^9$ is methyl.

In another embodiment of the compounds of Formula I-VI, each $R^7$ or $R^8$ is independently H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, $NR^{11}S(O)_p(OR^{11})$, —$NR^{11}SO_2NR^{11}R^{12}$, halogen, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl. In one aspect of this embodiment, $R^7$ or $R^8$ is H, $OR^{11}$, halogen, $(C_1-C_8)$alkyl, $(C_2-C_8)$alkenyl, or $(C_2-C_8)$alkynyl. In one aspect of this embodiment, $R^7$ and $R^8$ are each optionally substituted $(C_1-C_8)$alkyl. In one aspect of this embodiment, one of $R^7$ or $R^8$ is H and the other of $R^7$ or $R^8$ is optionally substituted $(C_1-C_8)$alkyl. In one aspect of this embodiment, $R^7$ is optionally substituted $(C_1-C_8)$alkyl and $R^8$ is optionally substituted $(C_3-C_7)$cycloalkyl. In another aspect of this embodiment, $R^7$ is H and $R^8$ is optionally substituted $(C_3-C_7)$cycloalkyl. In another aspect of this embodiment, $R^7$ is H and $R^8$ is cyclopropyl. In one aspect of this embodiment, one of $R^7$ or $R^8$ is halogen and the other of $R^7$ or $R^8$ is optionally substituted $(C_1-C_8)$alkyl. In one aspect of this embodiment, one of $R^7$ or $R^8$ is $OR^{11}$ and the other of $R^7$ or $R^8$ is optionally substituted $(C_1-C_8)$alkyl. In one aspect of this embodiment, $R^7$ and $R^8$ are each $CH_3$. In one aspect of this embodiment, one of $R^7$ or $R^8$ is H and the other of $R^7$ or $R^8$ is $CH_3$. In one aspect of this embodiment, one of $R^7$ or $R^8$ is halogen and the other of $R^7$ or $R^8$ is $CH_3$. In one aspect of this embodiment, one of $R^7$ or $R^8$ is $OR^{11}$ and the other of $R^7$ or $R^8$ is $CH_3$.

In another embodiment, provided is a compound of Formula I or Formula II represented by Formula VII or Formula VIII:

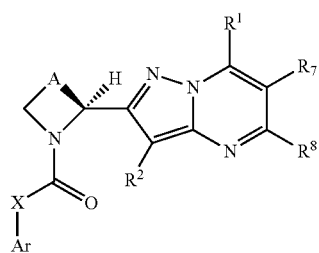

Formula VII

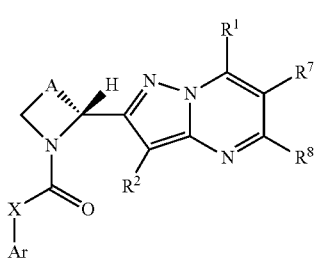

Formula VIII

In another embodiment, provided is a compound of Formula I or Formula II represented by Formula VIIa or Formula VIIIa:

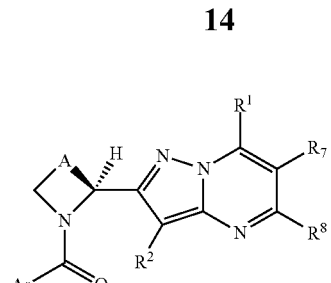

Formula VIIa

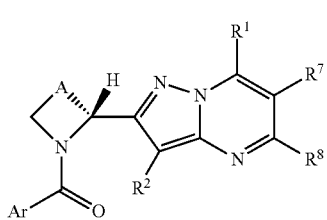

Formula VIIIa

In another embodiment, provided is a compound of Formula I or Formula II represented by Formula VIIb or Formula VIIIb:

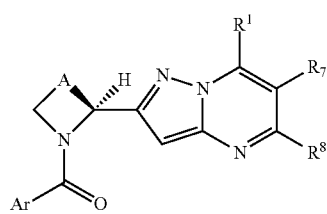

Formula VIIb

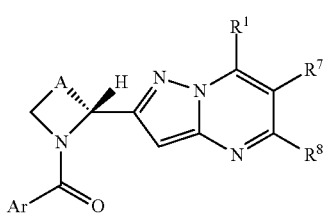

Formula VIIIb

In another embodiment, provided is a compound of Formula I or Formula II represented by Formula VIIc or Formula VIIIc:

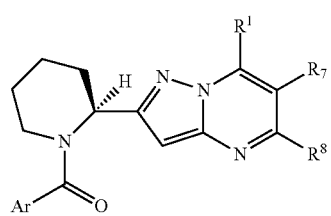

Formula VIIc

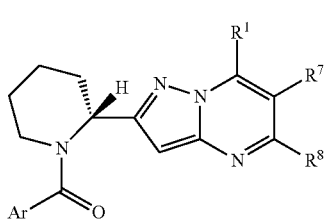

Formula VIIIc

In another embodiment, provided is a compound of Formula IX:

Formula IX

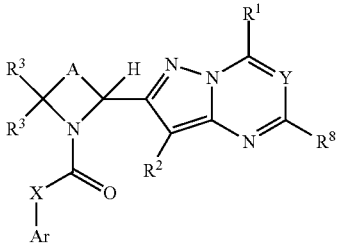

or a pharmaceutically acceptable salt or ester, thereof; wherein:

A is $-(C(R^4)_2)_n-$ wherein any one $C(R^4)_2$ of said $-(C(R^4)_2)_n-$ may be optionally replaced with $-O-$, $-S-$, $S(O)_p-$, NH or $NR^a$;

n is 3, 4, 5 or 6;

each p is 1 or 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1 to 5 $R^6$.

X is $-(CR^{13}R^{14})-$, $-N(CH_2R^{14})-$ or X is absent;

Y is N or $CR^7$;

each $R^1$, $R^2$, $R^3$, $R^4$, $R^5$, $R^6$, $R^7$ or $R^8$ is independently H, oxo, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl;

two $R^4$ on adjacent carbon atoms, when taken together, may form a double bond between the two carbons to which they are attached or may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

four $R^4$ on adjacent carbon atoms, when taken together, may form an optionally substituted $C_6$ aryl ring;

two $R^4$ on the same carbon atom, when taken together, may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

two $R^6$ on adjacent carbon atoms, when taken together, may form a $(C_3$-$C_7)$cycloalkyl ring wherein one carbon atom of said $(C_3$-$C_7)$cycloalkyl ring may be optionally replaced by $-O-$, $-S-$, $-S(O)_p-$, $-NH-$ or $-NR^a-$;

any $R^6$ adjacent to the obligate carbonyl group of said Ar, when taken together with $R^3$, may form a bond or a $-(C(R^5)_2)_m-$ group wherein m is 1 or 2;

any $R^6$ adjacent to the obligate carbonyl group of said Ar, when taken together with $R^2$, may form a bond;

each $R^a$ is independently $(C_1$-$C_8)$alkyl, $(C_1$-$C_8)$haloalkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl wherein any $(C_1$-$C_8)$alkyl, $(C_1$-$C_8)$haloalkyl, $(C_2$-$C_8)$alkenyl or $(C_2$-$C_8)$alkynyl of $R^a$ is optionally substituted with one or more OH, $NH_2$, $CO_2H$, $C_2$-$C_{20}$ heterocyclyl, and wherein any aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl of $R^a$ is optionally substituted with one or more OH, $NH_2$, $CO_2H$, $C_2$-$C_{20}$ heterocyclyl or $(C_1$-$C_8)$alkyl;

each $R^{11}$ or $R^{12}$ is independently H, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl, $(C_4$-$C_8)$carbocyclylalkyl, $-C(=O)R^a$, $-S(O)_pR^a$, or aryl$(C_1$-$C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S-$, $-S(O)_p-$, $-NH-$, $-NR^a-$ or $-C(O)-$;

$R^{13}$ is H or $(C_1$-$C_8)$alkyl;

$R^{14}$ is H, $(C_1$-$C_8)$alkyl, $NR^{11}R^{12}$, $NR^{11}C(O)R^{11}$, $NR^{11}C(O)OR^{11}$, $NR^{11}C(O)NR^{11}R^{12}$, $NR^{11}S(O)_pR^a$, $-NR^{11}S(O)_p(OR^{11})$ or $NR^{11}SO_pNR^{11}R^{12}$; and wherein each $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl of each $R^1$, $R^2$, $R^3$, $R^4$, $R^5$, $R^6$, $R^7$, $R^8$, $R^{11}$ or $R^{12}$ is, independently, optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1$-$C_8)$alkyl, $(C_1$-$C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $OC(=O)R^a$, $-OP(O)(OH)_2$ or $R^a$;

provided the compound is not:

(2-fluorophenyl)(2-(5-methyl-7-(trifluoromethyl)pyrazolo[1,5-a]pyrimidin-2-yl)piperidin-1-yl)methanone;

2-(7-hydroxy-5-methylpyrazolo[1,5-a]pyrimidin-2-yl)piperidin-1-yl)(3,4,5-trimethoxyphenyl)methanone;

4-fluoro-3-(2-(7-hydroxy-5-methylpyrazolo[1,5-a]pyrimidin-2-yl)piperidine-1-carbonyl)-N-methylbenzenesulfonamide;

N-(2-(2-(7-hydroxy-5-methylpyrazolo[1,5-a]pyrimidin-2-yl)piperidine-1-carbonyl)phenyl)methanesulfonamide;

(2-(5-ethyl-7-hydroxypyrazolo[1,5-a]pyrimidin-2-yl)piperidin-1-yl)(3,4,5-trimethoxyphenyl)methanone;

N-(2-(2-(5-ethyl-7-hydroxypyrazolo[1,5-a]pyrimidin-2-yl)piperidine-1-carbonyl)phenyl)methanesulfonamide;

(2-(7-hydroxy-5,6-dimethylpyrazolo[1,5-a]pyrimidin-2-yl)piperidin-1-yl)(3,4,5-trimethoxyphenyl)methanone;

N-(2-(2-(7-hydroxy-5,6-dimethylpyrazolo[1,5-a]pyrimidin-2-yl)piperidine-1-carbonyl)phenyl)methanesulfonamide; or (2-(6-fluoro-7-hydroxy-5-methylpyrazolo[1,5-a]pyrimidin-2-yl)piperidin-1-yl)(3,4,5-trimethoxyphenyl)methanone.

Specific values listed below for radicals, substituents, and ranges, are for illustration only; they do not exclude other defined values or other values within defined ranges for the radicals and substituents. The specific values listed below are specific values for compounds of Formulas I-IX. It is to be understood that reference to a general Formula includes all of the subformulas for that Formula. Therefore, reference to Formula VII includes Formulas VIIa, VIIb and VIIc unless otherwise stated and reference to Formulas I-IX includes Formulas I, Ia, II, IIa, III, IV, V, VI, VII, VIIa, VIIb, VIIc, VIII, VIIIa, VIIIb, VIIIc and IX unless otherwise stated.

In one embodiment the invention includes compounds of Formula I.

In another embodiment the invention includes compounds of Formula VII.

A specific value for $R^2$ is H.

A specific value for $R^3$ is H.

A specific value for Y is $CR^7$

A specific value for $R^7$ is H, halogen or $(C_1-C_8)$alkyl.

Another specific value for $R^7$ is H, fluoro, methyl or ethyl.

Another specific value for $R^7$ is methyl.

A specific value for n is 3 or 4.

A specific group of compounds are compounds wherein $R^4$ is H or optionally substituted $(C_1-C_8)$alkyl, or four $R^4$ on adjacent carbon atoms, when taken together, may form an optionally substituted $C_6$ aryl ring.

A specific group of compounds are compounds wherein one $R^4$ group is H, $CH_3$ or $CF_3$ and the remaining $R^4$ groups are H.

Another specific value for $R^4$ is H.

A specific value for A is $—(CH_2)_3—$, $—(CH_2)_4—$, $—CH_2—O—CH_2—$, $—CH_2—CH(CH_3)—CH_2—$, $—CH_2—CH(CF_3)—CH_2—$, $—CH_2—CH_2—CH(CH_3)—$ or the structure:

Another specific value for A is $—(CH_2)_3—$.

A specific value for X is $—CR^{13}(NR^{11}C(O)OR^{11})—$, $—CR^{13}(NR^{11}R^{12})—$, $—CR^{13}(NR^{11}S(O)_pR^a)—$ or X is absent.

Another specific value for X is $—CH(NHC(O)OC(CH_3)_3)—$, $—CH(NHC(O)OCH_3)—$, $—CH(NH_2)—$, $—CH(NHS(O)_2CH_3)—$, or X is absent.

A specific group of compounds are compounds wherein X is absent.

A specific value for $R^1$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $—C(=O)R^{11}$, $—C(=O)OR^{11}$, $—C(=O)NR^{11}R^{12}$, $—C(=O)SR^{11}$, $—S(O)_p(OR^{11})$, $—SO_2NR^{11}R^{12}$, $—NR^{11}S(O)_p(OR^{11})$, $—NR^{11}SO_pNR^{11}R^{12}$, $NR^{11}$, $NR^{11}C(=NR^{11})NR^{11}R^{12}$, halogen, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl, wherein any $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl of $R^1$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $—C(O)R^a$, $—C(O)H$, $—C(=O)OR^a$, $—C(=O)OH$, $—C(=O)N(R^a)_2$, $—C(=O)NHR^a$, $—C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $—OC(=O)R^a$, $—OP(O)(OH)_2$ or $R^a$, provided $R^1$ is not OH or $CF_3$ when $R^8$ is methyl or ethyl.

Another specific value for $R^1$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $—C(=O)R^{11}$, $—C(=O)OR^{11}$, $—C(=O)NR^{11}R^{12}$, $—C(=O)SR^{11}$, $—S(O)_p(OR^{11})$, $—SO_2NR^{11}R^{12}$, $—NR^{11}S(O)_p(OR^{11})$, $—NR^{11}SO_pNR^{11}R^{12}$, $NR^{11}$, $NR^{11}C(NR^{11})NR^{11}R^{12}$, halogen, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl, wherein any $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl of $R^1$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $—C(O)R^a$, $—C(O)H$, $—C(=O)OR^a$, $—C(=O)$ OH, $—C(=O)N(R^a)_2$, $—C(=O)NHR^a$, $—C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $—OC(=O)R^a$, $—OP(O)(OH)_2$ or $R^a$, provided $R^1$ is not OH or $CF_3$.

Another specific value for $R^1$ is H, $OR^{11}$, $NR^{11}R^{12}$, CN, $(C_1-C_8)$alkyl, $C_6-C_{20}$ aryl, $C_2-C_{20}$ heterocyclyl, or $(C_3-C_7)$cycloalkyl, wherein any $(C_1-C_8)$alkyl, $C_6-C_{20}$ aryl, $C_2-C_{20}$ heterocyclyl or $(C_3-C_7)$cycloalkyl of $R^1$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $—C(O)R^a$, $—C(O)H$, $—C(O)OR^a$, $—C(=O)OH$, $—C(=O)N(R^a)_2$, $—C(=O)NHR^a$, $—C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $—OC(=O)R^a$, $—OP(O)(OH)_2$ or $R^a$.

Another specific value for $R^1$ is H or $C_2-C_{20}$ heterocyclyl, wherein any $C_2-C_{20}$ heterocyclyl of $R^1$ is optionally substituted with or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $—C(O)R^a$, $—C(O)H$, $—C(=O)OR^a$, $—C(=O)OH$, $—C(=O)N(R^a)_2$, $—C(=O)NHR^a$, $—C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $—OC(=O)R^a$, $—OP(O)(OH)_2$ or $R^a$.

Another specific value for $R^1$ is H or $C_2-C_{20}$ heterocyclyl.

Another specific value for $R^1$ is:

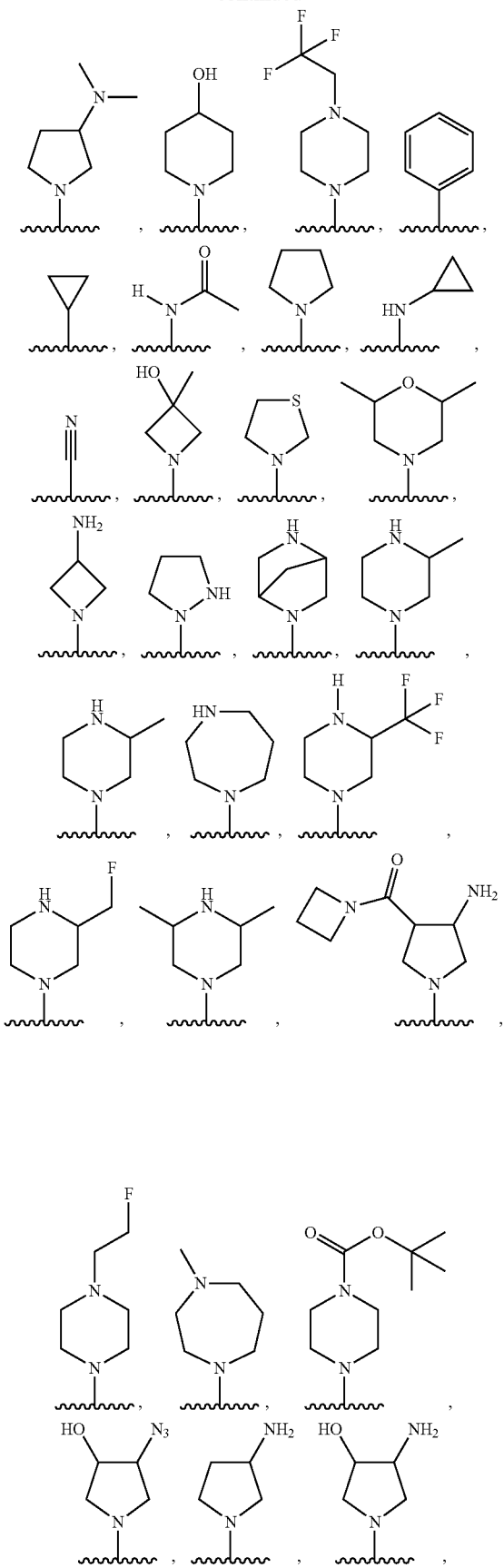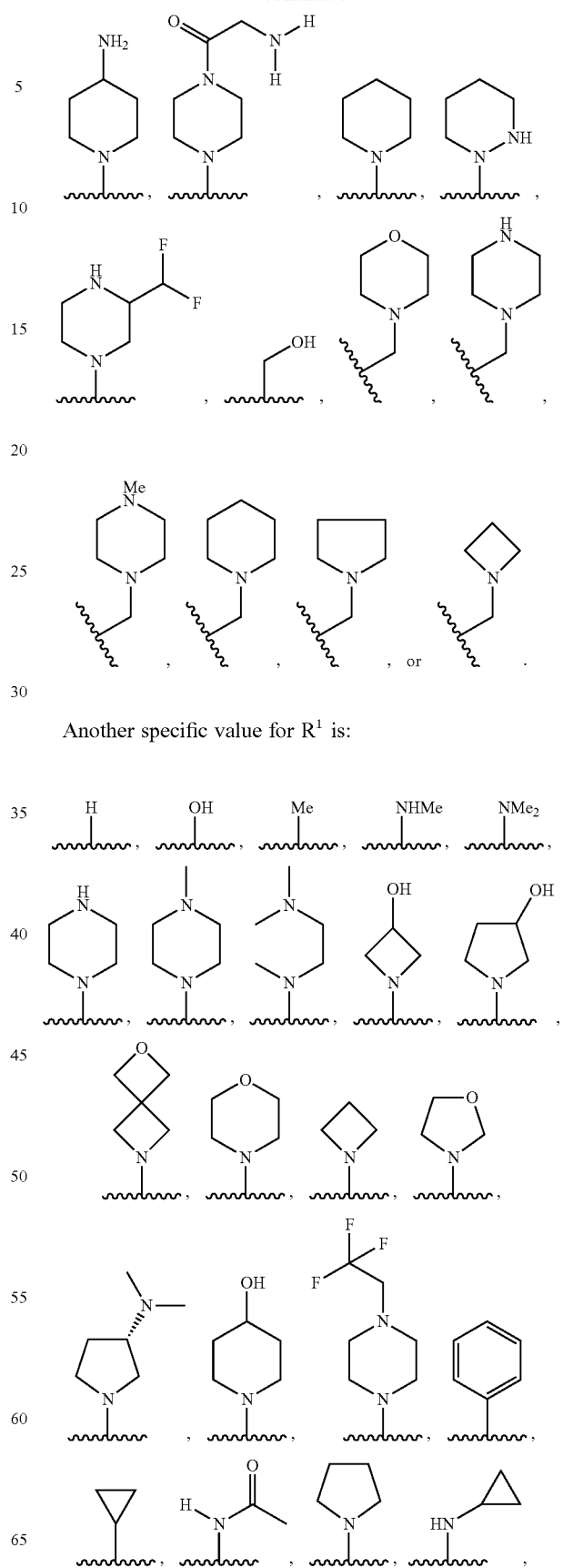
Another specific value for $R^1$ is:

-continued

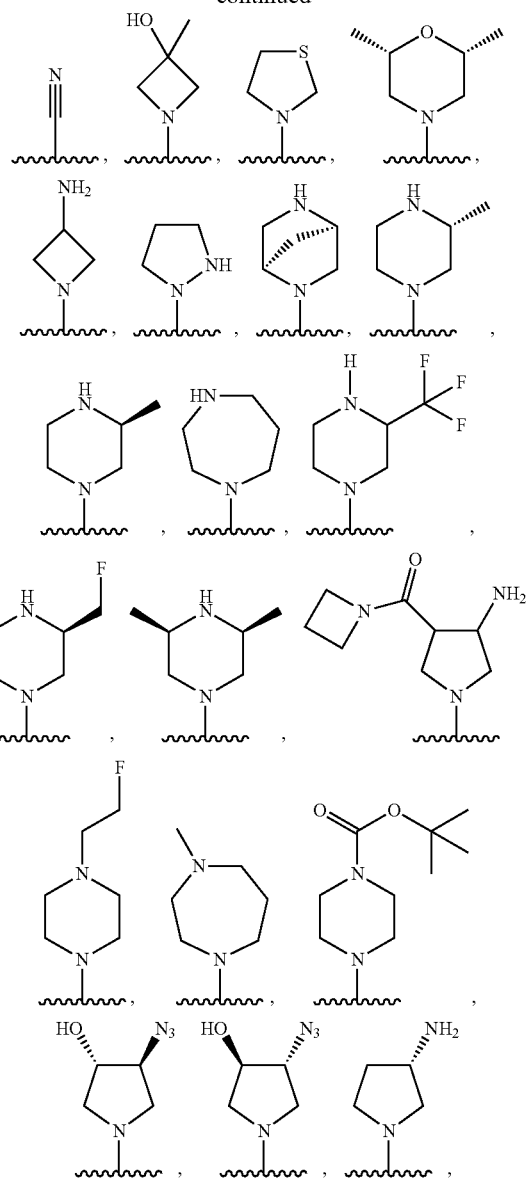

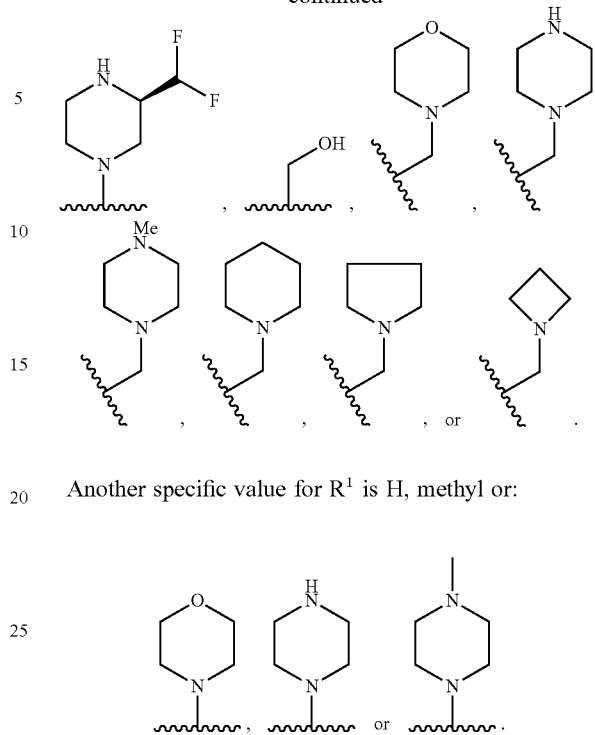

Another specific value for R¹ is H, methyl or:

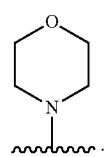

Another specific value for R¹ is H, methyl, morpholinyl, piperazinyl or N-methylpiperazinyl.
Another specific value for R¹ is H or:

Another specific value for R¹ is H or morpholinyl.
A specific value for Ar is a $C_6$-$C_{20}$ aryl group, wherein the $C_6$-$C_{20}$ aryl group is optionally substituted with 1 to 5 $R^6$.
Another specific value for Ar is phenyl optionally substituted with 1 to 5 $R^6$.
A specific value for $R^6$ is $OR^{11}$, $NR^{11}R^{12}$, $NR^{11}C(O)OR^{11}$, $NR^{11}C(O)OR^{11}$, CN, $NR^{11}S(O)_pR^a$, —C(=O)$NR^{11}R^{12}$, —$NR^{11}SO_pNR^{11}R^{12}$, halogen, ($C_1$-$C_8$)alkyl, ($C_2$-$C_8$)alkynyl, $C_6$-$C_{20}$ aryl, $C_2$-$C_{20}$ heterocyclyl or ($C_3$-$C_7$)cycloalkyl, wherein any $C_1$-$C_8$)alkyl, ($C_2$-$C_8$)alkynyl, $C_6$-$C_{20}$ aryl, $C_2$-$C_{20}$ heterocyclyl and ($C_3$-$C_7$)cycloalkyl of $R^6$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, ($C_1$-$C_8$)alkyl, ($C_1$-$C_8$)haloalkyl, —C(O)$R^a$, —C(O)H, —C(=O)$OR^a$, —C(=O)OH, —C(=O)$N(R^a)_2$, —C(=O)$NHR^a$, —C(=O)$NH_2$, $NHS(O)_pR^a$, $NR^aS(O)_pR^a$, NHC(O)$R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, =NH, =NOH, =$NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, —OC(=O)$R^a$, —OP(O)(OH)$_2$ or $R^a$.
Another specific value for $R^6$ is $NR^{11}S(O)_pR^a$, $NR^{11}C(O)OR^{11}$, $NR^{11}C(O)R^{11}$, ($C_1$-$C_8$)alkyl or halogen.

Another specific value for $R^6$ is $NR^{11}S(O)_pR^a$, $NR^{11}C(O)OR^{11}$ or halogen.
A specific value for Ar is:
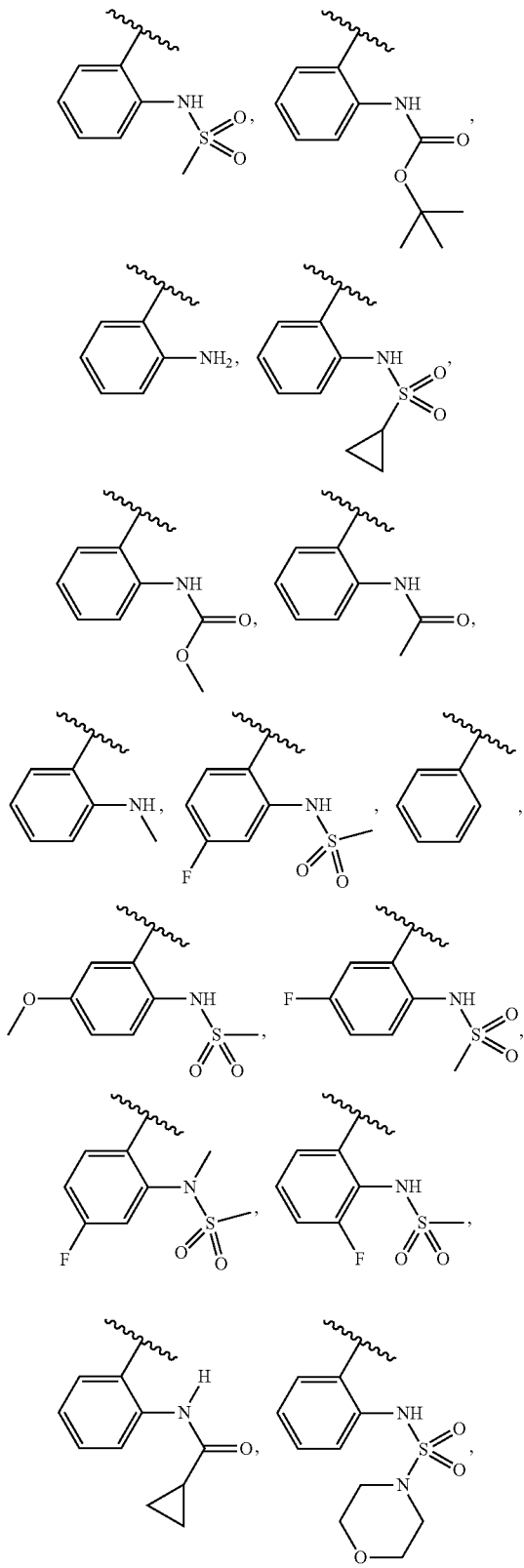
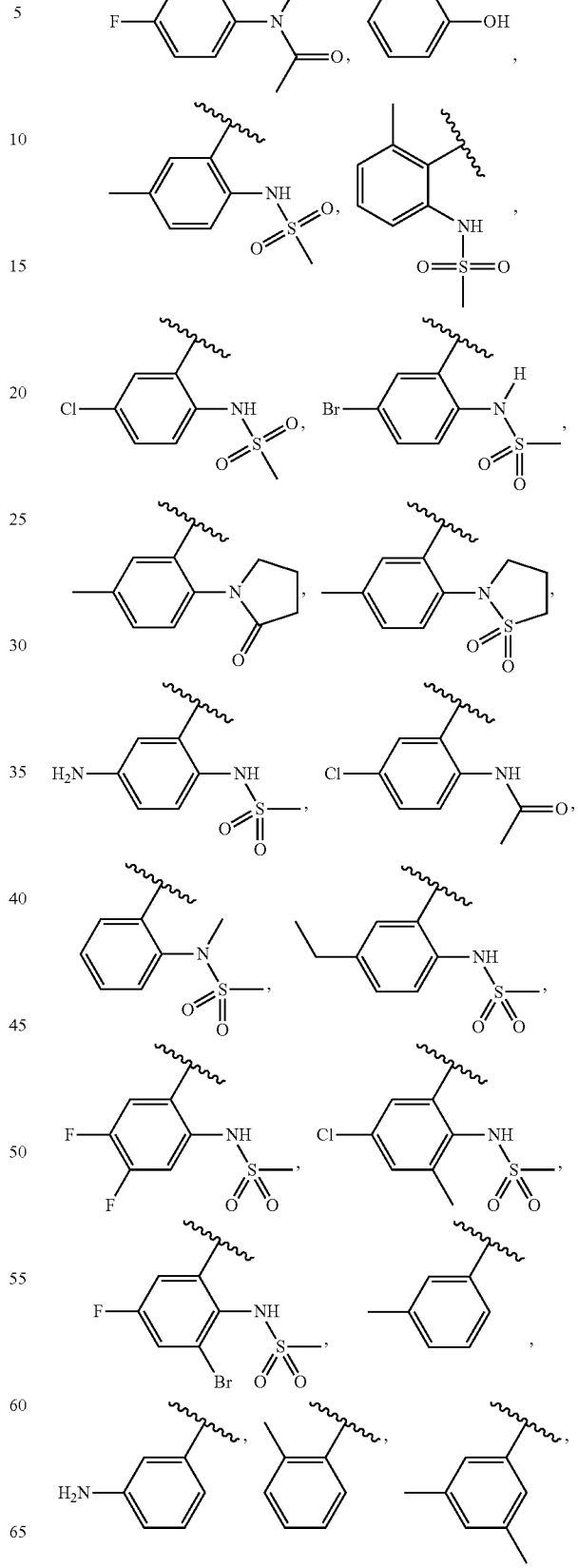

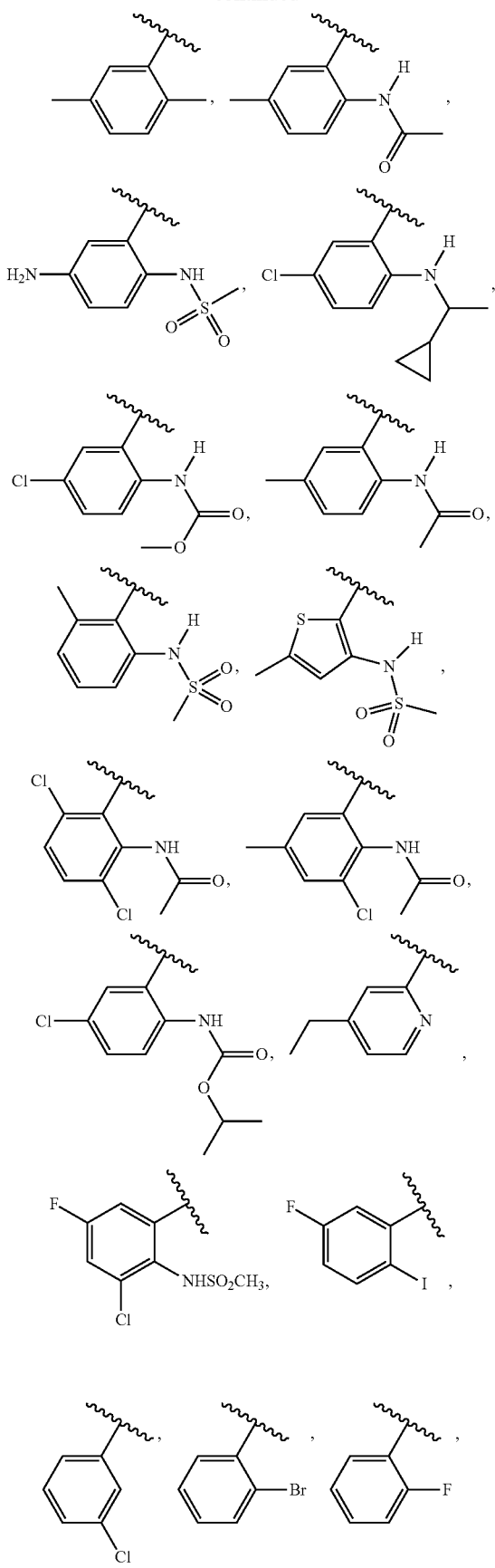
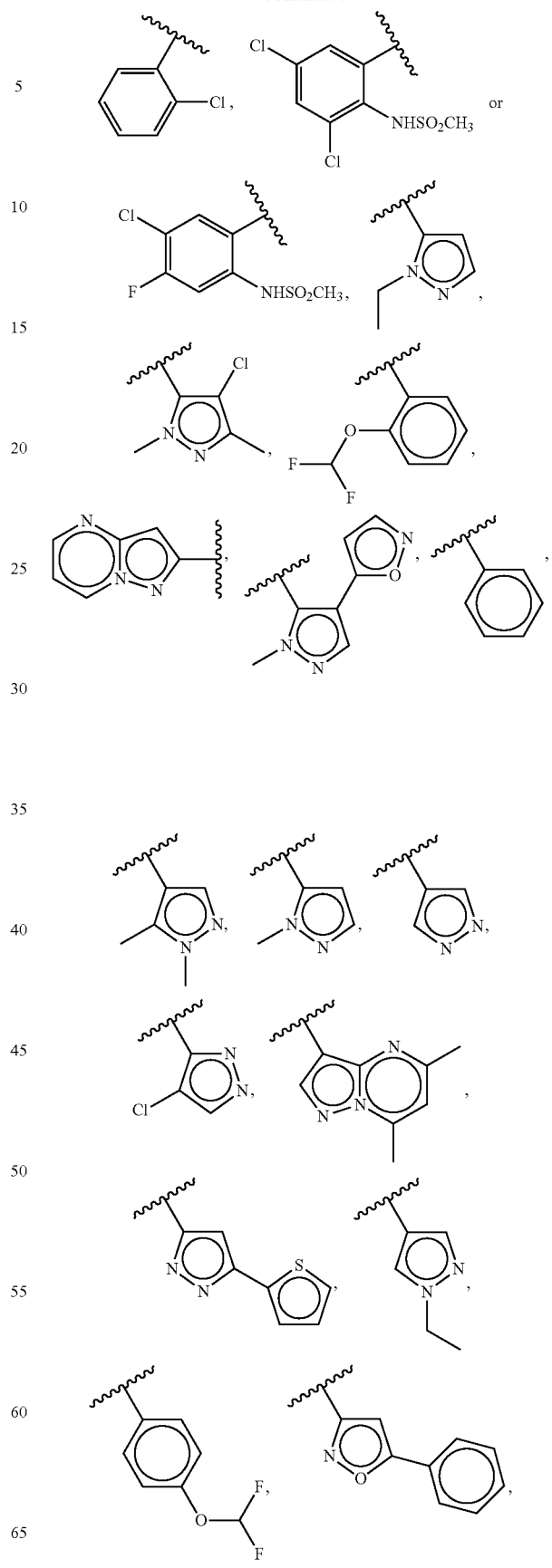

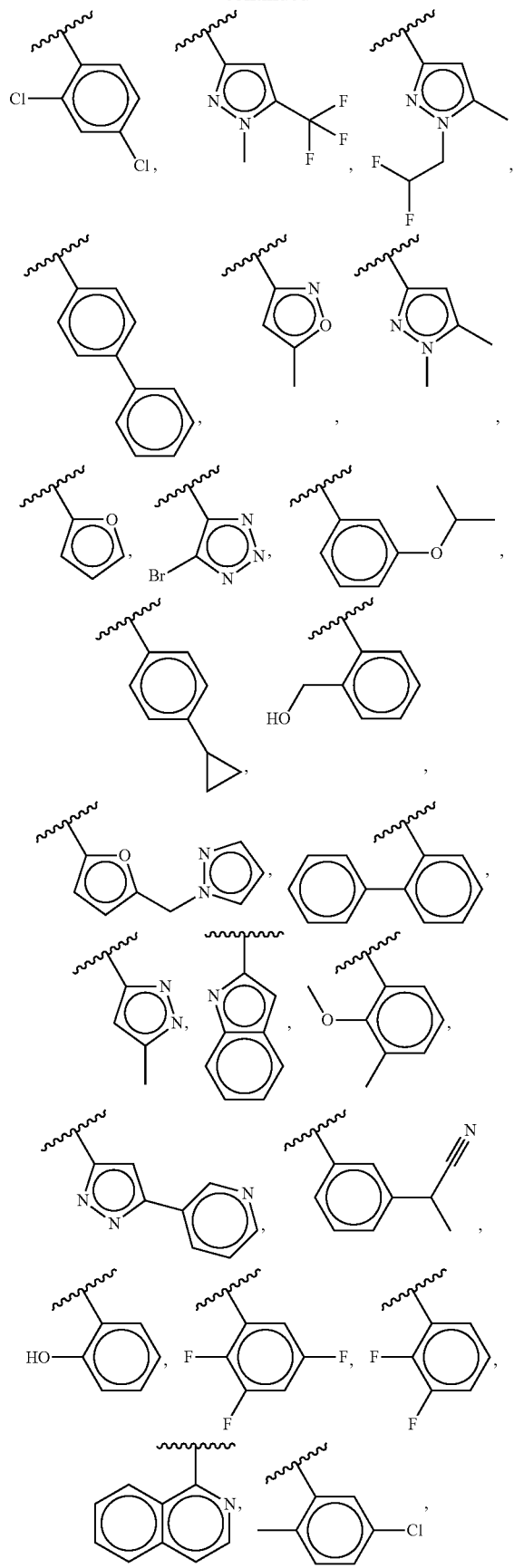
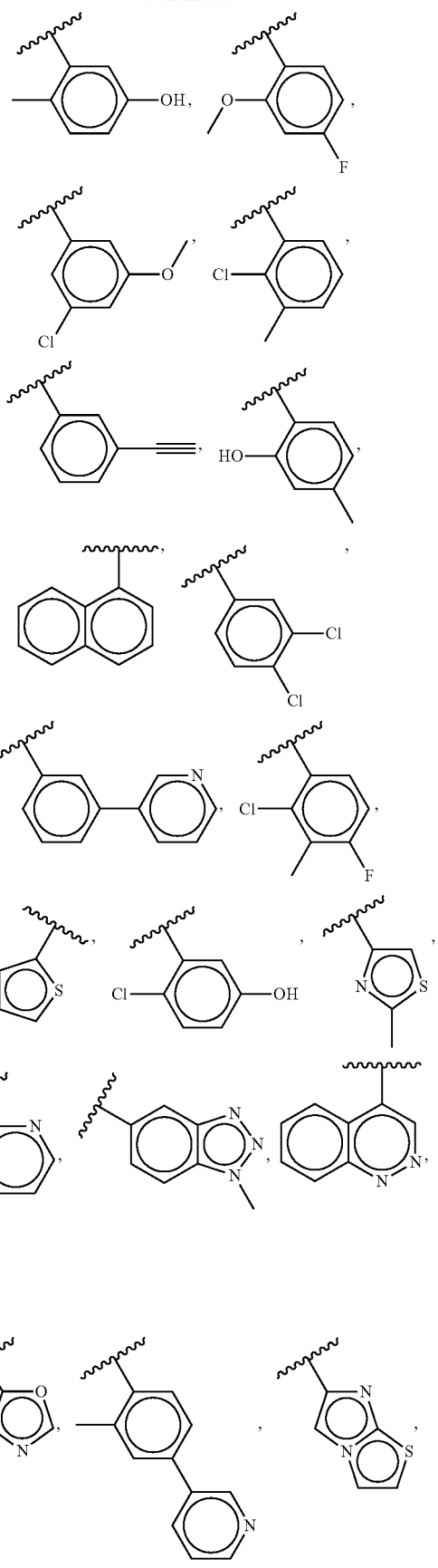

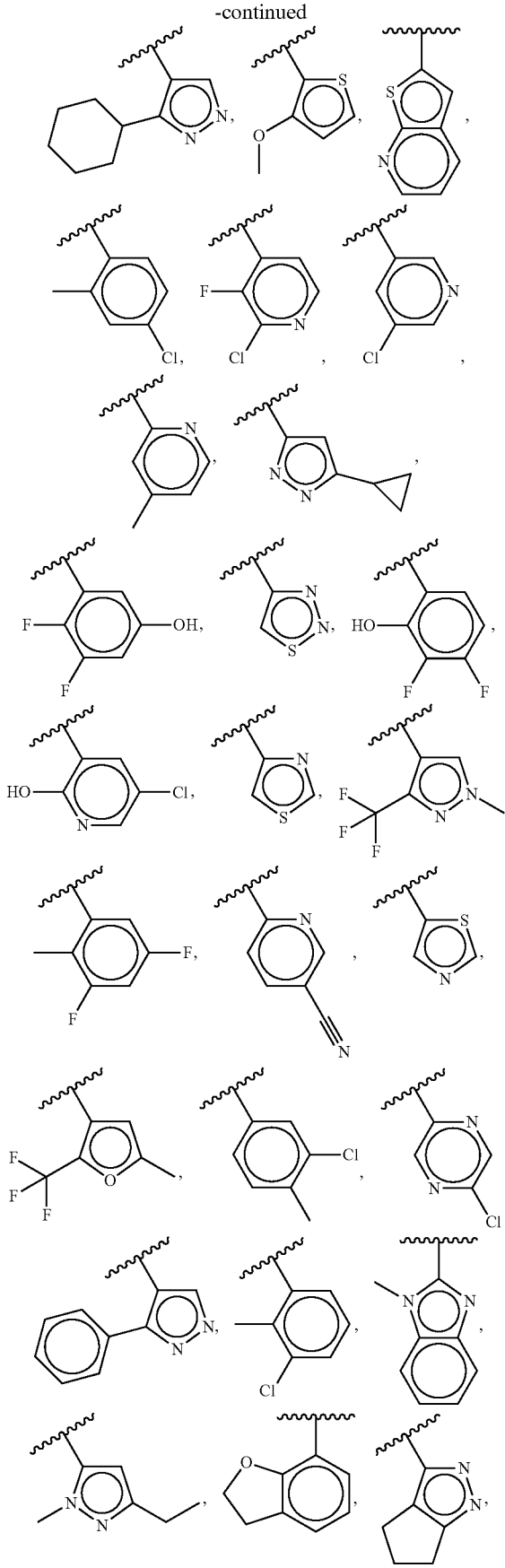
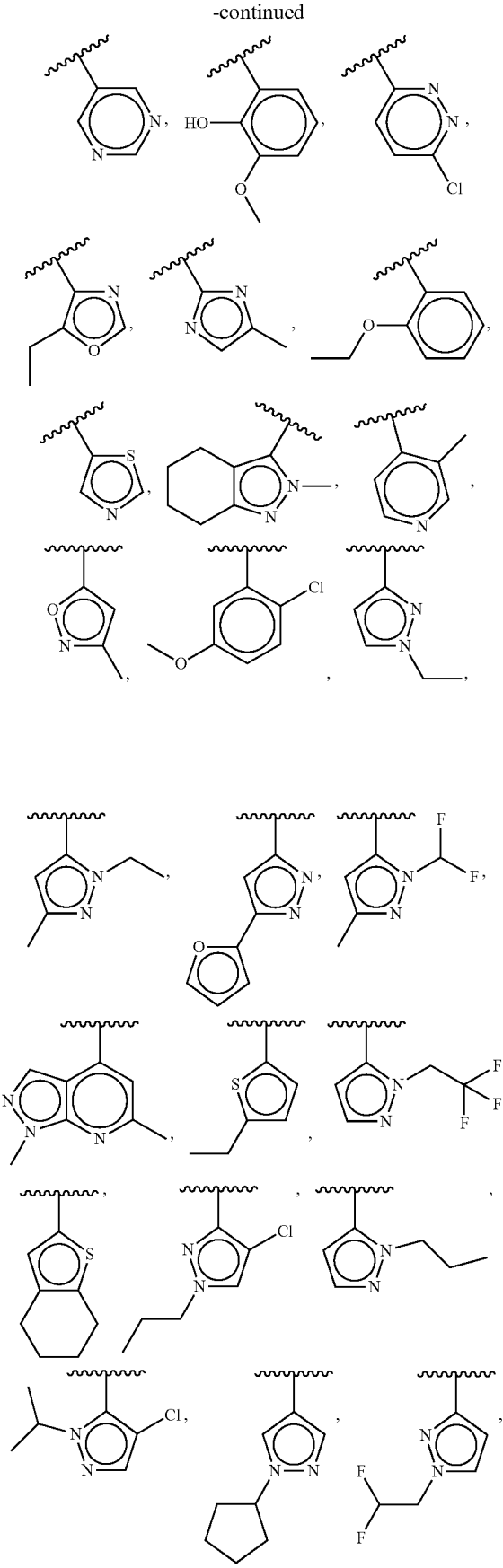

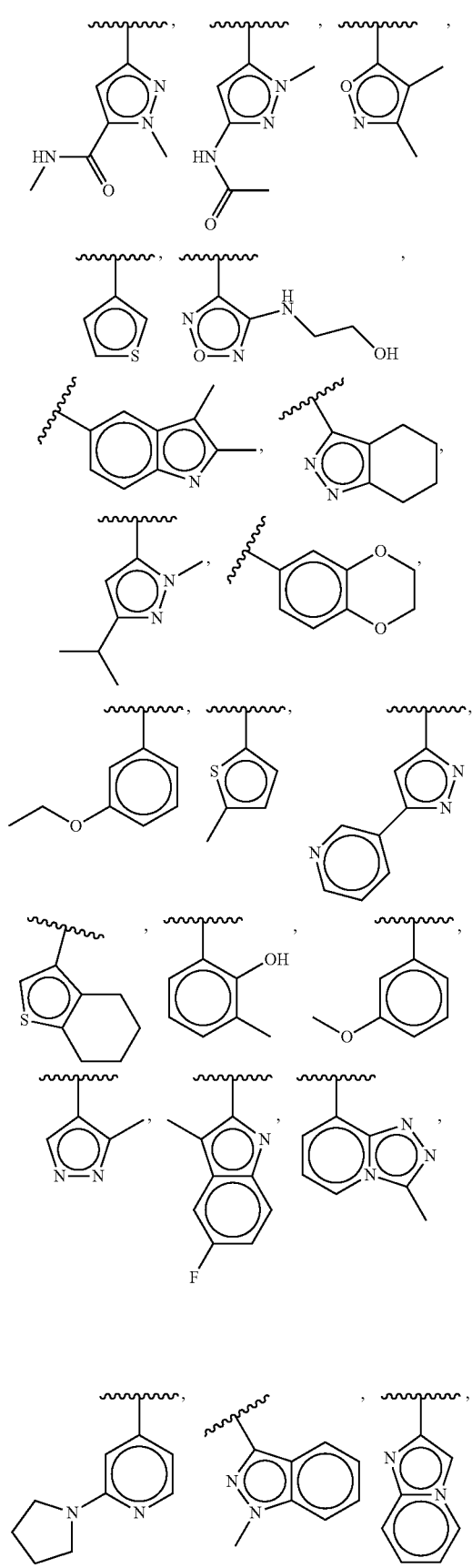
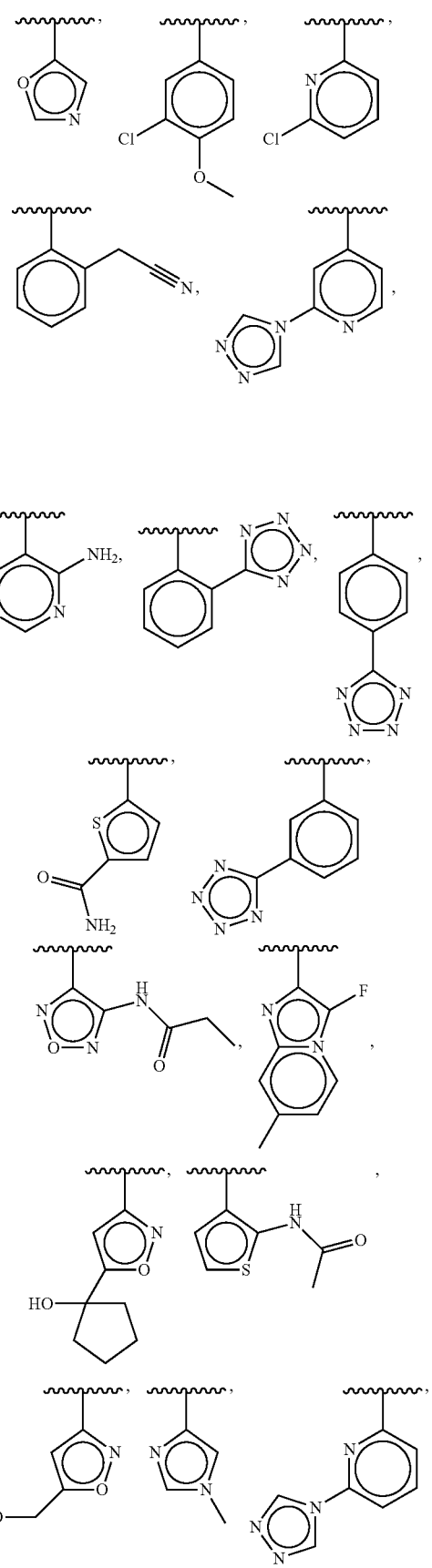

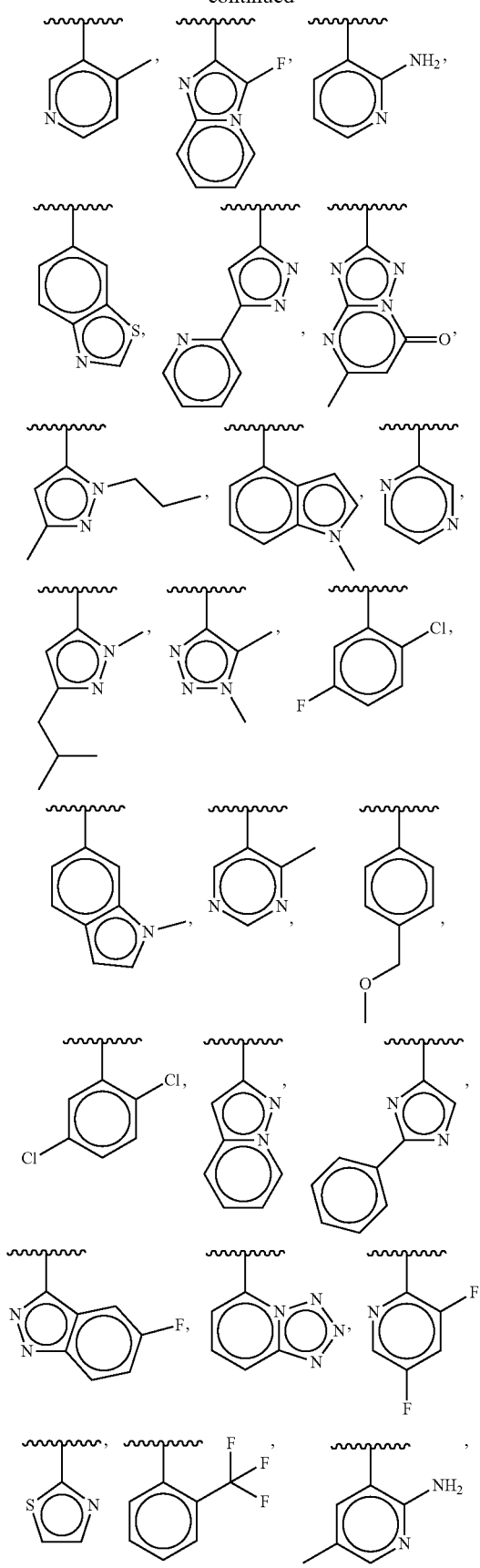
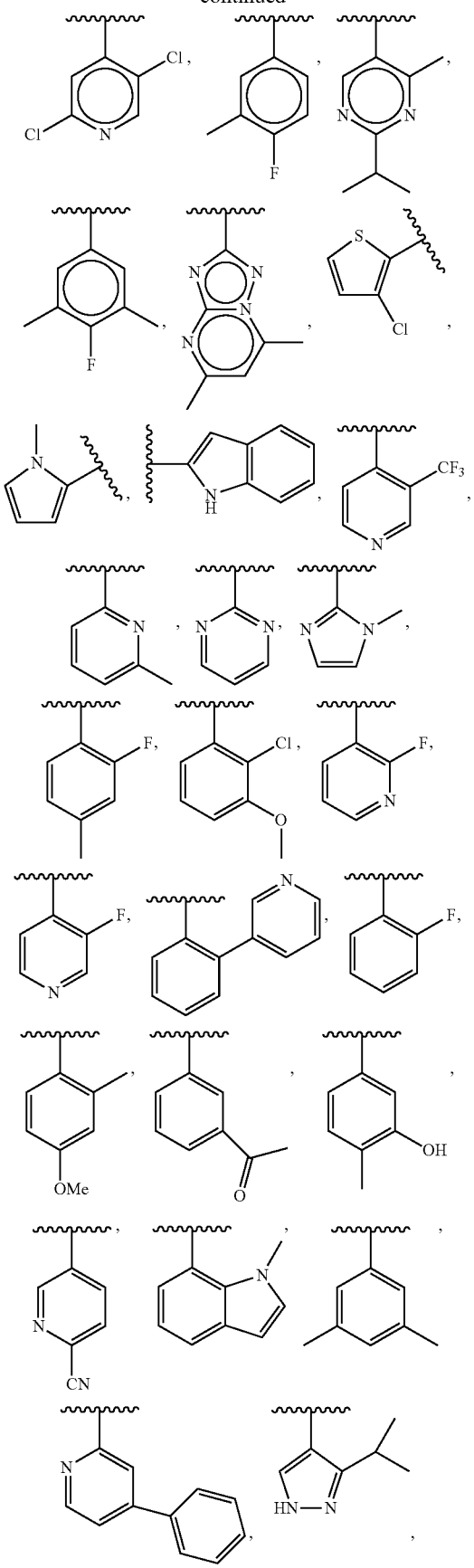

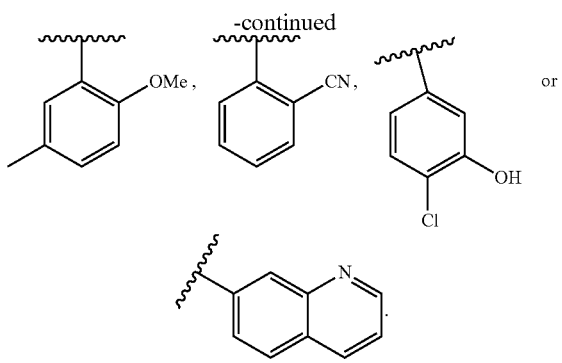

Another specific value for Ar is:

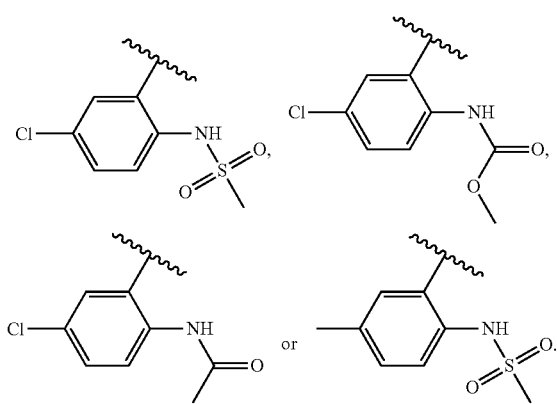

Another specific value for Ar is:

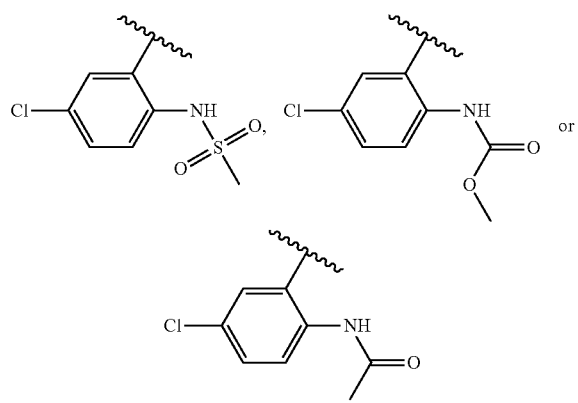

Another specific value for Ar is:

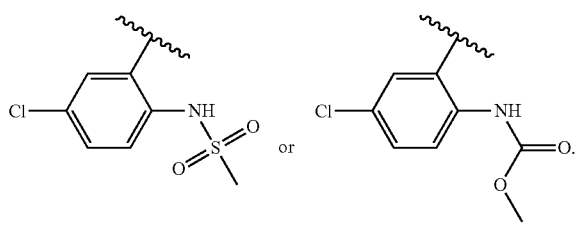 [SMILES: *c1cc(Cl)ccc1NS(C)(=O)=O ; *c1cc(Cl)ccc1NC(=O)OC]

A specific value for $R^8$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —C(=O)$R^{11}$, —C(=O)$OR^{11}$, —C(=O)$NR^{11}R^{12}$, —C(=O)$SR^{11}$, —S(O)($OR^{11}$), —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl, wherein any ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of $R^8$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, ($C_1$-$C_8$)alkyl, ($C_1$-$C_8$)haloalkyl, —C(O)$R^a$, —C(O)H, —C(=O)$OR^a$, —C(=O)OH, —C(=O)$N(R^a)_2$, —C(=O)$NHR^a$, —C(=O)$NH_2$, NHS(O)$_pR^a$, $NR^aS(O)_pR^a$, NHC(O)$R^a$, $NR^aC(O)R^a$, NHC(O)$OR^a$, $NR^aC(O)OR^a$, $NR^aC(O)NHR^a$, $NR^aC(O)N(R^a)_2$, $NR^aC(O)NH_2$, NHC(O)$NHR^a$, NHC(O)$N(R^a)_2$, NHC(O)$NH_2$, =NH, =NOH, =$NOR^a$, $NR^aS(O)_pNHR^a$, $NR^aS(O)_pN(R^a)_2$, $NR^aS(O)_pNH_2$, NHS(O)$_pNHR^a$, NHS(O)$_pN(R^a)_2$, NHS(O)$_pNH_2$, —OC(=O)$R^a$, —OP(O)(OH)$_2$ or $R^a$; provided $R^8$ is not methyl or ethyl when $R^1$ is OH or $CF_3$.

Another specific value for $R^8$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —C(=O)$R^{11}$, —C(=O)$OR^{11}$, —C(=O)$NR^{11}R^{12}$, —C(=O)$SR^{11}$, —S(O)$_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl, wherein any ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of $R^8$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, ($C_1$-$C_8$)alkyl, ($C_1$-$C_8$)haloalkyl, —C(O)$R^a$, —C(O)H, —C(=O)$OR^a$, —C(=O)OH, —C(=O)$N(R^a)_2$, —C(=O)$NHR^a$, —C(=O)$NH_2$, NHS(O)$_pR^a$, $NR^aS(O)_pR^a$, NHC(O)$R^a$, $NR^aC(O)R^a$, NHC(O)$OR^a$, $NR^aC(O)OR^a$, $NR^aC(O)NHR^a$, $NR^aC(O)N(R^a)_2$, $NR^aC(O)NH_2$, NHC(O)$NHR^a$, NHC(O)$N(R^a)_2$, NHC(O)$NH_2$, =NH, =NOH, =$NOR^a$, $NR^aS(O)_pNHR^a$, $NR^aS(O)_pN(R^a)_2$, $NR^aS(O)_pNH_2$, NHS(O)$_pNHR^a$, NHS(O)$_pN(R^a)_2$, NHS(O)$_pNH_2$, —OC(=O)$R^a$, —OP(O)(OH)$_2$ or $R^a$; provided $R^8$ is not methyl or ethyl.

Another specific value for $R^8$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —C(=O)$R^{11}$, —C(=O)$OR^{11}$, —C(=O)$NR^{11}R^{12}$, —C(=O)$SR^{11}$, —S(O)$_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, ($C_3$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl, wherein any ($C_3$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of $R^8$ is optionally substituted with one or more oxo, halogen, hydroxy, $NH_2$, CN, $N_3$, $N(R^a)_2$, $NHR^a$, SH, $SR^a$, $S(O)_pR^a$, $OR^a$, ($C_1$-$C_8$)alkyl, ($C_1$-$C_8$)haloalkyl, —C(O)$R^a$, —C(O)H, —C(=O)$OR^a$, —C(=O)OH, —C(=O)$N(R^a)_2$, —C(=O)$NHR^a$, —C(=O)$NH_2$, NHS(O)$_pR^a$, $NR^aS(O)_pR^a$, NHC(O)$R^a$, $NR^aC(O)R^a$, NHC(O)$OR^a$, $NR^aC(O)OR^a$, $NR^aC(O)NHR^a$, $NR^aC(O)N(R^a)_2$, $NR^aC(O)NH_2$, NHC(O)$NHR^a$, NHC(O)$N(R^a)_2$, NHC(O)$NH_2$, =NH, =NOH, =$NOR^a$, $NR^aS(O)_pNHR^a$, $NR^aS$ (O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

Another specific value for R$^8$ is H, NR$^{11}$R$^{12}$, NR$^{11}$C(=NR$^{11}$)NR$^{11}$R$^{12}$, halogen, (C$_1$-C$_8$)alkyl, (C$_2$-C$_8$)alkynyl, C$_6$-C$_{20}$ aryl, C$_2$-C$_{20}$ heterocyclyl or (C$_3$-C$_7$)cycloalkyl, wherein any (C$_1$-C$_8$)alkyl, (C$_2$-C$_8$)alkynyl, C$_6$-C$_{20}$ aryl, C$_2$-C$_{20}$ heterocyclyl, or (C$_3$-C$_7$)cycloalkyl of R$^8$ is optionally substituted with one or more oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

Another specific value for R$^8$ is C$_2$-C$_{20}$ heterocyclyl, wherein C$_2$-C$_{20}$ heterocyclyl is optionally substituted with one or more oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

Another specific value for R$^8$ is C$_2$-C$_{20}$ heterocyclyl, wherein C$_2$-C$_{20}$ heterocyclyl is optionally substituted with one or more hydroxy, NH$_2$, CN or —OP(O)(OH)$_2$.

Another specific value for R$^8$ is pyrrolidinyl or azetidinyl, wherein pyrrolidinyl or azetidinyl is optionally substituted with one or more oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

Another specific value for R$^8$ is pyrrolidinyl or azetidinyl, wherein pyrrolidinyl or azetidinyl is optionally substituted with one or more hydroxy, NH$_2$, CN or —OP(O)(OH)$_2$.

Another specific value for R$^8$ is:

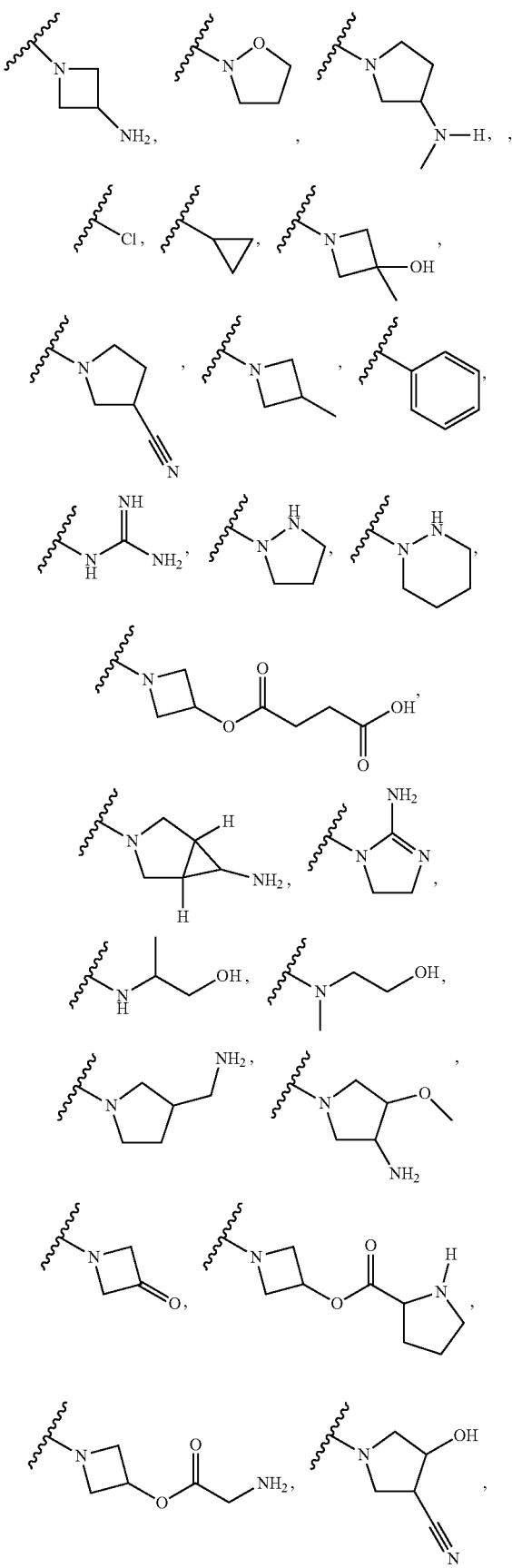

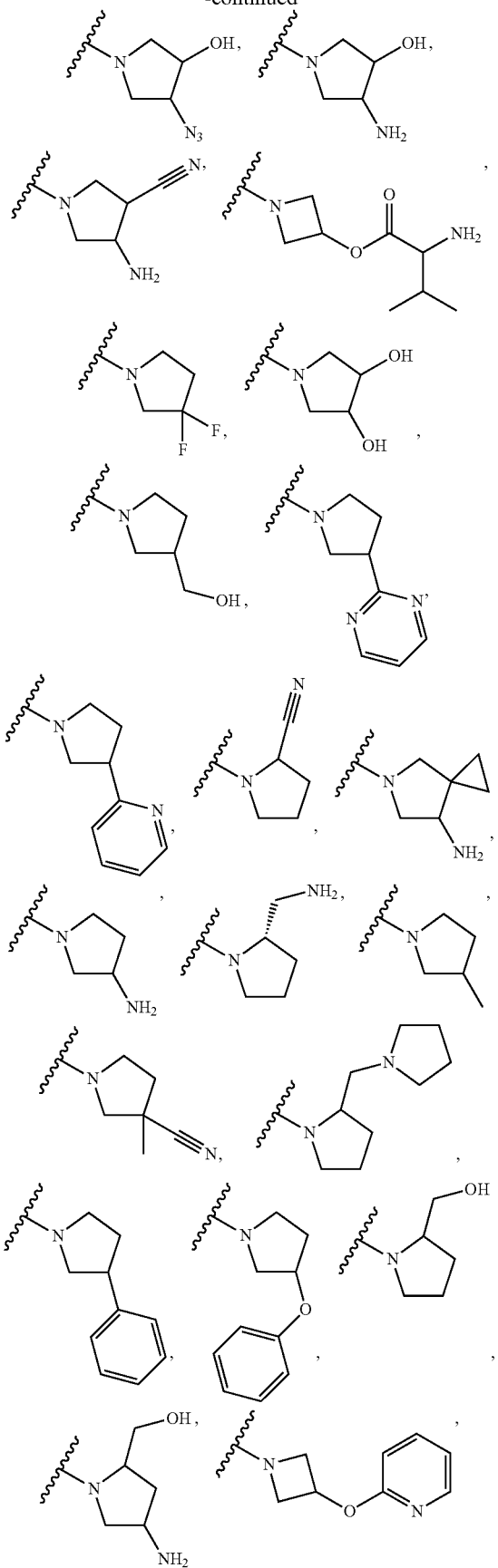
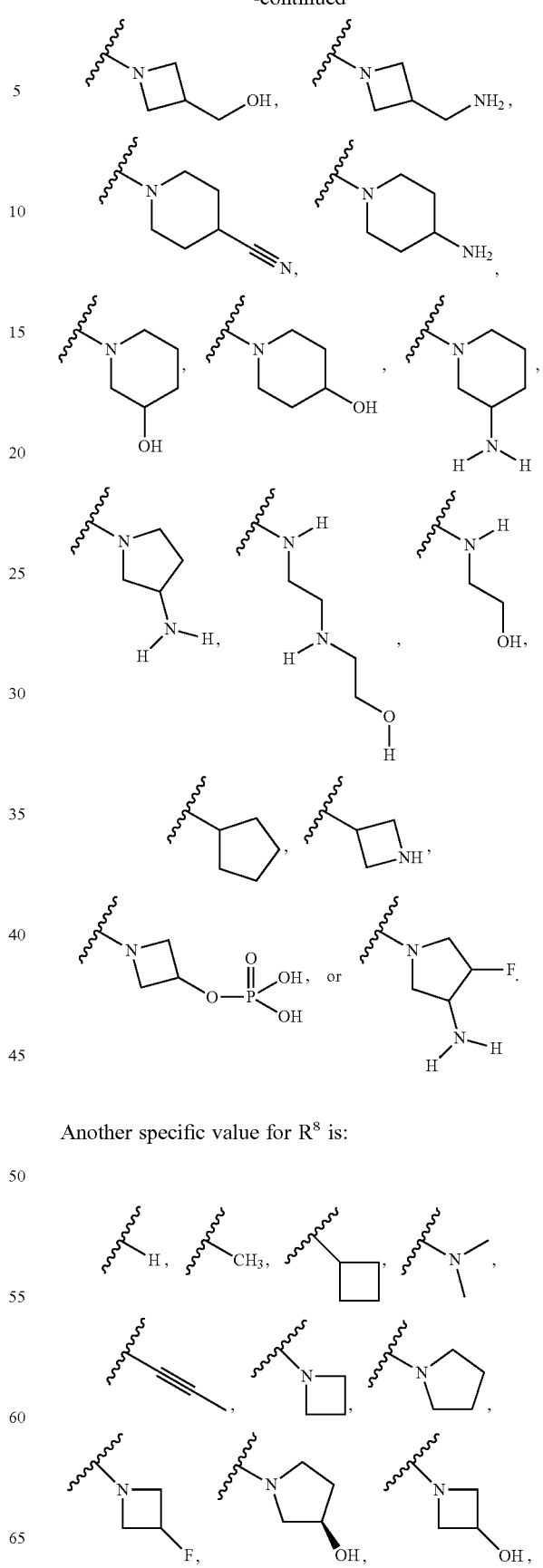
Another specific value for $R^8$ is:

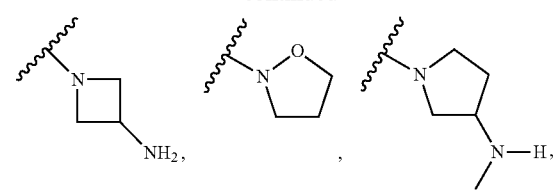
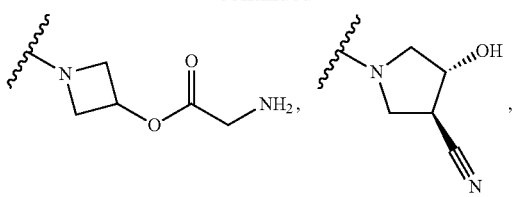

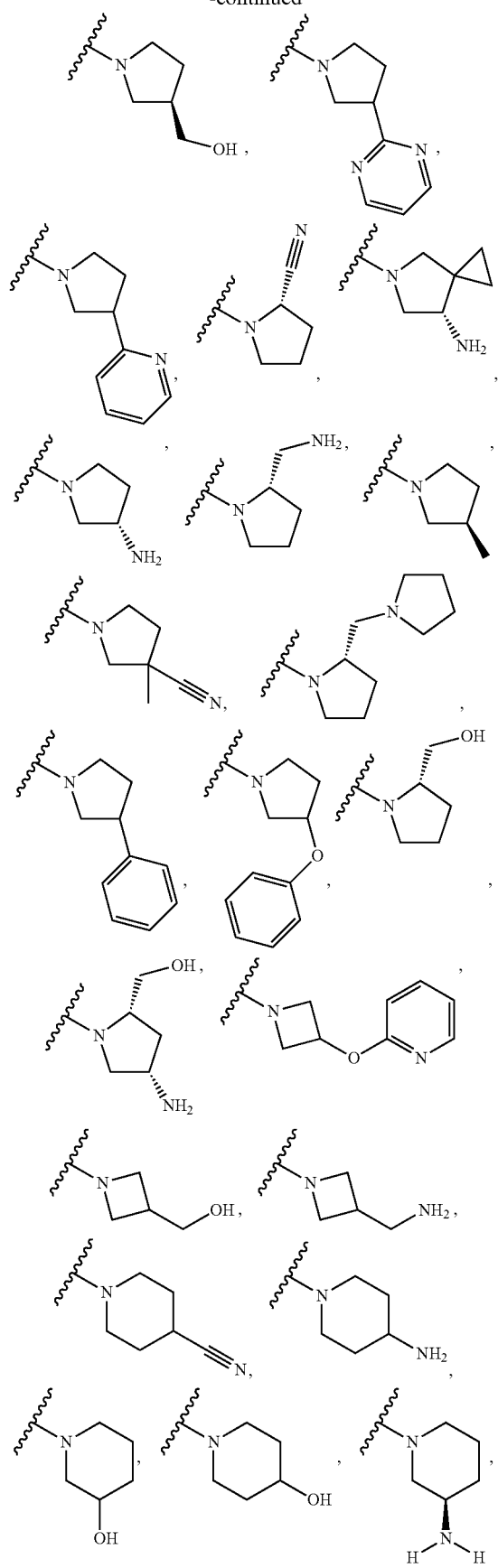
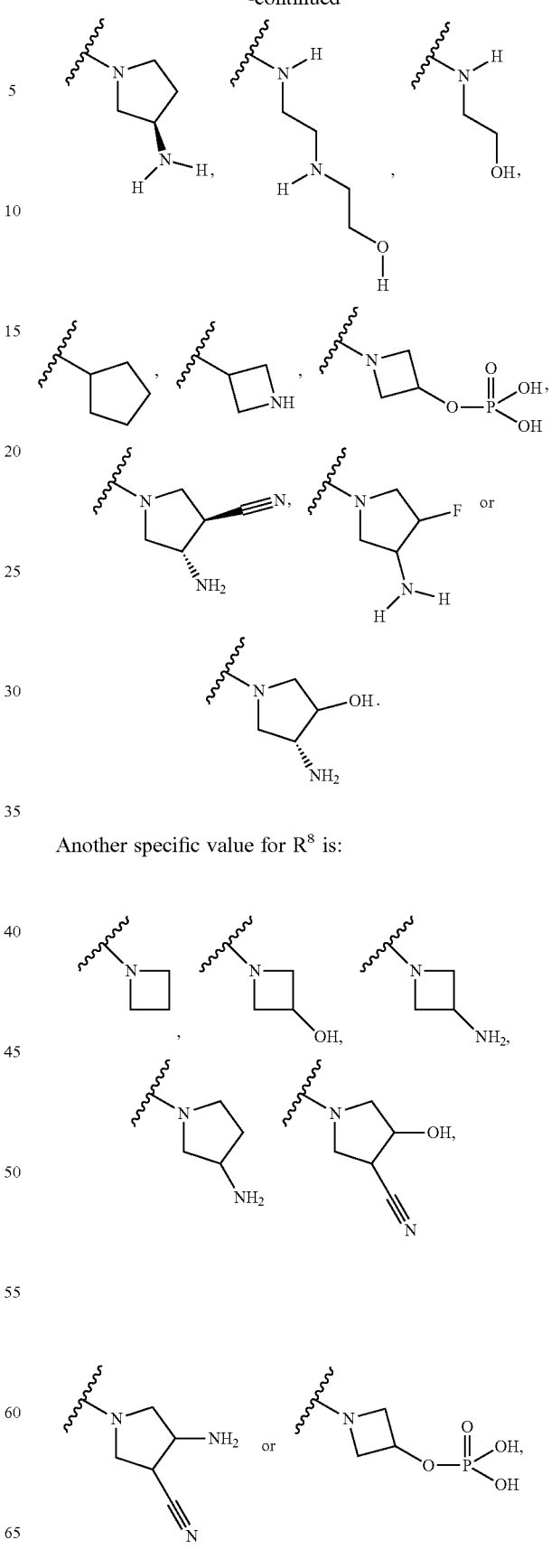
Another specific value for $R^8$ is:

Another specific value for R⁸ is:

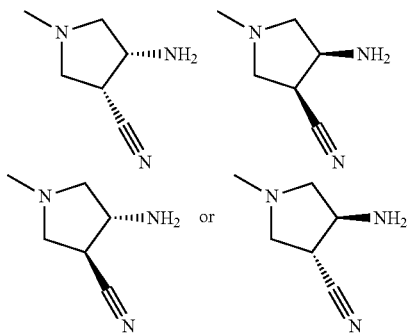

Another specific value for R⁸ is:

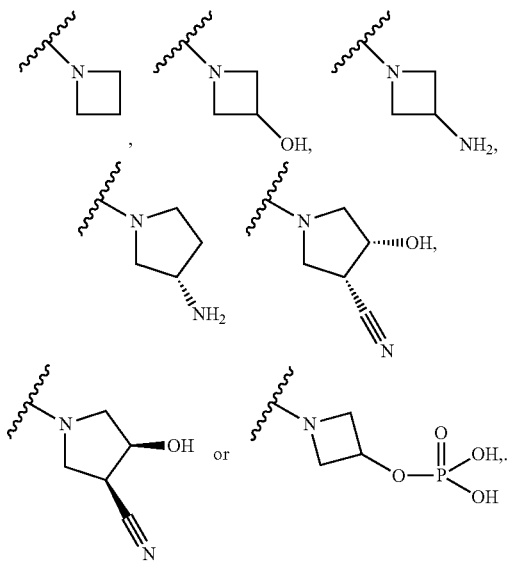

In one embodiment the compounds of Formulas I-IX do not include:
(2-fluorophenyl)(2-(5-methyl-7-(trifluoromethyl)pyrazolo [1,5-a]pyrimidin-2-yl)piperidin-1-yl)methanone;
2-(7-hydroxy-5-methylpyrazolo[1,5-a]pyrimidin-2-yl)piperidin-1-yl)(3,4,5-trimethoxyphenyl)methanone;
4-fluoro-3-(2-(7-hydroxy-5-methylpyrazolo[1,5-a]pyrimidin-2-yl)piperidine-1-carbonyl)-N-methylbenzenesulfonamide;
N-(2-(2-(7-hydroxy-5-methylpyrazolo[1,5-a]pyrimidin-2-yl)piperidine-1-carbonyl)phenyl)methanesulfonamide;
(2-(5-ethyl-7-hydroxypyrazolo[1,5-a]pyrimidin-2-yl)piperidin-1-yl)(3,4,5-trimethoxyphenyl)methanone;
N-(2-(2-(5-ethyl-7-hydroxypyrazolo[1,5-a]pyrimidin-2-yl) piperidine-1-carbonyl)phenyl)methanesulfonamide;
(2-(7-hydroxy-5,6-dimethylpyrazolo[1,5-a]pyrimidin-2-yl) piperidin-1-yl)(3,4,5-trimethoxyphenyl)methanone;
N-(2-(2-(7-hydroxy-5,6-dimethylpyrazolo[1,5-a]pyrimidin-2-yl)piperidine-1-carbonyl)phenyl)methanesulfonamide; or
(2-(6-fluoro-7-hydroxy-5-methylpyrazolo[1,5-a]pyrimidin-2-yl)piperidin-1-yl)(3,4,5-trimethoxyphenyl)methanone.

In another embodiment, provided is a method of treating a Pneumovirinae infection in a mammal in need thereof by administering a therapeutically effective amount of a compound of Formula IX:

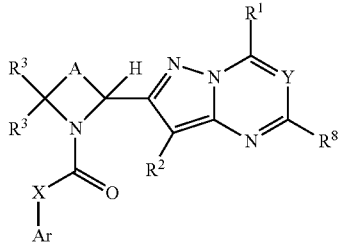

Formula IX or a pharmaceutically acceptable salt or ester thereof: wherein:

A is —(C(R⁴)₂)ₙ— wherein any one C(R⁴)₂ of said —(C(R⁴)₂)ₙ— may be optionally replaced with —O—, —S—, S(O)ₚ—, NH or NRᵃ;

n is 3, 4, 5 or 6;

each p is 1 or 2;

Ar is a C₂-C₂₀ heterocyclyl group or a C₆-C₂₀ aryl group, wherein the C₂-C₂₀ heterocyclyl group or the C₆-C₂₀ aryl group is optionally substituted with 1 to 5 R⁶;

X is —(CR¹³R¹⁴)—, —N(CH₂R¹⁴)— or X is absent;

Y is N or CR⁷;

each R¹, R², R³, R⁴, R⁵, R⁶, R⁷ or R⁸ is independently H, oxo, OR¹¹, NR¹¹R¹², NR¹¹C(O)R¹¹, NR¹¹C(O)OR¹¹, NR¹¹C(O)NR¹¹R¹², N₃, CN, NO₂, SR¹¹, S(O)ₚRᵃ, NR¹¹S (O)ₚRᵃ, —C(=O)R¹¹, —C(=O)OR¹¹, —C(=O)NR¹¹R¹², —C(=O)SR¹¹, —S(O)ₚ(OR¹¹), —SO₂NR¹¹R¹², —NR¹¹S (O)ₚ(OR¹¹), —NR¹¹SO ₚNR¹¹R¹², NR¹¹C(=NR¹¹) NR¹¹R¹², halogen, (C₁-C₈)alkyl, (C₂-C₈)alkenyl, (C₂-C₈) alkynyl, aryl(C₁-C₈)alkyl, C₆-C₂₀ aryl, C₂-C₂₀ heterocyclyl, (C₃-C₇)cycloalkyl or (C₄-C₈)carbocyclylalkyl;

two R⁴ on adjacent carbon atoms, when taken together, may form a double bond between the two carbons to which they are attached or may form a (C₃-C₇)cycloalkyl ring wherein one carbon atom of said (C₃-C₇)cycloalkyl ring may be optionally replaced by —O—, —S—, —S(O)ₚ—, —NH— or —NRᵃ—;

four R⁴ on adjacent carbon atoms, when taken together, may form an optionally substituted C₆ aryl ring;

two R⁴ on the same carbon atom, when taken together, may form a (C₃-C₇)cycloalkyl ring wherein one carbon atom of said (C₃-C₇)cycloalkyl ring may be optionally replaced by —O—, —S—, —S(O)ₚ—, —NH— or —NRᵃ—;

two R⁶ on adjacent carbon atoms, when taken together, may form a (C₃-C₇)cycloalkyl ring wherein one carbon atom of said (C₃-C₇)cycloalkyl ring may be optionally replaced by —O—, —S—, —S(O)ₚ—, —NH— or —NRᵃ—;

any R⁶ adjacent to the obligate carbonyl group of said Ar, when taken together with R³, may form a bond or a —(C(R⁵)₂)ₘ— group wherein m is 1 or 2;

any R⁶ adjacent to the obligate carbonyl group of said Ar, when taken together with R², may form a bond;

each Rᵃ is independently (C₁-C₈)alkyl, (C₁-C₈)haloalkyl, (C₂-C₈)alkenyl, (C₂-C₈)alkynyl, aryl(C₁-C₈)alkyl, C₆-C₂₀ aryl, C₂-C₂₀ heterocyclyl, (C₃-C₇)cycloalkyl or (C₄-C₈)carbocyclylalkyl wherein any (C₁-C₈)alkyl, (C₁-C₈)haloalkyl, (C₂-C₈)alkenyl or (C₂-C₈)alkynyl of Rᵃ is optionally substituted with one or more OH, NH₂, CO₂H, C₂-C₂₀ heterocyclyl, and wherein any aryl(C₁-C₈)alkyl, C₆-C₂₀ aryl, C₂-C₂₀ heterocyclyl, (C₃-C₇)cycloalkyl or (C₄-C₈)carbocyclylalkyl of Rᵃ is optionally substituted with one or more OH, NH₂, CO₂H, C₂-C₂₀ heterocyclyl or (C₁-C₈)alkyl;

each $R^{11}$ or $R^{12}$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $C_6\text{-}C_{20}$ aryl, $C_2\text{-}C_{20}$ heterocyclyl, $(C_3\text{-}C_7)$cycloalkyl, $(C_4\text{-}C_8)$carbocyclylalkyl, $-C(=O)R^a$, $-S(O)_pR^a$, or aryl$(C_1\text{-}C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S-$, $-S(O)_p-$, $-NH-$, $-NR^a-$ or $-C(O)-$;

$R^{13}$ is H or $(C_1\text{-}C_8)$alkyl;

$R^{14}$ is H, $(C_1\text{-}C_8)$alkyl, $NR^{11}R^{12}$, $NR^{11}C(O)R^{11}$, $NR^{11}C(O)OR^{11}$, $NR^{11}C(O)NR^{11}R^{12}$, $NR^{11}S(O)_pR^a$, $-NR^{11}S(O)_p(OR^{11})$ or $NR^{11}SO_pNR^{11}R^{12}$; and wherein each $(C_1\text{-}C_8)$alkyl, $(C_2\text{-}C_8)$alkenyl, $(C_2\text{-}C_8)$alkynyl, aryl$(C_1\text{-}C_8)$alkyl, $C_6\text{-}C_{20}$ aryl, $C_2\text{-}C_{20}$ heterocyclyl, $(C_3\text{-}C_7)$cycloalkyl or $(C_4\text{-}C_8)$carbocyclylalkyl of each $R^1$, $R^2$, $R^3$, $R^4$, $R^5$, $R^6$, $R^7$, $R^8$, $R^{11}$ or $R^{12}$ is, independently, optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1\text{-}C_8)$alkyl, $(C_1\text{-}C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, NHS$(O)_pNHR^a$, $NHS(O)_pN(R^a)_2$, $NHS(O)_pNH_2$, $-OC(=O)R^a$, $-OP(O)(OH)_2$ or $R^a$.

In another embodiment, provided is a method of treating a Pneumovirinae infection in a mammal in need thereof by administering a therapeutically effective amount of a racemate, enantiomer, diastereomer, tautomer, polymorph, pseudopolymorph, amorphous form, hydrate or solvate of a compound of Formula IX (compound of Formula IX as described above for the method of treating a Pneumovirinae infection), or a pharmaceutically acceptable salt or ester thereof.

In another embodiment, provided is a method treating a respiratory syncytial virus infection in a mammal in need thereof by administering a therapeutically effective amount of a compound of Formula IX (compound of Formula IX as described above for the method of treating a Pneumovirinae infection), or a pharmaceutically acceptable salt or ester thereof.

In another embodiment, provided is a method of treating a respiratory syncytial virus infection in a mammal in need thereof by administering a therapeutically effective amount of a racemate, enantiomer, diastereomer, tautomer, polymorph, pseudopolymorph, amorphous form, hydrate or solvate of a compound of a compound of Formula IX (compound of Formula IX as described above for the method of treating a Pneumovirinae infection), or a pharmaceutically acceptable salt or ester thereof.

In another embodiment, provided is a method of treating a Pneumovirinae infection in a mammal in need thereof by administering a therapeutically effective amount of a compound of Formula IX (compound of Formula IX as described above for the method of treating a Pneumovirinae infection), or a pharmaceutically acceptable salt or ester thereof, in combination with a pharmaceutically acceptable diluent or carrier.

In another embodiment, provided is a method of treating a Pneumovirinae infection in a mammal in need thereof by administering a therapeutically effective amount of a compound of Formula IX (compound of Formula IX as described above for the method of treating a Pneumovirinae infection), or a pharmaceutically acceptable salt or ester thereof in combination with at least one additional therapeutic agent.

In another embodiment, provided is a method of treating a Pneumovirinae infection in a mammal in need thereof, by administering a therapeutically effective amount of a combination pharmaceutical agent comprising:

a) a first pharmaceutical composition comprising a compound of Formula IX (compound of Formula IX as described above for the method of treating a Pneumovirinae infection); or a pharmaceutically acceptable salt or ester thereof; and b) a second pharmaceutical composition comprising at least one additional therapeutic agent active against infectious Pneumovirinae viruses.

In another embodiment, provided is a method of treating a respiratory syncytial virus infection in a mammal in need thereof, by administering a therapeutically effective amount of a combination pharmaceutical agent comprising:

a) a first pharmaceutical composition comprising a compound of Formula IX (compound of Formula IX as described above for the method of treating a Pneumovirinae infection); or a pharmaceutically acceptable salt or ester thereof; and b) a second pharmaceutical composition comprising at least one additional therapeutic agent active against infectious respiratory syncytial viruses.

In another embodiment, provided is the use of a compound of Formula IX (compound of Formula IX as described above for the method of treating a Pneumovirinae infection), or a pharmaceutically acceptable salt and/or ester thereof to treat a viral infection caused by a Pneumovirinae virus or a respiratory syncytial virus.

Some embodiments of the compounds of Formula I-IX specify that two $R^4$ on adjacent carbon atoms, when taken together, may form a double bond between the two carbons to which they are attached or may form a $(C_3\text{-}C_7)$cycloalkyl ring wherein one carbon atom of said $(C_3\text{-}C_7)$cycloalkyl ring may be optionally replaced by $-O-$, $-S-$, $-S(O)_p-$, $-NH-$ or $-NR^a-$. Non-limiting examples of these embodiments are:

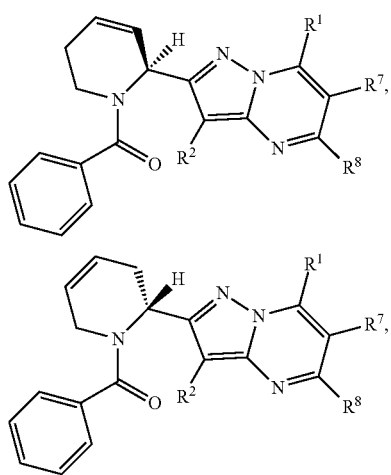

-continued

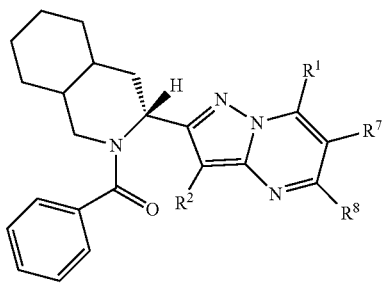

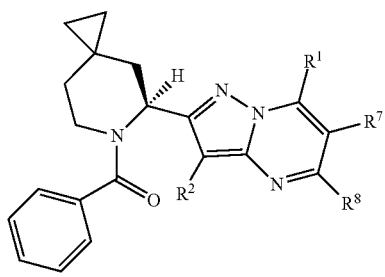

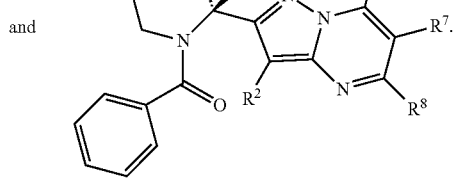

and 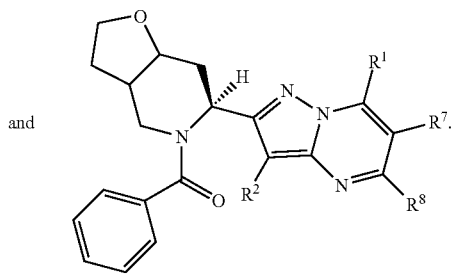

Some embodiments of the compounds of Formula I-IX specify that four $R^4$ on adjacent carbon atoms, when taken together, may form an optionally substituted $C_6$ aryl ring. Non-limiting examples of these embodiments are:

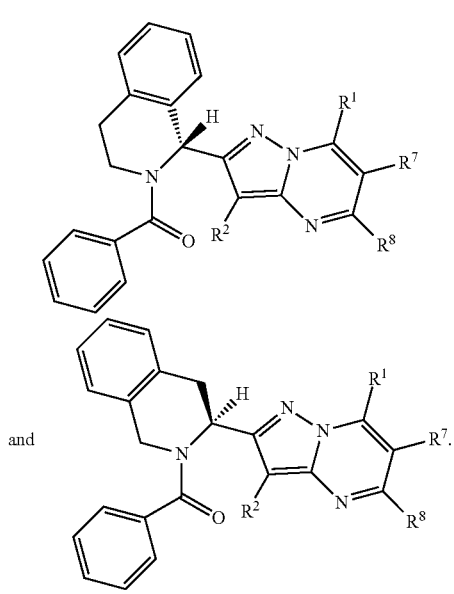

Some embodiments of the compounds of Formula I-IX specify that two $R^4$ on the same carbon atom, when taken together, may form a $(C_3-C_7)$cycloalkyl ring wherein one carbon atom of said $(C_3-C_7)$cycloalkyl ring may be optionally replaced by —O—, —S—, —S(O)$_p$—, —NH— or —NR$^a$—. Non-limiting examples of these embodiments are:

Some embodiments of the compounds of Formula I-II specify that two $R^6$ on adjacent carbon atoms, when taken together, may form a $(C_3-C_7)$cycloalkyl ring wherein one carbon atom of said $(C_3-C_7)$cycloalkyl ring may be optionally replaced by —O—, —S—, —S(O)$_p$—, —NH— or —NR$^a$—. Non-limiting examples of these embodiments are:

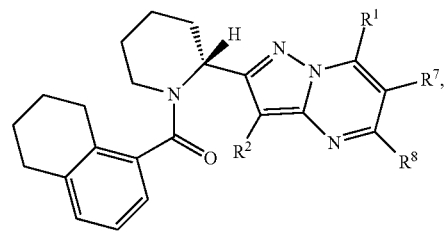

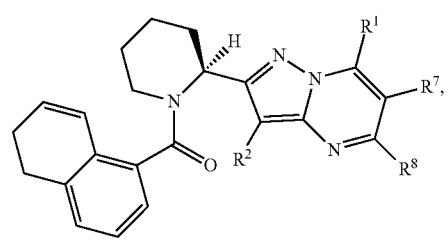

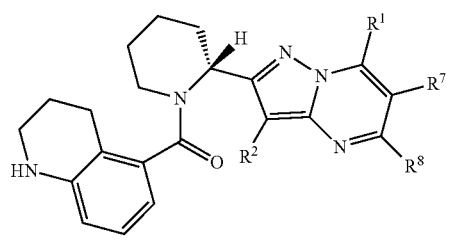

51

-continued and 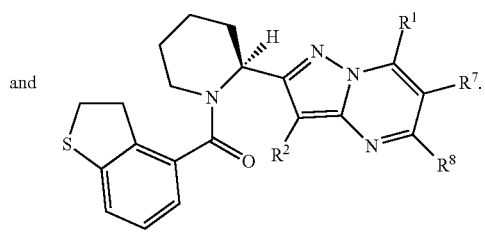

Some embodiments of the compounds of Formula I-II specify that any $R^6$ adjacent to the obligate carbonyl group of Ar, when taken together with $R^3$, may form a bond or a —$(C(R_5)_2)_m$— group wherein m is 1 or 2. Non-limiting examples of these embodiments are:

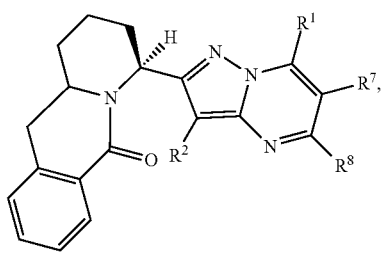

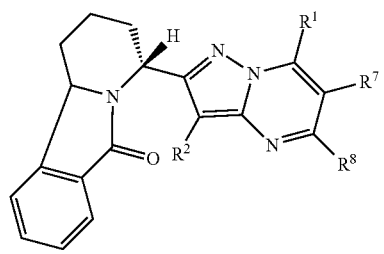

and 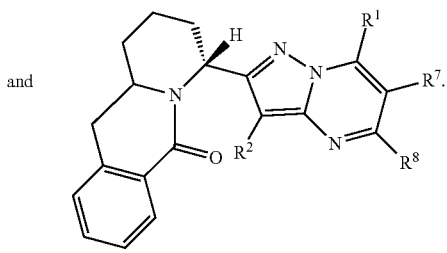

Some embodiments of the compounds of Formula I-II specify that any $R^6$ adjacent to the obligate carbonyl group Ar, when taken together with $R^2$, may form a bond. Non-limiting examples of these embodiments are:

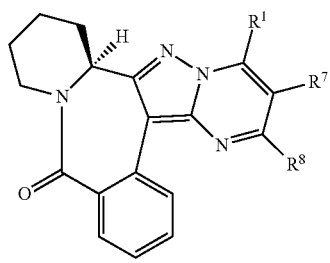

52

-continued and 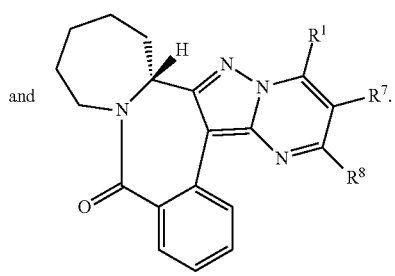

In another embodiment, the compounds of Formula I are selected from the group consisting of:

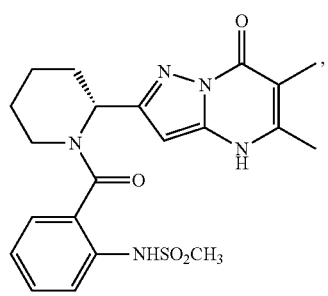

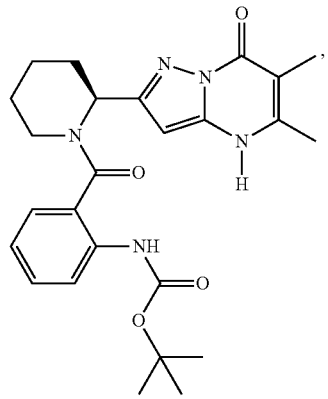

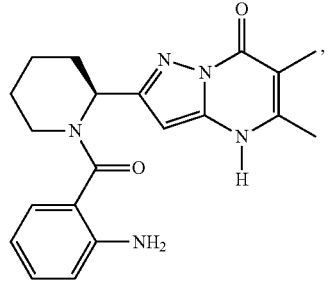

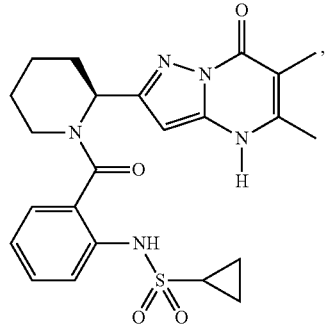

53
-continued
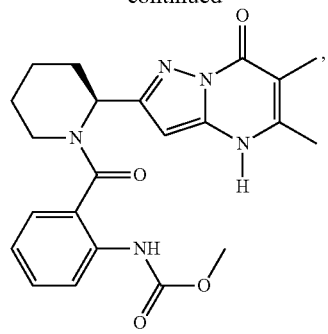
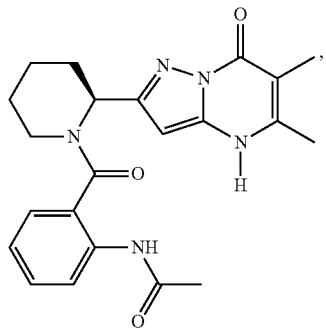
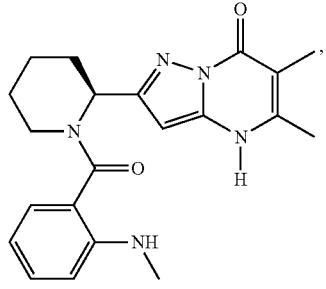
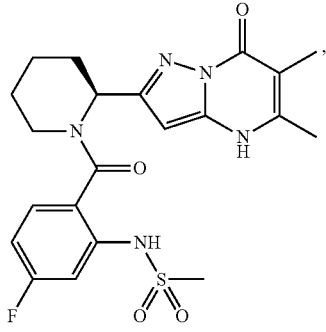
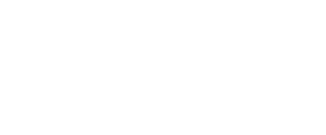
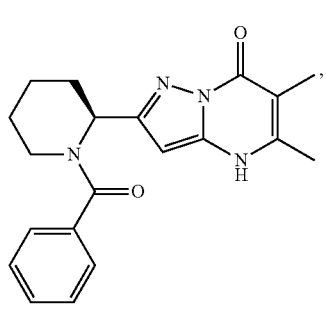
54
-continued
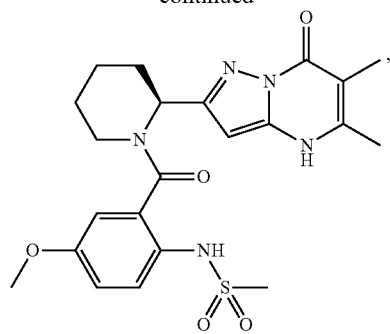
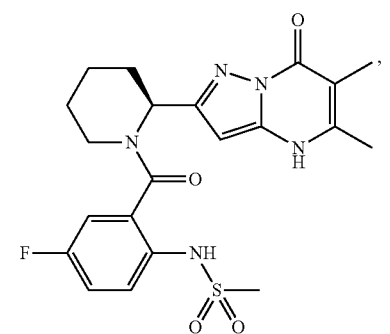
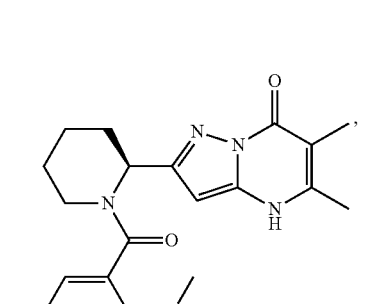
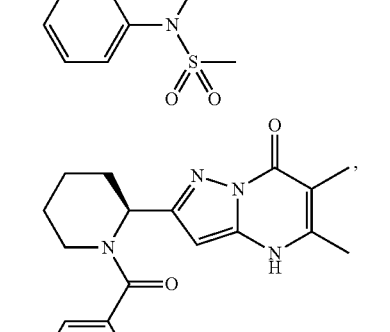
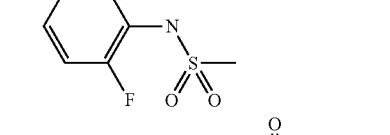
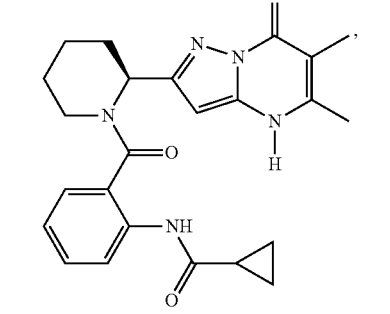

55
-continued
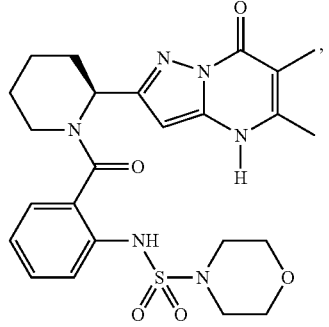
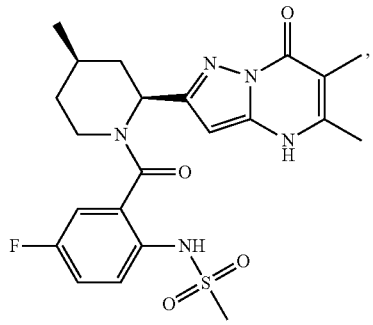
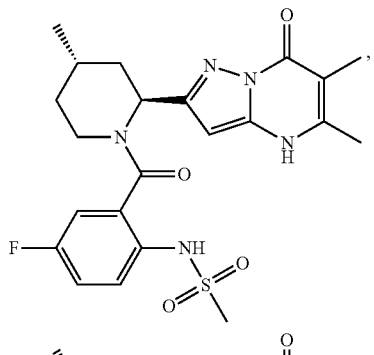
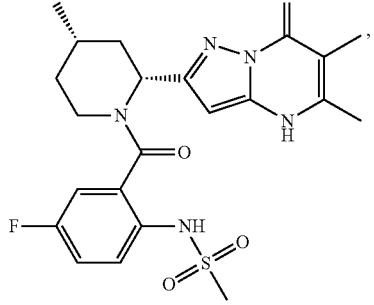
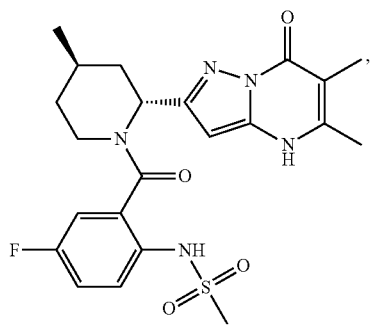
56
-continued
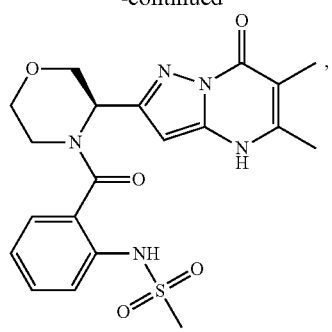

57
-continued
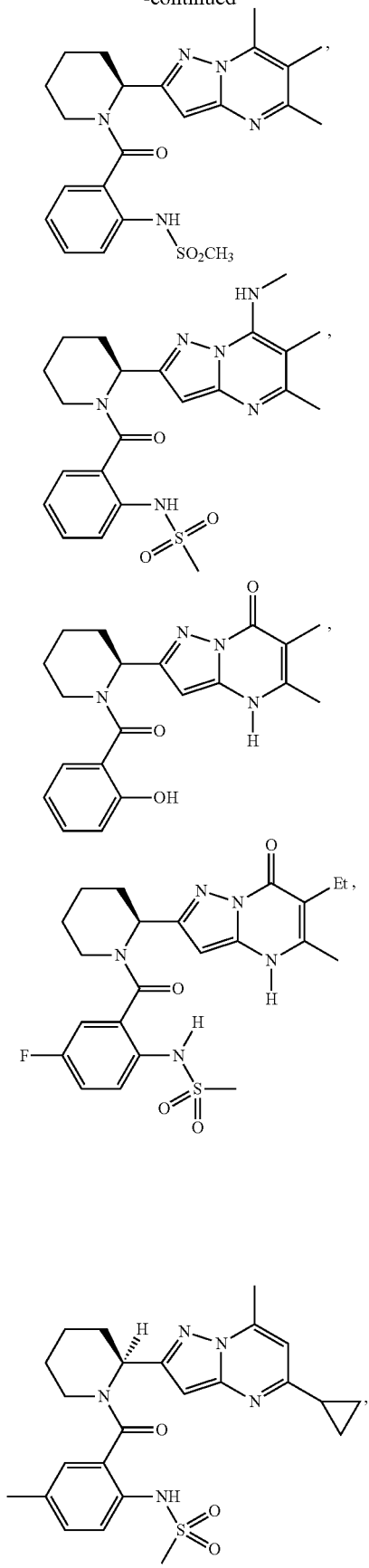
58
-continued
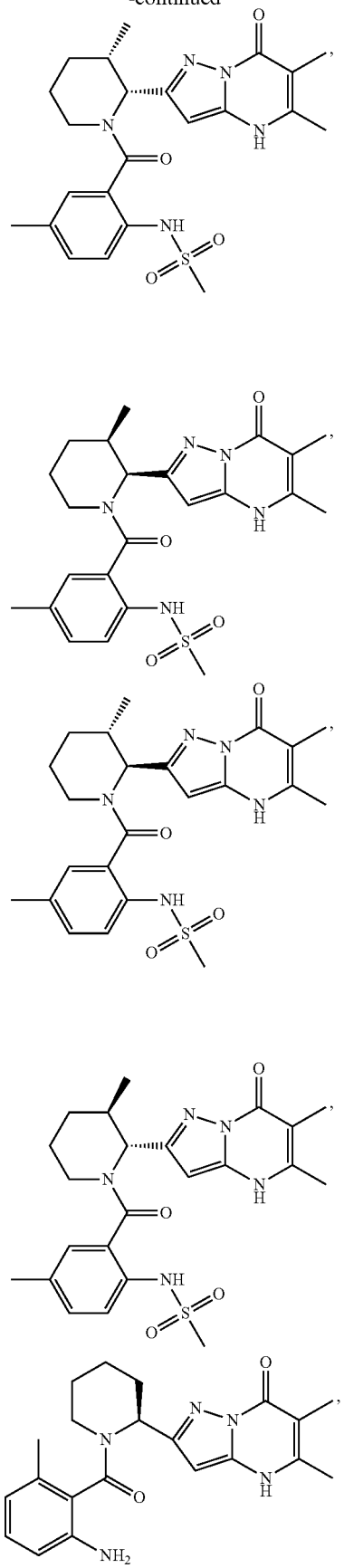

-continued
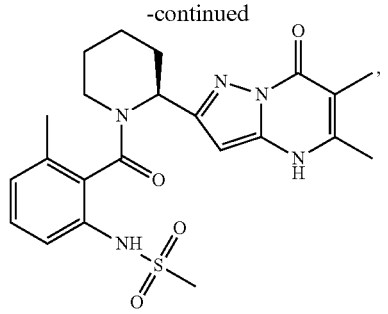
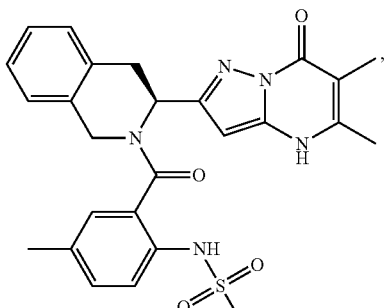
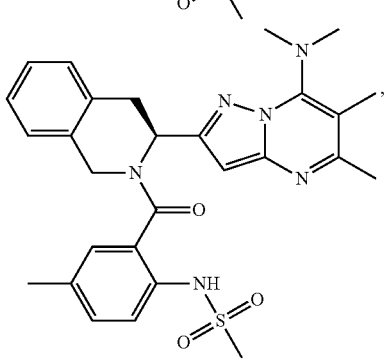
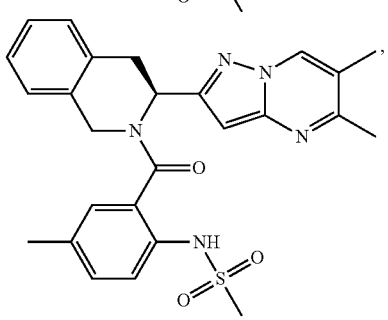
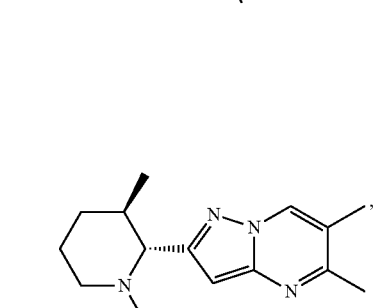
-continued
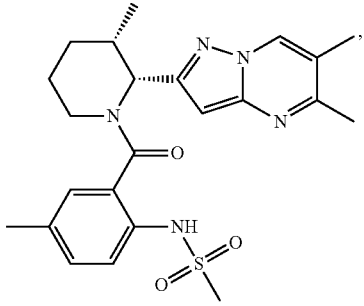
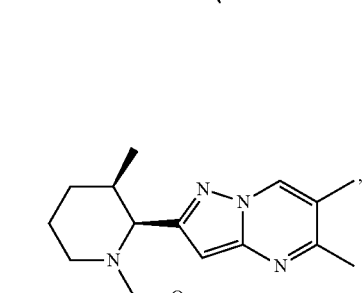
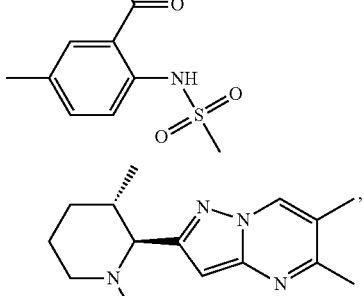
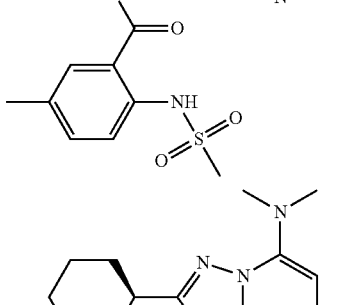
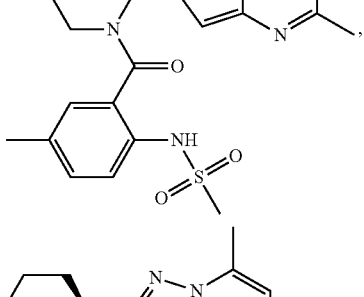
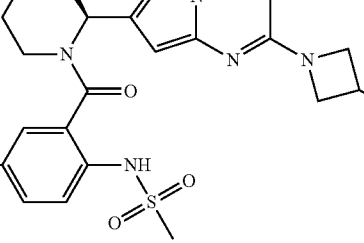

61
-continued
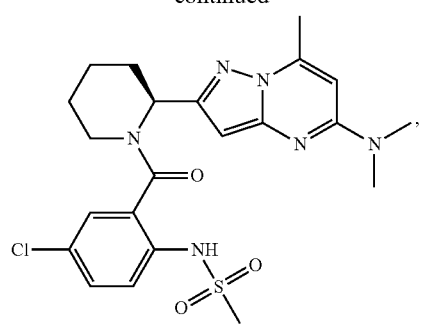
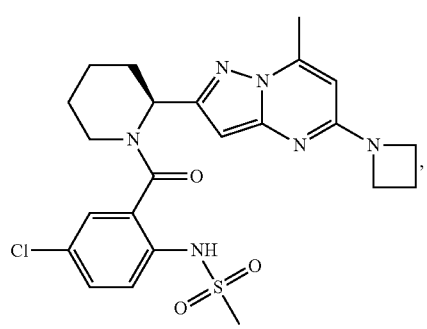
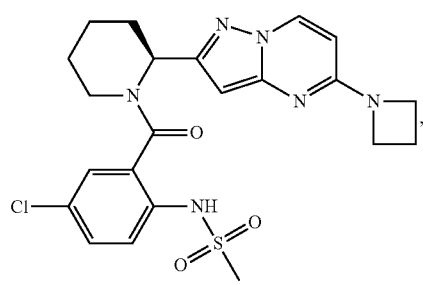
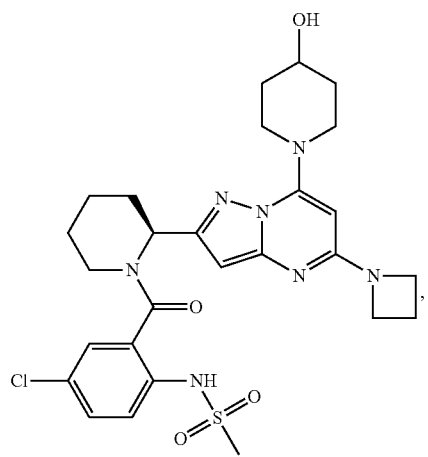
62
-continued
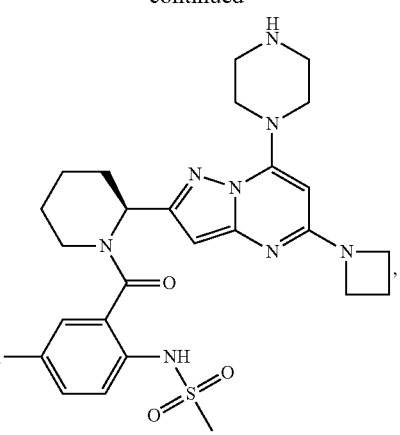
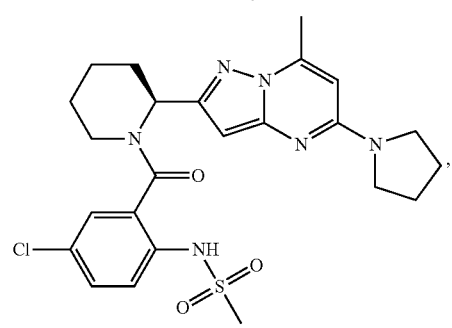
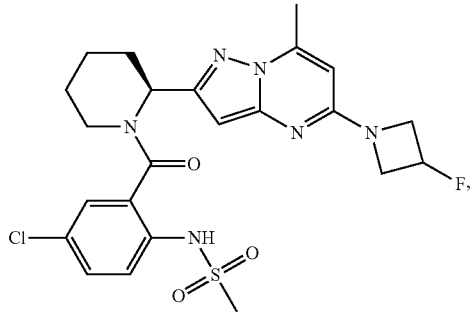
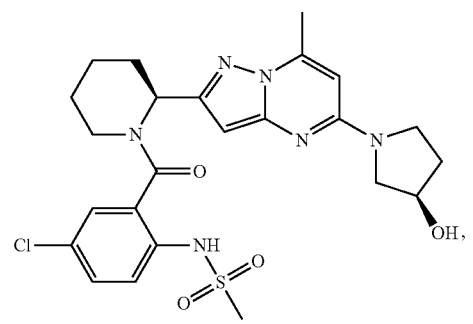
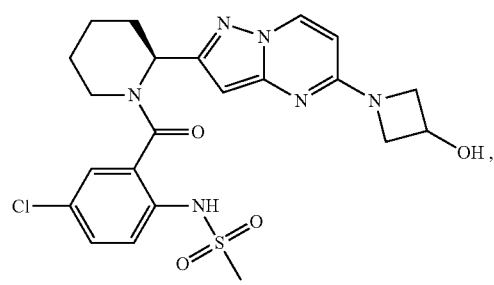

63
-continued
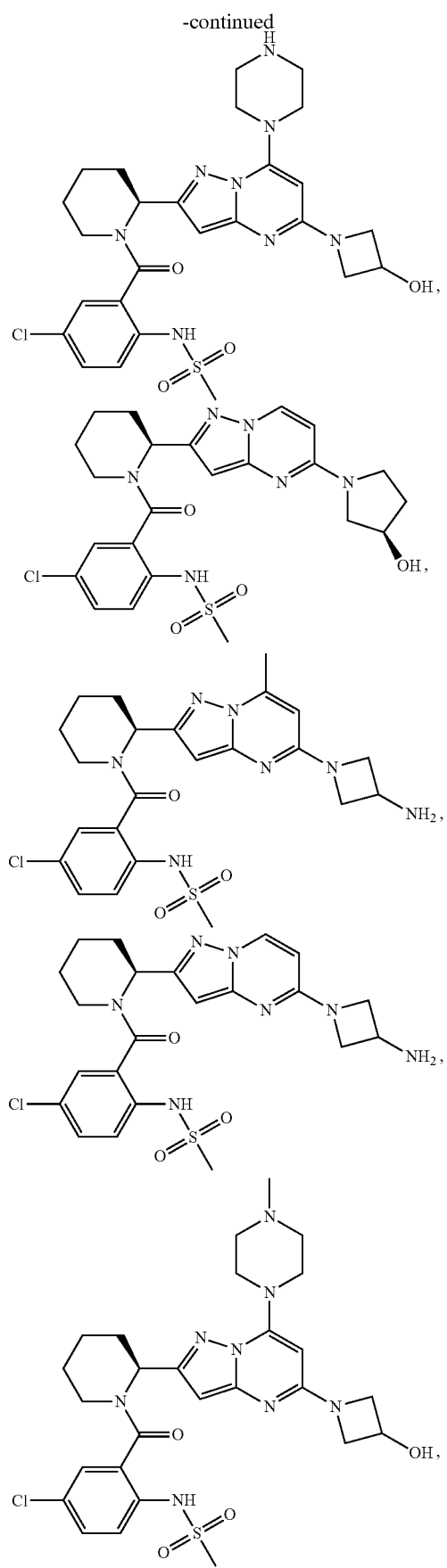
64
-continued
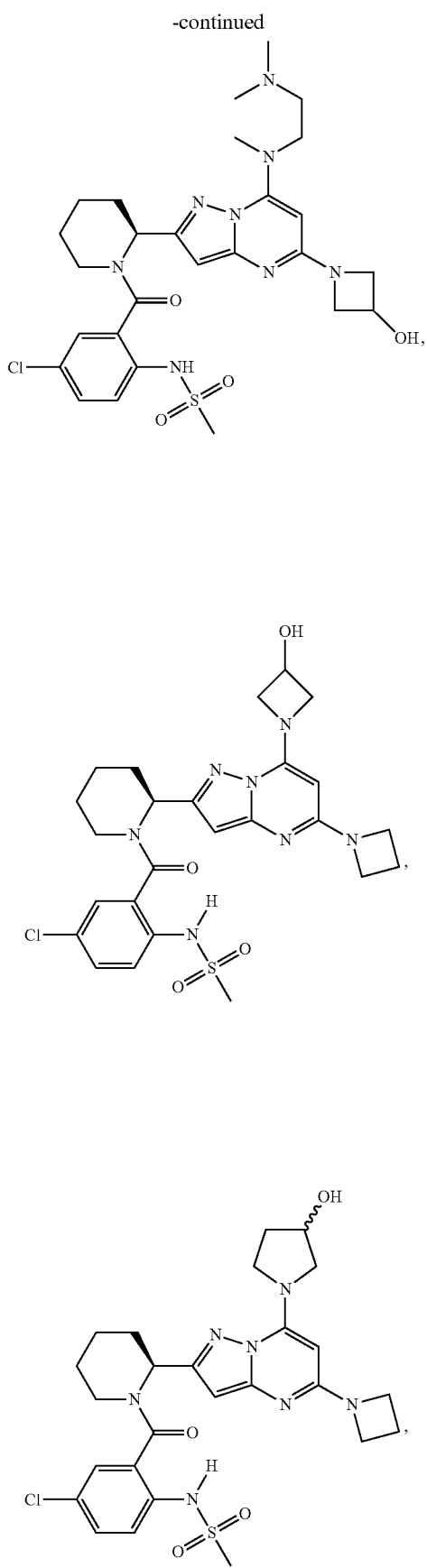

65
-continued
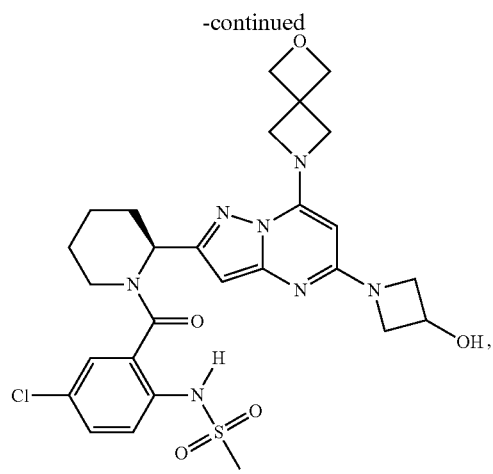
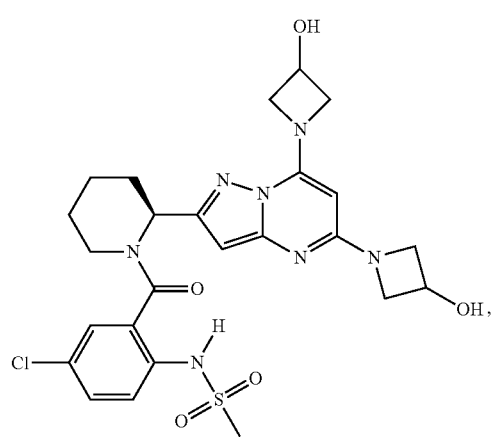
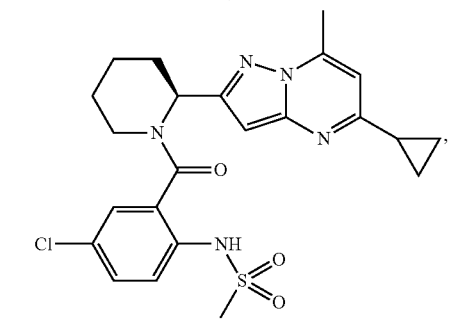
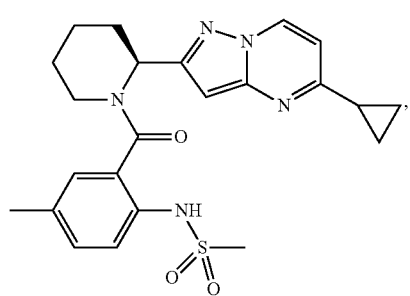
66
-continued
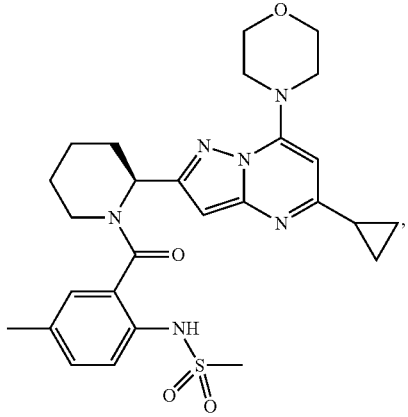
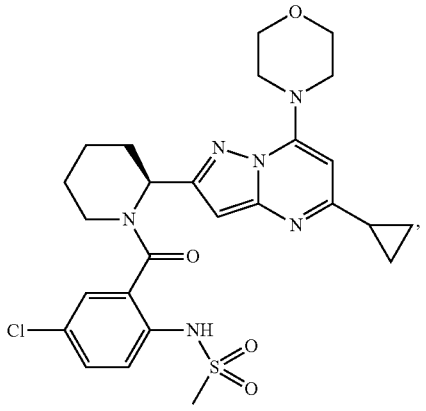
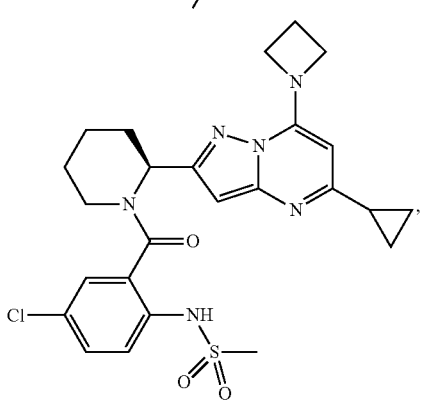
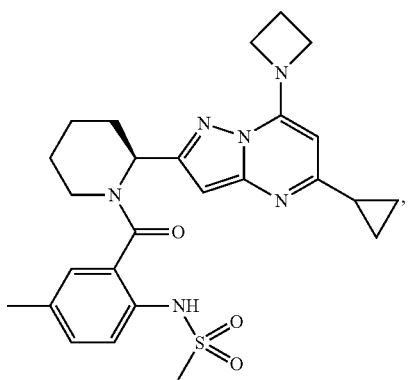

67
-continued
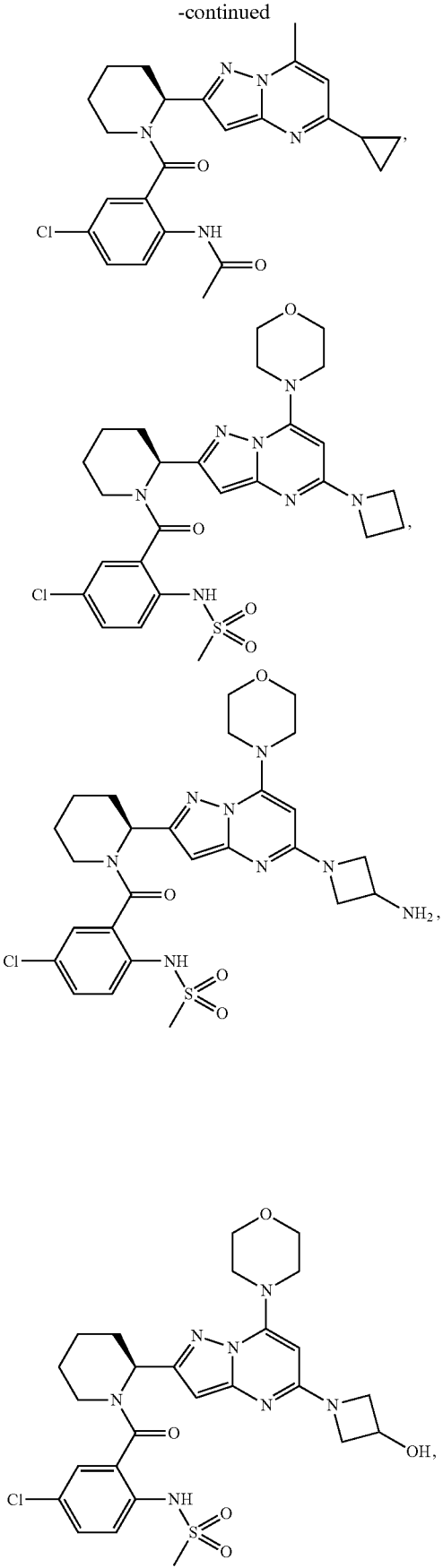
68
-continued
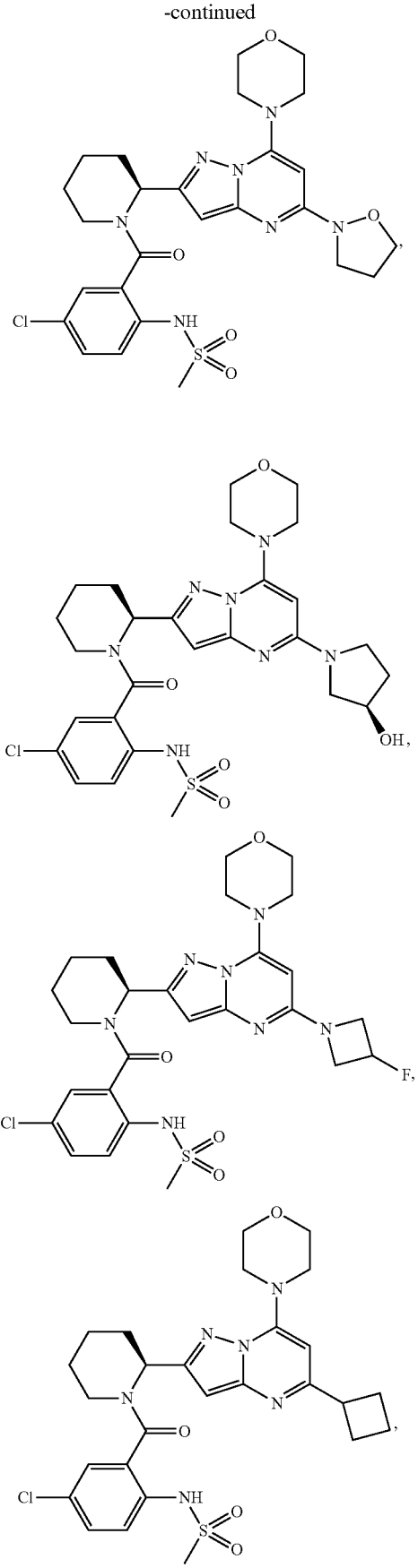

69
-continued
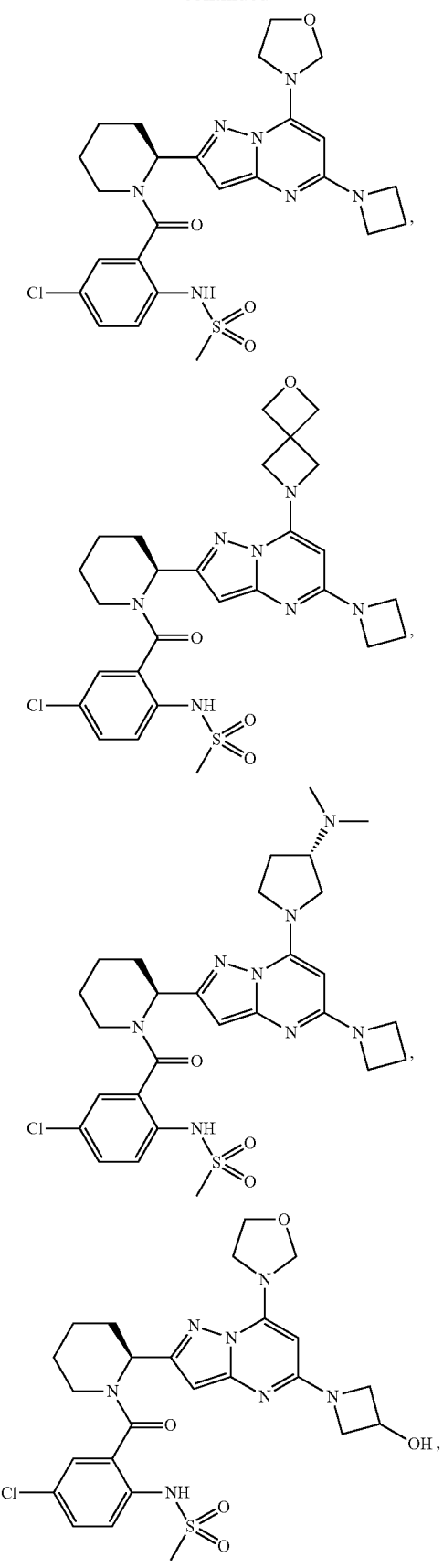
70
-continued
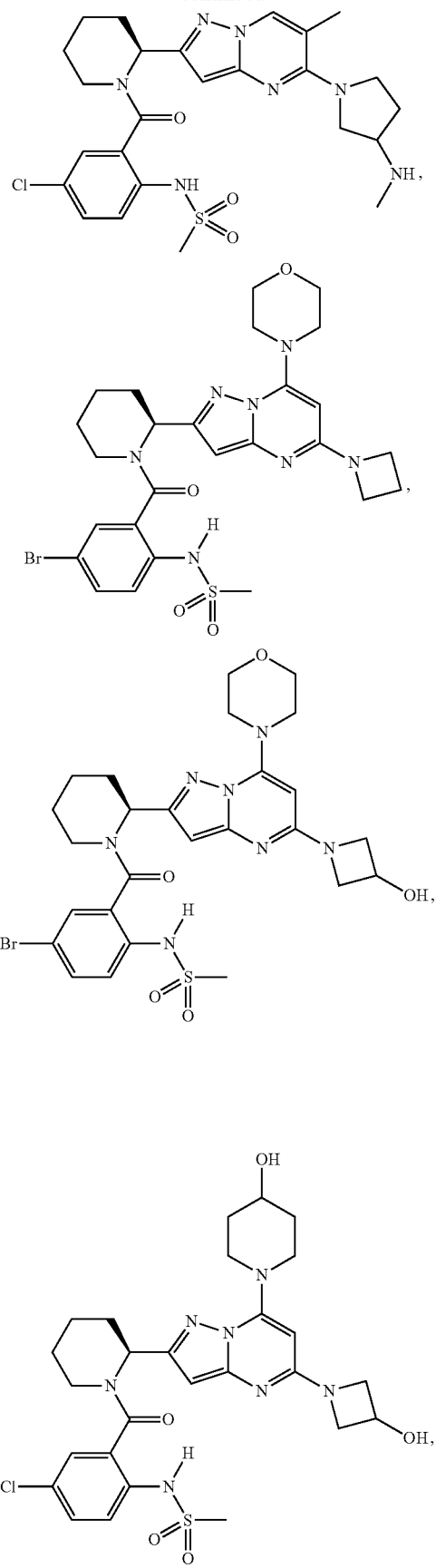

-continued
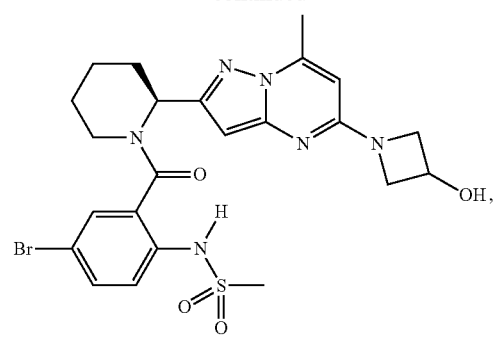
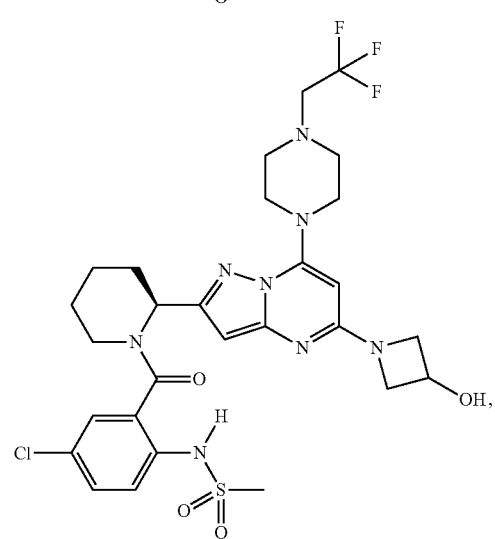
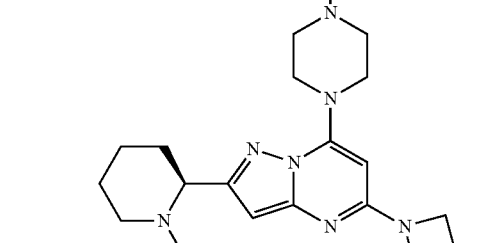
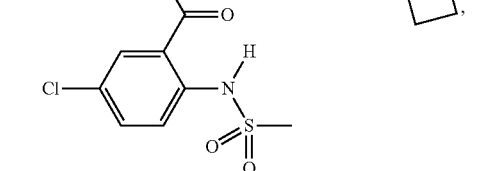
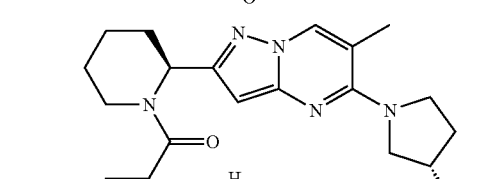
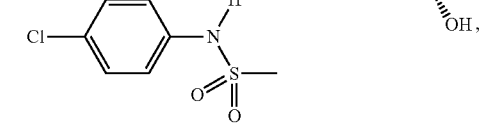
-continued
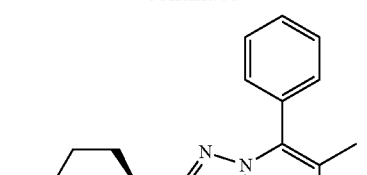
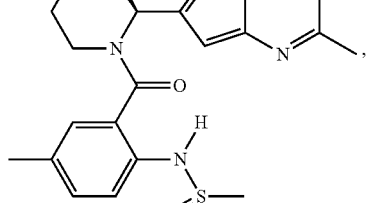
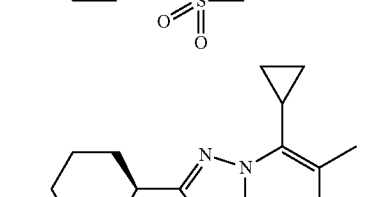
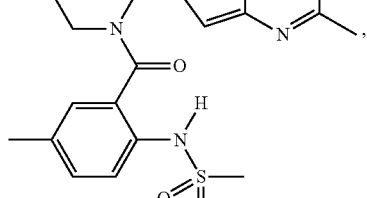
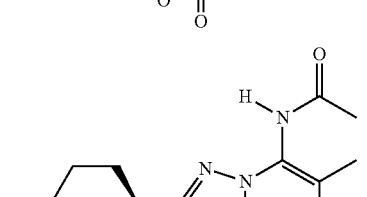
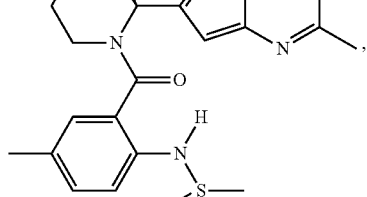
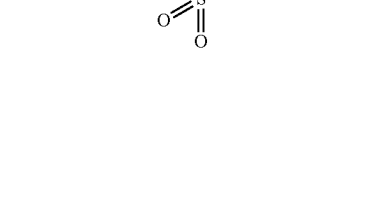
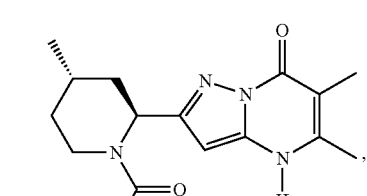
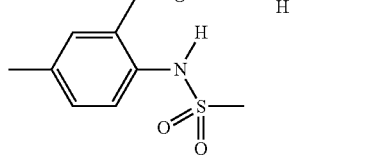

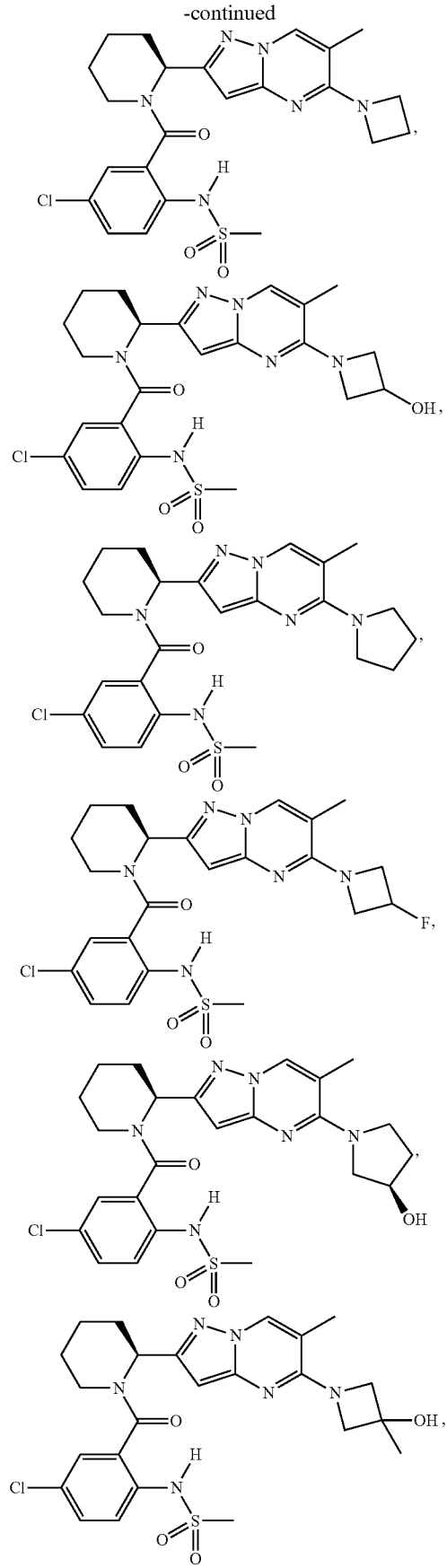
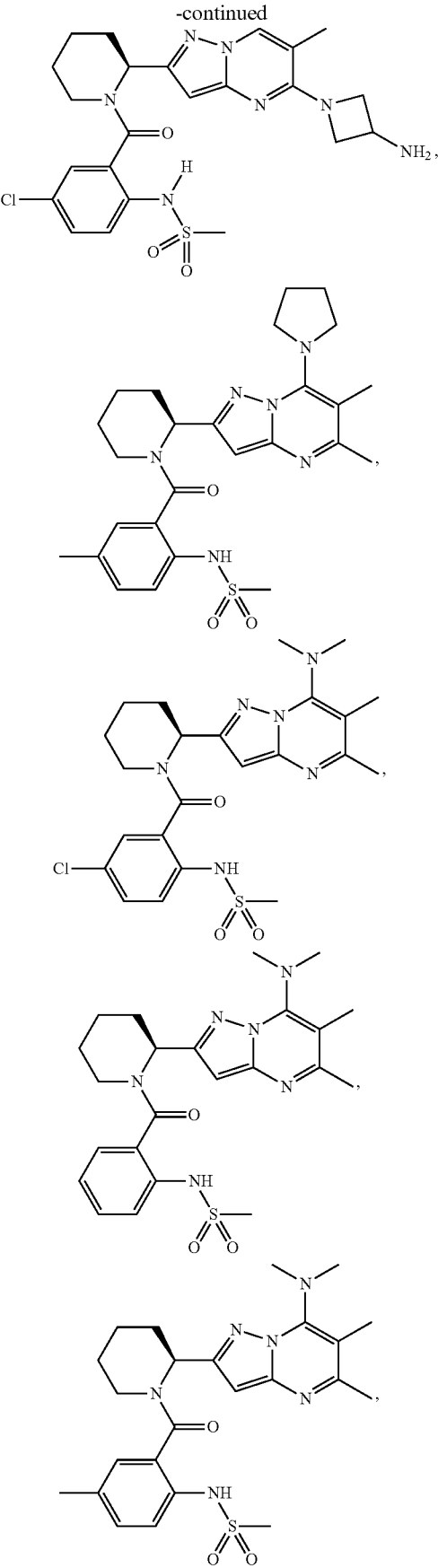

75
-continued
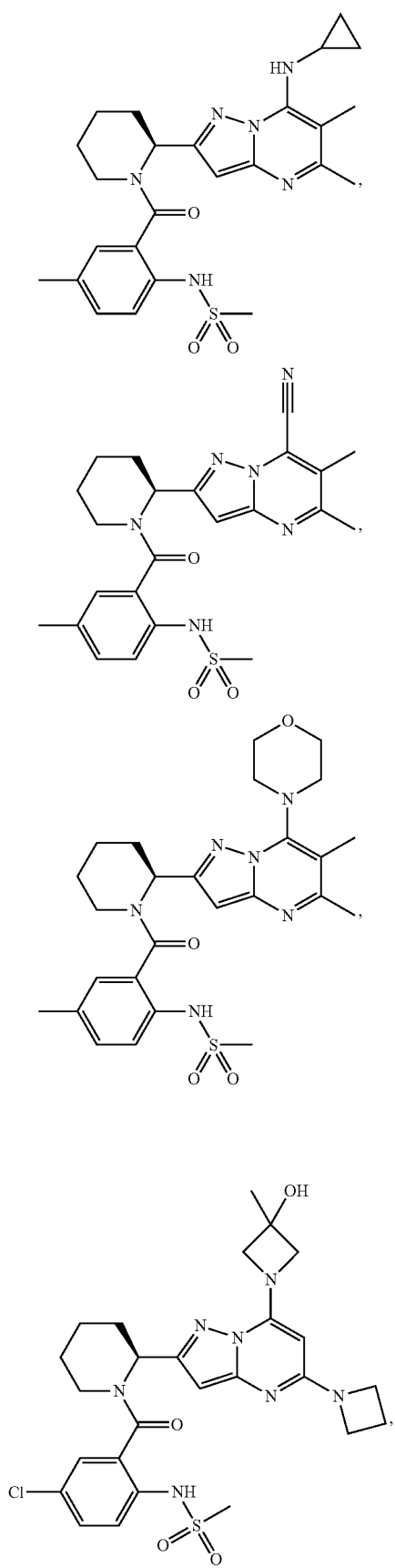
76
-continued
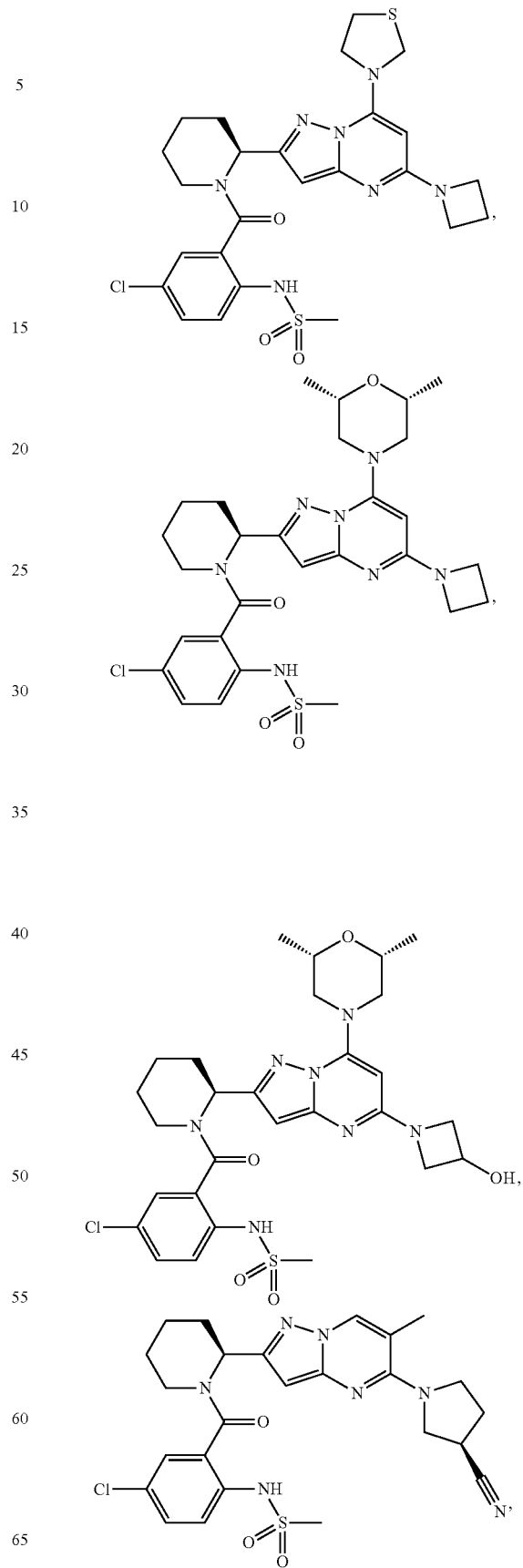

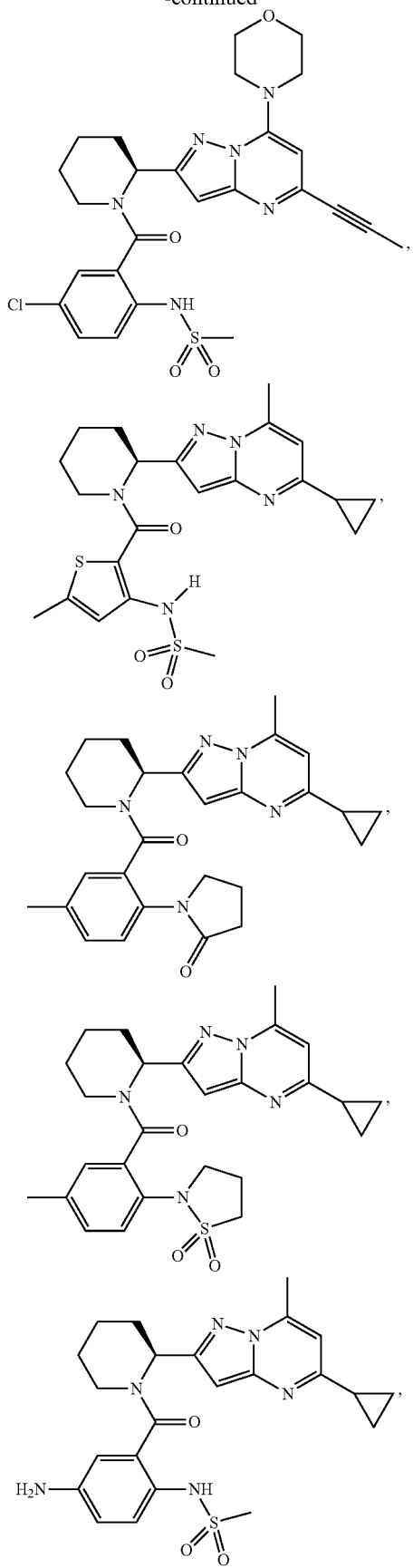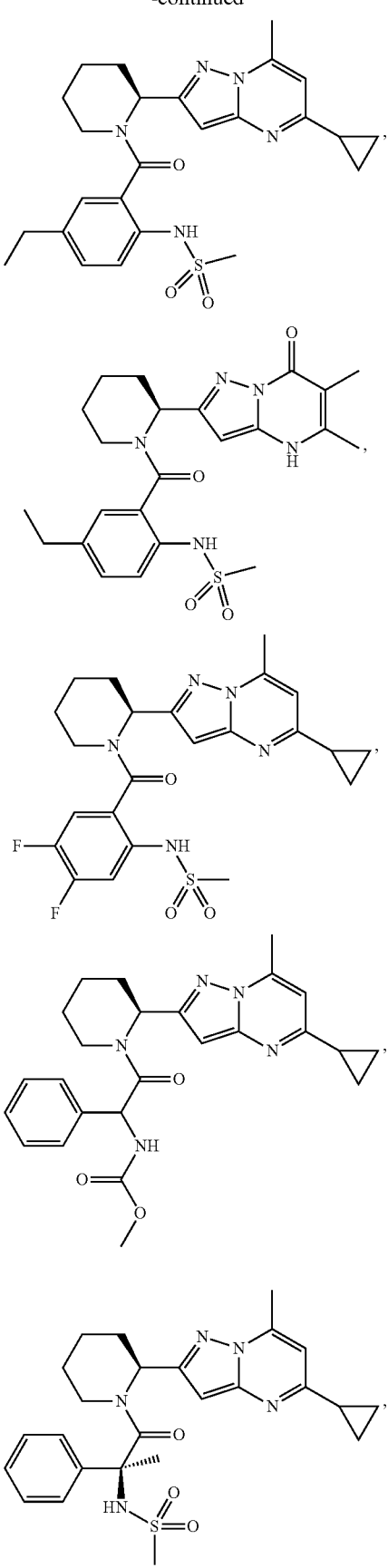

-continued
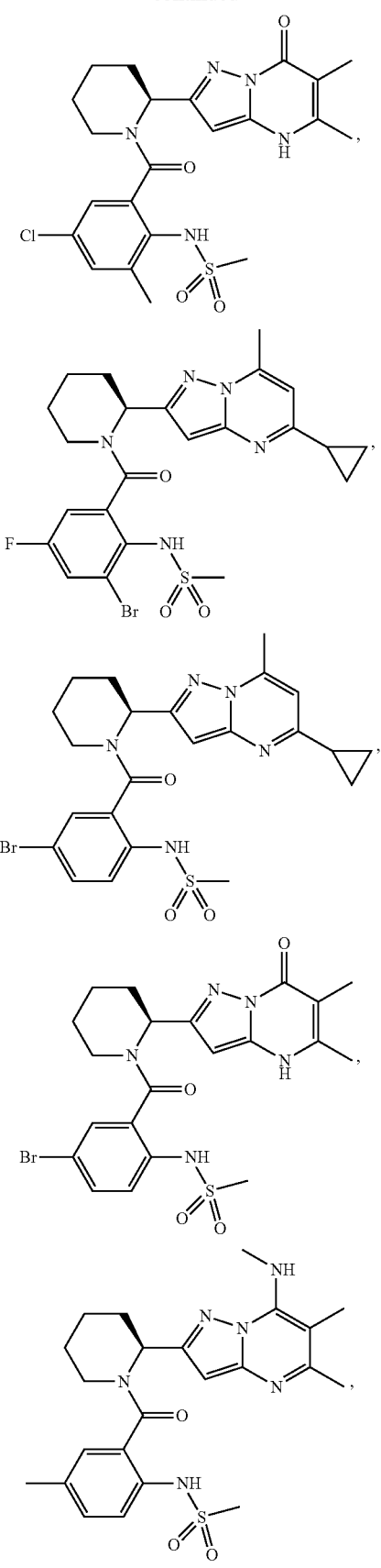
-continued
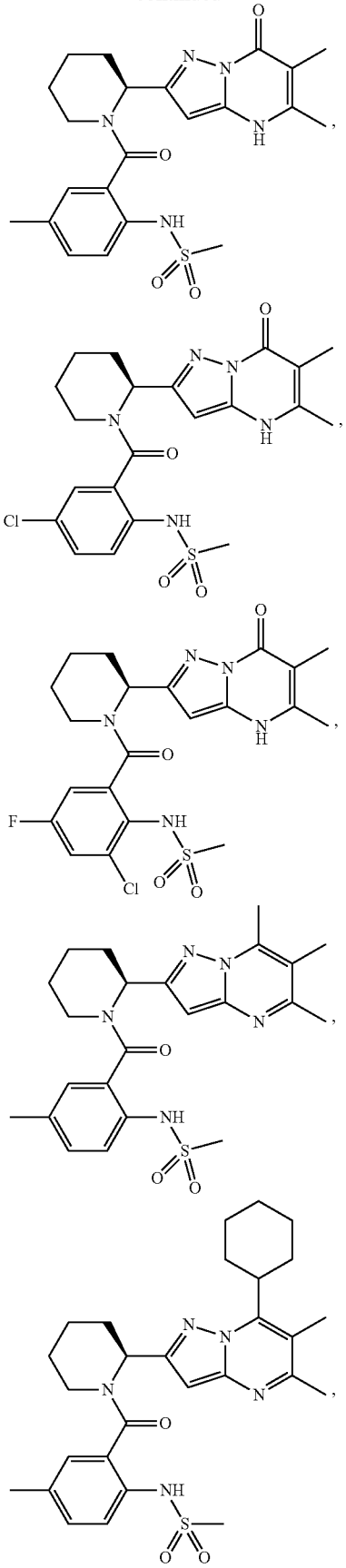

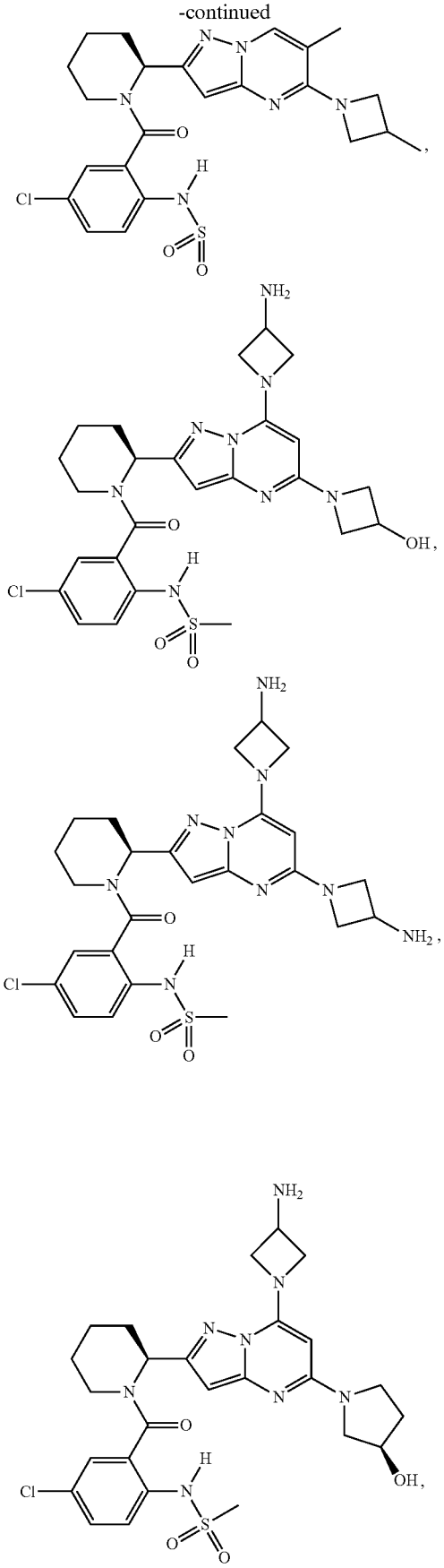
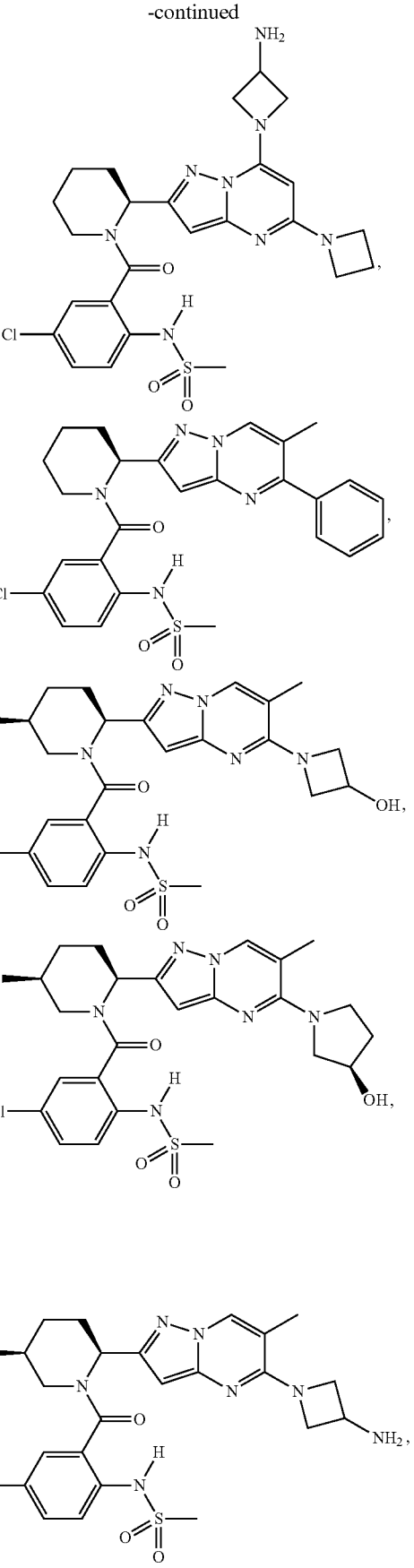

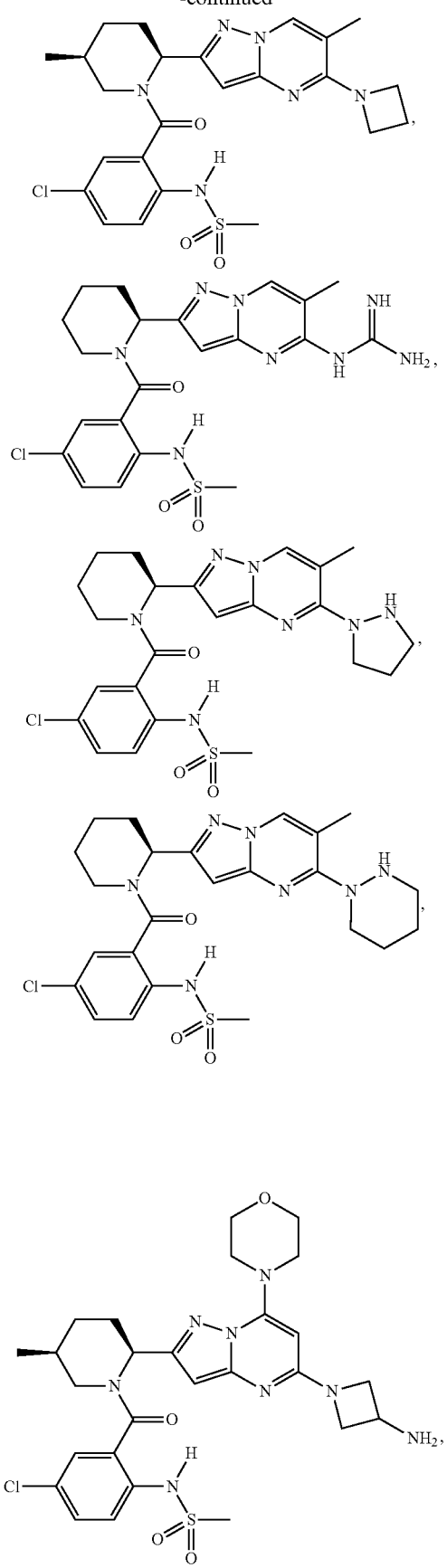
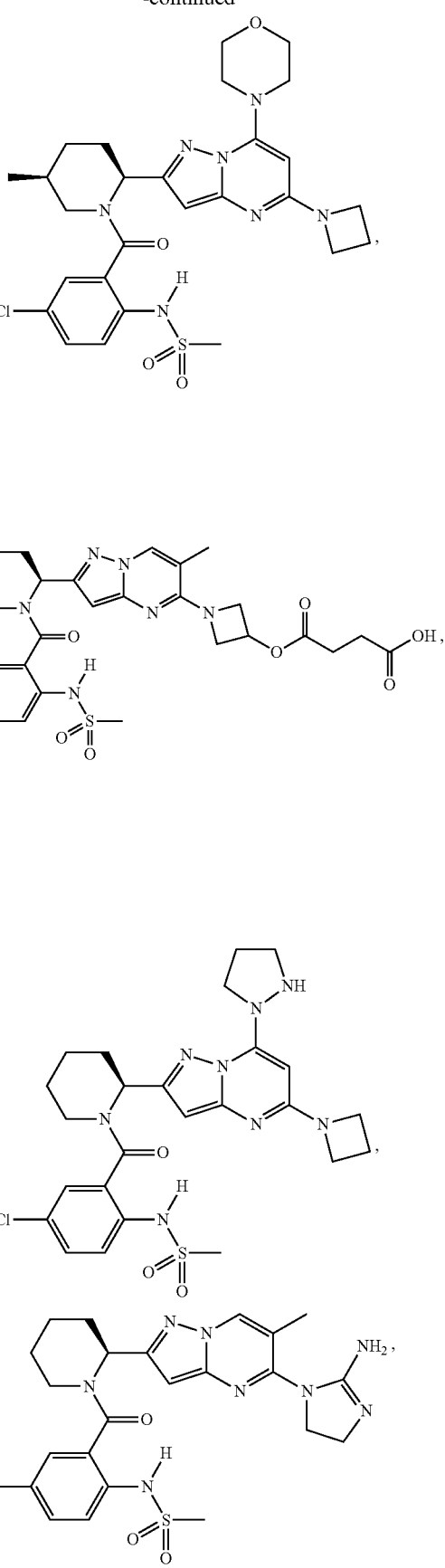

85
-continued
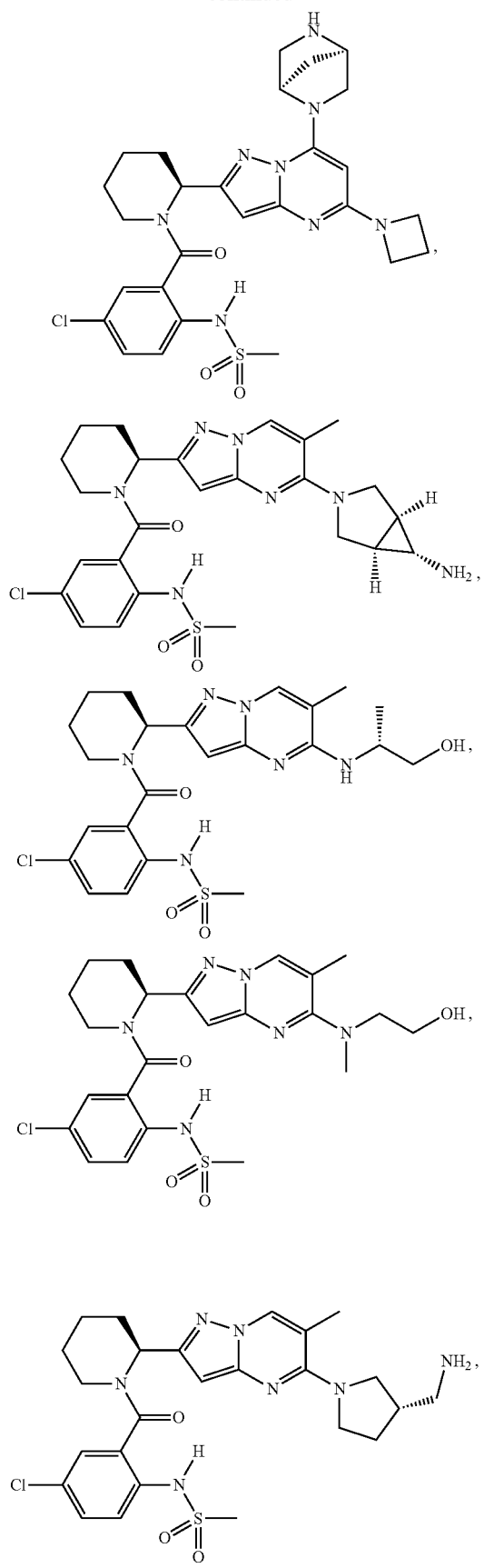
86
-continued
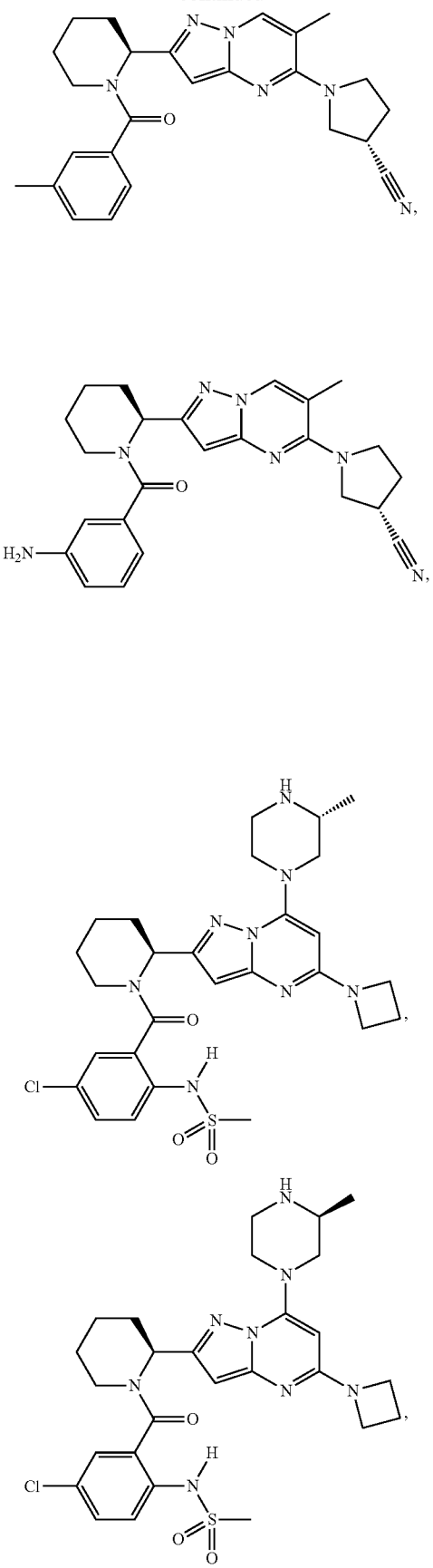

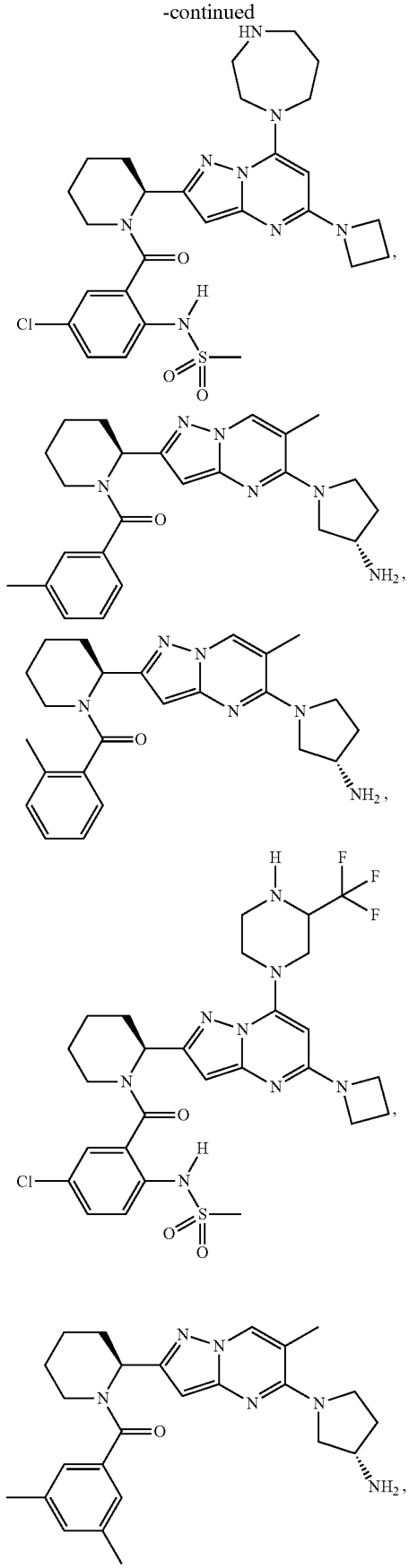
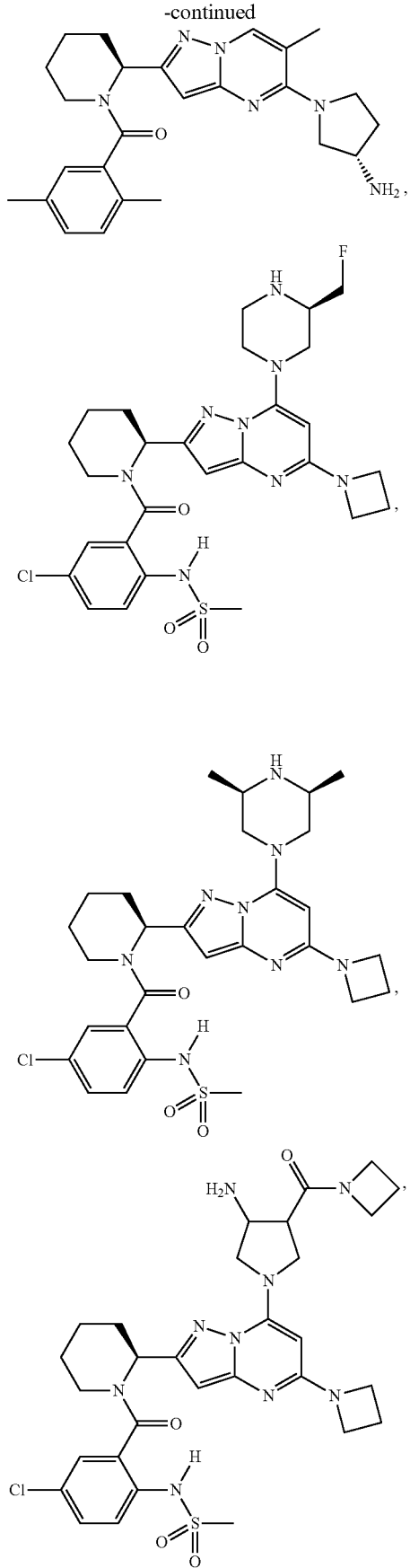

-continued
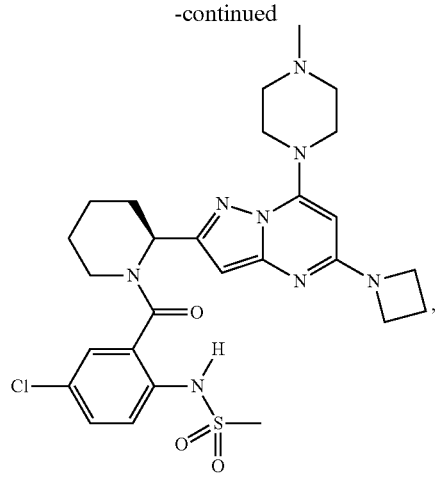
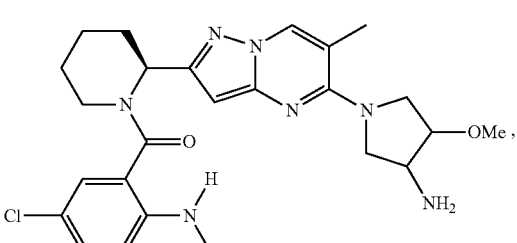
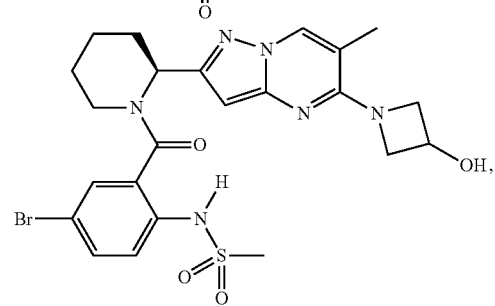
-continued
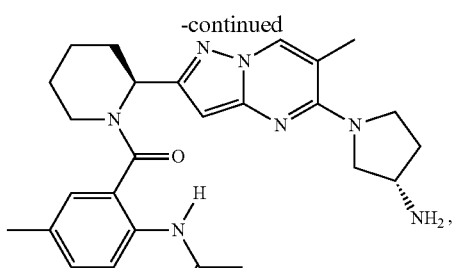
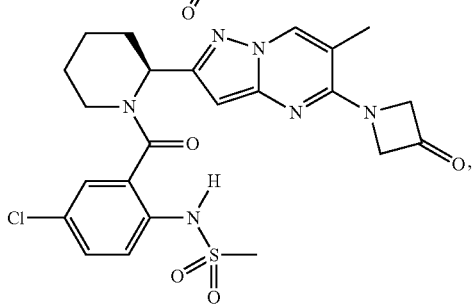
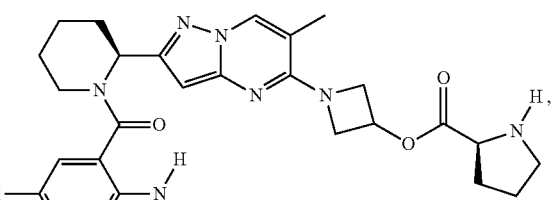
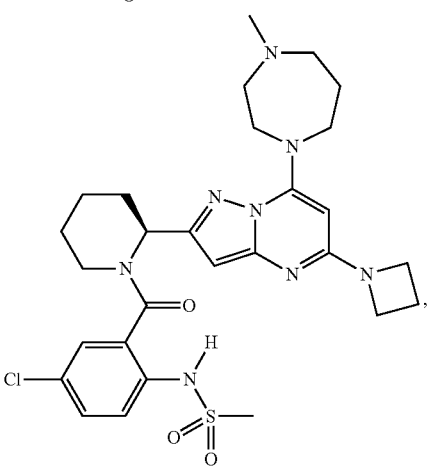

91
-continued
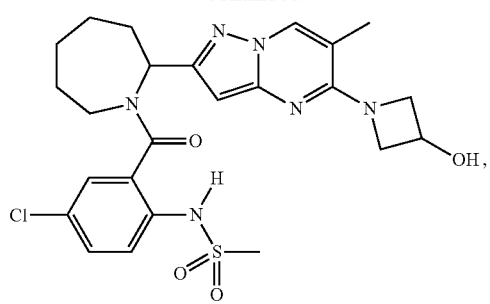
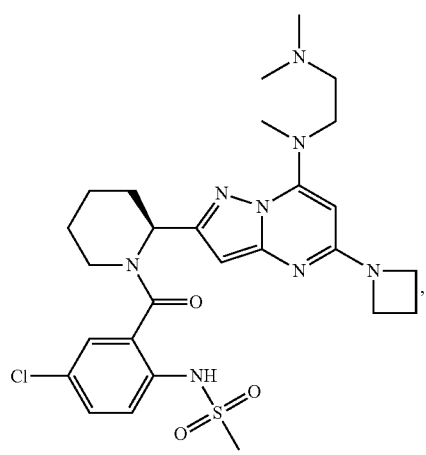
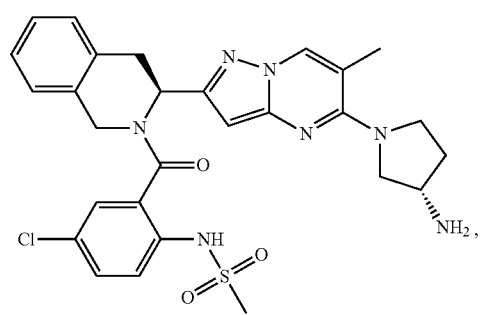
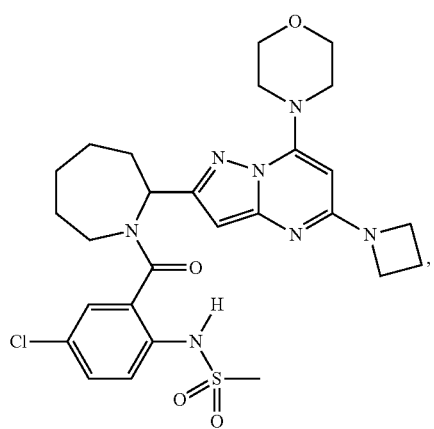
92
-continued
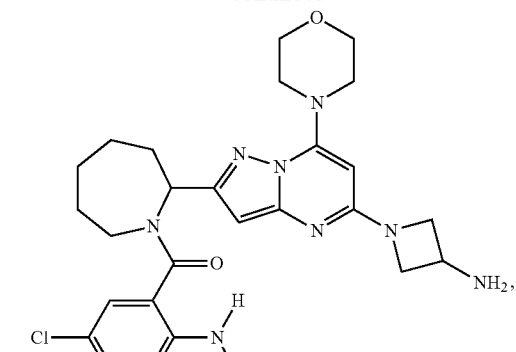
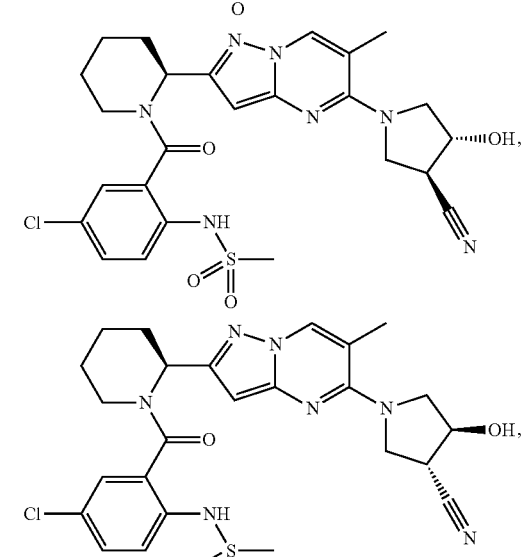
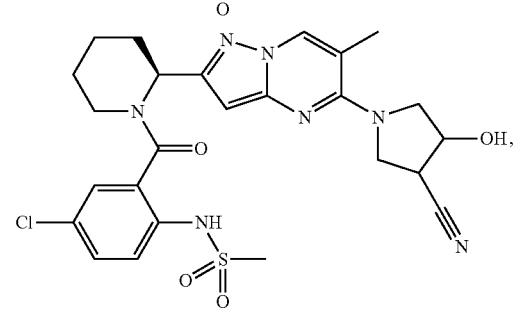
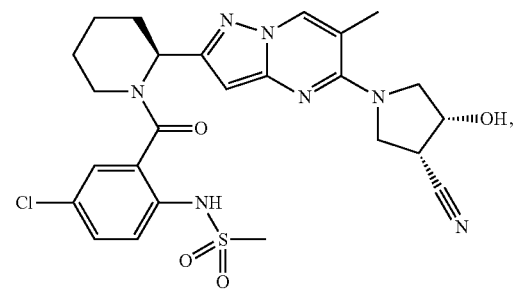

93
-continued
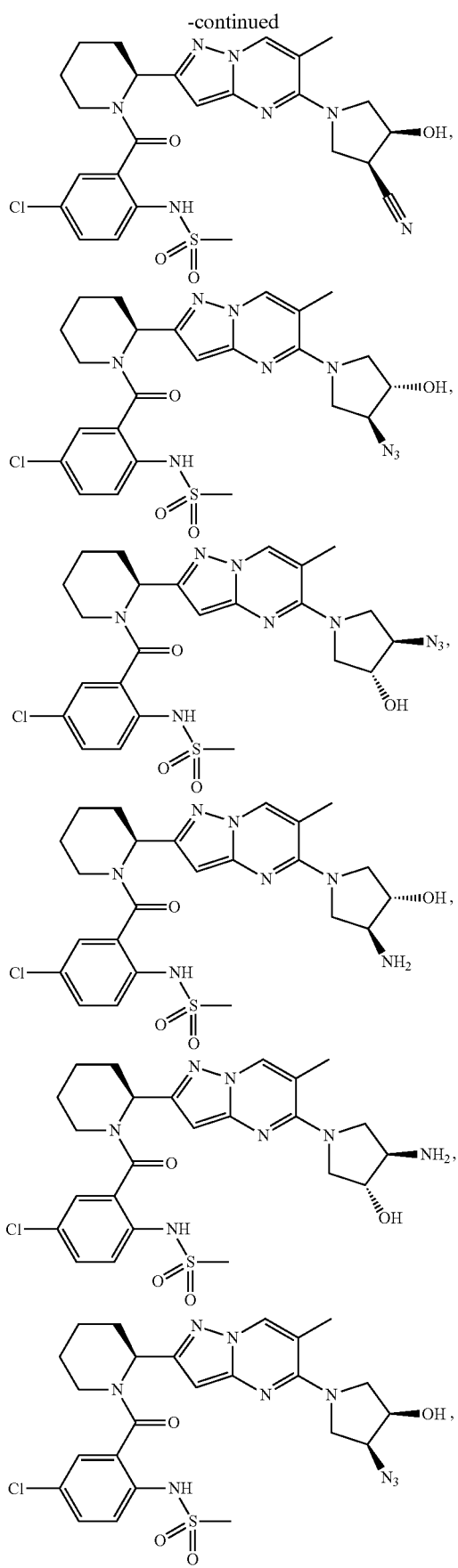
94
-continued
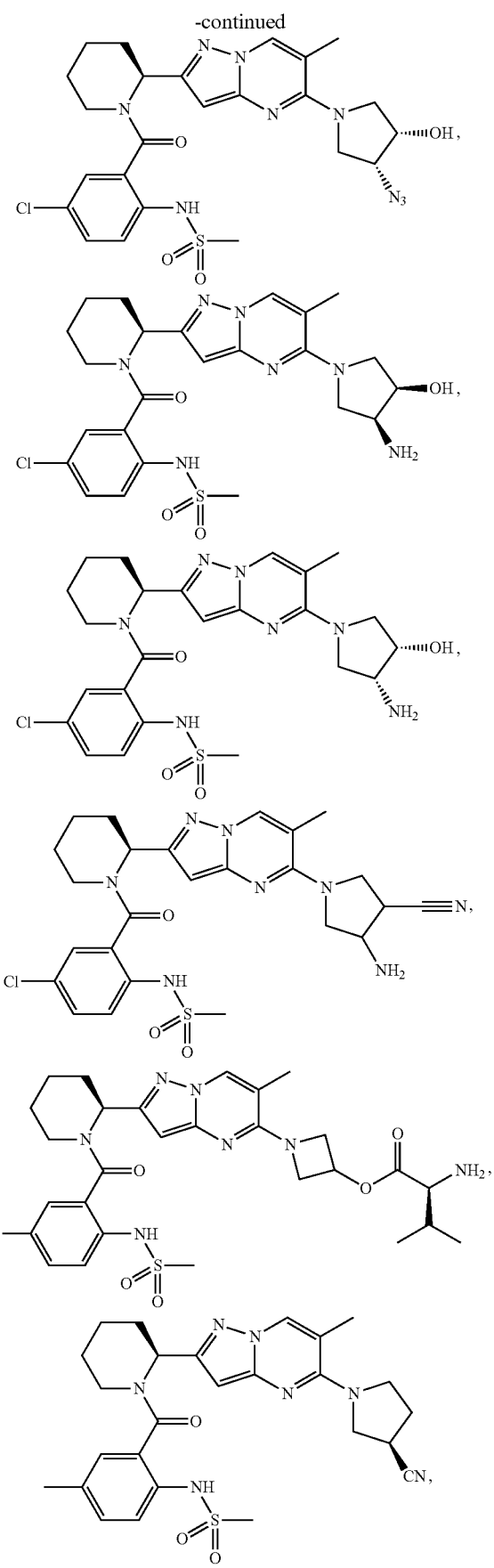

95
-continued
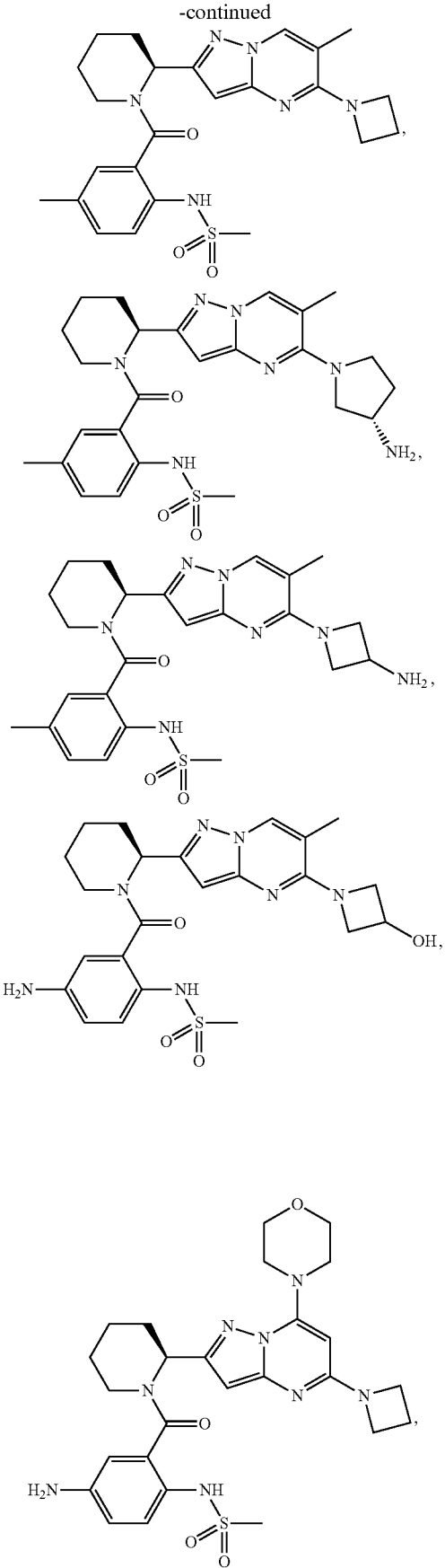
96
-continued
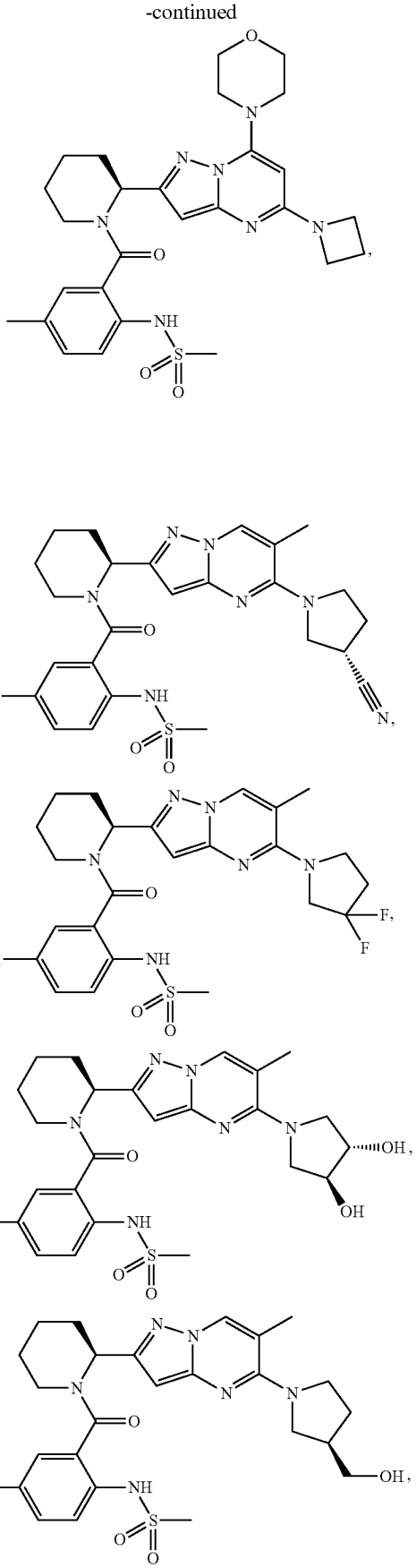

-continued
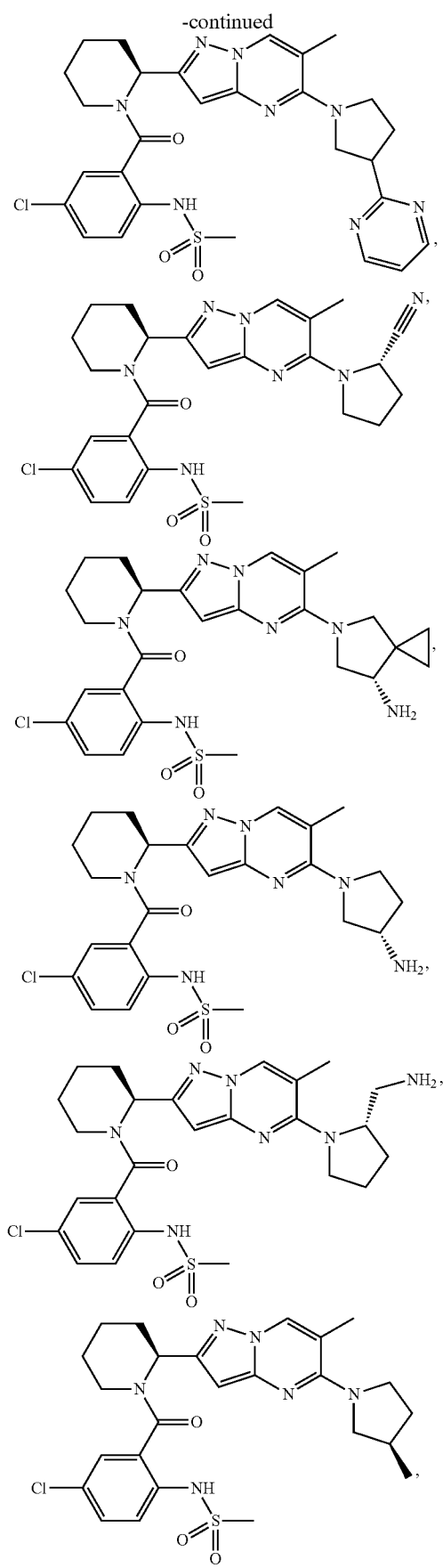
-continued
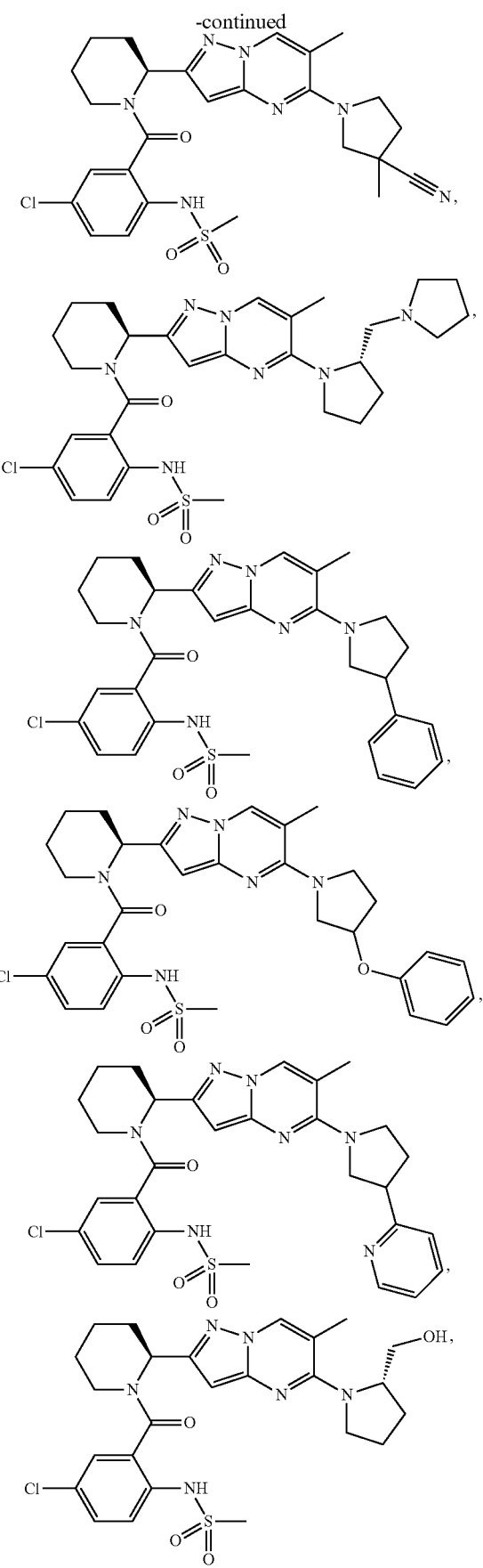

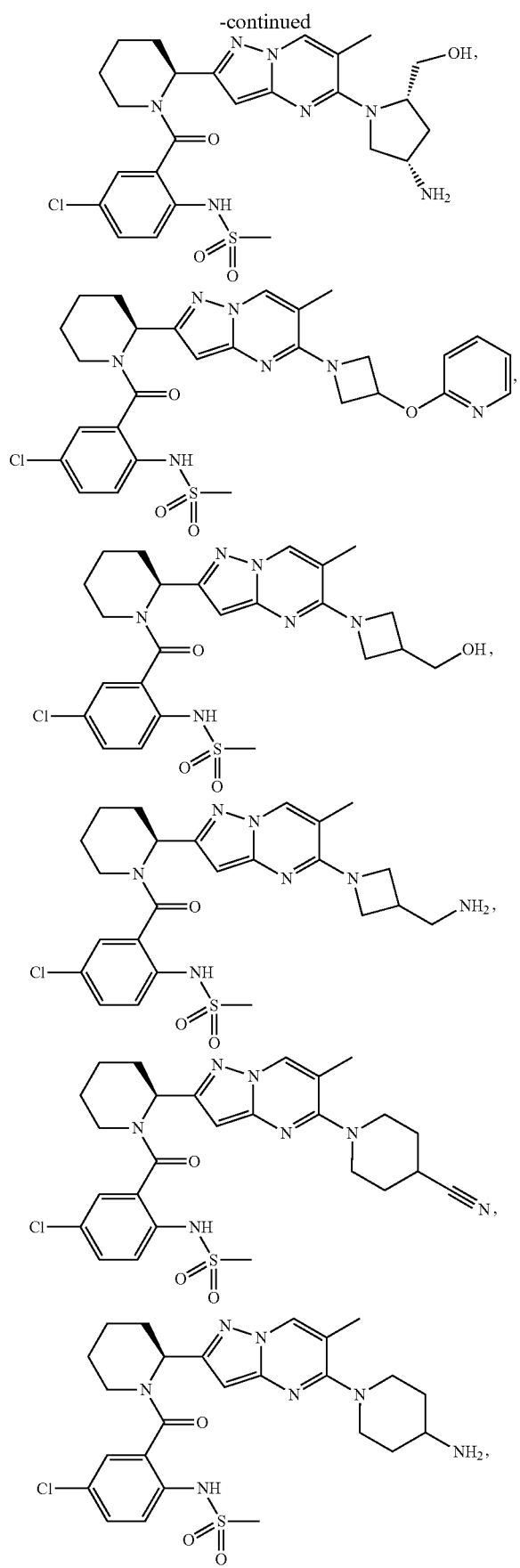
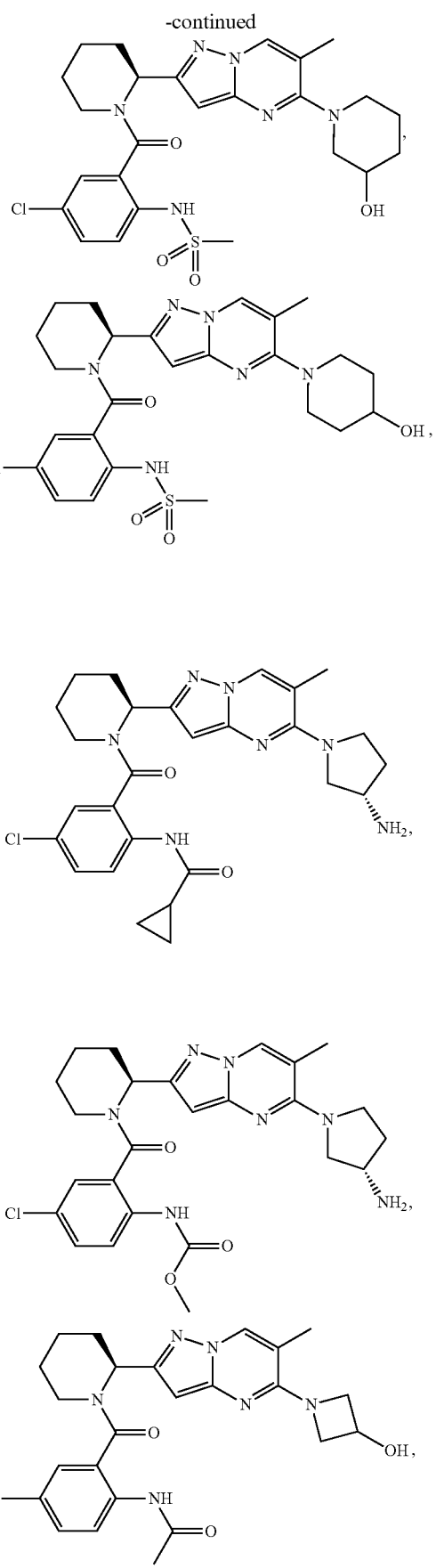

101
-continued
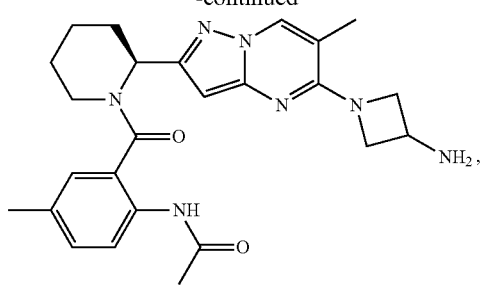
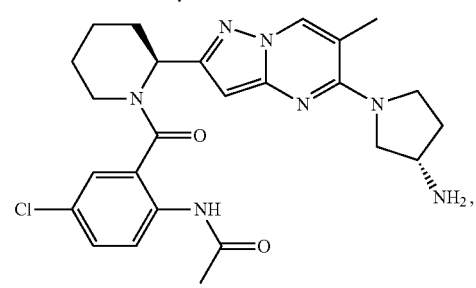
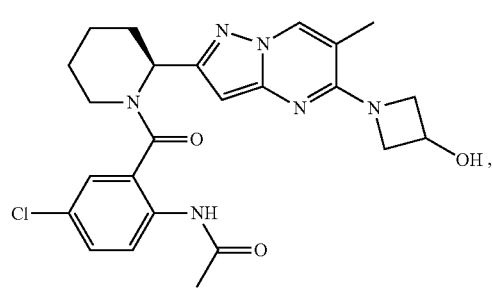
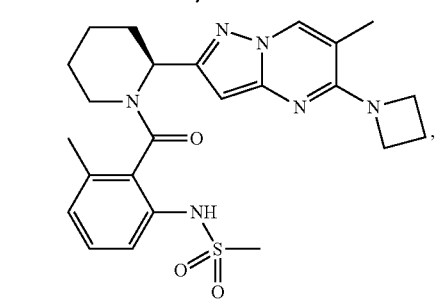
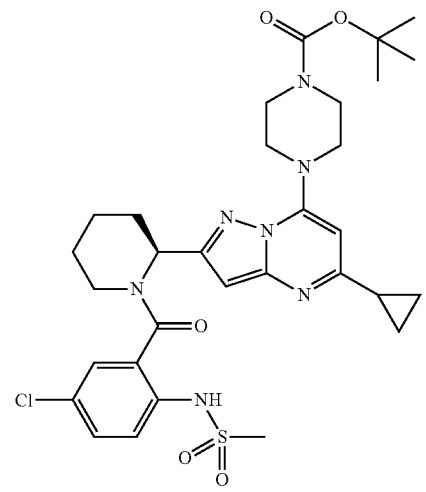
102
-continued
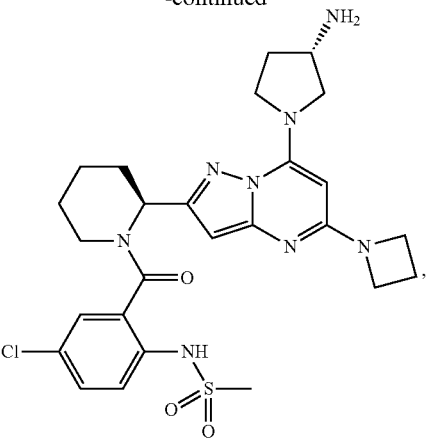
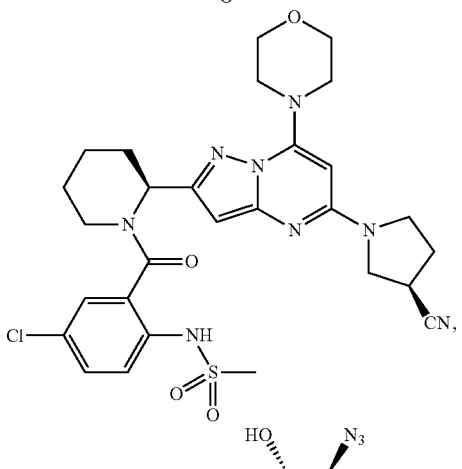
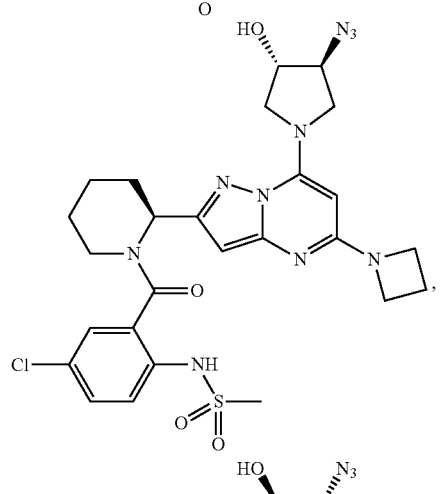
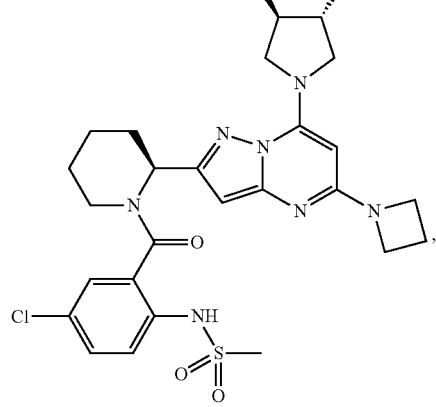

103
-continued
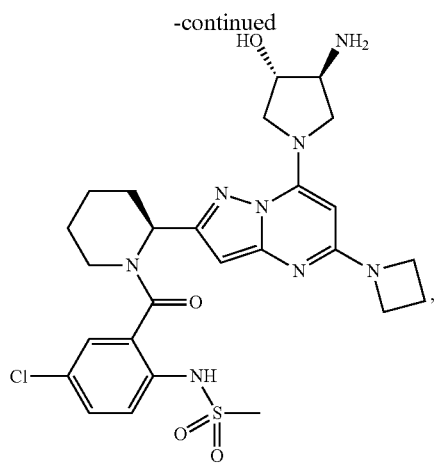
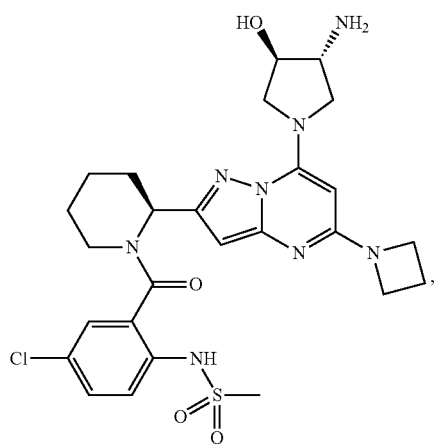
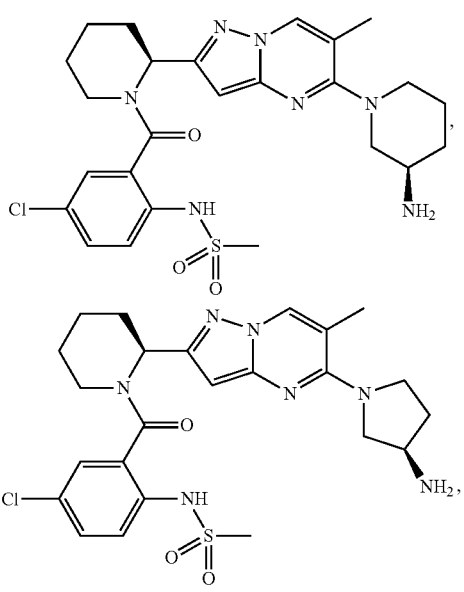
104
-continued
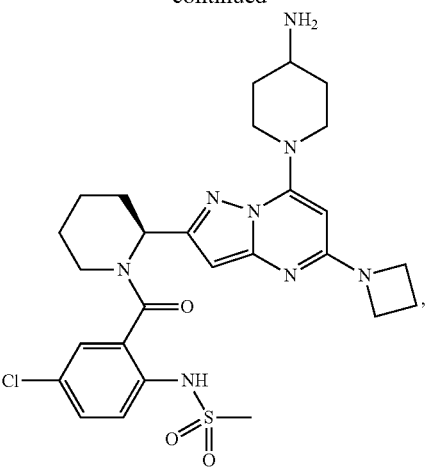
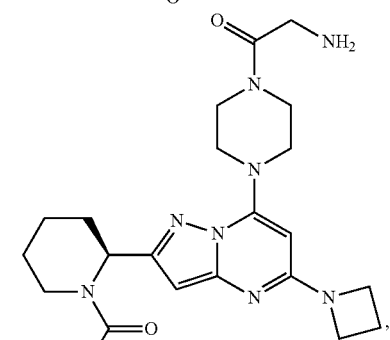
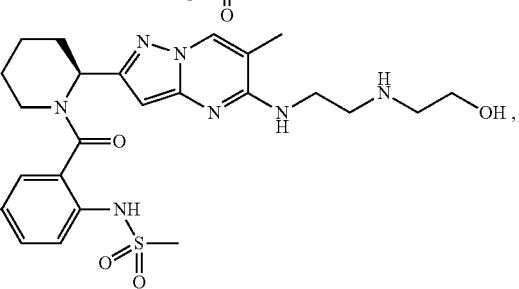
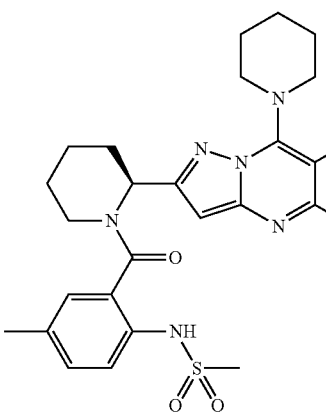

105
-continued
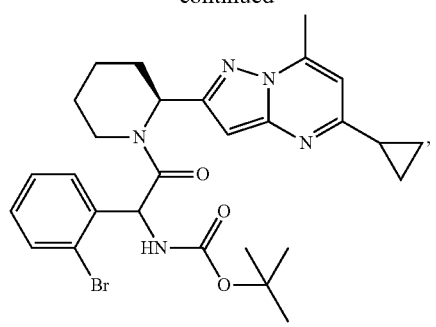
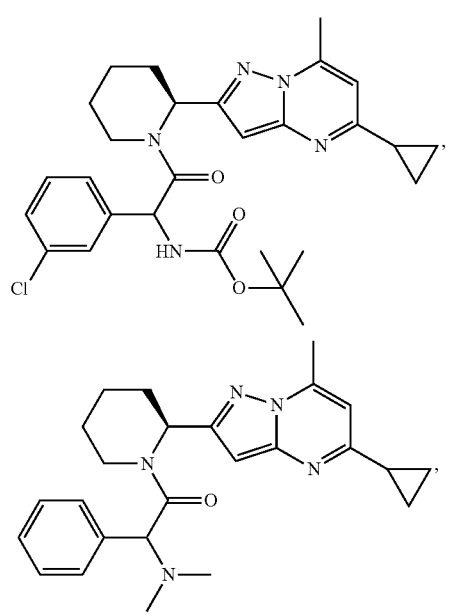
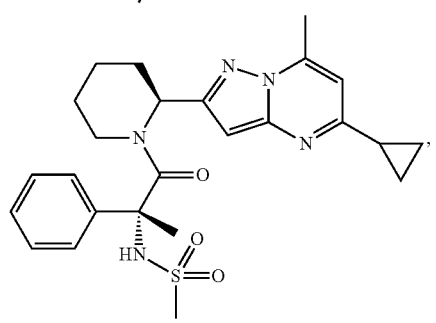
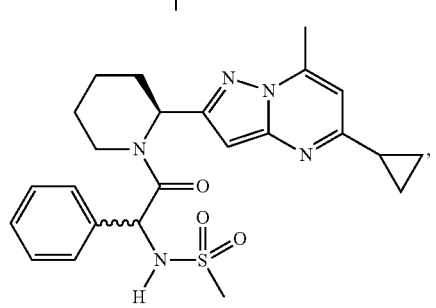
106
-continued
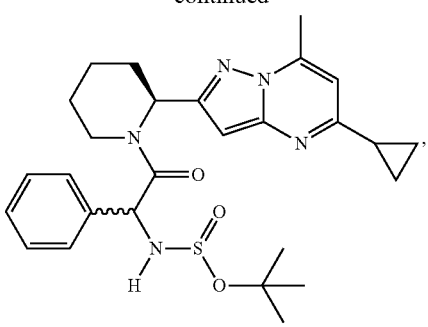
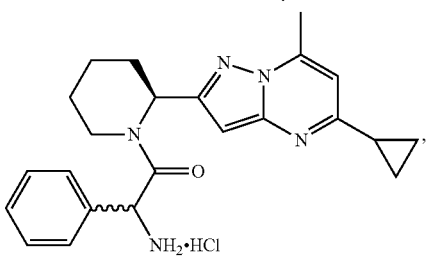
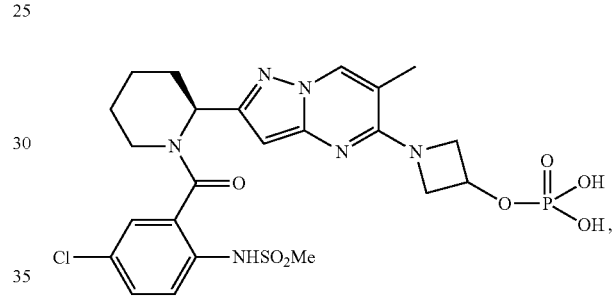
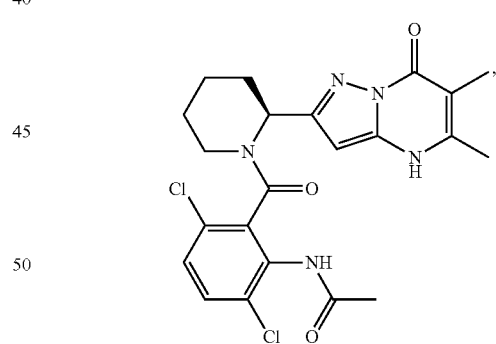
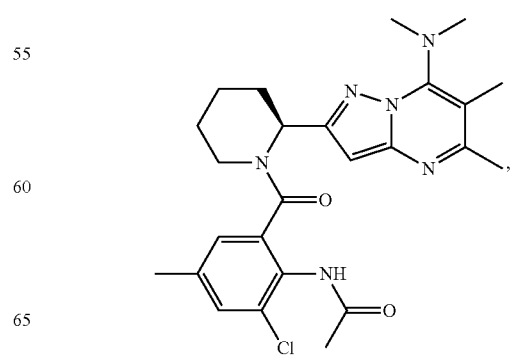

107
-continued
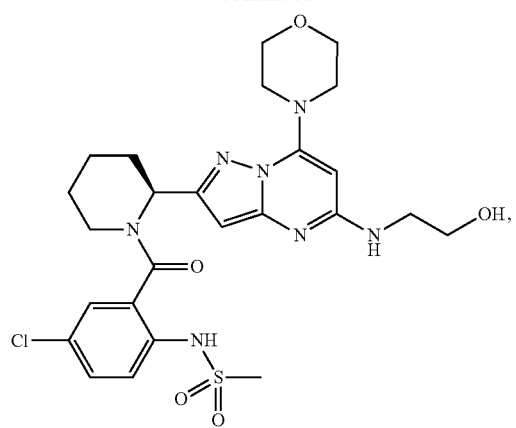
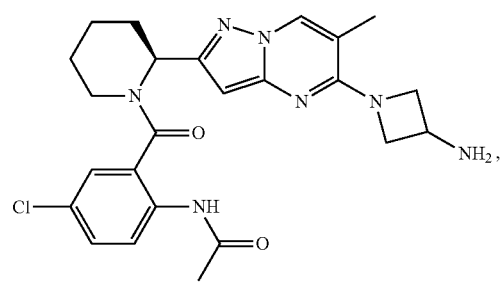
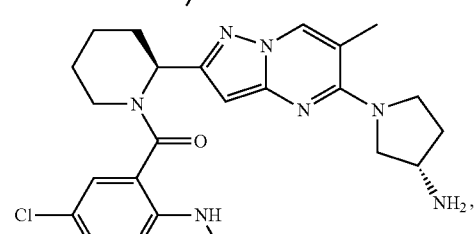
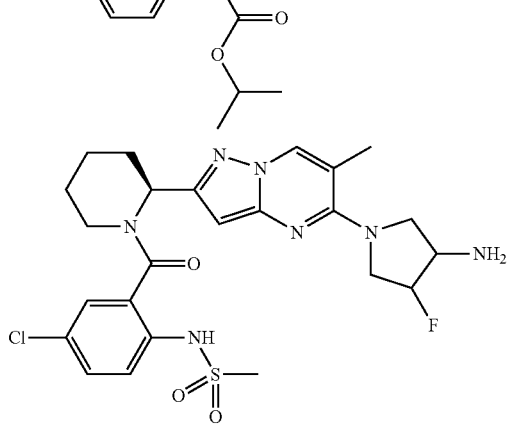
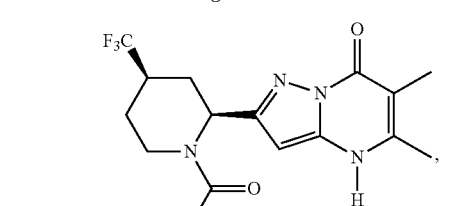
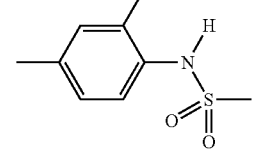
108
-continued
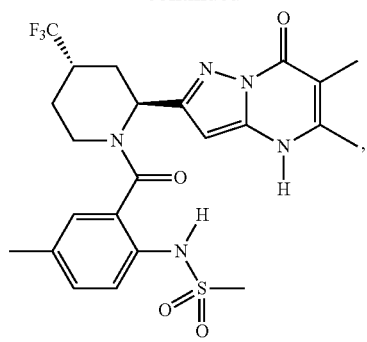
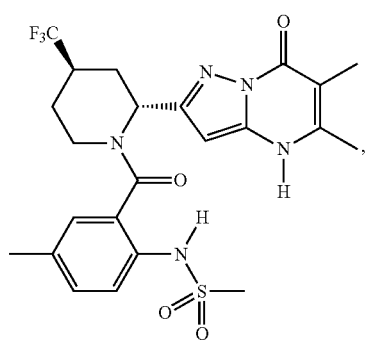
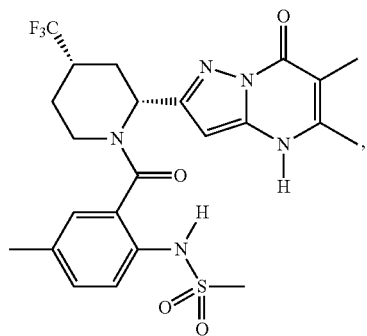
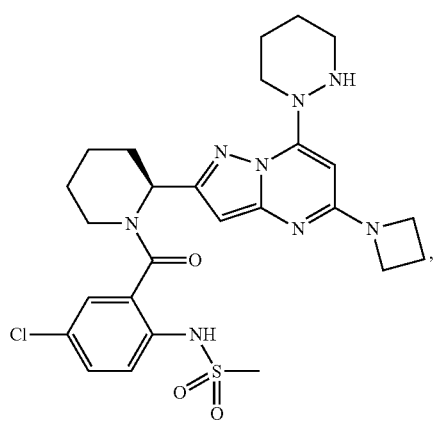

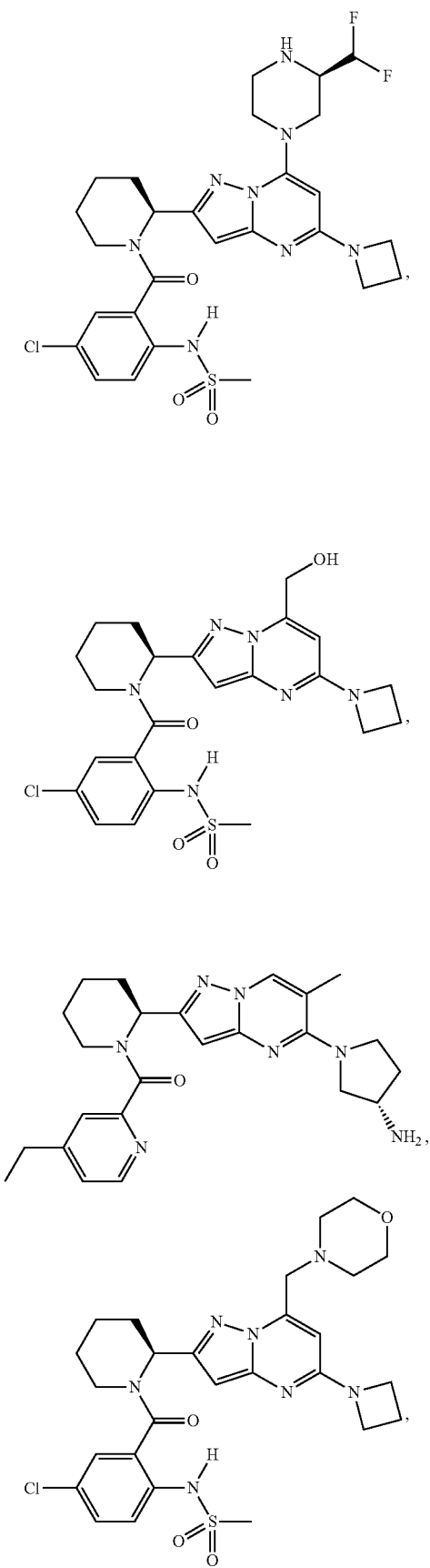
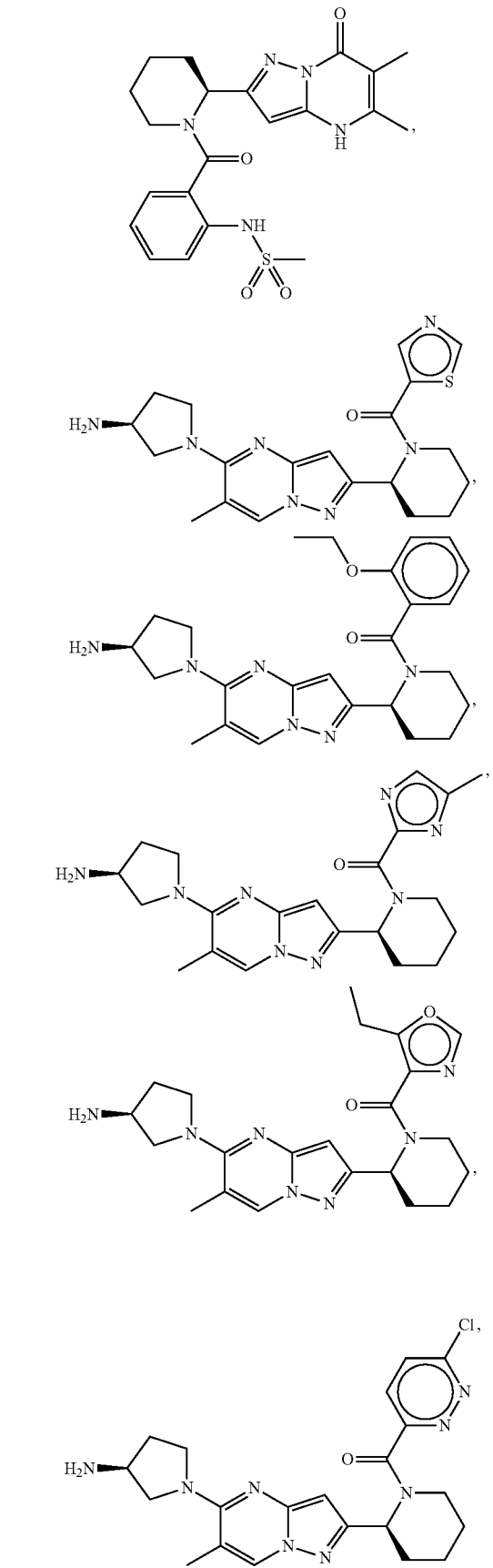

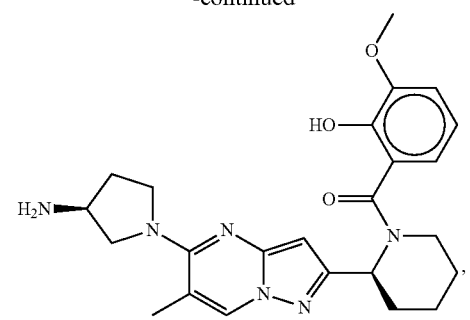
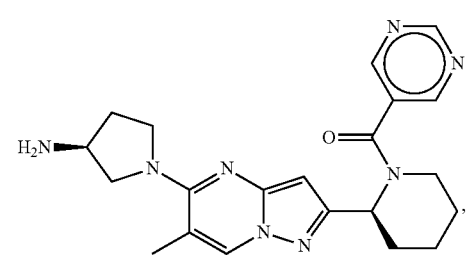
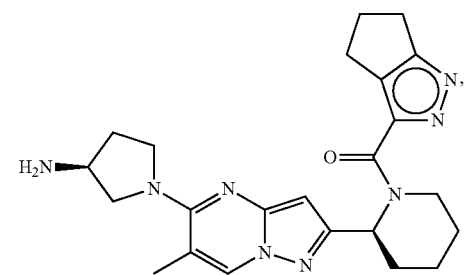
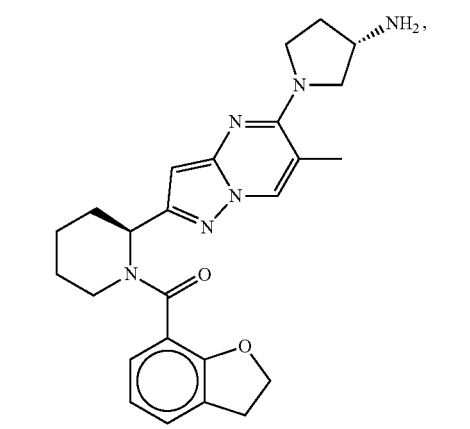
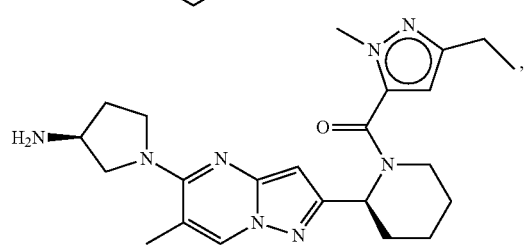
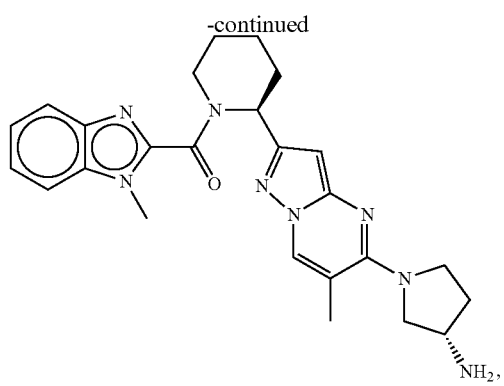
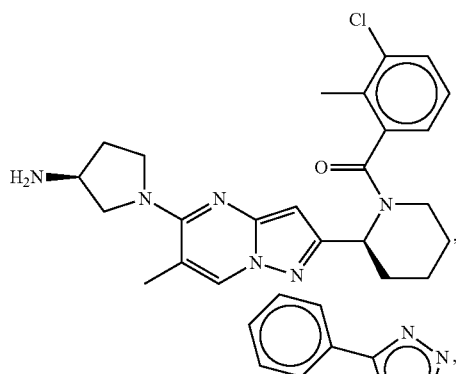
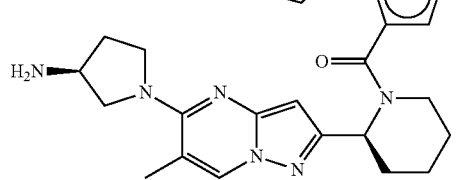
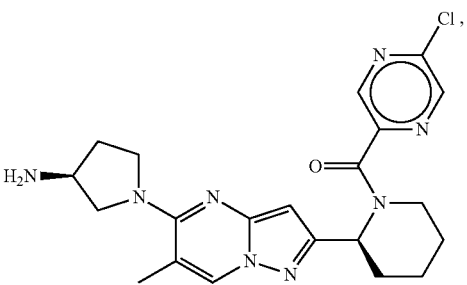
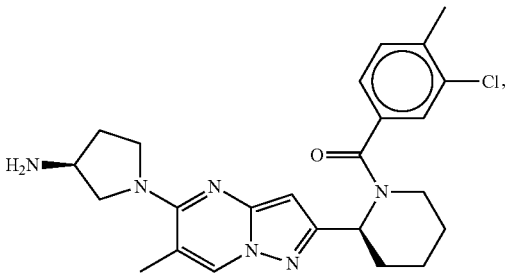
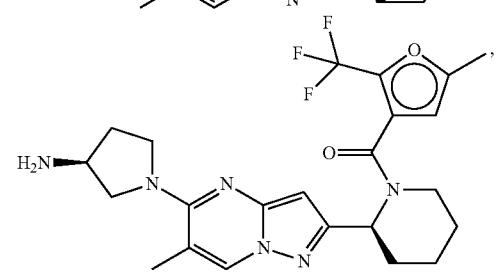

113
-continued
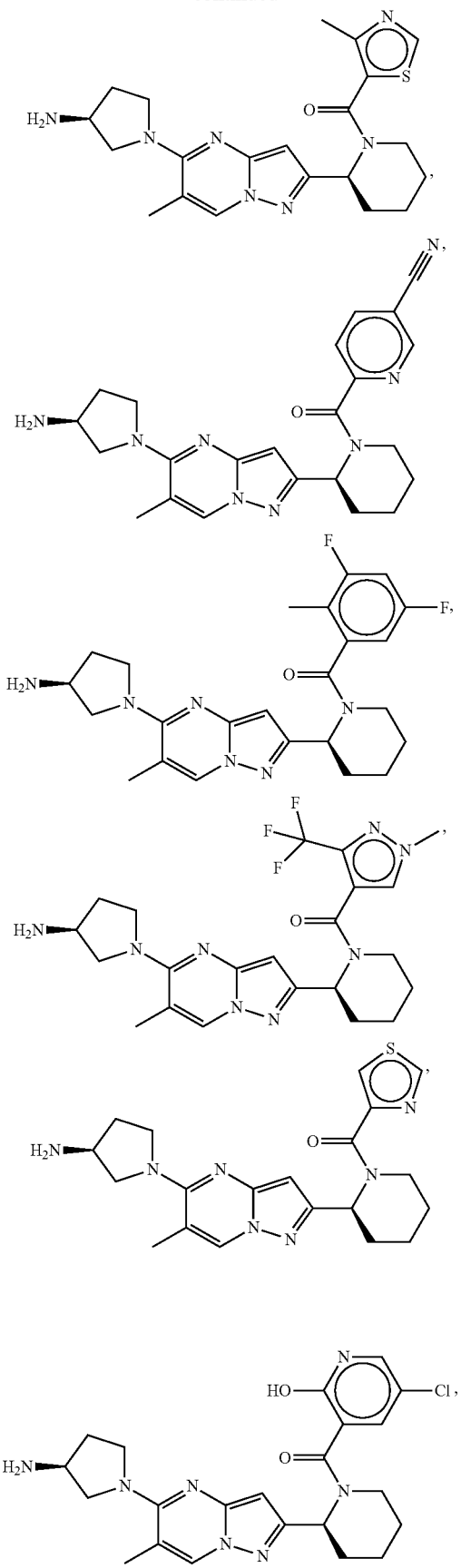
114
-continued
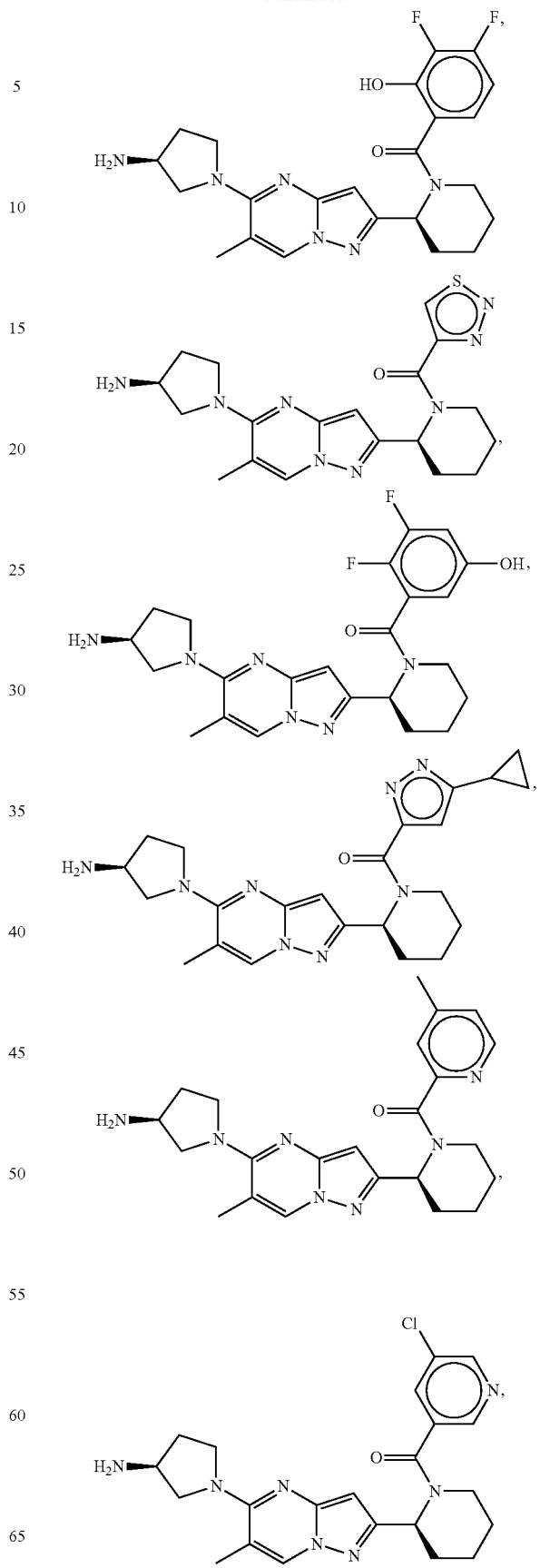

115
-continued
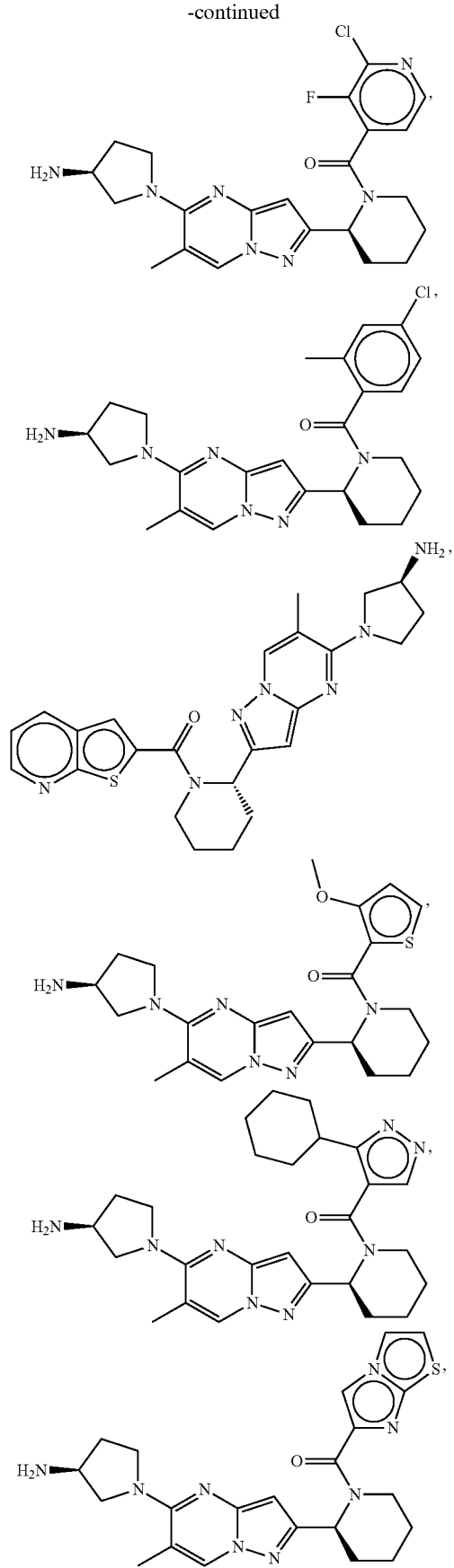
116
-continued
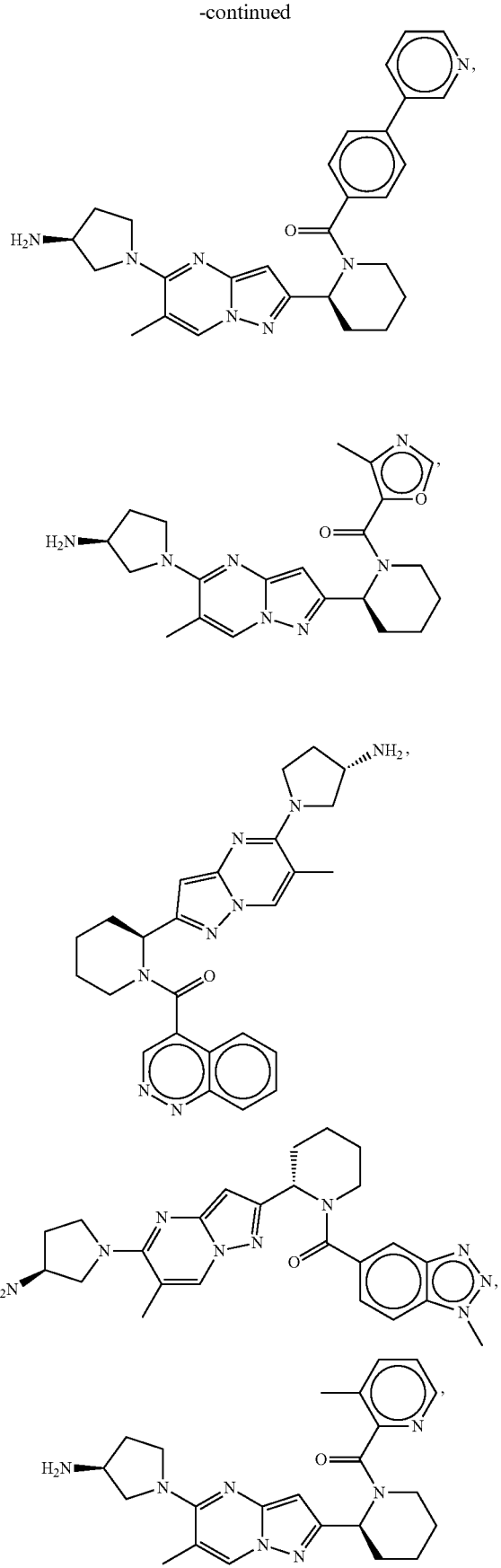

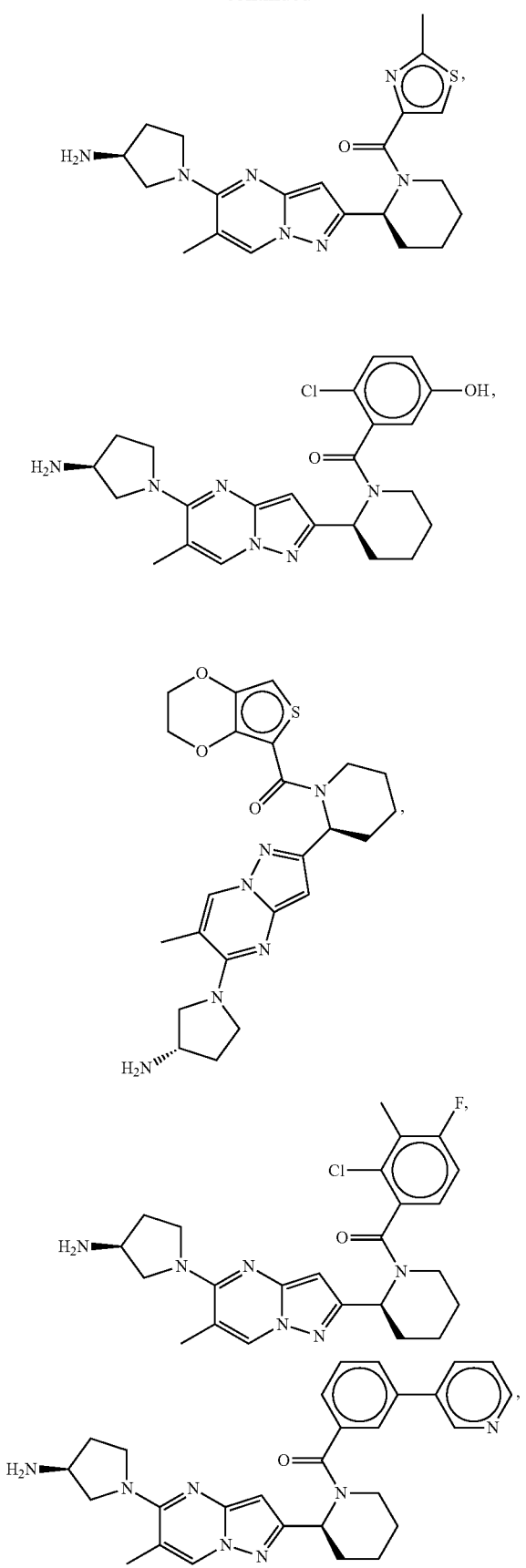
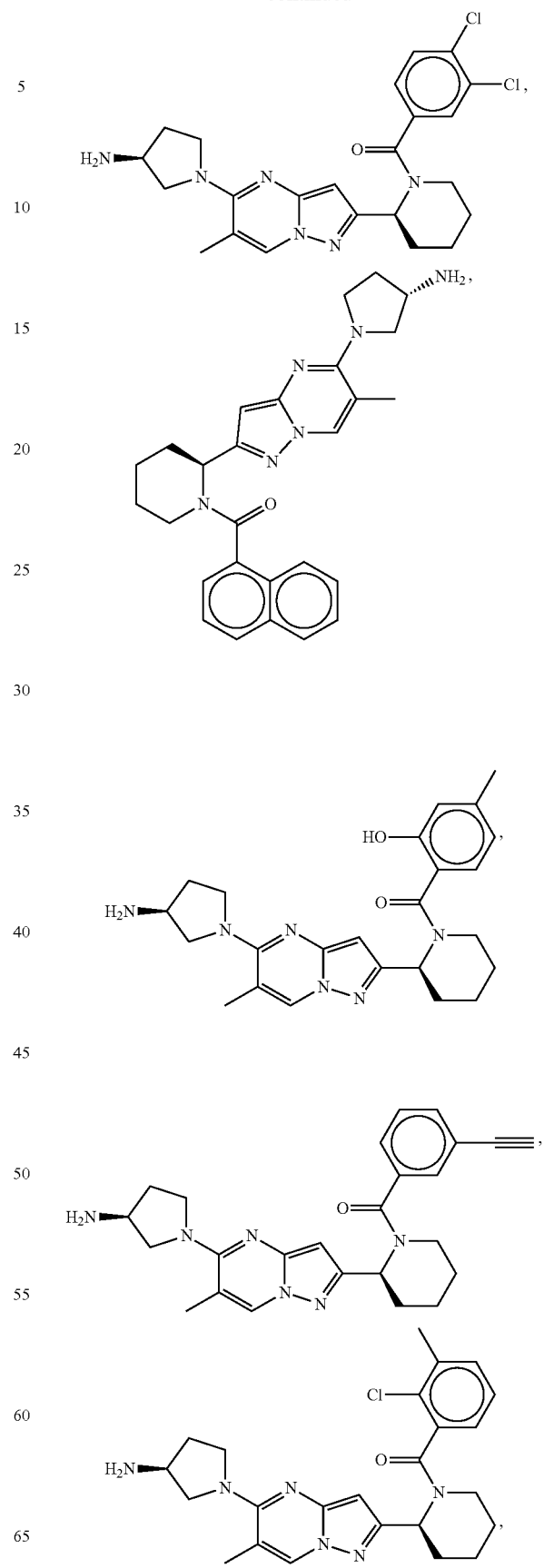

119
-continued
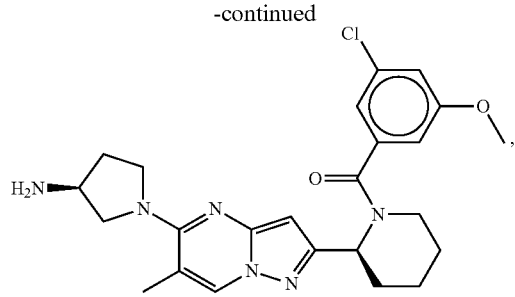
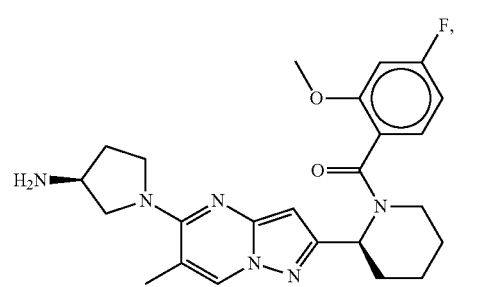
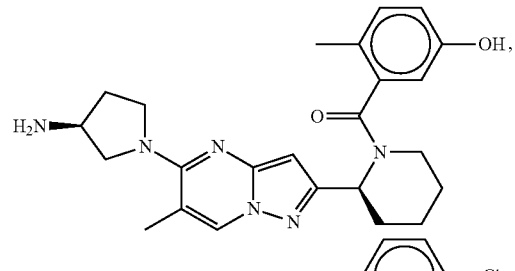
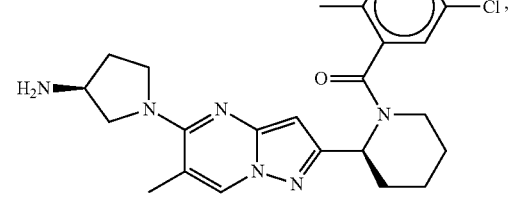
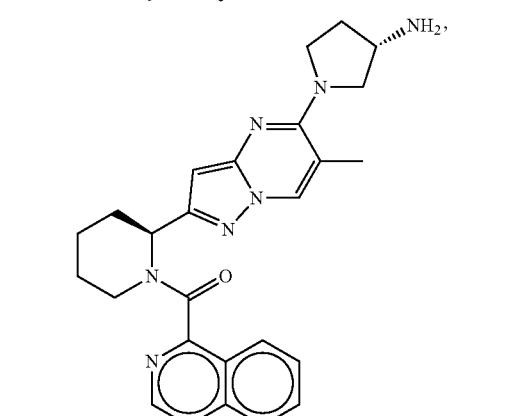
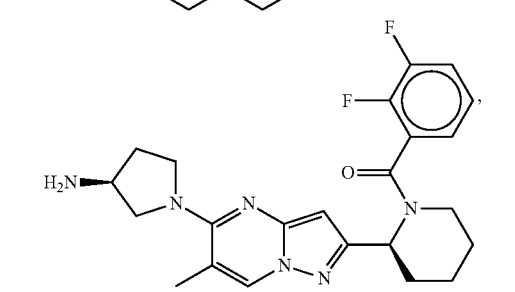
120
-continued
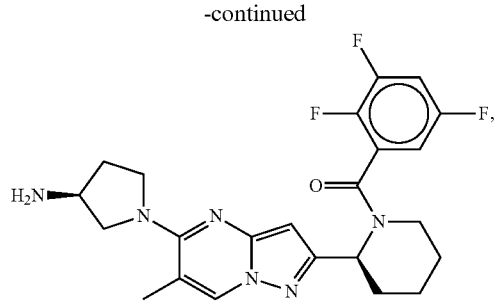
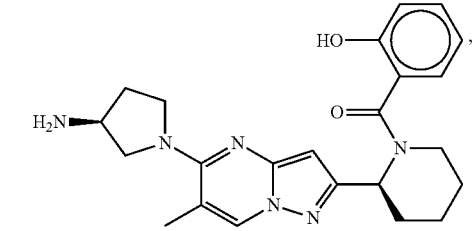
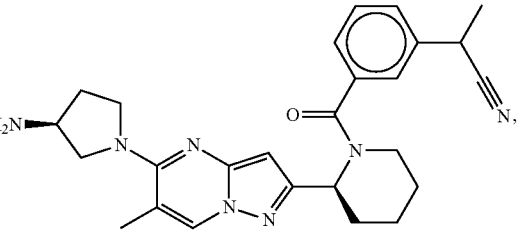
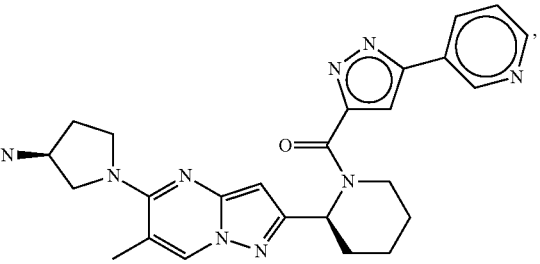
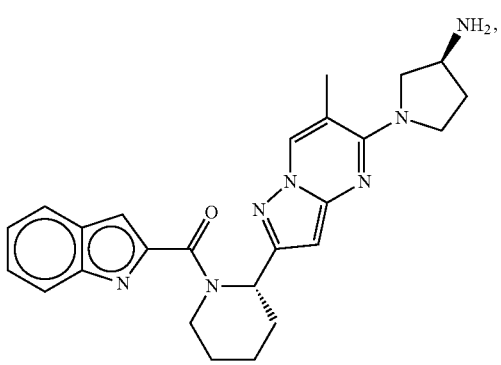
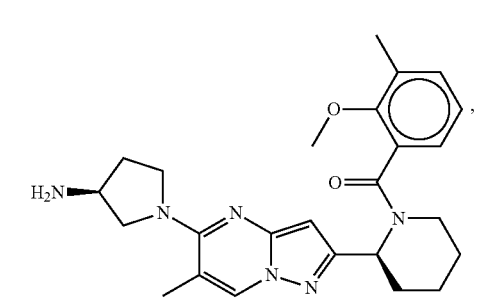

121
-continued
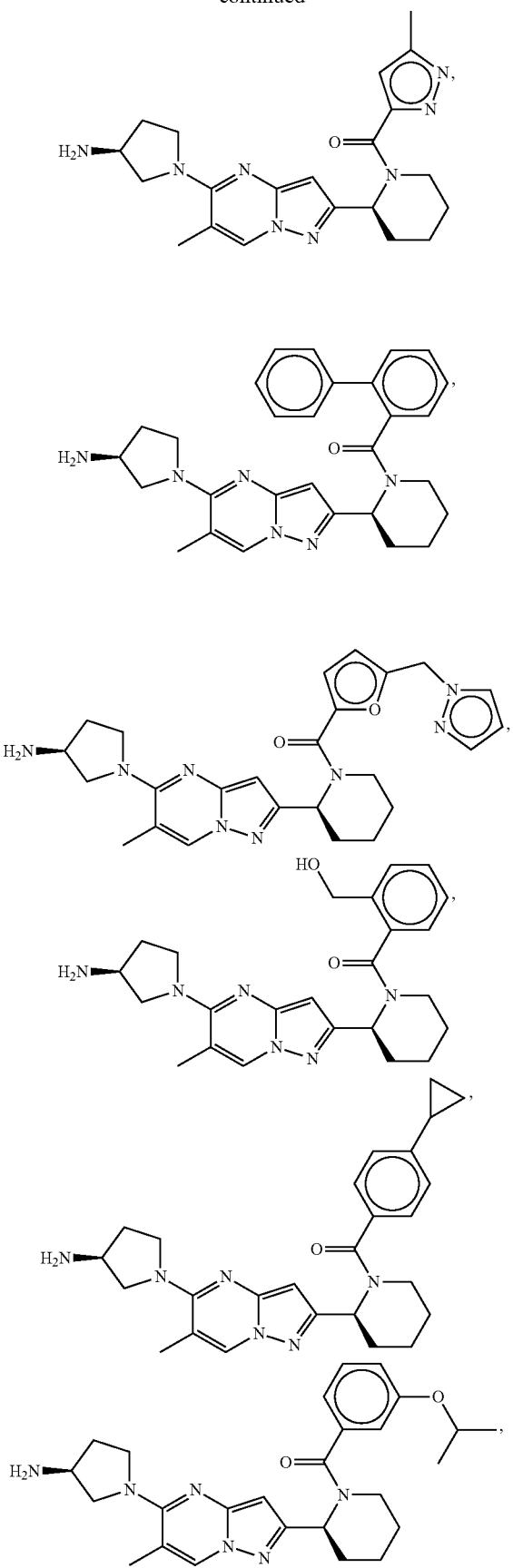
122
-continued
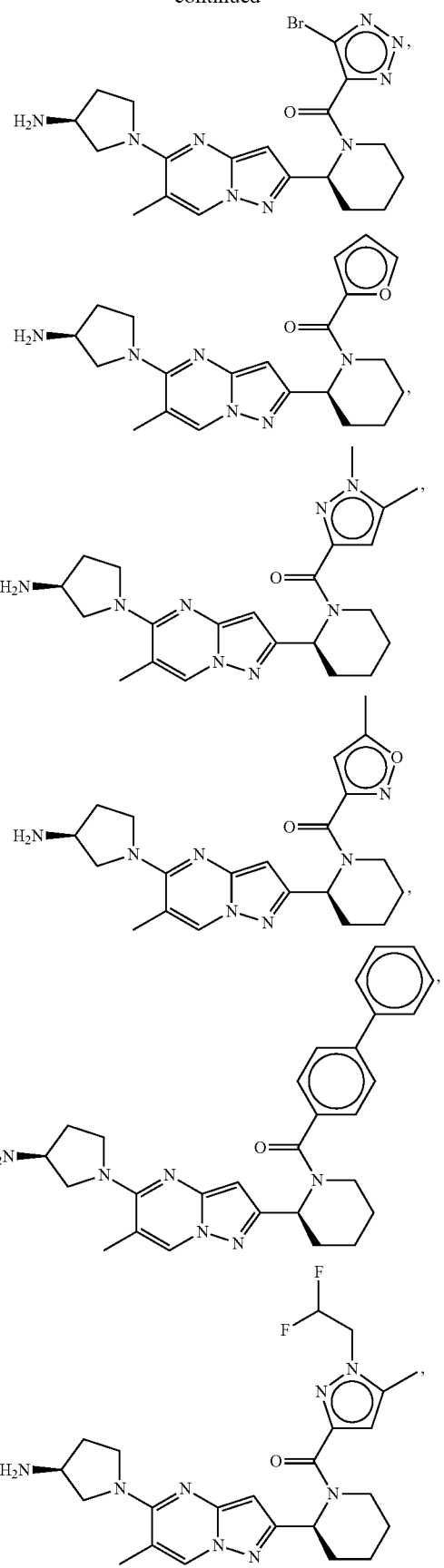

123
-continued
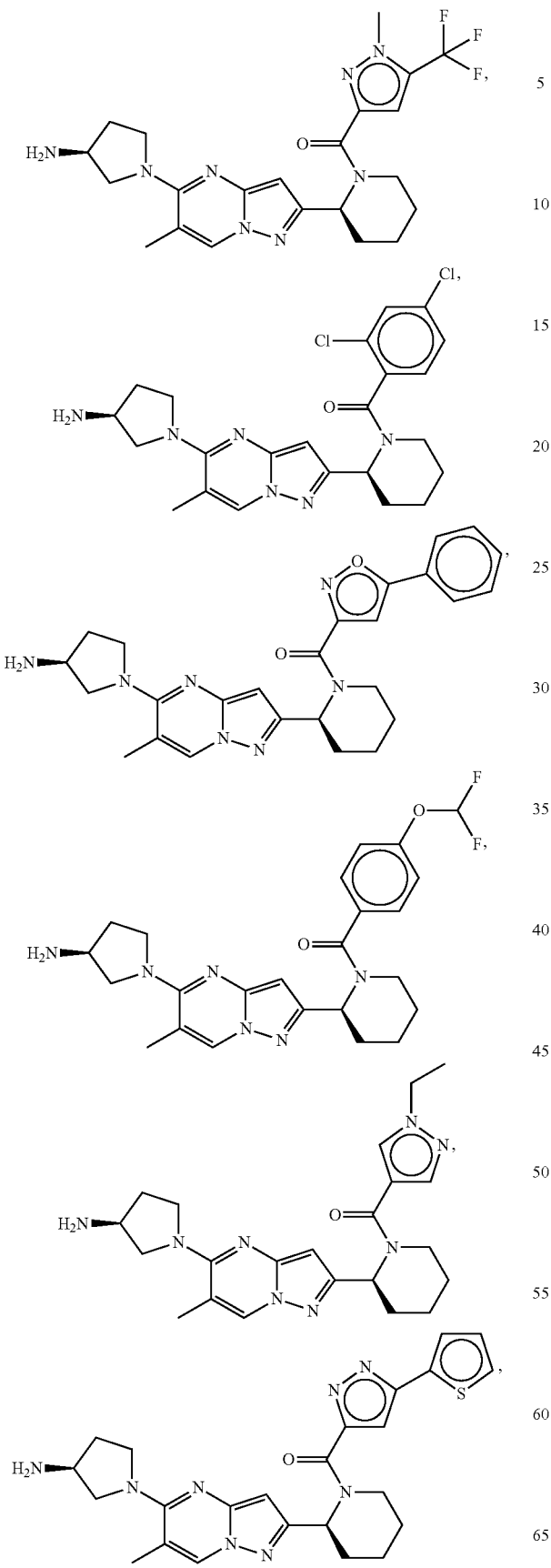
124
-continued
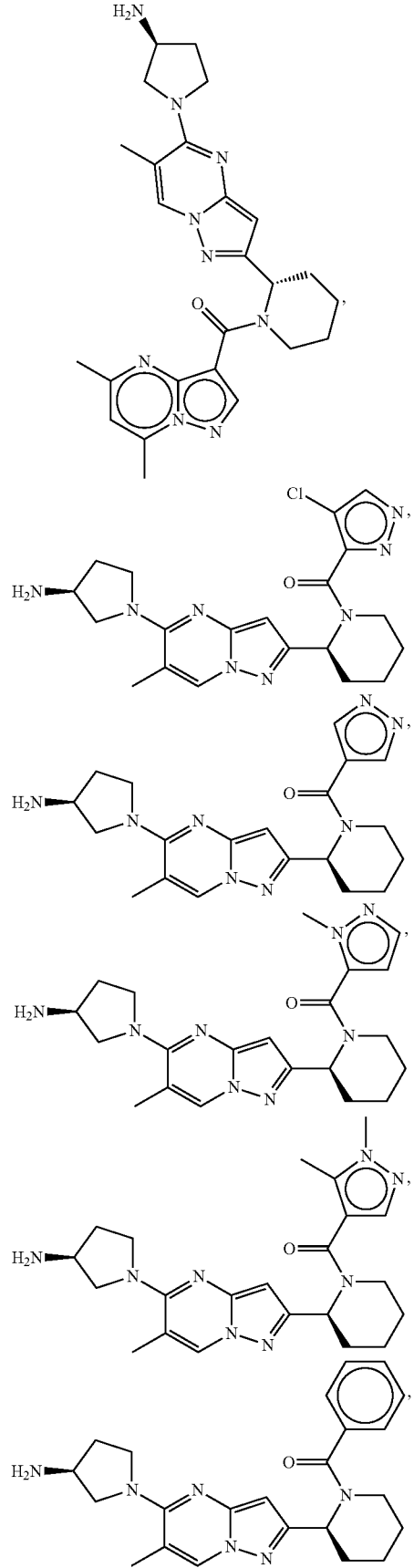

125
-continued
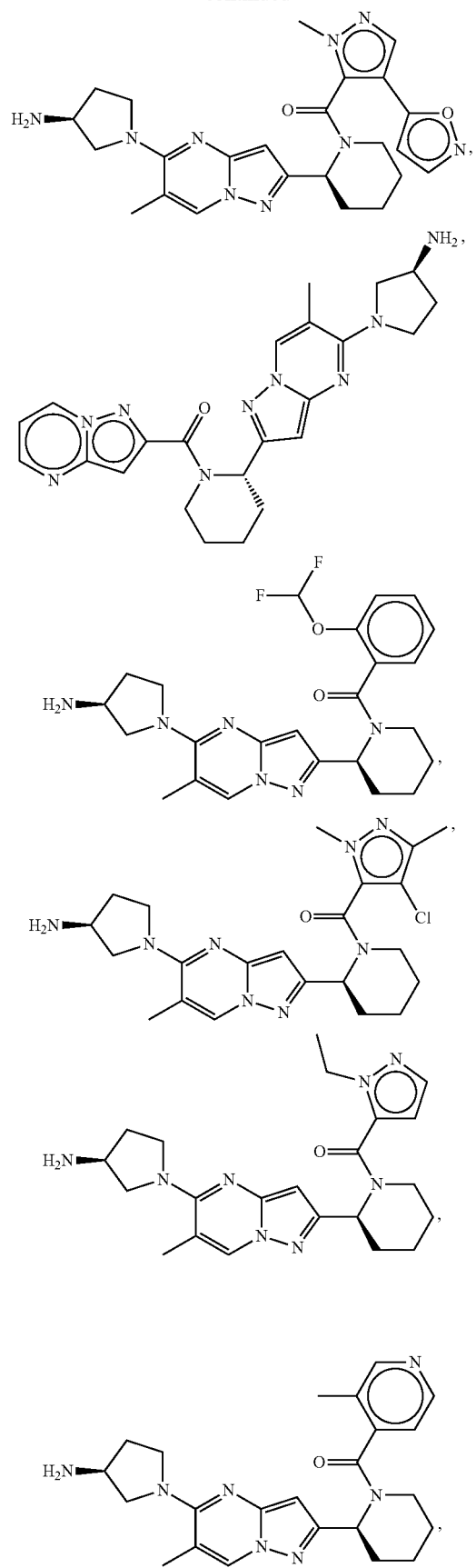
126
-continued
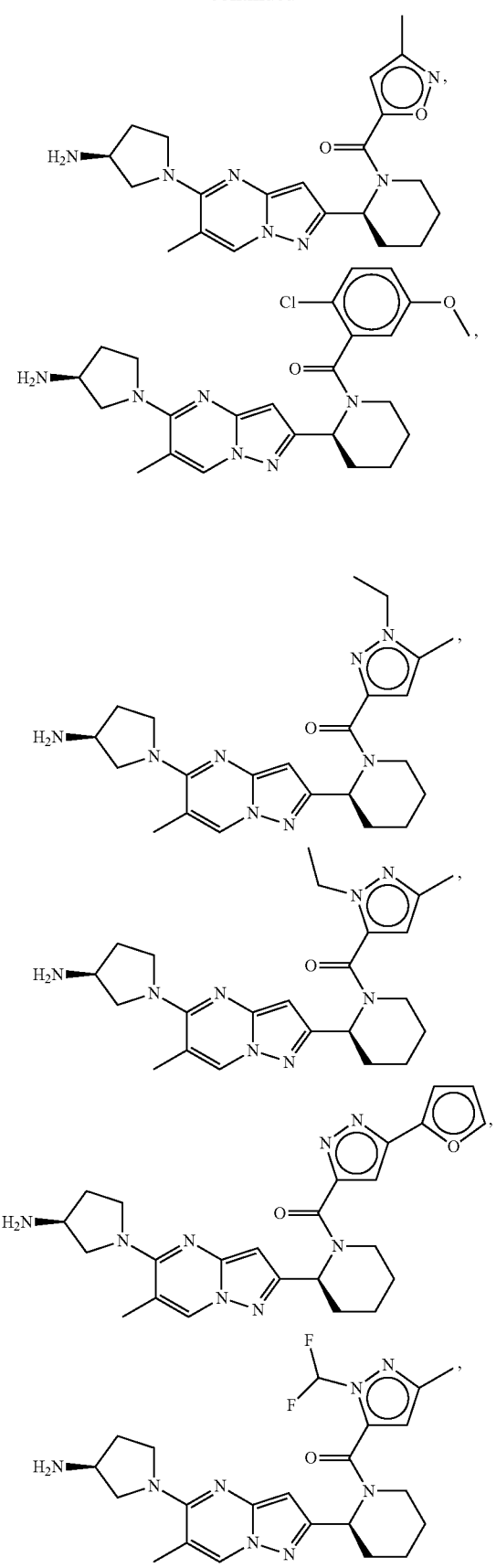

127
-continued
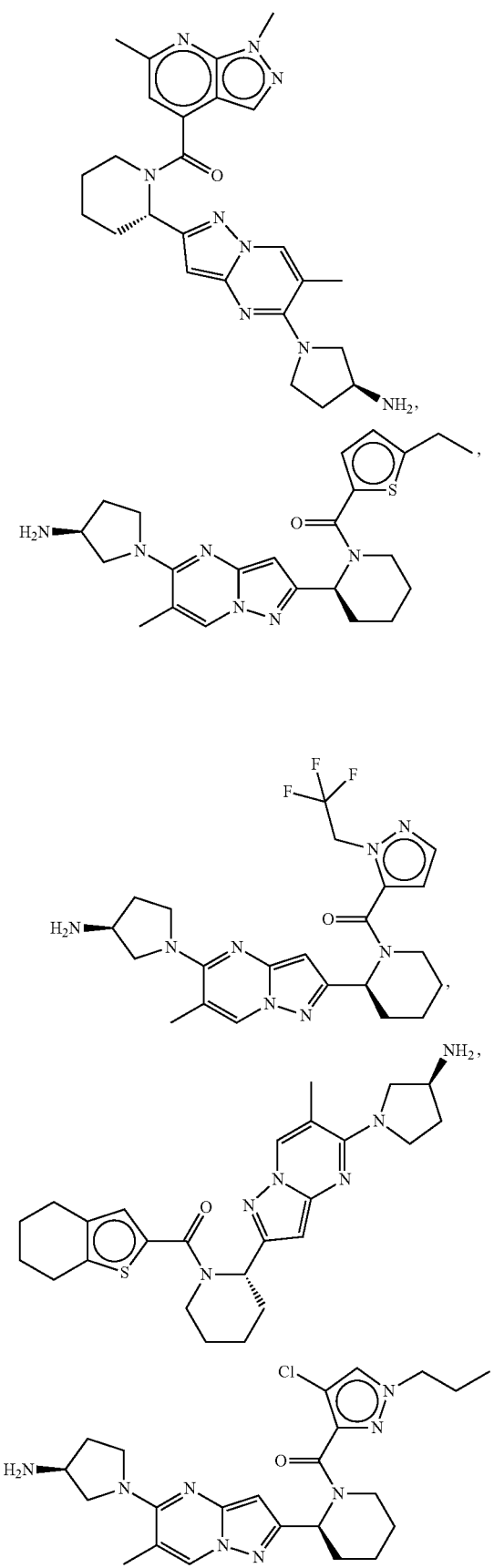
128
-continued
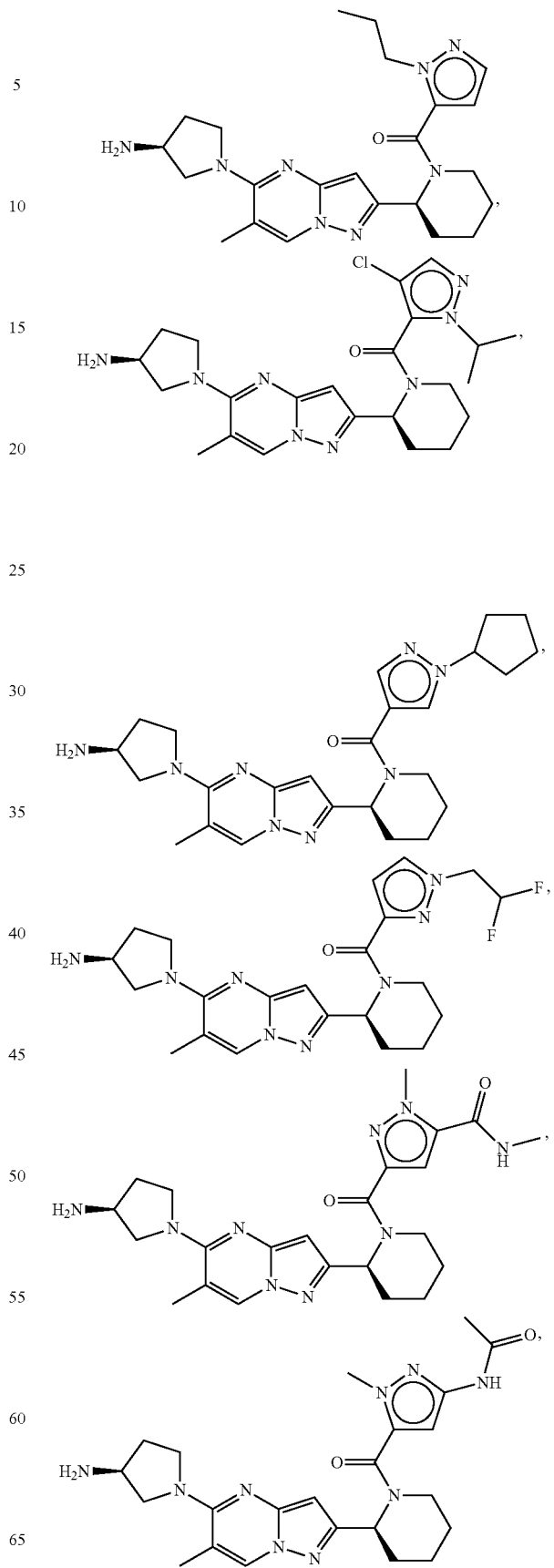

129
-continued
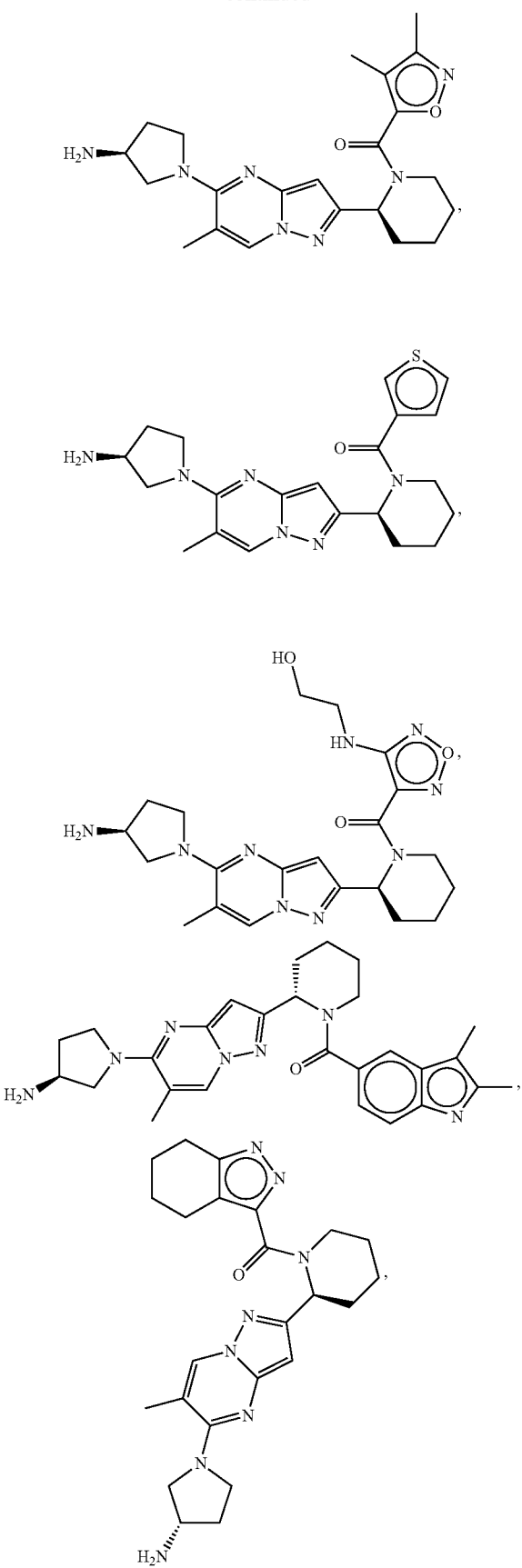
130
-continued
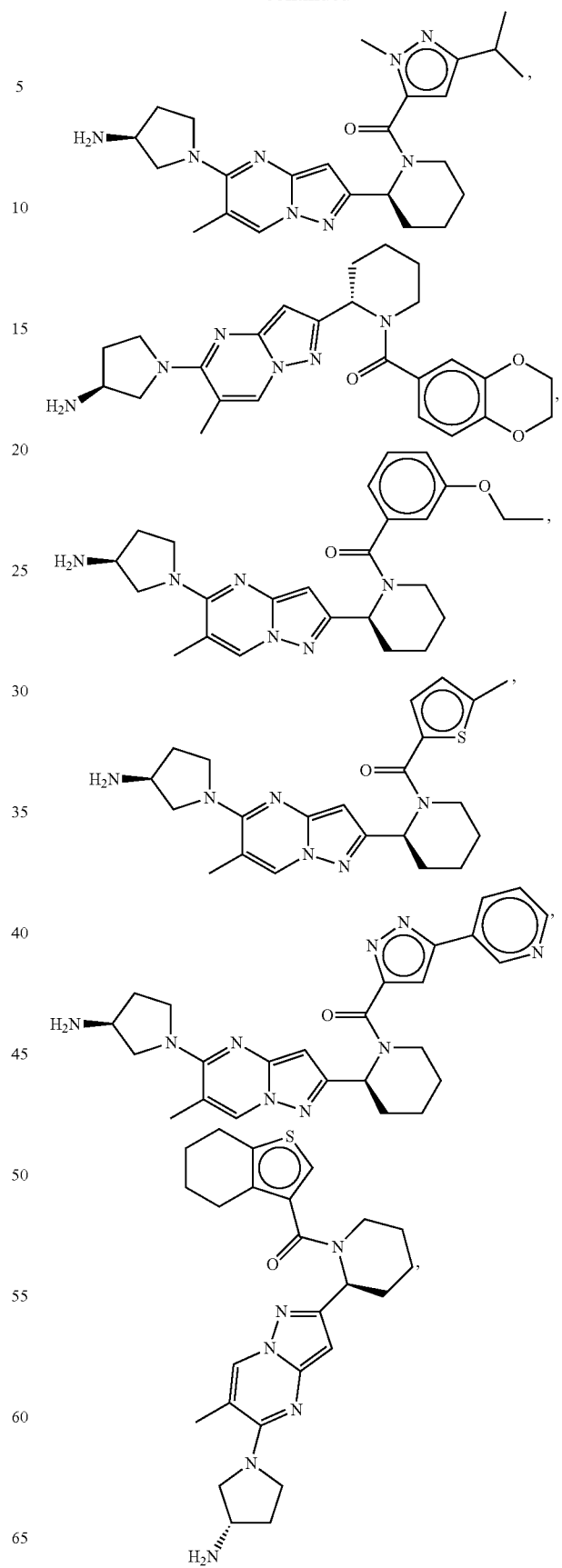

131
-continued
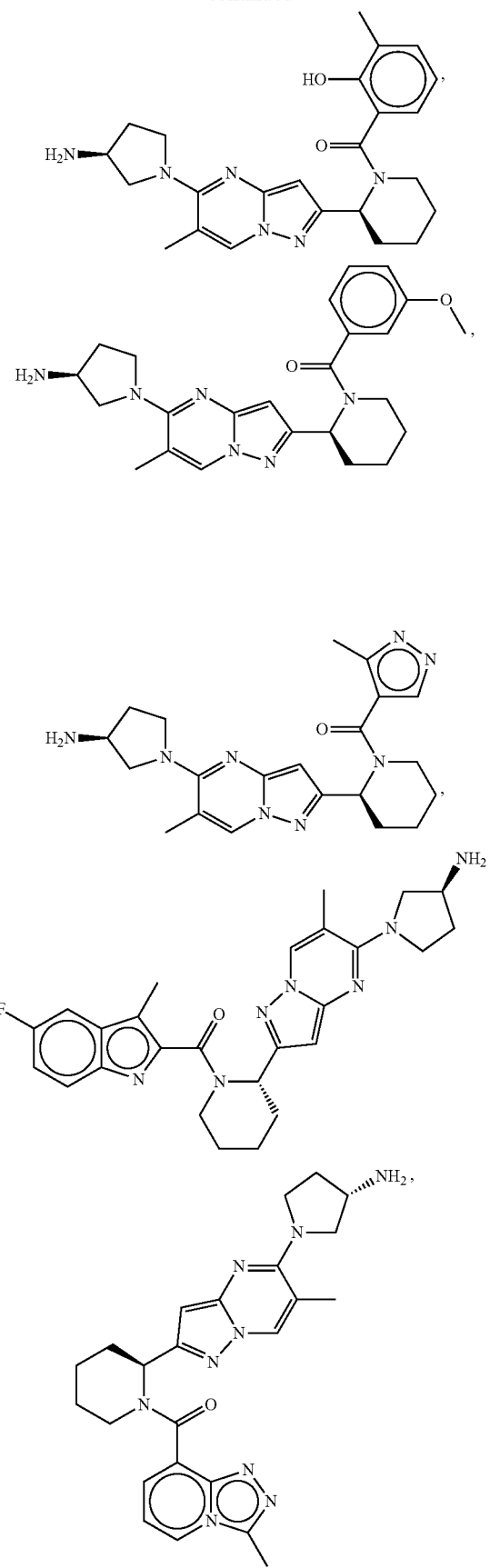
132
-continued
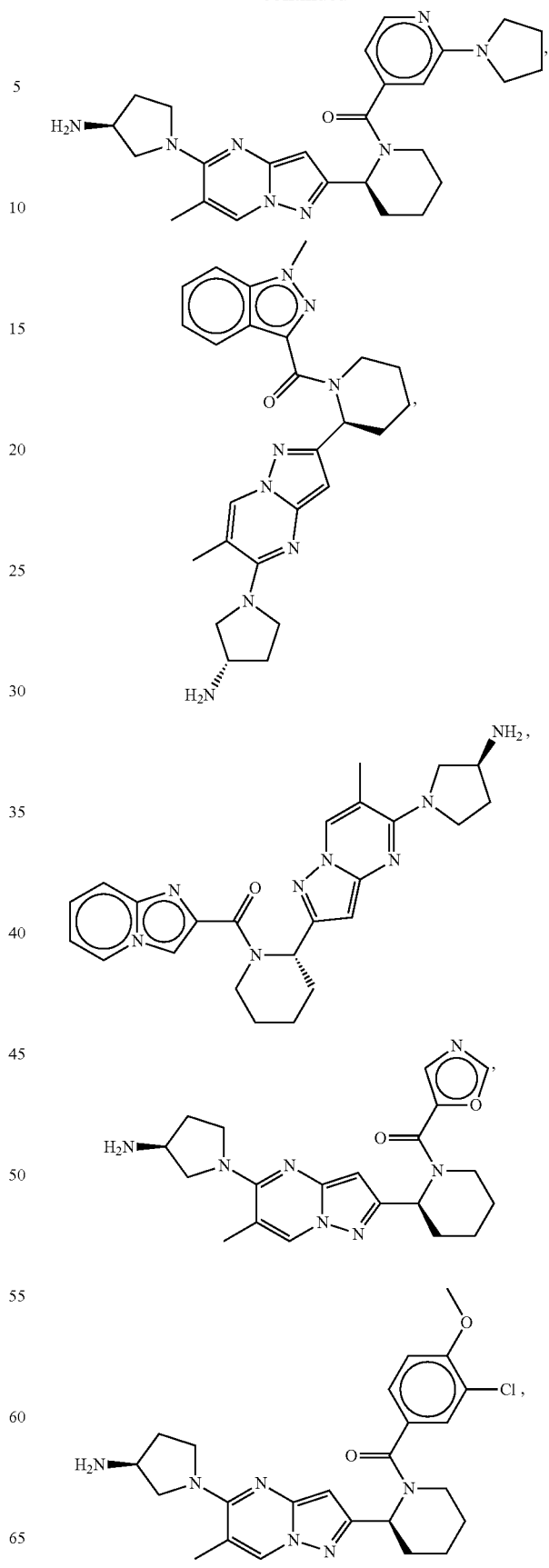

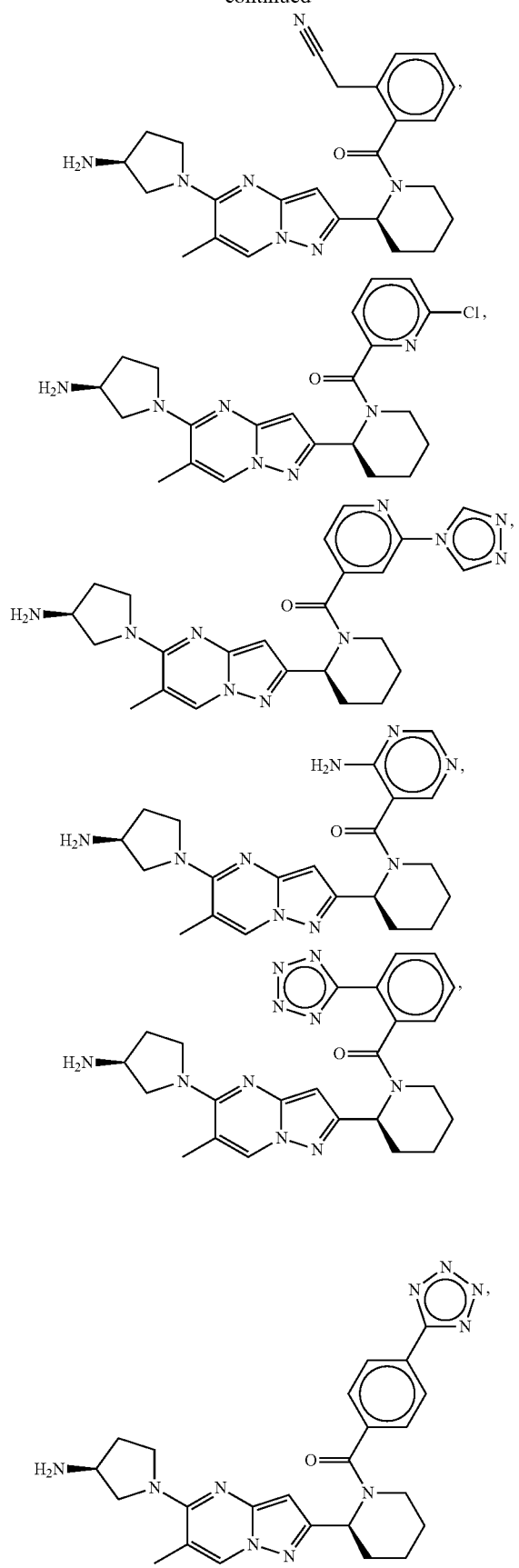
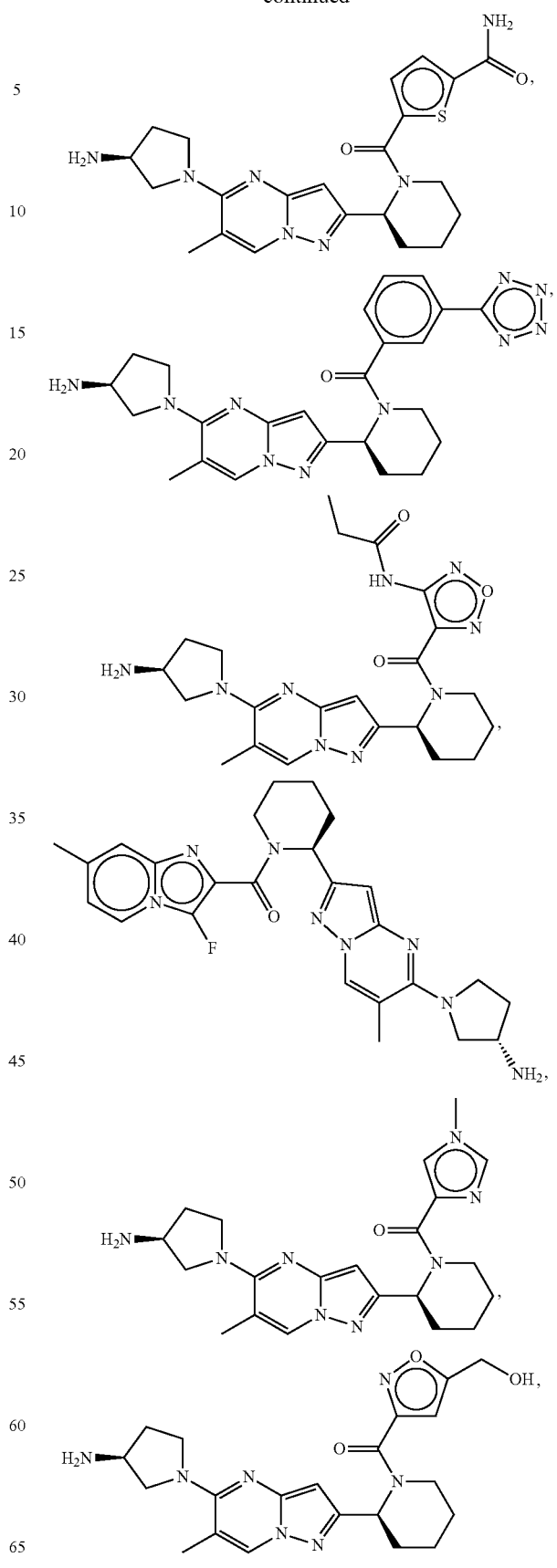

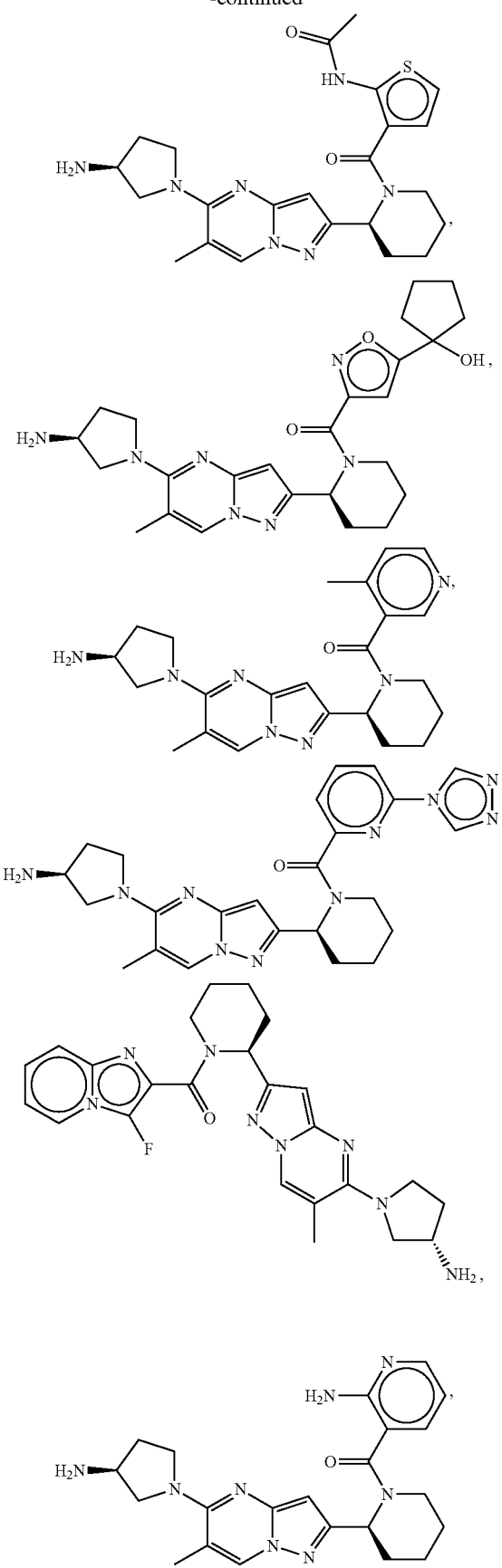
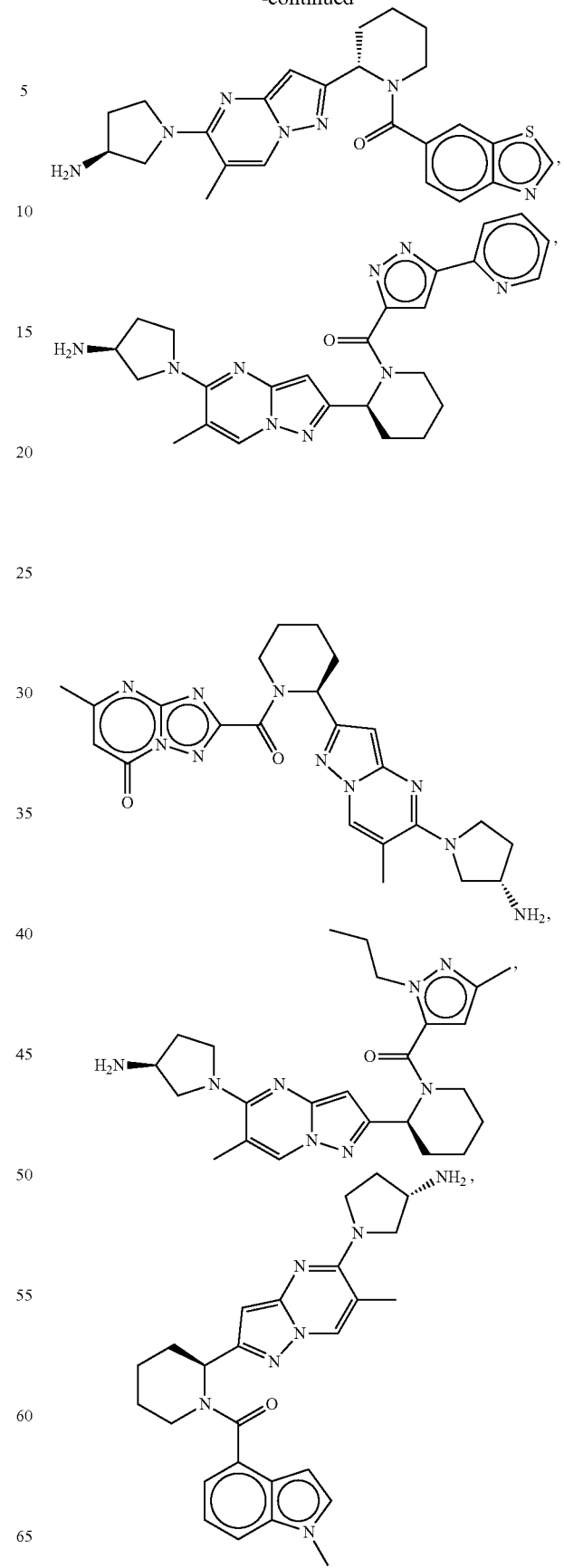

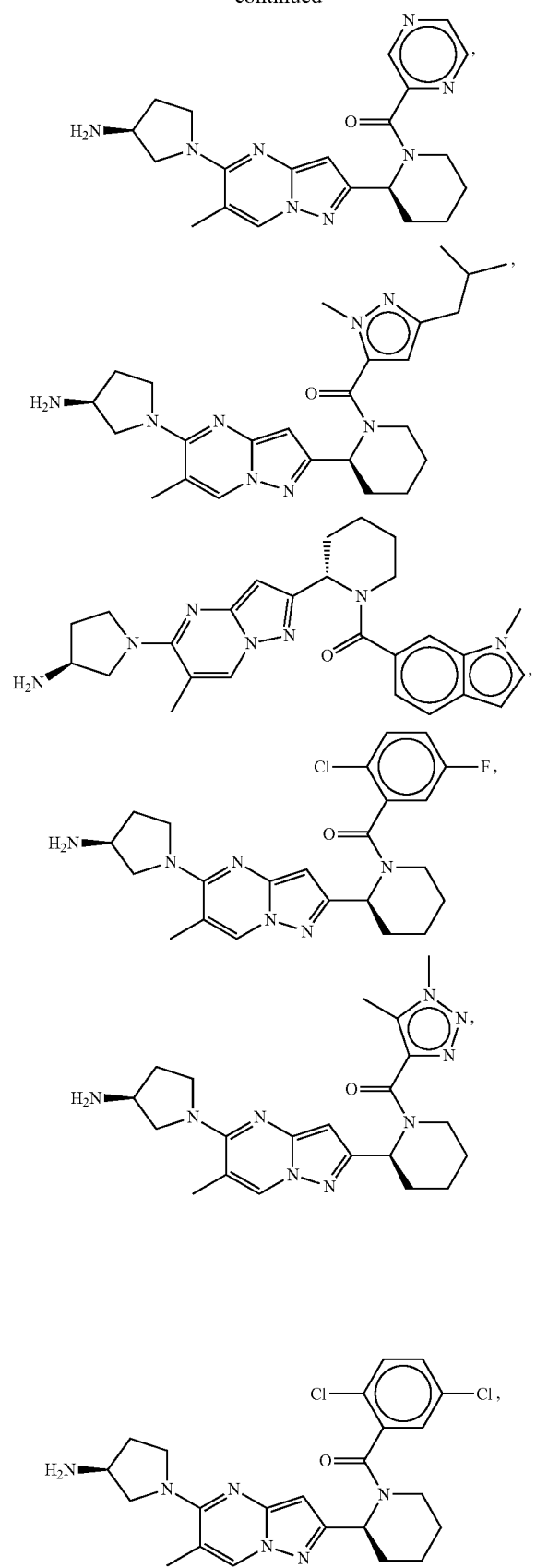
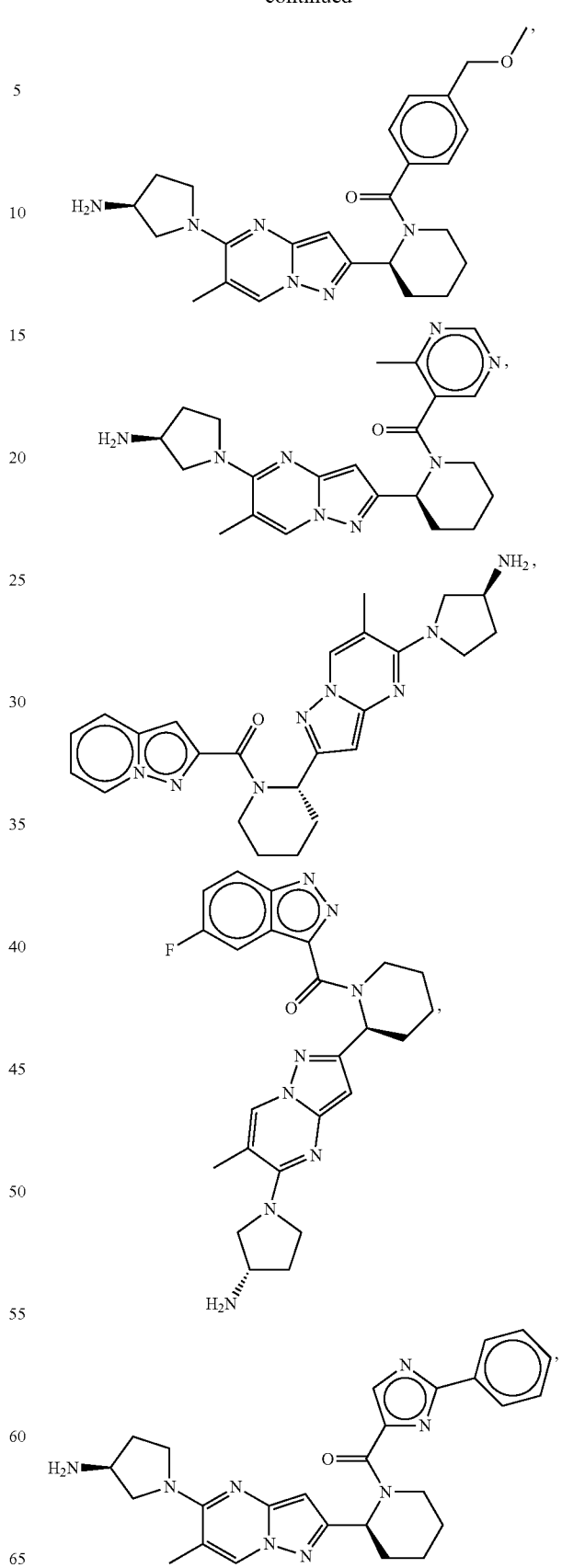

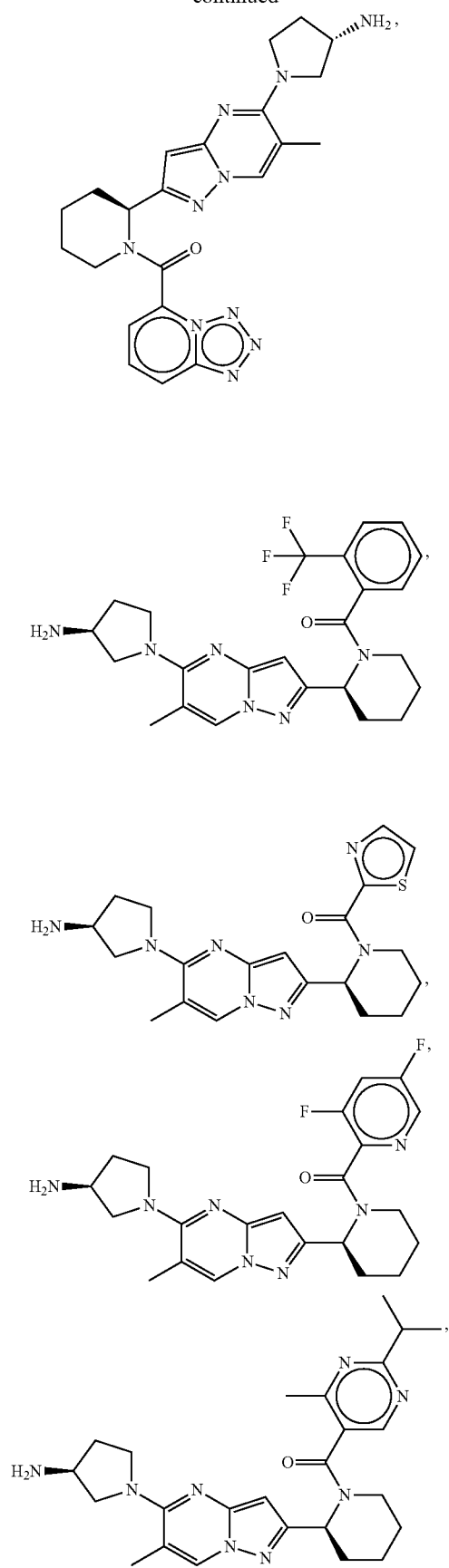
and pharmaceutically acceptable salts and esters thereof.
In another embodiment, the compounds of Formula I-IX are selected from the group consisting of:

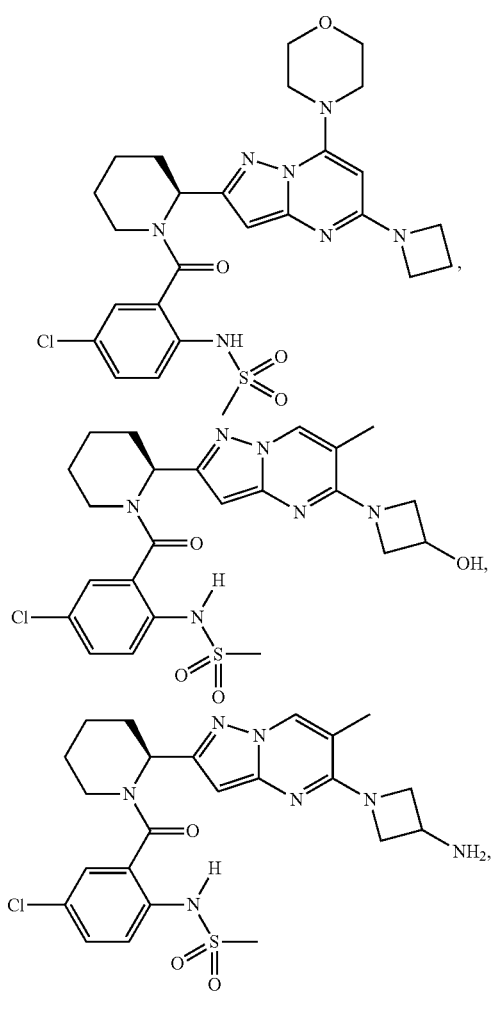
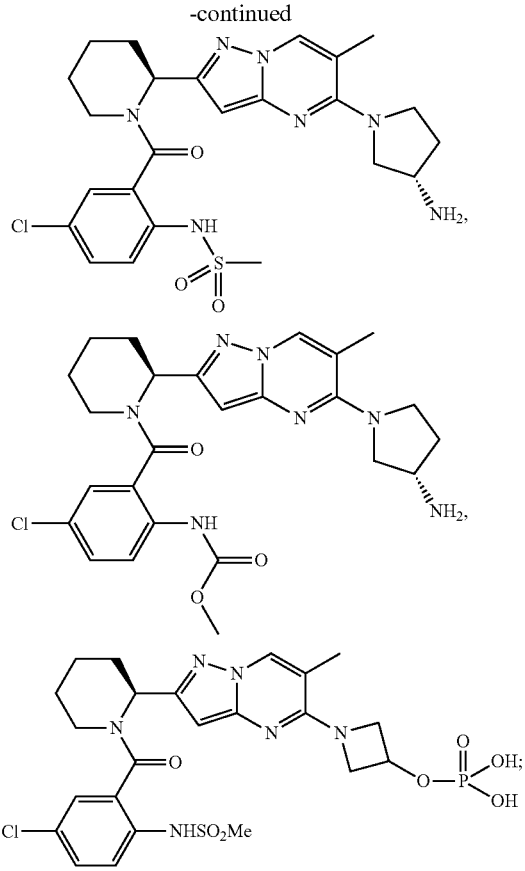
and pharmaceutically acceptable salts and esters thereof.
In another embodiment, the compounds of Formula I-IX are selected from the group consisting of:
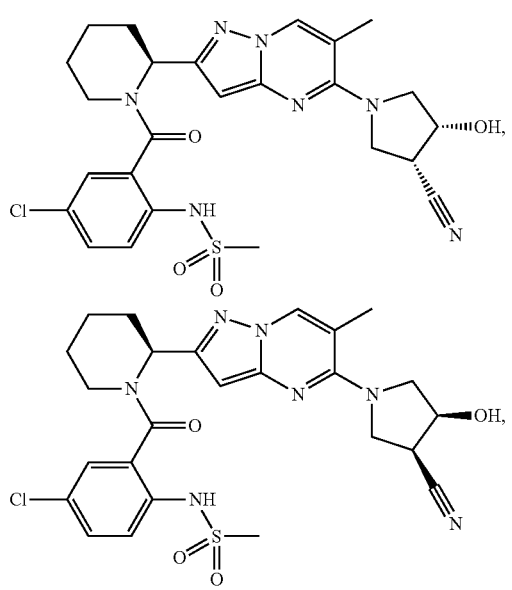
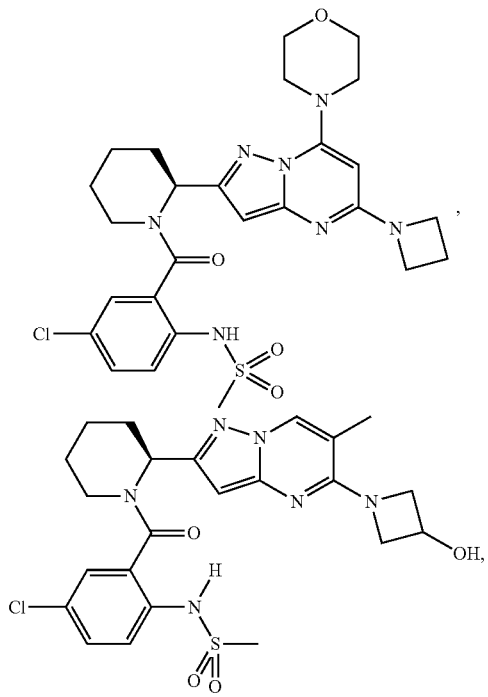

-continued
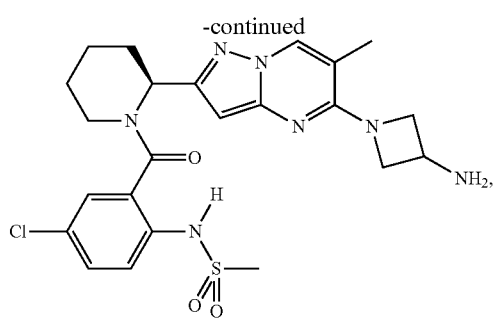
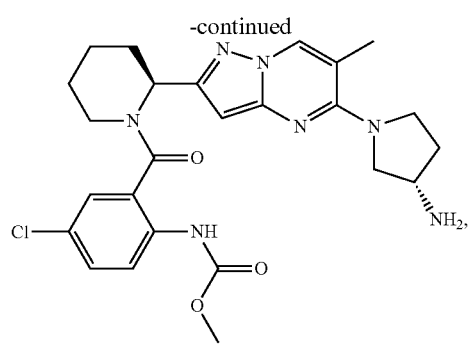
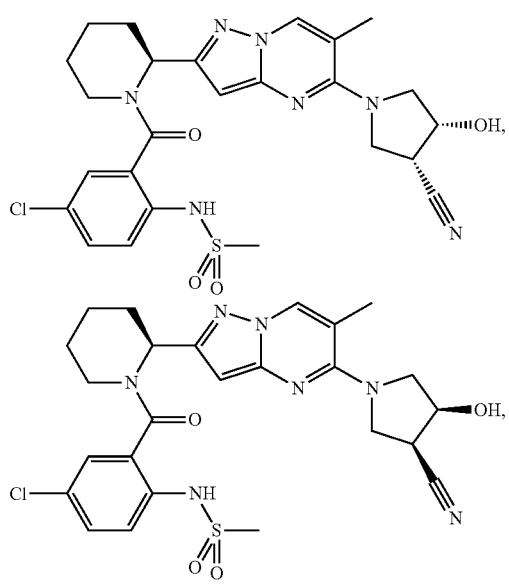
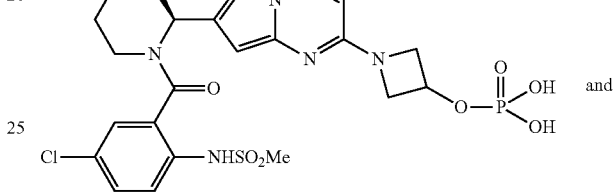
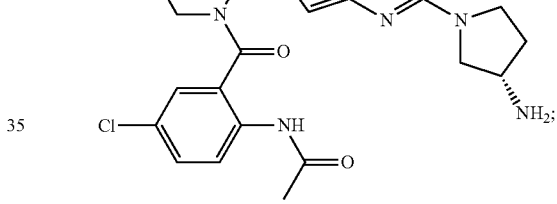
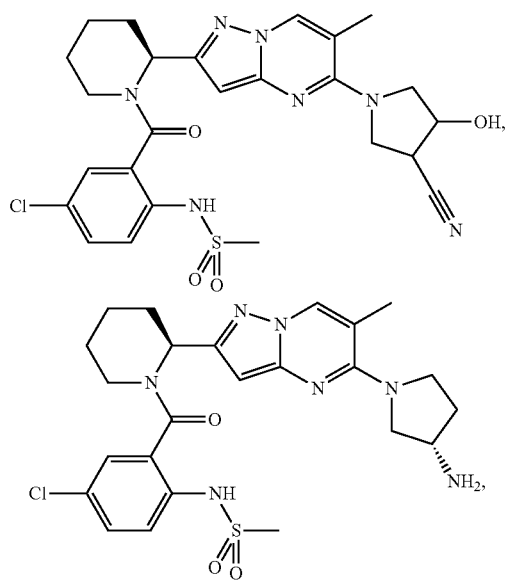
and pharmaceutically acceptable salts and esters thereof.
In another embodiment the compounds of Formula I-IX are selected from the compounds described in any one of Examples 258-412, and salts thereof.
In another embodiment, the compounds of Formula I-IX are selected from the group consisting of:
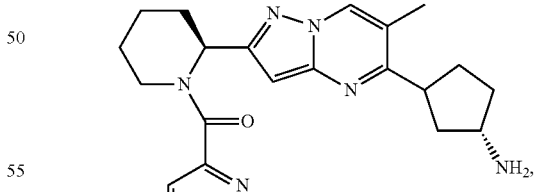
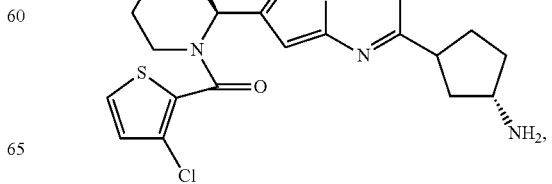

145
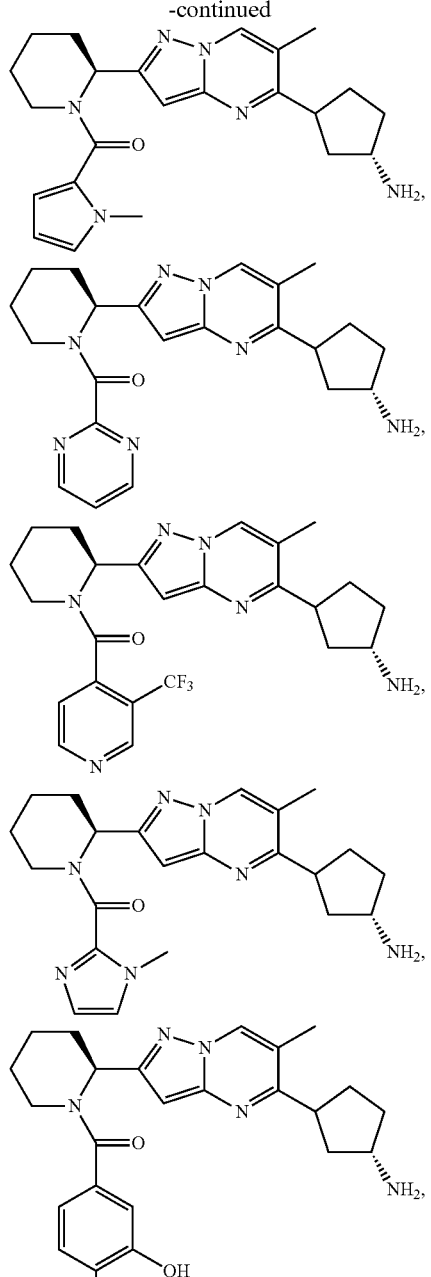
146
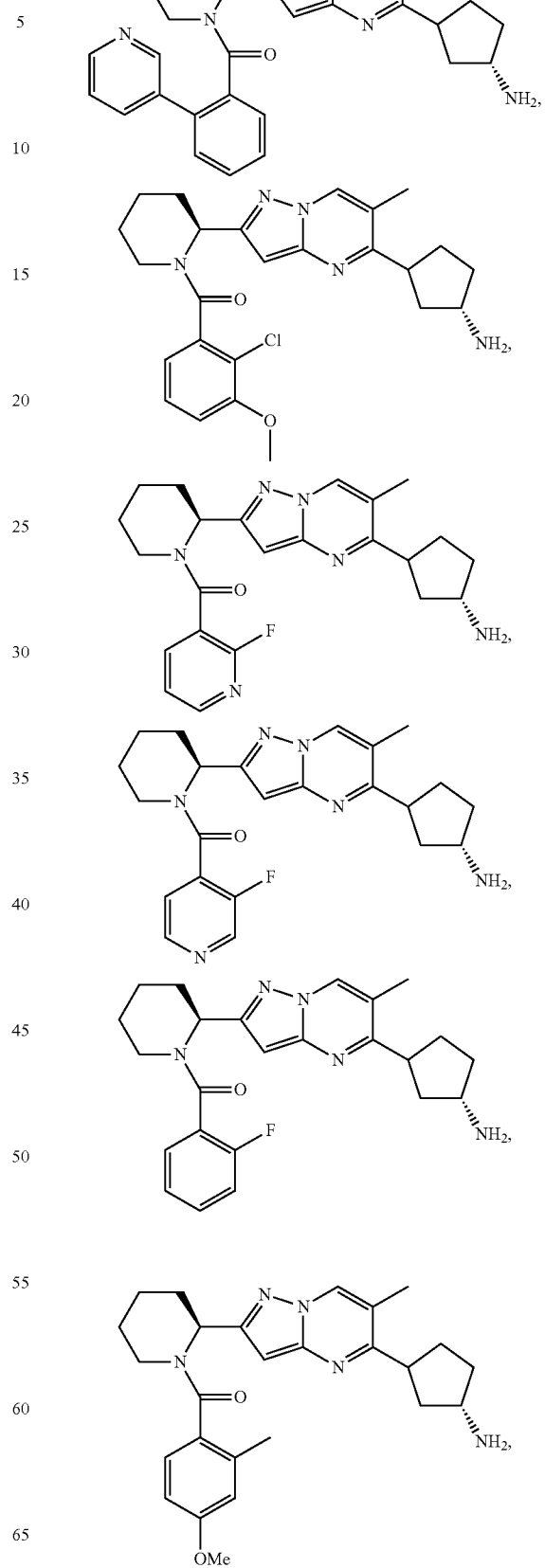

-continued

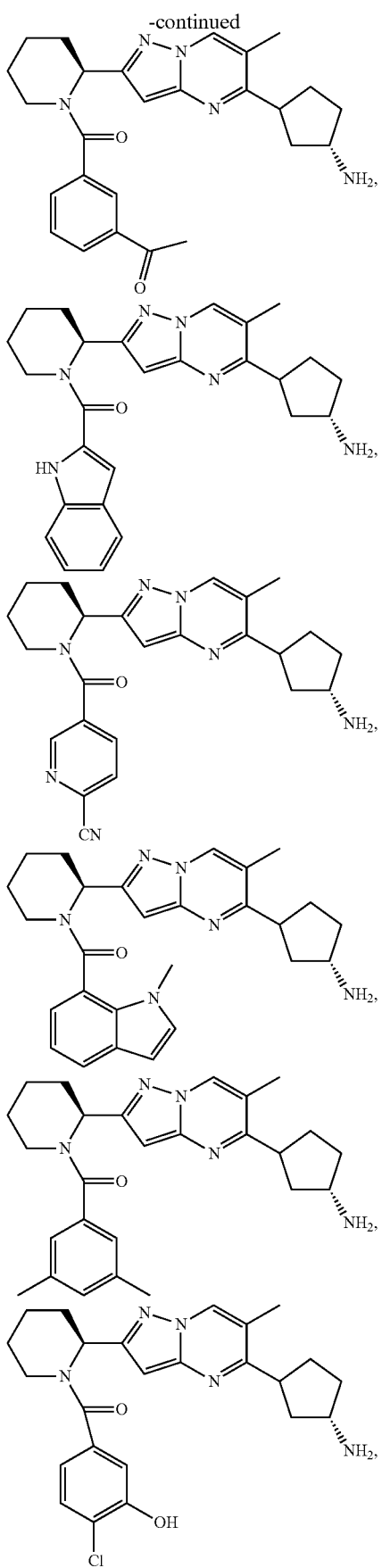

-continued

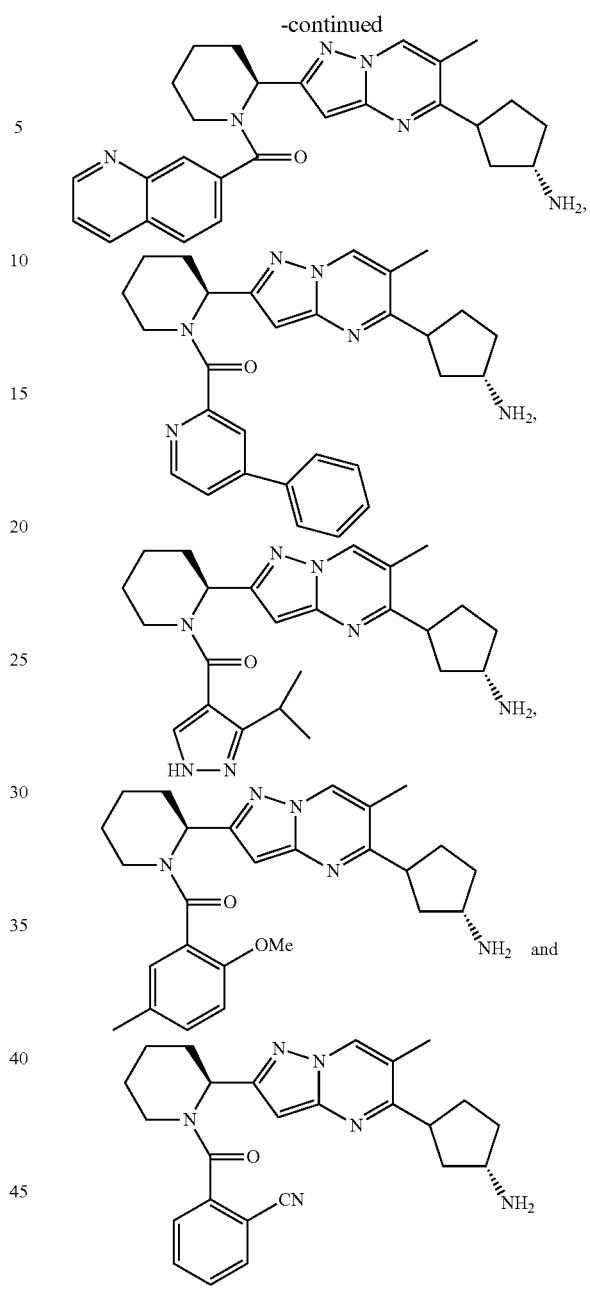

and pharmaceutically acceptable salts and esters thereof.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Amino" refers generally to a nitrogen radical which can be considered a derivative of ammonia, having the formula —$N(X)_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —$N(alkyl)_2$, —NH(alkyl), —$N(carbocyclyl)_2$, —NH(carbocyclyl), —$N(heterocyclyl)_2$, —NH(heterocyclyl), —$N(aryl)_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —$NH_2$, —$NH(CH_3)$, —$N(CH_3)_2$, —$NH(CH_2CH_3)$, —$N(CH_2CH_3)_2$, —NH(phenyl), —$N(phenyl)_2$, —NH(benzyl), —$N(benzyl)_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —$N(alkylene-C(O)—OH)_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or $sp^3$ carbon atom, but also an $sp^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl, respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b{}_2$, —N$^+$R$^b{}_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b{}_2$, —S(=O)$_2$—, —S(=O)$_2$OH, —S(=O)$_2$R$^b$, —OS(=O)$_2$OR$^b$, —S(=O)$_2$NR$^b{}_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b{}_2$, —C(S)NR$^b{}_2$, —C(=NR$^b$)NR$^b{}_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IX should be selected in order to provide a compound which is sufficiently stable to provide a pharmaceutically useful compound which can be formulated into an acceptably stable pharmaceutical composition. Compounds of Formula I-VI which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

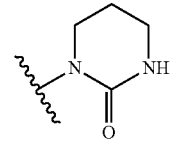 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

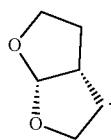

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclypethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 7 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or Spiro. Non-limiting examples of monocyclic carbocycles include cyclopropyl, cyclobutyl, cyclopentyl, 1-cyclopent-1-enyl, 1-cyclopent-2- enyl, 1-cyclopent-3-enyl, cyclohexyl, 1-cyclohex-1-enyl, 1-cyclohex-2-enyl, 1-cyclohex-3-enyl, bicyclo[3.1.0]hex-6-yl and the like.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I-IX (e.g., an optionally substituted aryl group) refers to a moiety wherein all substitutents are hydrogen or wherein one or more of the hydrogens of the moiety may be replaced by substituents such as those listed under the definition of "substituted" or as otherwise indicated.

The term "optionally replaced" in reference to a particular moiety of the compound of Formula I-IX (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

Selected substituents comprising the compounds of Formula I-IX may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

Unless otherwise specified, the carbon atoms of the compounds of Formula I-IX are intended to have a valence of four. In some chemical structure representations where carbon atoms do not have a sufficient number of variables attached to produce a valence of four, the remaining carbon substituents needed to provide a valence of four should be assumed to be hydrogen. For example,

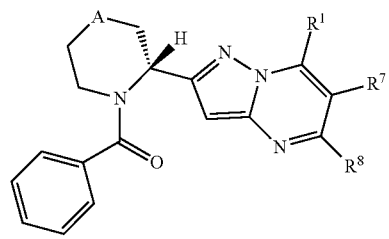

has the same meaning as

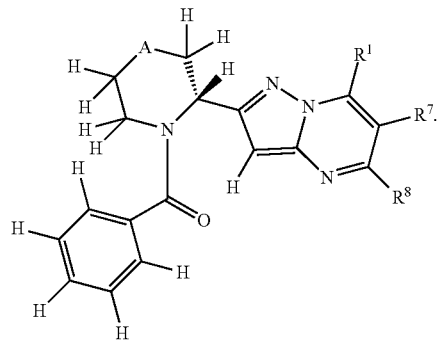

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with, for example any phosphate or phosphonate prodrug compounds of the invention, include but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

It is to be noted that all enantiomers, diastereomers, and racemic mixtures, tautomers, atropisomers, polymorphs, pseudopolymorphs of compounds within the scope of Formula I-IX and pharmaceutically acceptable salts thereof are embraced by the present invention. All mixtures of such enantiomers and diastereomers are within the scope of the present invention.

A compound of Formula I-IX and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-IX and their pharmaceutically acceptable salts.

A compound of Formula I-IX and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IX and their pharmaceutically acceptable salts.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I-IX present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I-IX, the specific activity of the composition, the delivery device employed, the physical characteristics of the composition, its intended use, as well as patient considerations such as severity of the disease state, patient cooperation, etc., and can readily be determined by one skilled in the art and in reference to the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

It is to be understood that the compositions herein comprise compounds of the invention in their un-ionized, as well as zwitterionic form, and combinations with stoichiometric amounts of water as in hydrates.

The compounds of the invention, exemplified by Formula I-IX may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another. Non-limiting examples of enantiomers of the instant invention are represented in Formula I-VI shown below wherein one position of chirality is marked with an asterisk.

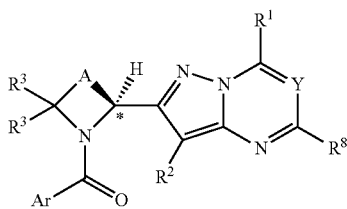

Formula I

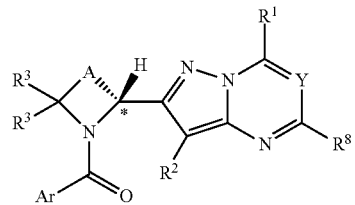

Formula II

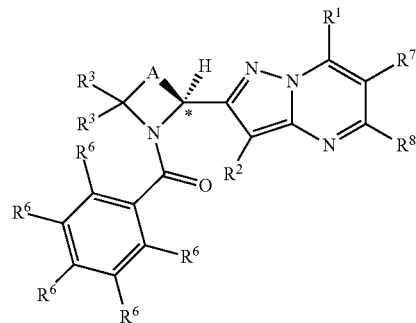

Formula III

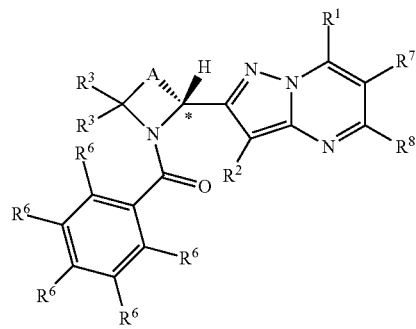

Formula IV

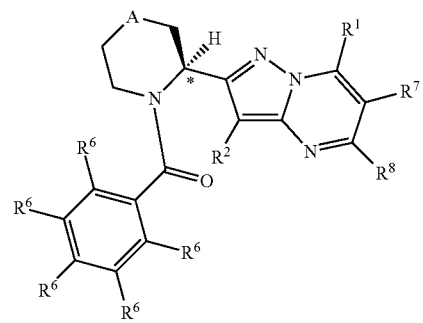

Formula V

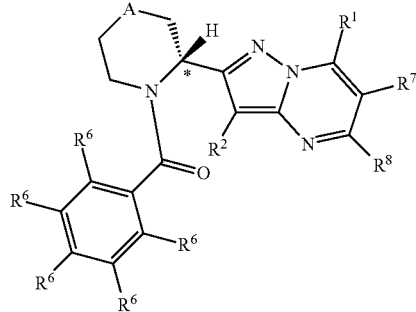

Formula VI

161
-continued

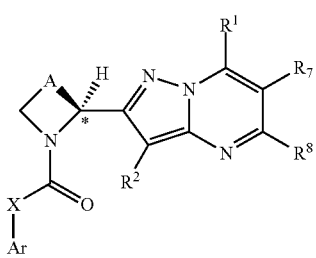
Formula VII

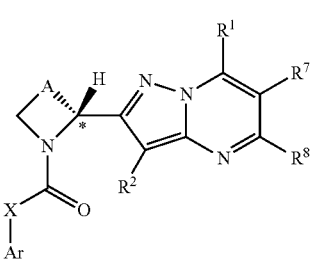
Formula VIII

The chirality at the asterisk position is a feature of the invention of Formulas I-VIII. In one embodiment, the compounds of the invention of Formula I-VIII are at least 60% a single enantiomer at the asterisk position. Preferably, the compounds of the invention of Formulas I-VIII are at least 70% a single enantiomer at the asterisk position, more preferably at least 80% a single enantiomer, more preferably at least 90% a single enantiomer and most preferably at least 95% a single enantiomer. In one embodiment the preferred stereochemistry at the carbon marked with an asterisk as shown above for Formula I-VIII is the (S) stereochemistry. In another embodiment the stereochemistry at the carbon marked with an asterisk as shown above for Formula I-VIII is the (R) stereochemistry.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of Formula I-IX also include molecules that incorporate isotopes of the atoms specified in the particular molecules. Non-limiting examples of these isotopes include D, T, $^{14}C$, $^{13}C$ and $^{15}N$.

162

Whenever a compound described herein is substituted with more than one of the same designated group, e.g., "R" or "R¹", then it will be understood that the groups may be the same or different, i.e., each group is independently selected. Wavy lines, ∼∼∼∼, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention. A non-limiting example of tautomerism in the compounds of Formula I-IX is shown below as tautomer A and tautomer B.

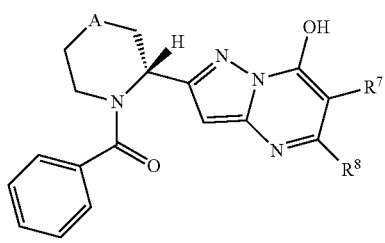
Tautomer A

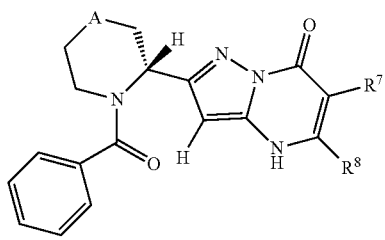
Tautomer B

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

In another aspect, the invention is a novel, efficacious, safe, nonirritating and physiologically compatible inhalable composition comprising a compound of Formula I-IX, or a pharmaceutically acceptable salt thereof, suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 µm. Preferably, the compound of Formula I-IX is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 µm and about 5 µm using a nebulizer able to aerosolize the formulation of the compound of Formula I-IX into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method of the invention, the aerosol formulation for nebulization delivers a therapeutically efficacious dose of the compound of Formula I-IX to the site of Pneumovirinae infection sufficient to treat the Pneumovirinae infection. The amount of drug administered must be adjusted to reflect the efficiency of the delivery of a therapeutically efficacious dose of the compound of Formula I-IX. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formula I-IX into the airways. In a preferred embodiment, at least about 30 to about 50% of the active compound is delivered. More preferably, about 70 to about 90% of the active compound is delivered.

In another embodiment of the instant invention, a compound of Formula I-IX or a pharmaceutically acceptable salt thereof, is delivered as a dry inhalable powder. The compounds of the invention are administered endobronchially as a dry powder formulation to efficacious deliver fine particles of compound into the endobronchial space using dry powder or metered dose inhalers. For delivery by DPI, the compound of Formula I-IX is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound of Formula I-IX before processing into particles of the required sizes. In another embodiment, excipients are blended with the particles of the required size to aid in dispersion of the drug particles, for example by using lactose as an excipient.

Particle size determinations are made using devices well known in the art. For example a a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula I-IX is delivered as a dry powder using a device such as a dry powder inhaler or other dry powder dispersion devices. Non-limiting examples of dry powder inhalers and devices include those disclosed in U.S. Pat. No. 5,458,135; U.S. Pat. No. 5,740,794; U.S. Pat. No. 5,775,320; U.S. Pat. No. 5,785,049; U.S. Pat. No. 3,906,950; U.S. Pat. No. 4,013,075; U.S. Pat. No. 4,069,819; U.S. Pat. No. 4,995,385; U.S. Pat. No. 5,522,385; U.S. Pat. No. 4,668,218; U.S. Pat. No. 4,667,668; U.S. Pat. No. 4,805,811 and U.S. Pat. No. 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm, and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula I-IX, or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another preferred embodiment, a compound of Formula I-IX is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234. In preferred embodiments, a compound of Formula I-IX, or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof.

Many of the infections of the Pneumovirinae viruses are respiratory infections. Therefore, additional active therapeutics used to treat respiratory symptoms and sequelae of infection may be used in combination with the compounds of Formula I-IX. The additional agents are preferably administered orally or by direct inhalation. For example, other preferred additional therapeutic agents in combination with the compounds of Formula I-IX for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formula I-IX are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflamatory agents working through anti-inflamatory cascade mechanisms are also useful as additional therapeutic agents in combination with the compounds of Formula I-IX for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethyl-amino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formula I-IX are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formula I-IX are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formula I-IX for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-dithiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formula I-IX may also be combined with mucolytic agents to treat both the infection and symptoms of respiratory infections. A non-limiting example of a mucolytic agent is ambroxol. Similarly, the compounds of Formula I-IX may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). The compounds of Formula I-IX may also be combined with nebulized hypertonic saline particularly when the Pneumovirinae virus infection is complicated with bronchiolitis. The combination of the compounds of Formula I-IX with hypertonic saline may also comprise any of the additional agents discussed above. In a preferred aspect, nebulized about 3% hypertonic saline is used.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of treating Pneumovirinae virus infection in a patient, comprising: administering to the patient a therapeutically effective amount of a compound of Formula I-IX, or a pharmaceutically acceptable salt, solvate, and/or ester thereof.

In still yet another embodiment, the present application provides for methods of treating Pneumovirinae virus infection in a patient, comprising: administering to the patient a therapeutically effective amount of a compound of Formula I-IX, or a pharmaceutically acceptable salt, solvate, and/or ester thereof, and at least one additional active therapeutic agent.

In still yet another embodiment, the present application provides for methods of treating Human respiratory syncytial virus infection in a patient, comprising: administering to the patient a therapeutically effective amount of a compound of Formula I-IX, or a pharmaceutically acceptable salt, solvate, and/or ester thereof, and at least one additional active therapeutic agent.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver, lung or other metabolic organ, or within cells in general.

Tissue Distribution

It has also been discovered that certain compounds of the invention show high lung to plasma ratios which may be beneficial for therapy. One particular group of compounds of the invention that demonstrate this property are compounds that include an amine functional group.

General schemes 1-4 describe methods that were used to prepare compounds of the invention. The general methods described in these schemes can also be used to prepare additional compounds of the invention.

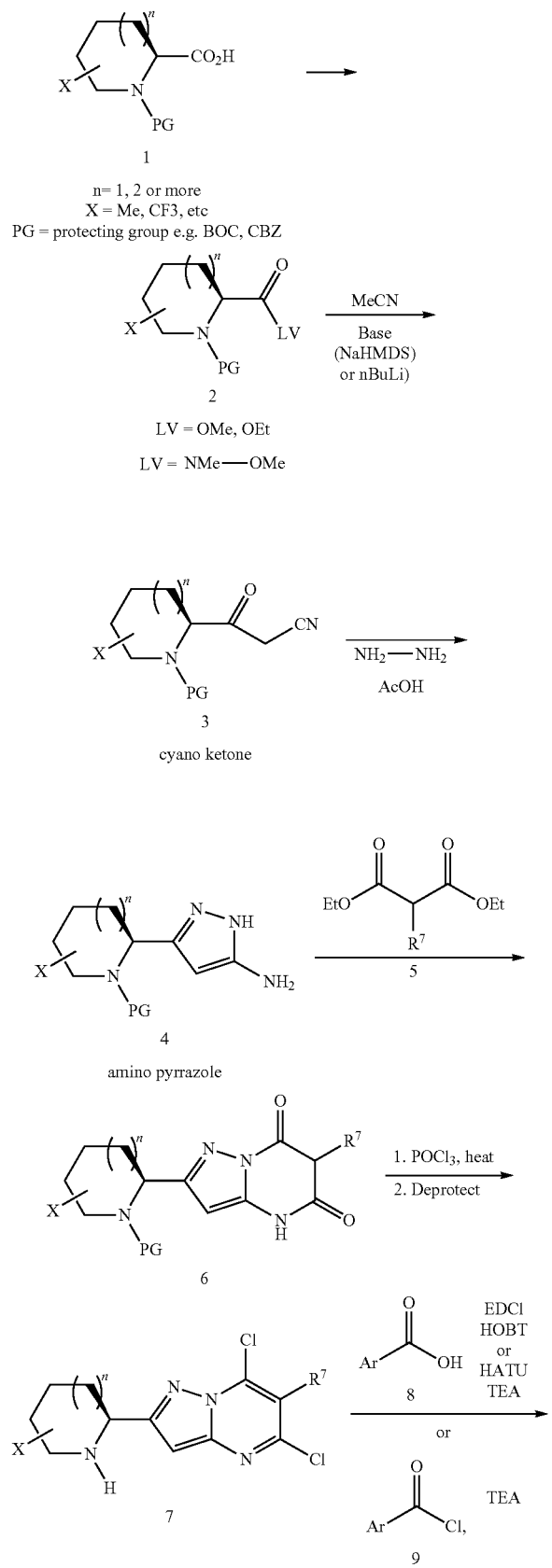

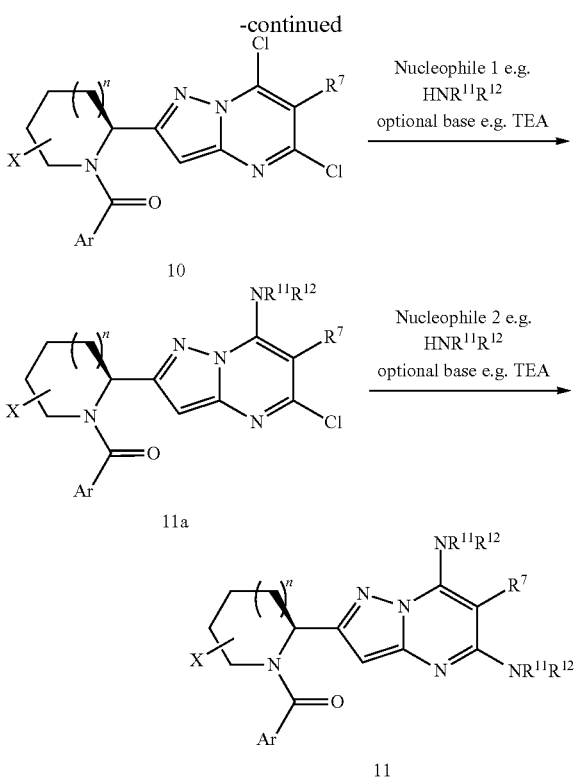

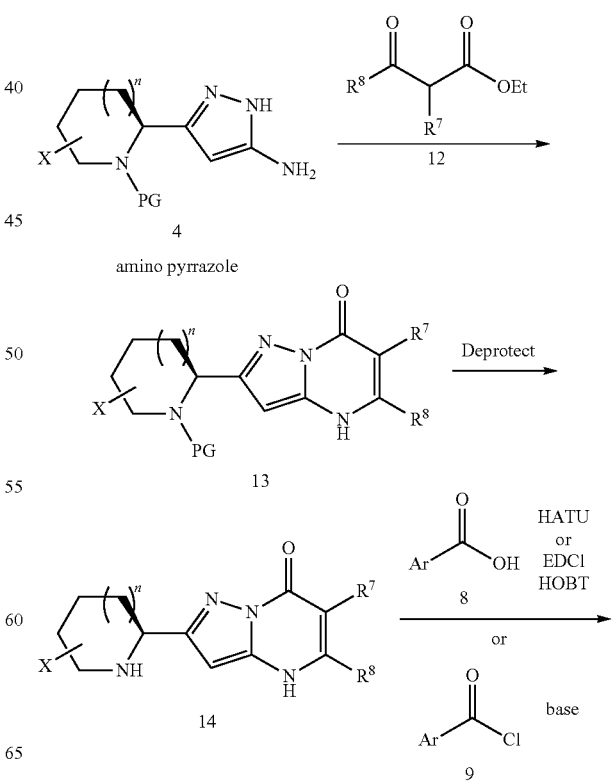

The general scheme shown describes the methods under which the claimed compounds can be prepared. The starting material is a protected (PG) cycloaminoalkyl ring that can be 6-, 7- or larger size ring and also contain substituents around the ring. For example piperidine or azepane rings. Importantly, there is a carboxyl group on the carbon atom adjacent to the ring nitrogen that preferably has the (S) stereochemistry e.g. (S)-piperidine-2-carboxylic acid. Protecting groups on the cycloaminoalkyl ring nitrogen are preferably BOC or CBZ and can be introduced or removed during the synthesis using methods described in; Green and Wutts, Protecting groups in Organic Synthesis 3$^{rd}$ Edition. In the forward scheme, the carboxylic acid group on the N-protected cyclicaminoheterocycle 1 is first activated with a leaving group (e.g. 2). Typical leaving groups are alkyl ester (e.g. methyl or ethyl ester) and these are generated by treatment of the carboxylic acid with the appropriate alcohol under non- or low-aqueous acidic conditions (e.g. methanol and concentrated sulfuric acid) or by treatment with methyl iodide in the presence of a base e.g. Cesium carbonate. Alternatively the acid can be activated as the Weinreb amide using standard peptide coupling procedures e.g. EDCI/HOBT, HATU, DCC, etc. Once the acid is activated as the ester or Weinreb amide, the addition of an acetonitrile anion is performed. The anion is generated from acetonitrile and a strong base e.g. sodium hexamethyl disilazide (NaHMDS) or alkyl lithium bases e.g. nBuLi, and when reacted with the ester or Weinreb amide generates the cyano ketone 3. Reaction of the cyano ketone with hydrazine acetate salt then generates the aminopyrrazole intermediate 4. This is a key intermediate in the formation of the bicyclic heterocycles 6 with different sidechains through different condensation reactions. In General Scheme 1 the condensation with a malonate 5 is described, the other general schemes 2-6 highlight other condensation reactions that generate alternative substitutions. Condensation of amino pyrrazole 4 with malonate 5 generates the bicyclic analog 6. Treatment of 6 with neat POCl$_3$ under elevated temperature (in some cases hindered bases like lutidine can improve the reaction) then affords the dichloride 7. Under the POCl$_3$ conditions acidic labile protecting groups e.g. BOC are typically removed but if this is partial further treatment with acid e.g. 4N HCl in dioxane can be used to remove remaining BOC protected material. If other protecting groups are utilized then procedures described in Green and Wutts, Protecting groups in Organic Synthesis 3$^{rd}$ Edition can be used to remove the protecting group. The unprotected NH in the cycloaminoalkyl ring on 7 is acylated to provide 10 using standard standard procedures of either peptide coupling of acids (8) using HATU/triethylamine or generation of the acid chloride (9) using thionyl or oxalyl chloride and then addition to compound 7 in the presence of a base e.g. triethylamine or diisopropylamine. Displacement of the chloride adjacent to the bridgehead nitrogen on 10 can be effected with nucleophiles, typically at room temperature to provide 11a. A typical nucleophile would be an amine that can be reacted in the absence or presence of a base such as triethylamine. The second and less reactive chloride is then displaced typically at elevated temperatures above 50° C. The result of these nucleophilic amine displacements are compounds of structure 11.

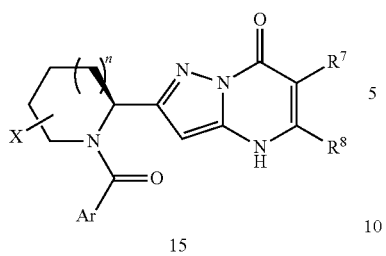

An alternative condensation of the aminopyrrazole using beta-keto esters 12 (e.g. 2-methylaceto acetate) in the presence of acid (acetic acid) at elevated temperature leads to the pyrrazo-pyrimidinone scaffold 13. Deprotection of the protecting group using conditions as described in Green and Wutts, Protecting groups in Organic Synthesis 3$^{rd}$ Edition then allows the free amine 14 to be acylated by a variety of acids 8 or acid chlorides 9 as described in general scheme 1 to produces the final compounds (structure 15).

A further alternative cyclization on amino pyrrazole 4 involves treatment with an acrylate e.g. 16 in the presence of base e.g. cesium carbonate, and heat to generate 17. Further treatment of 17 to active that OH as a leaving group can include conversion to chloride 18 using POCl$_3$ and heat. Acidic protecting groups e.g. BOC can be removed under the POCl$_3$ conditions, or if not, following procedures outlined in Green and Wutts, Protecting groups in Organic Synthesis 3$^{rd}$ Edition, any protecting groups can be removed. The free NH compound 18 is then acylated as previously described in General scheme 1 to give 19. Finally the chloride can be displaced by nucleophiles to generate the compounds (e.g. 20) as described in General Scheme 1.

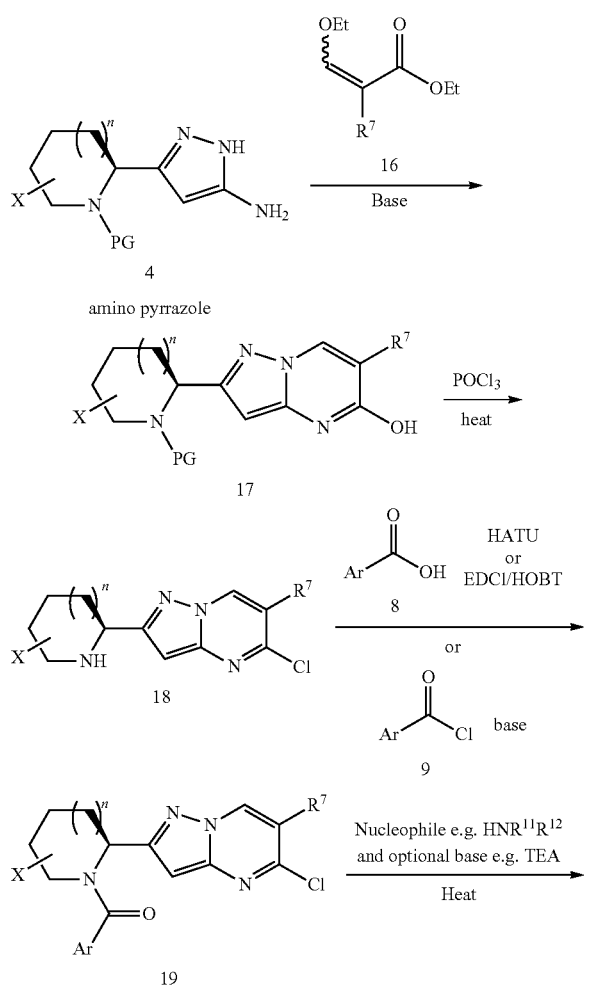

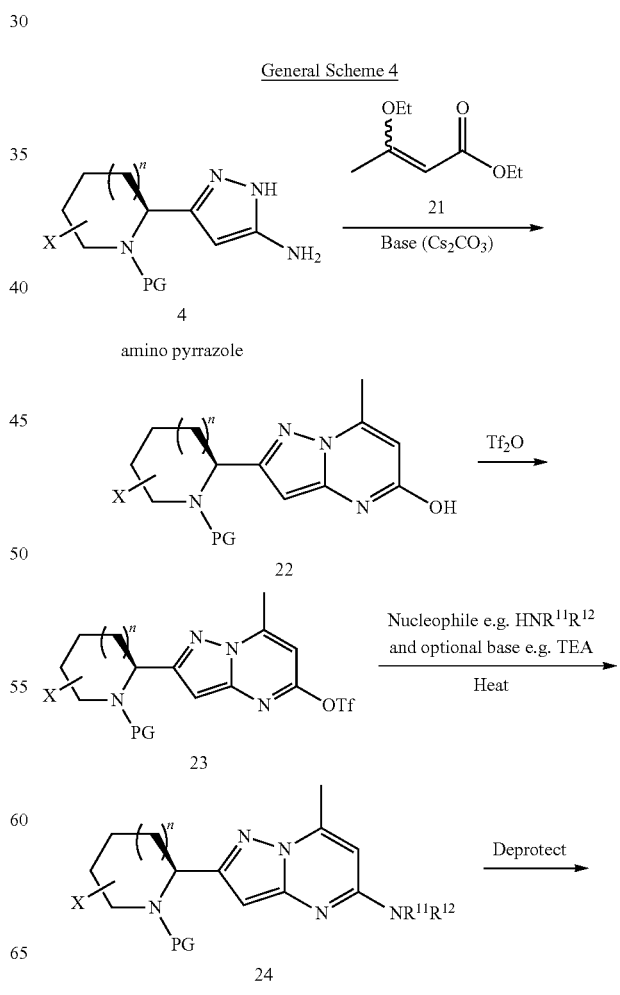

179
-continued

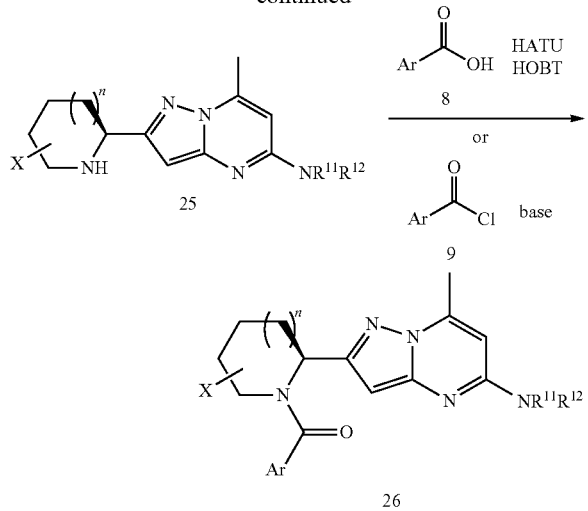

A further alternative cyclization on amino pyrrazole 4 involves treatment with an acrylate e.g. 16 in the presence of base e.g. cesium carbonate and heat to generate 22. Further treatment of 22 to active that OH as a leaving group can include conversion to chloride 18 using $POCl_3$ and heat; or an alternative leaving groups can be the triflate 23, generated by treatment with triflic anhydride in the presence of base. Triflate 23 is then reacted with the nucleophile to generate the product 24. The protecting group is then removed following procedures outlined in Green and Wutts, Protecting groups in Organic Synthesis $3^{rd}$ Edition to provide 25. The free NH compound 25 is then acylated as previously described in general scheme 1 to give 26.

In all the schemes cited the nucleophilic displacement of the reactive chloride or triflate on the bicyclic ring can be performed with alternative reagents to amines, to generate products that are not nitrogen linked. For example treatment of the chloride with KCN and base introduces cyano group. Carbon nucleophiles can be introduced using cross coupling reactions e.g. Stille reaction of alkyl stannanes in the presence of palladium catalysts at elevated temperatures. Aryl and heteroaryl boronic acids can be introduced in Suzuki couplings with Pd(PPh3)4 to introduce an aryl or heteroaryl rings. Grignard additions to the chloride in the presence of Fe(AcAc)3 can introduce small alkyl groups and alkyl rings e.g. cyclobutane onto the bicyclic scaffold.

The $HNR^{11}R^{12}$ moieties of the schemes can also be a $C_2$-$C_{20}$ heterocyclyl with a reactive nucleophile in the heterocyclyl (e.g. a nitrogen). Thus, the resulting compounds can have a $C_2$-$C_{20}$ heterocyclyl at the positions indicated by the —$NR^{11}R^{12}$ fragment.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| $Ac_2O$ | acetic anhydride |
| AIBN | 2,2'-azobis(2-methylpropionitrile) |
| Bn | benzyl |

TABLE 1-continued

List of abbreviations and acronyms.

| Abbreviation | Meaning |
| --- | --- |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

The invention will now be illustrated by the preparation of the following non-limiting compounds of the invention. It is to be understood that certain intermediates described herein may also be compounds of the invention.

Preparation of Compounds

Intermediate 1

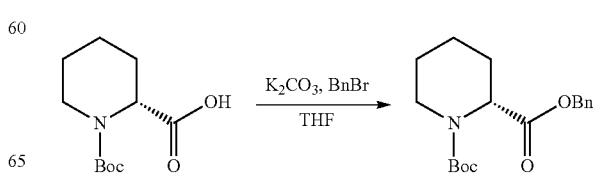

N-Boc-(R)-piperidine-2-carboxylic acid (4.5 g, 20 mmol) was dissolved in anhydrous THF (100 mL) and stirred in an ice bath. Potassium carbonate (4.1 g, 30 mmol) was added in one portion. Benzyl bromide (2.6 mL, 22 mmol) was added dropwise over 10 minutes. Cooling was removed and the reaction stirred for 16 hours. DMF (10 mL) was added and the reaction was stirred for 72 h. Diluted reaction with ethyl acetate and then washed with saturated aqueous sodium bicarbonate solution and then saturated aqueous sodium chloride solution. Dried organic extract over anhydrous sodium sulfate and then concentrated under reduced pressure to give intermediate 1 as a colorless light oil (5.9 g, 86%).

$^{1}$H NMR (CDCl$_3$, 300 MHz): δ 7.35 (m, 5H), 5.20 (m, 2H), 4.95-4.46 (m, 1H), 4.01-3.94 (m, 1H), 2.93 (m, 1H), 2.24 (m, 1H), 1.68-1.64 (m, 4H), 1.45-1.38 (m, 9H), 1.27-1.18 (m, 1H).

Intermediate 2

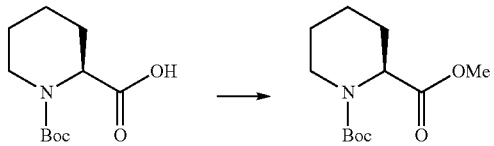 [SMILES: CC(C)(C)OC(=O)N1CCCC[C@H]1C(=O)O ; COC(=O)[C@@H]1CCCCN1C(=O)OC(C)(C)C]

N-Boc-(S)-piperidine-2-carboxylic acid (5.0 g, 22 mmol) in DMF (100 mL) was treated with Cs$_2$CO$_3$ (3.5 g, 10.9 mmol) and MeI (1.5 mL, 24 mmol). The mixture was stirred for 4 hours and diluted with MTBE (250 mL). The mixture was washed with water (2 100 mL) and saturated sodium chloride solution (1 100 mL). The solution was dried over anhydrous sodium sulfate and concentrated to afford the ester intermediate 2 (5.1 g crude, 96%) as an oil which was used without further purification $^{1}$H NMR (CDCl$_3$, 300 MHz): δ 4.80 (m, 1H), 3.97 (m, 1H), 3.73 (s, 3H), 2.93 (m, 1H), 2.18 (app d, J=13.2 Hz, 1H), 1.67 (m, 2H), 1.45 (br s, 10H), 1.20 (app t, J=13.5 Hz, 1H).

R$_f$=0.90 (30% EtOAc-hexanes);

Intermediate 3

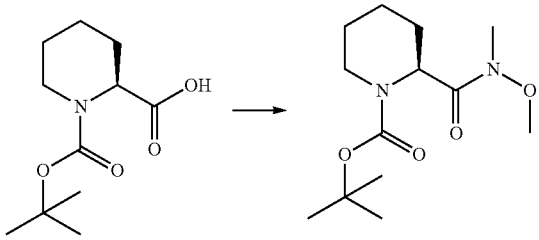 [SMILES: CC(C)(C)OC(=O)N1CCCC[C@H]1C(=O)O ; CON(C)C(=O)[C@@H]1CCCCN1C(=O)OC(C)(C)C]

(S)-1-Boc-piperidine-2-carboxylic acid (25 g, 109 mmol, Sigma-Aldrich) in DMF (500 mL) was treated sequentially with McNHOMe.HCl (11.2 g, 115 mmol), N-methylmorpholine (36 mL, 327 mmol), HOBt (16.2 g, 120 mmol), and EDCI (23 g, 120 mmol) and stirred for 18 h. The solution was diluted with EtOAc (1000 mL) and washed with H$_2$O (2 500 mL) and saturated NaCl solution (500 mL). The solution was dried over MgSO$_4$, filtered and concentrated. The residue was subjected to a 330 g SiO$_2$ Combiflash High Performance Gold column (0-100% EtOAc-hexanes gradient) to afford the Weinreb amide intermediate 3 (18.4 g, 61%) as a clear oil:

$^{1}$H NMR (CDCl$_3$, 300 MHz): δ 5.06 (br m, 1H), 3.93 (br m, 1H), 3.77 (br s, 3H), 3.18 (s, 3H), 2.01 (app d, J=13.5 Hz, 1H), 1.71 (m, 4H), 1.45 (s, 9H);

LCMS (ESI) m/z 273 [M+H]$^+$, t$_R$=2.31 min;

HPLC (RP: 6-98% MeCN—H$_2$O gradient, 0.05% TFA modifier) t$_R$=4.423 min.

R$_f$=0.60 (50% EtOAc-hexanes);

Intermediate 4

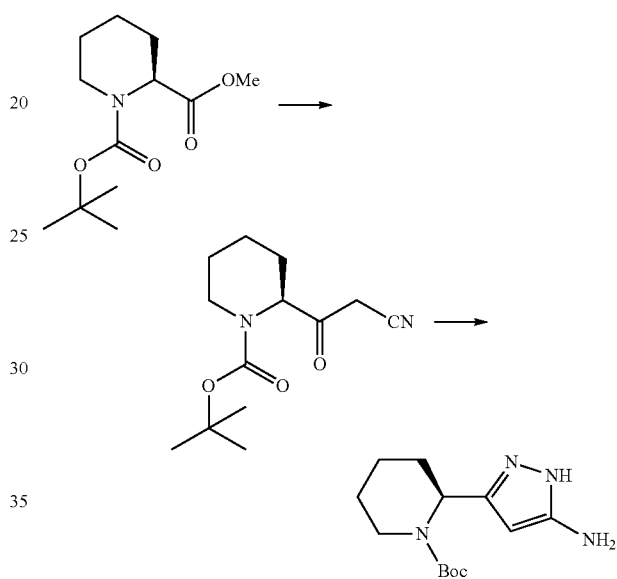

To a solution of acetonitrile (5 ml, 93.8 mmol) in dry THF (50 ml) at −78° C. was added dropwise NaN(TMS)$_2$ (34 ml, 68 mmol, 2M in hexanes). The solution was warmed up to −40° C. and stirred for 20 min. The solution was then cooled down to −78° C. and a solution of the ester (Intermediate 2) (7.6 g, 31.1 mmol) in THF (20 ml) was added dropwise. The solution was warmed up to −40° C. and stirred for 2 h. The solution was then cooled down to −78° C. and a solution of acetic acid (4.8 ml, 80 mmol) in THF (20 ml) added dropwise. The solution was then warmed to RT and volatiles were removed under reduced pressure at 40° C. The resulting residue was dissolved in EtOAc (300 mL) and the organic phase was washed 2× each with brine. Volatiles were removed under reduced pressure at 40° C.

$^{1}$H NMR (DMSO, 300 MHz) δ 4.63 (br s, 1H), 4.18-4.13 (m, 1H), 3.82-3.78 (m, 1H), 3.65 (s, 2H), 2.85-2.63 (m, 1H), 1.65-1.52 (m, 9H), 1.38 (s, 9H).

LCMS m/z: 153 [M−Boc group+H], t$_R$=2.50 min.

The residue was dissolved in EtOH (150 ml) and hydrazine acetate (4.5 g, 47 mmol) was added. The solution was stirred for 16 h at RT. Volatiles were removed under reduced pressure at 40° C., EtOAc added (200 ml) and the organic phase washed with aqueous dilute NaHCO$_3$, then H$_2$O followed by brine. Volatiles were removed under reduced pressure at 40° C., the resulting residue was purified by silica gel column (DCM/MeOH, gradient from 0% to 20%) to afford the product intermediate 4 (7.5 g, 90%) as a oil.

LCMS m/z [M+H]⁺ $C_{13}H_{22}N_4O_2$ requires: 266.34. Found 266.84

HPLC (min, purity) $t_R$=2.13, 100%

¹H NMR (DMSO, 300 MHz) 11.20 (br s, 1H), 5.09 (m, 1H), 5.07 (s, 1H), 4.67 (br s, 2H), 3.81 (app d, J=12.0 Hz, 1H), 2.72 (app br t, J=12.0 Hz, 1H), 2.08 (app d, J=12.9 Hz, 1H), 1.57 (m, 4H), 1.39 (s, 9H); MS (ESI) m/z 267 [M+H]⁺, $t_R$=1.97 min. (3.5 min method). HPLC (Chiral: Chiralpak AD-H, isocratic n-heptane-isopropanol 70:30). $t_R$ (desired)=22.42 min, $t_R$ (enantiomer of desired isomer)=25.67 min; % ee=93.

Intermediate 4 Via Weinreb Amide

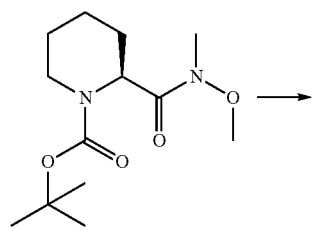

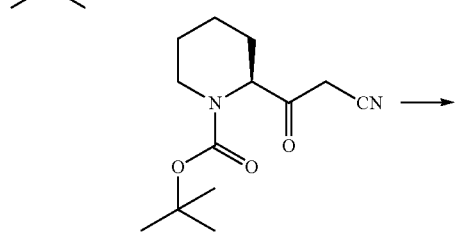

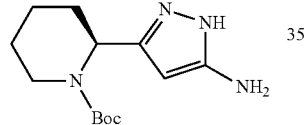

MeCN (3.20 mL, 60.7 mmol) in THF (50 mL) was cooled to −78° C. under Ar. NaHMDS solution (1.0 M in THF, 36.8 mL, 36.8 mmol) was added dropwise over 5 min, during which time an off-white suspension had formed. The suspension was warmed to −20° C. and stirred for 20 min. The suspension was cooled to −78° C. and transferred via cannula to the Weinreb amide intermediate 3 (5.02 g, 18.4 mmol) in THF (50 mL) at −78° C. over 5 min. The suspension is warmed to −45° C. and stirred for 3 h, during which time the suspension became a yellow solution. The solution was cooled to −78° C. and AcOH (4.2 mL in 10 mL THF, 73.6 mmol) was added dropwise. The solution was warmed to room temperature and diluted with EtOAc (100 mL). The solution was washed with H₂O (50 mL) and saturated NaCl solution (50 mL). The solution was dried over MgSO₄ and concentrated to afford the cyano ketone as a yellow oil which was used without further purification.

The crude α-cyano ketone was used in the next reaction with hydrazine acetate to synthesize desired amino pyrazole intermediate 4 as described above.

MS (ESI) m/z 267 [M+H]⁺, $t_R$=1.81 min.

HPLC (RP: 6-98% MeCN—H₂O gradient, 0.05% TFA modifier) $t_R$=3.212 min (>95% purity @ 254 nM).

HPLC (Chiral: Chiralpak AD-H 250 4.6 mm, 5 micron; isocratic n-heptane-isopropanol 70:30) $t_R$ (a isomer, desired)=22.35 min, $t_R$ (b isomer)=25.78 min; α=1.15; % ee=>90%, Intermediate 5

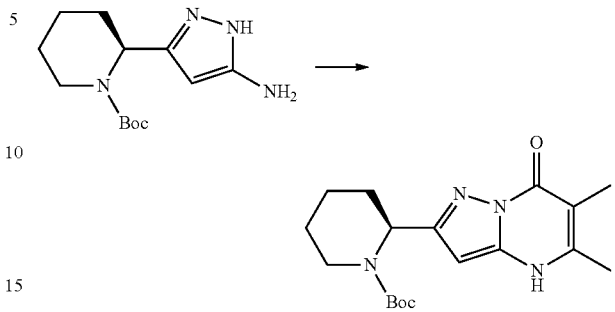

To a solution of the pyrazole intermediate 4 (7.2 g, 27.1 mmol) in acetic acid (100 ml) was added 2-methyl acetoacetate (3.9 ml, 27.1 nM) and the solution stirred at 100° C. for 45 min. Volatiles were removed under reduced pressure at 40° C., and the resulting residue was purified by silica gel column (DCM/MeOH, gradient from 0% to 20%) to afford the product intermediate 5 (7.23 g, 77%) as an oil.

¹H-NMR (DMSO, 400 MHz): 7.26 (s, 1H), 5.79 (s, 1H), 5.42 (s, 1H), 3.99 (m, 1H), 2.81 (m, 1H), 2.56 (m, 1H), 2.36 (m, 3H), 2.08 (m, 3H), 1.76 (m, 3H), 1.53-1.28 (m, 14H).

LCMS m/z [M+H]⁺ $C_{18}H_{26}N_4O_3$ requires: 346.42. Found 347.07

HPLC Tr (min), purity %: 1.45, 100%.

Intermediate 6

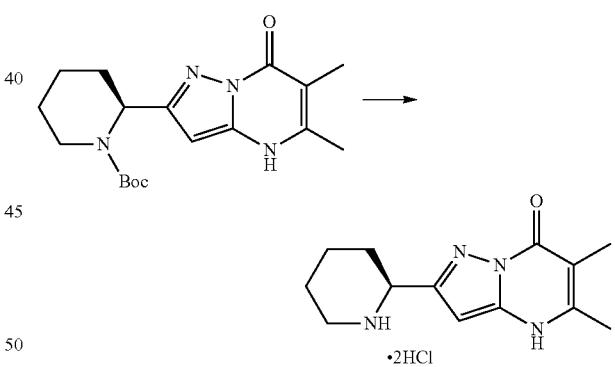

A 4N solution of hydrogen chloride in dioxane (20 mL, 80 mmol) was added to a mixture of N-Boc piperdine intermediate 5 (1.12 g, 3.26 mmol) in anhydrous dioxane (20 mL), forming a white precipitate after 5-10 minutes. Reaction mixture was stirred 65 hours and concentrated under reduced pressure to yield unprotected intermediate 6 as a white solid (1.14 g, 99%).

¹H-NMR (DMSO, 300 MHz): δ 12.67 (s, 1H), 9.43 (m, 1H), 9.30 (m, 1H), 6.27 (s, 1H), 4.70 (br s, 1H), 4.39 (t, J=10.2 Hz, 1H), 3.28 (d, J=14.1 Hz, 1H), 3.02 (m, 1H), 2.32 (s, 3H), 2.15 (d, J=10.8 Hz, 1H), 1.96 (s, 3H), 1.84-1.55 (m, 5H)

LCMS m/z [M+H]⁺ $C_{13}H_{18}N_4O$ requires: 247.15. Found 247.07

Intermediate 7

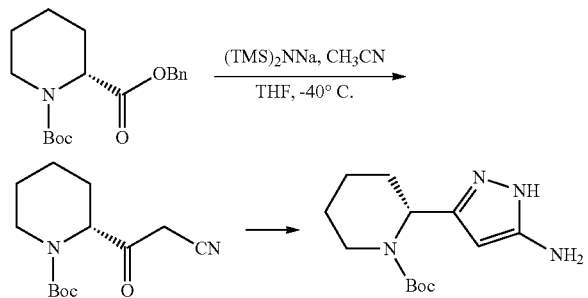

Dissolved anhydrous acetonitrile (131 uL, 2.5 mmol) in anhydrous THF (2 mL) and stirred under argon in a dry ice/acetonitrile bath at (−40° C.). Added 1N sodium bis(trimethylsilyl)amide in THF (2 mL, 2 mmol) dropwise. Resulting reaction mixture was stirred for 45 minutes at −40 C. Dissolved N-Boc-(R)-piperidine-2-carboxylic acid benzyl ester intermediate 1 (319 mg, 1 mmol) in anhydrous THF (5 mL) and stirred under argon in a dry ice/acetonitrile bath (−40° C.). Above reaction mixture was then added to the anion solution dropwise. Reaction was then stirred for 90 minutes at −40° C. Added acetic acid (229 uL, 4 mmol) and stirred for 30 minutes. Diluted with ethyl acetate (amount approx) and washed with saturated aqueous sodium chloride solution. Dried organic extract over anhydrous sodium sulfate and then concentrated under reduced pressure. Purified with Combiflash (linear gradient from 0-40% EtOAc in hexanes) to afford the cyano ketone (68 mg, 26%).

$^1$H NMR (CDCl$_3$, 300 MHz): δ 4.66 (m, 1H), 3.82 (m, 1H), 3.57 (s, 2H), 2.98 (m, 1H), 2.15 (m, 1H), 1.69-1.64 (m, 4H), 1.48 (s, 9H), 1.42 (m, 1H).

Dissolved the cyano ketone (68 mg, 0.26 mmol) in ethanol (4 mL). Added HOAc (15 uL, 0.26 mmol) and then hydrazine hydrate (13 uL, 0.26 mmol). Stirred at room temperature for 18 hours. Concentrated under reduced pressure. Purified residue by Combiflash (linear gradient from 0-10% MeOH in EtOAc) to afford intermediate 7 (42 mg, 71%).

$^1$H NMR (CDCl$_3$, 300 MHz): δ 5.41 (s, 1H), 5.31 (m, 1H), 4.86 (bs, 2H), 4.00 (m, 1H), 2.87 (m, 1H), 2.18 (m, 1H), 1.78-1.53 (m, 4H), 1.47 (s, 9H), 1.40 (m, 1H)

LCMS m/z [M+H]$^+$ 266.9

Intermediate 8

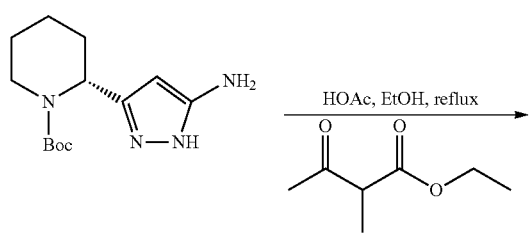

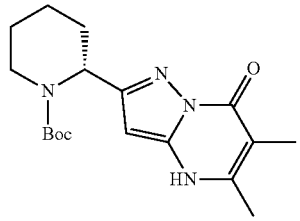

Dissolved amino-pyrazole intermediate 7 (42 mg, 0.185 mmol) in EtOH (5 mL). Added HOAc (32 uL, 0.555 mmol) and keto ester (24 uL, 0.185 mmol). Stirred at reflux for 2 hrs. Added additional HOAc (21 uL, 2 eq) and keto ester (4.8 uL, 0.2 eq). Stirred at reflux for 3 hrs. Concentrated under reduced pressure. Purified with Combiflash (linear gradient from 0-10% MeOH in EtOAc) to afford intermediate 8 (41 mg, 64%).

LCMS m/z [M+H]$^+$ 346.9

Intermediate 9

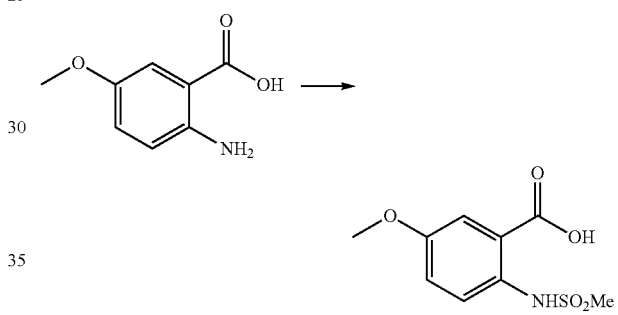

To a mixture of 2-amino-5-methoxybenzoic acid (350 mg, 2.10 mmol) in 3.5 mL of water, Na$_2$CO$_3$ (344 mg, 3.25 mmol) was added, slowly forming a solution. Methane sulfonyl chloride (0.18 mL, 2.28 mmol) was added slowly and reaction mixture stirred at room temperature for 24 hours. Reaction mixture was then quenched with 3.5 mL of 1N HCl$_{(aq)}$, forming a precipitate, and filtered, washing with 1N HCl$_{(aq)}$. Drying in-vacuo for 2 hours yielded intermediate 9 (453 mg, 88%) as a pink-purple solid.

$^1$H-NMR (DMSO, 300 MHz): δ 10.12 (s, 1H), 7.51-7.45 (m, 2H), 7.25-7.22 (m, 1H), 3.77 (s, 3H), 3.05 (s, 3H)

LCMS m/z [M+H]$^+$ C$_9$H$_{11}$NO$_5$S requires: 246.05. Found 246.12

Intermediate 10

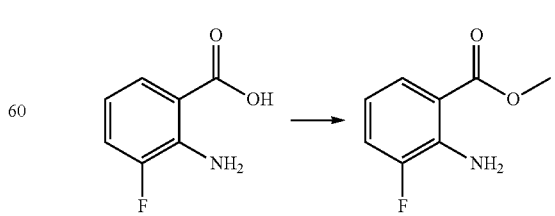

A solution of 2-amino-3-fluorobenzoic acid (559 mg, 3.62 mmol) and 1.7 mL of concentrated H$_2$SO$_4$ in 11 mL of anhydrous methanol was heated for 66 hours. After cooling to room temperature, methanol was concentrated under reduced pressure. Residue was taken up in 30 mL of water and added to a separatory funnel. Solid sodium carbonate was added slowly until gas evolution ceased (pH 9-10). Aqueous layer was extracted with ethyl acetate (3×40 mL). The combined organic layers were washed with 100 mL sat. NaHCO$_{3(aq)}$ and 100 mL of Brine, separated, dried (MgSO$_4$), filtered, and concentrated under reduced pressure. Column chromatography (5% Ethyl Acetate in Hexanes) yielded intermediate 10 (491 mg, 80%) as a white solid.

$^1$H-NMR (CDCl$_3$, 300 MHz): δ 7.66-7.63 (m, 1H), 7.15-7.08 (m, 1H), 6.60-6.55 (m, 1H), 5.40 (br s, 2H), 3.89 (s, 3H),

LCMS m/z [M+H]$^+$ C$_8$H$_8$FNO$_2$ requires: 170.05. Found 170.10

Intermediate 11

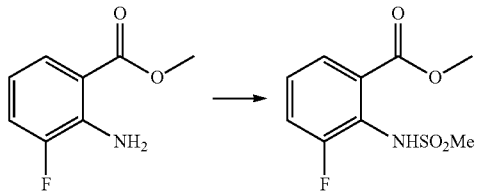

To a mixture of methyl 2-amino-3-fluorobenzoate (intermediate 10) (334 mg, 1.97 mmol) and pyridine (0.41 mL, 4.95 mmol) in 5.5 mL of dichloromethane at 0° C., was added slowly methanesulfonyl chloride (0.40 mL, 4.95 mmol). Mixture was warmed to room temperature and stirred overnight. HPLC indicated ~48% conversion to desired product. Pyridine (0.55 mL) and 0.50 mL of methanesulfonyl chloride (approximately 6.8 mmol each) was then added at room temperature. After a total of 40 hours, reaction mixture was quenched with 10 mL of 1N HCl. After 5 minutes of stirring, mixture was poured into 20 mL of water. Aqueous layer was extracted with ethyl acetate (3×30 mL). The combined organic layers were washed with 100 mL of 1N HCl$_{(aq)}$ and 100 mL Brine, separated, dried (MgSO$_4$), filtered, and concentrated under reduced pressure. Column chromatography (15-50% Ethyl Acetate in Hexanes) yielded intermediate 11 (360 mg, 74%) as a white solid.

$^1$H-NMR (CDCl$_3$, 300 MHz): δ 9.79 (s, 1H), 7.83 (d, J=7.8 Hz, 1H), 7.35 (m, 1H), 7.19-7.17 (m, 1H), 3.96 (s, 3H), 7.21 3.35 (s, 3H)

LCMS m/z [M+H]$^+$ C$_9$H$_{10}$FNO$_4$S requires: 248.03. Found 248.08

Intermediate 12

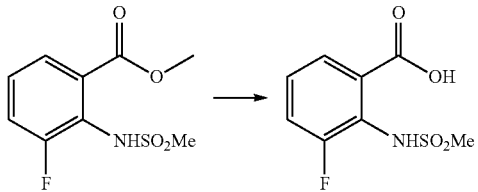

A solution of NaOH in water (2.85 M, 3 mL, 8.55 mmol) was added to a solution of methyl 3-fluoro-2-(methylsulfonamido)benzoate (intermediate 11) in 8.5 mL of THF with strong stirring. Reaction mixture was stirred at room temperature over night. Mixture was then acidified with 15 mL of 1N HCl and extracted with ethyl acetate (3×30 mL). The combined organic layers were washed 80 mL of Brine, separated, dried (MgSO$_4$), filtered, and concentrated under reduced pressure to yield intermediate 12 as a white solid (284 mg, 91%).

$^1$H-NMR (DMSO, 300 MHz): δ 9.77 (s, 1H), 7.70-7.68 (m, 1H), 7.57-7.50 (m, 1H), 7.38-7.33 (m, 1H), 3.15 (s, 3H)

LCMS m/z [M+H]$^+$ C$_9$H$_{10}$FNO$_4$S requires: 234.02. Found 234.09

Intermediate 13

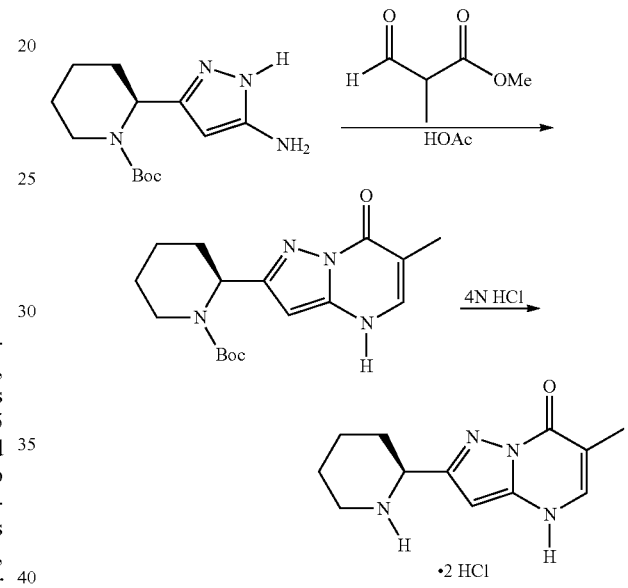

Intermediate 4 (330 mg, 1.2 mmol) in EtOH (12 mL) was treated with methyl 2-methyl-3-oxopropanoate (433 mg, 3.7 mmol) and HOAc (710 µL, 12.4 mmol) and the mixture was stirred overnight at 100° C. The mixture was concentrated and purified via SiO$_2$ column chromatography (40 g SiO$_2$ Combiflash HP Gold Column, 0-100% EtOAc/hexanes gradient) to afford crude intermediate compound as a crude white solid. The crude intermediate compound was treated with 4 N HCl/dioxanes (5 mL) and stirred 16 h. The mixture was concentrated to afford intermediate 13 (395 mg, >100%) as a crude off-white solid.

Intermediate 14

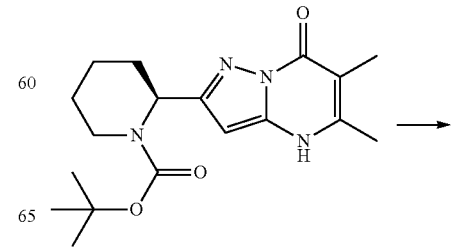

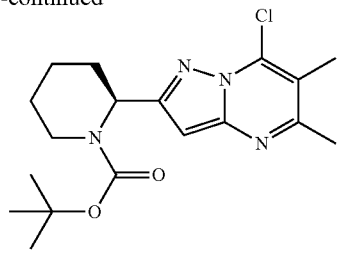

The intermediate 5 (0.3 g, 0.867 mmol), and DMAP (0.117 g, 0.958 mmol) were dissolved in anhydrous pyridine (15 mL) and placed under nitrogen with stirring. $POCl_3$ (0.567 ml, 6.07 mmol) was added neat and the reaction was heated to 100° C. for 2 hours. The reaction was monitored by LC/MS. When it was complete in about 2 hours the reaction was cooled to room temperature and solvents were removed by rotary evaporation. The residue was redissolved in 200 ml DCM and washed with 200 ml water. The organic layer was collected dried over $MgSO_4$(anh), filtered and then evaporated. The product was purified by column chromatography using ethyl acetate (25%) in hexanes to elute intermediate 14 (0.234 g, 0.643 mmol, 74%)

$^1$H-NMR ($CD_3CN$, 300 MHz): δ1.45 (m, 11H), 1.64 (m, 2H), 1.87 (m 1H), 2.39 (m 4H), 2.55 (s, 3H), 2.95 (t, 1H), 4.04 (d, 1H), 5.57 (d, 1H), 6.39 (s, 1H).

Intermediate 15

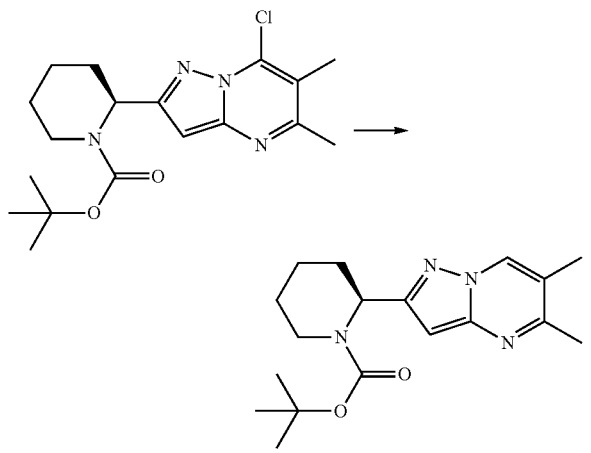

The starting intermediate 14 (0.06 g, 0.165 mmol), along with sodium acetate (0.027 g, 0.330 mmol) were dissolved in absolute ethanol (10 mL). Solid Pd/C (5% by wt) (0.030 g) was added and the reaction was placed under a balloon of hydrogen for 20 minutes. Catalyst was filtered off using a 40 micron syringe filter. The solvent was removed by rotary evaporation. The residue was taken up in DCM and loaded onto a silica gel column. The intermediate 15 was eluted with a 0 to 50% EtOAc in hexanes gradient. (Yield~40 mg, 0.121 mmol, 73%).

$^1$H-NMR ($CD_3CN$, 300 MHz): δ1.45 (m, 11H), 1.64 (m, 2H), 1.87 (m, 1H), 2.25 (s, 3H), 2.38 (d, 1H), 2.51 (s, 3H), 2.95 (t, 1H), 4.02 (d, 1H), 5.55 (d, 1H), 6.25 (s, 1H), 8.41 (s, 1H).

Intermediate 16

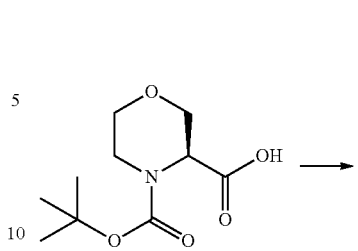

Dissolved S-Morpholine-3,4-dicarboxylic acid 4-tert-butyl ester (463 mg, 2 mmol) in anhydrous DMF (5 mL) and stirred at room temperature. Added sodium carbonate (318 mg, 3 mmol) in one portion. Added iodomethane (137 uL, 2.2 mmol). Stirred for 3 hours. Diluted reaction with ethyl acetate and washed with saturated aqueous sodium bicarbonate solution and then saturated aqueous sodium chloride solution. Dried organic extract over anhydrous sodium sulfate and then concentrated under reduced pressure to give intermediate 16 as a colorless light oil (474 mg, 96% crude)

$^1$H NMR ($CDCl_3$, 300 MHz): δ 4.60-4.25 (m, 2H), 3.95-3.60 (m, 5H), 3.60-3.20 (m, 2H), 1.49-1.45 (m, 9H).

Intermediate 17

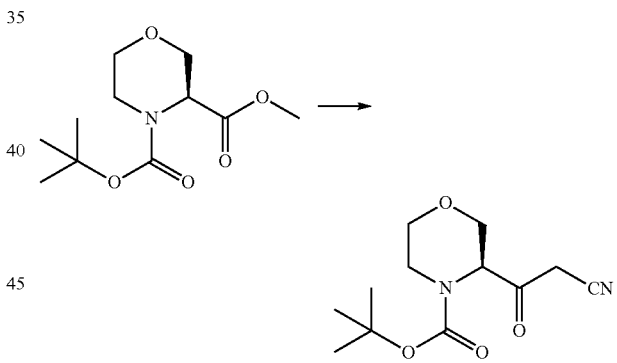

Added anhydrous acetonitrile (254 uL, 4.82 mmol) to anhydrous THF (2 mL) and stirred under Argon in a dry ice/acetonitrile bath (−40° C.). Added 1N sodium bis(trimethylsilyl)amide in THF (3.86 mL, 3.86 mmol) dropwise. Resulting reaction mixture was stirred for 60 minutes. Dissolved intermediate 16 (474 mg, 1.93 mmol) in anhydrous THF (5 mL) and stirred under Argon in a dry ice/acetonitrile bath (−40° C.). Above reaction mixture was then added to the solution dropwise. Reaction was then stirred for 5 hrs under the same conditions. Added acetic acid (442 uL, 7.72 mmol) and stirred for 15 minutes. Diluted with ethyl acetate and washed with 5% aqueous citric acid solution, saturated aqueous sodium bicarbonate solution and saturated aqueous sodium chloride solution. Dried organic extract over anhydrous sodium sulfate and then concentrated under reduced pressure. Purified with Combiflash silica gel column (linear gradient from 0-40% EtOAc in hexanes) to provide intermediate 17 (200 mg, 40%)

¹H NMR (CDCl₃, 300 MHz): δ 4.58 (m, 1H), 4.35 (m, 1H), 3.95-3.66 (m, 3H), 3.61 (s, 2H), 3.50 (m, 1H), 3.45 (m, 1H), 1.47 (s, 9H).

Intermediate 18

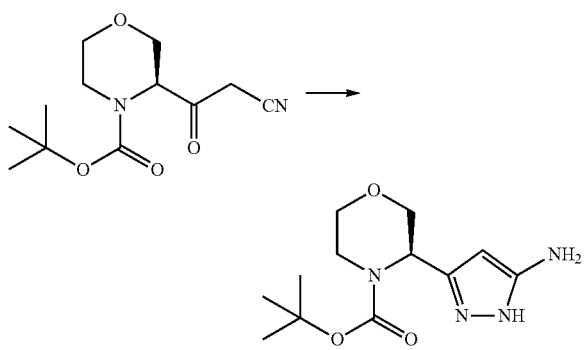

Dissolved intermediate 17 (200 mg, 0.78 mmol) in ethanol (10 mL). Added HOAc (134 uL, 2.36 mmol) and then hydrazine hydrate (175 uL, 2.36 mmol). Stirred at room temperature for 4 hrs. Concentrated under reduced pressure. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Combiflash silica gel column (linear gradient from 0-10% MeOH in EtOAc) to provide intermediate 18 (128 mg, 62%).

¹H NMR (CDCl₃, 300 MHz): δ 5.66 (s, 1H), 5.12 (s, 1H), 4.35 (m, 1H), 3.95-3.75 (m, 3H), 3.57 (m, 1H), 3.20 (m, 1H), 1.48 (s, 9H).

LCMS m/z [M+H]⁺ 268.9

Intermediate 19

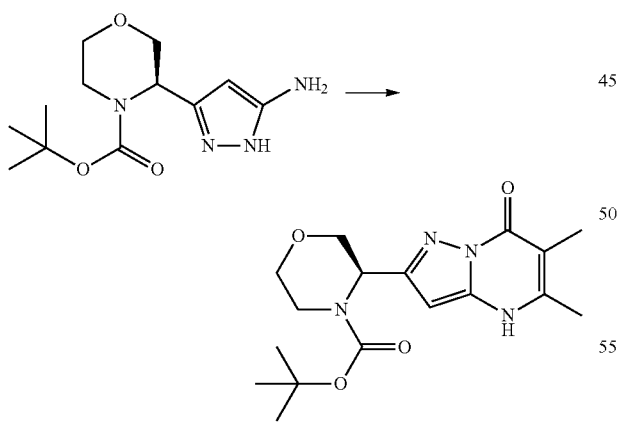

Dissolved intermediate 18 (128 mg, 0.48 mmol) in EtOH (10 mL). Added HOAc (274 uL, 4.8 mmol) and ethyl-2-methyl acetoacetate (230 uL, 1.43 mmol). Stirred at reflux for 4 hrs. Concentrated under reduced pressure. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Combiflash silica gel column (linear gradient from 0-10% MeOH in DCM) to afford intermediate 19 (156 mg, 93%)

¹H NMR (CDCl₃, 300 MHz): δ 5.26 (s, 1H), 4.40 (m, 1H), 3.90-3.80 (m, 4H), 3.58 (m, 1H), 3.16 (m, 1H), 2.54 (s, 3H), 2.10 (s, 3H), 1.46 (s, 9H).

LCMS m/z [M+H]⁺ 348.9

Intermediate 20

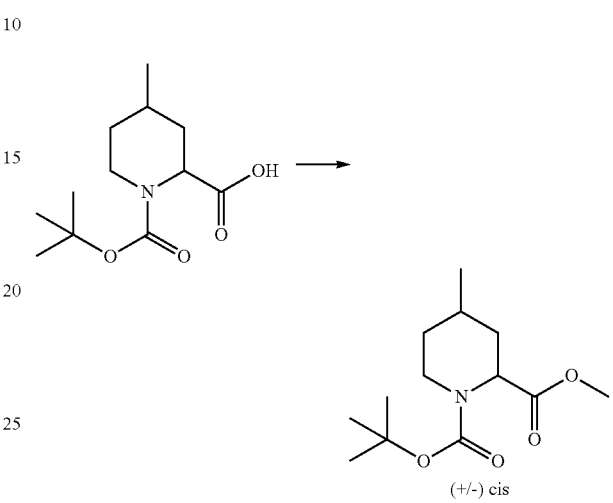

Dissolved (+,−) cis Boc-4-methyl pipecolinic acid (468 mg, 2 mmol) in anhydrous DMF (5 mL) and stirred at room temperature. Added sodium carbonate (318 mg, 3 mmol) in one portion. Added iodomethane (137 uL, 2.2 mmol). Stirred for 16 hours. Diluted reaction with ethyl acetate and washed with saturated aqueous sodium bicarbonate solution and then saturated aqueous sodium chloride solution. Dried organic extract over anhydrous sodium sulfate and then concentrated under reduced pressure to give the mixture of cis isomers, intermediate 20 as a colorless light oil (443 mg, 86%). Material was used without further purification.

¹H NMR (CDCl₃, 300 MHz): δ 4.34 (m, 1H), 3.73 (s, 3H), 3.60-3.35 (m, 2H), 1.97-1.74 (m, 4H), 1.44 (s, 9H), 1.34 (m, 2H), 0.95 (d, J=6.6 Hz, 3H).

Intermediate 21

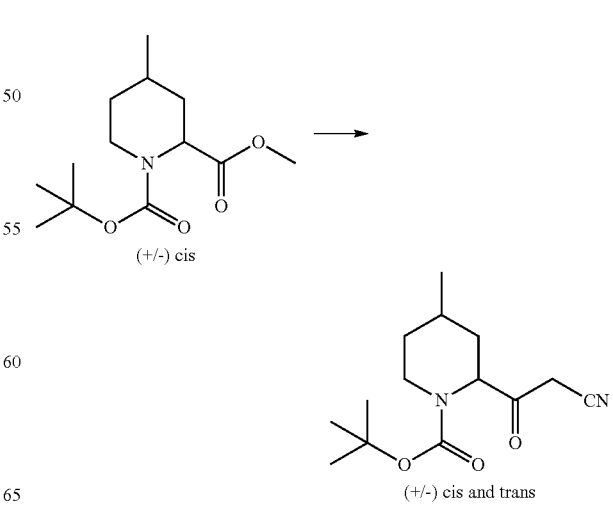

Dissolved anhydrous acetonitrile (226 uL, 4.3 mmol) in anhydrous THF (4 mL) and stirred under Argon in a dry ice/acetonitrile bath (−40° C.). Added 1N sodium bis(trimethylsilyl)amide in THF (3.44 mL, 3.44 mmol) dropwise. Resulting reaction mixture was stirred for 2 hrs. Dissolved intermediate 20 (443 mg, 1.72 mmol) in anhydrous THF (10 mL) and stirred under Argon in a dry ice/acetonitrile bath (−40° C.). Above reaction mixture was then added to the solution dropwise. Reaction was then stirred for 3 hrs under the same conditions. Added acetic acid (394 uL, 6.88 mmol) and stirred for 60 minutes. Diluted with ethyl acetate and washed with 5% aqueous citric acid solution, saturated aqueous sodium bicarbonate solution and saturated aqueous sodium chloride solution. Dried organic extract over anhydrous sodium sulfate and then concentrated under reduced pressure. Purified with Combiflash silica gel column (linear gradient from 0-40% EtOAc in hexanes) to afford intermediate 21 as a mixture of (+/−) cis and (+/−) trans isomers (340 mg, 74%).

$^1$H NMR (CDCl$_3$, 300 MHz): δ 3.90-3.71 (m, 2H), 3.37 (m, 1H), 2.97 (m, 1H), 1.97-1.56 (m, 4H), 1.46 (s, 9H), 1.25 (m, 2H), 1.01-0.94 (m, 3H).

Intermediate 22

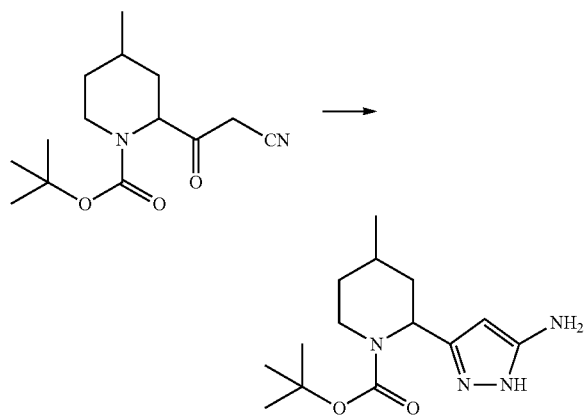

Dissolved intermediate 21 isomer mixture (340 mg, 1.27 mmol) in ethanol (20 mL). Added HOAc (219 uL, 3.83 mmol) and then hydrazine hydrate (286 uL, 3.83 mmol). Stirred at room temperature for 16 hrs. Concentrated under reduced pressure. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Combiflash silica gel column (linear gradient from 0-10% MeOH in MeOH) to afford intermediate 22 as a mixture of all stereoisomers (179 mg, 50%).

$^1$H NMR (CDCl$_3$, 300 MHz): δ 5.48 (m, 1H), 5.08 (m, 1H), 3.85 (m, 1H), 3.22 (m, 1H), 2.10 (m, 1H), 1.88 (m, 2H), 1.48-1.27 (m, 11H), 1.00-0.92 (m, 3H).
LCMS m/z [M+H]$^+$ 280.9

Intermediate 23 and 24

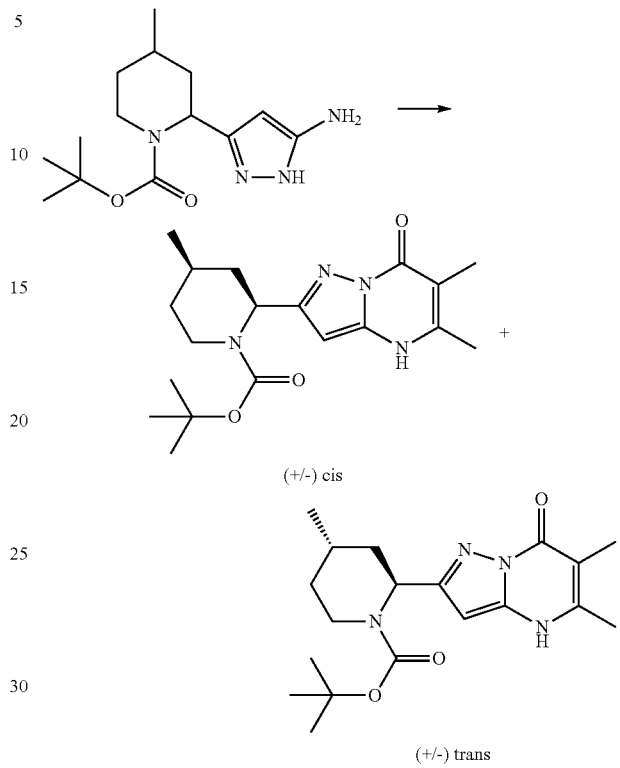

Dissolved intermediate 22 (179 mg, 0.638 mmol) in EtOH (10 mL). Added HOAc (365 uL, 6.38 mmol) and ethyl-2-methyl acetoacetate (307 uL, 1.95 mmol). Stirred at reflux for 4 hrs. Concentrated under reduced pressure. Purified with C$_{18}$ Prep HPLC to give (+,−) cis intermediate 23 as the major product and (+,−) trans intermediate 24 products (23 cis-89 mg, 24 trans-47 mg, 59% total).

Intermediate 23 (+,−)cis: $^1$H NMR (CDCl$_3$, 300 MHz): δ 6.02 (s, 1H), 4.97 (m, 1H), 3.66-3.44 (m, 2H), 2.70 (m, 2H), 2.38 (m, 3H), 2.26-1.8 (m, 5H), 1.46 (s, 9H), 1.31 (m, 1H), 0.94 (m, 3H).

Intermediate 24 (+/−) trans: $^1$H NMR (CDCl$_3$, 300 MHz): δ 5.82 (s, 1H), 5.48 (bs, 1H), 4.07 (m, 1H), 2.90 (m, 1H), 2.51 (m, 1H), 2.37 (s, 3H), 2.07 (s, 3H), 1.60-1.25 (m, 12H), 1.09 (m, 1H), 0.93 (d, J=6.0 Hz, 3H).
LCMS m/z [M+H]$^+$ 360.9

Intermediate 25

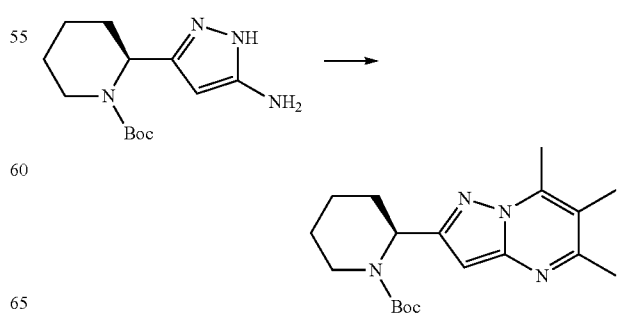

To a solution of the pyrazole intermediate 4 (0.5 g, 2.2 mM) in acetic acid (5 ml) was added 3-methylpentane-2,4-dione (0.25 g, 2.2 mM) and the solution stirred at 90° C. for 30 min. Volatiles were removed under reduced pressure at 40° C., and the resulting residue was purified by silica gel column (DCM/MeOH, gradient from 0% to 10%) to afford the product intermediate 25 (0.353 g, 47%) as a viscous oil.

$^1$H-NMR (DMSO, 400 MHz): δ 6.31 (s 1H), 5.58 (s 1H), 4.06 (d, J=12.8, 1H), 2.92 (m 1H), 2.79 (m 3H), 2.58 (s, 3H), 2.52 (m 1H), 2.30 (s 3H), 1.91 (m 1H), 1.57-1.40 (m, 12H).

LCMS m/z [M+H]$^+$ C$_{19}$H$_{28}$N$_4$O$_2$ requires: 344.45. Found 345.20

HPLC Tr (min), purity %: 5.96, 95%.

Intermediate 26

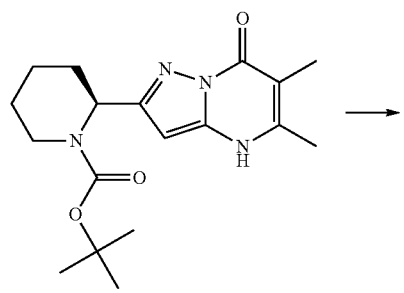

Intermediate 5 (0.3 g, 0.867 mmol), and DMAP (0.117 g, 0.958 mmol) were dissolved in anhydrous pyridine (15 mL) and placed under nitrogen with stirring. POCl$_3$ (0.567 ml, 6.07 mmol) was added neat and the reaction was heated to 100° C. for 2 hours. The reaction was monitored by LC/MS. When it was complete in about 2 hours the reaction was cooled to room temperature and solvents were removed by rotary evaporation. The residue was redissolved in 200 ml DCM and washed with 200 ml water. The organic layer was collected dried over MgSO$_4$(anh), filtered and then evaporated. The product was purified by column chromatography using ethyl acetate (25%) in hexanes to elute intermediate 26 (0.234 g, 0.643 mmol, 74%).

$^1$H-NMR (CD$_3$CN, 300 MHz): δ 1.45 (m, 11H) 1.64 (m, 2H), 1.87 (m, 1H), 2.39 (m, 4H), 2.55 (s, 3H), 2.95 (t, 1H), 4.04 (d, 1H), 5.57 (d, 1H), 6.39 (s, 1H).

Intermediate 27

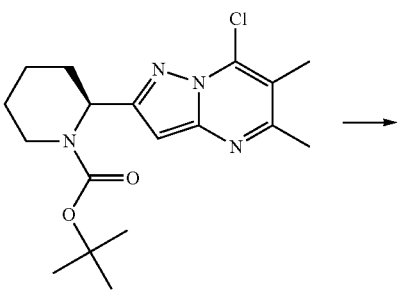

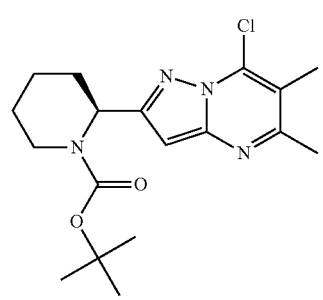

The intermediate 26 (0.110 g, 0.301 mmol), was dissolved in 1,4-dioxane 5 ml. Methyl amine (40% in water) (2 mL) was added and the reaction was stirred for 2 hr. Solvents were removed by rotary evaporation. The residue was taken up in DCM and loaded onto a silica gel column. The product, intermediate 27, was eluted with a 0 to 80% EtOAc in hexanes gradient (98 mg, 0.272 mmol, 90%).

$^1$H-NMR (CD$_3$CN, 300 MHz): δ 1.45 (m, 11H), 1.60 (m, 2H), 1.82 (m, 1H), 2.30 (s, 3H), 2.40 (m, 1H, 2.42 (s, 3H), 2.95 (t, 1H), 3.35 (d, 3H), 4.01 (d, 1H), 5.49 (m, 1H), 6.00 (s, 1H), 6.29 (bs, 1H).

Intermediate 28

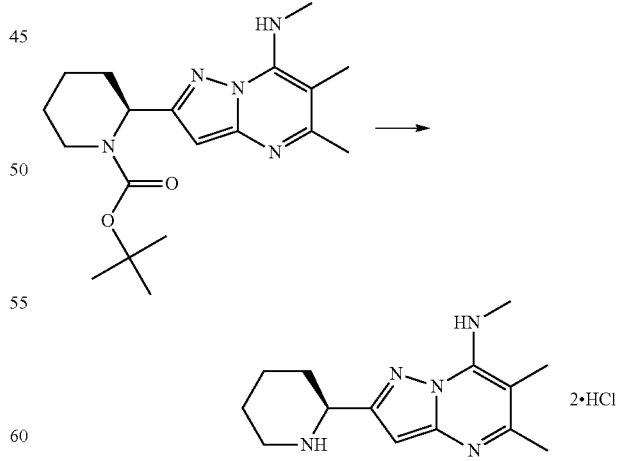

The intermediate 27 (0.10 g, 0.28 mmol), was dissolved in anhydrous 1,4-dioxane (6 ml). With stirring under nitrogen 4N HCl in dioxane (3 ml) was added via syringe. The reaction was stirred for 2 hours at room temperature while monitoring by LC/MS. When the reaction was complete solvent was removed by rotary evaporation. The product, intermediate 28 was taken forward without further purification after it was characterized by LC/MS (Yield~73 mg, 0.28 mmol, 100%).

LCMS m/z [M+H]+ 261

Intermediate 29

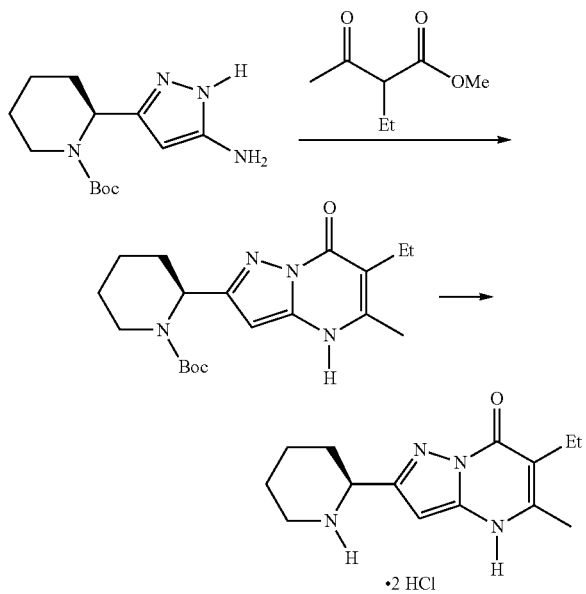

Intermediate 4 (292 mg, 1.1 mmol) in EtOH (11 mL) was treated with methyl 2-ethyl-3-oxobutanoate (471 μL, 3.3 mmol) and HOAc (629 μL, 11.0 mmol) and the mixture was stirred overnight at 100° C. The mixture was concentrated and purified via SiO$_2$ column chromatography (40 g SiO$_2$ Combiflash HP Gold Column, 0-100% EtOAc/hexanes gradient) to afford intermediate pyrrazolo-pyrimidione as a white solid (328 mg, 82%). The intermediate was then treated with 4 N HCl/dioxanes (5 mL) and stirred 16 h. The mixture was concentrated to afford intermediate 29 (395 mg, >100%) as a crude off-white solid.

Intermediate 30

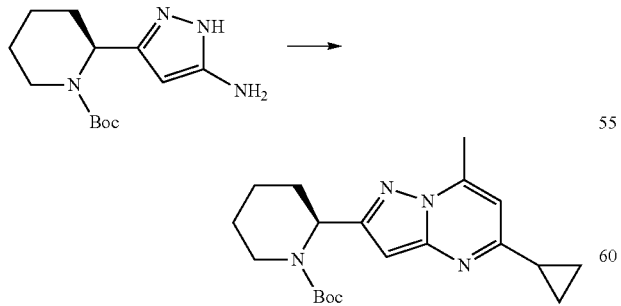

To a solution of the pyrazole intermediate 4 (3.22 g, 12.08 mM) in acetic acid (25 ml) was added 1-cyclopropyl-1,3-butanedione (2.28 g, 18.13 mM) and the solution stirred at 120° C. for 30 min. Volatiles were removed under reduced pressure at 40° C., and the resulting residue was purified by silica gel column (Hexane/EtOAc, gradient from 0% to 50%) to afford intermediate 30 (1.72 g, 26%).

$^1$H-NMR (CDCl$_3$, 400 MHz): δ 6.44 (s 1H), 6.28 (s 1H), 5.58 (s, 1H), 4.13-4.04 (m, 1H), 2.96-2.92 (m, 1H), 2.67 (s, 3H), 2.46-2.42 (m, 1H), 2.14-1.85 (m, 4H), 1.47 (s, 9H), 1.13-1.02 (m, 6H).

LCMS m/z [M+H]+ C$_{20}$H$_{28}$N$_4$O$_2$ requires: 357.46. Found 357.13

Intermediate 31

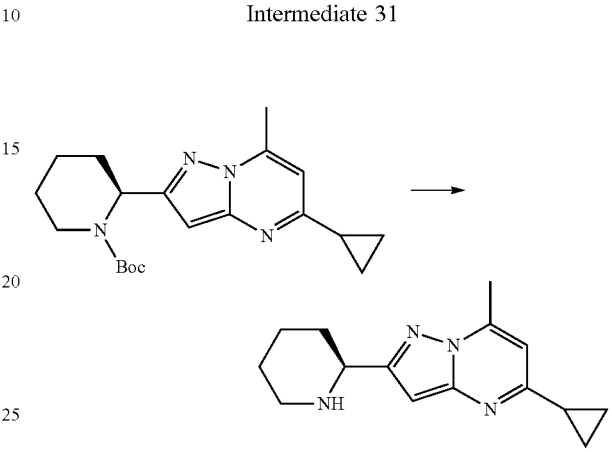

The intermediate 30 (0.60 g, 1.68 mmol), was dissolved in anhydrous 1,4-dioxane (6 ml). With stirring under nitrogen 4N HCl in dioxane (3 ml) was added via syringe. The reaction was stirred for 2 hours at room temperature while monitoring by LC/MS. When the reaction was complete solvent was removed by rotary evaporation. The product, intermediate 31 was taken forward without further purification (Yield 0.55 g, 100%).

$^1$H-NMR (CH$_3$OD, 400 MHz): δ 6.95 (d, J=1.2 Hz, 1H), 6.73 (s, 1H), 4.64 (d, J=12 Hz, 1H), 11), 3.52-3.51 (m, 1H), 3.23-3.20 (m, 1H), 2.86 (s 3H), 2.40-2.02 (m, 2H), 2.26-1.81 (m, 5H), 1.41-1.30 (m, 4H).

LCMS m/z [M+H]+ C$_{15}$H$_{20}$N$_4$ requires: 257.35. Found 257.15

HPLC Tr (min), purity %: 1.65, 98%.

Compound 1

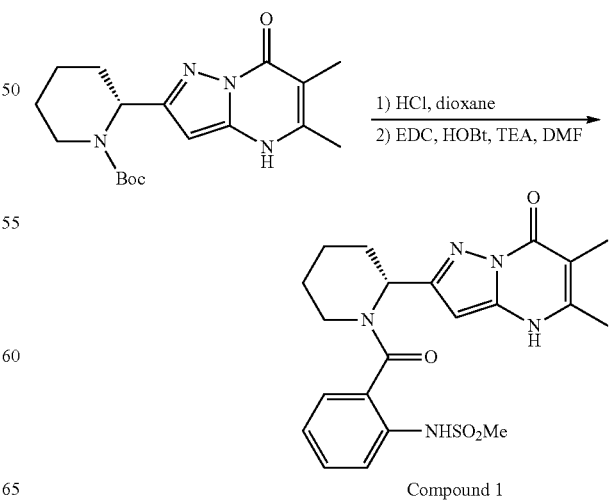

Compound 1

Dissolved boc material intermediate 8 (41 mg, 0.12 mmol) in MeOH (1 mL). Added 4N HCl in dioxane (2 mL) and stirred for 1 hr. Concentrated under reduced pressure. Dried under high vacuum. Dissolved material in anhydrous DMF and took half of the volume (17 mg, 0.059 mmol) for next reaction. Added to a mixture of EDC (12.5 uL, 0.071 mmol), HOBt (9 mg, 0.059 mmol) and sulfonamide benzoic acid (13 mg, 0.059 mmol) in anhydrous DMF (500 uL). Stirred for 15 mins. Added TEA (21 uL, 0.148 mmol) and stirred for 16 hrs. Diluted with ethyl acetate and washed with saturated aqueous sodium chloride solution. Dried organic extract over anhydrous sodium sulfate and then concentrated under reduced pressure. Purified with Combiflash (linear gradient from 0-10% MeOH in DCM). Final purification with Prep HPLC to yield compound 1 (3.6 mg, 14%).

$^1$H NMR (CD$_3$OD, 300 MHz): δ 7.52-7.30 (m, 4H), 6.09 (bs, 1H), 3.58-3.30 (m, 2H), 3.14 (s, 3H), 2.45 (m, 1H), 2.38 (s, 3H), 2.09 (s, 3H), 2.04 (m, 1H), 1.74-1.61 (m, 4H)

LCMS m/z [M+H]$^+$ 444.1

Compound 2

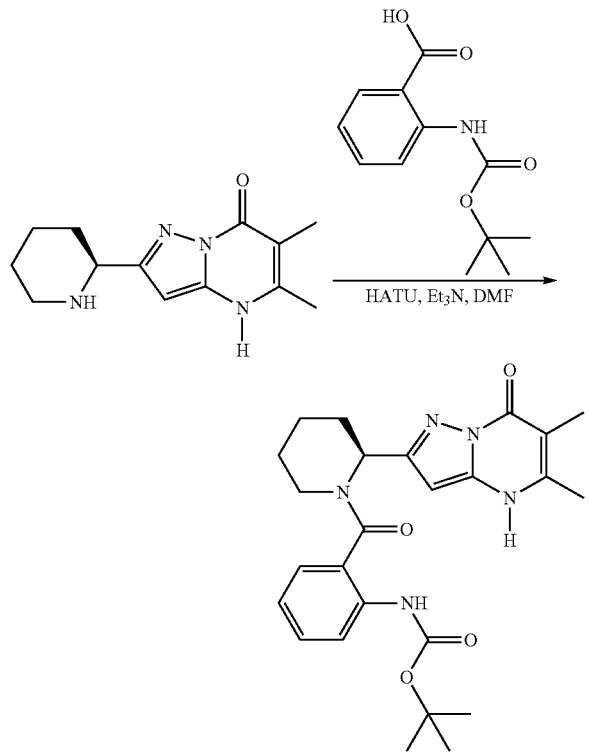

Compound 2

To a solution of boc-2-aminobenzoic acid (75 mg, 0.32 mmol) in DMF (4 mL) was added HATU (137 mg, 0.36 mmol) the solution stirred under N$_2$ at RT for 10 mins. To the above solution was added intermediate 6 (60 mg, 0.24 mmol) and Et$_3$N (0.05 mL). The reaction mixture was stirred at RT for 5 h. The volatile were removed under reduced pressure at 40° C. and the resulting residue was purified by preparative HPLC (MeCN in H$_2$O with a gradient from 0% to 95%) to afford compound 2 (91 mg, 80%) as a white powder after lyophilization.

$^1$H-NMR (CD$_3$CN, 300 MHz): δ 9.78 (s, 1H), 7.93 (d, J=5.1 Hz, 1H), 7.40-7.38 (m, 2H), 7.12 (s, 1H), 5.93 (s, 1H), 3.10 (mc, 3H), 2.31 (s, 3H), 2.00 (s, 3H), 1.72-1.51 (m, 6H), 1.44 (s, 9H).

LCMS m/z [M−H]$^+$ C$_{25}$H$_{31}$N$_5$O$_4$ requires: 464.54. Found 464.34

HPLC Tr (min), purity %: 1.83, 98%

Compound 3

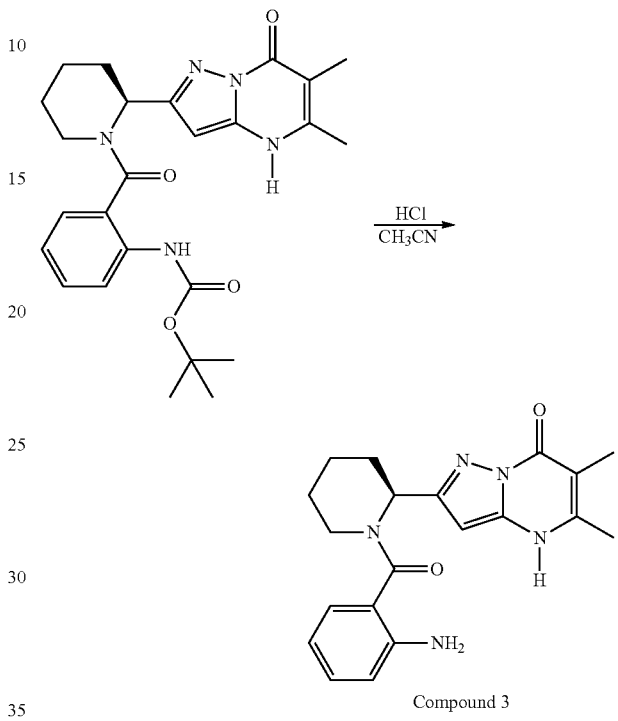

Compound 3

To a solution of compound 2 (420 mg) in CH$_3$CN (10 mL) was added 2N HCl (5 mL). The solution was stirred at RT overnight. The volatile were removed under reduced pressure at 40° C. and the resulting residue was purified by preparative HPLC (MeCN in H$_2$O with a gradient from 0% to 95%) to afford compound 3 (330 mg, 100%) as a white powder after lyophilization.

$^1$H-NMR (CD$_3$CN, 300 MHz): δ 12.16 (s, 1H), 7.22 (t, J=6.9 Hz, 1H), 7.06 (d, J=8.4 Hz, 1H), 6.61 (mc, 2H), 6.03 (s, 1H), 3.96 (mc, 3H), 2.31 (s, 3H), 1.98 (s, 3H), 1.75-1.48 (m, 6H),

LCMS m/z [M+H]$^+$ C$_{20}$H$_{23}$N$_5$O$_2$ requires: 366.43. Found 366.54

HPLC Tr (min), purity %: 1.72, 98%

Compound 4

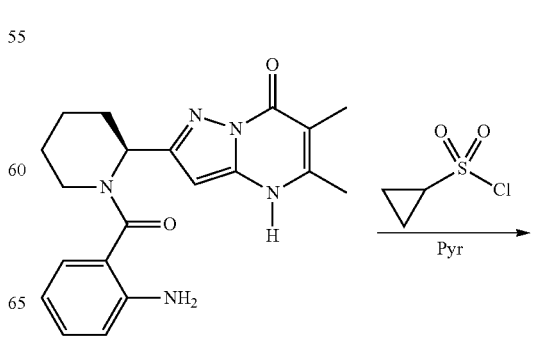

-continued

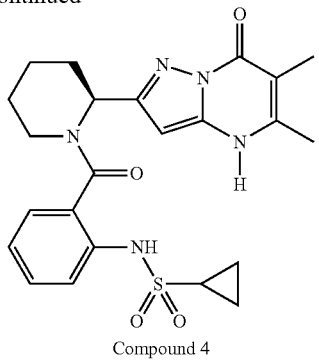

Compound 4

To a solution of compound 3 (25 mg, 0.068 mmol) in Pyridine (1.0 mL) was added Cyclopropane sulfonyl chloride (96 mg, 0.68 mmol) at −10° C. The temperature was raised slowly to RT and stirred overnight. The volatile were removed under reduced pressure at 40° C. and the resulting residue was purified by preparative HPLC (MeCN in H₂O with a gradient from 0% to 95%) to afford compound 4 (29 mg, 90%) as a white powder after lyophilization.

¹H-NMR (CD$_3$CN, 300 MHz): δ 12.07 (s, 1H), 9.07 (s, 1H), 7.44 (mc, 3H), 6.00 (s, 1H), 5.92 (s, 1H), 3.70 (mc, 5H), 2.87 (s, 1H), 2.29 (s, 3H), 1.95 (s, 3H), 1.62-0.50 (mc, 4H), 0.92 (mc, 4H).

LCMS m/z [M−H]⁺ C$_{20}$H$_{23}$N$_5$O$_2$ requires: 470.56. Found 470.07

HPLC Tr (min), purity %: 2.29, 98%

Compound 5

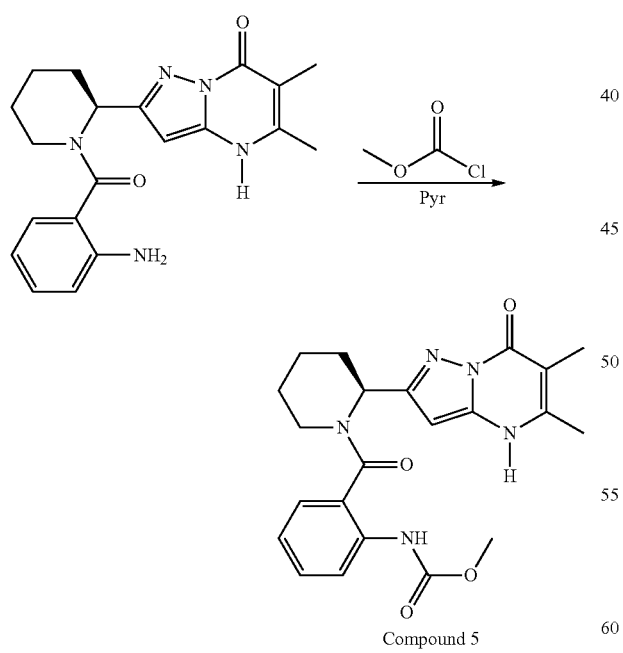

Compound 5

To a solution of compound 3 (8 mg, 0.022 mmol) in Pyridine (1.0 mL) was added Methyl Chloroformate (0.1 mL) and the reaction mixture was stirred at RT for 10 mins. The volatile were removed under reduced pressure at 40° C. and the resulting residue was purified by preparative HPLC (MeCN in H₂O with a gradient from 0% to 95%) to afford compound 5 (9 mg, 97%) as a white powder after lyophilization.

¹H-NMR (CD$_3$CN, 300 MHz): δ 9.92 (s, 1H), 8.27 (s, 1H), 7.88 (s, 1H), 7.40 (d, J=9.0 Hz, 1H), 7.15 (s, 1H), 5.94 (s, 1H), 3.68 (S, 3H), 3.30 (mc, 5H), 2.32 (s, 1H), 2.05 (s, 3H), 1.71-1.56 (m, 4H).

LCMS m/z [M+H]⁺ C$_{22}$H$_{25}$N$_5$O$_4$ requires: 424.47. Found 423.96

HPLC Tr (min), purity %: 2.03, 98%

Compound 6

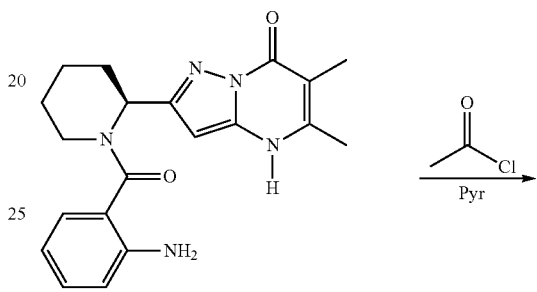

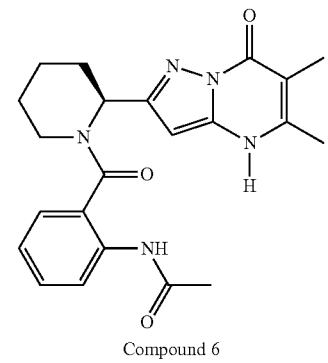

Compound 6

To a solution of compound 3 (10 mg, 0.028 mmol) in Pyridine (1.0 mL) was added Acetyl Chloride (0.1 mL) and the reaction mixture was stirred at RT for 10 mins. The volatile were removed under reduced pressure at 40° C. and the resulting residue was purified by preparative HPLC (MeCN in H₂O with a gradient from 0% to 95%) to afford compound 6 (10 mg, 91%) as a white powder after lyophilization.

¹H-NMR (CD$_3$CN, 300 MHz): δ 9.68 (s, 1H), 7.32 (t, J=6.6 Hz, 1H), 7.13 (d, J=9.1 Hz, 1H), 6.56 (mc, 2H), 5.83 (s, 1H), 3.30 (mc, 3H), 2.35 (s, 3H), 2.25 (s, 3H), 2.03 (s, 3H), 1.79-1.53 (m, 6H).

LCMS m/z [M+H]⁺ C$_{22}$H$_{25}$N$_5$O$_4$ requires: 408.47. Found 408.85

HPLC Tr (min), purity %: 1.92, 98%

Compound 7

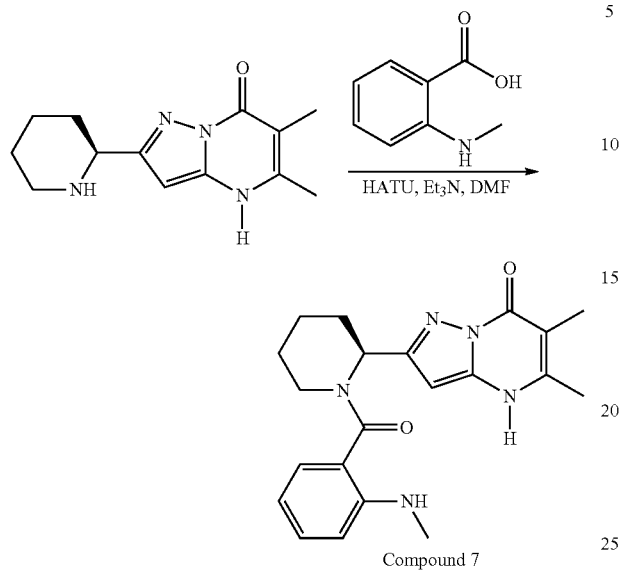

Compound 7

To a solution of 2-Methylaminobenzoic acid (34 mg, 0.23 mmol) in DMF (1.0 mL) was added HATU (92 mg, 0.24 mmol) the solution stirred under $N_2$ at RT for 10 mins. To the above solution was added intermediate 6 (28 mg, 0.11 mmol) and $Et_3N$ (0.03 mL). The reaction mixture was stirred at RT overnight. The volatile were removed under reduced pressure at 40° C. and the resulting residue was purified by preparative HPLC (MeCN in $H_2O$ with a gradient from 0% to 95%) to afford compound 7 (16 mg, 37%) as a white powder after lyophilization.

$^1$H-NMR (DMSO, 300 MHz): δ 12.15 (s, 1H), 7.22 (t, J=6.6 Hz, 1H), 7.05 (d, J=7.5 Hz, 1H), 6.61 (s, 2H), 6.03 (s, 1H), 3.86 (mc, 3H), 3.58 (s, 3H), 2.31 (s, 3H), 1.98 (s, 3H), 1.63-1.32 (m, 6H).

LCMS m/z [M−H]$^+$ $C_{21}H_{25}N_5O_2$ requires: 380.46. Found 380.28

HPLC Tr (min), purity %: 1.92, 98%

Compound 8

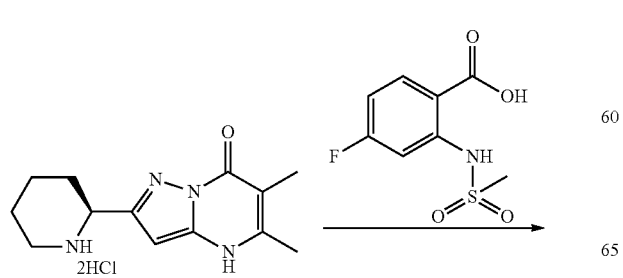

-continued

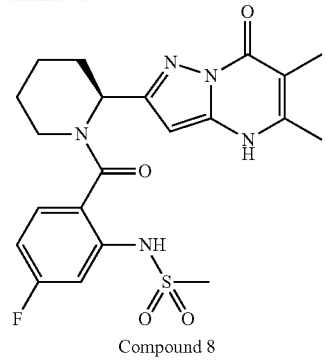

Compound 8

HATU (237.1 mg, 0.624 mmol) was added to a solution of 4-fluoro-2-(methylsulfonamido)benzoic acid (127.1 mg, 0.548 mmol) in 5 mL of anhydrous DMF at room temperature. After 15 min of stirring, intermediate 6 (133.2 mg, 0.418 mmol) was added followed immediately by triethylamine (0.22 mL, 1.58 mmol). Reaction mixture stirred at room temperature overnight under argon. Mixture was then poured into 50 mL of $H_2O$ and extracted three times with 50 mL of ethyl acetate. The combined organic layers were washed with 100 mL Brine, dried ($MgSO_4$), filtered, and concentrated under reduced pressure leaving a residue. Product was purified by silica gel column chromatography (0-10% Methanol in Dichloromethane) and then prep HPLC (15-100% Acetonitrile (with 0.1% trifluoroacetic acid) in water (with 0.1% trifluoroacetic acid)) to yield compound 8 (143 mg, 60%) as a white solid, trifluoroacetate salt, after lyophilization.

$^1$H-NMR (CDCl$_3$, 300 MHz): δ 10.05 (s, 1H) 9.53 (s, 1H), 7.41 (t, J=7.2 Hz, 1H), 7.30-7.25 (m, 1H), 6.97-6.91 (m, 1H), 5.99 (s, 1H), 5.67 (s, 1H), 5.07 (br s, 1H), 3.53 (m, 1H), 3.42 (s, 3H), 2.22 (m, 1H), 2.19 (s, 3H), 1.96 (s, 3H), 1.94 (m, 1H), 1.67 (m, 2H), 1.44 (m, 2H)

LCMS m/z [M+H]$^+$ $C_{21}H_{24}FN_5O_4S$ requires: 462.15. Found 462.10

Compound 9

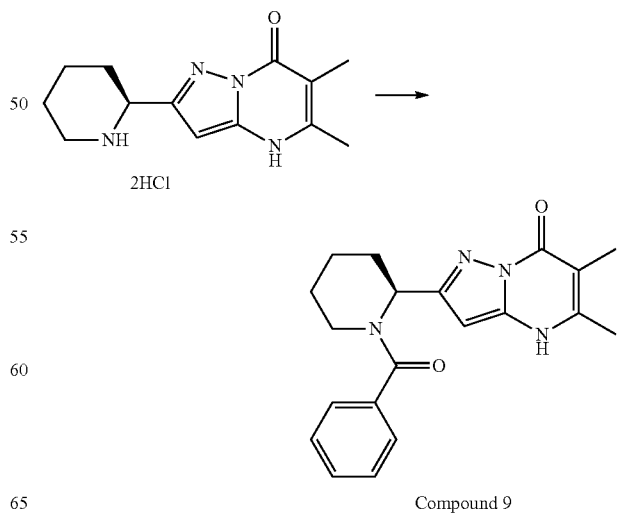

Compound 9

To a mixture of intermediate 6 (128.1 mg, 0.401 mmol) in 4 mL of anhydrous CH$_2$Cl$_2$ under argon was added triethylamine (0.20 mL, 1.44 mmol) at room temperature. After 5 minutes of stirring, benzoyl chloride (0.050 mL, 0.442 mmol) was added slowly and solution was stirred overnight. Reaction mixture was quenched with 3 mL of water with stirring. After 10 min, reaction mixture was taken up in 35 mL of ethyl acetate, poured into 20 mL of water, and separated. The aqueous layer was then extracted with ethyl acetate (2×30 mL). The combined organic layers were washed with 30 mL of 1N HCl$_{(aq)}$, 30 mL of saturated NaHCO$_{3(aq)}$, 30 mL of brine, dried (MgSO$_4$), filtered, and concentrated under reduced pressure leaving a residue. Product was purified by silica gel column chromatography (2-10% Methanol in Dichloromethane) and then prep HPLC (15-100% Acetonitrile (with 0.1% trifluoroacetic acid) in water (with 0.1% trifluoroacetic acid)) to yield compound 9 (35 mg, 19%) as a white solid, trifluoroacetate salt, after lyophilization.

$^1$H-NMR (CDCl$_3$, 300 MHz): δ 12.01 (s, 1H), 7.41-7.31 (m, 5H), 6.09 (s, 1H), 5.87 (s, 1H), 3.61 (d, J=12.6 Hz, 1H), 3.19 (m, 1H), 2.97 (m, 1H), 2.55 (d, J=12.9 Hz, 1H), 2.15 (s, 3H), 2.03 (s, 3H), 1.90-1.55 (m, 4H)

LCMS m/z [M+H]$^+$ C$_{20}$H$_{22}$N$_4$O$_2$ requires: 351.17. Found 351.12

HPLC Tr (min), purity %: 17.3, 97%

Compound 10

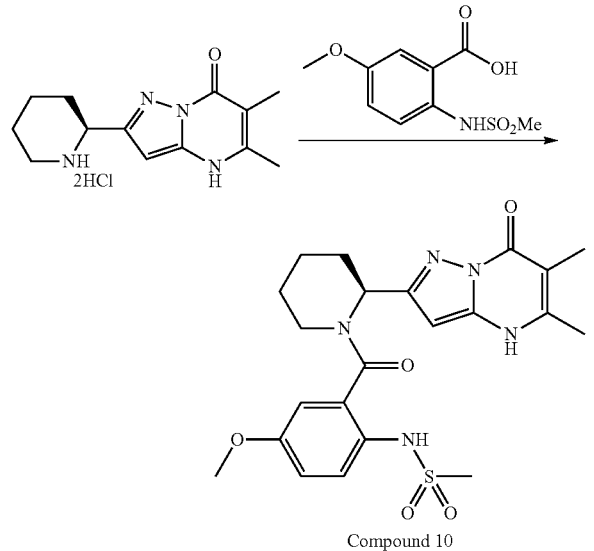

Compound 10

HATU (230.1 mg, 0.605 mmol) was added to a solution of 5-methoxy-2-(methylsulfonamido)benzoic acid (intermediate 9) (129.2 mg, 0.527 mmol) in 4 mL of anhydrous DMF at room temperature. After 15 min of stirring, intermediate 6 (128.4 mg, 0.403 mmol) was added followed immediately by triethylamine (0.20 mL, 1.43 mmol). Reaction mixture stirred at room temperature for 18 hours under argon. Mixture was then poured into 40 mL of H$_2$O and extracted three times with 40 mL of ethyl acetate. The combined organic layers were washed with 80 mL Brine, dried (MgSO$_4$), filtered, and concentrated under reduced pressure leaving a residue. Product was purified by silica gel column chromatography (0-10% Methanol in Dichloromethane) and then prep HPLC (15-100% Acetonitrile (with 0.1% trifluoroacetic acid) in water (with 0.1% trifluoroacetic acid)) to yield compound 10 (56 mg, 30%) as a white solid, trifluoroacetate salt, after lyophilization.

$^1$H-NMR (CDCl$_3$, 300 MHz): δ 8.62 (s, 1H), 7.44 (d, J=9.3 Hz, 1H), 7.01-6.91 (m, 2H), 6.02 (s, 1H), 5.77 (s, 1H), 4.15 (br s, 2H), 3.85 (s, 3H), 3.49 (m, 2H), 3.32 (s, 3H), 2.27 (s, 3H), 2.20 (m, 1H), 2.01 (s, 3H), 1.99 (m, 1H), 1.70-1.25 (m, 3H)

LCMS m/z [M+H]$^+$ C$_{22}$H$_{27}$N$_5$O$_5$S requires: 474.17. Found 474.04

HPLC Tr (min), purity %: 17.3, 99%

Compound 11

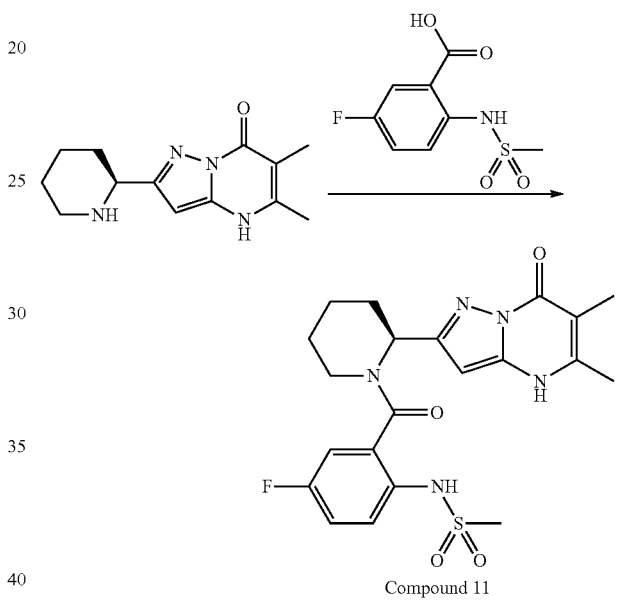

Compound 11

HATU (105.8 mg, 0.278 mmol) was added to a solution of 5-fluoro-2-(methylsulfonamido)benzoic acid (57.1 mg, 0.246 mmol) in 3 mL of anhydrous DMF at room temperature. After 15 min of stirring, intermediate 6 (44.8 mg, 0.182 mmol) was added followed immediately by triethylamine (0.040 mL, 0.288 mmol). Reaction mixture stirred at room temperature for 24 hours under argon. Mixture was then poured into a mixture of 40 mL of 1:1 water/brine and extracted three times with 40 mL of ethyl acetate. The combined organic layers were washed with 50 mL of 1:1 water/brine, dried (MgSO$_4$), filtered, and concentrated under reduced pressure leaving a residue. Product was purified by silica gel column chromatography (0-10% Methanol in Dichloromethane) and then prep HPLC (15-100% Acetonitrile (with 0.1% trifluoroacetic acid) in water (with 0.1% trifluoroacetic acid)) to yield compound 11 (61 mg, 58%) as a white solid, trifluoroacetate salt, after lyophilization.

$^1$H-NMR (CDCl$_3$, 300 MHz): δ 8.89 (s, 1H), 7.49 (m, 1H), 7.18-7.10 (m, 2H), 6.01 (s, 1H), 5.81 (s, 1H), 3.67 (br s, 2H), 3.50 (m, 2H), 3.37 (s, 3H), 2.27 (s, 3H), 2.22 (m, 1H), 2.02 (s, 3H), 2.00 (m, 1H), 1.70-1.25 (m, 3H)

LCMS m/z [M+H]$^+$ C$_{21}$H$_{24}$FN$_5$O$_4$S requires: 462.15. Found 462.04

HPLC Tr (min), purity %: 18.0, 99.7%

Compound 12

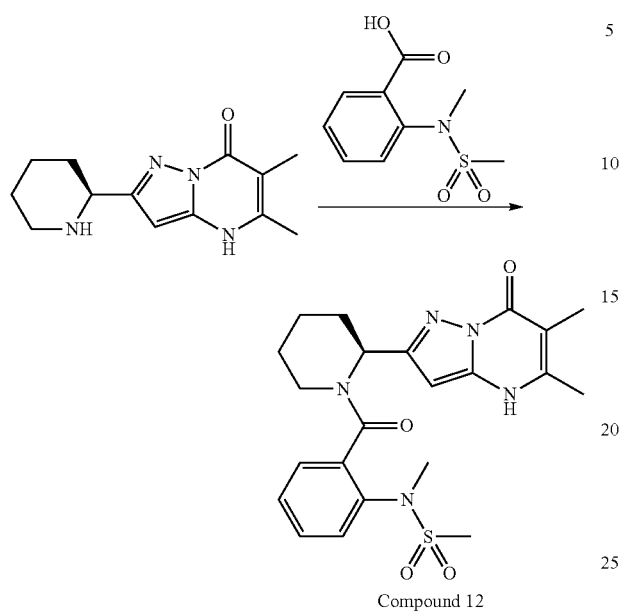

Compound 12

HATU (114.9 mg, 0.302 mmol) was added to a solution of 2-(N-methylmethylsulfonamido)benzoic acid (61.1 mg, 0.268 mmol) in 4 mL of anhydrous DMF at room temperature. After 15 min of stirring, intermediate 6 (49.5 mg, 0.201 mmol) was added followed immediately by triethylamine (0.042 mL, 0.300 mmol). Reaction mixture stirred at room temperature for 18 hours under argon. Mixture was then poured into 40 mL of H$_2$O and extracted three times with 40 mL of ethyl acetate. The combined organic layers were washed with 80 mL 1:1 water/Brine, dried (MgSO$_4$), filtered, and concentrated under reduced pressure leaving a residue. Product was purified by silica gel column chromatography (0-10% Methanol in Dichloromethane) and then prep HPLC (15-100% Acetonitrile (with 0.1% trifluoroacetic acid) in water (with 0.1% trifluoroacetic acid)) to yield compound 12 (34.2 mg, 30%) as a white solid, trifluoroacetate salt, after lyophilization.

$^1$H-NMR (CDCl$_3$, 300 MHz): δ 7.51-7.34 (m, 4H), 6.37 (s, 1H), 6.10 (s, 1H), 4.38 (br s, 1H), 3.53 (d, J=12.9 Hz, 1H), 3.32 (s, 3H), 3.07 (s, 3H) 3.06 (m, 1H), 2.59 (d, J=14.1 Hz, 1H), 2.35 (s, 3H), 2.06 (s, 3H), 1.94 (m, 1H), 1.72-1.50 (m, 4H)

LCMS m/z [M+H]$^+$ C$_{22}$H$_{27}$N$_5$O$_4$S requires: 458.18. Found 458.03

HPLC Tr (min), purity %: 17.3, 96%

Compound 13

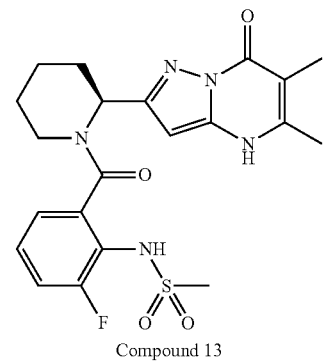

Compound 13

HATU (180 mg, 0.473 mmol) was added to a solution of 3-fluoro-2-(methylsulfonamido)benzoic acid (Intermediate 12) (95.3 mg, 0.409 mmol) in 4.5 mL of anhydrous DMF at room temperature. After 20 min of stirring, intermediate 6 (99.9 mg, 0.313 mmol) was added followed immediately by triethylamine (0.15 mL, 1.09 mmol). Reaction mixture stirred at room temperature overnight under argon. Mixture was then poured into 40 mL of 3:1 H$_2$O:brine and extracted three times with 40 mL of ethyl acetate. The combined organic layers were washed with 50 mL of water and 30 mL of Brine, dried (MgSO$_4$), filtered, and concentrated under reduced pressure leaving a residue. Product was purified by silica gel column chromatography (0-10% Methanol in Dichloromethane) and then prep HPLC (15-100% Acetonitrile (with 0.1% trifluoroacetic acid) in water (with 0.1% trifluoroacetic acid)) to yield compound 13 (61 mg, 34%) as a white solid, trifluoroacetate salt, after lyophilization.

$^1$H-NMR (CDCl$_3$, 300 MHz): δ 9.38 (s, 1H) 7.31-7.15 (m, 3H), 6.09 (s, 1H), 5.97 (s, 1H), 4.33 (br s, 1H), 3.61 (s, 3H), 3.33 (m, 2H), 2.43 (m, 1H), 2.26 (m, 1H), 2.21 (s, 3H) 2.04 (s, 3H) 1.68 (m, 1H), 1.50 (m, 1H), 1.24 (m, 1H)

LCMS m/z [M+H]$^+$ C$_{21}$H$_{24}$FN$_5$O$_4$S requires: 462.15. Found 462.09

HPLC Tr (min), purity %: 5.08, 99%

Compound 14

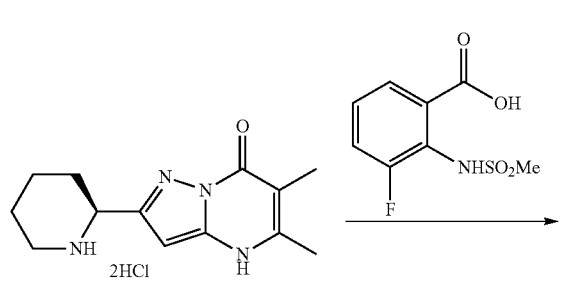

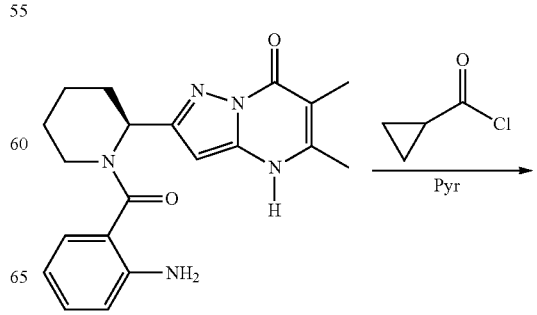

Compound 14

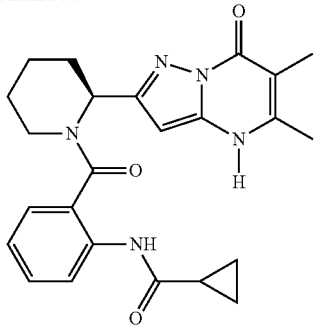

To a solution of compound 3 (6 mg, 0.016 mmol) in Pyridine (1.0 mL) was added Cyclopropanecarbonyl chloride (17 mg, 0.16 mmol) at RT. The reaction was completed in 5 mins. The volatile were removed under reduced pressure at 40° C. and the resulting residue was purified by preparative HPLC (MeCN in H$_2$O with a gradient from 0% to 95%) to afford compound 14 (5 mg, 71%) as a white powder after lyophilization.

$^1$H-NMR (CD$_3$CN, 300 MHz): δ 10.22 (s, 1H), 7.95-7.86 (m, 2H), 7.44 (s, 1H), 6.78-6.43 (m, 2H), 5.47 (s, 1H), 2.82 (mc, 5H), 2.58 (s, 3H), 2.37-2.15 (m, 4H), 1.40 (s, 3H), 1.35-1.30 (mc, 5H).

LCMS m/z [M+H]$^+$ C$_{24}$H$_{27}$N$_5$O$_3$ requires: 434.50. Found 433.98

HPLC Tr (min), purity %: 2.19, 98%

Compound 15

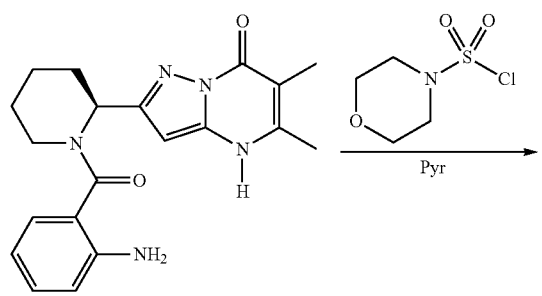

Compound 15

To a solution of compound 3 (13 mg, 0.036 mmol) in pyridine (1.0 mL) was added 4-Morpholinesulfonyl chloride (67 mg, 0.36 mmol) at RT, The reaction was heated at 70° overnight. The volatile were removed under reduced pressure at 40° C. and the resulting residue was purified by preparative HPLC (MeCN in H$_2$O with a gradient from 0% to 95%) to afford compound 15 (12 mg, 67%) as a white powder after lyophilization.

$^1$H-NMR (CD$_3$CN, 300 MHz): δ 9.84 (s, 1H), 7.64 (d, J=9.3 Hz, 1H), 7.46 (d, J=8.1 Hz, 1H), 7.22 (s, 1H), 5.98 (s, 1H), 3.60 (t, J=4.5 Hz, 1H), 3.22 (t, J=4.5 Hz, 1H), 2.32-2.30 (m, 4H), 2.05 (s, 3H), 1.96 (s, 3H), 1.75-1.64 (mc, 5H).

LCMS m/z [M+H]$^+$ C$_{24}$H$_{30}$N$_6$O$_5$S requires: 515.60. Found 515.04

HPLC Tr (min), purity %: 2.23, 98%

Compound 16

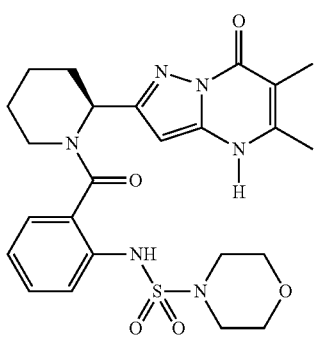

Compound 16

To a solution of 2-Acetimido-5-fluorobenzoic acid (63 mg, 0.32 mmol) in DMF (4 mL) was added HATU (134 mg, 0.35 mmol) the solution stirred under N$_2$ at RT for 10 mins. To the above solution was added Intermediate 6 (40 mg, 0.16 mmol) and Et$_3$N (0.05 mL). The reaction mixture was stirred at RT for 5 h. The volatile were removed under reduced pressure at 40° C. and the resulting residue was purified by preparative HPLC (MeCN in H$_2$O with a gradient from 0% to 95%) to afford compound 16 (5 mg, 7%) as a white powder after lyophilization.

$^1$H-NMR (CD$_3$CN, 300 MHz): δ 12.21 (s, 1H), 7.50 (s, 1H), 7.26-7.24 (m, 2H), 6.87 (s, 1H), 5.93 (s, 1H), 3.32-3.30 (m, 4H), 2.29 (s, 3H), 2.06 (s, 3H), 1.74 (s, 3H), 1.60-1.43 (mc, 5H).

LCMS m/z [M+H]$^+$ C$_{22}$H$_{24}$FN$_5$O$_3$ requires: 426.46. Found 426.01

HPLC Tr (min), purity %: 2.14, 98%

Compound 17

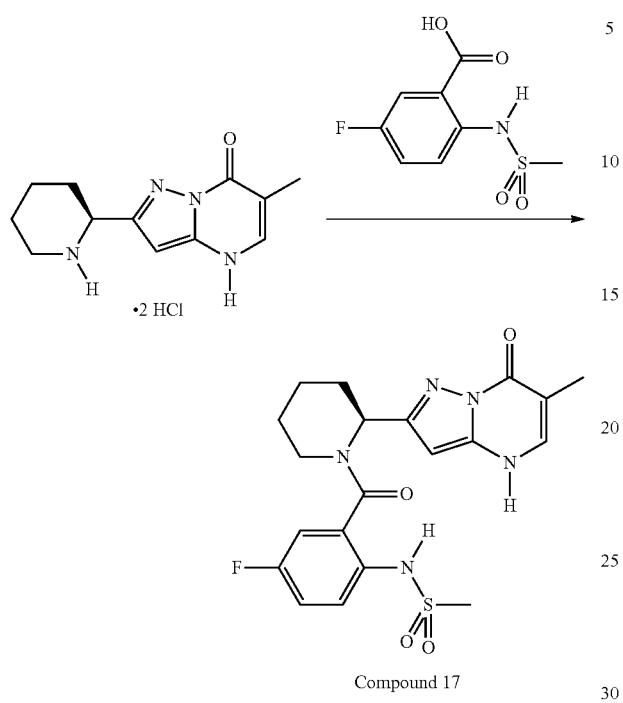

HATU (707 mg, 0.186 mmol) was added to a solution of 5-fluoro-2-(methylsulfonamido)benzoic acid (376 mg, 0.1.61 mmol) in DMF (5 mL) and stirred 15 min. Intermediate 13 (395 mg, 1.24 mmol) and triethylamine (865 µL, 6.20 mmol) were added and the mixture was stirred overnight. The mixture was poured into H$_2$O (50 mL) and extracted with ethyl acetate (3×50 mL). The combined organic layers were washed with saturated sodium chloride solution (50 mL) and dried over MgSO$_4$. Purification via SiO$_2$ column chromatography (80 g SiO$_2$ Combiflash HP Gold Column, 0-10% MeOH/CH$_2$Cl$_2$) followed by preparative HPLC (5-100% MeCN/H$_2$O, 0.1% trifluoroacetic acid modifier) afforded Compound 17 (23.6 mg, 4%) as a white solid (TFA salt).

$^1$H NMR (CD$_3$OD, 300 MHz) 7.49 (m, 1H), 7.24 (m, 2H), 6.05 (br m, 114), 3.44 (m, 1H), 3.31 (s, 3H), 2.43 (br m, 1H), 2.12 (s, 3H), 1.45 (br m, 5H);

LCMS m/z [M+H]$^+$ 448;

HPLC (RP: 6-98% MeCN—H$_2$O gradient, 0.05% TFA modifier) t$_R$=3.854 min (>95% purity @ 254 nM).

Compound 18

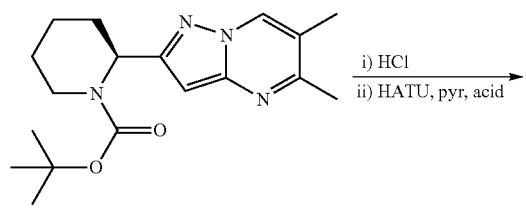

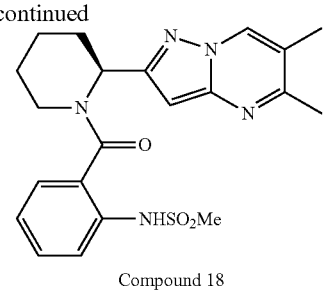

Compound 18

The starting material intermediate 15 (0.04 g, 0.121 mmol), was dissolved in anhydrous 1,4-dioxane (2 ml). With stirring under nitrogen 4N HCl in dioxane (4 ml) was added via syringe. The reaction was stirred for 2 hours at room temperature while monitoring by LC/MS. When the reaction was complete solvent was removed by rotary evaporation to provide a residue that was then dissolved in DMF (3 mL). (Yield~28 mg, 0.121 mmol, 100%). MS: [232, M$^{+1}$]. In a separate reaction vessel, 0-Benzoic acid methanesulfamide (0.039 g, 0.183 mmol), HATU (0.116 g, 0.305 mmol), and pyridine (29 ul, 0.366 mmol), were dissolved in anhydrous DMF (5 ml). The reaction mixture was stirred under nitrogen for 2 hours to activate the acid. When activation was approximately 80% complete by LC/MS (2 hr) the piperidine solution in DMF (0.028 g, 0.121 mmol), along with DIPEA (86 ul, 0.488 mmol) were added. The reaction was stirred overnight while monitoring by LC/MS. Solvents were removed by rotary evaporation. The residue was taken up in DCM (100 ml) and washed with water (5×100 ml). The organic layer was collected, dried over MgSO$_4$, filtered and evaporated. The residue was taken up in DCM and columned on silica gel using a gradient of 0 to 10% MeOH to provide compound 18: DCM. (Yield~32.45 mg, 0.076 mmol, 62%).

$^1$H-NMR (CD$_3$CN, 300 MHz): δ 1.50 (m, 2H), 1.74 (m, 1H), 2.20 (bs, 1H), 2.31 (s, 3H), 2.43 (s, 1H), 2.99 (s, 3H), 3.10 (m, 1H), 3.35 (m, 1H), 6.22-6.46 (m, 1H), 7.25-7.70 (m, 4H), 8.80-9.00 (m, 1H).

Compound 19

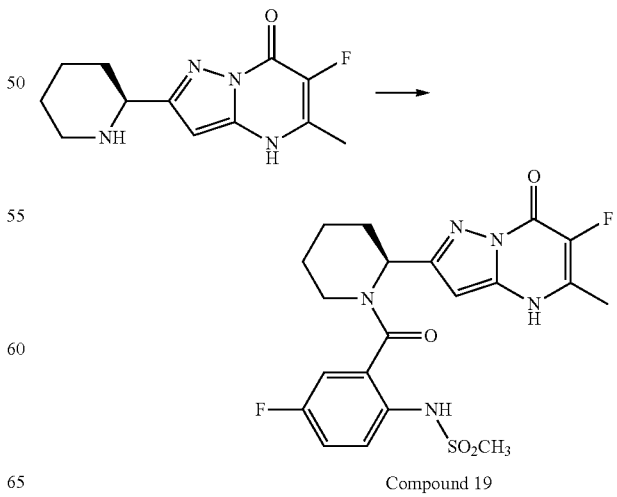

The piperidine starting material was purchased from Asinex Ltd. Using the general method above for compound 11, 0.035 g (19%) colourless powder of compound 19 was obtained.

¹H-NMR (CD₃CN, 400 MHz): δ 7.34 (s 1H), 7.08 (d, 2H, J=5.6 Hz), 5.88 (s 1H), 4.86 (m, 1H), 4.33 (s, br. 1H), 4.33 (s, br. 1H), 3.28 (s, br. 1H), 3.26 (s, br. 1H), 3.06 (s, 3H), 2.4-1.4 (m, 4H).

¹⁹F-NMR (CH₃CN, 400 MHz): δ−75.97

LCMS m/z [M+H]⁺ C₂₀H₂₁F₂N₅O₄S requires: 465.47. Found 466.03

HPLC Tr (min), purity %: 2.09, 100%.

Compound 20: N-{2-[3-(5,6-Dimethyl-7-oxo-4,7-dihydro-pyrazolo[1,5-a]pyrimidin-2-yl)-morpholine-4-carbonyl]-phenyl}-methanesulfonamide

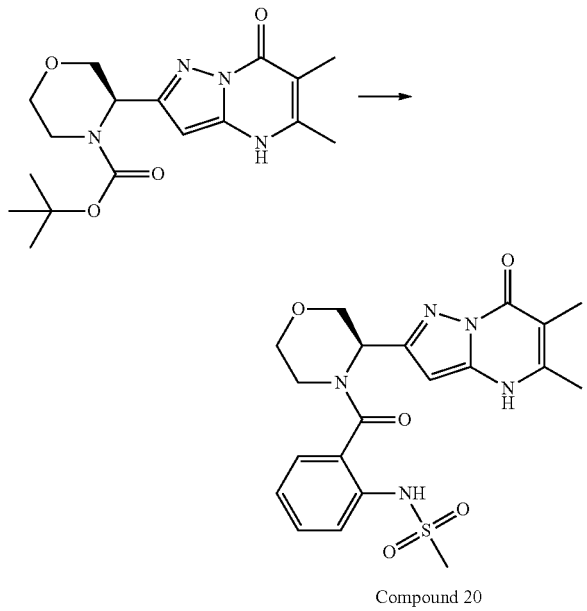

Compound 20

Dissolved intermediate 19 (77 mg, 0.22 mmol) in MeOH (0.5 mL). Added 4N HCl in dioxane (3 mL) and stirred for 1 hr. Concentrated under reduced pressure. Dried under high vacuum. Mixed 2-methanesulfonylamino-benzoic acid (72 mg, 0.335 mmol) with HATU (127 mg, 0.335 mmol) and dissolved in anhydrous DMF (2 mL). Stirred for 30 minutes. Dissolved 5,6-Dimethyl-2-morpholin-3-yl-4H-pyrazolo[1,5-a]pyrimidin-7-one hydrochloride in anhydrous DMF (2 mL) and added to the reaction. Added triethylamine (92 uL, 0.66 mmol) and stirred for 12 hrs. Diluted with ethyl acetate and washed with 5% aqueous citric acid solution and saturated aqueous sodium chloride solution. Dried organic extract over anhydrous sodium sulfate and then concentrated under reduced pressure. Purified with Combiflash silica gel column (linear gradient from 0-10% MeOH in DCM). Final purification with C₁₈ Prep HPLC to provide compound 20 (41 mg, 42%).

¹H NMR (CD₃OD, 300 MHz): δ 7.48-7.28 (m, 4H), 6.15 (s, 1H), 5.80 (bs, 1H), 4.46 (m, 1H), 4.02-3.68 (m, 5H), 3.14 (s, 3H), 2.38 (s, 3H), 2.08 (s, 3H).

LCMS m/z [M+H]⁺ 446.1

Compound 21 (cis)

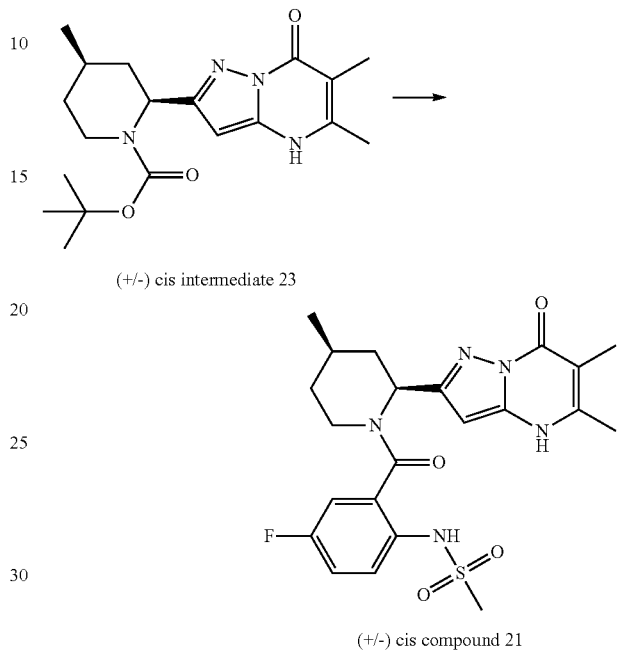

Dissolved (+/−)-cis-intermediate 23 in MeOH (1 mL). Added 4N HCl in dioxane (3 mL) and stirred for 2 hr. Concentrated under reduced pressure. Dried under high vacuum. Mixed 5-Fluoro-2-methanesulfonylamino-benzoic acid (63 mg, 0.272 mmol) with HATU (113 mg, 0.296 mmol) and dissolved in anhydrous DMF (2 mL) in a separate flask. Stirred for 30 minutes. Dissolved product from above, hydrochloride (89 mg, 0.247 mmol) in anhydrous DMF (2 mL) and added to the benzoic acid mixture. Added triethylamine (103 uL, 0.741 mmol) and stirred for 16 hrs. Concentrated under reduced pressure. Purified with C₁₈ Prep HPLC to provide compound 21 as a mixture of cis isomers (61 mg, 52%).

¹H NMR (CD₃OD, 300 MHz): (+,−)cis: δ 7.51 (m, 1H), 7.21 (m, 2H), 6.09 (s, 1H), 5.00 (bs, 1H), 3.66 (m, 2H), 3.11 (s, 3H), 2.38 (m, 3H), 2.27 (m, 1H), 2.09 (s, 3H), 2.04 (m, 3H), 1.37 (m, 1H), 0.92 (d, J=6.3 Hz, 3H).

LCMS m/z [M+H]⁺ 476.1

Compound 22 (trans)

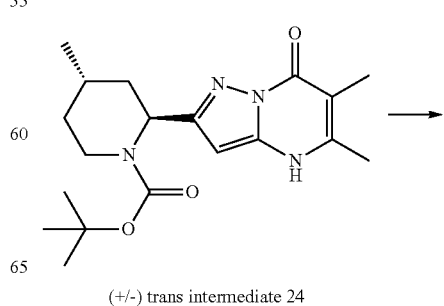

(+/−) trans intermediate 24

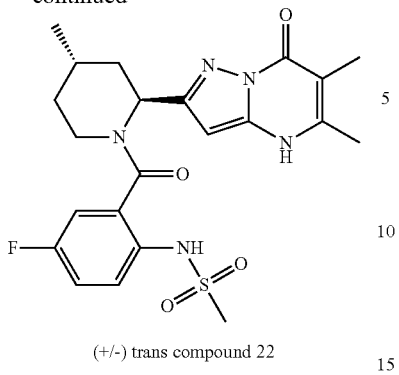

(+/−) trans compound 22

Dissolved (+/−) trans intermediate 24 in MeOH (1 mL). Added 4N HCl in dioxane (3 mL) and stirred for 2 hr. Concentrated under reduced pressure. Dried under high vacuum. Mixed 5-Fluoro-2-methanesulfonylamino-benzoic acid (33 mg, 0.143 mmol) with HATU (59 mg, 0.156 mmol) and dissolved in anhydrous DMF (2 mL) in a separate flask. Stirred for 30 minutes. Dissolved product from above, hydrochloride (47 mg, 0.13 mmol) in anhydrous DMF (2 mL) and added to the benzoic acid mixture. Added triethylamine (54 uL, 0.39 mmol) and stirred for 16 hrs. Concentrated under reduced pressure. Purified with $C_{18}$ Prep HPLC. Yield the trans product compound 22 as a mixture of trans isomers (46 mg, 74%).

$^1$H NMR (CD$_3$OD, 300 MHz): (+,−)trans: δ 7.49 (m, 1H), 7.25 (m, 2H), 6.12 (m, 1H), 4.95-4.85 (m, 1H), 3.47 (m, 2H), 3.11 (s, 3H), 2.45 (m, 1H), 2.38 (m, 3H), 2.09 (s, 3H), 1.73-1.50 (m, 3H), 1.30 (m, 1H), 0.99 (d, J=5.7 Hz, 3H).

LCMS m/z [M+H]$^+$ 476.1

Compound 23 and Compound 24. Isomerically Pure Enantiomers of Compound 22 Racemic Mixture Trans mixture compound 22 (38 mg) was resolved using Chiralpak AD-H column eluting with heptane/IPA (7:3) to provide the isomer A (first peak), Compound 23 (9.4 mg), followed by the isomer B (second peak), Compound 24 (10.4 mg)

Compound 25: 5,6-Dimethyl-2-(S)-piperidin-2-yl-4H-pyrazolo[1,5-a]pyrimidin-7-one

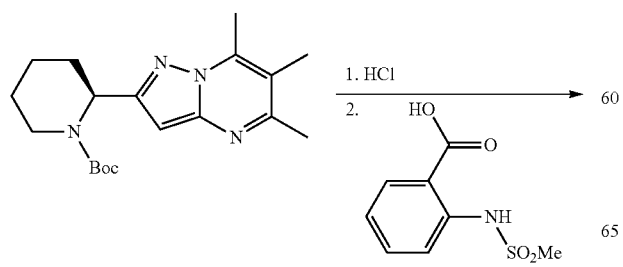

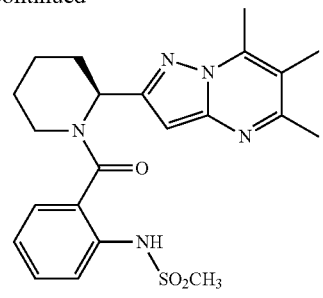

Compound 25

Intermediate 25 (0.35 g, 1.0 mM) was dissolved in HOAc (20 ml) and conc. aequ. HCl (2 ml) and stirred 2 h. The solution was concentrated under reduced pressure to yield the unprotected intermediate as an oil (0.45 g). The sulphonamide (0.2 g, 0.93 mM) was suspended in DMF (2 ml) and pyridine was added (0.3 ml) followed by HATU (0.26 g, 0.93 mM). The clear solution was stirred for 2 h at RT. A solution of above intermediate in DMF and DIPEA (added dropwise to adjust pH>8) was then added and stirred for 6 h. Preparative HPLC (0-95% MeCN in water) afforded compound 25 was a white powder (0.083 g, 20%).

$^1$H-NMR (DMSO, 300 MHz): δ 8.00 (s, 1H), 7.51 (m, 3H), 7.30 (m, 1H), 6.5 (s, 1H), 6.10 (br s, 3H), 2.98 (s, 3H), 2.83 (s, 3H), 2.59 (s, 3H), 2.33 (s, 3H), 1.99-1.95 (m, 1H), 1.74-1.60 (m, 4H).

LCMS m/z [M+H]$^+$ C$_{22}$H$_{27}$N$_5$O$_3$S requires: 441.55. Found 442.13

HPLC Tr (min), purity %: 2.76, 95%.

Compound 26

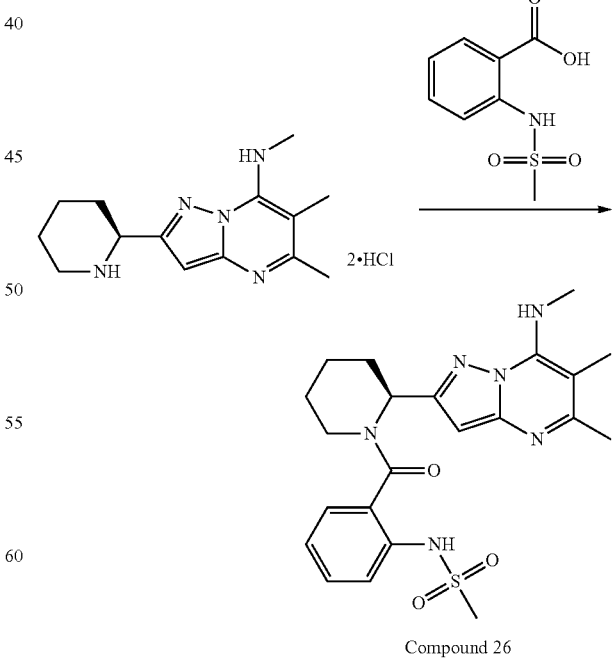

Compound 26

O-Benzoic acid methanesulfonamide (0.060 g, 0.28 mmol), HATU (0.213 g, 0.56 mmol), and pyridine (68 ul, 0.84 mmol), were dissolved in anhydrous DMF (8 ml). The reaction was stirred under nitrogen for 2 hours to activate the acid. When activation was approximately 80% complete by LC/MS (2 hr) the piperidine intermediate 28 (0.073 g, 0.28 mmol), along with DIPEA (96 ul, 0.56 mmol) were added dissolved in DMF (4 ml). The reaction was stirred overnight while monitoring by LC/MS. Solvents were removed by rotary evaporation. The residue was taken up in DCM (100 ml) and washed with water (5×100 ml). The organic layer was collected, dried over MgSO$_4$, filtered and evaporated. The residue was taken up in DCM and columned on silica gel using a gradient of 0 to 10% MeOH: DCM to afford compound 26 (65 mg, 0.143 mmol, 51%).

$^1$H-NMR (CD$_3$CN, 300 MHz): δ 1.58 (m, 2H), 1.75 (m, 2H), 2.22 (s, 1H), 2.40 (s, 3H), 2.42 (s, 1H), 2.44 (s, 3H), 3.01 (m, 4H), 3.39 (m, 3H), 6.20 (s, 1H), 6.37 (m, 1H), 7.25-7.60 (m, 4H), 8.36 (bs, 1H).

Compound 27

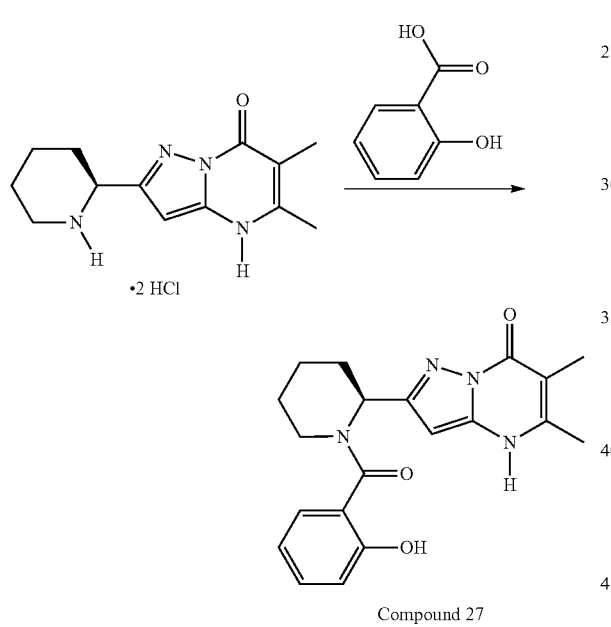

Compound 27

HATU (170 mg, 0.45 mmol) was added to a solution of salicylic acid (54 mg, 0.39 mmol) in DMF (5 mL) and stirred 15 min. Intermediate 6 (95 mg, 0.30 mmol) and triethylamine (124 µL, 0.89 mmol) were added and the mixture was stirred overnight. The mixture was poured into H$_2$O (50 mL) and extracted with ethyl acetate (3×50 mL). The combined organic layers were washed with saturated sodium chloride solution (50 mL) and dried over MgSO$_4$. The material in THF/MeOH/H$_2$O (3:2:1, 5 mL) was treated with LiOH (250 mg) and stirred 2 h. The mixture was acidified with AcOH (pH ~2) and the mixture was poured into H$_2$O (50 mL) and extracted with ethyl acetate (3×50 mL). The combined organic layers were washed with saturated sodium chloride solution (50 mL) and dried over MgSO$_4$. Purification via SiO$_2$ column chromatography (40 g SiO$_2$ Combiflash HP Gold Column, 0-10% MeOH/CH$_2$Cl$_2$) followed by preparative HPLC (5-100% MeCN/H$_2$O, 0.1% trifluoroacetic acid modifier) afforded Compound 27 (9.4 mg, 9%) as a white solid (TFA salt).

$^1$H NMR (CD$_3$OD, 300 MHz) 7.25 (m, 2H), 6.89 (m, 2H), 6.11 (br s, 1H), 2.62 (br m, 1H), 2.39 (s, 3H), 2.09 (s, 3H), 1.94 (m, 1H), 1.60 (br m, 5H);
LCMS m/z [M+H]$^+$ 367;
HPLC (RP: 6-98% MeCN—H$_2$O gradient, 0.05% TFA modifier) t$_R$=4.430 min (>95% purity @ 254 nM).

Compound 28

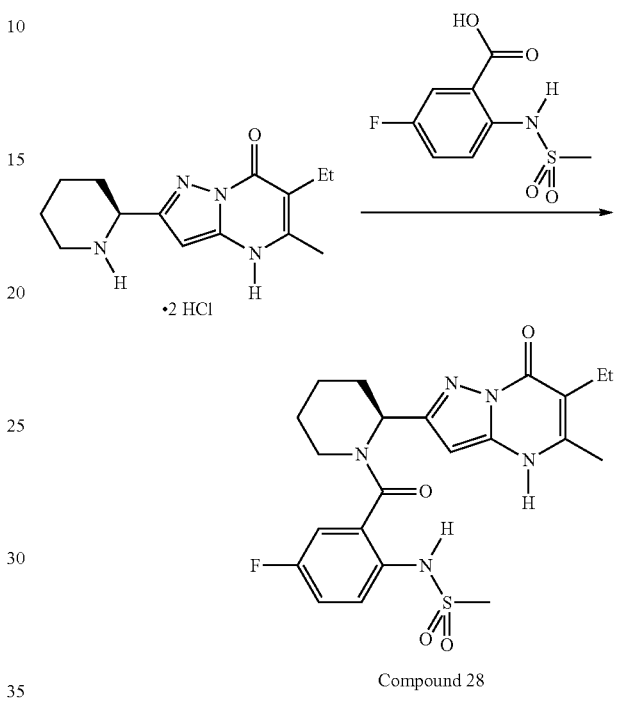

Compound 28

HATU (137 mg, 0.36 mmol) was added to a solution of 5-fluoro-2-(methylsulfonamido)benzoic acid (73 mg, 0.31 mmol) in DMF (5 mL) and stirred 15 min. Intermediate 29 (87 mg original Boc material, 0.24 mmol) and triethylamine (100 µL, 0.72 mmol) were added and the mixture was stirred overnight. The mixture was poured into H$_2$O (50 mL) and extracted with ethyl acetate (3×50 mL). The combined organic layers were washed with saturated sodium chloride solution (50 mL) and dried over MgSO$_4$. Purification via SiO$_2$ column chromatography (4 g SiO$_2$ Combiflash HP Gold Column, 0-10% MeOH/CH$_2$Cl$_2$) followed by preparative HPLC (5-100% MeCN/H$_2$O, 0.1% trifluoroacetic acid modifier) afforded Compound 28 (5.3 mg, 5%) as a white solid (TFA salt).
LCMS m/z [M+H]$^+$ 476;
HPLC (RP: 6-98% MeCN—H$_2$O gradient, 0.05% TFA modifier) t$_R$=3.867 min (>95% purity @ 254 nM).

Compound 29

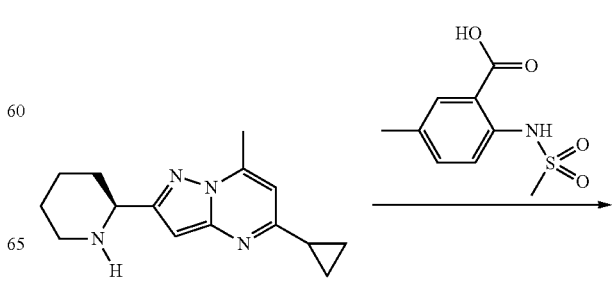

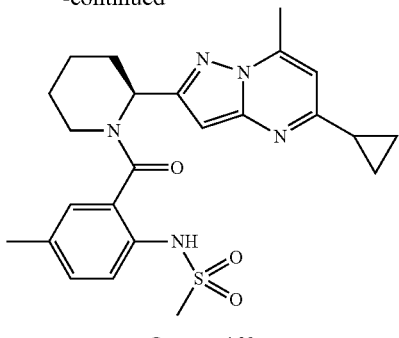

Compound 29

2-methanesulfonamido-5-methylbenzoic acid (1.0 g, 4.36 mmol), HATU (1.5 g, 5.2 mmol) were dissolved in anhydrous DMF (8 ml). After activation for 1 hour, to the above solution was added intermediate 31 (0.32 g, 1.25 mmol) and triethylamine (0.17 ml). The reaction was stirred under nitrogen for 5 hours. Solvents were removed by rotary evaporation. The residue purified with preparatory HPLC to provide compound 29. (Yield 0.56 g, 90%).

$^1$H-NMR (DMSO, 400 MHz): δ 7.40-7.31 (m, 3H), 6.72 (s, 1H), 6.27 (s 1H), 2.92 (s, 3H), 2.36 (s, 2H), 2.10-1.90 (m, 2H), 1.96 (s, 3H), 1.67-1.48 (m, 3H), 1.08-1.02 (m, 2H).

LCMS m/z [M+H]$^+$ $C_{24}H_{29}N_6O_3S$ requires: 468.58. Found 468.20

HPLC Tr (min), purity %: 2.92, 98%.

Intermediate 32

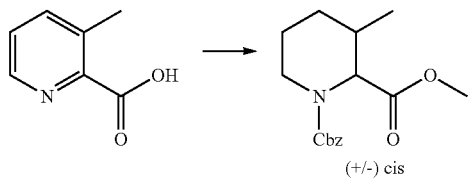

3-Methylpicolinic acid (10 g, 72.9 mmol) in EtOH (80 mL) and water (80 mL) was treated with PtO2 (4 g) and placed under a H2 atmosphere (60 psi). The mixture was shaken vigorously for 18 h, and then the PtO2 was degassed via vacuum for 30 min. The mixture was filtered through a Celite pad, which was washed with EtOH (3 50 mL) and H2O (3 80 mL). The solution was concentrated to afford (+/−) cis-3-methylpiperidine-2-carboxylic acid, which was used without further purification.

(+/−)-Cis-3-methylpiperidine-2-carboxylic acid (10.4 g, 72.9 mmol) in 1,4-dioxane (200 mL) and 1 N NaOH (218 mL, 219 mmol) was treated with CBzCl (15.4 mL, 109 mmol) and stirred for 18 h. The mixture concentrated and the resulting solid was suspended in EtOAc (200 mL) and the mixture was filtered. The solids were washed with EtOAc (3 50 mL) and the solution was dried over MgSO4. The solution was concentrated to afford (+/−)-cis-1-(benzyloxycarbonyl)-3-methylpiperidine-2-carboxylic acid, which was used without further purification.

(+/−) Cis-1-(benzyloxycarbonyl)-3-methylpiperidine-2-carboxylic acid (20.2 g, 72.9 mmol) in MeOH (300 mL) was cooled to 0° C. and treated with SOCl2 (13.3 mL, 182 mmol). The mixture was warmed to ambient temperature and stirred for 18 h. The mixture concentrated. Crude material was purified with silica gel column (0-20% EtOAc in hexanes) to give intermediate 32. Yield: 2.6 g, 8%

$^1$H NMR (400 MHz, CD$_3$OD): δ 7.34 (m, 5H), 5.18-5.03 (m, 2H), 4.74 (d, J=4.8 Hz, 1H), 3.99 (m, 1H), 3.68 (m, 3H), 3.31 (m, 1H), 1.89 (m, 1H), 1.75 (m, 1H), 1.62-1.45 (m, 2H), 1.33 (m, 1H), 1.02 (m, 3H).

LC/MS (m/z): 291.9 [M+H]$^+$

Intermediate 33

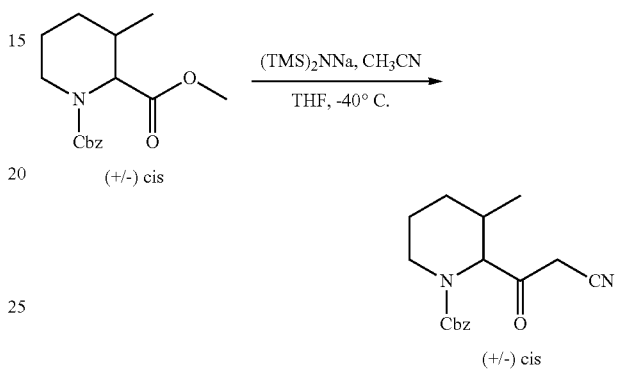

Dissolved anhydrous acetonitrile (1.4 mL, 26.6 mmol) in anhydrous THF (10 mL) and stirred under Argon in a dry ice/acetonitrile bath (−40° C.). Added 1N sodium bis(trimethylsilyl)amide in THF (17.7 mL, 17.7 mmol) dropwise over 20 mins. Resulting reaction mixture was stirred for 1 hr. under same conditions.

Dissolved intermediate mixture of isomers 32 (2.6 g, 8.8 mmol) in anhydrous THF (10 mL) and stirred under Argon at −78° C. which was then transferred to reaction mixture dropwise. Reaction was stirred for 6 hrs. under Argon in at −40° C. Added acetic acid (2 mL, 34.4 mmol) and the reaction was slowly warmed to r.t. Diluted with ethyl acetate and washed with 5% aqueous citric acid solution, saturated aqueous sodium bicarbonate solution and saturated aqueous sodium chloride solution. Dried organic extract over anhydrous sodium sulfate and then concentrated under reduced pressure. Crude residue was purified with silica gel column (linear gradient from 0-30% EtOAc in hexanes) to yield intermediate 33 as a mixture of isomers (1.2 g, 45%).

$^1$H NMR (400 MHz, CD$_3$OD): δ 7.36 (m, 5H), 5.15 (m, 2H), 4.78 (m, 1H), 3.96 (m, 1H), 3.05-2.90 (m, 1H), 1.88 (m, 1H), 1.72 (m, 1H), 1.60-1.49 (m, 3H), 1.08 (m, 3H).

LC/MS (m/z): 300.9 [M+H]$^+$

Intermediate 34

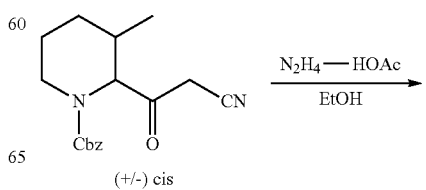

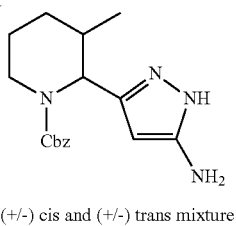

(+/−) cis and (+/−) trans mixture

Dissolved intermediate isomer mixture 33 (1.2 g, 4 mmol) in ethanol (40 mL). Added HOAc (1.8 mL, 32 mmol) and then hydrazine hydrate (1.2 mL, 16 mmol). Stirred at room temperature for 9 hrs. Added more HOAc (1 mL) and hydrazine hydrate (0.6 mL) and stirred for 20 hrs. Concentrated under reduced pressure. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with silica gel column (linear gradient from 0-5% MeOH in DCM) to give a mixture of both (+/−) cis and (+/−) trans products, intermediate 34 (0.9 g, 72%).

$^1$H NMR (400 MHz, CD$_3$OD): δ 7.31 (m, 5H), 5.70-5.50 (m, 1H), 5.15 (m, 3H), 4.04 (m, 1H), 3.05-2.90 (m, 1H), 2.39 (m, 1H), 1.90-1.70 (m, 3H), 1.58-1.38 (m, 3H), 1.11-0.79 (m, 3H).

LC/MS (m/z): 315.1 [M+H]$^+$

Intermediate 35

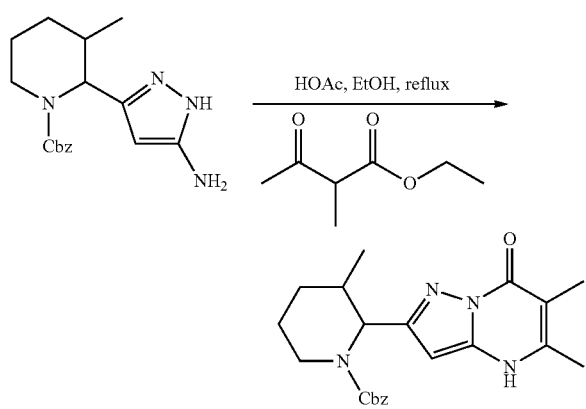

Dissolved intermediate 34 isomer mixture (0.9 g, 2.86 mmol) in EtOH (50 mL). Added HOAc (3.3 mL, 57.2 mmol) and ethyl-2-methyl acetoacetate (2.3 mL, 14.3 mmol). Stirred at reflux for 2 hrs. Concentrated under reduced pressure. Diluted with ethyl acetate and washed with saturated aqueous sodium bicarbonate solution and saturated aqueous sodium chloride solution. Dried organic extract over anhydrous sodium sulfate and then concentrated under reduced pressure. Crude residue was purified with silica gel column (linear gradient from 0-10% MeOH in DCM) to yield intermediate 35 (diastereomeric mixture of cis and trans isomers, 1.1 g, 98%).

$^1$H NMR (400 MHz, CD$_3$OD): δ 7.32 (m, 5H), 5.95-5.82 (m, 1H), 5.39-5.21 (m, 1H), 5.16-5.05 (m, 2H), 4.10 (m, 1H), 3.02-2.78 (m, 1H), 2.36 (m, 3H), 2.09 (m, 3H), 2.00-1.75 (m, 3H), 1.58-1.38 (m, 2H), 1.16-0.85 (m, 3H).

LC/MS (m/z): 395.1 [M+H]$^+$

Compound 30 and 31

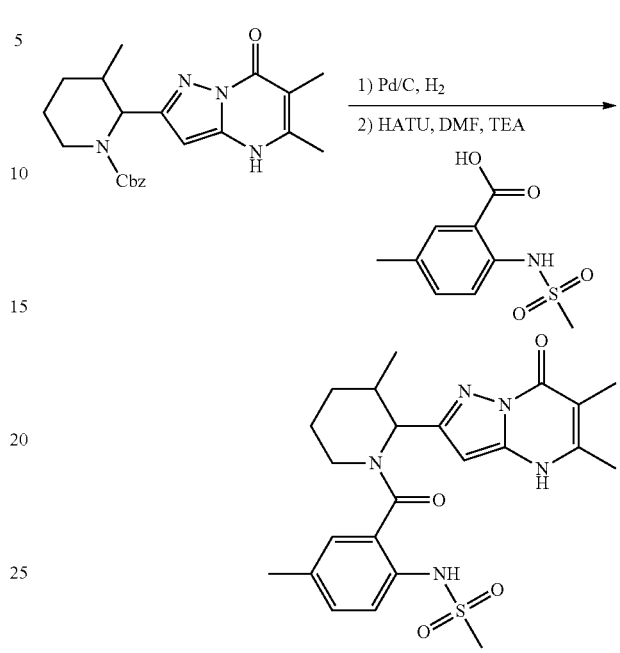

Dissolved intermediate 43 isomer mixture (benzyl 2-(5,6-dimethyl-7-oxo-4,7-dihydropyrazolo[1,5-a]pyrimidin-2-yl)-3-methylpiperidine-1-carboxylate) (50 mg, 0.126 mmol) in MeOH. Added Pd/C and stirred under atmosphere hydrogen for 2 hrs. Filtered reaction through Celite and washed with MeOH. Concentrated under reduced pressure and dried under high vacuum. Mixed 5-methyl-2-(methylsulfonamido)benzoic acid (32 mg, 0.139 mmol) with HATU (63 mg, 0.167 mmol) and dissolved in anhydrous DMF (500 uL). Stirred for 1 hr. Dissolved 5,6-dimethyl-2-(3-methylpiperidin-2-yl)pyrazolo[1,5-a]pyrimidin-7(4H)-one from hydrogenation in anhydrous DMF (500 uL) and added to the reaction. Added triethylamine (384 uL, 2.75 mmol) and stirred for 16 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified crude material with C$_{18}$ Prep HPLC to give compound 30, (9 mg) as the first eluting product, and compound 31 (13 mg) as the second eluting material.

Compound 30, (First Eluting Peak)

$^1$H NMR (400 MHz, CD$_3$OD): δ 7.38-7.26 (m, 3H), 7.12 (m, 1H), 6.12-5.93 (m, 1H), 3.85-3.40 (m, 2H), 3.00 (s, 3H), 3.25-2.80 (m, 1H), 2.38-2.34 (m, 6H), 2.09 (m, 3H), 1.93-1.60 (m, 3H), 1.26 (m, 2H), 1.12 (m, 2H), 0.99-0.87 (m, 3H).

LC/MS (m/z): 472.2 [M+H]$^+$

Compound 31 (Second Eluting Peak)

$^1$H NMR (400 MHz, CD$_3$OD): δ 7.37-7.24 (m, 3H), 6.07 (m, 1H), 3.09 (s, 3H), 2.78 (m, 1H), 2.38 (m, 6H), 2.08 (m, 3H), 1.86 (m, 2H), 1.53 (m, 2H), 1.40 (m, 1H), 1.30 (m, 3H).

LC/MS (m/z): 472.1 [M+H]$^+$

Intermediate 36

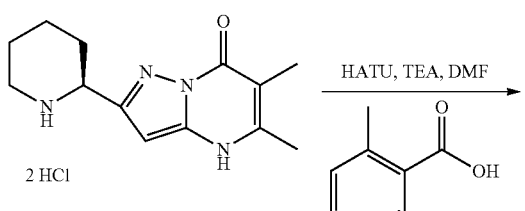

Mixed 2-amino-6-methyl-benzoic acid (24 mg, 0.157 mmol) with HATU (60 mg, 0.157 mmol) and dissolved in anhydrous DMF (500 uL). Stirred for 1 hr. Dissolved intermediate 6 ((S)-5,6-dimethyl-2-(piperidin-2-yl)pyrazolo[1,5-a]pyrimidin-7(4H)-one hydrochloride) (25 mg, 0.078 mmol) in anhydrous DMF (500 uL) and added to the reaction. Added triethylamine (54 uL, 0.39 mmol) and stirred for 16 hrs. Diluted with ethyl acetate and washed with saturated aqueous sodium bicarbonate solution and saturated aqueous sodium chloride solution. Dried organic extract over anhydrous sodium sulfate and then concentrated under reduced pressure to give crude intermediate 36 (19 mg), which was used in the next step without purification.

Compound 32

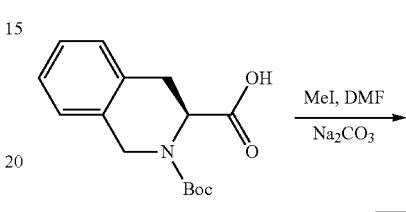

Dissolved (S)-2-(1-(2-amino-6-methylbenzoyl)piperidin-2-yl)-5,6-dimethylpyrazolo[1,5-a]pyrimidin-7(4H)-one (intermediate 36) (19 mg, 0.05 mmol) in anhydrous pyridine (500 uL) and added methanesulfonyl chloride (4.7 uL, 0.06 mmol) and stirred for 16 hrs. Concentrated under reduced pressure. Purified crude material with C$_{18}$ Prep HPLC to give compound 32. Yield: 6.9 mg, 19% over 2 steps.

$^1$H NMR (300 MHz, CDCl$_3$): δ 9.03 (m, 1H), 7.31 (m, 2H), 7.11 (m, 1H), 6.21 (m, 1H), 5.89 (m, 1H), 3.40-3.25 (m, 5H), 2.44-2.25 (m, 8H), 2.04-1.97 (m, 4H), 1.67-1.25 (m, 4H).

LC/MS (n/z): 458.1 [M+H]$^+$

Intermediate 37

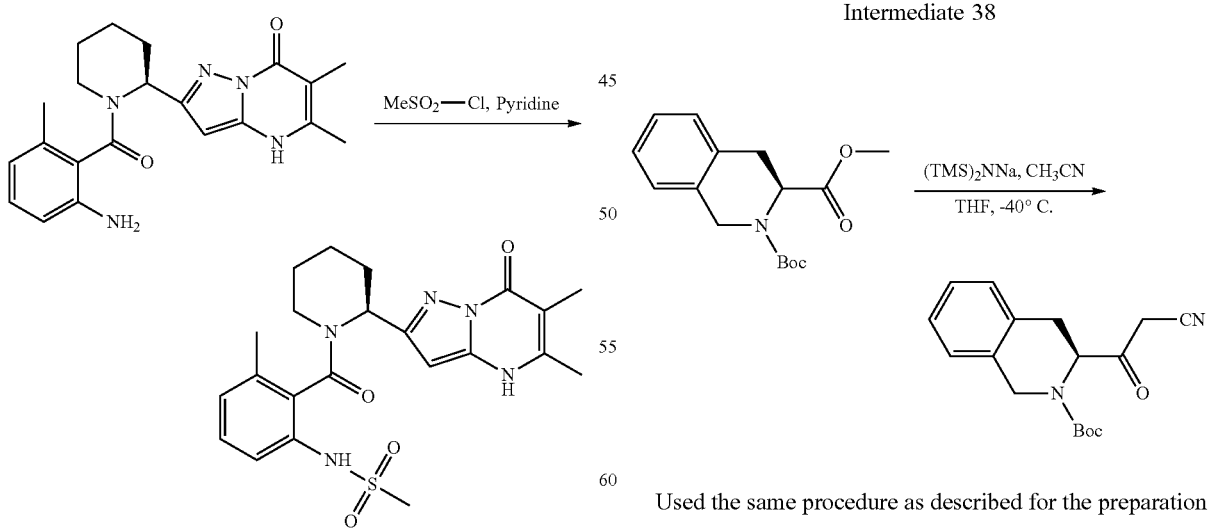

Used the procedure as described for the preparation of intermediate 16 but with (S)-2-(tert-butoxycarbonyl)-1,2,3,4-tetrahydroisoquinoline-3-carboxylic acid instead. Starting material acid (500 mg, 1.8 mmol) gave intermediate 37 (515 mg, 98% yield).

$^1$H NMR (300 MHz, CDCl$_3$): δ 7.12 (m, 4H), 5.14-4.77 (m, 1H), 4.72-4.45 (m, 2H), 3.65 (m, 3H), 3.23-3.15 (m, 2H), 1.53-1.46 (m, 9H).

Intermediate 38

Used the same procedure as described for the preparation of intermediate 17, using intermediate 37 (515 mg, 1.77 mmol) gave cyanoketone intermediate 38 (419 mg, 79% yield).

LC/MS (m/z): 299.0 [M−H]$^−$

Intermediate 39

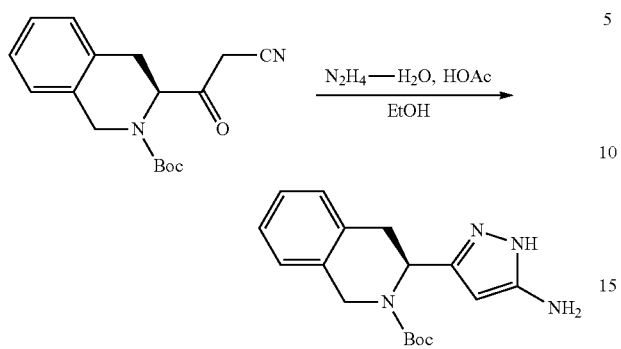

Used the same procedure as described for the preparation of intermediate 18. Starting material cyanoketone intermediate 38 (419 mg, 1.4 mmol) gave intermediate 39 (320 mg, 73% yield).

LC/MS (m/z): 314.9 [M+H]$^+$

Intermediate 40

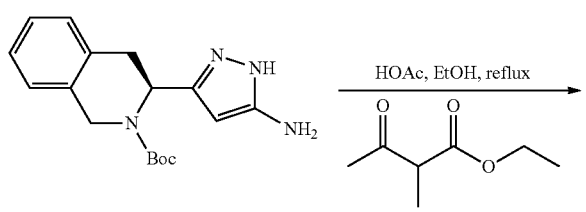

Condensation with keto ester was done on intermediate 39 using the same procedure as described for the preparation of intermediate 19, the product was then deprotected following the procedure described for that of intermediate 6. Starting material aminopyrazole intermediate 39 (320 mg, 1.02 mmol) gave intermediate 40 (357 mg, 97% yield).

LC/MS (m/z): 295.1 [M+H]$^+$

Compound 33

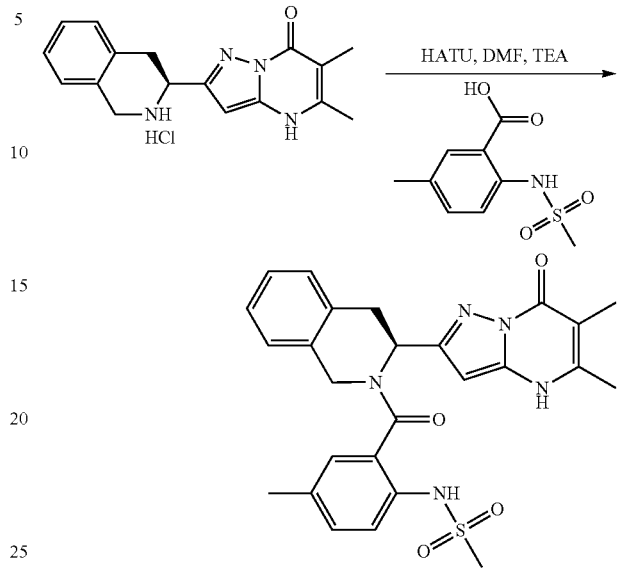

Mixed 5-methyl-2-(methylsulfonamido)benzoic acid (23 mg, 0.1 mmol) with HATU (46 mg, 0.12 mmol) and dissolved in anhydrous DMF (500 uL). Stirred for 1 hr. Added Intermediate 40 (S)-5,6-dimethyl-2-(1,2,3,4-tetrahydroisoquinolin-3-yl)pyrazolo[1,5-a]pyrimidin-7(4H)-one hydrochloride (33 mg, 0.1 mmol) and then TEA (70 uL, 0.5 mmol). Stirred for 2 hrs. Diluted reaction with acetonitrile (1 mL) and purified with Prep HPLC to give title compound 33 (28.5 mg, 46% yield).

$^1$H NMR (400 MHz, CD$_3$OD): δ 7.41-6.89 (m, 7H), 6.10-5.95 (m, 1H), 5.30-5.18 (m, 1H), 4.61-4.54 (m, 2H), 3.52-3.40 (m, 2H), 3.06-2.99 (m, 3H), 2.36-2.24 (m, 6H), 2.00-1.98 (m, 3H).

LC/MS (m/z): 506.1 [M+H]$^+$

Intermediate 41

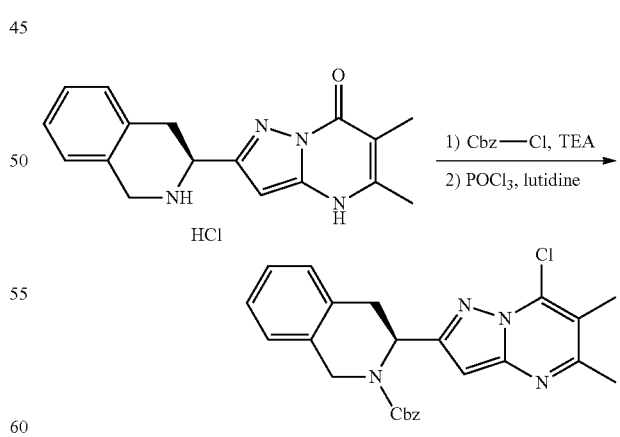

Mixed intermediate 40 (S)-5,6-dimethyl-2-(1,2,3,4-tetrahydroisoquinolin-3-yl)pyrazolo[1,5-a]pyrimidin-7(4H)-one hydrochloride (271 mg, 0.819 mmol) with anhydrous DMF (3 mL). Added triethylamine to give pH 9-10. Added Cbz-Cl (138 uL, 0.983 mmol) dropwise and then stirred for 2 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with silica gel column (0-10% MeOH in DCM) to give the CBZ protected pyrimidinone (277 mg). LC/MS (m/z): 429.1 [M+H]+

Dissolved material in 2,6-lutidine (5 mL). Added POCl₃ (118 uL, 1.29 mmol) and stirred @120° C. under Ar(g) for 30 mins. Added more 2,6-lutidine (5 mL) and POCl₃ (xs) and stirred @120° C. under Ar(g) for 60 mins. Concentrated under reduced pressure and purified with silica gel column (0-50% EtOAc in hexanes) to give intermediate 41 (190 mg, 52% yield).

¹H NMR (400 MHz, CDCl₃): δ 7.41-7.13 (m, 9H), 6.00-5.70 (m, 1H), 5.30-5.18 (m, 2H), 5.10-4.60 (m, 2H), 3.55-125 (m, 2H), 2.60 (s, 3H), 2.36 (s, 3H).

LC/MS (m/z): 447.1 [M+H]+

Compound 34

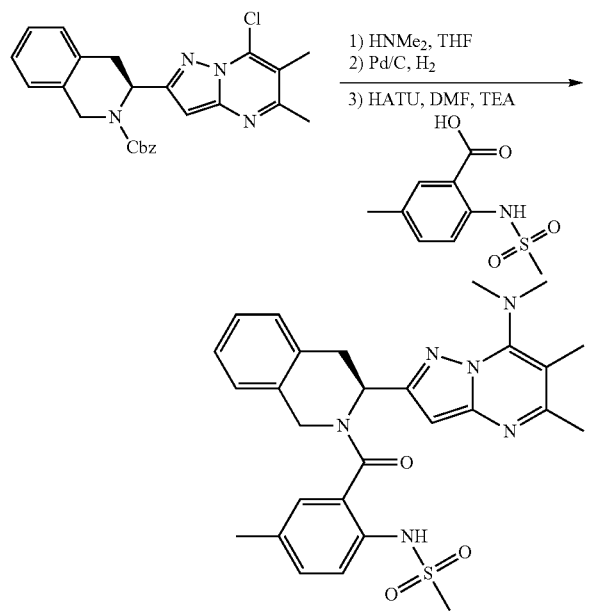

Dissolved intermediate 41 (S)-benzyl-3-(7-chloro-5,6-dimethylpyrazolo[1,5-a]pyrimidin-2-yl)-3,4-dihydroisoquinoline-2(1H)-carboxylate (45 mg, 0.1 mmol) in 2M dimethylamine in THF (5 mL). Stirred for 8 hrs. Concentrated under reduced pressure. Dissolved the resulting material in MeOH, added Pd/C and stirred under atm H₂(g) for 16 hrs. Filtered through Celite and concentrated under reduced pressure. Mixed 5-methyl-2-(methylsulfonamido) benzoic acid (25 mg, 0.11 mmol) with HATU (46 mg, 0.12 mmol) and dissolved in anhydrous DMF (2 mL). Stirred for 1 hr. Dissolved hydrogenation product in anhydrous DMF (1.5 mL) and added to the reaction. Added TEA (42 uL, 0.3 mmol). Stirred for 2 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Prep HPLC to give compound 34 (14.9 mg, 23% yield).

¹H NMR (400 MHz, CD₃OD): δ 7.39-6.89 (m, 7H), 6.49-6.11 (m, 1H), 6.30-5.44 (m, 1H), 5.17-4.54 (m, 2H), 3.65-3.45 (m, 2H), 3.39 (s, 3H), 3.34 (s, 3H), 3.02-2.91 (m, 3H), 2.54-2.50 (m, 3H), 2.38-2.25 (m, 6H).

LC/MS (m/z): 533.2 [M+H]+

Compound 35

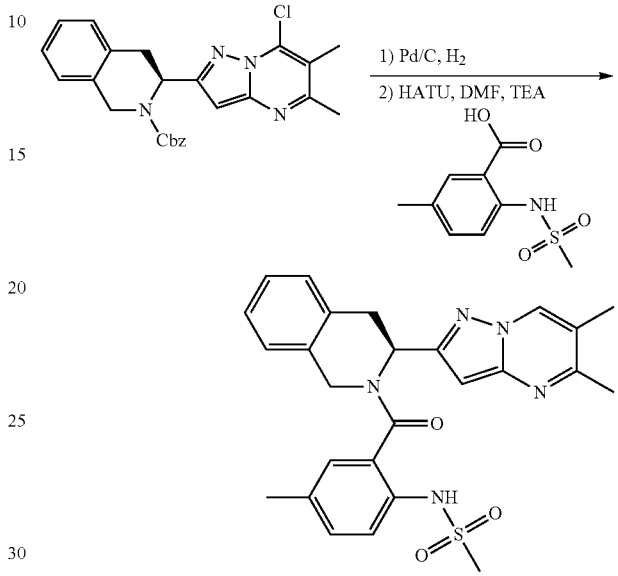

Dissolved intermediate 41 (S)-benzyl-3-(7-chloro-5,6-dimethylpyrazolo[1,5-a]pyrimidin-2-yl)-3,4-dihydroisoquinoline-2(1H)-carboxylate (70 mg, 0.15 mmol) in THF/MeOH (2 mL:2 mL). Added TEA (44 uL, 0.31 mmol) and Pd/C and stirred under atm H₂(g) for 4 hrs. Filtered through Celite and concentrated under reduced pressure. Mixed 5-methyl-2-(methylsulfonamido)benzoic acid (39 mg, 0.171 mmol) with HATU (71 mg, 0.6 mmol) and dissolved in anhydrous DMF (2 mL). Stirred for 1 hr. Dissolved hydrogenation product in anhydrous DMF (2 mL) and added to the reaction. Added TEA (130 uL, 0.93 mmol). Stirred for 16 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Prep HPLC to give compound 35 (32.5 mg, 36% yield).

¹H NMR (400 MHz, CD₃OD): δ 8.81-8.58 (m, 1H), 7.60-6.83 (m, 7H), 6.39 (m, 1H), 5.34-5.17 (m, 1H), 4.41 (s, 1H), 3.50-3.34 (m, 2H), 3.03-2.94 (m, 3H), 2.47-2.45 (m, 3H), 2.38-2.34 (m, 3H), 2.24-2.23 (m, 3H).

LC/MS (m/z): 490.1 [M+H]+

Intermediate 42

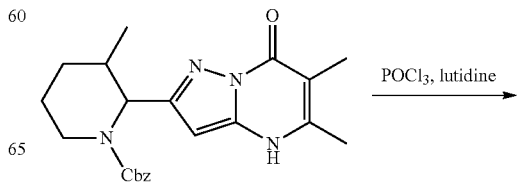

-continued

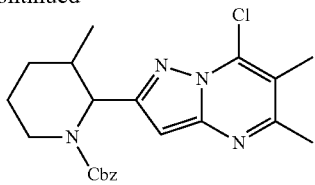

Dissolved benzyl 2-(5,6-dimethyl-7-oxo-4,7-dihydropyrazolo[1,5-a]pyrimidin-2-yl)-3-methylpiperidine-1-carboxylate (intermediate 35) (200 mg, 0.51 mmol) in 2,6-lutidine (1 mL). Added POCl₃ (93 uL, 1.01 mmol) and stirred @120° C. under Ar(g) for 3 hrs. Concentrated under reduced pressure and purified with silica gel column (0-50% EtOAc in hexanes) to give intermediate 42 (mixture of (+/−) cis and (+/−) trans isomers, 158 mg, 74% yield).

$^1$H NMR (400 MHz, CD$_3$OD): δ 7.32-7.20 (m, 5H), 6.40 (s, 1H), 5.45-5.32 (m, 1H), 5.18 (s, 2H), 4.15-4.05 (m, 1H), 3.10-3.15 (m, 1H), 2.59 (s, 3H), 2.44 (s, 3H), 1.90-1.40 (m, 3H), 1.21 (m, 3H), 0.85 (m, 1H).

LC/MS (m/z): 413.2 [M+H]$^+$

Compound 36

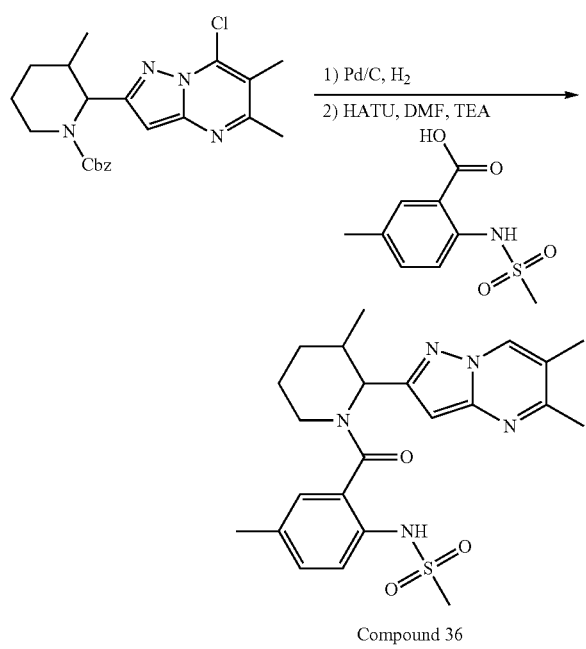

Compound 36

Dissolved intermediate 42 (benzyl-2-(7-chloro-5,6-dimethylpyrazolo[1,5-a]pyrimidin-2-yl)-3-methyl-piperidine-1-carboxylate) (52 mg, 0.126 mmol) in MeOH (2 mL). Added TEA (35 uL, 0.278 mmol) and Pd/C and stirred under atm H$_2$(g) for 1 hr. Filtered through Celite and concentrated under reduced pressure. Mixed 5-methyl-2-(methylsulfonamido)benzoic acid (32 mg, 0.139 mmol) with HATU (63 mg, 0.167 mmol) and dissolved in anhydrous DMF (1 mL). Stirred for 1 hr. Dissolved hydrogenation product in anhydrous DMF (1 mL) and added to the reaction. Added TEA (58 uL, 0.417 mmol). Stirred for 16 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Prep HPLC to give title compound 36 ((+/−) mixture of one diastereoisomer, 25.2 mg, 35% yield).

$^1$H NMR (400 MHz, CD$_3$OD): δ 8.95-8.70 (m, 1H), 7.55-7.25 (m, 3H), 6.51 (m, 1H), 5.94 (m, 1H), 3.16 (m, 1H), 2.91 (m, 3H), 2.72 (m, 1H), 2.54 (s, 3H), 2.38 (s, 3H), 2.31 (s, 3H), 1.90-1.50 (m, 3H), 1.32 (m, 4H).

LC/MS (m/z): 456.2 [M+H]$^+$

Compound 37 and 38

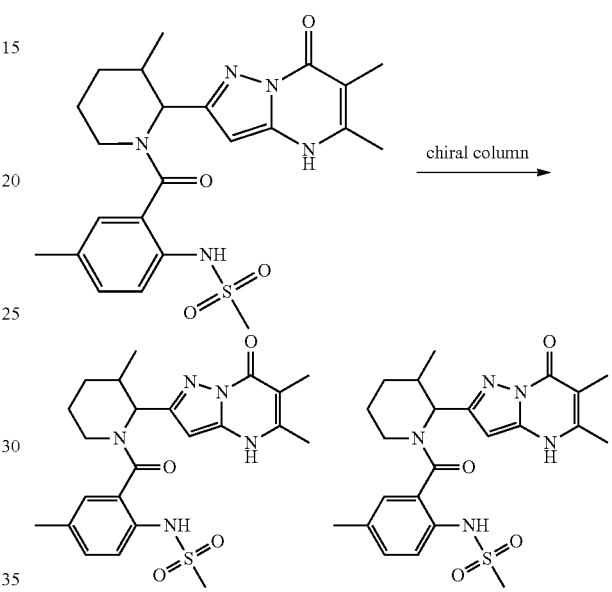

Compound 30 (6.7 mg) was resolved using Chiralpak IC column using MeOH:EtOH (1:1) as mobile phase to give title compound 37 as the first eluting compound and 38 as the second eluting compound (2.5 mg each).

Intermediate 43

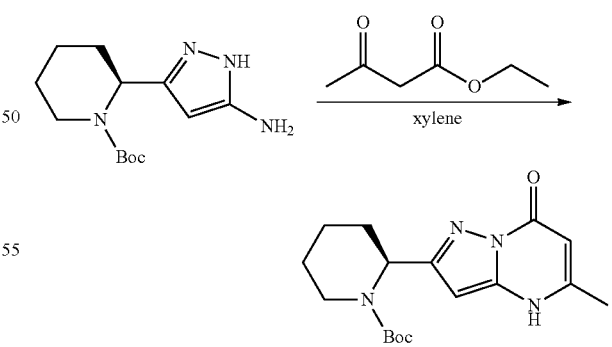

Dissolved Intermediate 4 (266 mg, 1 mmol) in xylene (5 mL). Added ethyl acetoacetate (140 uL, 1.1 mmol) and stirred @140° C. for 1.5 hr. Added more ethyl acetoacetate (50 uL) and stirred @140° C. for 1 hr. Concentrated under reduced pressure and purified with silica gel column (0-10% MeOH in EtOAc) to give intermediate 43 (145 mg, 44% yield).

¹H NMR (400 MHz, DMSO): δ 5.75 (s, 1H), 5.53 (s, 1H), 5.30 (bs, 1H), 3.90-3.86 (m, 1H), 2.75 (m, 1H), 2.31 (m, 1H), 2.25 (s, 3H), 1.68 (m, 1H), 1.54 (m, 2H), 1.40-1.25 (m, 11H).

LC/MS (m/z): 332.9 [M+H]⁺

Intermediate 44

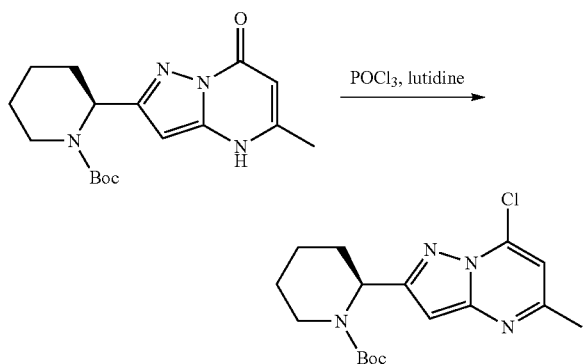

Dissolved intermediate 43 (S)-tert-butyl-2-(5-methyl-7-oxo-4,7-dihydropyrazolo[1,5-a]pyrimidin-2-yl) piperidine-1-carboxylate (145 mg, 0.436 mmol) in 2,6-lutidine (0.5 mL). Added POCl₃ (80 uL, 0.872 mmol) and stirred @120° C. for 1 hr. Concentrated under reduced pressure and purified with silica gel column (0-50% EtOAc in hexanes) to give intermediate 44 (5 mg, 3% yield).

¹H NMR (400 MHz, CD₃OD): δ 7.10 (s, 1H), 6.42 (s, 1H), 5.57 (m, 1H), 4.05 (m, 1H), 2.96 (m, 1H), 2.56 (s, 3H), 2.48 (m, 1H), 1.89 (m, 1H), 1.64 (m, 2H), 1.52-1.47 (m, 11H).

LC/MS (m/z): 351.0 [M+H]⁺

Compound 39

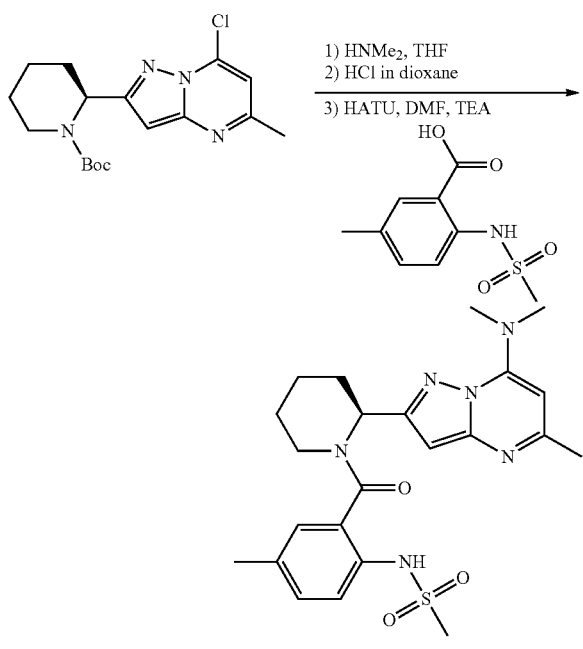

Dissolved intermediate 44 (S)-tert-butyl-2-(7-chloro-5-methylpyrazolo[1,5-a]pyrimidin-2-yl)piperidine-1-carboxylate (5 mg, 0.014 mmol) in 2M dimethylamine in THF (5 mL). Stirred for 1 hr. Concentrated under reduced pressure. Dissolved the resulting material in EtOAc and washed with saturated aqueous sodium chloride solution. Dried organic extract over anhydrous sodium sulfate and then concentrated under reduced pressure. Dissolved in 4N HCl in dioxane (1 mL) and stirred for 1 hr. Concentrated under reduced pressure and dried under high vacuum. Mixed 5-methyl-2-(methylsulfonamido)benzoic acid (4.3 mg, 0.019 mmol) with HATU (7.4 mg, 0.0196 mmol) and dissolved in anhydrous DMF (200 uL). Stirred for 1 hr. Dissolved de-Boc product in anhydrous DMF (300 uL) and added to the reaction. Added TEA (10 uL, 0.07 mmol). Stirred for 2 hrs. Diluted with MeOH and purified with Prep HPLC to give compound 39 (6.2 mg, 76% yield).

¹H NMR (400 MHz, CD₃OD): δ 7.34-7.20 (m, 3H), 6.50-6.10 (m, 1H), 6.33 (s, 1H), 3.75 (bs, 6H), 3.55-3.20 (m, 1H), 3.00 (s, 3H), 2.54 (s, 3H), 2.50-2.05 (m, 2H), 2.39 (s, 3H), 1.80-1.60 (m, 4H).

LC/MS (m/z): 471.2 [M+H]⁺

Intermediate 45

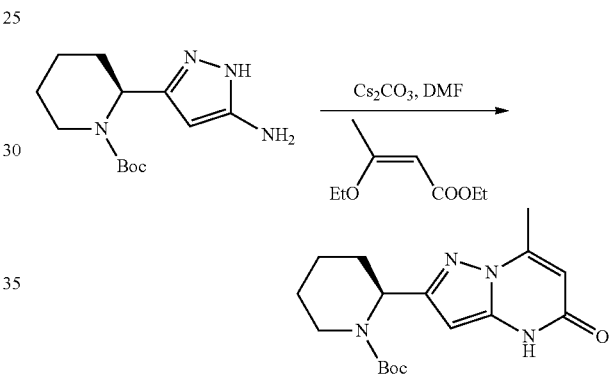

Dissolved intermediate 4 (10 g, 37.5 mmol) in anhydrous DMF (60 mL). Added ethyl 3-ethoxy-2-butenoate (11 g, 67.5 mmol) and cesium carbonate (18 g, 56.3 mmol). Stirred @110° C. for 48 hrs. Cooled to room temperature. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with silica gel column (0-80% EtOAc in hexanes) to give intermediate 45 (9.55 g, 77% yield).

¹H NMR (400 MHz, CD₃OD): δ 5.86 (s, 1H), 5.73 (s, 1H), 5.40 (m, 1H), 4.00 (m, 1H), 2.91 (m, 1H), 2.54 (s, 3H), 2.36 (m, 1H), 1.80 (m, 1H), 1.63 (m, 2H), 1.58-1.45 (m, 11H).

LC/MS (m/z): 333.1 [M+H]⁺

Intermediate 46

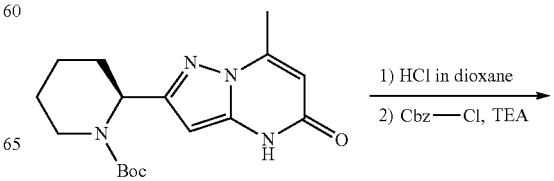

-continued

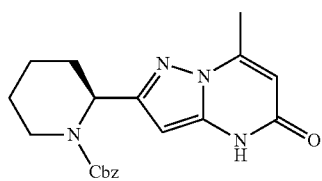

Dissolved intermediate 45 ((S)-tert-butyl-2-(7-methyl-5-oxo-4,5-dihydropyrazolo[1,5-a]pyrimidin-2-yl) piperidine-1-carboxylate) (1.68 g, 5 mmol) in 4N HCl in dioxane (5 mL) and stirred for 1 hr. Concentrated under reduced pressure and dried under high vacuum to give solid which was then mixed with THF (10 mL) and TEA (2.1 mL, 15 mmol). Added Cbz-Cl (739 uL, 5.25 mmol) dropwise. Stirred for 1 hr. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with silica gel column (0-80% EtOAc in hexanes) to give intermediate 46 (929 mg, 51% yield).

$^1$H NMR (400 MHz, CD$_3$OD): δ 7.31 (m, 5H), 5.85 (s, 1H), 5.74 (s, 1H), 5.47 (m, 1H), 5.20-5.10 (m, 2H), 4.08 (m, 1H), 3.05 (m, 1H), 2.50 (s, 3H), 2.34 (m, 1H), 1.85 (m, 1H), 1.63-1.51 (m, 4H).

LC/MS (m/z): 367.2 [M+H]$^+$

Intermediate 47

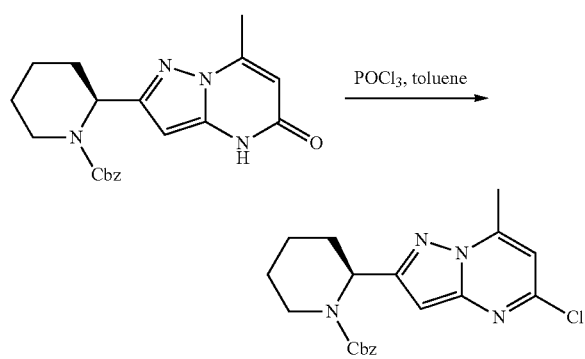

Mixed intermediate 46 ((S)-benzyl-2-(7-methyl-5-oxo-4,5-dihydropyrazolo[1,5-a]pyrimidin-2-yl) piperidine-1-carboxylate) (848 mg, 2.3 mmol) with toluene (7 mL). Added POCl$_3$ (635 uL, 6.94 mmol) and stirred @ 110° C. for 1.5 hr. Concentrated under reduced pressure. Dissolved with ethyl acetate and washed with saturated aqueous sodium bicarbonate solution twice and saturated aqueous sodium chloride solution. Dried organic extract over anhydrous sodium sulfate and then concentrated under reduced pressure. Purified with silica gel column (0-30% EtOAc in hexanes) to give intermediate 47 (425 mg, 48% yield).

$^1$H NMR (400 MHz, CD$_3$OD): δ 7.29 (m, 5H), 6.88 (s, 1H), 6.40 (s, 1H), 5.64 (m, 1H), 5.21-5.10 (m, 2H), 4.12 (m, 1H), 3.08 (m, 1H), 2.68 (s, 3H), 2.41 (m, 1H), 1.94 (m, 1H), 1.67-1.49 (m, 4H).

LC/MS (m/z): 385.0 [M+H]$^+$

Compound 40

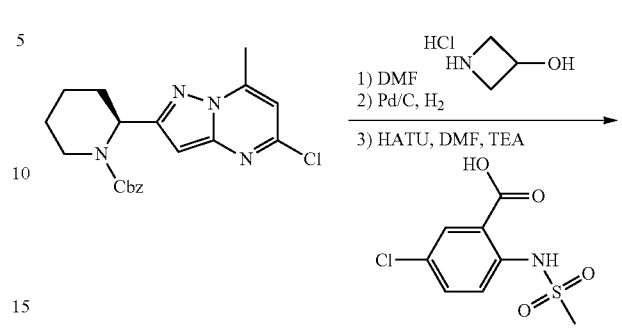

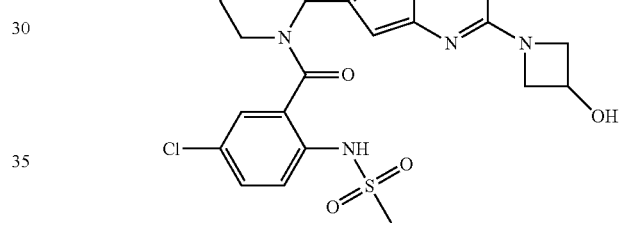

Dissolved intermediate 47 ((S)-benzyl-2-(5-chloro-7-methylpyrazolo[1,5-a]pyrimidin-2-yl)piperidine-1-carboxylate) (43 mg, 0.109 mmol) in DMF (500 uL). Added 3-hydroxyazetidine hydrogen chloride (120 mg, 1.09 mmol) and TEA (304 uL, 2.18 mmol). Stirred @ 70° C. for 2 hrs. Cooled to room temperature. Dissolved with ethyl acetate and washed with saturated aqueous sodium bicarbonate solution twice and saturated aqueous sodium chloride solution. Dried organic extract over anhydrous sodium sulfate and then concentrated under reduced pressure. Dissolved material in MeOH, added Pd/C and stirred under atm H$_2$(g) for 1 hr. Filtered through Celite and concentrated under reduced pressure.

Mixed 5-chloro-2-(methylsulfonamido)benzoic acid (28 mg, 0.109 mmol) with HATU (42 mg, 0.109 mmol) and dissolved in anhydrous DMF (300 uL). Stirred for 1 hr. Dissolved hydrogenation product in anhydrous DMF (300 uL) and added to the reaction. Added TEA (30 uL, 0.218 mmol). Stirred for 12 hrs. Diluted with acetonitrile and purified with Prep HPLC to give compound 40 (22 mg, 32% yield).

$^1$H NMR (400 MHz, CD$_3$OD): δ 7.49 (m, 3H), 6.26 (m, 1H), 6.08 (m, 1H), 4.78 (m, 1H), 4.57 (m, 2H), 4.14 (m, 2H), 3.47-3.34 (m, 2H), 3.01 (m, 4H), 2.76 (s, 3H), 2.40-2.05 (m, 2H), 1.73-1.50 (m, 4H).

LC/MS (m/z): 519.2 [M+H]$^+$

Compound 41

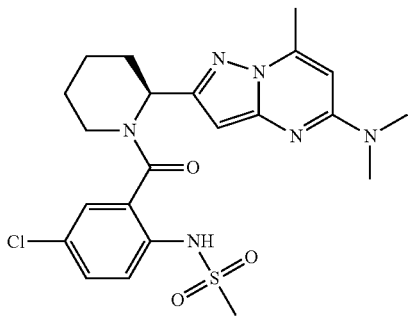 [SMILES: Cc1cc(N(C)C)nc2cc([C@@H]3CCCCN3C(=O)c3cc(Cl)ccc3NS(C)(=O)=O)nn12]

Used the procedure as described for the preparation of compound 40 (4.6 mg) and intermediate 47, except substituting dimethylamine for the hydroxyl azetidine.

$^1$H NMR (400 MHz, CD$_3$OD): δ 7.53-7.40 (m, 3H), 6.40 (m, 1H), 5.97 (m, 1H), 4.58 (m, 1H), 3.45 (m, 1H), 3.15 (s, 6H), 2.98 (m, 3H), 2.70 (s, 3H), 2.35-2.20 (m, 1H), 2.03 (m, 1H), 1.71-1.55 (m, 4H).

LC/MS (m/z): 491.2 [M+H]$^+$

Intermediate 48

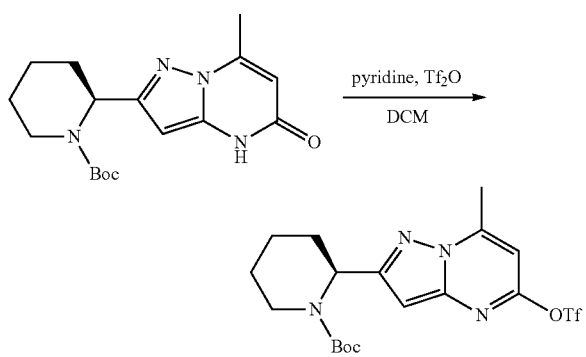

Dissolved intermediate 46 (S)-tert-butyl-2-(7-methyl-5-oxo-4,5-dihydropyrazolo[1,5-a]pyrimidin-2-yl) piperidine-1-carboxylate (100 mg, 0.3 mmol) in anhydrous DCM (3 mL) and @ 0° C. under nitrogen. Added pyridine (121 uL, 1.5 mmol). Added trifluoromethane sulfonic anhydride (76 uL, 0.45 mmol) dropwise. Warmed to room temperature and stirred for 2 hrs. Added more pyridine (300 uL) and Tf$_2$O (76 uL). Stirred for 2 hrs. Concentrated under reduced pressure. Dissolved with ethyl acetate and washed with saturated aqueous sodium bicarbonate solution twice and saturated aqueous sodium chloride solution. Dried organic extract over anhydrous sodium sulfate and then concentrated under reduced pressure. Purified with silica gel column (0-20% EtOAc in hexanes) to give intermediate 48 (97 mg, 70% yield).

$^1$H NMR (400 MHz, CD$_3$OD): δ 6.85 (s, 1H), 6.51 (s, 1H), 5.59 (m, 1H), 4.05 (m, 1H), 2.97 (m, 1H), 2.82 (s, 3H), 2.48 (m, 1H), 1.91 (m, 1H), 1.65 (m, 2H), 1.55-1.45 (m, 11H).

LC/MS (m/z): 365.1 [M+H]$^+$

Intermediate 49

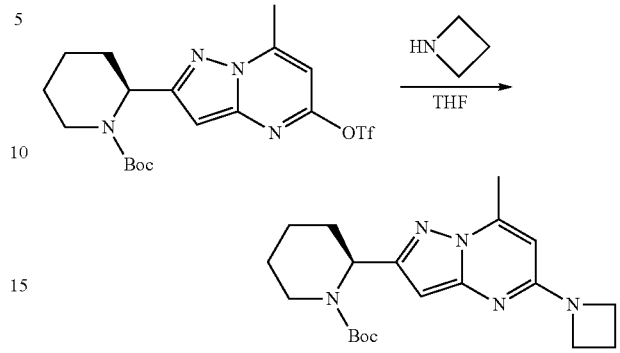

Dissolved (S)-tert-butyl-2-(7-methyl-5-(trifluoromethylsulfonyloxy)pyrazolo[1,5-a] pyrimidin-2-yl)piperidine-1-carboxylate) (46 mg, 0.1 mmol) in THF (1 mL). Added azetidine (68 uL, 1 mmol). Stirred @ 70° C. for 2 hrs. Cooled to room temperature. Dissolved with ethyl acetate and washed with saturated aqueous sodium bicarbonate solution twice and saturated aqueous sodium chloride solution. Dried organic extract over anhydrous sodium sulfate and then concentrated under reduced pressure. Purified with silica gel column (0-60% EtOAc in hexanes) to give intermediate 49 (29 mg, 78% yield).

$^1$H NMR (400 MHz, CD$_3$OD): δ 5.96 (s, 1H), 5.84 (s, 1H), 5.44 (m, 1H), 4.15-4.11 (m, 4H), 4.01 (m, 1H), 2.96 (m, 1H), 2.58 (s, 3H), 2.45-2.38 (m, 3H), 1.81 (m, 1H), 1.62 (m, 2H), 1.53-1.45 (m, 11H).

LC/MS (m/z): 372.2 [M+H]$^+$

Compound 42

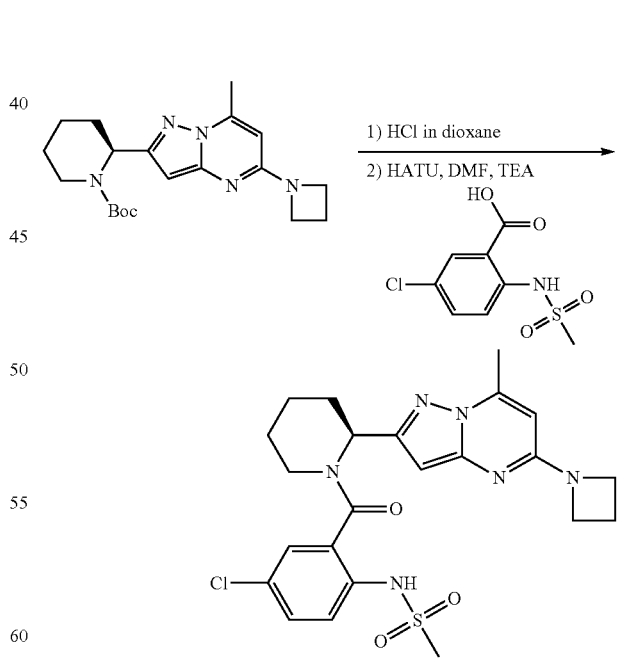

Dissolved intermediate (S)-tert-butyl-2-(5-(azetidin-1-yl)-7-methylpyrazolo[1,5-a]pyrimidin-2-yl) piperidine-1-carboxyl (Intermediate 49) (29 mg, 0.078 mmol) in 4N HCl in dioxane (1 mL) and stirred for 1 hr. Concentrated under reduced pressure.

Mixed 5-chloro-2-(methylsulfonamido)benzoic acid (20 mg, 0.082 mmol) with HATU (36 mg, 0.094 mmol) and dissolved in anhydrous DMF (1 mL). Stirred for 1.5 hr. Dissolved above amine in anhydrous DMF (1 mL) and added to the reaction. Added TEA (44 uL, 0.312 mmol). Stirred for 12 hrs. Diluted with ethyl acetate and washed with saturated aqueous sodium bicarbonate solution twice and saturated aqueous sodium chloride solution. Dried organic extract over anhydrous sodium sulfate and then concentrated under reduced pressure. Purified with Prep HPLC to give compound 42 (24 mg, 61% yield).

$^1$H NMR (400 MHz, CD$_3$OD): δ 7.52 (m, 3H), 6.15-5.92 (m, 2H), 4.90-4.58 (m, 1H), 4.17-4.13 (m, 4H), 3.42 (m, 1H), 3.01 (m, 1H), 2.81 (s, 3H), 2.67 (s, 3H), 2.35-2.20 (m, 2H), 2.05 (m, 1H), 1.75-1.50 (m, 4H).

LC/MS (m/z): 503.3 [M+H]$^+$

Intermediate 51

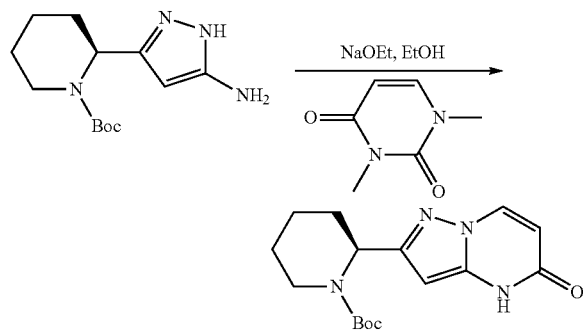

Mixed intermediate 4 (1.33 g, 5 mmol) with dimethyl uracil (771 mg, 5.5 mmol) in anhydrous EtOH (12 mL). Added 3M sodium ethoxide in ethanol (5.83 mL, 17.5 mmol). Stirred @90° C. for 3 hrs. Cooled to room temperature. Diluted with ethyl acetate and washed with saturated aqueous sodium bicarbonate solution twice and saturated aqueous sodium chloride solution. Dried organic extract over anhydrous sodium sulfate and then concentrated under reduced pressure. Purified with silica gel column (0-60% EtOAc in hexanes) to give intermediate 51 (1.27 g, 80% yield).

$^1$H NMR (400 MHz, CD$_3$OD): δ 8.29 (d, J=7.6 Hz, 1H), 5.78 (d, J=8.0 Hz, 1H), 5.70 (s, 1H), 5.40 (m, 1H), 4.01 (m, 1H), 2.89 (m, 1H), 2.34 (m, 1H), 1.80 (m, 1H), 1.63 (m, 2H), 1.54-1.45 (m, 11H).

LC/MS (m/z): 319.0 [M+H]$^+$

Intermediate 52

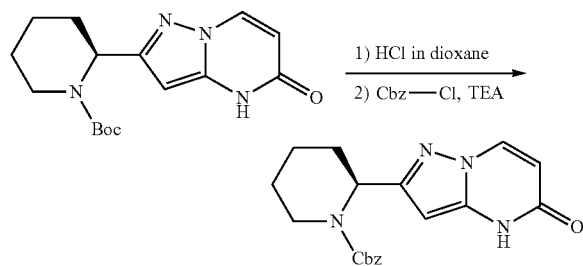

Dissolved intermediate 51 ((S)-tert-butyl-2-(5-oxo-4,5-dihydropyrazolo[1,5-a]pyrimidin-2-yl)piperidine-1-carboxylate) (1.35 g, 4.27 mmol) in 4N HCl in dioxane (10 mL) and stirred for 1 hr. Concentrated under reduced pressure and dried under high vacuum. Mixed with THF (20 mL) and TEA (1.8 mL, 12.8 mmol). Added Cbz-Cl (630 uL, 4.48 mmol) dropwise. Stirred for 2 hrs. Diluted with ethyl acetate and washed with saturated aqueous sodium bicarbonate solution and saturated aqueous sodium chloride solution. Dried organic extract over anhydrous sodium sulfate and then concentrated under reduced pressure to give solid which was then suspended in a mixture of DCM/hexanes (4 mL:80 mL). Collected solid and dried under high vacuum to give intermediate 52 (1.25 g, 83% yield).

$^1$H NMR (400 MHz, CD$_3$OD): δ 8.29 (d, J=7.6 Hz, 1H), 7.33 (m, 5H), 5.98 (d, J=8.0 Hz, 1H), 5.71 (s, 1H), 5.48 (m, 1H), 5.20-5.11 (m, 2H), 4.10 (m, 1H), 3.01 (m, 1H), 2.32 (m, 1H), 1.87 (m, 1H), 1.67-1.47 (m, 4H).

Intermediate 53

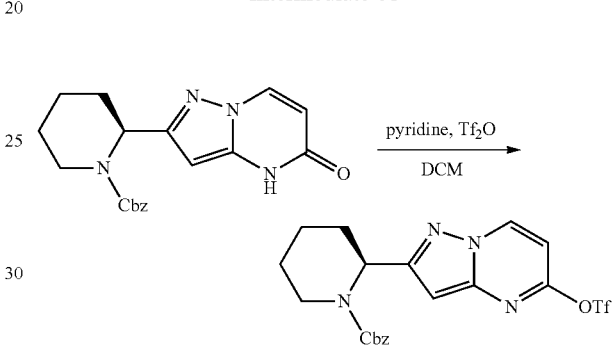

Dissolved intermediate 52 ((S)-benzyl-2-(5-oxo-4,5-dihydropyrazolo[1,5-a]pyrimidin-2-yl)piperidine-1-carboxylate) (462 mg, 1.31 mmol) in anhydrous DCM (10 mL) stirred under nitrogen. Added pyridine (530 uL, 6.55 mmol). Added trifluoromethane sulfonic anhydride (441 uL, 2.62 mmol) dropwise. Stirred for 1.5 hrs. Concentrated under reduced pressure. Dissolved with ethyl acetate and washed with 5% citric acid aqueous solution and saturated aqueous sodium chloride solution. Dried organic extract over anhydrous sodium sulfate and then concentrated under reduced pressure. Purified with silica gel column (0-20% EtOAc in hexanes) to give intermediate 53 (577 mg, 90% yield).

$^1$H NMR (400 MHz, CD$_3$OD): δ 9.03 (d, J=7.6 Hz, 1H), 7.31 (m, 5H), 6.90 (d, J=7.2 Hz, 1H), 6.50 (s, 1H), 5.66 (m, 1H), 5.22-5.12 (m, 2H), 4.13 (m, 1H), 3.05 (m, 1H), 2.44 (m, 1H), 1.93 (m, 1H), 1.68-1.48 (m, 4H).

Intermediate 54

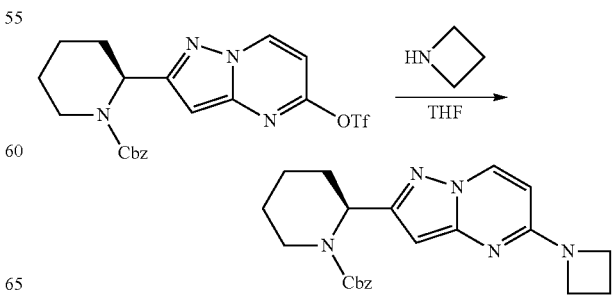

Dissolved intermediate 53 ((S)-benzyl-2-(5-(trifluoromethylsulfonyloxy)pyrazolo[1,5-a]pyrimidin-2-yl)piperidine-1-carboxylate) (115 mg, 0.237 mmol) in THF (1 mL). Added azetidine (161 uL, 2.37 mmol). Stirred @ 70° C. for 2 hrs. Cooled to room temperature. Diluted with ethyl acetate and washed with saturated aqueous sodium bicarbonate solution and saturated aqueous sodium chloride solution. Dried organic extract over anhydrous sodium sulfate and then concentrated under reduced pressure to give intermediate 54 (78 mg, 84% yield).

$^1$H NMR (400 MHz, CD$_3$OD): δ 8.31 (d, J=8.0 Hz, 1H), 7.33 (m, 5H), 6.12 (d, J=7.2 Hz, 1H), 5.83 (s, 1H), 5.53 (m, 1H), 5.16 (m, 2H), 4.19-4.15 (m, 4H), 4.09 (m, 2H), 3.03 (m, 1H), 2.48-2.40 (m, 2H), 2.35 (m, 1H), 1.86 (m, 1H), 1.64-1.49 (m, 4H).

LC/MS (m/z): 392.3 [M+H]$^+$

Compound 43

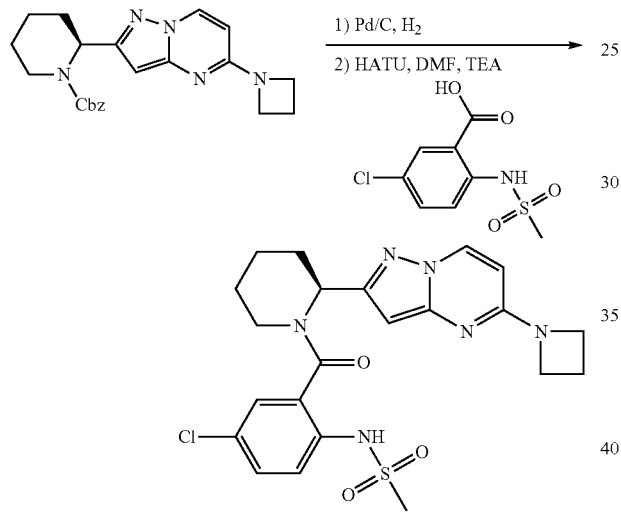

Dissolved intermediate 54 ((S)-benzyl-2-(5-(azetidin-1-yl)pyrazolo[1,5-a]pyrimidin-2-yl)piperidine-1-carboxylate) (78 mg) in MeOH, added Pd/C and stirred under atm H$_2$(g) for 1 hr. Filtered through Celite and concentrated under reduced pressure.

Mixed 5-chloro-2-(methylsulfonamido)benzoic acid (51 mg, 0.205 mmol) with HATU (78 mg, 0.205 mmol) and dissolved in anhydrous DMF (1 mL). Stirred for 1 hr. Dissolved hydrogenation product in anhydrous DMF (1 mL) and added to the reaction. Added TEA (52 uL, 0.374 mmol). Stirred for 16 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Prep HPLC to give compound 43 (49 mg, 54% yield).

$^1$H NMR (400 MHz, CD$_3$OD): δ 8.75-8.45 (m, 1H), 7.68-7.43 (m, 3H), 6.20-6.12 (m, 2H), 6.02-5.95 (m, 1H), 4.90-4.50 (m, 1H), 4.21-4.17 (m, 4H), 3.30-3.18 (m, 1H), 2.98-2.94 (m, 3H), 2.49-2.25 (m, 3H), 2.05 (m, 1H), 1.78-1.45 (m, 4H).

LC/MS (m/z): 489.2 [M+H]$^+$

Compound 44

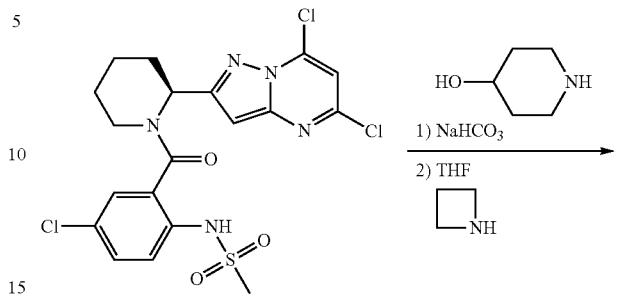

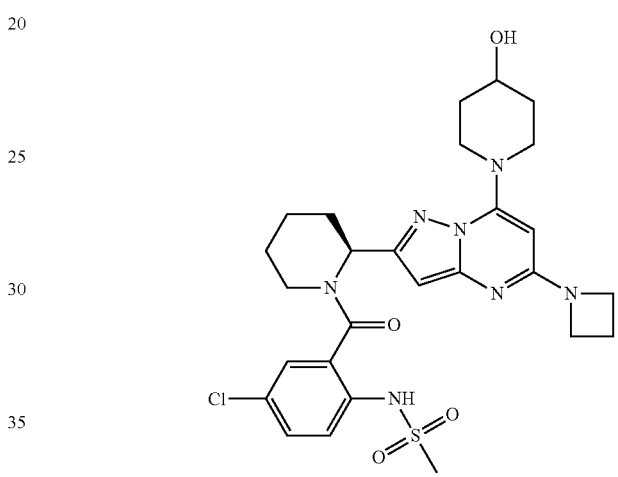

Dissolved intermediate 56 ((S)—N-(4-chloro-2-(2-(5,7-dichloropyrazolo[1,5-a]pyrimidin-2-yl)piperidine-1-carbonyl)phenyl)methanesulfonamide) (50 mg, 0.1 mmol) in THF (1.5 mL). Added hydroxypiperidine (10 mg, 0.1 mmol) and sodium bicarbonate (10 mg, 0.12 mmol). Stirred for 1.5 hrs. Diluted with ethyl acetate and washed with saturated aqueous sodium chloride solution. Dried organic extract over anhydrous sodium sulfate and then concentrated under reduced pressure. Dissolved in THF (2 mL). Added azetidine (68 uL, 1 mmol). Stirred @ 70° C. for 2 hrs. Concentrated under reduced pressure. Diluted with ethyl acetate and washed with saturated aqueous sodium chloride solution. Dried organic extract over anhydrous sodium sulfate and then concentrated under reduced pressure. Purified with Prep HPLC to give compound 44 (28 mg, 48% yield).

$^1$H NMR (400 MHz, CD$_3$OD): δ 7.50-7.40 (m, 3H), 6.18-5.95 (m, 1H), 5.25 (s, 1H), 4.25-4.15 (m, 6H), 3.93 (m, 1H), 3.56-3.40 (m, 3H), 3.04 (m, 3H), 2.51 (m, 2H), 2.40-2.05 (m, 4H), 1.78-1.60 (m, 4H).

LC/MS (m/z): 588.3 [M+H]$^+$

Compound 45

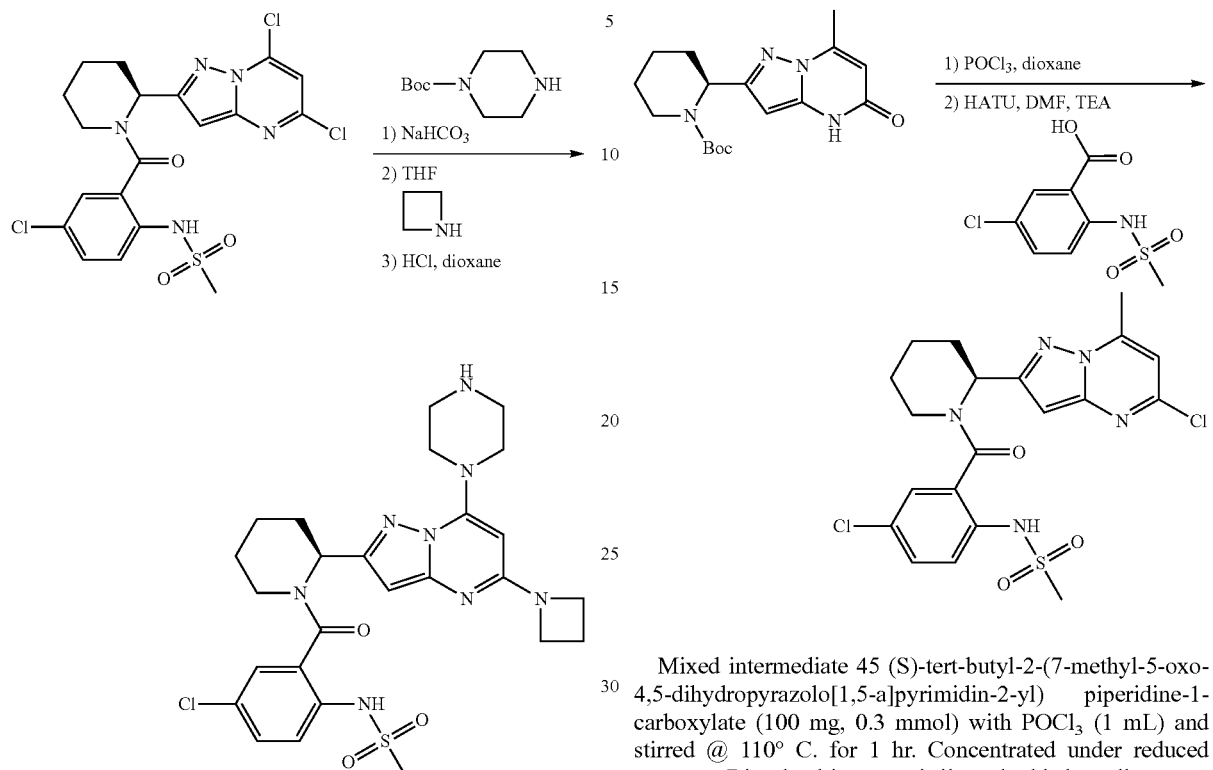

Dissolved intermediate 56 ((S)—N-(4-chloro-2-(2-(5,7-dichloropyrazolo[1,5-a]pyrimidin-2-yl)piperidine-1-carbonyl)phenyl)methanesulfonamide) (50 mg, 0.1 mmol) in THF (1.5 mL). Added Boc-piperazine (17 mg, 0.1 mmol) and sodium bicarbonate (10 mg, 0.12 mmol). Stirred for 2 hrs. Diluted with ethyl acetate and washed with saturated aqueous sodium chloride solution. Dried organic extract over anhydrous sodium sulfate and then concentrated under reduced pressure. Dissolved in THF (1.5 mL). Added azetidine (68 uL, 1 mmol). Stirred @ 70° C. for 2.5 hrs. Concentrated under reduced pressure. Diluted with ethyl acetate and washed with saturated aqueous sodium chloride solution. Dried organic extract over anhydrous sodium sulfate and then concentrated under reduced pressure. Dissolved in 4N HCl in dioxane (2 mL) and stirred for 1 hr. Concentrated under reduced pressure. Purified with Prep HPLC to give compound 45 (26.9 mg, 44% yield).

$^1$H NMR (400 MHz, CD$_3$OD): δ 7.50-7.40 (m, 3H), 6.28-6.04 (m, 2H), 5.46 (s, 1H), 4.42 (m, 4H), 4.15 (m, 4H), 3.75 (m, 1H), 3.68 (m, 1H), 3.56 (m, 1H), 3.50 (s, 4H), 3.04 (s, 3H), 2.58 (m, 2H), 2.38-2.09 (m, 2H), 1.75-1.60 (m, 4H).

LC/MS (m/z): 573.3 [M+H]$^+$

Intermediate 55

Mixed intermediate 45 (S)-tert-butyl-2-(7-methyl-5-oxo-4,5-dihydropyrazolo[1,5-a]pyrimidin-2-yl) piperidine-1-carboxylate (100 mg, 0.3 mmol) with POCl$_3$ (1 mL) and stirred @ 110° C. for 1 hr. Concentrated under reduced pressure. Dissolved in acetonitrile and added small amount of MeOH. Stirred at 0° C. for 30 mins. Collected solid and dried under high vacuum.

Mixed 5-chloro-2-(methylsulfonamido)benzoic acid (47 mg, 0.187 mmol) with HATU (71 mg, 0.187 mmol) and dissolved in anhydrous DMF (1 mL). Stirred for 1 hr. Dissolved amine hydrogen chloride (49 mg, 0.17 mmol) in anhydrous DMF (1 mL) and added to the reaction. Added TEA (71 uL, 0.51 mmol). Stirred for 16 hrs. Diluted with ethyl acetate and washed with saturated aqueous sodium chloride solution twice. Dried organic extract over anhydrous sodium sulfate and then concentrated under reduced pressure. Purified with silica gel column (0-50% EtOAc in hexanes) to give intermediate 55 (57 mg, 39% yield).

LC/MS (m/z): 482.2 [M+H]$^+$

Compound 46

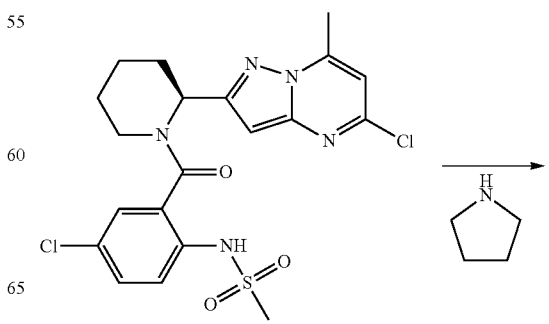

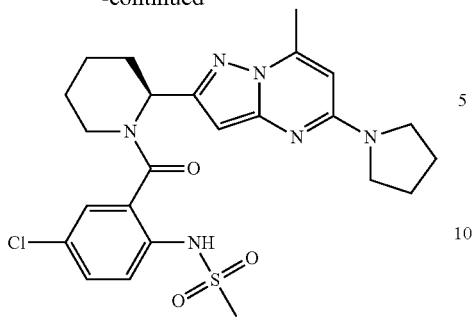

Dissolved intermediate 55 (S)—N-(4-chloro-2-(2-(5-chloro-7-methylpyrazolo[1,5-a]pyrimidin-2-yl) piperidine-1-carbonyl)phenyl)methanesulfonamide (19 mg, 0.039 mmol) in THF (1.5 mL). Added pyrrolidine (33 uL, 0.39 mmol). Stirred @ 70° C. for 2 hrs. Concentrated under reduced pressure. Purified with Prep HPLC to give compound 46 (13.9 mg, 56% yield).

$^1$H NMR (400 MHz, CD$_3$OD): δ 7.49 (m, 3H), 6.56 (s, 1H), 6.35-6.10 (m, 1H), 3.71 (m, 4H), 3.50-5.35 (m, 2H), 3.02 (s, 3H), 2.81 (s, 3H), 2.38-2.09 (m, 6H), 1.74-1.56 (m, 4H).

LC/MS (m/z): 517.3 [M+H]$^+$

Compound 47

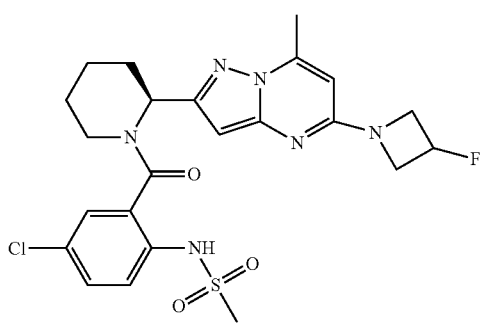 [SMILES: Cc1cc(N2CC(F)C2)nc2cc([C@@H]3CCCCN3C(=O)c3cc(Cl)ccc3NS(C)(=O)=O)nn12]

Used the same procedures as described for the synthesis of compound 46 except replacing pyrrolidine with the fluoro azetidine to provide compound 47 (13.9 mg, 56%)

$^1$H NMR (400 MHz, CD$_3$OD): δ 7.50 (m, 3H), 6.27 (s, 1H), 6.10 (m, 1H), 5.60-5.46 (m, 1H), 4.65 (m, 2H), 4.42 (m, 2H), 3.46 (m, 1H), 3.30 (s, 3H), 3.04 (s, 3H), 2.77 (s, 3H), 2.40-2.05 (m, 2H), 1.76-1.55 (m, 4H).

LC/MS (m/z): 521.2 [M+H]$^+$

Compound 48

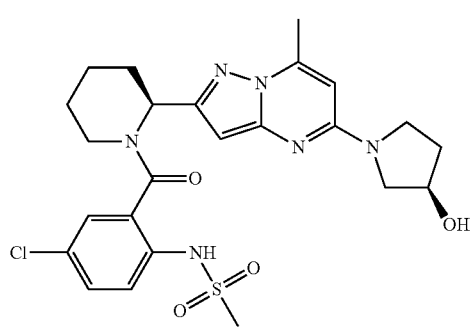 [SMILES: Cc1cc(N2CC[C@@H](O)C2)nc2cc([C@@H]3CCCCN3C(=O)c3cc(Cl)ccc3NS(C)(=O)=O)nn12]

Used the same procedures as described for the synthesis of compound 46 except replacing pyrrolidine with the (R)-hydroxy pyrroldine to provide compound 48 (6.5 mg, 26%).

$^1$H NMR (400 MHz, CD$_3$OD): δ 7.50 (m, 3H), 6.55 (s, 1H), 6.30-6.10 (m, 1H), 4.64 (m, 2H), 3.81-3.45 (m, 6H), 3.02 (s, 3H), 2.81 (s, 3H), 2.40-2.05 (m, 4H), 1.76-1.55 (m, 4H).

LC/MS (m/z): 533.3 [M+H]$^+$

Compound 49

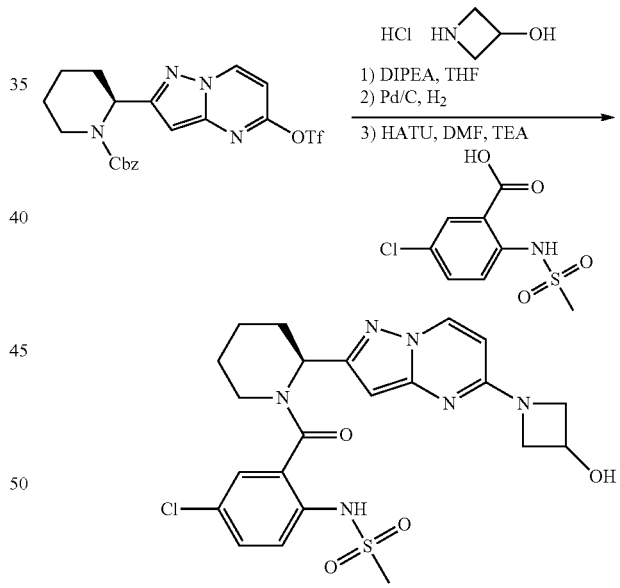

Dissolved intermediate 53 ((S)-benzyl-2-(5-(trifluoromethylsulfonyloxy)pyrazolo[1,5-a]pyrimidin-2-yl) piperidine-1-carboxylate) (57.7 mg, 0.118 mmol) in THF (1 mL). Added 3-hydroxy azetidine HCl (129 mg, 1.18 mmol) and DIPEA (247 uL, 1.42 mmol). Stirred @ 70° C. for 2 hrs. Cooled to room temperature. Diluted with ethyl acetate and washed with saturated aqueous sodium bicarbonate solution and saturated aqueous sodium chloride solution. Dried organic extract over anhydrous sodium sulfate and then concentrated under reduced pressure. Dissolved in MeOH, added Pd/C and stirred under atm H$_2$(g) for 1 hr. Filtered through Celite and concentrated under reduced pressure.

Mixed 5-chloro-2-(methylsulfonamido)benzoic acid (32 mg, 0.13 mmol) with HATU (49 mg, 0.13 mmol) and dissolved in anhydrous DMF (1 mL). Stirred for 1 hr. Dissolved hydrogenation product in anhydrous DMF (1 mL) and added to the reaction. Added TEA (41 uL, 0.295 mmol). Stirred for 2 hrs. Diluted with ethyl acetate and washed with saturated aqueous sodium bicarbonate solution and saturated aqueous sodium chloride solution. Dried organic extract over anhydrous sodium sulfate and then concentrated under reduced pressure. Purified with Prep HPLC to provide compound 49 (35 mg, 48% yield).

$^1$H NMR (400 MHz, CD$_3$OD): δ 8.85-8.50 (m, 1H), 7.66-7.43 (m, 3H), 6.30 (m, 1H), 6.18-6.12 (m, 1H), 4.77 (m, 1H), 4.54 (m, 2H), 4.10 (m, 2H), 3.35-3.22 (m, 2H), 2.96 (s, 3H), 2.42 (m, 1H), 2.04 (m, 1H), 1.76-1.45 (m, 4H).

LC/MS (m/z): 505.2 [M+H]$^+$

Compound 50

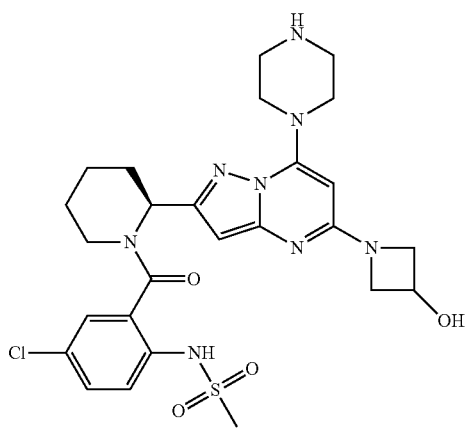 [SMILES: CS(=O)(=O)Nc1ccc(Cl)cc1C(=O)N1CCCC[C@H]1c1cc2nc(N3CC(O)C3)cc(N3CCNCC3)n2n1]

Used the same procedures as described for the synthesis of compound 45 except substituting the corresponding reagents to provide compound 50 (11 mg, 35%).

$^1$H NMR (400 MHz, CD$_3$OD): δ 7.50-7.40 (m, 3H), 6.28-6.04 (m, 2H), 5.50 (s, 1H), 4.62 (m, 2H), 4.14 (m, 6H), 334 (m, 1H), 3.66 (m, 1H), 3.56 (m, 1H), 3.51 (s, 4H), 3.04 (s, 3H), 2.38-2.09 (m, 2H), 1.75-1.60 (m, 4H).

LC/MS (m/z): 589.2 [M+H]$^+$

Compound 51

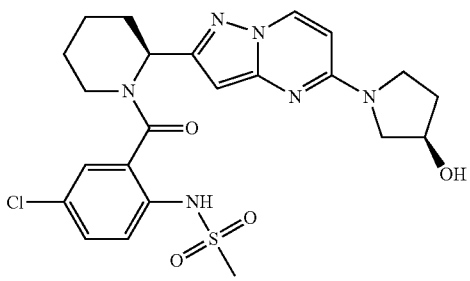 [SMILES: CS(=O)(=O)Nc1ccc(Cl)cc1C(=O)N1CCCC[C@H]1c1cc2nc(N3CC[C@@H](O)C3)ccn2n1]

Used the same procedures as described for the synthesis of compound 49 starting from intermediate 53, except using the appropriate (R)-hydroxyl pyrrolidine compound 51 (29 mg, 46%) was obtained.

$^1$H NMR (400 MHz, CD$_3$OD): δ 8.92-8.60 (m, 1H), 7.67-7.44 (m, 3H), 6.59 (m, 1H), 6.25-6.14 (m, 1H), 4.62 (m, 1H), 3.81 (m, 3H), 3.66 (m, 1H), 3.35-3.24 (m, 2H), 2.97 (s, 3H), 2.42 (m, 1H), 2.24-2.04 (m, 3H), 1.77-1.45 (m, 4H).

LC/MS (m/z): 519.2 [M+H]$^+$

Compound 52

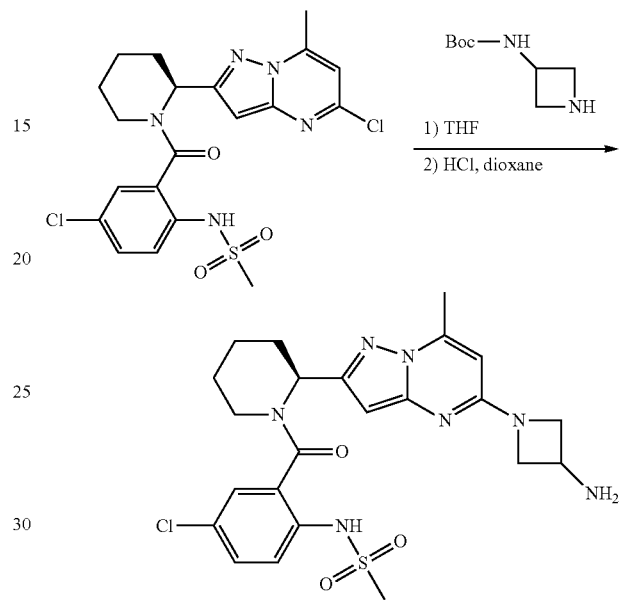

Dissolved intermediate 55 (S)—N-(4-chloro-2-(2-(5-chloro-7-methylpyrazolo[1,5-a]pyrimidin-2-yl) piperidine-1-carbonyl)phenyl)methanesulfonamide (10 mg, 0.021 mmol) in THF (2 mL). Added 3-N-Boc-amino azetidine (36 mg, 0.21 mmol). Stirred @ 70° C. for 2 hrs. Concentrated under reduced pressure. Dissolved in 4N HCl in dioxane (2 mL) and stirred for 1 hr. Concentrated under reduced pressure. Purified with Prep HPLC to give compound 52 (10 mg, 75% yield).

$^1$H NMR (400 MHz, CD$_3$OD): δ 7.51 (m, 3H), 6.19 (s, 1H), 6.10 (m, 1H), 4.55 (m, 3H), 4.27-4.20 (m, 3H), 3.40 (m, 1H), 2.99 (s, 3H), 2.73 (s, 3H), 2.38-2.05 (m, 2H), 1.72-1.56 (m, 4H).

LC/MS (m/z): 518.3 [M+H]$^+$

Compound 53

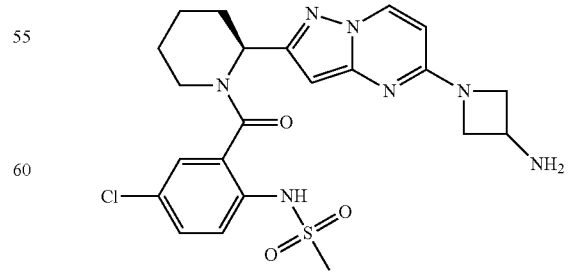

Used the same procedures as described for the preparation of compound 46 to give compound 53 (36 mg, 58%).

¹H NMR (400 MHz, CD₃OD): δ 8.90-8.58 (m, 1H), 7.67-7.44 (m, 3H), 6.25 (m, 1H), 6.11 (m, 1H), 4.53 (m, 2H), 4.27 (m, 1H), 4.18 (m, 2H), 3.22 (m, 1H), 2.99 (s, 3H), 2.38-2.30 (m, 1H), 2.03 (m, 1H), 1.75-1.45 (m, 4H).

LC/MS (m/z): 504.2 [M+H]⁺

Compound 54

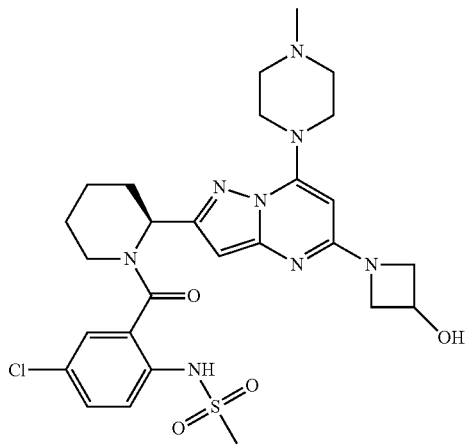 [SMILES: CN1CCN(c2cc(N3CC(O)C3)nc3cc([C@@H]4CCCCN4C(=O)c4cc(Cl)ccc4NS(C)(=O)=O)nn23)CC1]

Used the same procedures as described for the preparation of compound 44 to give compound 54 (6 mg, 17%)

¹H NMR (400 MHz, CD₃OD): δ 7.49 (m, 3H), 6.28-6.04 (m, 1H), 5.50 (s, 1H), 4.80 (m, 2H), 4.55 (m, 4H), 4.14 (m, 3H), 3.70-3.45 (m, 6H), 3.04 (s, 3H), 3.00 (s, 3H), 2.38-2.09 (m, 2H), 1.75-1.60 (m, 4H).

LC/MS (m/z): 603.3 [M+H]⁺

Compound 55

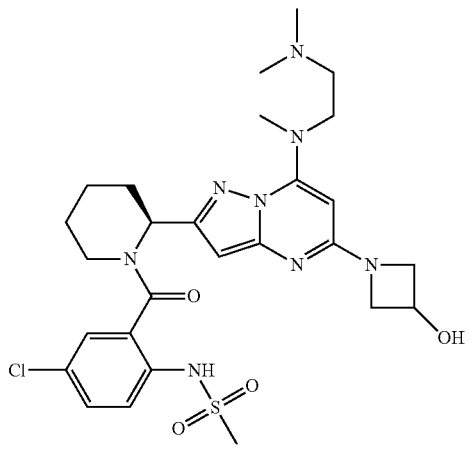 [SMILES: CN(C)CCN(C)c1cc(N2CC(O)C2)nc2cc([C@@H]3CCCCN3C(=O)c3cc(Cl)ccc3NS(C)(=O)=O)nn12]

Used the same procedures as described for the preparation of compound 44 to give compound 55 (1.1 mg, 4%).

¹H NMR (400 MHz, CD₃OD): δ 7.50-7.40 (m, 3H), 6.08-5.85 (m, 1H), 5.25 (s, 1H), 4.68 (m, 1H), 4.33 (m, 2H), 4.15-3.95 (m, 2H), 3.88 (m, 3H), 3.11 (s, 3H), 2.91-2.70 (m, 5H), 2.45-2.25 (m, 7H), 2.05 (m, 1H), 1.75-1.60 (m, 4H).

LC/MS (m/z): 605.3 [M+H]⁺

Intermediate 56

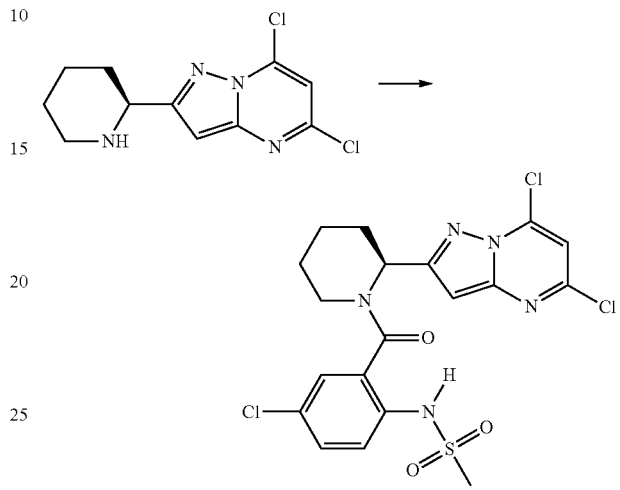

To a suspension of (5-chloro-2-(methylsulfonamido)benzoic acid) (0.7 g, 2.8 mM) in DCM (6 ml) was added oxalylchloride (2 M in DCM, 6 ml, 12 mM) and DMF (5 microliter) and the stirred for 3 h at RT. Volatiles were removed under vacuum and the residue dissolved in DCM (20 ml). With ice-water bath cooling, the amine intermediate 64 (0.78 g, 2.54 mM) and ET₃N (0.55 g) was added and stirred for 10 min, then 30 min at RT. The reaction mixture was diluted with DCM (100 ml) and washed 3× with water. Volatiles were remove and the residue purified on silica gel (hexane/AcOEt=1/1). The product, intermediate 56, was obtained as a colorless oil in 75% purity and used without further purification in the next step.

Compound 56

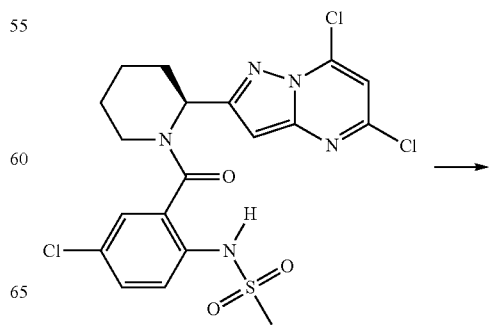

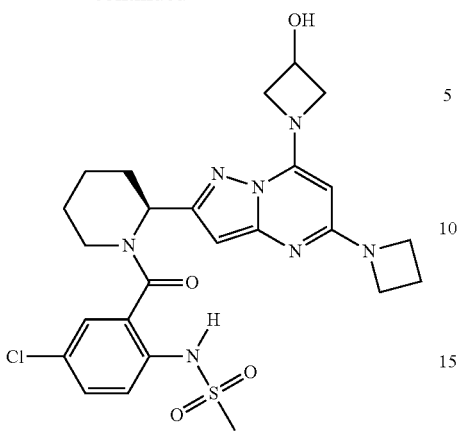

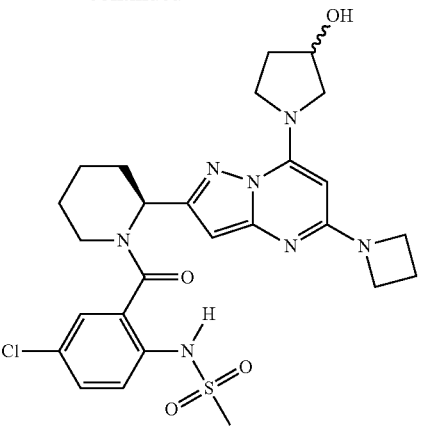

Intermediate 56 (0.033 g, 0.065 mM) was stirred with 3-hydroxyazetidine (0.0071 g, 0.065 mM) and NaHCO₃ (0.1 ml, aequ. sat.) in MeCN (4 ml) for 2 h. Additional 3-hydroxyazetidine (0.0071 g, 0.065 mM) was added and the solution heated to 50° C. for 1 h. Azetidine (0.5 ml) was then added and the solution stirred for 1 h at to 70° C. Volatiles were removed under reduced pressure at 40° C. and the resulting residue was purified by preparative HPLC (MeCN in H₂O with a gradient from 5% to 95%) to afford compound 56 (14 mg, 39%) as a white powder after lyophilization.

¹H-NMR (DMSO, 400 MHz): δ 7.8 (s, br., 1H), 7.52-7.42 (m, 3H), 6.05 (s, br., 2H), 4.73 (s, 1H), 4.59 (s, 1H), 4.24 (m, 3H), 3.03 (s, 1H), 2.9-2.05 (m, 9H), 1.96 (m, 4H), 1.71 (s, br., 2H), 1.60 (s, br., 2H).

LCMS m/z [M+H]⁺ C₂₅H₃₀ClN₇O₄S requires: 559.18. Found 560.23

HPLC Tr (min), purity %: 2.24, 98%.

Compound 57

Intermediate 56 (0.030 g, 0.059 mM) was stirred with 3-hydroxypyrrolidine (0.0051 g, 0.065 mM) and NaHCO₃ (0.2 ml, aequ. sat.) in MeCN (4 ml) for 2 h. Additional 3-hydroxyazetidine (0.0051 g, 0.065 mM) was added and the solution heated to 50° C. for 1 h. Azetidine (0.5 ml) was then added and the solution stirred for 1 h at to 70° C. Volatiles were removed under reduced pressure at 40° C. and the resulting residue was purified by preparative HPLC (MeCN in H₂O with a gradient from 5% to 95%) to afford compound 57 (17 mg, 50%) as a white powder after lyophilization.

¹H-NMR (DMSO, 400 MHz): δ 7.8 (s, br., 1H), 7.52-7.42 (m, 3H), 6.05 (s, br., 2H), 4.79 (s, 1H), 4.58 (s, 1H), 4.25 (m, 3H), 3.05 (m, 2H), 2.9-2.05 (m, 11H), 1.96 (m, 4H), 1.71 (s, br., 2H), 1.61 (s, br., 2H).

LCMS m/z [M+H]⁺ C₂₆H₃₂ClN₇O₄$_S$ requires: 573.19. Found 574.30

HPLC Tr (min), purity %: 2.41, 98%.

Compound 58

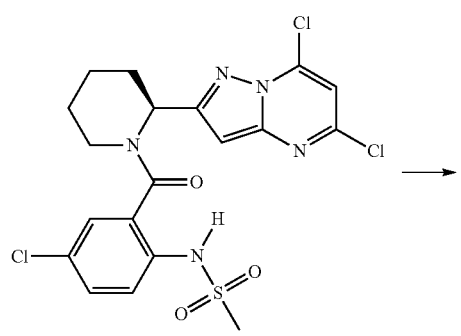

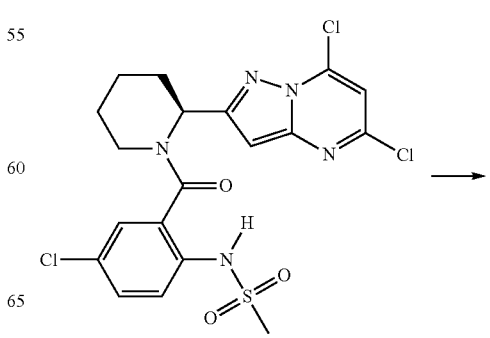

-continued

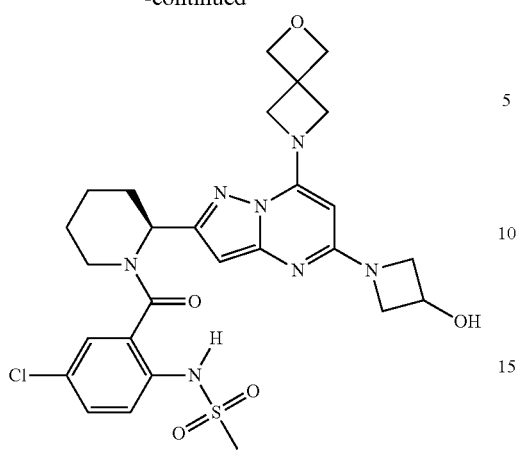

Intermediate 56 (0.034 g, 0.067 mM) was stirred with 2-Oxa-6-aza-spiro[3.3]heptane (0.006 g, 0.067 mM) and NaHCO₃ (0.2 ml, aequ. sat.) in MeCN (4 ml) for 2 h. Additional 2-Oxa-6-aza-spiro[3.3]heptane (0.006 g, 0.067 mM) was added and the solution heated to 50° C. for 1 h. 3-Hydroxyazetidine HCl-salt (0.3 g) and Et₃N (0.2 ml) was then added and the solution stirred for 1 h at to 70° C. Volatiles were removed under reduced pressure at 40° C. and the resulting residue was purified by preparative HPLC (MeCN in H₂O with a gradient from 5% to 95%) to afford compound 58 (2.1 mg, 5%) as a white powder after lyophilization.

¹H-NMR (DMSO, 400 MHz): δ 7.95 (s, br., 1H), 7.40-7.33 (m, 3H), 5.6 (s, br., 2H), 4.73 (s, 1H), 4.59 (m, 3H), 4.51 (s, br., 1H), 4.45-4.37 (m, 3H), 4.12 (t, J=8, 1H), 3.68-6.65 (m, 2H), 3.54 (s, 1H), 2.87 (s, 1H), 2.05-1.87 (m, 10H), 1.60-1.57 (m, 2H), 1.46 (s, br., 2H).

LCMS m/z [M+H]⁺ C₂₇H₃₂ClN₇O₅S requires: 601.19. Found 602.27

HPLC Tr (min), purity %: 1.92, 98%.

Compound 59

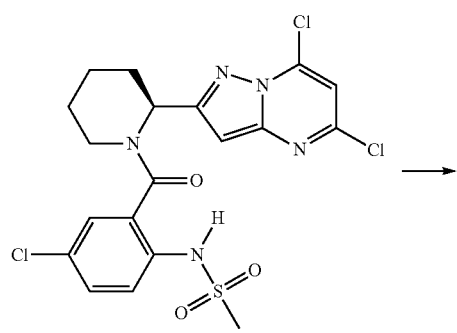

-continued

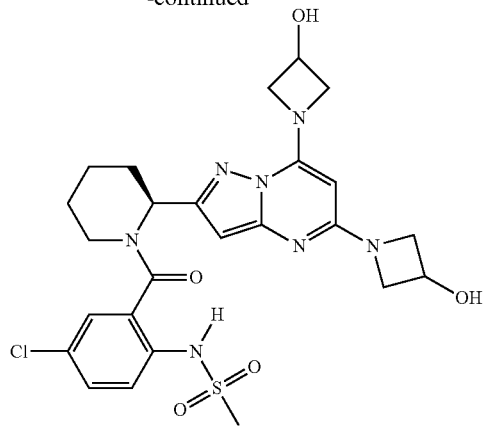

Intermediate 56 (0.034 g, 0.067 mM) was stirred with 3-Hydroxyazetidine HCl-salt (0.148 g) and Et₃N (0.18 ml) in MeOH (4 ml) for 16 h at 70° C. Volatiles were removed under reduced pressure at 40° C. and the resulting residue was purified by preparative HPLC (MeCN in H₂O with a gradient from 5% to 95%) to afford compound 59 (7.8 mg, 20%) as a white powder after lyophilization.

¹H-NMR (DMSO, 400 MHz): δ 9.20 (s, br., 1H), 7.46-7.37 (m, 3H), 5.80 (m, 2H), 5.71 (s, 1H), 5.62 (d, J=5.6 Hz, 1H), 4.81 (s, br., 1H), 4.67 (s, br., 1H), 4.52-4.38 (m, 3H), 4.09 (t, J=7.6, 1H), 3.94 (m, 2H), 3.25-2.60 (m, br., 2H), 2.47-2.02 (m, 2H), 2.05-1.87 (m, 8H), 1.52-1.16 (m, 2H).

LCMS m/z [M+H]⁺ C₂₅H₃₀ClN₇O₅S requires: 575.7. Found 576.26

HPLC Tr (min), purity %: 1.82, 98%.

Compound 60

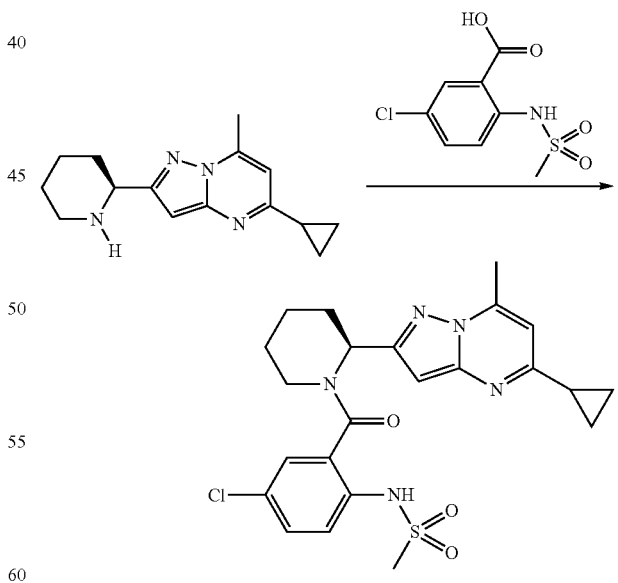

2-methanesulfonamido-5-chlorobenzoic acid (0.1 g, 4.36 mmol), HATU (0.15 g, 0.52 mmol) were dissolved in anhydrous DMF (2 ml). After activation for 1 hour, to the above solution was added intermediate 31 (0.32 g, 1.25 mmol) and triethylamine (0.17 ml). The reaction was stirred under nitrogen for 5 hours. Solvents were removed by rotary evaporation. The residue purified with preparatory HPLC to provide compound 60. (Yield 0.56 g, 90%).

$^1$H-NMR (DMSO, 400 MHz): δ 7.40 (m, 3H), 6.61 (s, 1H), 6.4 (s, br., 1H), 6.38 (s, br., 1 h), 6.05 (s, br., 1H), 4.95 (s, br., 1H), 4.40 (s, br., 1H), 3.06 (s, br., 1H, 2.86 (s, 3H), 2.01 (s, 3H), 1.86 (s, br., 4H), 1.60 (s, br., 2H), 1.45 (s, br., 2H), 1.00 (m, 4H).

LCMS m/z [M+H]$^+$ $C_{23}H_{26}ClN_5O_3S$ requires: 487.14. Found 488.19

HPLC Tr (min), purity %: 2.84, 98%.

Intermediate 57

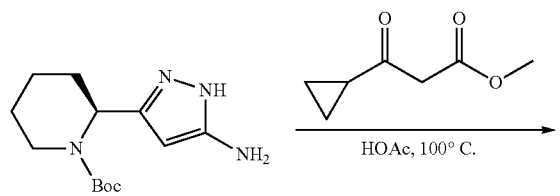

Intermediate 4 (5 g, 0.02 mol) in HOAc (20 mL) was treated with 3-cyclopropyl-3-oxopropanoic acid methyl ester (14 g, 0.1 mmol) and the mixture was stirred overnight at 100° C. The mixture was concentrated and purified via SiO$_2$ column chromatography (40 g SiO$_2$ Combiflash HP Gold Column, 0-100% EtOAc/hexanes gradient) to afford intermediate 57 (4 g, 83%).

LCMS m/z [M+H]$^+$ $C_{19}H_{26}N_4O_3$ requires: 359.20. Found 359.10

HPLC Tr (min), purity %: 2.45, 98%

Intermediate 58

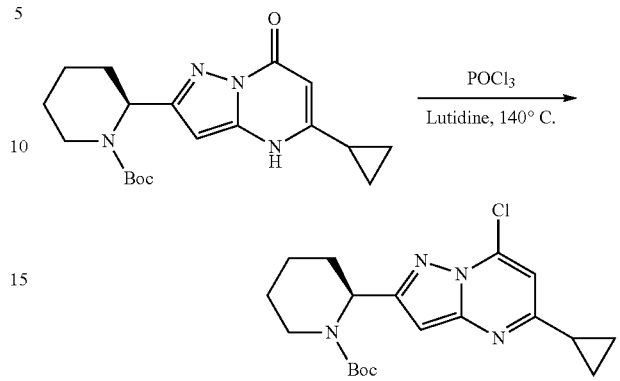

Starting material intermediate 57 (400 mg, 1.1 mol) was dissolved in lutidine (5 ml), to the mixture was added POCl$_3$ (340 mg, 2.2 mmol) and the mixture was heated at 140° C. The reaction was completed in 30 mins. The mixture was concentrated and purified via SiO$_2$ column chromatography (40 g SiO$_2$ Combiflash HP Gold Column, 0-100% EtOAc/hexanes gradient) to afford intermediate 58 (388 mg, 92%).

LCMS m/z [M+H]$^+$ $C_{19}H_{25}ClN_4O_2$ requires: 377.17. Found 377.11

HPLC Tr (min), purity %: 3.21, 98%

Intermediate 59

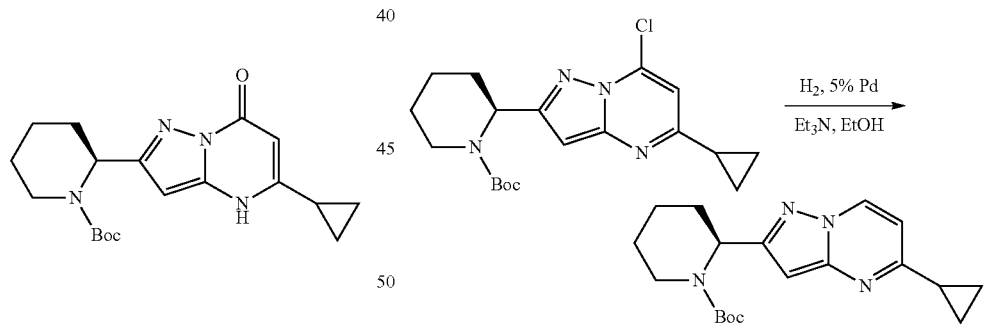

Starting material intermediate 58 (400 mg, 1.1 mmol) was dissolved in EtOH (10 ml), to the mixture was added 5% Pd on carbon (20 mg, 0.053 mmol) and Et$_3$N (0.5 ml). The mixture was heated under hydrogen balloon at RT for 1.5 h. The mixture was filtered and filtrate was concentrated and purified via SiO$_2$ column chromatography to afford intermediate 59 (283 mg, 80%).

LCMS m/z [M+H]$^+$ $C_{19}H_{26}N_4O_2$ requires: 343.21. Found 343.13

HPLC Tr (min), purity %: 2.93, 98%

Compound 61

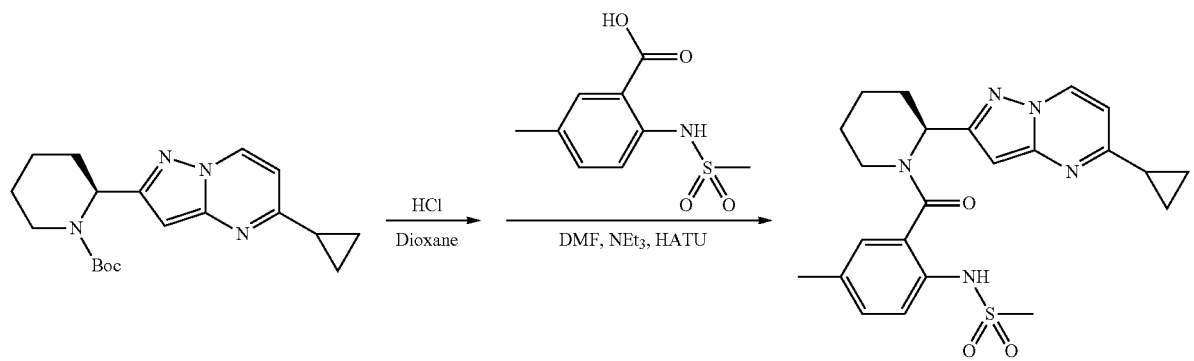

Starting material intermediate 59 (283 mg) was dissolved in 10 ml of dioxane, to the solution was added concentrated HCl (1 ml). The reaction was completed in 30 mins, solvent was evaporated and the residue was used in the next step. 2-methanesulfonamido-5-methylbenzoic acid (55 mg, 0.24 mmol), HATU (122 mg, 0.32 mmol) were dissolved in anhydrous DMF (2 ml). After activation for 1 hour, to the above solution was added previous step crude product (50 mg, 0.16 mmol) and triethylamine (50 μl). The reaction was stirred under nitrogen for 20 mins. Solvents were removed by rotary evaporation. The residue was purified with prep HPLC to provide compound 61. (Yield 31 mg, 43%).

$^1$H-NMR (CD$_3$OD, 400 MHz): δ 9.04 (s, 1H), 7.54 (d, J=8.0 Hz, 1H), 7.30 (d, J=8.0 Hz, 1H), 7.21 (s, 1H), 6.82 (d, J=7.2 Hz, 1H), 6.45 (s, 1H), 6.23-6.22 (m, 1H), 4.58 (s, 2H), 3.31 (s, 3H), 3.00-2.91 (m, 3H), 2.48-2.38 (m, 3H), 2.12-2.06 (m, 2H), 1.75-1.73 (m, 2H), 1.52 (s, 2H), 1.13 (s, 3H).

LCMS m/z [M+H]$^+$ C$_{23}$H$_{27}$N$_5$O$_3$S requires: 454.56. Found 454.13

HPLC Tr (min), purity %: 2.89, 98%

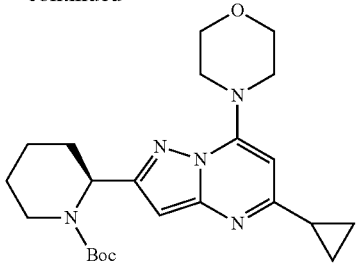

Starting material intermediate 58 (200 mg, 0.55 mmol) was dissolved in morpholine (10 ml), the mixture was stirred at RT for 30 mins. The mixture was concentrated and purified via SiO$_2$ column chromatography to afford intermediate 60 (200 mg, 88%).

LCMS m/z [M+H]$^+$ C$_{23}$H$_{33}$N$_5$O$_3$ requires: 428.26. Found 428.17

HPLC Tr (min), purity %: 2.90, 98%

Compound 62

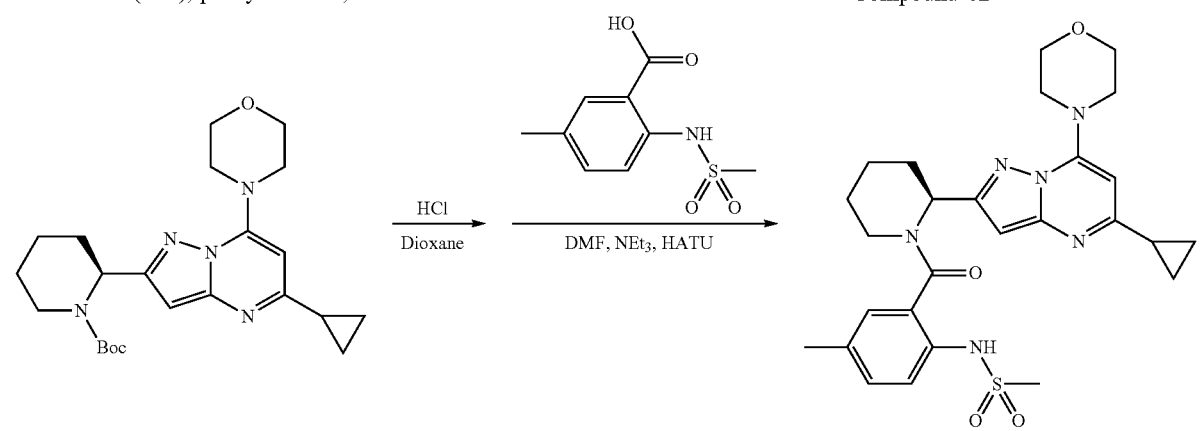

Intermediate 60

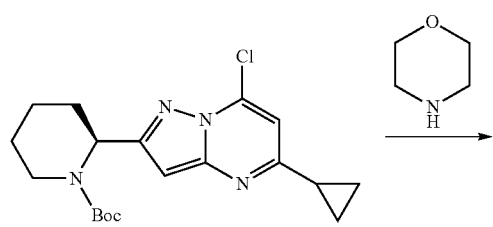

Starting material intermediate 60 (200 mg) was dissolved in 10 ml of dioxane, to the solution was added concentrated HCl (1 ml). The reaction was completed in 30 mins, solvent was evaporated and the residue was used in the next step. 2-methanesulfonamido-5-methylbenzoic acid (43 mg, 0.19 mmol), HATU (95 mg, 0.26 mmol) were dissolved in anhydrous DMF (2 ml). After activation for 1 hour, to the above solution was added previous step crude product (50 mg, 0.13 mmol) and triethylamine (50 μl). The reaction was stirred under nitrogen for 1 h. Solvents were removed by rotary evaporation. The residue was purified with preparatory HPLC to provide compound 62. (Yield 37 mg, 45%).

¹H-NMR (CD₃OD, 400 MHz): δ 7.40 (bs, 2H), 7.28 (s, 1H), 7.23 (s, 1H), 3.92-3.88 (m, 6H), 3.70 (bs, 4H), 2.95 (bs, 4H), 2.38-2.10 (m, 5H), 1.71-1.59 (m, 5H), 1.08-1.03 (m, 4H).

LCMS m/z [M+H]⁺ $C_{27}H_{34}N_6O_4S$ requires: 539.24. Found 539.27

HPLC Tr (min), purity %: 2.60, 98%

3.04-2.94 (m, 3H), 2.91-2.80 (m, 3H), 2.57-2.48 (m, 3H), 2.22-2.16 (m, 2H), 1.76-1.74 (m, 2H), 1.51 (s, 2H).

LCMS m/z [M+H]⁺ $C_{26}H_{31}ClN_6O_4S$ requires: 559.18. Found 559.24

HPLC Tr (min), purity %: 2.74, 98%

Compound 63

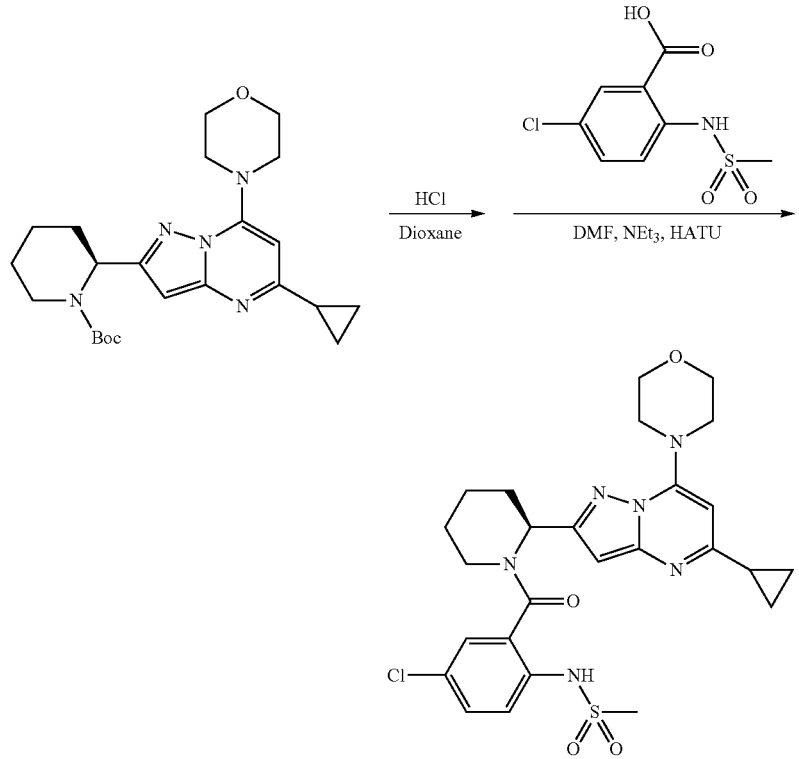

Starting material intermediate 60 (200 mg) was dissolved in 10 ml of dioxane, to the solution was added concentrated HCl (1 ml). The reaction was completed in 30 mins, solvent was evaporated and the residue was used in the next step. 2-methanesulfonamido-5-chlorobenzoic acid (20 mg, 0.08 mmol), HATU (38 mg, 0.1 mmol) were dissolved in anhydrous DMF (2 ml). After activation for 1 hour, to the above solution was added previous step crude product (20 mg, 0.05 mmol) and triethylamine (40 μl). The reaction was stirred under nitrogen for 1 h. Solvents were removed by rotary evaporation. The residue was purified with preparatory HPLC to provide compound 63. (Yield 9 mg, 26%).

¹H-NMR (CD₃OD, 400 MHz): δ 8.78 (s, 1H), 7.65 (d, J=7.2 Hz, 1H), 7.25 (d, J=7.2 Hz, 1H), 7.18 (s, 1H), 6.68 (s, 1H), 6.11 (s, 1H), 4.46 (s, 2H), 3.83 (s, 5H), 3.81 (s, 3H),

Intermediate 61

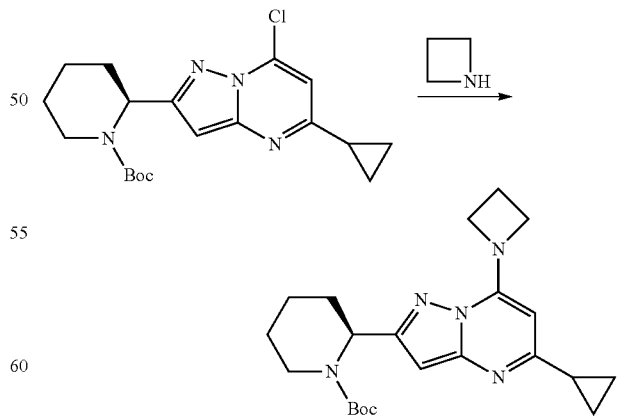

Starting material intermediate 58 (0.46 g) was dissolved in azetidine (2 g), the mixture was stirred at RT for 30 mins. The mixture was concentrated and purified via SiO₂ column chromatography to afford intermediate 61 (0.4 g, 83%).

LCMS m/z [M+H]+ C22H31N5O2 requires: 398.25. Found 398.15

HPLC Tr (min), purity %: 2.25, 98%

Compound 64

1H-NMR (CD3OD, 400 MHz): δ 7.32 (bs, 1H), 7.16 (bs, 2H), 5.98 (s, 1H), 5.41 (s, 1H), 4.44 (bs, 6H), 2.84 (bs, 4H), 2.44-2.38 (m, 3H), 1.89-1.82 (m, 1H), 1.59-1.45 (m, 4H), 0.91-0.84 (m, 5H).

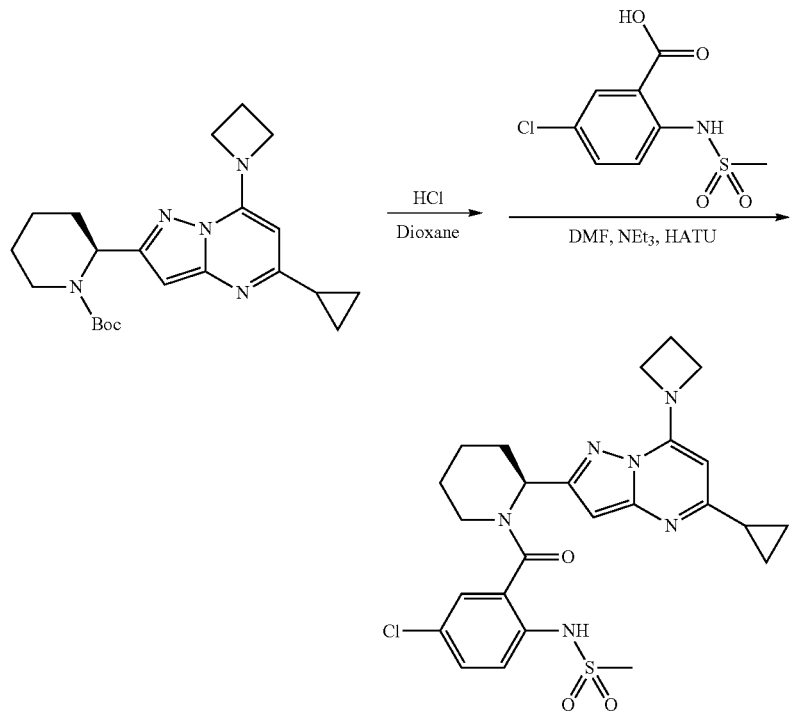

Starting material intermediate 61 (400 mg) was dissolved in 10 ml of dioxane, to the solution was added concentrated HCl (1 ml). The reaction was completed in 30 mins, solvent was evaporated and the residue was used in the next step. 2-methanesulfonamido-5-chlorobenzoic acid (45 mg, 0.18 mmol), HATU (93 mg, 0.25 mmol) were dissolved in anhydrous DMF (2 ml). After activation for 1 hour, to the above solution was added previous step crude product (50 mg, 0.12 mmol) and triethylamine (50 μl). The reaction was stirred under nitrogen for 1 h. Solvents were removed by rotary evaporation. The residue was purified with preparatory HPLC to provide compound 64. (Yield 37 mg, 80%).

LCMS m/z [M+H]+ C25H29ClN6O3S requires: 529.17. Found 529.19

HPLC Tr (min), purity %: 2.16, 98%

Compound 65

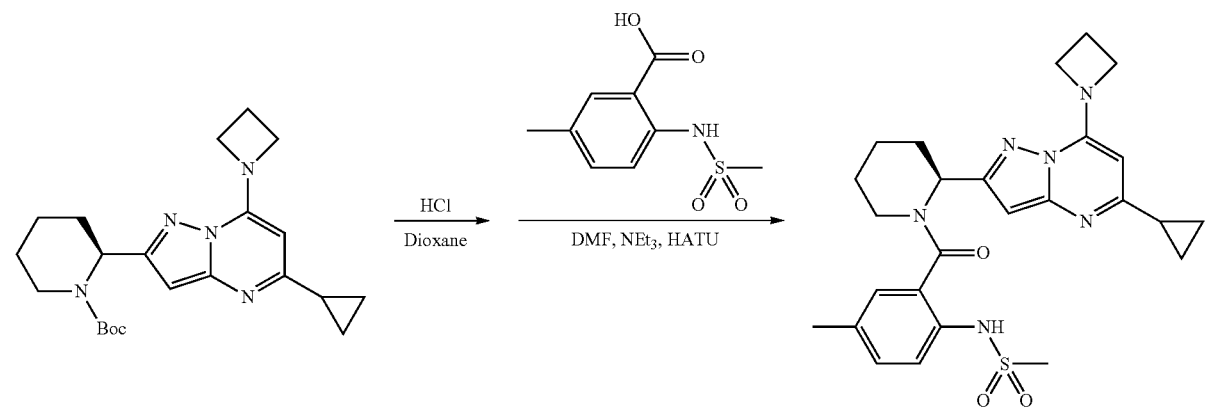

Starting material intermediate 61 (400 mg) was dissolved in 10 ml of dioxane, to the solution was added concentrated HCl (1 ml). The reaction was completed in 30 mins, solvent was evaporated and the residue was used in the next step. 2-methanesulfonamido-5-methylbenzoic acid (41 mg, 0.18 mmol), HATU (93 mg, 0.25 mmol) were dissolved in anhydrous DMF (2 ml). After activation for 1 hour, to the above solution was added previous step crude product (50 mg, 0.12 mmol) and triethylamine (50 μl). The reaction was stirred under nitrogen for 1 h. Solvents were removed by rotary evaporation. The residue was purified with preparatory HPLC to provide compound 65. (Yield 44 mg, 64%).

$^1$H-NMR (CD$_3$OD, 400 MHz): δ 7.28 (bs, 1H), 7.11 (bs, 2H), 6.05 (s, 1H), 5.44 (s, 1H), 4.46 (bs, 6H), 3.23-3.21 (m, 4H), 2.89 (bs, 3H), 2.43-2.36 (m, 2H), 2.27-2.19 (m, 3H), 1.90-1.83 (m, 1H), 1.60 (bs, 3H), 0.92-0.90 (m, 4H).

LCMS m/z [M+H]$^+$ C$_{26}$H$_{32}$N$_6$O$_3$S requires: 509.23. Found 509.21

HPLC Tr (min), purity %: 2.12, 98%

Intermediate 62

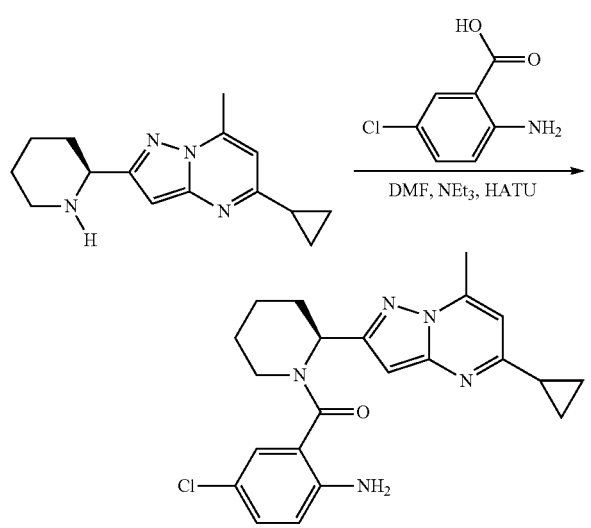

2-Amino-5-chlorobenzoic acid (55 mg, 0.32 mmol), HATU (152 mg, 0.4 mmol) were dissolved in anhydrous DMF (2 ml). After activation for 1 hour, to the above solution was added intermediate 31 (50 mg, 0.2 mmol) and triethylamine (50 μl). The reaction was stirred under nitrogen for 5 hours. Solvents were removed by rotary evaporation. The residue were purified with preparatory HPLC to provide intermediate 62 (Yield 54 mg, 68%).

LCMS m/z [M+H]$^+$ C$_{22}$H$_{24}$ClN$_5$O requires: 410.17. Found 410.15

HPLC Tr (min), purity %: 3.06, 98%

Compound 66

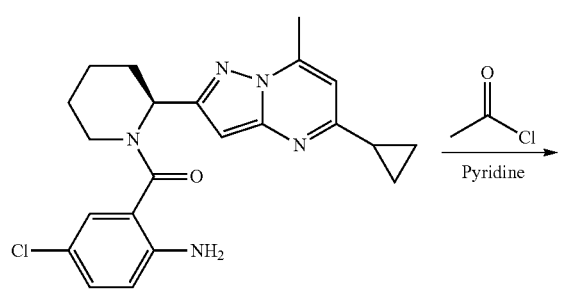

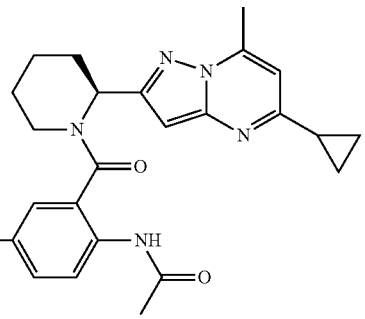

To a solution of intermediate 62 (49 mg, 0.12 mmol) in pyridine (2.0 mL) was added acetyl chloride (11 mg, 0.14 mmol) at RT, The reaction was completed in 5 mins. The volatile were removed under reduced pressure at 40° C. and the resulting residue was purified by preparative HPLC (MeCN in H$_2$O with a gradient from 0% to 95%) to afford compound 66 (46 mg, 85%) as a white powder after lyophilization.

$^1$H-NMR (CD$_3$OD, 400 MHz): δ 7.49-7.38 (m, 3H), 6.64 (s, 1H), 6.33-6.26 (m, 1H), 6.02 (s, 1H), 3.39 (s, 1H), 2.65 (s, 3H), 2.42 (bs, 3H), 2.20 (bs, 3H), 2.03-1.93 (m, 6H), 1.63 (bs, 2H), 1.50 (bs, 2H), 1.03 (s, 1H), 1.01 (s, 3H).

LCMS m/z [M+H]$^+$ C$_{24}$H$_{26}$ClN$_5$O$_2$ requires: 452.18. Found 452.04

HPLC Tr (min), purity %: 2.93, 98%

Intermediate 63

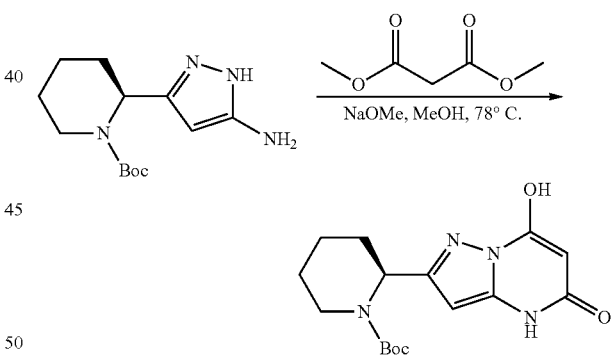

Intermediate 4 (3 g, 0.02 mol) was dissolved in MeOH (30 ml), to the solution was added dimethyl malonate (2.6 ml, 0.02 mmol) and 10% NaOMe in MeOH (25 ml, 0.1 mmol). The reaction mixture was heated at 78° C. for 5 h. Solvent was evaporated, the residue was redissolved in EtOAc (20 mL), HOAc was added to make the solution slightly acidic, washed with brine, organic solvent was evaporated, the residue was purified by silica gel column chromatography to afford intermediate 63 (3 g, 78%).

LCMS m/z [M+H]$^+$ C$_{16}$H$_{22}$N$_4$O$_4$ requires: 335.16. Found 335.05

HPLC Tr (min), purity %: 2.82, 98%

Intermediate 64

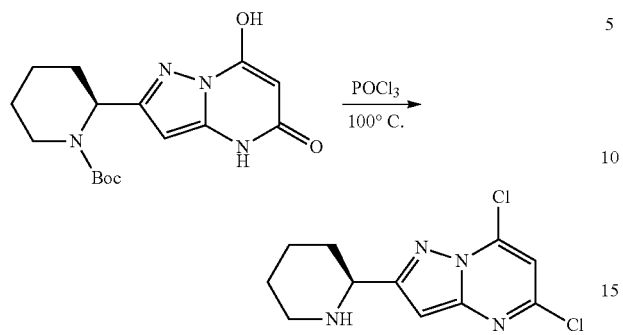

Intermediate 63 (10 g) was added to neat POCl₃ (25 ml), the reaction mixture was heated at 100° C. for 3 h. Solvent was evaporated, to the residue was added MeOH until no bubble formed. Then 30 mL of acetonitrile was added to the above residue, orange solid precipitated out of mixture to afford intermediate 64 (7.4 g, 92%).

LCMS m/z [M+H]⁺ $C_{11}H_{12}N_4Cl_2$ requires: 271.04. Found 271.07

HPLC Tr (min), purity %: 1.78, 98%

Intermediate 65

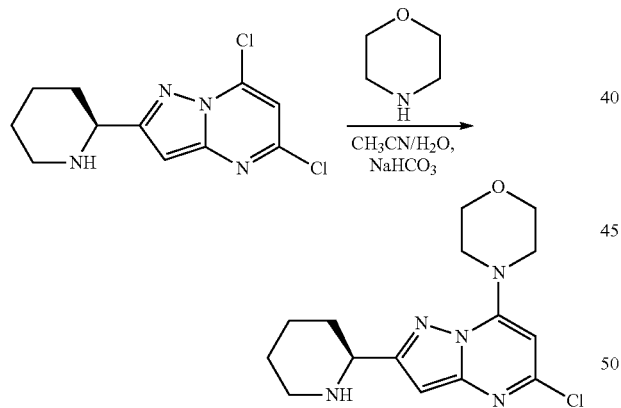

Intermediate 64 (4.2 g, 15.5 mmol) was added to CH₃CN (40 ml) and H₂O (40 ml), to the above mixture was added NaHCO₃ (2.6 G, 31 mmol) and morpholine (1.35 g, 15.5 mmol). The reaction mixture was stirred at RT for 30 mins, solvents were evaporated and to the residue was added 20 ml of DCM, the mixture was filtered and filtrate was evaporated to give intermediate 65 (4.5 g, 91%).

LCMS m/z [M+H]⁺ $C_{15}H_{20}ClN_5O$ requires: 322.14. Found 322.10

HPLC Tr (min), purity %: 1.81, 98%

Intermediate 66

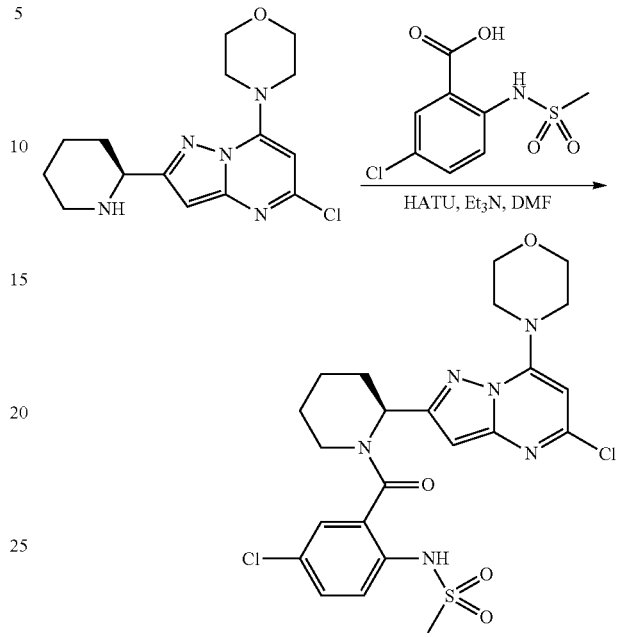

2-Amino-5-chlorobenzoic acid (5 g, 19.94 mmol), HATU (9.5, 24.92 mmol) were dissolved in anhydrous DMF (50 ml). After activation for 1 hour, to the above solution was added intermediate 65 (4 g, 12.46 mmol) and triethylamine (6.93 ml). The reaction was stirred under nitrogen for 2 hours. Solvents were removed by rotary evaporation. The residue was purified with silica gel column chromatography to provide intermediate 66. (Yield 4.7 g, 68%).

LCMS m/z [M+H]⁺ $C_{23}H_{26}Cl_2N_6O_4S$ requires: 553.11. Found 553.16

HPLC Tr (min), purity %: 2.72, 98%

Compound 67

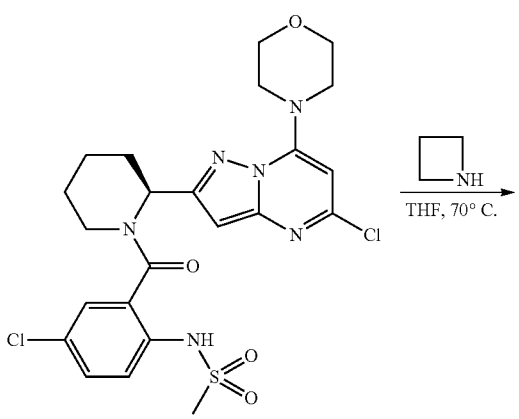

-continued

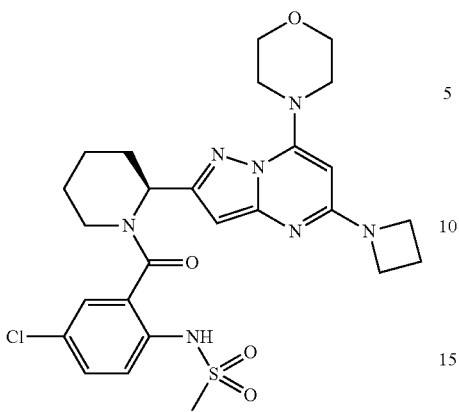

Intermediate 66 (7 g, 12.66 mmol) was dissolved in azetidine (8 g), the mixture was stirred at 70° C. for 30 mins. The mixture was concentrated and purified via SiO$_2$ column chromatography to afford compound 67 (6 g, 83%).

$^1$H-NMR (CD$_3$OD, 400 MHz): δ 7.46 (bs, 3H), 6.13-5.85 (m, 2H), 4.15-4.07 (m, 4H), 3.91-3.89 (m, 5H), 3.53 (bs, 5H), 3.31-3.30 (m, 5H), 2.99 (s, 3H), 2.43-2.37 (m, 3H), 1.70-1.62 (m, 5H).

LCMS m/z [M+H]$^+$ C$_{26}$H$_{32}$ClN$_7$O$_4$S requires: 574.19. Found 574.19

HPLC Tr (min), purity %: 2.32, 98%

Compound 68

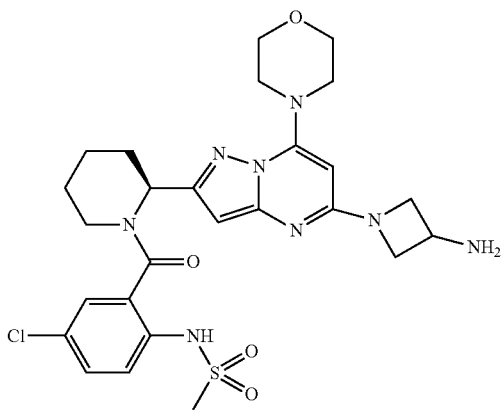 [SMILES: CS(=O)(=O)Nc1ccc(Cl)cc1C(=O)N1CCCC[C@H]1c1cc2nc(N3CC(N)C3)cc(N3CCOCC3)n2n1]

The title compound was prepared in an analogous way as described for compound 52 starting from intermediate 66.

$^1$H-NMR (CD$_3$OD, 400 MHz): δ 7.35 (bs, 3H), 5.95 (bs, 2H), 4.41-4.37 (m, 3H), 4.16-4.11 (m, 2H), 4.11-4.05 (m, 3H), 4.03-3.80 (m, 5H), 3.80 (bs, 3H), 3.20-3.16 (m, 2H), 2.90 (m, 3H), 1.62-1.57 (m, 4H).

LCMS m/z [M+H]$^+$ C$_{26}$H$_{33}$ClN$_8$O$_4$S requires: 589.20. Found 589.30

HPLC Tr (min), purity %: 2.20, 98%

Compound 69

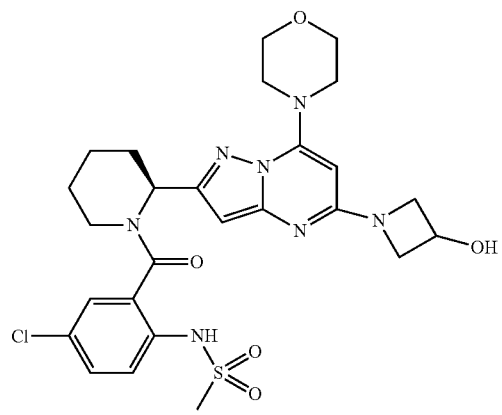 [SMILES: CS(=O)(=O)Nc1ccc(Cl)cc1C(=O)N1CCCC[C@H]1c1cc2nc(N3CC(O)C3)cc(N3CCOCC3)n2n1]

The title compound what prepared in an analogous way as described for compound 67 starting from intermediate 64.

$^1$H-NMR (CD$_3$OD, 400 MHz): δ 7.34 (bs, 4H), 5.28 (s, 1H), 4.27-4.24 (m, 4H), 3.83-3.81 (m, 8H), 3.46-3.39 (m, 6H), 2.89 (bs, 5H), 1.62 (bs, 4H).

LCMS m/z [M+H]$^+$ C$_{26}$H$_{32}$ClN$_7$O$_5$S requires: 590.11. Found 590.18

HPLC Tr (min), purity %: 2.2, 98%

Compound 70

The title compound what prepared in an analogous way as described for compound 67 starting from intermediate 64.

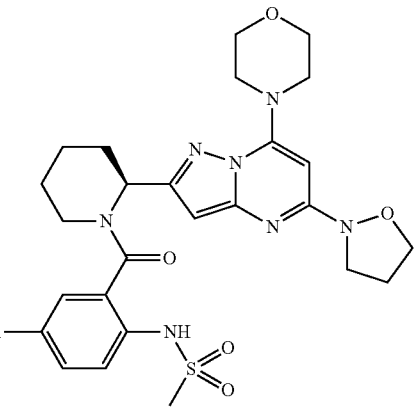

$^1$H-NMR (CD$_3$OD, 400 MHz): δ 7.38 (bs, 4H), 6.03 (bs, 1H), 3.96-3.95 (m, 4H), 3.76-3.64 (m, 6H), 2.92 (bs, 6H), 2.27 (t, J=6.8 Hz, 4H), 1.63 (bs, 4H), 1.29-1.26 (m, 1H).

LCMS m/z [M+H]$^+$ C$_{26}$H$_{32}$ClN$_7$O$_5$S requires: 590.19. Found 590.30

HPLC Tr (min), purity %: 2.97, 98%

Compound 71

The title compound what prepared in an analogous way as described for compound 67 starting from intermediate 64.

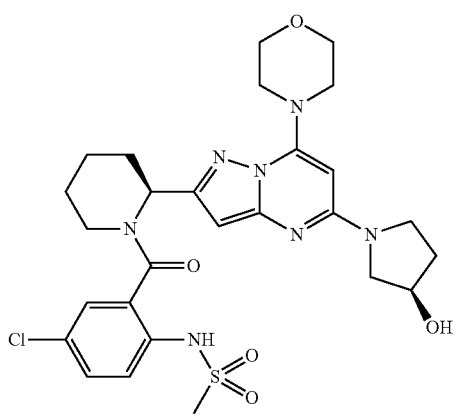 [SMILES: CS(=O)(=O)Nc1ccc(Cl)cc1C(=O)N1CCCC[C@H]1c1cc2nc(N3CC[C@@H](O)C3)cc(N3CCOCC3)n2n1]

$^1$H-NMR (CD$_3$OD, 400 MHz): δ 7.35-7.20 (m, 4H), 5.41 (s, 1H), 5.94-5.97 (bs, 1H), 3.83 (bs, 5H), 3.55-3.44 (m, 4H), 2.83 (bs, 4H), 2.69 (t, J=6.8 Hz, 4H), 2.29-1.94 (m, 5H), 1.60-1.51 (m, 4H).

LCMS m/z [M+H]$^+$ C$_{27}$H$_{34}$ClN$_7$O$_5$S requires: 604.20. Found 604.28

HPLC Tr (min), purity %: 2.33, 98%

Compound 72

The title compound what prepared in an analogous way as described for compound 67 starting from intermediate 64.

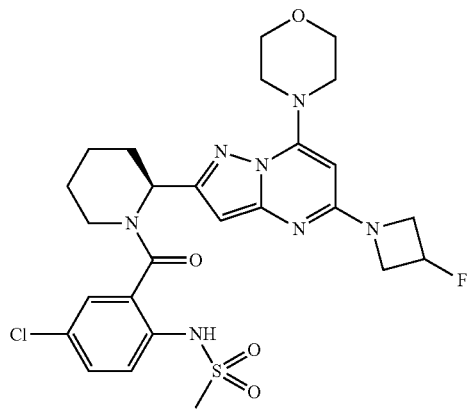 [SMILES: CS(=O)(=O)Nc1ccc(Cl)cc1C(=O)N1CCCC[C@H]1c1cc2nc(N3CC(F)C3)cc(N3CCOCC3)n2n1]

$^1$H-NMR (CD$_3$OD, 400 MHz): δ 7.35 (bs, 4H), 6.05 (bs, 1H), 5.32 (s, 1H), 4.37-4.29 (m, 2H), 4.28-4.06 (m, 2H), 4.04-3.81 (m, 5H), 3.83-3.61 (m, 7H), 2.89 (bs, 5H), 1.61-1.53 (m, 4H).

LCMS m/z [M+H]$^+$ C$_{26}$H$_{31}$ClFN$_7$O$_4$S requires: 592.18. Found 592.22

HPLC Tr (min), purity %: 2.85, 98%

Compound 73

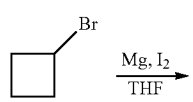

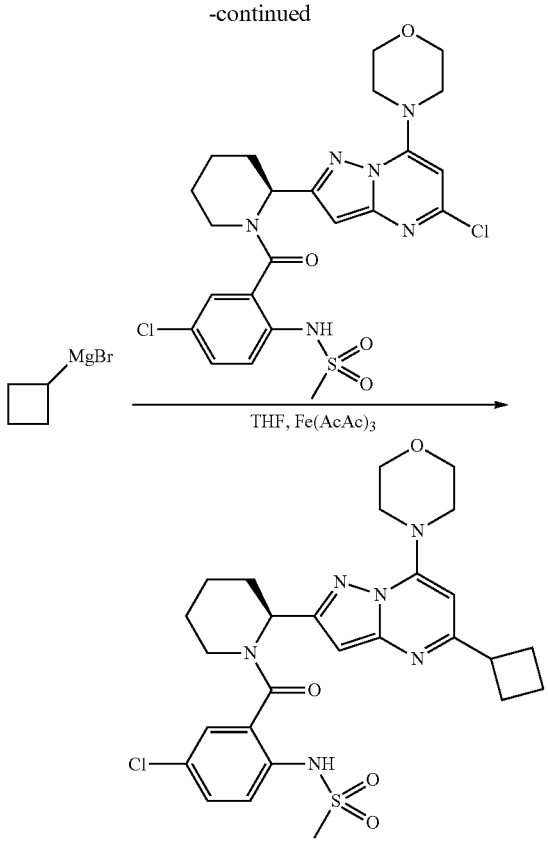

Cyclobutyl Bromide (300 mg, 0.22 mmol) was dissolved in THF (1 ml), to the mixture were added Mg (5 mg, 0.44 mmol) and catalytic amount of I$_2$. The reaction mixture was stirred at RT for 2 h. To the above mixture were added intermediate 66 (10 mg, 0.018 mmol) and Fe(AcAc)$_3$ (0.005 mmol). The reaction mixture was stirred at RT overnight. The volatile were removed under reduced pressure at 40° C. and the resulting residue was purified by preparative HPLC (MeCN in H$_2$O with a gradient from 0% to 95%) to afford compound 73 (3 mg, 30%) as a white powder after lyophilization.

$^1$H-NMR (CD$_3$OD, 400 MHz): δ 7.39 (bs, 3H), 6.23 (bs, 2H), 4.46 (bs, 5H), 3.85-3.82 (m, 3H), 3.82-3.28 (m, 3H), 3.21-3.16 (m, 2H), 2.92 (s, 3H), 2.33-2.26 (m, 4H), 2.05-1.98 (m, 2H), 1.83-1.81 (m, 1H), 1.64-1.44 (m, 4H).

LCMS m/z [M+H]$^+$ C$_{27}$H$_{33}$ClN$_6$O$_4$S requires: 573.20. Found 573.22

HPLC Tr (min), purity %: 3.00, 98%

Compound 74

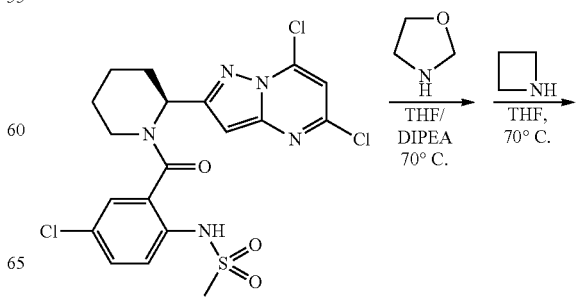

Compound 76

The title compound what prepared in an analogous way as described for compound 67 starting from intermediate 64.

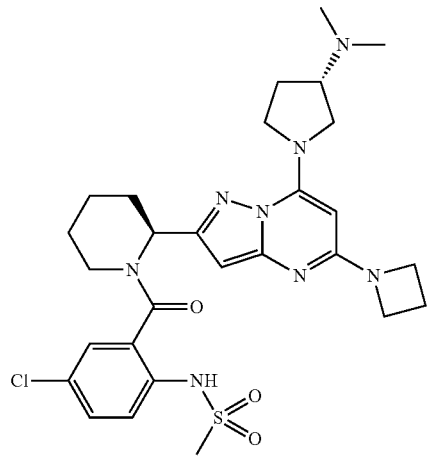

¹H-NMR (CD₃OD, 400 MHz): δ 7.36 (bs, 3H), 7.29 (bs, 1H), 4.17 (bs, 8H), 3.94 (bs, 3H), 2.92 (bs, 8H), 2.53 (bs, 2H), 2.42 (bs, 3H), 2.21-2.12 (m, 2H), 1.64 (bs, 5H).

LCMS m/z [M+H]⁺ C₂₈H₃₇ClN₈O₃S requires: 601.24. Found 601.08

HPLC Tr (min), purity %: 1.79, 98%

Compound 77

The title compound what prepared in an analogous way as described for compound 74 starting from intermediate 56.

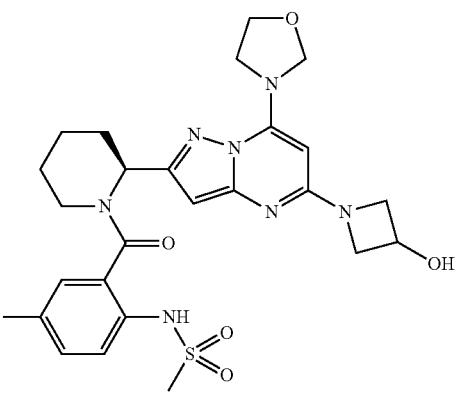

¹H-NMR (CD₃OD, 400 MHz): δ 7.43 (bs, 3H), 7.37 (bs, 1H), 5.62 (bs, 3H), 4.53-4.49 (m, 3H), 4.22 (bs, 3H), 4.10-4.06 (m, 2H), 3.82 (bs, 3H), 3.06 (bs, 5H), 1.75 (bs, 5H).

LCMS m/z [M+H]⁺ C₂₅H₃₀ClN₇O₅S requires: 576.17. Found 576.27

HPLC Tr (min), purity %: 1.98, 98%

Compound 78

The title compound what prepared in an analogous way as described for compound 85 starting from intermediate 73

-continued

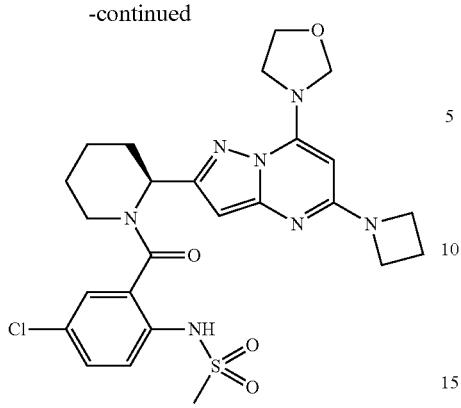

Intermediate 56 (30 mg, 0.06 mmol) was dissolved in THF (2 ml) and to the solution were added 1,3-oxazolidine (4.4 mg, 0.06 mmol) and DIPEA (0.3 ml). The reaction mixture was heated at 70° C. for 2 h. Then azetidine (0.2 ml) was added to the above solution and heated at 70° C. for 2 h. The volatile were removed under reduced pressure at 40° C. and the resulting residue was purified by preparative HPLC (MeCN in H₂O with a gradient from 0% to 95%) to afford compound 74 (20 mg, 62%) as a white powder after lyophilization.

¹H-NMR (CD₃OD, 400 MHz): δ 7.49-7.47 (m, 4H), 7.37 (bs, 1H), 6.01 (bs, 1H), 5.61 (s, 2H), 4.22 (bs, 4H), 3.81 (bs, 3H), 2.59-2.55 (m, 4H), 2.39-2.31 (m, 2H), 2.04-1.93 (m, 3H), 1.74 (bs, 6H).

LCMS m/z [M+H]⁺ C₂₅H₃₀ClN₇O₄S requires: 560.18. Found 560.17 HPLC Tr (min), purity %: 2.06, 98%

Compound 75

The title compound what prepared in an analogous way as described for compound 67 starting from intermediate 64.

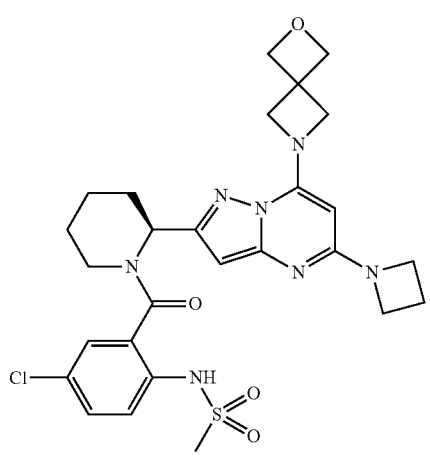 [SMILES: CS(=O)(=O)Nc1ccc(Cl)cc1C(=O)N1CCCC[C@H]1c1cc2nc(N3CCC3)cc(N3CC4(COC4)C3)n2n1]

¹H-NMR (CD₃OD, 400 MHz): δ 7.50 (bs, 3H), 7.41 (s, 1H), 6.01 (bs, 1H), 4.31-4.27 (m, 6H), 3.75 (s, 1H), 3.07 (bs, 5H), 2.54 (t, J=7.2 Hz, 3H), 2.38 (bs, 2H), 2.17-2.03 (m, 3H), 1.74 (bs, 6H).

LCMS m/z [M+H]⁺ C₂₇H₃₂ClN₇O₄S requires: 586.19. Found 586.16

HPLC Tr (min), purity %: 1.94, 98%

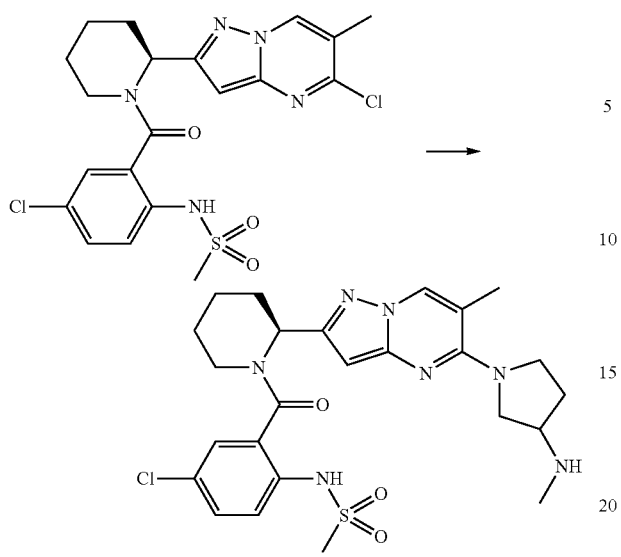

¹H-NMR (CD₃OD, 400 MHz): δ 8.71 (s, 1H), 8.42 (s, 1H), 7.68 (d, J=8.8 Hz, 1H), 7.48 (d, J=10.8 Hz, 2H), 7.44 (d, J=2.4 Hz, 1H), 6.13 (s, 1H), 4.01-3.92 (m, 3H), 3.89-3.81 (m, 5H), 3.35-3.25 (m, 2H), 3.01-2.93 (m, 5H), 2.26-2.21 (m, 2H), 2.03 (bs, 2H), 1.75-1.72 (m, 3H), 1.55 (s, 3H).

LCMS m/z [M+H]⁺ C₂₅H₃₂ClN₇O₃S requires: 546.20. Found 546.28

HPLC Tr (min), purity %: 1.96, 98%

Intermediate 67

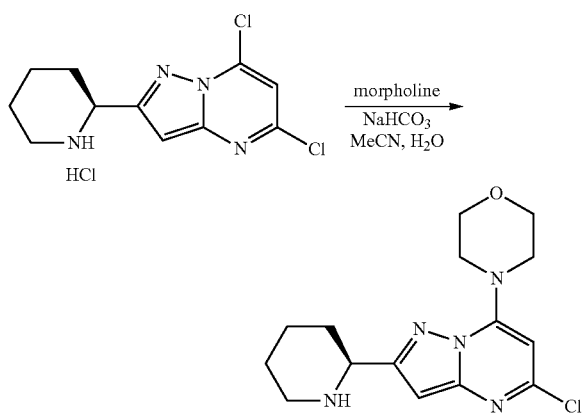

Morpholine (56.8 μL, 0.65 mmol) and sodium bicarbonate (109 mg, 1.30 mmol) were added to a solution of intermediate 64 (S)-5,7-dichloro-2-(piperidin-2-yl)pyrazolo[1,5-a]pyrimidine hydrochloride (200 mg, 0.65 mmol) in acetonitrile (1.65 mL) and water (1.65 mL) and the reaction mixture was stirred at room temperature. After 30 min, the reaction mixture was concentrated under reduced pressure. The crude residue was diluted with dichloromethane (50 mL) and the resulting suspension was filtered. The filtrate was concentrated under reduced pressure to afford the morpholine compound as a white solid (209 mg, 99%).

LCMS (ESI) m/z 322.45 [M+H]⁺, $t_R$=1.68 min.

$R_f$=0.17 (10% MeOH/CH₂Cl₂).

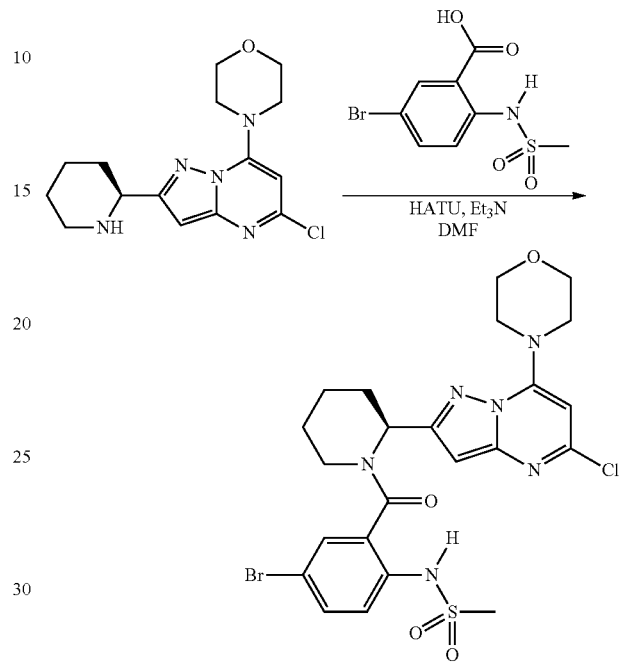

HATU (297 mg, 0.78 mmol) was added to a solution of 5-bromo-2-(methylsulfonamido)benzoic acid (210 mg, 0.72 mmol) in DMF (3.3 mL), and the reaction mixture was stirred at room temperature. After 1 h, morpholine intermediate above (209 mg, 0.65 mmol) and triethylamine (227 μL, 1.63 mmol) were added, and the reaction mixture was stirred at room temperature for 18 h. The reaction mixture was partitioned between ethyl acetate (150 mL) and water (150 mL), and the layers were separated. The organic layer was washed with water (150 mL), saturated aqueous sodium bicarbonate solution (50 mL), and saturated sodium chloride solution (50 mL), was dried over Na₂SO₄, and was concentrated under reduced pressure. The crude residue was purified via SiO₂ column chromatography (4 g SiO₂ Combiflash HP Gold Column, 0-100% ethyl acetate/hexanes) to afford intermediate 67 (348 mg, 89%) as a white solid.

¹H NMR (CDCl₃, 400 MHz): δ 8.15-7.62 (m, 1H), 7.51 (m, 3H), 6.49-6.14 (m, 1H), 6.10 (s, 1H), 5.14 (br s, 0.2H), 4.51 (br s, 0.2H), 4.01-3.51 (m, 9H), 3.33 (m, 1H), 2.95 (br s, 3H), 2.47-2.16 (m, 1H), 2.09-1.91 (m, 1H), 1.87-1.40 (m, 4H).

LCMS (ESI) m/z 597.25 [M+H]⁺, $t_R$=2.88 min.

HPLC $t_R$ (min), purity %: 4.76, 99%.

$R_f$=0.66 (EtOAc).

Compound 79

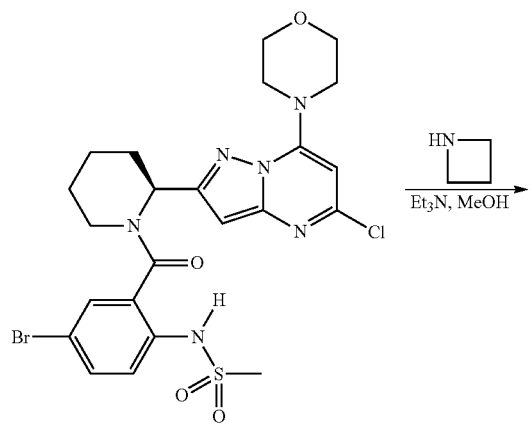

Compound 80

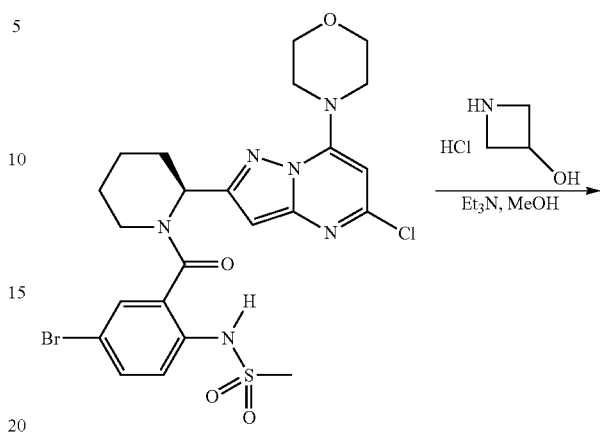

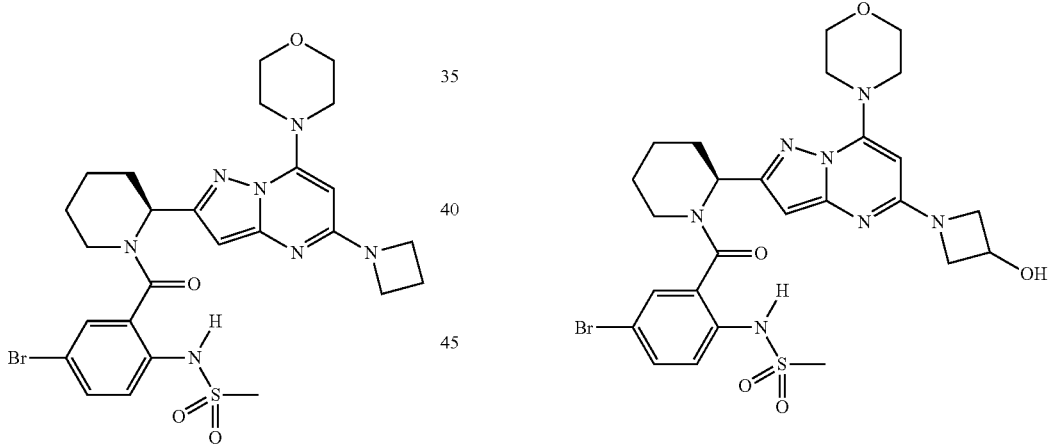

To a solution of intermediate 67 (30.0 mg, 0.05 mmol) in MeOH (1.00 mL) was added azetidine (57.0 mg, 1.00 mmol) and triethylamine (279 µL, 2.00 mmol), and the reaction mixture was stirred at 70° C. After 1 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 79 (30.4 mg, 98%) as a white solid.

$^1$H NMR (DMSO-d$_6$, 400 MHz): δ 9.34 (br s, 1H), 7.64-7.30 (m, 3H), 6.10-5.85 (m, 2H), 5.36 (s, 1H), 4.75 (br s, 0.5H), 4.38 (br d, 0.5H), 4.20-3.00 (m, 16H), 2.45-1.30 (m, 8H).

LCMS (ESI) m/z 618.36 [M+H]$^+$, t$_R$=2.37 min.

HPLC t$_R$ (min), purity %: 3.43, 99%.

R$_f$=0.33 (EtOAc).

To a solution of intermediate 67 (30.0 mg, 0.05 mmol) in MeOH (1.00 mL) was added 3-hydroxyazetidine hydrochloride (110 mg, 1.00 mmol) and triethylamine (279 µL, 2.00 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 80 (28 mg, 99%) as a white solid.

$^1$H NMR (DMSO-d$_6$, 400 MHz): δ 9.34 (br s, 1H), 7.66-7.35 (m, 3H), 6.10-5.84 (m, 2H), 5.39 (s, 1H), 4.74 (br s, 0.5H), 4.58 (br s, 1H), 4.50-4.20 (m, 1.5H), 4.10-3.00 (m, 16H), 2.40-1.30 (m, 6H).

LCMS (ESI) m/z 634.34 [M+H]$^+$, t$_R$=2.25 min.

HPLC t$_R$ (min), purity %: 3.19, 99%.

R$_f$=0.30 (EtOAc).

275
Intermediate 68

276
Compound 81

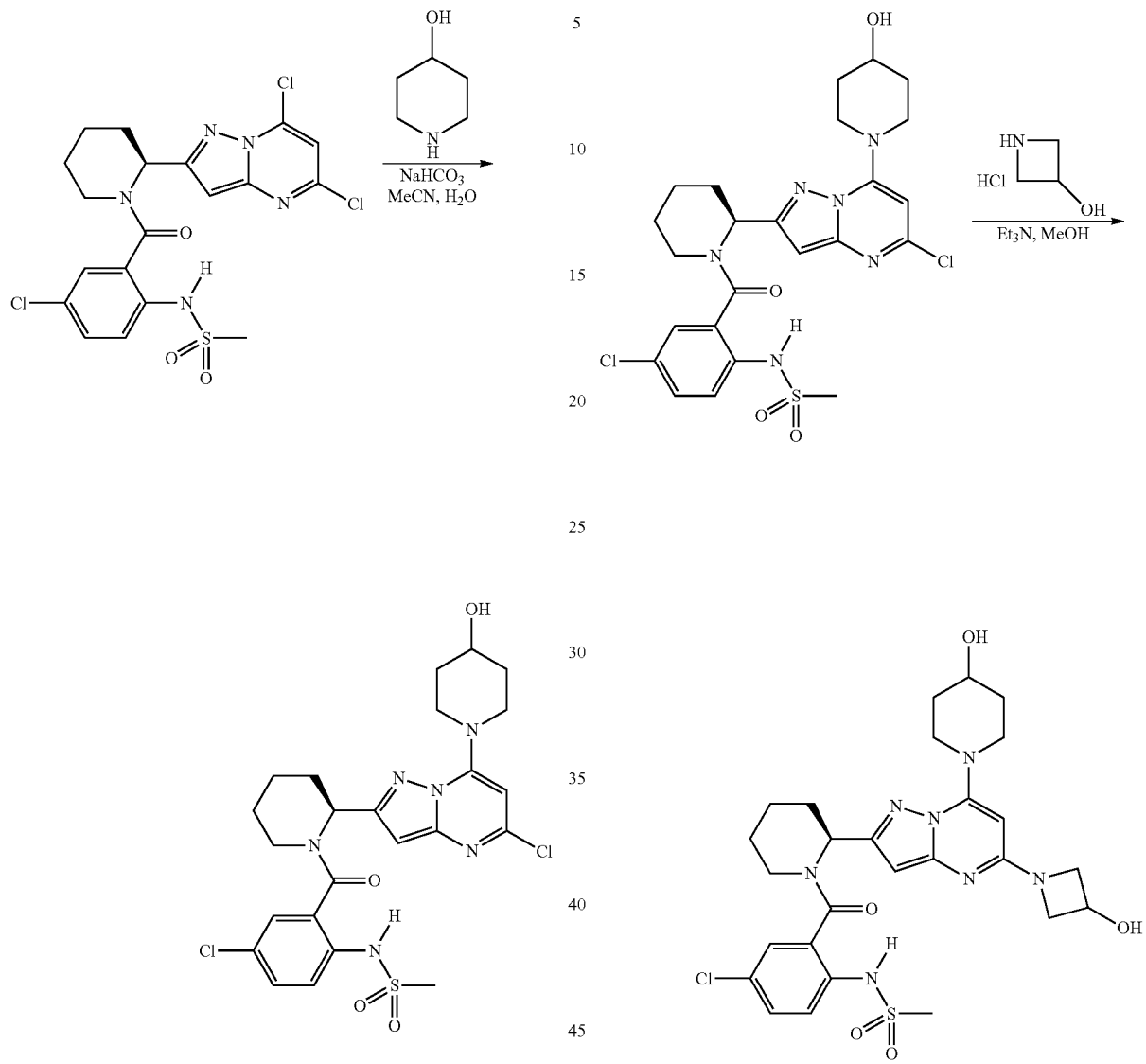

4-hydroxypiperidine (20.2 µL, 0.20 mmol) and sodium bicarbonate (33.0 mg, 0.40 mmol) were added to a solution of intermediate 56 (100 mg, 0.20 mmol) in acetonitrile (0.50 mL) and water (0.50 mL) and the reaction mixture was stirred at room temperature. After 30 min, the reaction mixture was partitioned between ethyl acetate (50 mL) and water (50 mL), and the layers were separated. The organic layer was washed with saturated aqueous sodium bicarbonate solution (50 mL) and saturated sodium chloride solution (50 mL), was dried over $Na_2SO_4$, and was concentrated under reduced pressure to afford intermediate 68 (114 mg, 99%) as a light orange solid.

$^1$H NMR (CDCl$_3$, 400 MHz): δ 8.15-7.11 (m, 4H), 6.43-5.94 (m, 2H), 5.12 (br s, 0.2H), 4.50 (br s, 0.2H), 4.28-3.91 (m, 3H), 3.81-3.15 (m, 4H), 2.93 (br s, 3H), 2.51-2.14 (m, 2H), 2.12-1.85 (m, 2H), 1.85-1.29 (m, 6H).

LCMS (ESI) m/z 567.37 [M+H]$^+$, $t_R$=2.66 min.

HPLC $t_R$ (min), purity %: 4.21, 90%.

$R_f$=0.46 (EtOAc).

To a solution of intermediate 68 (40.0 mg, 0.07 mmol) in MeOH (1.42 mL) was added 3-hydroxyazetidine hydrochloride (154 mg, 1.41 mmol) and triethylamine (396 µL, 2.84 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 81 (35.5 mg, 83%) as a white solid.

$^1$H NMR (CD$_3$OD, 400 MHz): δ 7.49 (br s, 3H), 6.10-5.60 (m, 2H), 5.34 (s, 1H), 4.72-4.66 (m, 1H), 4.30-4.45 (m, 1H), 4.35 (app t, J=8.0 Hz, 3H), 4.20-3.94 (m, 2H), 3.93-3.85 (m, 3H), 3.50-3.39 (m, 1H), 3.29-3.20 (m, 2H), 2.99 (br-s, 3H), 2.40-2.15 (m, 1H), 2.10-1.98 (m, 3H), 1.80-1.50 (m, 5H), 1.35-1.20 (m, 1H).

LCMS (ESI) m/z 604.44 [M+H]$^+$, $t_R$=2.03 min.

HPLC $t_R$ (min), purity %: 2.89, 89%.

$R_f$=0.50 (10% MeOH/CH$_2$Cl$_2$).

Intermediate 69

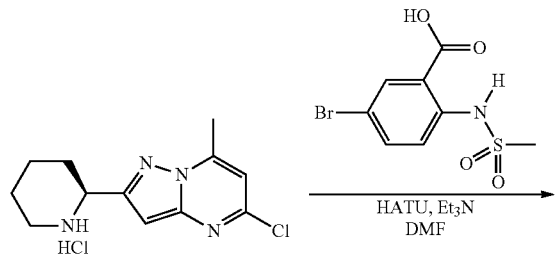

Compound 82

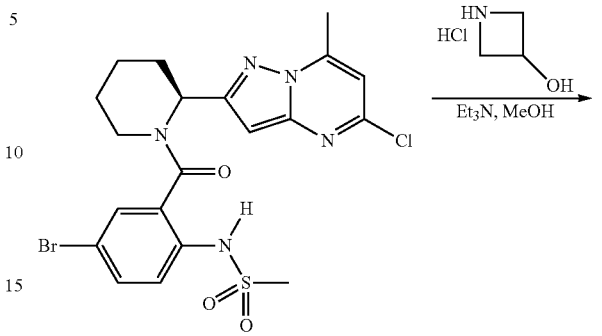

HATU (350 mg, 0.92 mmol) was added to a solution of 5-bromo-2-(methylsulfonamido)benzoic acid (247 mg, 0.84 mmol) in DMF (3.80 mL), and the reaction mixture was stirred at room temperature. After 1 h, the piperidine substrate (prepared as exemplified in the first step of conversion of Intermediate 46 to intermediate 55) (220 mg, 0.77 mmol) and triethylamine (267 µL, 1.90 mmol) were added, and the reaction mixture was stirred at room temperature for 17 h. The reaction mixture was partitioned between ethyl acetate (100 mL) and water (100 mL), and the layers were separated. The organic layer was washed with saturated aqueous sodium bicarbonate solution (100 mL) and saturated sodium chloride solution (100 mL), was dried over $Na_2SO_4$, and was concentrated under reduced pressure. The crude residue was purified via $SiO_2$ column chromatography (8 g $SiO_2$ Combiflash HP Gold Column, 0-100% ethyl acetate/hexanes) to afford intermediate 69 (342 mg, 85%) as a white solid.

$^1$H NMR ($CDCl_3$, 400 MHz): δ 7.93-7.64 (m, 1H), 7.62-7.40 (3H), 6.71 (s, 1H), 6.56-6.23 (m, 1H), 5.05 (br s, 0.2H), 4.57 (br s, 0.2H), 3.62-3.33 (m, 1H), 3.11-2.73 (m, 4H), 2.84 (s, 3H), 2.38-2.20 (m, 1H) 2.16-1.91 (m, 1H), 1.87-1.34 (m, 4H).

LCMS (ESI) m/z 526.32 [M+H]$^+$, $t_R$=3.03 min.

HPLC $t_R$ (min), purity %: 5.15, 90%.

$R_f$=0.68 (EtOAc).

To a solution of intermediate 69 (40.0 mg, 0.08 mmol) in MeOH (1.50 mL) was added 3-hydroxyazetidine hydrochloride (166 mg, 1.50 mmol) and triethylamine (424 µL, 3.00 mmol), and the reaction mixture was stirred at 70° C. After 3 h, the reaction mixture was allowed to cool to room temperature and was partitioned between ethyl acetate (50 mL) and water (25 mL). The layers were separated, and the organic layer was washed with saturated aqueous sodium bicarbonate solution (25 mL) and saturated sodium chloride solution (25 mL), was dried over $Na_2SO_4$, and was concentrated under reduced pressure. The crude residue was purified via $SiO_2$ column chromatography (4 g $SiO_2$ Combiflash HP Gold Column, 0-100% ethyl acetate/hexanes) to afford compound 82 (43 mg, 99%) as a white solid.

$^1$H NMR ($CD_3OD$, 400 MHz): δ 7.70-7.35 (m, 3H), 6.12-5.92 (m, 2H), 6.07 (s, 1H), 4.72-4.67 (m, 1H), 4.60-4.50 (m, 1H), 4.36 (app t, J=8.0 Hz, 2H), 3.92 (dd, J=9.6, 4.4 Hz, 2H), 3.50-3.45 (m, 1H), 2.98 (br s, 3H), 2.69 (s, 3H), 2.44-2.15 (m, 2H), 2.11-2.00 (m, 1H), 1.79-1.53 (m, 3H).

LCMS (ESI) m/z 563.2 [M+H]$^+$, $t_R$=2.20 min.

HPLC $t_R$ (min), purity %: 3.35, 99%.

$R_f$=0.50 (EtOAc).

279
Intermediate 70

280
Compound 83

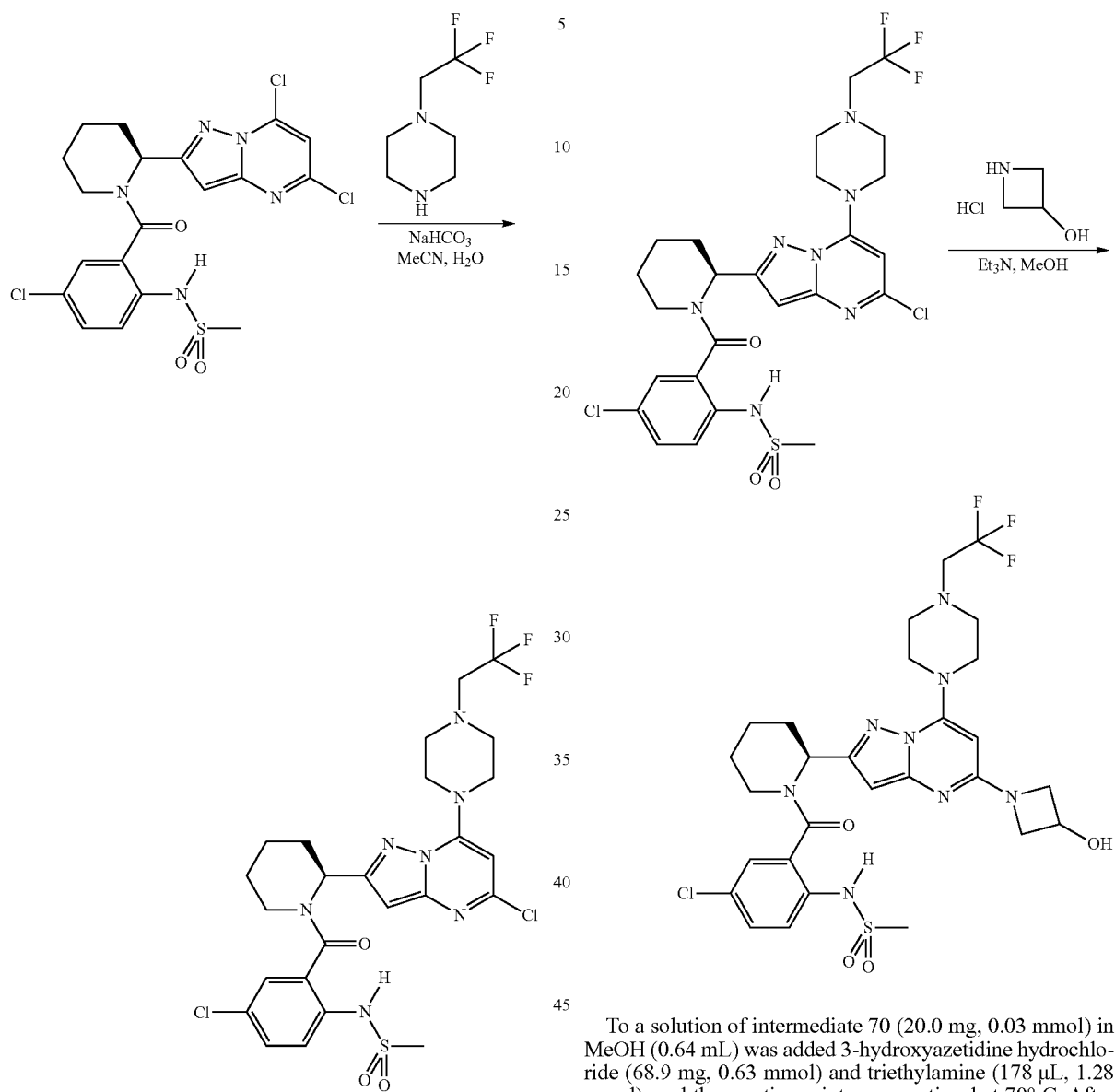

1-(2,2,2-trifluoroethyl)piperazine (32.6 mg, 0.16 mmol) and sodium bicarbonate (26.8 mg, 0.32 mmol) were added to a solution of intermediate 56 (80.0 mg, 0.16 mmol) in acetonitrile (0.40 mL) and water (0.40 mL) and the reaction mixture was stirred at room temperature. After 3 h, the reaction mixture was partitioned between ethyl acetate (20 mL) and water (50 mL), and the layers were separated. The organic layer was washed with saturated sodium chloride solution (50 mL), was dried over $Na_2SO_4$, and was concentrated under reduced pressure. The crude residue was purified via $SiO_2$ column chromatography (4 g $SiO_2$ Combiflash HP Gold Column, 0-100% ethyl acetate/hexanes) to afford intermediate 70 (79.1 mg, 78%) as a white solid.

LCMS (ESI) m/z 634.2 $[M+H]^+$, $t_R$=2.78 min.

HPLC $t_R$ (min), purity %: 5.37, 54%.

$R_f$=0.39 (EtOAc).

To a solution of intermediate 70 (20.0 mg, 0.03 mmol) in MeOH (0.64 mL) was added 3-hydroxyazetidine hydrochloride (68.9 mg, 0.63 mmol) and triethylamine (178 µL, 1.28 mmol), and the reaction mixture was stirred at 70° C. After 5 h, the reaction mixture was allowed to cool to room temperature and was partitioned between ethyl acetate (10 mL) and water (10 mL). The layers were separated, and the organic layer was washed with saturated aqueous sodium bicarbonate solution (10 mL) and saturated sodium chloride solution (10 mL), was dried over $Na_2SO_4$, and was concentrated under reduced pressure. The crude residue was purified via $SiO_2$ column chromatography (4 g $SiO_2$ Combiflash HP Gold Column, 0-100% ethyl acetate/hexanes) to afford compound 83 (9.4 mg, 44%) as a white solid.

$^1$H NMR ($CD_3OD$, 400 MHz): δ 7.54-7.34 (m, 3H), 6.30-5.95 (m, 2H), 5.31 (s, 1H), 4.81-4.74 (m, 1H), 4.58-4.48 (m, 2H), 4.14-4.08 (m, 2H), 4.03-3.85 (m, 4H), 3.48 (quintet, J=1.6, 1H), 3.23-3.08 (m, 1H), 3.07-3.00 (m, 2H), 2.96-2.89 (app t, J=5.2 Hz, 4H), 2.40-2.00 (m, 2H), 1.80-1.56 (m, 4H).

LCMS (ESI) m/z 671.3 $[M+H]^+$, $t_R$=2.18 min.

HPLC $t_R$ (min), purity %: 4.07, 99%.

$R_f$=0.39 (EtOAc).

Compound 84

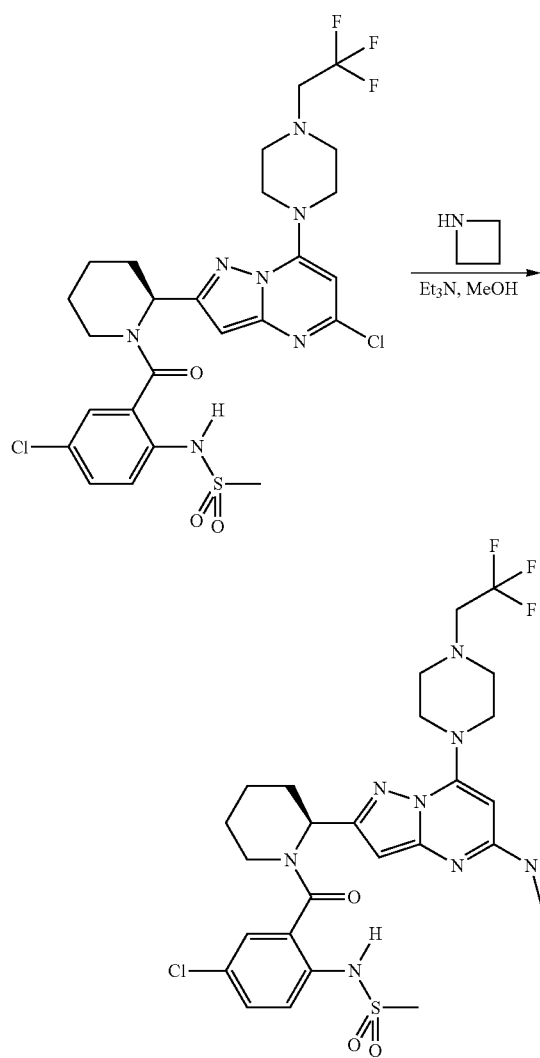

To a solution of intermediate 70 (20.0 mg, 0.03 mmol) in MeOH (0.64 mL) was added azetidine (42.0 µL, 0.63 mmol) and triethylamine (178 µL, 1.28 mmol), and the reaction mixture was stirred at 70° C. After 2 h, the reaction mixture was allowed to cool to room temperature and was partitioned between ethyl acetate (10 mL) and water (10 mL). The layers were separated, and the organic layer was washed with saturated aqueous sodium bicarbonate solution (10 mL) and saturated sodium chloride solution (10 mL), was dried over $Na_2SO_4$, and was concentrated under reduced pressure. The crude residue was purified via $SiO_2$ column chromatography (4 g $SiO_2$ Combiflash HP Gold Column, 0-100% ethyl acetate/hexanes) to afford compound 84 (6.2 mg, 30%) as a white solid.

$^1$H NMR (CD$_3$OD, 400 MHz): δ 7.67-7.27 (m, 3H), 6.14-5.74 (m, 2H), 5.32 (s, 1H), 4.14 (app t, J=7.2 Hz, 4H), 3.67-3.43 (m, 2H), 3.20-3.08 (m, 2H), 3.01-2.95 (m, 2H), 2.92 (app t, J=4.8 Hz, 4H), 2.41 (quintet, J=6.8 Hz, 2H), 2.20-1.99 (m, 2H), 1.76-1.54 (m, 4H).
LCMS (ESI) m/z 655.3 [M+H]$^+$, $t_R$=2.32 min.
HPLC $t_R$ (min), purity %: 3.81, 99%.
$R_f$=0.50 (EtOAc).

Intermediate 71

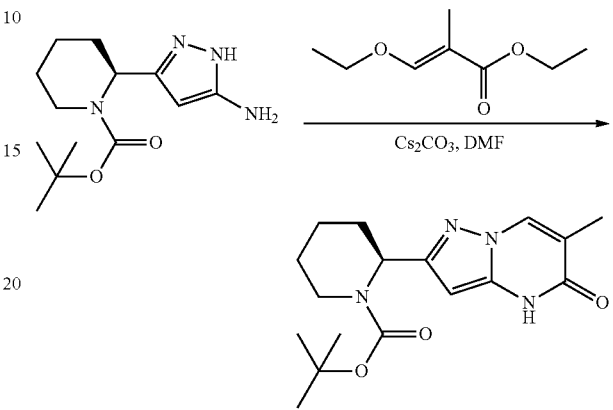

(E)-ethyl-3-ethoxy-2-methylacrylate (11.8 g, 67.6 mmol) and $Cs_2CO_3$ (22.0 g, 67.6 mmol) were added to a solution of intermediate 4 (12.0 g, 45.1 mmol) at room temperature and the reaction mixture was heated to 130° C. After 17 h, the reaction mixture was allowed to cool to room temperature and was concentrated under reduced pressure. The crude residue was diluted with ethyl acetate (250 mL) and was filtered. The resulting filtrate was concentrated under reduced pressure and the residue was purified via $SiO_2$ column chromatography (330 g $SiO_2$ Combiflash HP Gold Column, 0-100% ethyl acetate/hexanes) to afford intermediate 71 (8.58 g, 57%) as a light yellow solid.

$^1$H NMR (CDCl$_3$, 400 MHz): δ 12.01 (br s, 1H), 7.99 (s, 1H), 5.73 (s, 1H), 5.42 (br s, 1H), 4.01 (br d, J=12.2 Hz, 1H), 2.81 (br t, J=11.2 Hz, 1H), 2.29 (d, J=13.5 Hz, 1H), 2.07 (d, J=1.1 Hz, 3H), 1.87-1.69 (m, 1H), 1.68-1.41 (m, 4H), 1.48 (s, 9H). $^{13}$C NMR (CDCl$_3$, 100 MHz): δ 162.87, 156.34, 155.43, 140.16, 135.00, 113.29, 86.50, 79.75, 28.41, 27.79, 25.27, 21.00, 19.88, 13.38.
LCMS (ESI) m/z 333.0 [M+H]$^+$, $t_R$=2.24 min.
HPLC $t_R$ (min), purity %: 3.969, 99%.
$R_f$=0.50 (EtOAc).
Chiral HPLC, 98% ee (Chiralpak IC 5 mM, 4.6 150 mm, 10-95% MeCN/H$_2$O, 0.05% trifluoroacetic acid modifier) (S)-isomer $t_R$=22.234 min, (R)-isomer $t_R$=20.875 min.

Intermediate 72

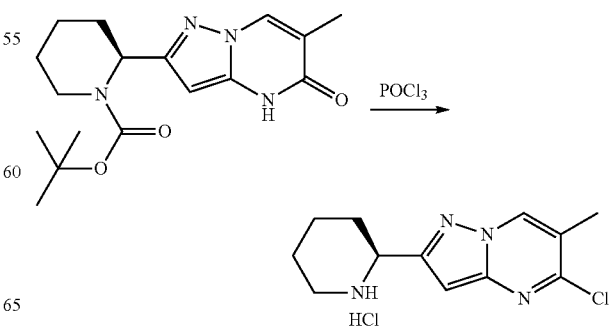

POCl₃ (5.60 mL, 59.8 mmol) was added to intermediate 71 (993.4 mg, 2.99 mmol) at room temperature and the reaction mixture was heated to 100° C. After 2 h, the reaction mixture was allowed to cool to room temperature and was concentrated under reduced pressure to afford intermediate 72 as an orange semi-solid, which was used directly in the following step.

¹H NMR (DMSO-d₆, 400 MHz): δ 9.40 (br d, J=7.6 Hz, 1H), 9.27-9.16 (m, 2H), 6.85 (s, 1H), 4.54 (t, J=112.4 Hz, 1H), 3.32 (d, J=12.8 Hz, 1H), 3.08 (q, J=8.81 Hz, 1H), 2.33 (s, 3H), 2.23-2.14 (m, 1H), 1.92-1.61 (m, 5H).

LCMS (ESI) m/z 251.1 [M+H]⁺, $t_R$=0.21 min.
HPLC $t_R$=2.35 min.

Intermediate 73

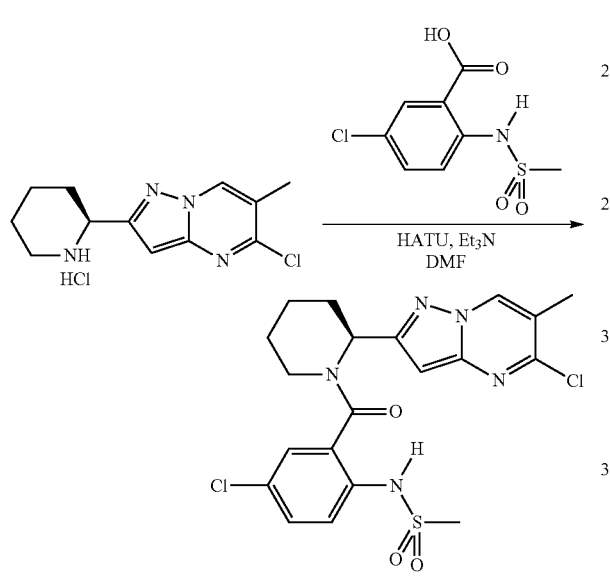

HATU (1.37 g, 3.59 mmol) was added to a solution of 5-chloro-2-(methylsulfonamido)benzoic acid (823 mg, 3.29 mmol) in DMF (15.0 mL), and the reaction mixture was stirred at room temperature. After 1 h, a solution of crude intermediate 72 (220 mg, 2.99 mmol) in DMF (1 mL) was added followed by the addition of triethylamine (2.00 mL, 14.3 mmol), and the reaction mixture was stirred at room temperature for 19 h. The reaction mixture was partitioned between ethyl acetate (250 mL) and saturated aqueous sodium bicarbonate solution (200 mL), and the layers were separated. The organic layer was washed with saturated aqueous sodium bicarbonate solution (200 mL) and saturated sodium chloride solution (200 mL), was dried over Na₂SO₄, and was concentrated under reduced pressure. The crude residue was purified via SiO₂ column chromatography (12 g SiO₂ Combiflash HP Gold Column, 0-100% ethyl acetate/hexanes) to afford intermediate 73 (736.2 mg, 51% (2-steps)) as a white solid.

¹H NMR (CDCl₃, 400 MHz): δ 10.05 (br s, 0.2H), 9.13 (br s, 8.95 (br s, 1H), 8.81 (br s, 0.2H), 7.70 (d, J=8.8 Hz, 1H), 7.56 (d, J=8.8 Hz, 0.2H), 7.40 (dd, J=8.8, 2.4 Hz, 1H), 7.33 (d, J=2.4 Hz, 1H), 7.31 (d, J=4.4 Hz, 0.2H), 6.45 (s, 1H), 6.40 (br s, 0.2H), 6.28 (br d, J=4.4 Hz, 1H), 5.01 (br s, 0.2H), 4.54 (br d, J=14.0 Hz, 0.2H), 3.35 (br d, J=13.2 Hz, 1H), 3.15-3.03 (m, 1H), 2.92 (s, 3H), 2.39 (s, 3H), 2.13-1.98 (m, 1H), 1.90-1.59 (m, 2H), 1.59-1.31 (m, 3H). ¹³C NMR (CDCl₃, 100 MHz): δ 167.09, 156.12, 153.13, 147.86, 135.68, 131.79, 131.66, 131.38, 130.12, 125.91, 125.44, 117.08, 93.74, 47.65, 44.07, 39.81, 27.83, 25.47, 19.78, 16.90.

LCMS (ESI) m/z 482.1 [M+H]⁺, $t_R$=2.79 min.
HPLC $t_R$ (min), purity %: 5.438, 99%
$R_f$=0.47 (50% EtOAc/hexanes).
Chiral HPLC, 99% ee (Chiralpak IC 5 mM, 4.6 150 mm, 10-95% MeCN/H₂O, 0.05% trifluoroacetic acid modifier) (S)-isomer $t_R$=29.739 min, (R)-isomer $t_R$=29.495 min.

Compound 85

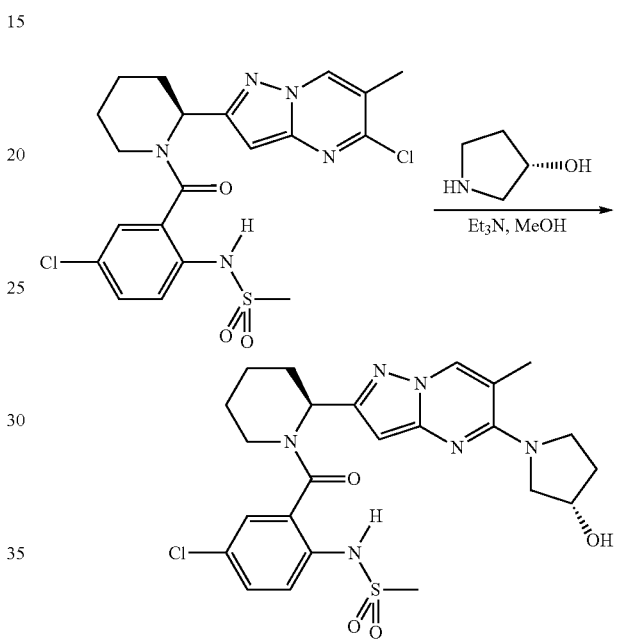

To a solution of intermediate 73 (20.0 mg, 0.04 mmol) in MeOH (0.84 mL) was added (S)-3-hydroxypyrrolidine (72.5 mg, 0.83 mmol) and triethylamine (234 µL, 1.68 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H₂O, 0.1% trifluoroacetic acid modifier) to afford compound 85 (17.7 mg, 65%) as a white solid. (TFA Salt)

¹H NMR (CDCl₃, 400 MHz): δ 8.90 (s, 1H), 8.64 (br s, 0.7H), 8.52 (br s, 0.15H), 8.45 (br s, 0.15H), 7.70 (d, J=8.8 Hz, 1H), 7.57 (br d, J=12 Hz, 0.2H), 7.41 (dd, J=8.8, 2.8 Hz, 1H), 7.33 (d, J=2.4 Hz, 1H), 6.44 (br s, 1H), 6.17 (d, J=4.4 Hz, 1H), 4.75 (br s, 1H), 4.61 (br s, 0.2H), 4.39-4.27 (m, 1H), 4.24-4.14 (m, 1H), 4.12-4.03 (m, 1H), 3.34 (br d, J=13.6 Hz, 1H), 3.16-3.04 (m, 2H), 2.92 (s, 3H), 2.80 (s, 0.4H), 2.56 (s, 3H), 2.41 (s, 0.6H), 2.38-2.26 (m, 2H), 2.24-1.99 (m, 2H), 1.84-1.75 (br d, J=12.4 Hz, 1H), 1.64-1.42 (m, 2H), 1.41-1.29 (m, 1H).

LCMS (ESI) m/z 533.2 [M+H]⁺, $t_R$=2.41 min.
HPLC $t_R$ (min), purity %: 3.80, 99%.
$R_f$=0.5 (EtOAc).

Intermediate 74

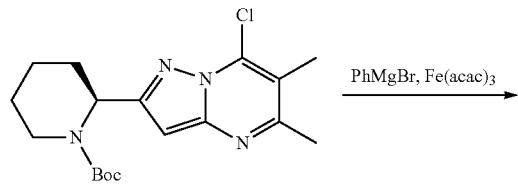

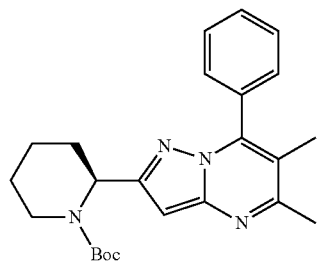

Intermediate 14 (244 mg, 0.68 mmol) in THF/NMP 7:1 (8 mL) was treated with Fe(acac)₃ (66 mg, 0.19 mmol) and placed under Ar. The mixture was treated dropwise with PhMgBr (508 µL, 1.015 mmol, 2.0 M) and the mixture was stirred overnight. The mixture was treated with saturated NH₄Cl/Na₂EDTA (100 µL) poured into EtOAc (100 mL) and H₂O (50 mL). The organic layer was washed with H₂O (50 mL) and saturated sodium chloride solution (50 mL), then dried over MgSO₄. Purification via SiO₂ column chromatography (40 g SiO₂ Combiflash HP Gold Column, 0-100% EtOAc/hexanes) afforded intermediate 74 (9 mg, 3%) as a white solid:

LCMS m/z [M+H]⁺407, [M+Na]⁺429.

Compound 86

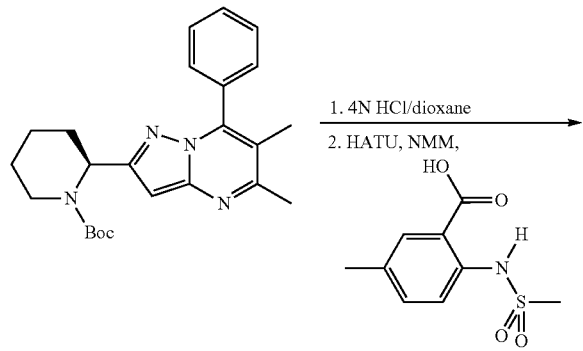

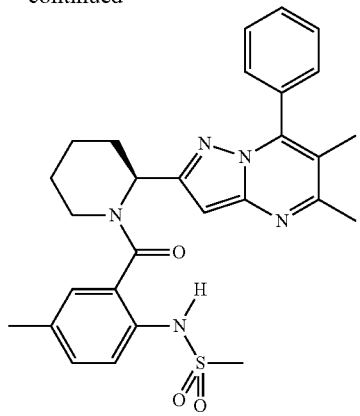

Intermediate 74 (9 mg, 0.02 mmol) was treated with 4 N HCl/dioxane (1 mL) and stirred at for 3 h. The mixture was concentrated and treated with DMF (1 mL), HATU (13 mg, 0.03 mmol), N-methylmorpholine (15 µL, 0.11 mmol), and 5-methyl-2-(methylsulfonamido)benzoic acid (7 mg, 0.03 mmol). The mixture was stirred overnight then poured into EtOAc (100 mL) and H₂O (50 mL). The organic layer was washed with H₂O (50 mL) and saturated sodium chloride solution (50 mL), then dried over MgSO₄. Purification via preparative HPLC (5-100% MeCN/H₂O, 0.1% trifluoroacetic acid modifier) afforded compound 86 (1 mg, 9%) as a white solid (TFA salt):

m/z [M+H]⁺518, [M+Na]⁺540.

HPLC (RP: 6-98% MeCN—H₂O gradient, 0.05% TFA modifier) t$_R$=5.236 min (>95% purity @ 254 nM).

Intermediate 75

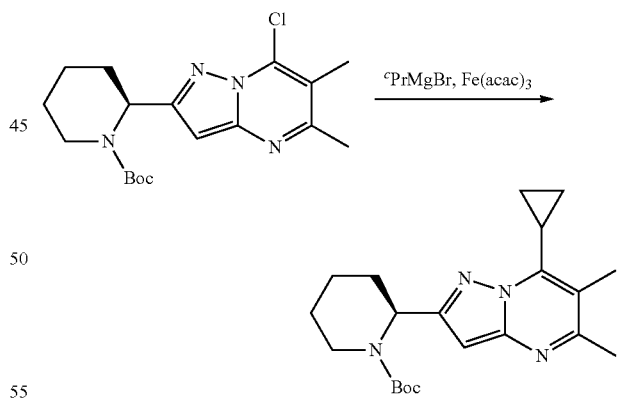

Intermediate 14 (247 mg, 0.68 mmol) in THF/NMP 7:1 (8 mL) was treated with Fe(acac)₃ (66 mg, 0.19 mmol) and placed under Ar. The mixture was treated dropwise with ᶜPrMgBr (2.07 mL, 1.015 mmol, 0.5 M) and the mixture was stirred overnight. The mixture was treated with saturated NH₄C/Na₂EDTA (100 µL) poured into EtOAc (100 mL) and H₂O (50 mL). The organic layer was washed with H₂O (50 mL) and saturated sodium chloride solution (50 mL), then dried over MgSO₄. Purification via SiO₂ column chromatography (40 g SiO₂ Combiflash HP Gold Column, 0-100%

EtOAc/hexanes) afforded intermediate 75 (16 mg, 6%) as a white solid:

LCMS m/z [M+H]$^+$371, [M+Na]$^+$393.

Compound 87

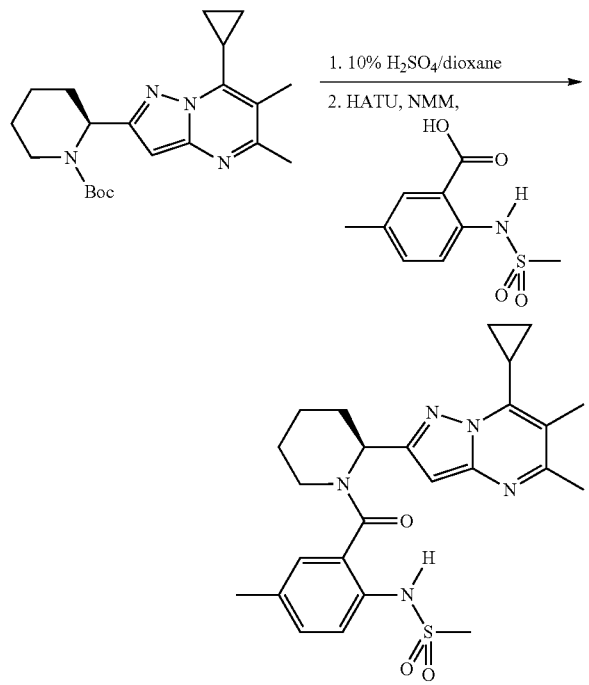

Intermediate 75 (9 mg, 0.02 mmol) was treated with 10% H$_2$SO$_4$/dioxane (1 mL) and stirred at for 3 h. The mixture was concentrated and treated with DMF (1 mL), HATU (25 mg, 0.06 mmol), N-methylmorpholine (30 µL, 0.21 mmol), and 5-methyl-2-(methylsulfonamido) benzoic acid (13 mg, 0.06 mmol). The mixture was stirred overnight then poured into EtOAc (100 mL) and H$_2$O (50 mL). The organic layer was washed with H$_2$O (50 mL) and saturated sodium chloride solution (50 mL), then dried over MgSO$_4$. Purification via preparative HPLC (5-100% MeCN/H$_2$O, 0.1% trifluoroacetic acid modifier) afforded compound 87 (0.7 mg, 3%) as a white solid (TFA salt):

m/z [M+H]$^+$482.

HPLC (RP: 6-98% MeCN—H$_2$O gradient, 0.05% TFA modifier) t$_R$=5.118 min (>95% purity @ 254 nM).

Intermediate 76

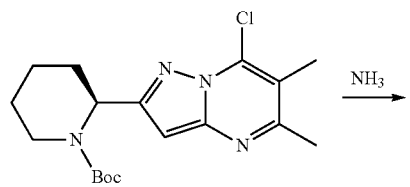

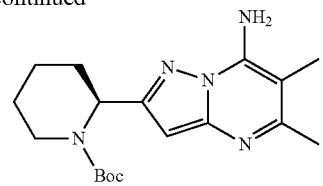

Intermediate 14 (610 mg, 1.67 mmol) was treated with NH$_3$ (10 mL) and heated at 80° C. overnight. The mixture was cooled and NH$_3$ was removed with degassing. The mixture was suspended in MeOH and filtered through a medium glass fitted funnel to afford intermediate 76 (375 mg, 65%) as a white solid:

LCMS m/z [M+H]$^+$346.

Intermediate 77

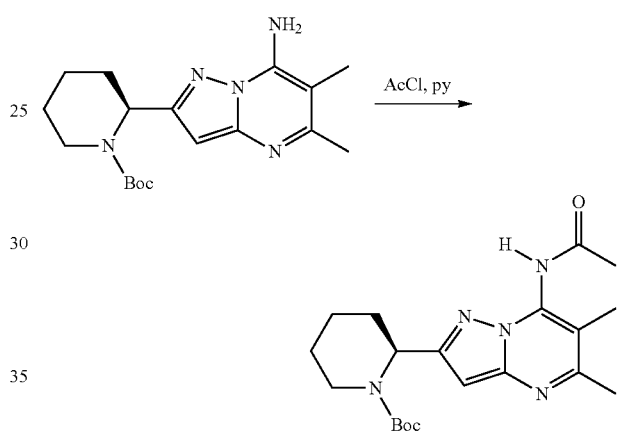

Intermediate 76 (185 mg, 0.53 mmol) in CH$_2$Cl$_2$ (5 mL) was treated with pyridine (430 µL, 5.3 mmol) and AcCl (113 µL, 1.6 mmol) and stirred overnight. The mixture was poured into EtOAc (100 mL) and H$_2$O (50 mL). The organic layer was washed with H$_2$O (50 mL) and saturated sodium chloride solution (50 mL), then dried over MgSO$_4$. Purification via SiO$_2$ column chromatography (40 g SiO$_2$ Combiflash HP Gold Column, 0-100% EtOAc/hexanes) afforded intermediate 77 (29 mg, 6%) as a white solid:

LCMS m/z [M+2H]$^+$389.

Compound 88

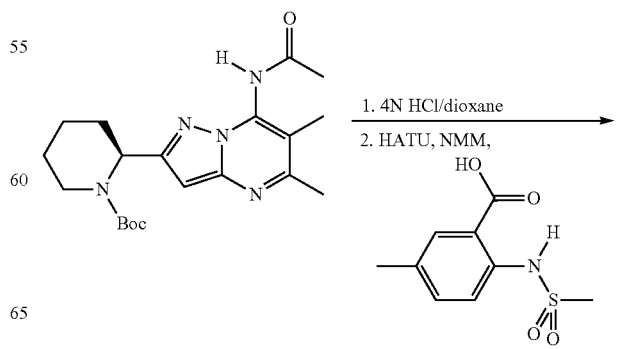

-continued

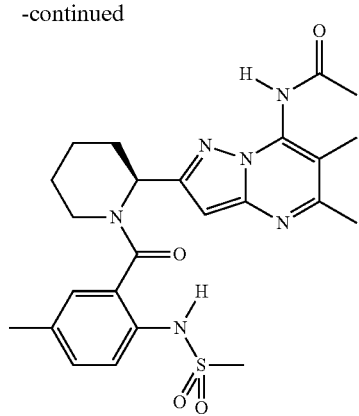

Intermediate 77 (29 mg, 0.07 mmol) was treated with 4 N HCl/dioxane (2 mL) and stirred at for 3 h. The mixture was concentrated and treated with DMF (2 mL), HATU (39 mg, 0.1 mmol), N-methylmorpholine (50 μL, 0.34 mmol), and 5-methyl-2-(methylsulfonamido)benzoic acid (20 mg, 0.09 mmol). The mixture was stirred overnight then poured into EtOAc (100 mL) and H$_2$O (50 mL). The organic layer was washed with H$_2$O (50 mL) and saturated sodium chloride solution (50 mL), then dried over MgSO$_4$. Purification via preparative HPLC (5-100% MeCN/H$_2$O, 0.1% trifluoroacetic acid modifier) afforded compound 88 (8 mg, 22%) as a white solid (TFA salt):

$^1$H-NMR (CD$_3$CN, 400 MHz): δ 7.31 (m, 3H), 6.71 (s, 1H), 6.27 (s 1H), 2.92 (s, 3H), 2.36 (s, 2H), 1.91 (m, 2H), 1.96 (s, 3H), 1.68 (m, 3H).

m/z [M+H]$^+$499.

HPLC (RP: 15-100% MeCN—H$_2$O gradient, 0.05% TFA modifier) t$_R$=14.65 min (>95% purity @254 nM).

Compound 89

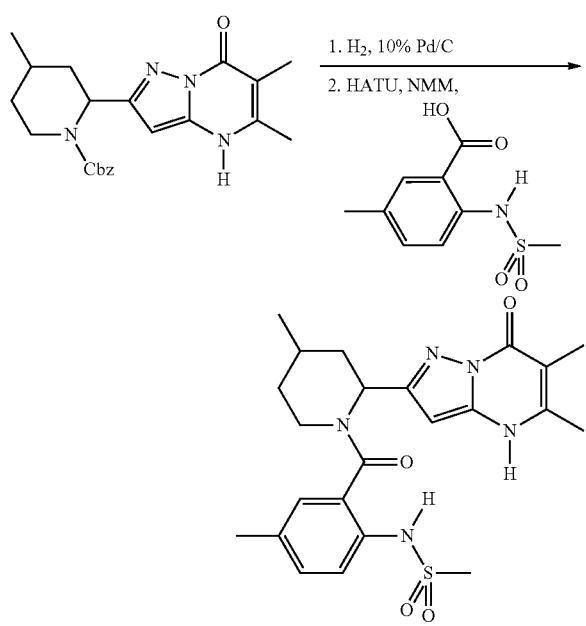

Cbz intermediate 203 (119 mg, 0.30 mmol) in EtOH (6 mL) was treated with 10% Pd/C (50 mg) and HOAc (18 mL, 0.33 mmol) and placed under H$_2$. The mixture was stirred overnight then filtered through Celite plug. The solution is concentrated and treated with DMF (6 mL), HATU (172 mg, 0.45 mmol), N-methylmorpholine (250 μL, 1.5 mmol), and 5-methyl-2-(methylsulfonamido)benzoic acid (90 mg, 0.29 mmol). The mixture was stirred overnight then poured into EtOAc (100 mL) and H$_2$O (50 mL). The organic layer was washed with H$_2$O (50 mL) and saturated sodium chloride solution (50 mL), then dried over MgSO$_4$. Purification via preparative HPLC (5-100% MeCN/H$_2$O, 0.1% trifluoroacetic acid modifier) afforded compound 89 as a mixture of isomers (5 mg, 3%) as a white solid (TFA salt):

m/z [M+H]$^+$472.

HPLC (RP: 6-98% MeCN—H$_2$O gradient, 0.05% TFA modifier) t$_R$=4.016 min (80% purity @ 254 nM).

Compound 90

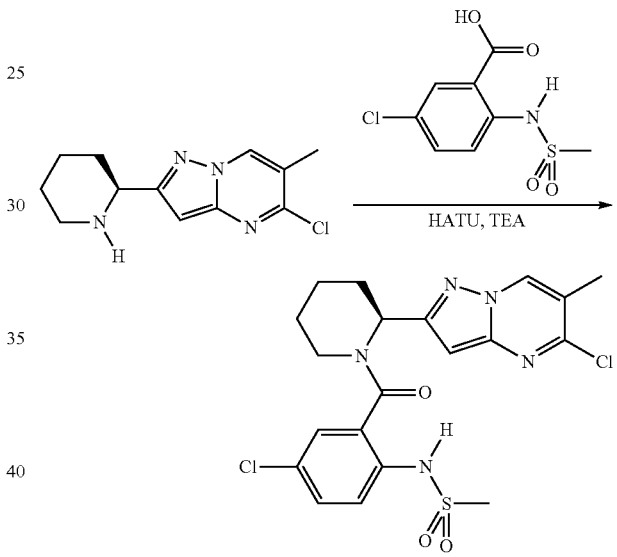

5-Chloro-2-(methylsulfonamido)benzoic acid (40 mg, 0.16 mmol) and HATU (69 mg, 0.18 mmol) in DMF (2 mL) were stirred for 1 h. Intermediate 72 (35 mg, 0.12 mmol) and TEA (42 μL, 0.30 mmol) and the mixture was stirred overnight. The mixture was stirred overnight then poured into EtOAc (100 mL) and H$_2$O (50 mL). The organic layer was washed with H$_2$O (50 mL) and saturated sodium chloride solution (50 mL), then dried over MgSO$_4$. Purification via preparative HPLC (5-100% MeCN/H$_2$O, 0.1% trifluoroacetic acid modifier) afforded compound 90 (also same as intermediate 73) (27 mg, 46%) as a white solid (TFA salt):

$^1$H-NMR (CDCl$_3$, 400 MHz): δ 9.13 (s, 1H), 8.94 (br s, 1H), 7.70 (d, J=6.6 Hz, 1H), 7.39 (d, J=6.6 Hz, 1H), 7.32 (s, 1H), 6.45 (s, 1H), 6.28 (d, J=3.3 Hz, 1H), 3.31 (d, J=9.9 Hz, 1H), 3.12 (m, 1H), 2.92 (s, 3H), 2.38 (s, 3H), 1.38-1.62 (m, 6H).

m/z [M+H]$^+$483, [M+Na]$^+$ 505.

HPLC (RP: 6-98% MeCN—H$_2$O gradient, 0.05% TFA modifier) t$_R$=5.261 min (95% purity @ 254 nM).

Compound 91

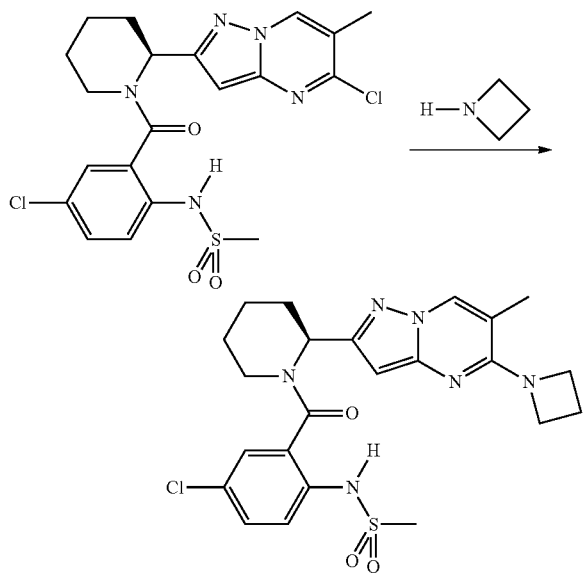

Compound 90 (9 mg, 0.02 mmol) in azetidine (1 mL) was stirred at 70° C. for 1 h. The solution was concentrated and purified via preparative HPLC (5-100% MeCN/H₂O, 0.1% trifluoroacetic acid modifier) to afford compound 91 (5 mg, 53%) as a white solid (TFA salt):

$^1$H-NMR (CD$_3$OD, 400 MHz): δ 8.65 (s, 1H), 7.67 (d, J=6.9 Hz, 1H), 7.48 (d, J=6.6 Hz, 1H), 7.43 (s, 1H), 6.10 (br d, 1H), 4.51 (br m, 1H), 2.51 (app t, 2H), 3.29 (m, 1H), 3.12 (m, 1H), 2.96 (s, 3H), 2.29 (s, 3H), 2.03 (br m, 2H), 1.35-1.75 (m, 6H).

m/z [M+H]$^+$504, [M+H]$^+$ 526.

HPLC (RP: 6-98% MeCN—H₂O gradient, 0.05% TFA modifier) t$_R$=4.197 min (>99% purity @ 254 nM).

Compound 92

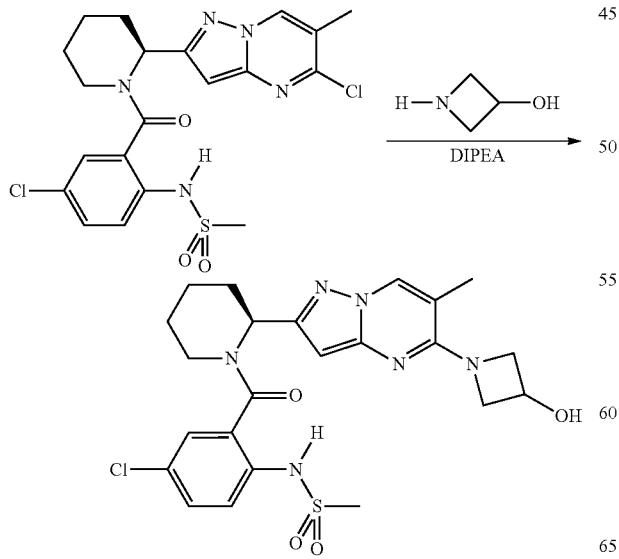

Compound 90 (9 mg, 0.02 mmol) in THF (1 mL) was treated with DIPEA (66 μL, 0.38 mmol) and 3-hydroxyazetidine.HCl (20 mg, 0.19 mmol). The mixture was stirred at 70° C. for 1.5 h. The solution was concentrated and purified via preparative HPLC (5-100% MeCN/H₂O, 0.1% trifluoroacetic acid modifier) to afford compound 92 (8 mg, 87%) as a white solid (data for TFA salt):

R$_f$=0.41 (EtOAc)

$^1$H-NMR (CDCl$_3$, 400 MHz, rotamer denoted by *): δ 9.30 (br s, 1H), 8.81 (s, 1H), 7.68 (d, J=6.6 Hz, 1H), 7.54 (d, J=6.3 Hz, 1H), 7.41 (s, 1H), 6.21 (s, 1H), 6.14 (d, J=4.0 Hz, 1H), 4.92* (br s, 1H, rotamer), 4.85* (br s, 1H, rotamer), 3.33 (app d, J=9.3 Hz, 1H), 3.12 (app t, J=8.7 Hz, 2H), 2.91 (s, 3H), 2.32 (s, 3H), 2.27 (m, 1H, unresolved), 2.00 (app t, J=10.5 Hz, 1H), 1.76 (d, J=9.9 Hz, 1H), 1.56 (app d, J=9.6 Hz, 1H), 1.45 (m, 1H), 1.27 (m, 1H).

m/z [M+H]$^+$520, [M+Na]$^+$542.

HPLC (RP: 6-98% MeCN—H₂O gradient, 0.05% TFA modifier) t$_R$=3.778 min (>99.9% purity @ 254 nM).

Chiral HPLC (Chiralpak IC 5 mM, 4.6 150 mm, 10-95% MeCN/H₂O, 0.05% trifluoroacetic acid modifier) (S)-isomer t$_R$=19.274 min, (R)-isomer t$_R$=19.773 min.

Compound 93

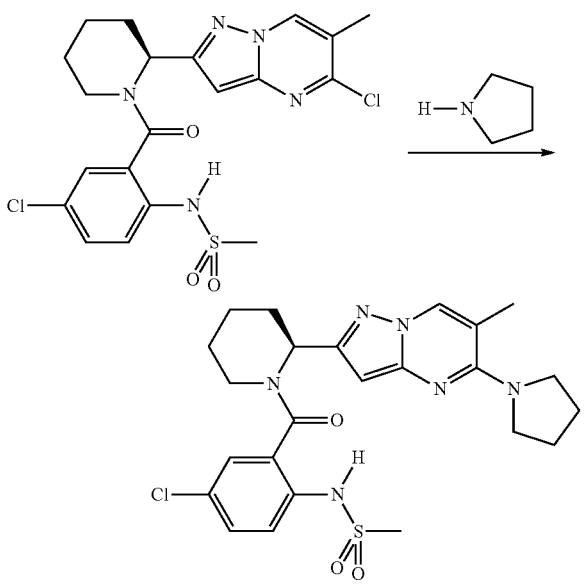

Compound 90 (9 mg, 0.02 mmol) in pyrrolidine (1 mL) was stirred at 70° C. for 1 h. The solution was concentrated and purified via preparative HPLC (5-100% MeCN/H₂O, 0.1% trifluoroacetic acid modifier) to afford compound 93 (5 mg, 53%) as a white solid (TFA salt):

$^1$H-NMR (CD$_3$OD, 400 MHz): δ 8.64 (s, 1H), 7.56 (d, J=6.3 Hz, 1H), 7.39 (d, J=6.6 Hz, 1H), 7.34 (s, 1H), 6.02 (br d, 1H), 3.80 (br m, 4H), 3.20 (m, 1H), 3.09 (s, 3H), 2.31 (m, 1H), 1.99 (br s, 6H), 1.93-1.36 (complex, 5H)

m/z [M+H]$^+$518, [M Na]$^+$540.

HPLC (RP: 6-98% MeCN—H₂O gradient, 0.05% TFA modifier) t$_R$=4.413 min (>95% purity @ 254 nM).

Compound 94

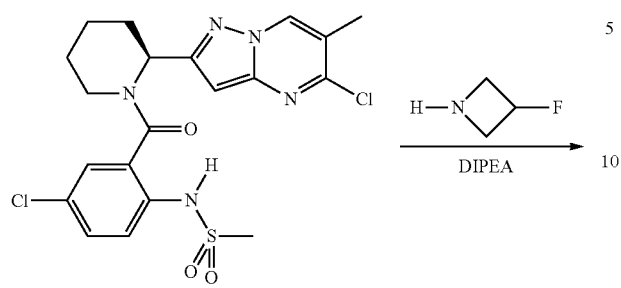
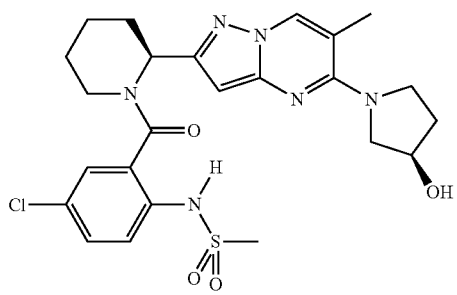

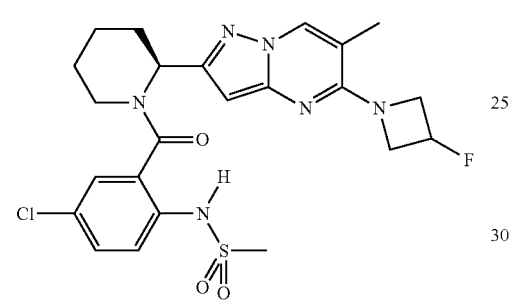

Compound 90 (20 mg, 0.04 mmol) in THF (3 mL) was treated with DIPEA (150 μL, 0.83 mmol) and 3-fluoroazetidine.HCl (46 mg, 0.4 mmol). The mixture was stirred at 70° C. for 1 h. The solution was concentrated and purified via preparative HPLC (5-100% MeCN/H₂O, 0.1% trifluoroacetic acid modifier) to afford compound 94 (13 mg, 60%) as a white solid (TFA salt):

¹H-NMR (CD₃CN, 400 MHz): δ 8.82 (s, 1H), 8.65 (s, 1H), 7.68 (m, 1H), 7.48 (m, 2H), 6.07 (s, 1H), 6.03 (m, 1H), 5.45 (s, 1H), 5.40 (s, 1H), 3.80 (br m, 4H), 3.20 (m, 1H), 2.95 (s, 3H), 2.31 (m, 1H), 1.99 (br s, 6H), 1.93-1.36 (m, 5H).

m/z [M+H]⁺ 522, [M+Na]⁺ 543.

HPLC (RP: 6-98% MeCN—H₂O gradient, 0.05% TFA modifier) $t_R$=4.937 min (>95% purity @ 254 nM).

Compound 95

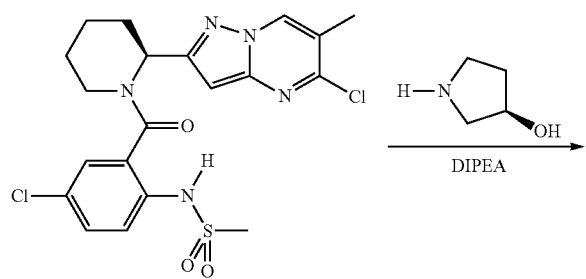

Compound 90 (15 mg, 0.03 mmol) in THF (3 mL) was treated with DIPEA (110 μL, 0.6 mmol) and (R)-pyrrolidin-3-ol.HCl (38 mg, 0.3 mmol). The mixture was stirred at 70° C. for 1 h. The solution was concentrated and purified via preparative HPLC (5-100% MeCN/H₂O, 0.1% trifluoroacetic acid modifier) to afford Compound 95 (13 mg, 60%) as a white solid (TFA salt):

m/z [M+H]⁺ 534.

HPLC (RP: 6-98% MeCN—H₂O gradient, 0.05% TFA modifier) $t_R$=3.761 min (>95% purity @ 254 nM).

Compound 96

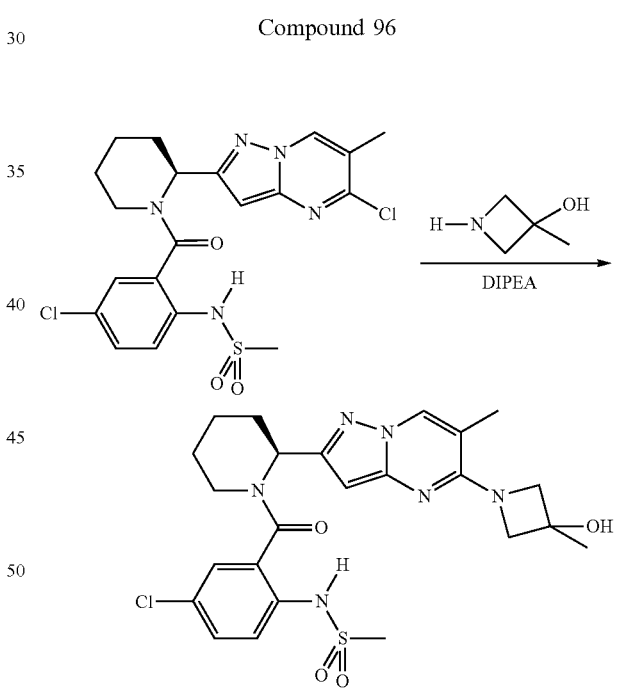

Compound 90 (30 mg, 0.06 mmol) in THF (6 mL) was treated with DIPEA (221 μL, 1.2 mmol) and 3-methylazetidin-3-ol.HCl (75 mg, 0.6 mmol). The mixture was stirred at 70° C. for 2 h. The solution was concentrated and purified via preparative HPLC (5-100% MeCN/H₂O, 0.1% trifluoroacetic acid modifier) to afford Compound 96 (19 mg, 57%) as a white solid (TFA salt):

m/z [M+H]⁺ 534.

HPLC (RP: 6-98% MeCN—H₂O gradient, 0.05% TFA modifier) $t_R$=3.959 min (>95% purity @ 254 nM).

Compound 97

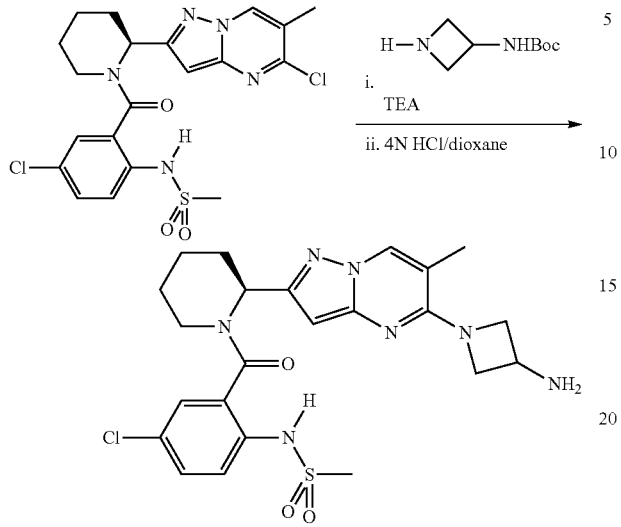

Compound 90 (47 mg, 0.1 mmol) in MeOH (1 mL) was treated with TEA (270 µL, 1.9 mmol) and tert-butyl azetidin-3-ylcarbamate (167 mg, 1.0 mmol). The mixture was stirred at 70° C. overnight. The solution was concentrated to afford the product as a white solid which was used without further purification: m/z [M+H]$^+$ 619, [M+Na]$^+$ 641. The product (60 mg, 0.1 mmol) was treated with 4 N HCl/dioxane (1 mL) and the mixture was stirred for 3 h. The solution was concentrated and purified via preparative HPLC (5-100% MeCN/H$_2$O, 0.1% trifluoroacetic acid modifier) to afford compound 97 (13 mg, 60%) as a white solid (TFA salt):

$^1$H-NMR (CD$_3$OD, 400 MHz): δ 8.84 (s, 1H), 8.38 (s, 1H), 7.70 (m, 1H), 7.47 (s, 1H), 7.43 (s, 1H), 6.10 (m, 1H), 4.63 (m, 1H), 4.28 (m, 2H), 4.18 (m, 2H), 3.20 (m, 2H), 3.01 (m, 1H), 2.97 (s, 3H), 2.40 (m, 1H), 2.25 (s, 3H), 2.05 (m, 1H), 1.75 (m, 1H), 1.55 (m, 1H), 1.45 (m, 1H).

m/z [M+H]$^+$ 519.

HPLC (RP: 6-98% MeCN—H$_2$O gradient, 0.05% TFA modifier) t$_R$=3.314 min (>95% purity @ 254 nM).

Intermediate 78

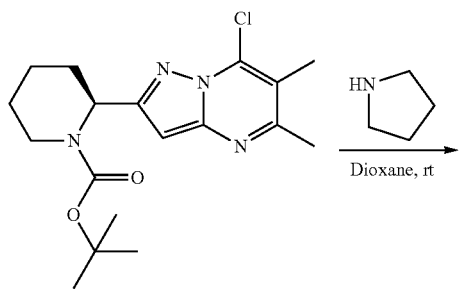

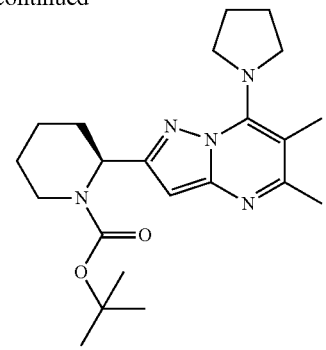

Pyrrolidine (7.4 mL, 89.3 mmol) was added to a solution of intermediate 14 (250 mg, 0.687 mmol) in 15 mL of dioxane at room temperature. Reaction mixture was stirred overnight. Solution was concentrated to ½ volume and was poured into 50 mL of water/50 mL Brine. Aqueous was extracted with ethyl acetate (3×70 mL) and combined organic was washed with 150 mL of 1:1 water:brine, dried (MgSO$_4$), filtered, and concentrated under reduced pressure. Silica gel column chromatography (20-50% Ethyl Acetate in Hexanes) yielded intermediate 78 (232 mg, 85%)

LCMS m/z [M+H]$^+$ C$_{22}$H$_{33}$N$_5$O$_2$ requires: 400.26. Found 400.20

Intermediate 79

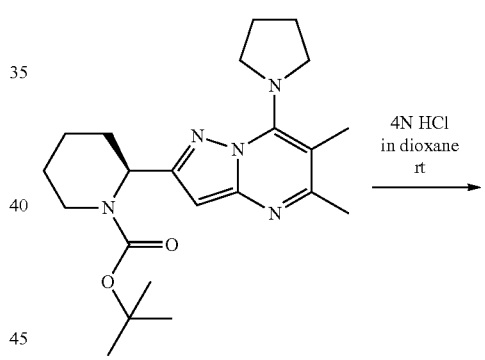

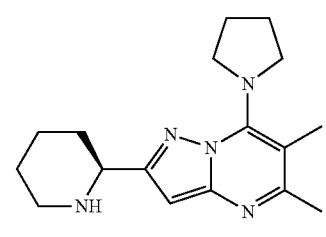

A 4N solution of hydrogen chloride in dioxane (7.0 mL, 28 mmol) was added to a mixture of N-Boc piperdine intermediate 78 (230 mg, 0.575 mmol) in anhydrous dioxane (16 mL), forming a white precipitate after 5-10 minutes. Reaction mixture was stirred 18 hours. Analytical HPLC indicated 86% conversion to desired product. Additional 2.5 mL of HCl in dioxane was then added and mixture was stirred for 1 hour and concentrated under reduced pressure to yield unprotected intermediate 79 as a white solid after drying in-vacuo, (236 mg, 99%, 90% purity), which was used in the next step without further purification.

¹H-NMR (DMSO, 400 MHz): δ 9.81 (s, 1H), 9.60 (m, 1H), 6.72 (s, 1H), 4.51 (t, 1H), 4.20 (m, 5H), 3.37 (m, 1H), 3.08 (m, 1H), 2.40 (m, 1H) 2.25 (s, 3H), 2.16 (m, 2H), 1.94 (s, 3H), 1.84-1.60 (m, 6H)

LCMS m/z [M+H]⁺ $C_{17}H_{25}N_5$ requires: 300.21. Found 300.20

Compound 98

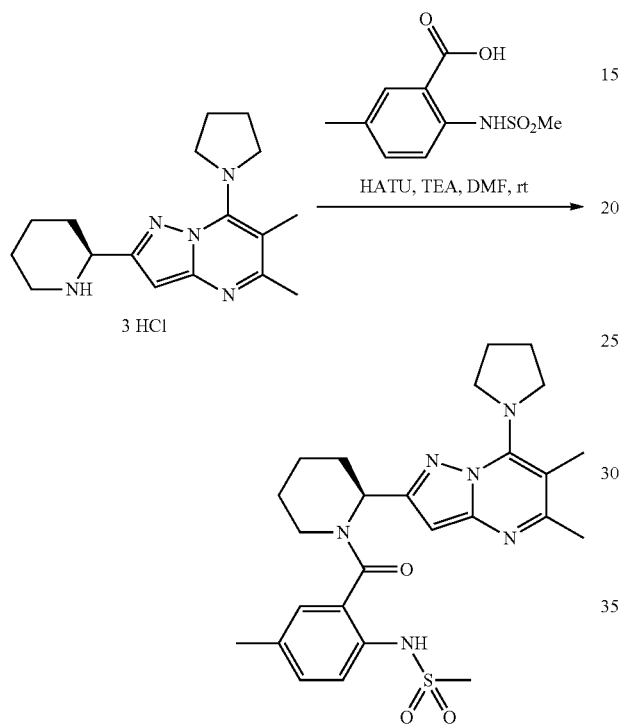

HATU (64.6 mg, 0.170 mmol) was added to a solution of 5-methyl-2-(methylsulfonamido)benzoic acid (34.1 mg, 0.159 mmol) in 5 mL of anhydrous DMF at room temperature. After 45 min of stirring, intermediate 79 (50.3 mg, 0.123 mmol) was added followed immediately by triethylamine (0.07 mL, 0.548 mmol). Reaction mixture stirred at room temperature overnight under argon. Mixture was then poured into 50 mL of H₂O and extracted three times with 50 mL of ethyl acetate. The combined organic layers were washed with 100 mL Brine, dried (MgSO₄), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 98 (51 mg, 66%) as a yellow off-white solid, trifluoroacetate salt, after lyophilization.

¹H-NMR (DMSO, 400 MHz): δ 9.08 (s, 1H) 7.35 (m, 2H), 7.13 (d, 1H), 6.41 (s, 1H), 6.01 (s, 1H), 4.18 (m, 4H), 4.11 (m, 2H), 3.42 (m, 1H), 3.13 (m, 1H), 3.01 (s, 3H), 2.40-2.05 (m, 3H), 2.32 (s, 3H), 2.23 (s, 3H), 1.94 (s, 3H), 1.93 (m, 1H), 1.66-1.35 (m, 4H).

LCMS m/z [M+H]⁺ $C_{26}H_{34}N_6O_3S$ requires: 511.24. Found 511.30

HPLC Tr (min), purity %: 5.50, 99%

Intermediate 80

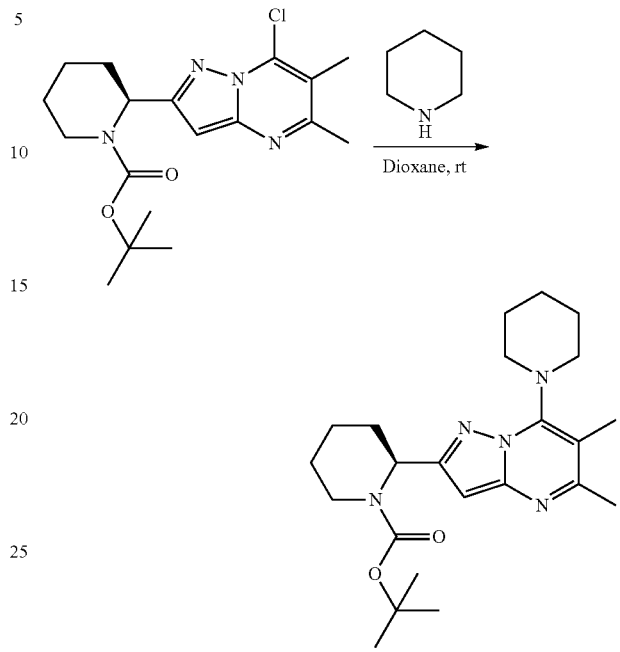

Piperidine (8.8 mL, 89.3 mmol) was added to a solution of intermediate 14 (247 mg, 0.679 mmol) in 16 mL of dioxane at room temperature. Reaction mixture was stirred overnight. Solution was concentrated to ½ volume and was poured into 35 mL of water/15 mL Brine. Aqueous was extracted with ethyl acetate (3×40 mL) and combined organic was washed with 100 mL of 1:1 water:brine, dried (MgSO4), filtered, and concentrated under reduced pressure. Desired product, intermediate 80 was recovered as a beige film (282 mg, 99%) and used without further purification.

LCMS m/z [M+H]⁺ $C_{23}H_{35}N_5O_2$ requires: 414.28. Found 414.48

Intermediate 81

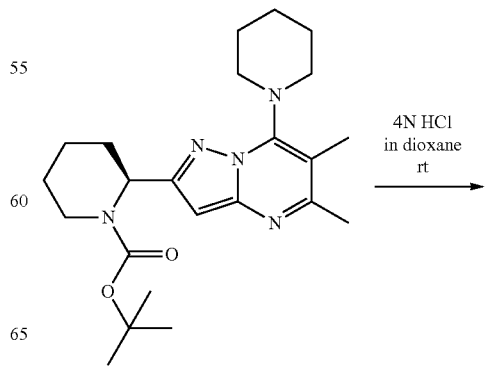

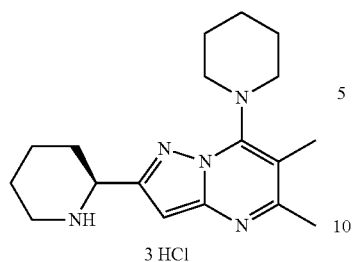

3 HCl

A 4N solution of hydrogen chloride in dioxane (8.0 mL, 32 mmol) was added to a mixture of N-Boc piperdine intermediate 80 (275 mg, 0.666 mmol) in anhydrous dioxane (17 mL), forming a light yellow precipitate after 5-10 minutes. Reaction mixture was stirred 18 hours at room temperature and concentrated under reduced pressure to yield unprotected intermediate 81 as a light yellow solid after drying in-vacuo, (280 mg, 99%) that was used in the next step without further purification.

LCMS m/z [M+H]$^+$ C$_{18}$H$_{27}$N$_5$ requires: 314.23. Found 314.30

Intermediate 82

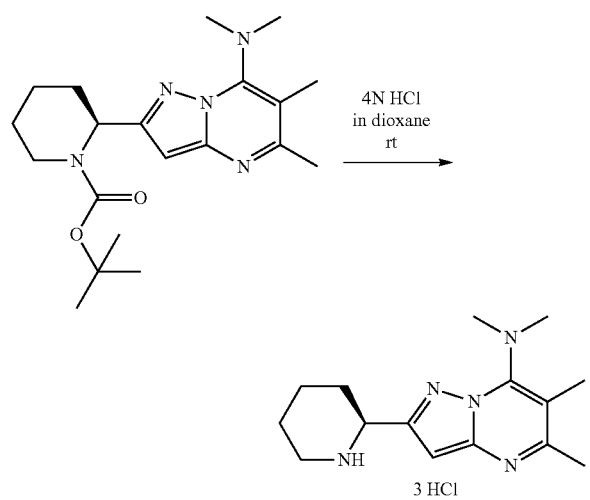

3 HCl

Following the procedure for the synthesis of intermediate 81 from 80 and 80 from Intermediate 14, intermediate 89 was synthesized as a yellow solid from intermediate 14 (232 mg, 99%).

$^1$H-NMR (DMSO, 400 MHz): δ 9.98 (s, 1H), 9.79 (s, 1H), 6.84 (s, 1H), 4.53 (m, 1H), 3.42 (s, 6H), 3.05 (m, 1H), 2.60 (s, 3H), 2.23 (s, 1H), 2.17 (m, 1H), 1.94-1.72 (m, 5H), 1.65 (m, 1H)

LCMS m/z [M+H]$^+$ C$_{15}$H$_{23}$N$_5$ requires: 274.20. Found 274.23

Compound 99

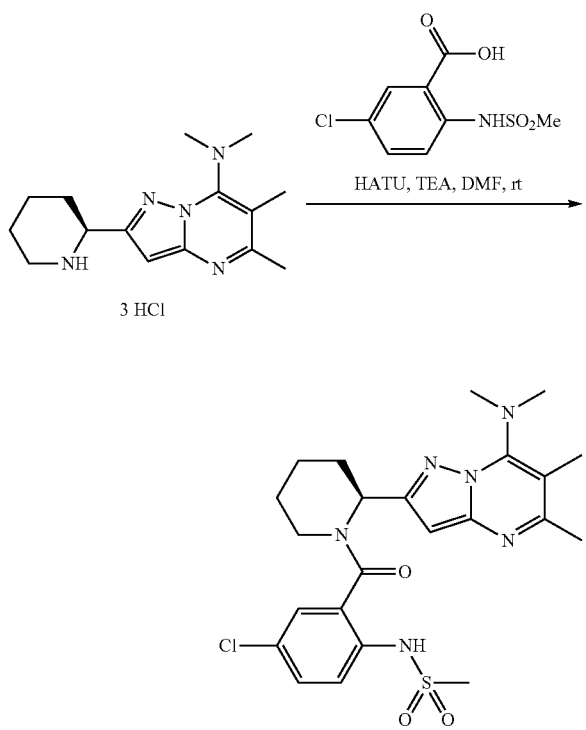

HATU (85.8 mg, 0.226 mmol) was added to a solution of 5-chloro-2-(methylsulfonamido)benzoic acid (48.6 mg, 0.194 mmol) in 8.0 mL of anhydrous DMF at room temperature. After 45 min of stirring, intermediate 82 (56.1 mg, 0.146 mmol) was added followed immediately by triethylamine (0.09 mL, 0.641 mmol). Reaction mixture stirred at room temperature overnight under argon. Mixture was then poured into 30 mL of H$_2$O and 10 mL brine and extracted three times with 30 mL of ethyl acetate. The combined organic layers were washed with 60 mL of 1:1 water:brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 99 (58 mg, 66%) as a white solid, trifluoroacetate salt, after lyophilization.

$^1$H-NMR (DMSO, 400 MHz): δ 9.34 (s, 1H) 7.45 (m, 3H), 6.43 (d, 1H), 6.01 (s, 1H), 5.67 (s, 1H), 4.61 (m, 1H), 3.35 (m, 1H), 3.25 (s, 3H), 3.19 (s, 3H), 3.07 (s, 3H), 2.48 (s, 3H), 2.38 (m, 1H), 2.22 (s, 3H), 2.01 (m, 1H), 1.70-1.41 (m, 3H).

LCMS m/z [M+H]$^+$ C$_{23}$H$_{29}$ClN$_6$O$_3$S requires: 505.17. Found 505.12

HPLC Tr (min), purity %: 5.39, 95%

Compound 100

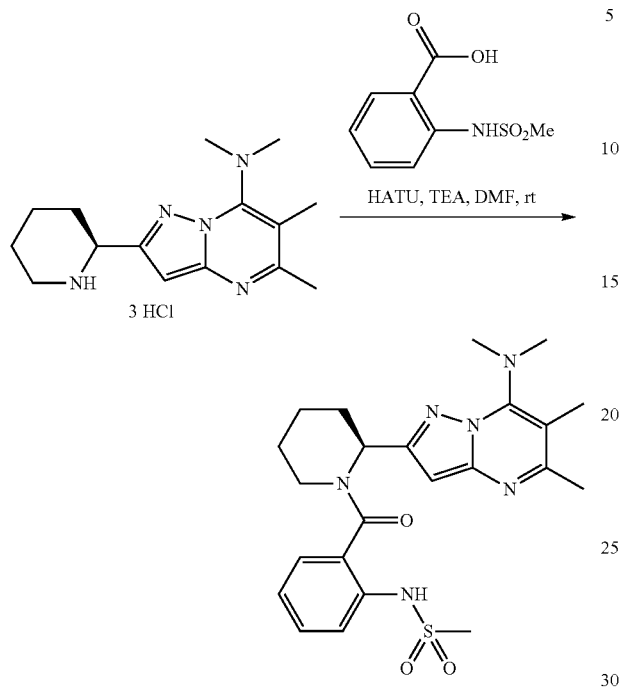

Following the procedure for the synthesis of compound 99, beginning with 2-(methylsulfonamido)benzoic acid (46.5 mg, 0.216 mmol) and intermediate 82 (56 mg, 0.146 mmol), compound 100 was synthesized as a white solid, trifluoroacetate salt, after lyophilisation (62.5 mg, 75%).

$^1$H-NMR (DMSO, 300 MHz): δ 9.15 (s, 1H), 7.45 (m, 4H), 6.49 (s, 1H), 6.36 (s, 1H), 6.03 (s, 1H), 3.28 (s, 6H), 3.4-3.21 (m, 2H), 3.06 (s, 3H), 3.01-2.85 (m, 1H), 2.44 (s, 3H), 2.22 (s, 3H), 2.05 (m, 1H), 1.71-1.38 (m, 4H).

LCMS m/z [M+H]$^+$ C$_{23}$H$_{30}$N$_6$O$_3$S requires: 471.21. Found 471.20

HPLC Tr (min), purity %: 4.99, 99%

Compound 101

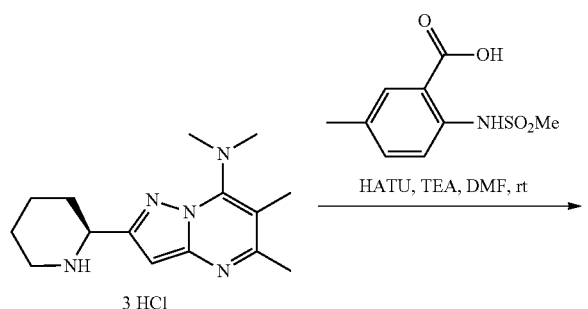

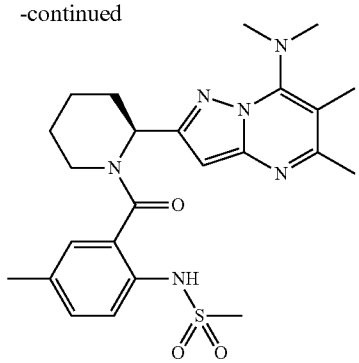

Following the procedure for the synthesis of compound 99, beginning with 5-methyl-2-(methylsulfonamido)benzoic acid (43.1 mg, 0.188 mmol) and intermediate 82 (45 mg, 0.130 mmol), compound 101 was synthesized as a light yellow solid, trifluoroacetate salt, after lyophilisation (33.2 mg, 43%).

$^1$H-NMR (DMSO, 400 MHz): δ 9.02 (s, 1H), 7.28 (m, 3H), 6.45 (s, 1H), 6.03 (s, 1H), 3.39 (m, 1H) 3.21 (s, 6H), 3.17 (m, 1H), 3.00 (s, 3H), 2.47 (s, 3H), 2.45 (m, 1H), 2.33 (m, 2H), 2.22 (s, 3H), 2.17 (m, 1H), 1.92 (m, 1H), 1.69-1.38 (m, 4H)

LCMS m/z [M+H]$^+$ C$_{24}$H$_{32}$N$_6$O$_3$S requires: 485.23. Found 485.19

HPLC Tr (min), purity %: 5.27, 99%

Intermediate 83

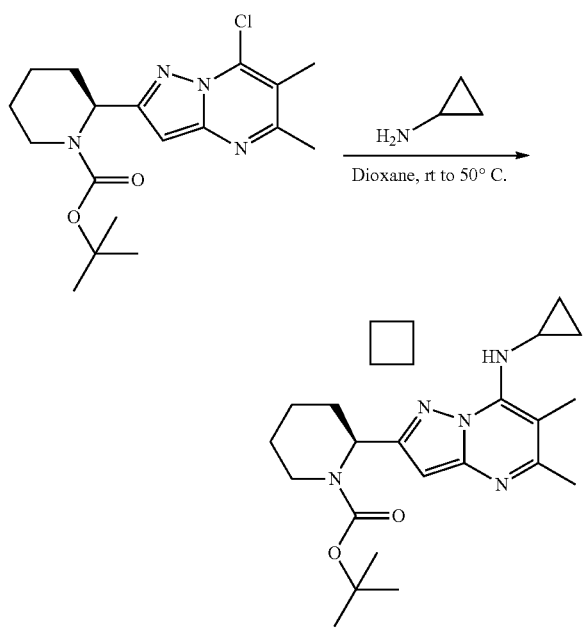

Cyclopropylamine (2.0 mL, 28.9 mmol) was added to a solution of intermediate 14 (130 mg, 0.357 mmol) in 8 mL of dioxane at room temperature. Reaction mixture was stirred overnight. HPLC indicated starting material remained. Reaction mixture was heated at 50° C. for 24 hours. Solution was concentrated under reduced pressure and residue was subjected to silica gel column chromatography (25-50% Ethyl Acetate in Hexanes. Desired product intermediate 83 was recovered as a clear film (65 mg, 47%).

LCMS m/z [M+H]$^+$ C$_{21}$H$_{31}$N$_5$O$_2$ requires: 386.25. Found 386.43

Intermediate 84

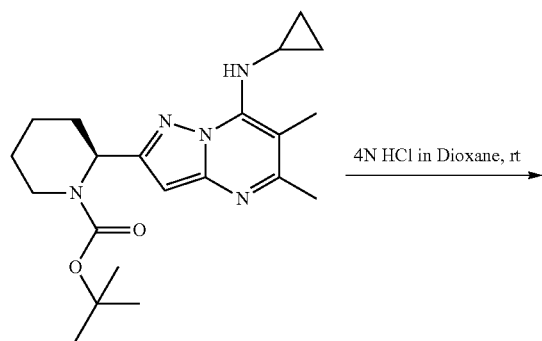

A 4N solution of hydrogen chloride in dioxane (1.2 mL, 4.8 mmol) was added to a mixture of intermediate 83 (65 mg, 0.168 mmol) in anhydrous dioxane (5.5 mL), forming a white precipitate after 5-10 minutes. Reaction mixture was stirred 18 hours at room temperature and concentrated under reduced pressure to yield intermediate 84 as a white solid after drying in-vacuo, (48 mg, 99%) that was used in the next step without further purification.

LCMS m/z [M+H]$^+$ C$_{16}$H$_{23}$N$_5$ requires: 286.20. Found 286.46

Compound 102

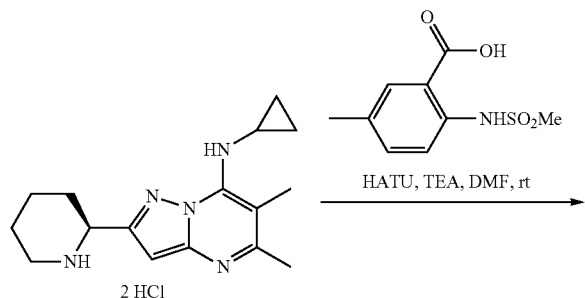

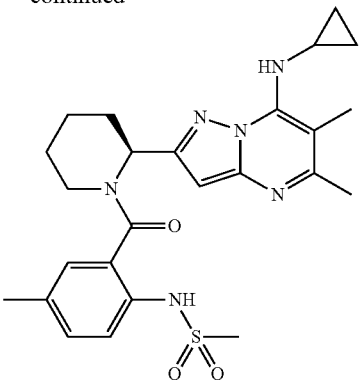

Following the procedure for the synthesis of compound 99, beginning with 5-methyl-2-(methylsulfonamido)benzoic acid (28.4 mg, 0.124 mmol) and intermediate 84 (33 mg, 0.093 mmol), compound 102 was synthesized as a white solid, trifluoroacetate salt, after lyophilisation (29.2 mg, 53%).

LCMS m/z [M+H]$^+$ C$_{25}$H$_{32}$N$_6$O$_3$S requires: 497.23. Found 497.39

HPLC Tr (min), purity %: 5.39, 99%

Intermediate 85

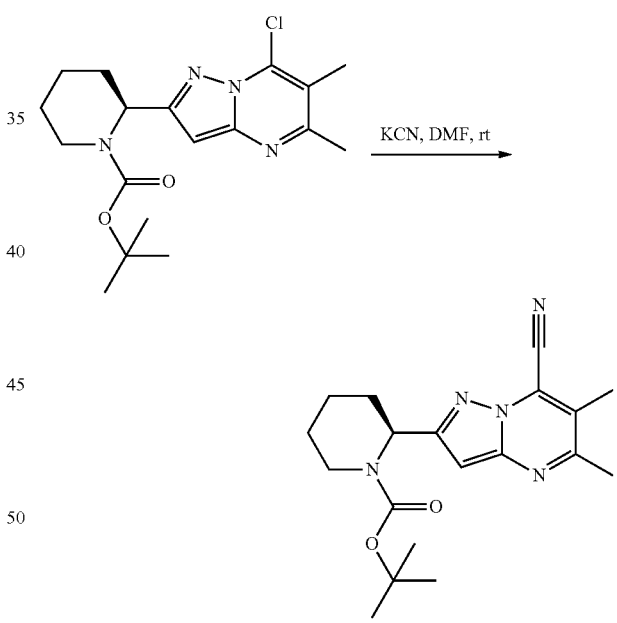

Potassium cyanide (175 mg, 2.69 mmol) was added to a solution of intermediate 14 (200 mg, 0.55 mmol) in 5 mL of anhydrous DMF at room temperature. After stirring for 65 hours, reaction mixture was poured into 50 mL of water and extracted with ethyl acetate (3×40 mL). Combined organics were washed with 100 mL of water and brine, dried (MgSO$_4$), filtered, and concentrated under reduced pressure to yield a residue. Silica gel column chromatography (15-30% ethyl acetate in hexanes) yielded intermediate 85 (111 mg, 57%) as a yellow film.

LCMS m/z [M+H]$^+$ C$_{19}$H$_{25}$N$_5$O$_2$ requires: 356.20. Found 356.08

Intermediate 86

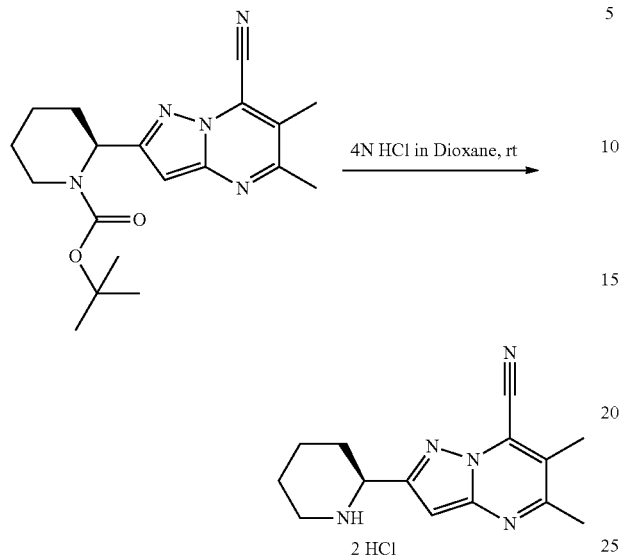

A 4N solution of hydrogen chloride in dioxane (4.0 mL, 60 mmol) was added to a mixture of intermediate 85 (110 mg, 0.31 mmol) in anhydrous dioxane (10 mL), forming a yellow precipitate after 5-10 minutes. Reaction mixture was stirred 18 hours at room temperature and concentrated under reduced pressure to yield intermediate 86 as a yellow solid after drying in-vacuo, (100 mg, 98%) that was used in the next step without further purification.

$^1$H-NMR (DMSO, 400 MHz): δ 9.57 (s, 2H), 7.07 (s, 1H), 4.57 (t, J=8.8 Hz, 1H), 3.34 (s, 3H), 3.07 (m, 1H), 2.54 (s, 3H), 2.15 (dd, J=13.8 Hz, 2.8 Hz, 1H), 1.97-1.76 (m, 5H), 1.68 (m, 1H)

LCMS m/z [M+H]$^+$ C$_{14}$H$_{17}$N$_5$ requires: 256.15. Found 256.09

Compound 103

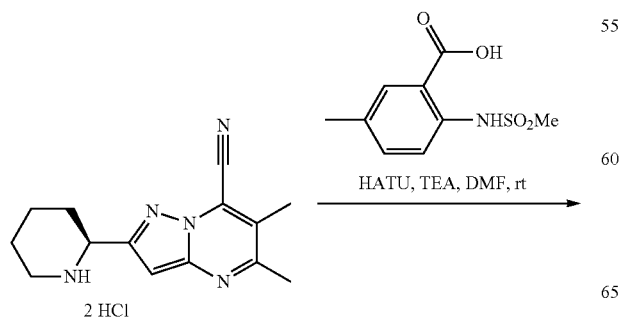

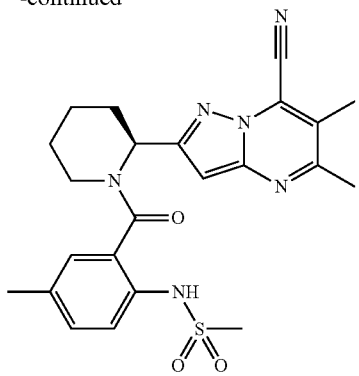

Following the procedure for the synthesis of compound 99, beginning with 5-methyl-2-(methylsulfonamido)benzoic acid (34.8 mg, 0.152 mmol) and intermediate 86 (40.6 mg, 0.123 mmol), compound 103 was synthesized as a yellow solid, trifluoroacetate salt, after lyophilisation (38.7 mg, 56%).

$^1$H-NMR (DMSO, 400 MHz): δ 9.03 (s, 1H), 7.26 (m, 3H), 6.85 (s, 1H), 6.07 (s, 1H), 3.37 (m, 1H), 3.14 (m, 1H), 3.05 (m, 1H), 3.02 (s, 3H), 2.59 (m, 1H), 2.57 (s, 3H), 2.34 (s, 3H), 2.17 (m, 1H), 1.94 (m, 1H), 1.70-1.30 (m, 5H)

LCMS m/z [M+H]$^+$ C$_{23}$H$_{26}$N$_6$O$_3$S requires: 467.18. Found 467.34

HPLC Tr (min), purity %: 6.72, 99%

Intermediate 87

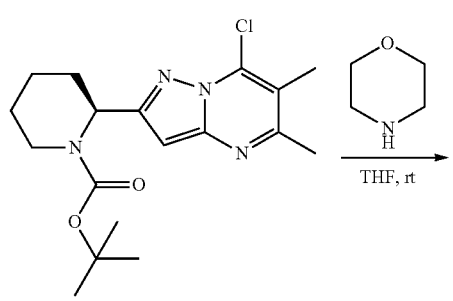

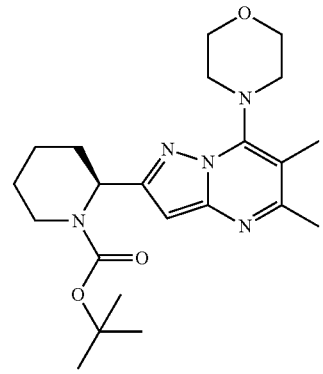

Morpholine (2.0 mL, 23.0 mmol) was added to a solution of intermediate 14 (75 mg, 0.206 mmol) in 3 mL of anhydrous THF at room temperature. Reaction mixture was stirred overnight. Solution was poured into 20 mL of water and aqueous was extracted with ethyl acetate (3×20 mL) and combined organic was washed with 100 mL of water, dried (MgSO4), filtered, and concentrated under reduced pressure. Desired product intermediate 87 was recovered as a clear film (77 mg, 90%) and used without further purification.

¹H-NMR (CDCl₃, 300 MHz): δ 6.31 (s, 1H), 5.59 (m, 1H), 4.07 (m, 1H), 3.91 (m, 5H), 3.58 (m, 5H), 2.91 (m, 1H), 2.54 (s, 3H), 2.52 (m, 1H), 2.40 (m, 2H), 2.25 (s, 3H), 1.84 (m, 1H), 1.47 (s, 9H).

LCMS m/z [M+H]⁺ C₂₂H₃₃N₅O₃ requires: 416.26. Found 416.49

Intermediate 88

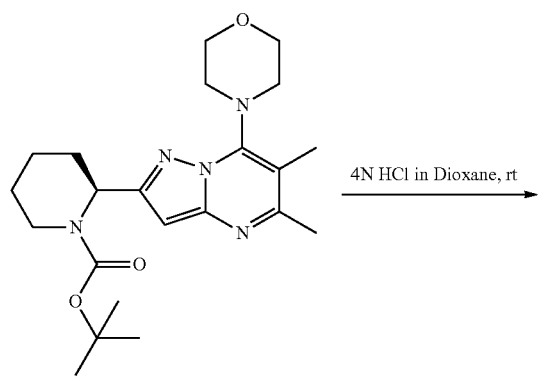

Compound 104

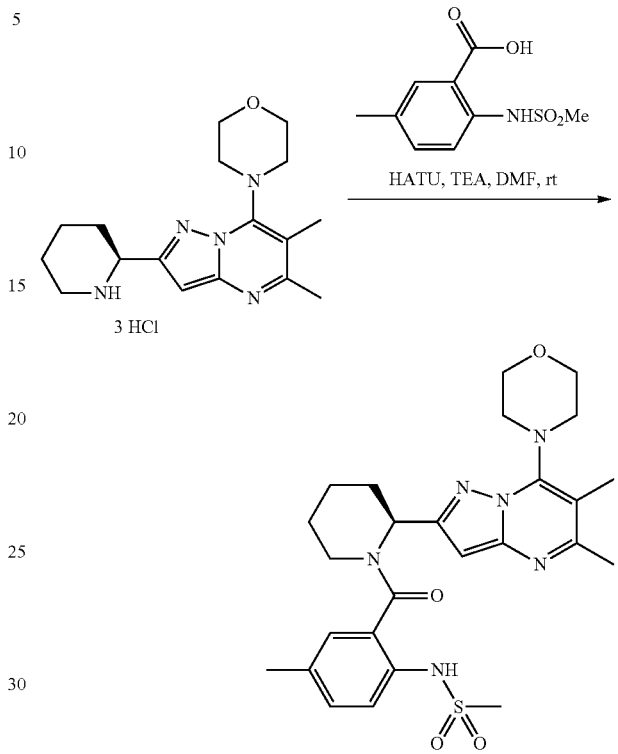

Following the procedure for the synthesis of compound 99, beginning with 5-methyl-2-(methylsulfonamido)benzoic acid (30.1 mg, 0.131 mmol) and intermediate 88 (40 mg, 0.095 mmol), compound 104 was synthesized as a white solid, trifluoroacetate salt, after lyophilization (36 mg, 59%).

¹H-NMR (DMSO, 400 MHz): δ 9.07 (s, 1H), 7.28 (m, 2H), 7.30 (s, 1H), 6.41 (d, 1H), 6.03 (s, 1H), 3.76 (m, 5H), 3.54 (s, 3H), 3.52 (m, 1H), 3.38 (m, 1H), 3.13 (m, 2H), 3.01 (s, 3H), 2.47 (s, 3H), 2.34 (m, 2H), 2.24 (s, 3H), 2.15 (m, 1H), 1.95 (m, 1H), 1.66-1.40 (m, 3H)

LCMS m/z [M+H]⁺ C₂₆H₃₄N₆O₄S requires: 527.24. Found 527.13

HPLC Tr (min), purity %: 5.10, 88%

Intermediate 89

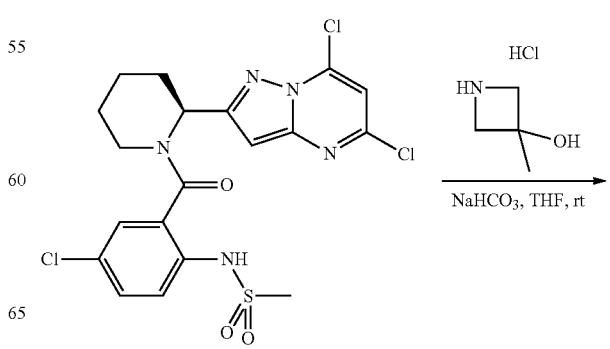

A 4N solution of hydrogen chloride in dioxane (2.3 mL, 9.2 mmol) was added to a mixture of intermediate 87 (75 mg, 0.180 mmol) in anhydrous dioxane (9 mL), forming a yellow precipitate after 5-10 minutes. Reaction mixture was stirred 18 hours at room temperature and concentrated under reduced pressure to yield intermediate 88 as a yellow solid after drying in-vacuo, (75 mg, 98%) that was used in the next step without further purification.

¹H-NMR (DMSO, 300 MHz): δ 9.29 (s, 1H), 9.04 (s, 1H), 6.62 (s, 1H), 4.49 (m, 1H), 3.80 (m, 1H), 3.41 (m, 3H), 3.13 (m, 3H), 2.32 (s, 6H), 2.29 (m, 1H), 1.84-1.61 (m, 8H), 1.30 (m, 2H)

LCMS m/z [M+H]⁺ C₁₇H₂₅N₅O requires: 316.21. Found 316.25

309
-continued

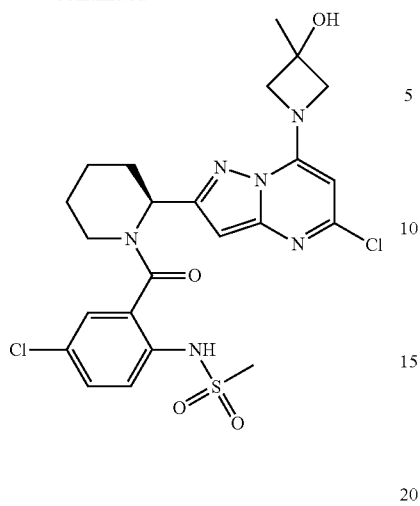

Intermediate 56 (31 mg, 0.062 mmol), 3-methylazetidin-3-ol hydrochloride (7.9 mg, 0.064 mmol), and sodium bicarbonate (13.1 mg, 0.156 mmol) were suspended in 2 mL of THF and stirred at room temperature for 36 hours. Mixture was poured into 10 mL of water and extracted with ethyl acetate (3×10 mL) and combined organic was washed with 20 mL of brine, dried (MgSO4), filtered, and concentrated under reduced pressure. Desired intermediate 89 was recovered as a white solid (34 mg, 99%) and used without further purification.

LCMS m/z [M+H]$^+$ C$_{23}$H$_{26}$Cl$_2$N$_6$O$_4$S requires: 553.11. Found 553.18

Compound 105

310
-continued

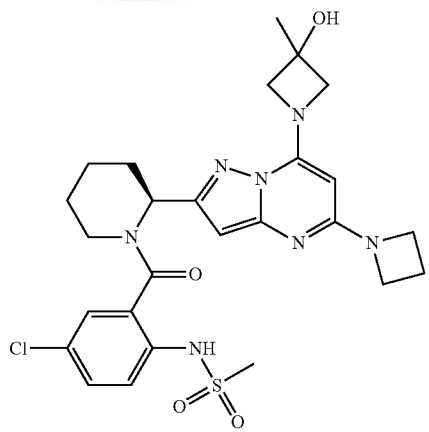

Azetidine (0.05 mL, 0.73 mmol) was added to a solution of intermediate 89 (34 mg, 0.062 mmol) in 2 mL of anhydrous THF. Mixture was heated at 70° C. overnight after which it was concentrated and residue was purified by prep HPLC (15-100% Acetonitrile (with 0.1% trifluoroacetic acid) in water (with 0.1% trifluoroacetic acid)) to yield compound 105 (24 mg, 56%) as a white solid, trifluoroacetate salt, after lyophilization.

$^1$H-NMR (DMSO, 400 MHz): δ 9.41 (s, 1H) 7.53 (m, 2H), 7.45 (m, 1H), 7.30 (s, 1H), 6.07 (s, 1H), 5.91 (d, 2H), 5.67 (s, 1H), 4.17 (m, 4H), 3.34 (d, 1H), 3.21-3.01 (m, 3H), 3.06 (s, 3H), 2.40 (m, 2H), 2.31 (m, 1H), 2.07-1.90 (m, 1H), 1.66-1.54 (m, 3H), 1.50-1.40 (m, 2H), 1.48 (s, 3H)

LCMS m/z [M+H]$^+$ C$_{26}$H$_{32}$ClN$_7$O$_4$S requires: 574.19. Found 574.12

HPLC Tr (min), purity %: 5.32, 95%

Intermediate 90

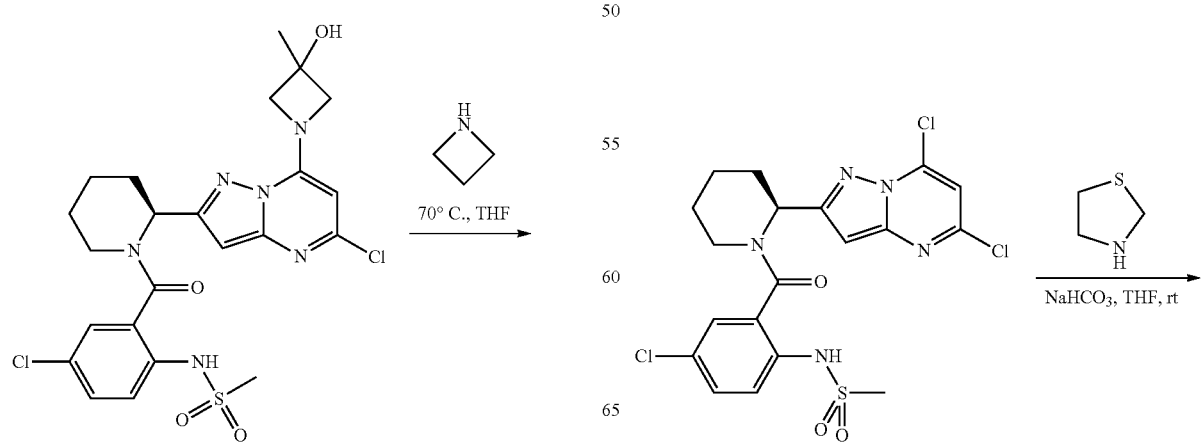

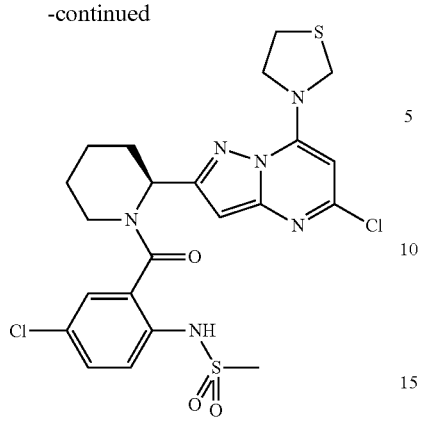

Following the procedure of intermediate 89, starting with intermediate 56 (37 mg, 0.074 mmol) and thiazolidine (0.0058 mL, 0.074 mmol), intermediate 90 (34 mg, 99%) was recovered as a film and used without further purification.

LCMS m/z [M+H]$^+$ C$_{22}$H$_{24}$Cl$_2$N$_6$O$_3$S$_2$ requires: 555.07. Found 555.09

Compound 106

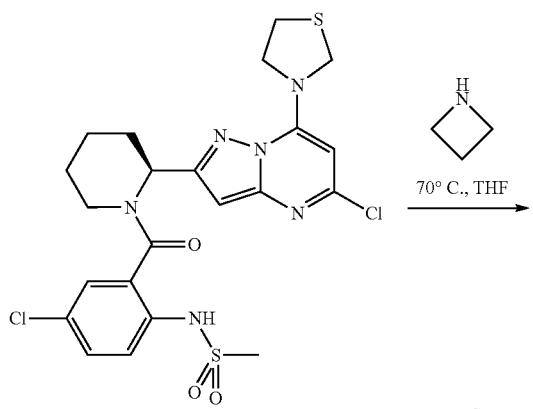

Following the procedure of compound 105, starting with intermediate 90 (34 mg, 0.061 mmol) and azetidine (0.040 mL, 0.60 mmol), compound 106 (36 mg, 86%) was isolated as a white solid, trifluoroacetate salt, after lyophilization.

$^1$H-NMR (DMSO, 400 MHz): δ 9.61 (s, 1H) 7.55-7.46 (m, 3H), 6.08 (s, 1H), 5.93 (d, 1H), 5.28 (m, 1H), 5.02 (m, 2H), 4.21-4.01 (m, 7H), 3.72 (m, 4H), 3.32 (m, 1H), 3.16 (t, 2H), 3.07 (s, 3H), 2.40-2.22 (m, 2H), 1.66-1.36 (m, 2H).

LCMS m/z [M+H]$^+$ C$_{25}$H$_{30}$ClN$_7$O$_3$S requires: 576.15. Found 576.40

HPLC Tr (min), purity %: 5.93, 89%

Intermediate 91

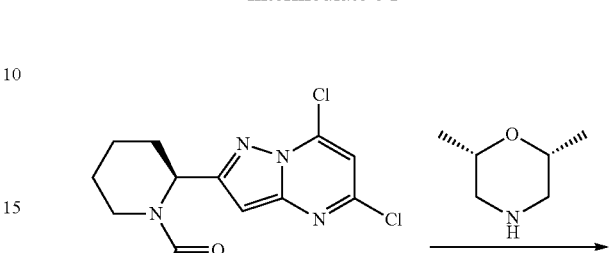

Following the procedure of intermediate 89, starting with intermediate 56 (34 mg, 0.068 mmol) and (0.0089 mL, 0.072 mmol), intermediate 91 (40 mg, 99%) was recovered as a clear solid and used without further purification.

LCMS m/z [M+H]$^+$ C$_{25}$H$_{30}$Cl$_2$N$_6$O$_4$S requires: 581.14. Found 581.33

Compound 107

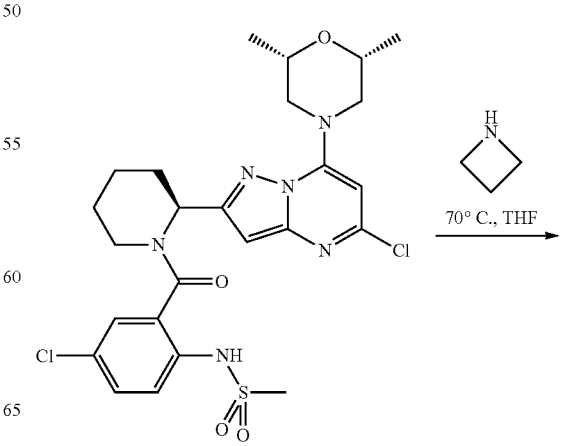

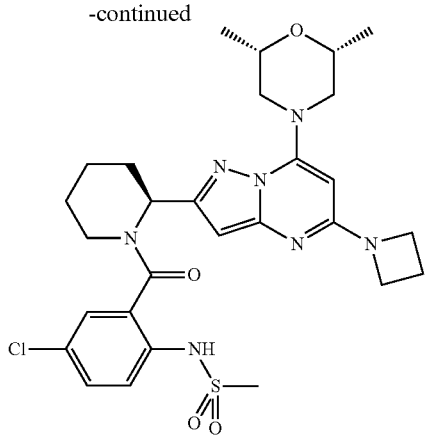

Following the procedure of compound 105, starting with intermediate 91 (40 mg, 0.068 mmol) and azetidine (0.045 mL, 0.68 mmol), compound 107 (43 mg, 87%) was isolated as a white solid, trifluoroacetate salt, after lyophilization.

LCMS m/z [M+H]$^+$ C$_{28}$H$_{36}$ClN$_7$O$_4$S requires: 602.22. Found 602.19

HPLC Tr (min), purity %: 5.95, 91%

Compound 108

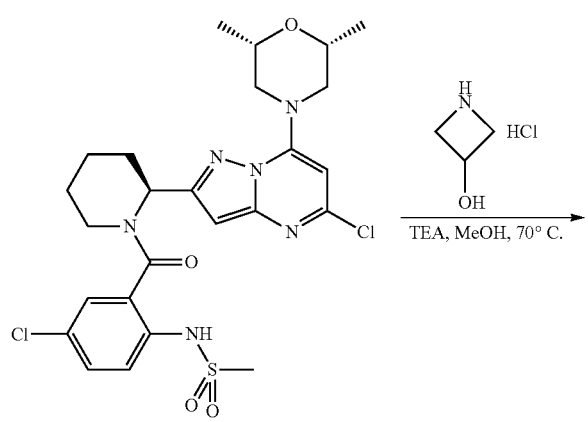

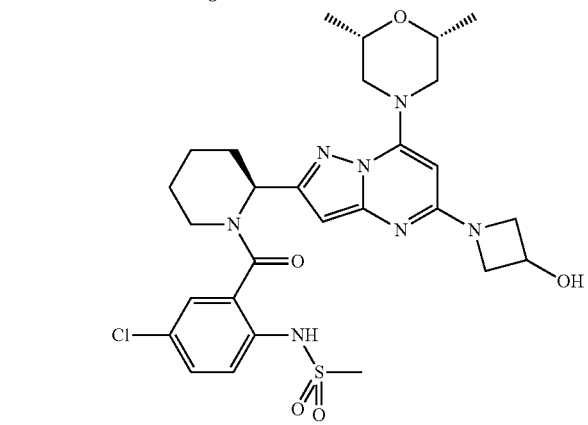

Azetidin-3-ol hydrochloride (77 mg, 0.7 mmol) and triethylamine (0.2 mL, 1.4 mmol) were added to a solution of intermediate 91 (43 mg, 0.074 mmol) in 2 mL of anhydrous methanol. Reaction mixture was heated at 70° C. overnight. Solution was cooled to room temperature and concentrated under reduced pressure. Residue was purified by prep HPLC (15-100% Acetonitrile (with 0.1% trifluoroacetic acid) in water (with 0.1% trifluoroacetic acid)) to yield compound 108 (32 mg, 59%) as a white solid, trifluoroacetate salt, after lyophilization.

$^1$H-NMR (DMSO, 400 MHz): δ 9.38 (s, 1H) 7.47 (m, 3H), 6.09 (s, 1H), 5.92 (d, 1H), 5.38 (s, 1H), 4.75 (m, 1H), 4.59 (m, 1H), 4.51-4.22 (m, 6H), 3.83 (m, 3H), 3.04 (s, 3H), 2.66 (m, 2H), 2.30 (m, 1H), 2.01 (m, 2H), 1.70-1.35 (m, 4H), 1.16-1.04 (m, 6H).

LCMS m/z [M+H]$^+$ C$_{28}$H$_{36}$ClN$_7$O$_5$S requires: 618.22. Found 618.42

HPLC Tr (min), purity %: 5.56, 99%

Compound 109

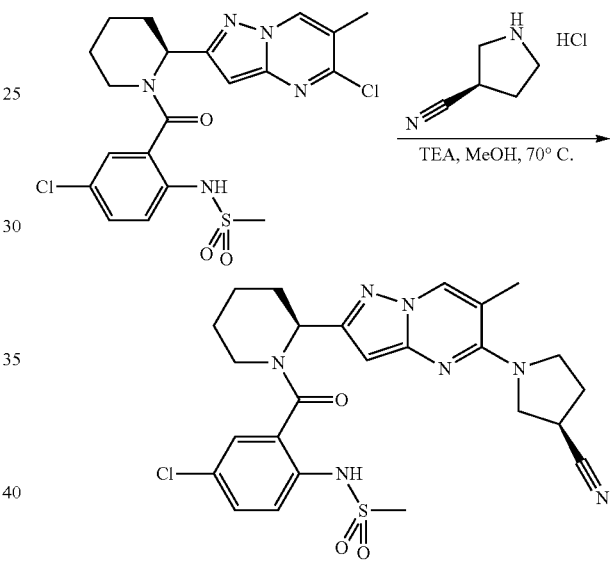

(R)-pyrrolidine-3-carbonitrile hydrochloride (82 mg, 0.618 mmol) and triethylamine (0.17 mL, 0.122 mmol) were added to a mixture of intermediate 73 (29.8 mg, 0.062 mmol) in 4 mL of anhydrous methanol. Reaction mixture was heated at 70° C. overnight. After cooling to room temperature, mixture was poured into 10 mL of water and extracted with ethyl acetate (3×20 mL). Combined organics were dried (MgSO$_4$), filtered, and concentrated under reduced pressure. Residue was purified by prep HPLC (15-100% Acetonitrile (with 0.1% trifluoroacetic acid) in water (with 0.1% trifluoroacetic acid)) to yield compound 109 (35 mg, 82%) as a white solid, trifluoroacetate salt, after lyophilization.

$^1$H-NMR (DMSO, 400 MHz): δ 9.23 (s, 1H) 8.53 (s, 1H), 7.52 (m, 2H), 7.42 (m, 1H), 6.15 (s, 1H), 5.97 (s, 1H), 3.96 (m, 1H), 3.85 (m, 3H), 3.50 (m, 1H), 3.21 (m, 1H), 3.06 (m, 1H), 3.04 (s, 3H), 2.37 (s, 3H), 2.33 (m, 2H), 2.20 (m, 1H), 1.91 (m, 1H), 1.67-1.27 (m, 4H).

LCMS m/z [M+H]$^+$ C$_{25}$H$_{28}$ClN$_7$O$_3$S requires: 542.17. Found 542.17

HPLC Tr (min), purity %: 7.17, 99%

Compound 110

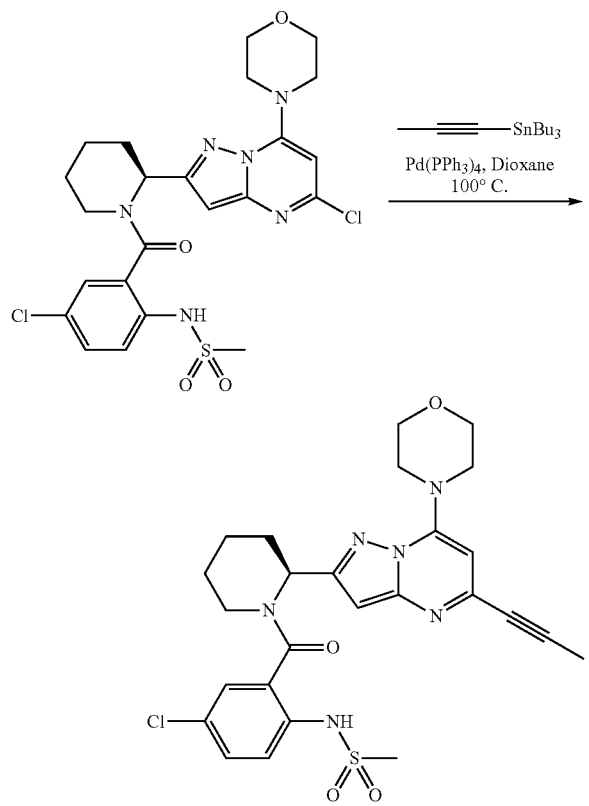

A mixture of intermediate 66 (52 mg, 0.094 mmol), tributyl(prop-1-ynyl)stannane (0.035 mL, 0.154 mmol), and Pd(PPh$_3$)$_4$ (69.8 mg, 0.060 mmol) in 2 mL of anhydrous dioxane was heated at 100° C. overnight under argon. Reaction mixture was cooled to room temperature and concentrated under reduced pressure. Residue was purified by prep HPLC (15-100% Acetonitrile (with 0.1% trifluoroacetic acid) in water (with 0.1% trifluoroacetic acid)) to yield compound 110 (13 mg, 19%) as a yellow solid, trifluoroacetate salt, after lyophilization.

$^1$H-NMR (DMSO, 400 MHz): δ 9.45 (s, 1H) 7.65-7.40 (m, 314), 6.41 (s, 1H), 6.08 (s, 1H), 3.81 (m, 5H), 3.58 (m, 1H), 3.44 (m, 1H), 3.20 (m, 2H), 3.09 (m, 2H), 3.05 (s, 3H), 2.42 (m, 2H), 2.17 (s, 3H), 2.11 (m, 1H), 1.55 (m, 3H).

LCMS m/z [M+H]$^+$ C$_{26}$H$_{29}$ClN$_6$O$_4$S requires: 557.15. Found 557.14

HPLC Tr (min), purity %: 5.89, 94%

Intermediate 92

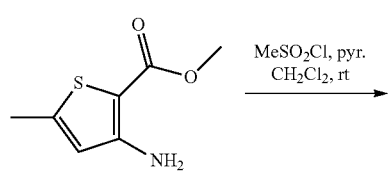

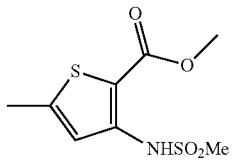

To a solution of methyl 3-amino-5-methylthiophene-2-carboxylate (497 mg, 2.91 mmol) and pyridine (0.71 mL, 8.77 mmol) in 10 mL of anhydrous CH$_2$CL$_2$, was added slowly methane sulfonylchloride (0.7 mL, 9.06 mmol). After stirring overnight, reaction mixture was quenched with 30 mL of 1N HCl$_{(aq)}$. Aqueous mixture was extracted with ethyl acetate (3×40 mL) and combined organic layers were washed with sat. CuSO$_{4(aq)}$ and then brine. Organics were dried (MgSO$_4$), filtered, and concentrated under reduced pressure to yield intermediate 92 (707 mg, 98%) as a peach colored solid that was used in the next step without further purification.

$^1$H-NMR (CDCl$_3$, 400 MHz): δ 9.41 (s, 1H), 7.11 (s, 1H), 3.85 (s, 3H), 3.06 (s, 3H), 2.49 (s, 3H).

LCMS m/z [M+H]$^+$ C$_8$H$_{11}$NO$_4$S$_2$ requires: 250.01. Found 250.09

Intermediate 93

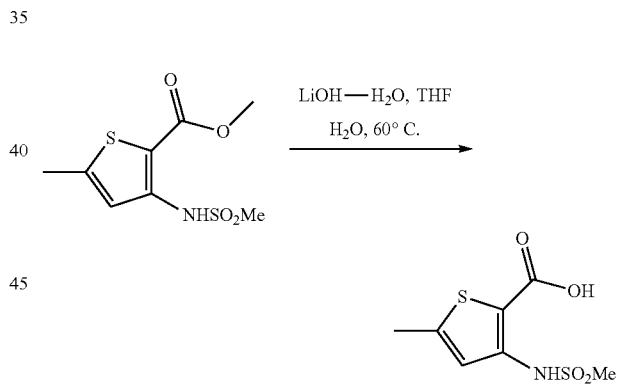

Lithium hydroxide monohydrate (1.0 g, 23.8 mmol) was added to a solution of intermediate 92 (695 mg, 2.8 mmol) in 25 mL of THF and 14 mL of water at room temperature. Reaction mixture was heated at 60° C. for one hour. After cooling to room temperature, reaction mixture was acidified with 70 mL of 1N HCl$_{(aq)}$ and extracted with ethyl acetate (3×50 mL). The combined organic layers were washed 80 mL of Brine, separated, dried (MgSO$_4$), filtered, and concentrated under reduced pressure to yield intermediate 93 as a yellow-white solid (650 mg, 99%).

$^1$H-NMR (DMSO, 300 MHz): δ 9.55 (s, 1H), 7.04 (s, 1H), 3.20 (s, 3H), 2.45 (s, 3H)

LCMS m/z [M+H]$^-$ C$_7$H$_9$NO$_4$S$_2$ requires: 234.00. Found 234.02

Compound 111

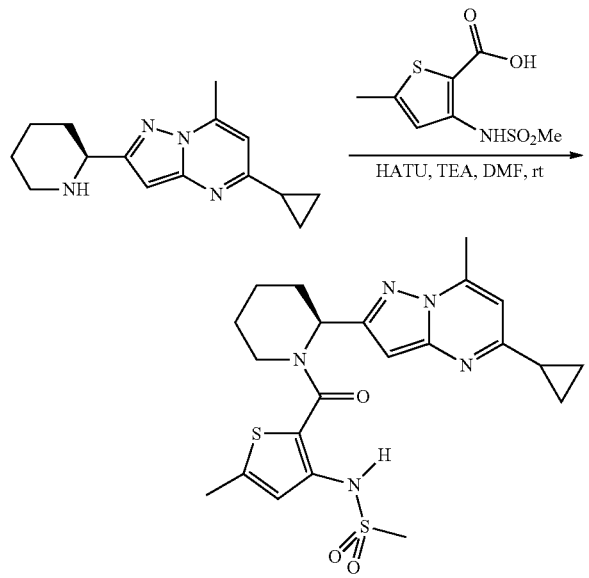

Following the procedure for the synthesis of compound 104, beginning with intermediate 31 (77.1 mg, 0.329 mmol) and a 0.5 M DMF solution of intermediate 93 (0.5 mL, 0.25 mmol), compound 116 was synthesized as an off-white solid, trifluoroacetate salt, after lyophilization. (91 mg, 62%).

$^1$H-NMR (DMSO, 300 MHz): δ 9.63 (s, 1H), 6.86 (s, 1H), 6.39 (s, 1H), 5.39 (s, 1H), 4.15 (m, 1H), 3.05 (s, 3H), 3.04 (m, 2H), 2.63 (s, 3H), 2.39 (s, 3H), 2.37 (m, 1H), 2.14 (m, 1H), 1.97 (m, 1H), 1.61-1.40 (m, 4H), 1.03 (m, 4H).

LCMS m/z [M+H]$^+$ C$_{22}$H$_{27}$N$_5$O$_3$S$_2$ requires: 474.16. Found 474.10

HPLC Tr (min), purity %: 7.18, 99%

Intermediate 94

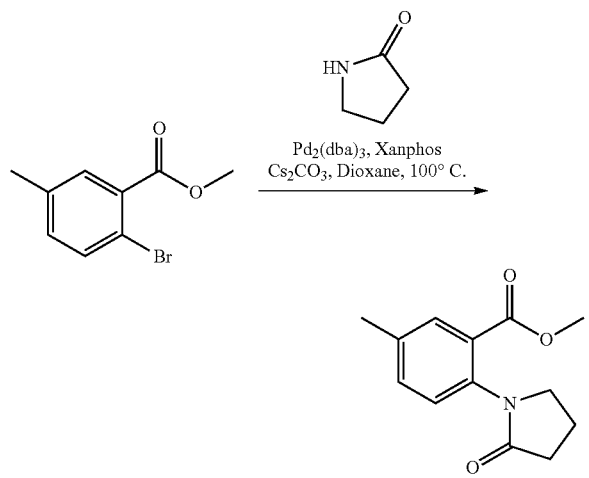

To an oven dried 25 mL round-bottom flask, methyl 2-bromo-5-methylbenzoate (356 mg, 1.55 mmol), 2-pyrrolidinone (0.15 mL, 1.95 mmol), cesium carbonate (739 mg, 2.27 mmol), Pd$_2$(dba)$_3$ (70.0 mg, 0.076 mmol), and Xanphos (134 mg, 0.231 mmol) were added and flask was placed under argon. Reagents were suspended in 8 mL of anhydrous dioxane and mixture was heated at 100° C. overnight. After cooling to room temperature, reaction mixture was filtered, washing with ethyl acetate. Combined filtrate was concentrated under reduced pressure and resulting film was purified by silica gel column chromatography (50-100% Ethyl Acetate in Hexanes) to yield intermediate 94 (335 mg, 92%) as a light yellow solid.

$^1$H-NMR (CDCl$_3$, 400 MHz): δ 7.77 (d, 1H), 7.37 (m, 1H), 7.15 (m, 1H), 3.86 (s, 3H), 3.81 (t, 2H), 2.56 (t, 2H), 2.38 (s, 3H), 2.22 (m, 2H).

LCMS m/z [M+H]$^+$ C$_{13}$H$_{15}$NO$_3$ requires: 234.11. Found 234.26

Intermediate 95

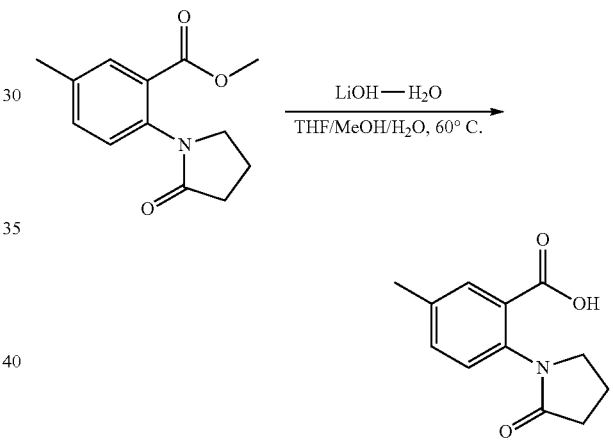

Lithium hydroxide monohydrate (305 mg, 7.26 mmol) was added to a solution of intermediate 94 (235 mg, 1.01 mmol) in 6 mL of 1:1:1 THF:MeOH:H$_2$O at room temperature. Reaction mixture was heated at 60° C. for two hours. After cooling to room temperature, reaction mixture was acidified with 15 mL of 1N HCl$_{(aq)}$ and extracted with ethyl acetate (3×20 mL). The combined organic layers were washed 50 mL of Brine, separated, dried (MgSO$_4$), filtered, and concentrated under reduced pressure to yield intermediate 95 as a light yellow solid (199 mg, 90%).

$^1$H-NMR (DMSO, 400 MHz): δ 12.7 (s, 1H), 7.58 (d, J=2 Hz, 1H), 7.38 (dd, J=8.2 Hz, 2 Hz, 1H), 7.20 (d, J=8.2 Hz, 1H), 3.69 (t, J=6.4 Hz, 2H), 2.32 (s, 3H), 2.30 (t, J=8.4 Hz, 2H), 2.07 (m, 2H).

LCMS m/z [M+H]$^+$ C$_{12}$H$_{13}$NO$_3$ requires: 218.09. Found 218.17

Compound 112

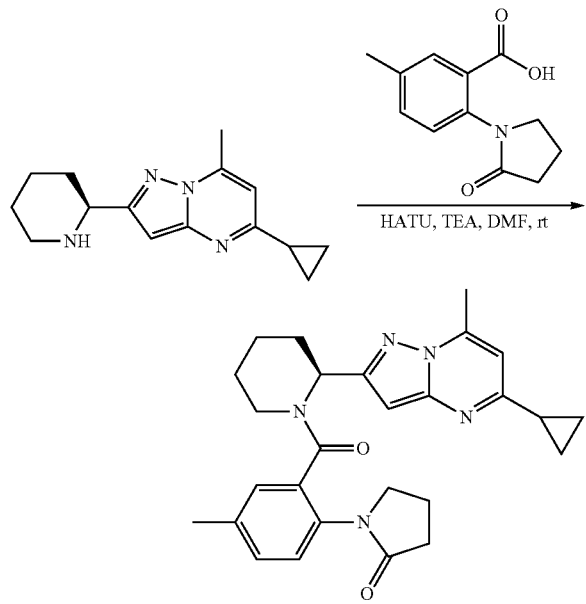

Following the procedure for the synthesis of compound 99, beginning with intermediate 95 (57.3 mg, 0.261 mmol) and a 0.5 M DMF solution of intermediate 31 (0.4 mL, 0.20 mmol), compound 112 was synthesized as a white solid, trifluoroacetate salt, after lyophilization. (29 mg, 28%).

$^1$H-NMR (DMSO, 400 MHz): δ 7.31 (m, 3H), 6.42 (d, 1H), 6.00 (dd, 1H), 3.71 (m, 3H), 3.44 (m, 1H), 3.11 (m, 1H), 2.66 (s, 3H), 2.41 (m, 4H), 2.13 (s, 3H), 2.11 (m, 1H), 1.91 (m, 1H), 1.62-1.35 (m, 5H), 1.03 (m, 4H).

LCMS m/z [M+H]$^+$ C$_{27}$H$_{31}$N$_5$O$_2$ requires: 458.25. Found 458.46

HPLC Tr (min), purity %: 6.31, 99%

Intermediate 96

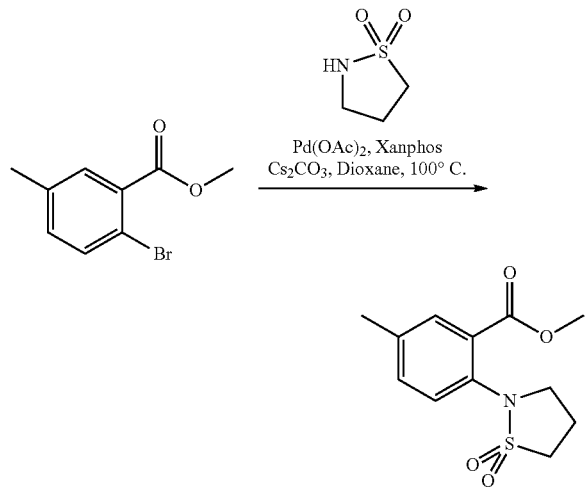

To an oven dried 50 mL round-bottom flask, methyl 2-bromo-5-methylbenzoate (352 mg, 1.54 mmol), sultam (236 mg, 1.95 mmol), cesium carbonate (732 mg, 2.25 mmol), palladium acetate (40.4 mg, 0.18 mmol), and Xanphos (136 mg, 0.235 mmol) were added and flask was placed under argon. Reagents were suspended in 8 mL of anhydrous dioxane and mixture was heated at 100° C. overnight. After cooling to room temperature, reaction mixture was filtered, washing with ethyl acetate. Combined filtrate was concentrated under reduced pressure and resulting film was purified by silica gel column chromatography (25-100% Ethyl Acetate in Hexanes) to yield intermediate 96 (322 mg, 78%) as a yellow off-white solid.

$^1$H-NMR (DMSO, 400 MHz): δ 7.75 (d, 1H), 7.44 (m, 1H), 7.35 (m, 1H), 3.89 (s, 3H), 3.81 (t, 2H), 3.28 (t, 2H), 2.55 (m, 2H), 2.39 (s, 3H).

LCMS m/z [M+H]$^+$ C$_{12}$H$_{15}$NO$_4$S requires: 270.07. Found 270.12

Intermediate 97

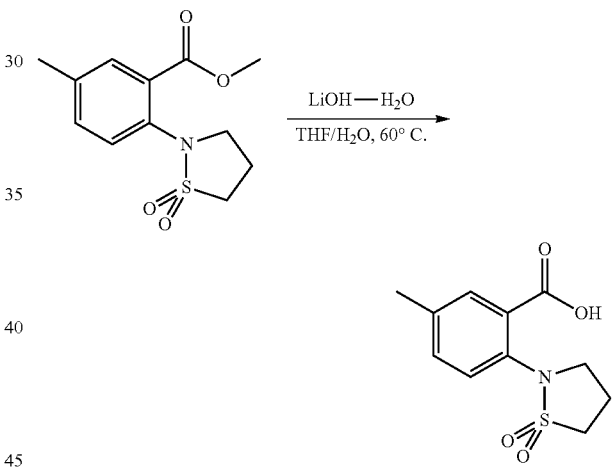

Lithium hydroxide monohydrate (496 mg, 11.8 mmol) was added to a solution of intermediate 96 (316 mg, 1.17 mmol) in 22 mL of THF and 12 mL of water at room temperature. Reaction mixture was heated at 60° C. for two hours. After cooling to room temperature, reaction mixture was acidified with 40 mL of 1N HCl$_{(aq)}$ and extracted with ethyl acetate (3×30 mL). The combined organic layers were washed 50 mL of Brine, separated, dried (MgSO$_4$), filtered, and concentrated under reduced pressure to yield intermediate 97 as a off-white solid (293 mg, 98%).

$^1$H-NMR (DMSO, 400 MHz): δ 12.9 (s, 1H), 7.57 (d, J=1.6 Hz, 1H), 7.41-7.34 (m, 2H), 3.66 (t, J=6.8 Hz, 2H), 3.28 (m, 2H), 2.37 (m, 2H), 2.33 (s, 3H).

LCMS m/z [M+H]$^-$ C$_{11}$H$_{13}$NO$_4$S requires: 254.06. Found 254.18

Compound 113

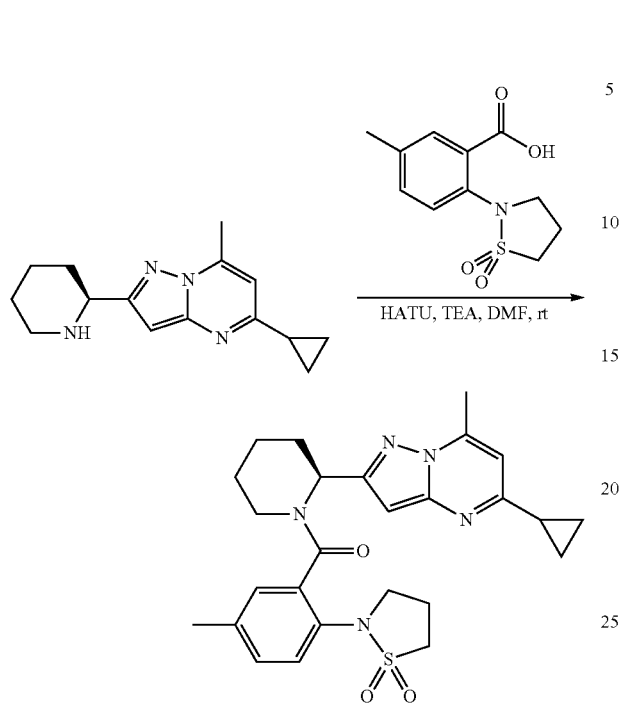

Following the procedure for the synthesis of compound 99, beginning with intermediate 31 (84.8, 0.332 mmol) and a 0.5 M DMF solution of intermediate 97 (0.5 mL, 0.25 mmol), compound 113 was synthesized as a white solid, trifluoroacetate salt, after lyophilization. (93 mg, 61%).

$^1$H-NMR (DMSO, 400 MHz): δ 8.81 (s, 1H), 7.48 (m, 1H), 7.31 (m, 1H), 7.24 (m, 1H), 6.87 (d, 1H), 6.60 (s, 1H), 6.46 (d, 1H), 6.01 (dd, 1H), 3.84-3.64 (m, 1H), 3.54-3.28 (m, 4H), 3.12 (m, 1H), 2.66 (s, 3H), 2.36 (s, 3H), 2.26 (m, 1H), 1.84-1.55 (m, 5H), 1.03 (m, 5H)

LCMS m/z [M+H]$^+$ C$_{26}$H$_{31}$N$_5$O$_3$S requires: 494.21. Found 494.07

HPLC Tr (min), purity %: 6.74, 99%

Compound 114

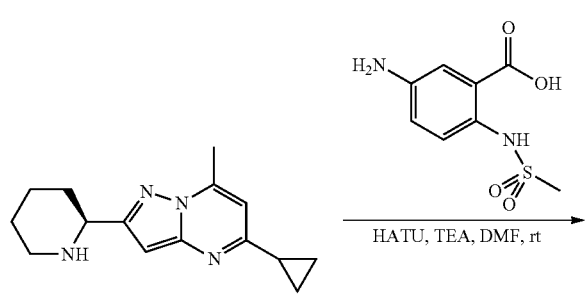

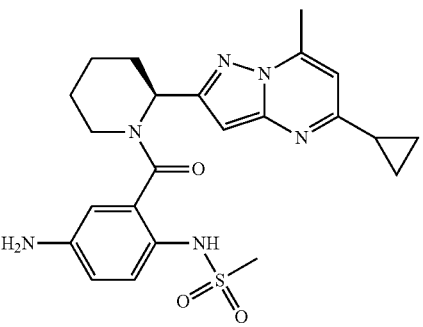

Following the procedure for the synthesis of compound 99, beginning with 5-amino-2-(methylsulfonamido)benzoic acid (45.5 mg, 0.198 mmol) and a 0.5 M DMF solution of intermediate 31 (0.30 mL, 0.15 mmol), compound 114 was synthesized as a white solid, trifluoroacetate salt, after lyophilization. (60.2 mg, 69%).

$^1$H-NMR (DMSO, 400 MHz): δ 8.75 (s, 1H), 7.19 (m, 1H), 6.84 (m, 3H), 6.4 (d, 2H), 6.01 (s, 1H), 3.39 (m, 1H), 3.18 (m, 1H), 2.97 (s, 3H), 2.68 (s, 3H), 2.12 (m, 1H), 1.86 (m, 1H), 1.61 (m, 2H), 1.46 (m, 3H), 1.04 (m, 5H)

LCMS m/z [M+H]$^+$ C$_{23}$H$_{28}$N$_6$O$_3$S requires: 469.19. Found 469.14

HPLC Tr (min), purity %: 5.20, 99%

Intermediate 98

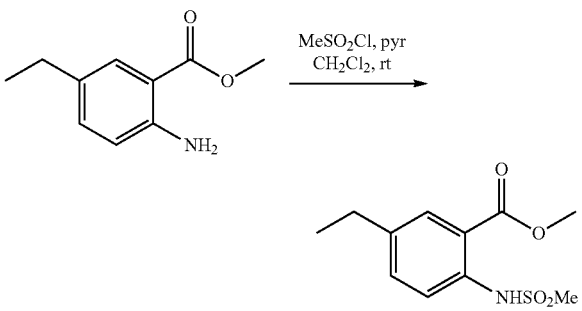

To a solution of methyl 2-amino-5-ethylbenzoate (569 mg, 3.18 mmol) and pyridine (0.70 mL, 8.72 mmol) in 15 mL of anhydrous CH$_2$CL$_2$, was added slowly methane sulfonylchloride (0.71 mL, 9.12 mmol). After stirring overnight, reaction mixture was quenched with 30 mL of 1N HCl$_{(aq)}$. Aqueous mixture was extracted with ethyl acetate (3×40 mL) and combined organic layers were washed with 1N HCl$_{(aq)}$ and then brine. Organics were dried (MgSO$_4$), filtered, and concentrated under reduced pressure to yield intermediate 98 (785 mg, 96%) as a brown oily residue that was used in the next step without further purification.

LCMS m/z [M+H]$^-$ C$_{11}$H$_{15}$NO$_4$S requires: 258.07. Found 258.20

Intermediate 99

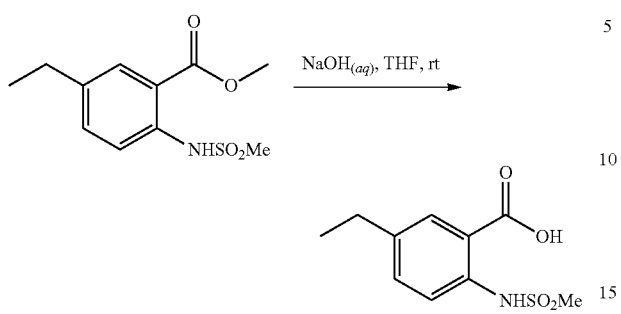

A 1.0 M solution of NaOH in water (16 mL, 16 mmol) was added to a solution of intermediate 98 (817 mg, 3.19 mmol) in 30 mL of THF with strong stirring. Reaction mixture was stirred at room temperature for twenty four hours. Mixture was then acidified with 40 mL of 1N HCl$_{(aq)}$ and extracted with ethyl acetate (3×60 mL). The combined organic layers were washed 100 mL of Brine, separated, dried (MgSO$_4$), filtered, and concentrated under reduced pressure to yield intermediate 99 as a tan solid (714 mg, 92%).

$^1$H-NMR (DMSO, 400 MHz): δ 13.8 (s, 1H), 10.5 (s, 1H), 7.82 (d, J=1.2 Hz, 1H), 7.48 (m, 2H), 3.13 (s, 3H), 2.59 (q, J=7.2 Hz, 2H), 1.15 (t, J=7.2 Hz, 3H).

LCMS m/z [M+H]$^-$ C$_{10}$H$_{13}$NO$_4$S requires: 242.06. Found 242.10

Compound 115

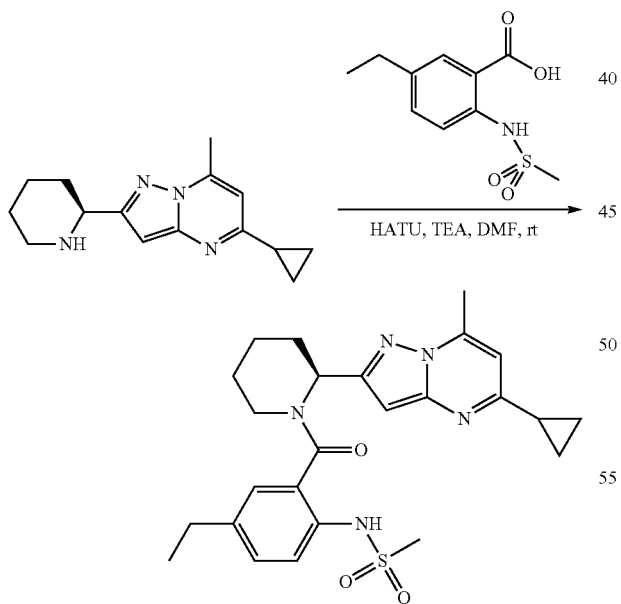

Following the procedure for the synthesis of compound 99, beginning with intermediate 31 (60.1 mg, 0.247 mmol) and the bis-hydrochloride salt of intermediate 99 (57 mg, 0.173 mmol), compound 115 was synthesized as a white solid, trifluoroacetate salt, after lyophilization. (67.8 mg, 66%).

$^1$H-NMR (DMSO, 400 MHz): δ 8.90 (s, 1H), 7.26 (m, 3H), 6.89 (s, 1H), 6.49 (d, 1H), 3.40-3.17 (m, 1H), 3.00 (s, 1H), 2.68 (s, 3H), 2.67 (m, 1H), 2.42 (m, 1H), 2.12 (m, 1H), 1.91 (m, 1H), 1.67-1.33 (m, 4H), 1.20 (t, 2H, J=8 Hz), 1.04 (m, 5H), 1.01 (s, 3H)

LCMS m/z [M+H]$^+$ C$_{25}$H$_{31}$N$_5$O$_3$S requires: 482.21. Found 482.38

HPLC Tr (min), purity %: 7.54, 99%

Compound 116

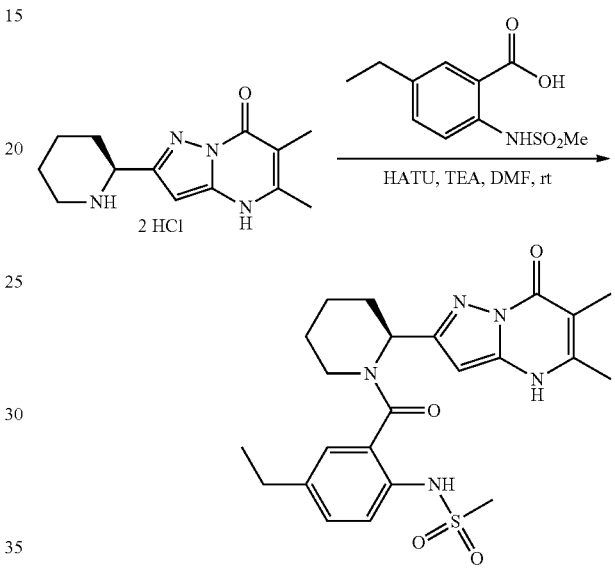

Following the procedure for the synthesis of compound 99, beginning with intermediate 99 (101 mg, 0.416 mmol) and the bis-hydrochloride salt of intermediate 6 (106 mg, 0.333 mmol), compound 116 was synthesized as a white solid, trifluoroacetate salt, after lyophilization (99.3 mg, 50%).

$^1$H-NMR (DMSO, 300 MHz): δ 12.1 (s, 1H), 9.15 (s, 1H), 7.25 (m, 3H), 5.97 (s, 1H), 4.31-4.15 (m, 3H), 3.39 (m, 1H), 3.12 (s, 3H), 3.11 (m, 1H), 2.64 (m, 1H), 2.42 (m, 1H), 2.30 (s, 3H), 1.95 (s, 3H), 1.94 (m, 1H), 1.65 (m, 1H), 1.46-1.21 (q, 2H), 1.18 (t, 3H)

LCMS m/z [M+H]$^+$ C$_{23}$H$_{29}$N$_5$O$_4$S requires: 472.20. Found 472.40

HPLC Tr (min), purity %: 5.73, 99%

Intermediate 100

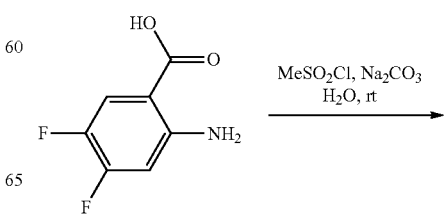

-continued

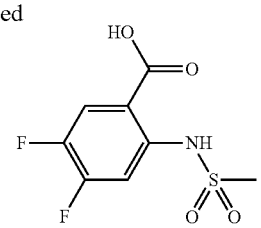

Sodium carbonate (4.1 g, 38.7 mmol) was added to a mixture of 2-amino-4,5-difluorobenzoic acid (704 mg, 4.07 mmol) in 6 mL of water. Methane sulfonylchloride (2.5 mL, 32.5 mmol) was added slowly (delayed exotherm). Reaction mixture was stirred at room temperature. Sodium carbonate (3.5 g) was added after one hour to maintain pH>8. HPLC indicates ~85% conversion to desired product. Methane sulfonylchloride (0.5 mL) was added and after one hour, reaction mixture was carefully quenched with 1N HCl$_{(aq)}$ until pH<2. Aqueous was extracted with ethyl acetate (3×60 mL) and combined organic layers were washed with brine, dried (MgSO$_4$), filtered, and concentrated to yield an off white solid. This solid was suspended in a minimal amount of dichloromethane, stirred for 20 min, filtered, and dried in-vacuo to yield intermediate 100 (586 mg, 60%) as a creamy white solid.

$^1$H-NMR (DMSO, 400 MHz): δ 10.6 (s, 1H), 7.97 (m, 1H), 7.53 (m, 1H), 3.24 (s, 3H)

LCMS m/z [M+H]$^+$ C$_8$H$_7$F$_2$NO$_4$S requires: 252.01. Found 252.09

Compound 117

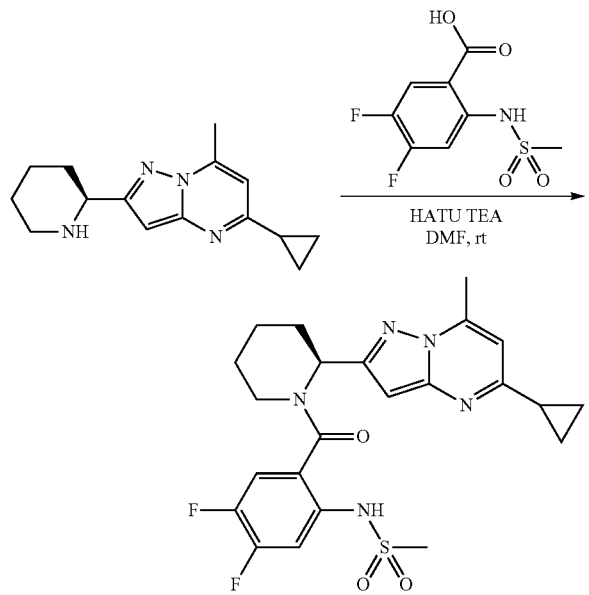

Following the procedure for the synthesis of compound 99, beginning with intermediate 100 (53.2 mg, 0.212 mmol) and a 0.5 M DMF solution of intermediate 31 (0.30 mL, 0.15 mmol), compound 117 was synthesized as a white solid, trifluoroacetate salt, after lyophilization. (53 mg, 59%).

$^1$H-NMR (DMSO, 400 MHz): δ 9.29 (s, 1H), 7.63 (m, 1H), 7.47 (m, 1H), 6.89 (s, 1H), 6.54 (d, 1H), 3.34 (m, 1H), 3.21 (m, 1H), 3.08 (s, 1H), 2.67 (s, 3H), 2.12 (m, 1H), 2.08-1.96 (m, 1H), 1.65-1.35 (m, 5H), 1.03 (m, 1H)

LCMS m/z [M+H]$^+$ C$_{23}$H$_{25}$F$_2$N$_5$O$_3$S requires: 490.16. Found 490.03

HPLC Tr (min), purity %: 7.28, 99%

Compound 118

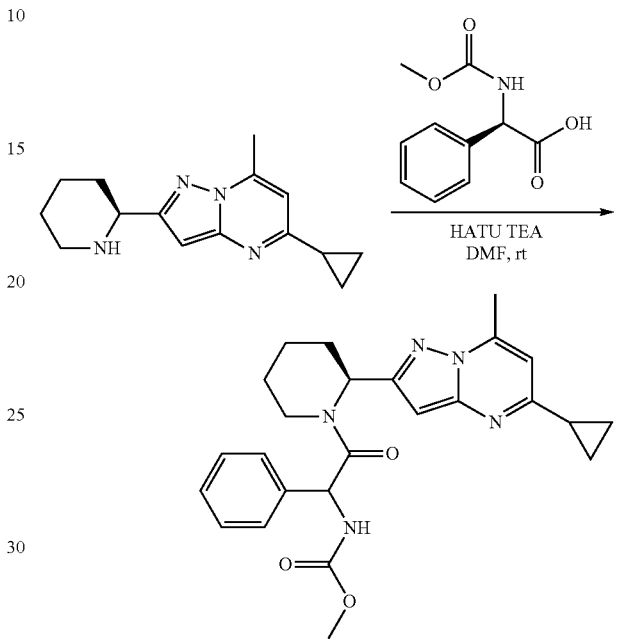

Following the procedure for the synthesis of compound 99, beginning with (R)-2-(methoxycarbonylamino)-2-phenylacetic acid (45.1 mg, 0.216 mmol) and a 0.5 M DMF solution of intermediate 31 (0.30 mL, 0.15 mmol), compound 118 was synthesized as a 1:1 mixture of diasteromers as a white solid, trifluoroacetate salt, after lyophilization. (69 mg, 82%).

$^1$H-NMR (DMSO, 400 MHz): δ 7.65 (d, 1H), 7.42 (m, 5H), 6.84 (m, 1H), 5.94 (m, 1H), 5.70 (m, 1H), 4.41 (m, 1H), 3.81 (m, 1H), 3.53 (s, 3H), 2.98 (tt, 1H), 2.63 (s, 3H), 2.37 (m, 1H), 2.14 (m, 1H), 1.55 (m, 4H), 1.31 (m, 1H), 1.03 (m, 4H).

LCMS m/z [M+H]$^+$ C$_{25}$H$_{29}$N$_5$O$_3$ requires: 448.23. Found 448.20

HPLC Tr (min), purity %: 6.83, 6.96, 1:1 mixture of diastereomers, 99%

Intermediate 101

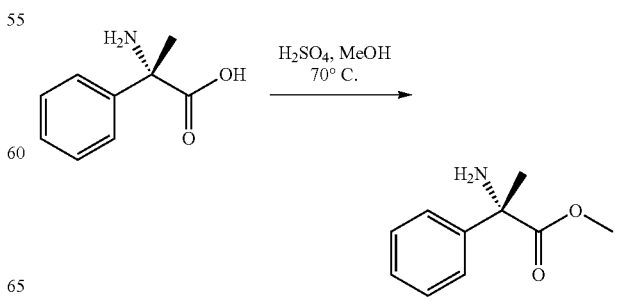

A solution of (S)-2-amino-2-phenylpropanoic acid (246.2 mg, 1.49 mmol) and 0.6 mL of concentrated H₂SO₄ in 6 mL of anhydrous methanol was heated overnight. After cooling to room temperature, methanol was concentrated under reduced pressure. Residue was taken up in 20 mL of water and added to a reparatory funnel. Solid sodium carbonate was added slowly until gas evolution ceased (pH 9-10). Aqueous layer was extracted with ethyl acetate (3×30 mL). The combined organic layers were washed with 80 mL sat. NaHCO$_{3(aq)}$ and 80 mL of Brine, separated, dried (MgSO₄), filtered, and concentrated under reduced pressure to yield intermediate 101 (117 mg, 44%) as a yellow-green oily residue.

¹H-NMR (DMSO, 400 MHz): δ 7.44 (m, 2H), 7.32 (m, 2H), 7.24 (m, 1H), 3.59 (s, 3H), 2.37 (s, 2H), 1.51 (s, 3H)

LCMS m/z [M+H]⁺ C₁₀H₁₃NO₂ requires: 180.09. Found 180.19

Intermediate 112

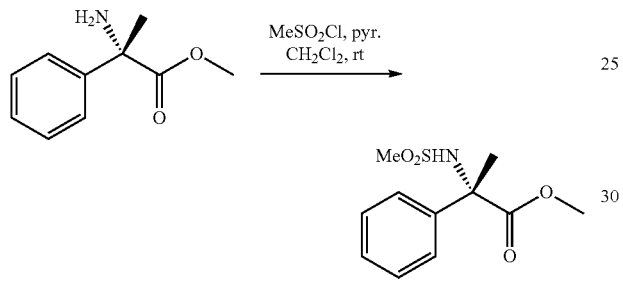

To a solution of intermediate 101 (116 mg, 0.647 mmol) and pyridine (0.16 mL, 1.98 mmol) in 4 mL of anhydrous CH₂CL₂, was added slowly methane sulfonylchloride (0.070 mL, 0.91 mmol). After stirring overnight, reaction mixture was quenched with 20 mL of 1N HCl$_{(aq)}$. Aqueous mixture was extracted with ethyl acetate (3×20 mL) and combined organic layers were washed with 1N HCl$_{(aq)}$ and then brine. Organics were dried (MgSO₄), filtered, and concentrated under reduced pressure to yield intermediate 102 (312 mg, 97%) as a yellow-green oily residue that was used in the next step without further purification.

LCMS m/z [M+H]⁺ C₁₁H₁₅NO₄S requires: 258.08. Found 258.19

Intermediate 113

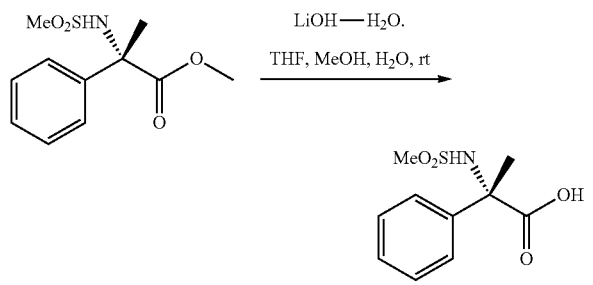

Lithium hydroxide monohydrate (169 mg, 4.02 mmol) was added to a solution of intermediate 102 (102 mg, 0.397 mmol) in 6 mL of 1:1:1 THF:MeOH:H₂O at room temperature. Reaction mixture was stirred overnight and then was acidified with 15 mL of 1N HCl$_{(aq)}$ and extracted with ethyl acetate (3×20 mL). The combined organic layers were washed 50 mL of Brine, separated, dried (MgSO₄), filtered, and concentrated under reduced pressure to yield intermediate 103 as a light green film (93.6 mg, 97%).

LCMS m/z [M+H]⁻ C₁₀H₁₃NO₄S requires: 242.06. Found 242.0

Compound 119

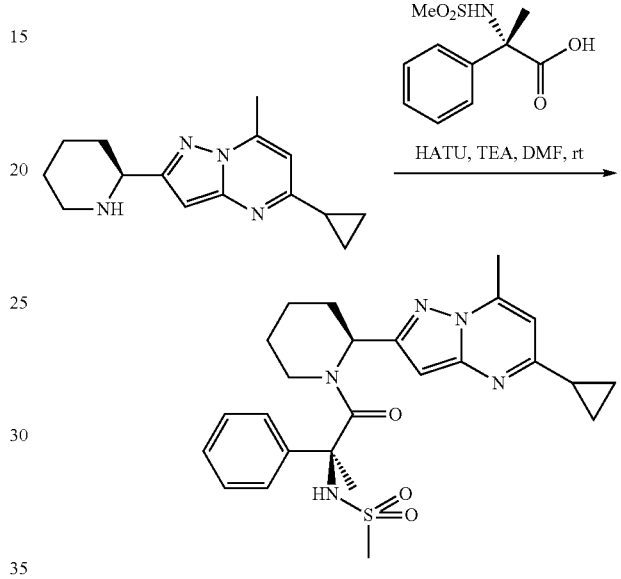

Following the procedure for the synthesis of compound 99, beginning with a 0.082 DMF solution of intermediate 103 (2.5 mL, 0.205 mmol) and a 0.5 M DMF solution of intermediate 31 (0.30 mL, 0.15 mmol), compound 119 was synthesized as a white solid, trifluoroacetate salt, after lyophilization. (6.2 mg, 7%).

¹H-NMR (DMSO, 300 MHz): δ 7.51-7.35 (m, 5H), 6.85 (s, 1H), 6.45 (s, 1H), 6.00 (s, 1H), 3.64 (m, 3H), 2.63 (s, 3H), 2.52 (s, 3H), 2.32 (m, 2H), 2.11 (m, 1H), 1.92 (s, 3H), 1.65 (m, 1H), 1.38 (m, 2H), 1.05 (m, 5H)

LCMS m/z [M+H]⁺ C₂₅H₃₁N₅O₃S requires: 482.21. Found 482.12

HPLC Tr (min), purity %: 7.22, 85%

Intermediate 104

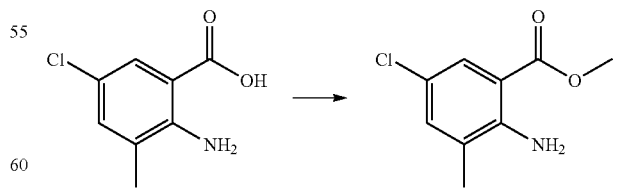

A solution of 2-amino-5-chloro-3-methylbenzoic acid (928 mg, 4.99 mmol) and 2.0 mL of concentrated H₂SO₄ in 15 mL of anhydrous methanol was heated for 66 hours. After cooling to room temperature, methanol was concentrated under reduced pressure. Residue was taken up in 50 mL of water and added to a separatory funnel. Solid sodium carbonate was added slowly until gas evolution ceased (pH 9-10). Aqueous layer was extracted with ethyl acetate (3×50 mL). The combined organic layers were washed with 100 mL sat. NaHCO$_{3(aq)}$ and 100 mL of Brine, separated, dried (MgSO$_4$), filtered, and concentrated under reduced pressure to yield intermediate 104 (817 mg, 83%) as a brown solid, which was used without further purification.

$^1$H-NMR (CDCl$_3$, 300 MHz): δ 7.75 (d, J=2.7 Hz, 1H), 7.17 (d, J=2.7 Hz, 1H), 5.83 (br s, 2H), 3.88 (s, 3H), 2.16 (s, 3H)

LCMS m/z [M+H]$^+$ C$_9$H$_{10}$ClNO$_2$ requires: 200.04. Found 200.10

Intermediate 105

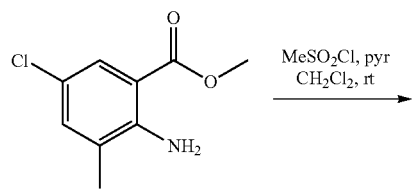

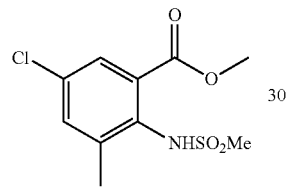

To a solution of intermediate 104 (392 mg, 1.97 mmol) and pyridine (0.45 mL, 5.68 mmol) in 9 mL of anhydrous CH$_2$CL$_2$, was added slowly methane sulfonylchloride (0.46 mL, 5.66 mmol). After stirring overnight, an addition 0.7 mL of pyridine and methane sulfonylchloride were each added reaction mixture stirred for two hour. It was then quenched with 30 mL of 1N HCl$_{(aq)}$. Aqueous mixture was extracted with ethyl acetate (3×40 mL) and combined organic layers were washed with 1N HCl$_{(aq)}$ and then brine. Organics were dried (MgSO$_4$), filtered, and concentrated under reduced pressure to yield a light yellow film. Silica gel column chromatography (0-50% Ethyl Acetate in Hexanes) yielded intermediate 105 (330, 60%) as a light yellow solid.

$^1$H-NMR (CDCl$_3$, 300 MHz): δ 8.47 (s, 1H), 7.86 (d, J=2.4 Hz, 1H), 7.50 (d, J=2.4 Hz, 1H), 3.96 (s, 3H), 2.90 (s, 3H), 2.53 (s, 3H)

LCMS m/z [M+H]$^+$ C$_{10}$H$_{12}$ClNO$_4$S requires: 278.03. Found 278.08

Intermediate 106

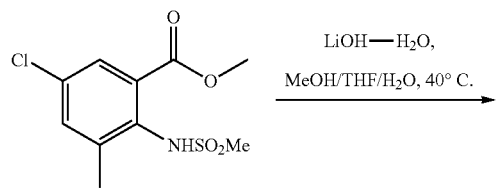

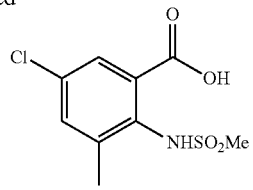

Lithium hydroxide monohydrate (228 mg, 5.43 mmol) was added to a solution of intermediate 105 (120 mg, 0.433 mmol) in 3 mL of 1:1:1 THF:MeOH:H$_2$O at room temperature. Reaction mixture was heated at 50° C. for four hours. After cooling to room temperature, reaction mixture was acidified with 20 mL of 1N HCl$_{(aq)}$ and extracted with ethyl acetate (3×20 mL). The combined organic layers were washed 50 mL of Brine, separated, dried (MgSO$_4$), filtered, and concentrated under reduced pressure to yield intermediate 106 as a white solid (114 mg, 100%).

$^1$H-NMR (DMSO, 300 MHz): δ 9.2 (s, 1H), 7.59 (m, 2H), 2.96 (s, 3H), 2.37 (s, 3H)

LCMS m/z [M+H]$^-$ C$_9$H$_{10}$ClNO$_4$S requires: 264.00. Found 264.09

Compound 120

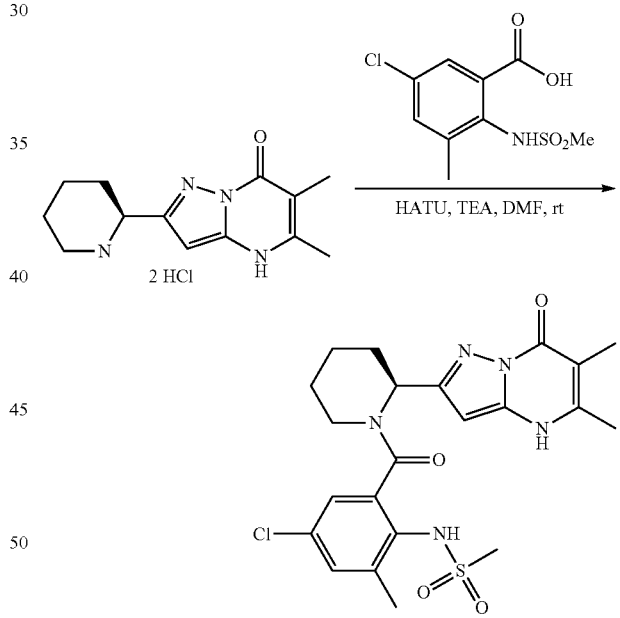

Following the procedure for the synthesis of compound 99, using intermediate 106 (67.3 mg, 0.252 mmol) and intermediate 6 (61.6 mg, 0.193 mmol), compound 120 was synthesized as an off-white solid, trifluoroacetate salt, after lyophilization. (49 mg, 43%).

$^1$H-NMR (DMSO, 300 MHz): δ 12.1 (s, 1H), 9.0 (s, 1H) 7.46-7.2 (m, 2H), 6.10 (s, 1H), 5.91 (s, 1H), 4.05 (m, 1H), 3.21 (m, 1H), 3.11 (s, 3H), 2.45 (m, 1H), 2.40 (s, 3H), 2.30 (s, 3H), 1.99 (s, 3H), 1.65-1.27 (m, 4H)

LCMS m/z [M+H]$^+$ C$_{22}$H$_{26}$ClN$_5$O$_4$S requires: 492.14 Found 492.09

HPLC Tr (min), purity %: 5.67, 99%

Intermediate 107

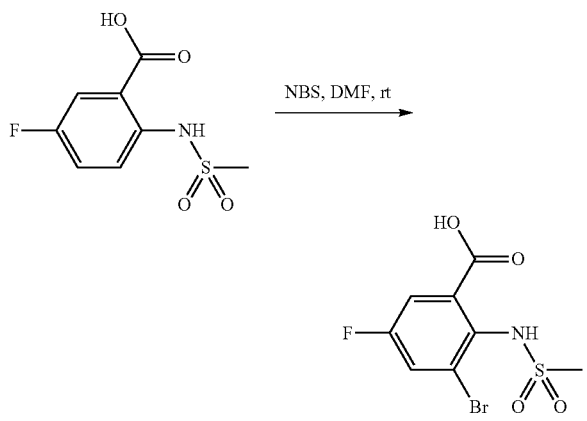

N-Bromosuccinimide (919 mg, 3.32 mmol) was added to a solution of 5-fluoro-2-(methylsulfonamido)benzoic acid (701 mg, 3.01 mmol) in 11 mL of anhydrous DMF. After stirring overnight, reaction mixture was poured into 100 mL of water and 50 mL of brine and extracted with ethyl acetate (3×100 mL). Combined organic layers were washed with 300 mL of 1:1 water:brine, dried (MgSO$_4$), filtered, and concentrated under reduced pressure to yield intermediate 107 (910 mg, 97%).

$^1$H-NMR (DMSO, 400 MHz): δ 11.1 (s, 1H), 9.50 (s, 1H), 7.90 (d, J=3.6 Hz, 1H), 7.56 (d, J=3.6 Hz, 1H), 4.70 (br s, 1H), 4.39 (t, J=10.2 Hz, 1H), 3.28 (d, J=14.1 Hz, 1H), 3.01 (s, 3H)

LCMS m/z [M+H]$^+$ C$_8$H$_7$BrFNO$_4$S requires: 309.93. Found 309.97

Compound 121

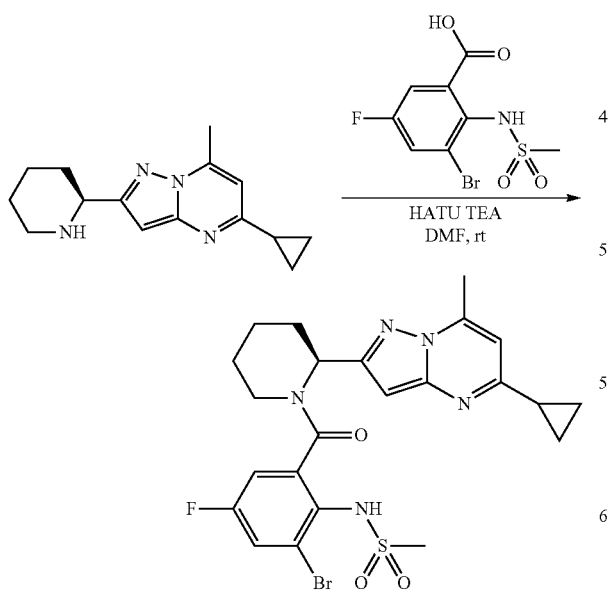

Following the procedure for the synthesis of compound 99, beginning with intermediate 107 (61.2 mg, 0.196 mmol) and a 0.5 M DMF solution of intermediate 31 (0.30 mL, 0.15 mmol), compound 121 was synthesized as a white solid, trifluoroacetate salt, after lyophilization. (69.3 mg, 70%).

LCMS m/z [M+H]$^+$ C$_{23}$H$_{25}$BrFN$_5$O$_3$S requires: 550.08. Found 550.04

HPLC Tr (min), purity %: 6.93, 99%

Intermediate 108

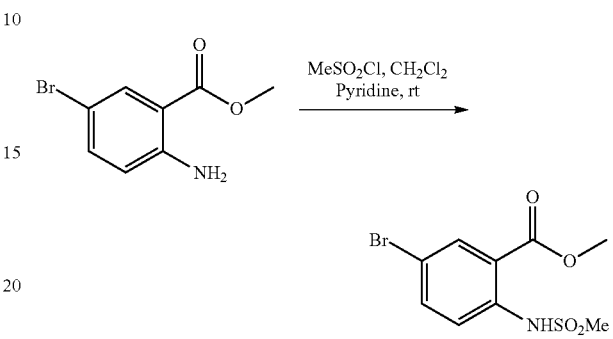

To a solution of methyl 2-amino-5-bromobenzoate (7.38 g, 32.0 mmol) and pyridine (6.3 mL, 81.5 mmol) in 100 mL of anhydrous CH$_2$CL$_2$, was added slowly methane sulfonyl-chloride (6.5 mL, 79.9 mmol). After stirring overnight, reaction mixture was quenched with 100 mL of 1N HCl$_{(aq)}$. Aqueous mixture was extracted with ethyl acetate (3×120 mL) and combined organic layers were washed 200 mL brine. Organics were dried (MgSO$_4$), filtered, and concentrated under reduced pressure to yield intermediate 108 as an off white solid. Silica gel column chromatography (0-30% Ethyl Acetate in Hexanes), yielded intermediate C—C (9.35 g, 95%) as a white off-white solid.

$^1$H-NMR (CDCl$_3$, 300 MHz): δ 10.4 (s, 1H), 8.22 (s, 1H), 7.63 (s, 2H), 3.96 (s, 3H), 3.05 (s, 3H)

LCMS m/z [M+H]$^+$ C$_9$H$_{10}$BrNO$_4$S requires: 307.95. Found 308.06

Intermediate 109

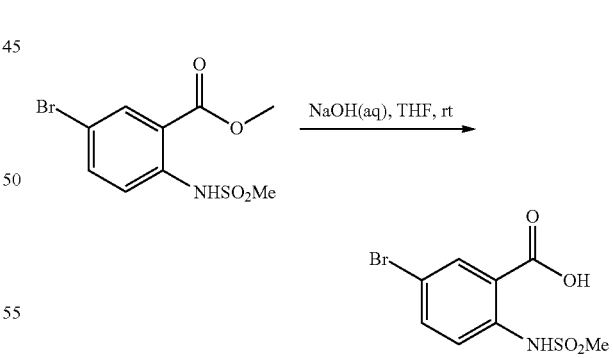

A 2.65 M solution of NaOH in water (2.65 mL, 7.02 mmol) was added to a solution of intermediate 108 in 9 mL of THF with strong stirring. Reaction mixture was stirred at room temperature over night. Mixture was then acidified with 10 mL of 1N HCl and extracted with ethyl acetate (3×20 mL). The combined organic layers were washed 30 mL of Brine, separated, dried (MgSO$_4$), filtered, and concentrated under reduced pressure to yield intermediate 109 as a white solid (338 mg, 98%).

¹H-NMR (DMSO, 300 MHz): δ 10.6 (s, 1H), 8.05 (s, 1H), 7.79 (d, 1H), 7.55 (d, 1H), 3.18 (s, 3H)

LCMS m/z [M+H]⁻ C₈H₈BrNO₄S requires: 291.94. Found 291.90

Compound 122

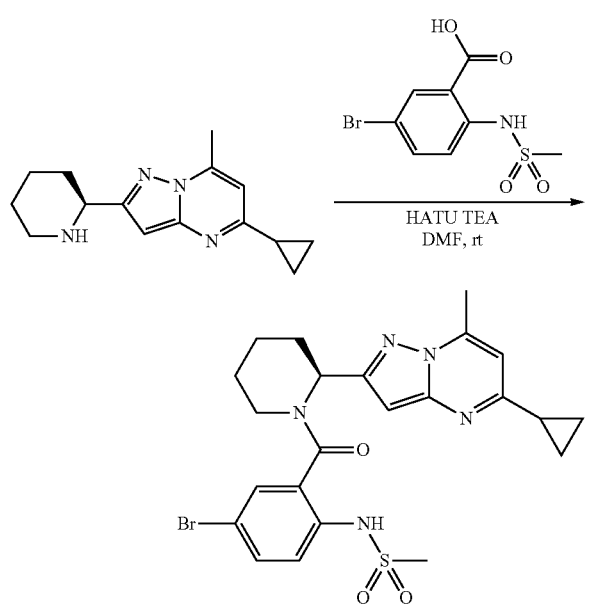

Following the procedure for the synthesis of compound 99, beginning with intermediate 109 (58.6 mg, 0.199 mmol) and a 0.5 M DMF solution of intermediate 31 (0.30 mL, 0.15 mmol), compound 122 was synthesized as an white solid, trifluoroacetate salt, after lyophilization. (71 mg, 73%).

¹H-NMR (DMSO, 400 MHz): δ 9.39 (s, 1H), 7.61 (m, 2H), 7.40 (m, 1H), 6.92 (s, 1H), 6.53 (d, 1H), 6.01 (s, 1H), 4.44 (m, 1H), 3.25 (m, 1H), 3.04 (s, 3H), 2.79 (m, 1H), 2.68 (s, 3H), 2.40-1.91 (m, 3H), 1.64-1.25 (m, 4H), 1.02 (m, 3H).

LCMS m/z [M+H]⁺ C₂₃H₂₆BrN₅O₃S requires: 532.09. Found 532.05

HPLC Tr (min), purity %: 7.52, 99%

Compound 123

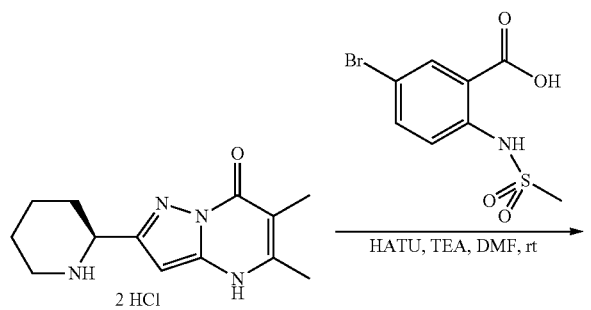

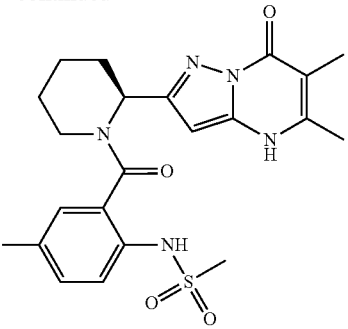

Following the procedure for the synthesis of compound 13, using intermediate 109 (85.2 mg, 0.290 mmol) and intermediate 6 (73.1 mg, 0.229 mmol), compound 123 was synthesized as a white solid, trifluoroacetate salt, after lyophilization. (83 mg, 57%).

¹H-NMR (DMSO, 300 MHz): δ 12.1 (s, 1H), 9.61 (s, 1H), 9.30 (m, 1H), 7.65 (m, 2H), 7.38 (m, 1H), 6.01 (m, 1H), 3.08 (m, 1H), 3.05 (s, 3H), 2.39 (m, 1H), 2.34 (s, 3H), 1.99 (s, 3H), 1.97 (m, 1H), 1.84-1.45 (m, 4H)

LCMS m/z [M+H]⁺ C₂₁H₂₄BrN₅O₄S requires: 522.07. Found 522.25

HPLC Tr (min), purity %: 5.81, 99%

Compound 124

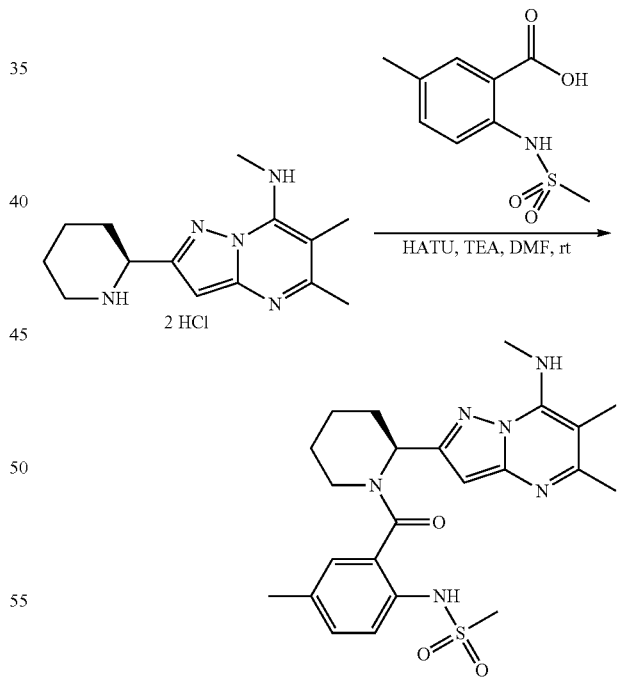

HATU (52.4 mg, 0.138 mmol) was added to a solution of 5-methyl-2-(methylsulfonamido)benzoic acid (26.8 mg, 0.117 mmol) in 2.1 mL of anhydrous DMF at room temperature. After 45 min of stirring, intermediate 28 (30.4 mg, 0.091 mmol) was added followed immediately by triethylamine (0.044 mL, 0.315 mmol). Reaction mixture stirred at room temperature overnight under argon. Mixture was then poured into 20 mL of H₂O and 10 mL of brine and extracted three times with 20 mL of ethyl acetate. The combined organic layers were washed with 60 mL of 1:1 water:brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 129 (34.3 mg, 65%) as a white solid, trifluoroacetate salt, after lyophilization.

$^1$H-NMR (DMSO, 300 MHz): δ 9.08 (s, 1H), 8.68 (s, 1H), 7.30-7.21 (m, 2H), 7.13 (m, 1H), 6.39 (s, 1H), 6.00 (s, 1H), 3.40 (m, 1H), 3.11 (m, 1H), 3.01 (s, 3H), 2.91 (m, 1H), 2.33 (s, 3H), 2.30 (m, 2H), 2.20 (s, 3H), 2.17 (m, 1H), 1.94 (m, 1H), 1.75-1.38 (m, 5H).

LCMS m/z [M+H]$^+$ C$_{23}$H$_{30}$N$_6$O$_3$S requires: 471.21. Found 471.42

HPLC Tr (min), purity %: 5.03, 99%

Compound 125

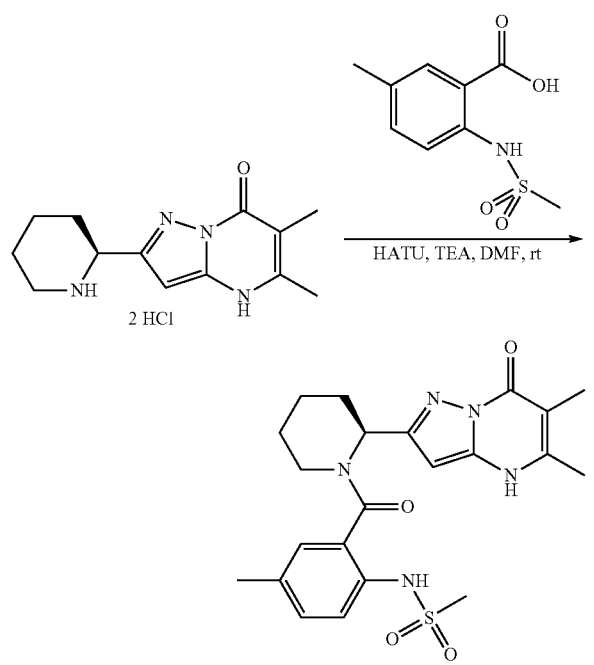

Following the procedure for the synthesis of compound 13, using 5-methyl-2-(methylsulfonamido)benzoic acid (96.1 mg, 0.419 mmol) and intermediate 6 (101 mg, 0.317 mmol), compound 125 was synthesized as a white solid, trifluoroacetate salt, after lyophilization (113 mg, 63%).

$^1$H-NMR (CDCl$_3$, 300 MHz): δ 10.3 (s, 1H), 8.94 (s, 1H) 7.55-7.40 (m, 1H), 7.35-7.18 (m, 2H), 6.01 (s, 1H), 5.74 (br m, 2H), 3.51 (m, 2H), 3.38 (s, 3H), 2.38 (s, 3H), 2.23 (s, 3H), 2.21 (m, 1H) 1.99 (s, 3H) 1.97 (m, 1H), 1.80-1.2 (m, 3H)

LCMS m/z [M+H]$^+$ C$_{22}$H$_{27}$N$_5$O$_4$S requires: 458.18. Found 458.12

HPLC Tr (min), purity %: 5.33, 95%

Compound 126

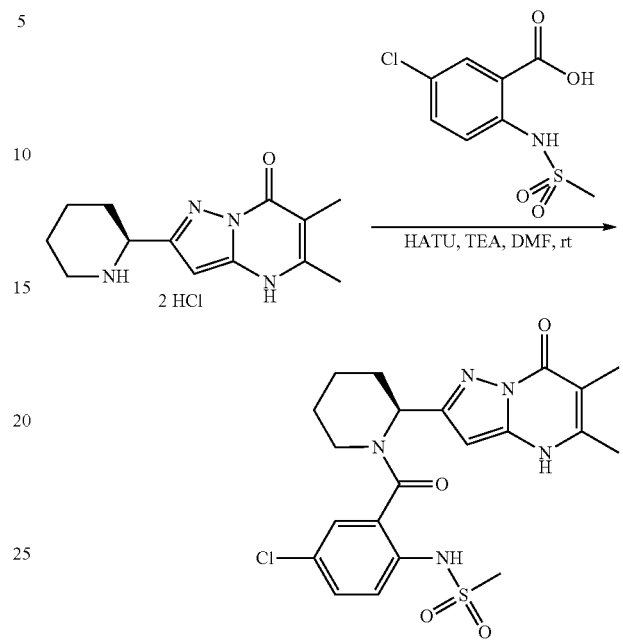

Following the procedure for the synthesis of compound 13, using 5-chloro-2-(methylsulfonamido)benzoic acid (140 mg, 0.562 mmol) and intermediate 6 (138 mg, 0.433 mmol mg, 0.317 mmol), compound 126 was synthesized as a white solid, trifluoroacetate salt, after lyophilization (184 mg, 73%).

$^1$H-NMR (DMSO, 300 MHz): δ 12.1 (s, 1H), 9.59 (s, 1H) 7.51 (m, 3H), 6.05 (s, 1H), 5.90 (s, 1H), 4.05 (m, 1H), 3.31 (m, 1H), 3.25 (s, 3H), 2.40 (m, 1H), 2.35 (s, 3H), 1.99 (s, 3H), 1.97 (m, 1H), 1.75-1.30 (m, 4H)

LCMS m/z [M+H]$^+$ C$_{21}$H$_{24}$ClN$_5$O$_4$S requires: 478.12. Found 478.07

HPLC Tr (min), purity %: 5.67, 99%

Intermediate 110

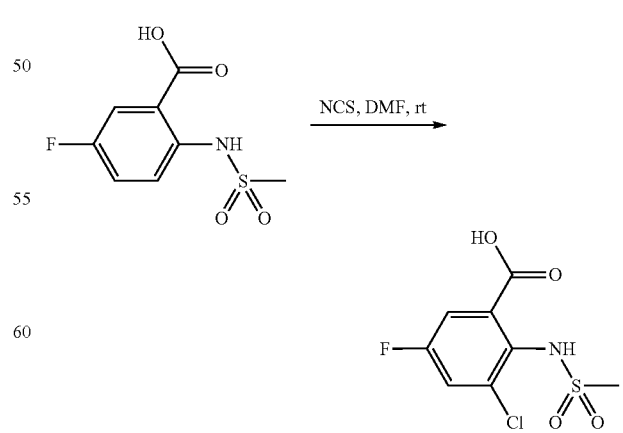

N-chlorosuccinimide (528 mg, 3.95 mmol) was added to a solution of 5-fluoro-2-(methylsulfonamido)benzoic acid (705 mg, 3.03 mmol) in 9 mL of anhydrous DMF. After stirring overnight, reaction mixture was poured into 100 mL of water and 50 mL of brine and extracted with ethyl acetate (3×100 mL). Combined organic layers were washed with 300 mL of 1:1 water:brine, dried (MgSO$_4$), filtered, and concentrated under reduced pressure to yield intermediate 110 (746 mg, 93%).

$^1$H-NMR (DMSO, 400 MHz): δ 9.5 (s, 1H), 7.76 (dd, J$_{HF}$=8 Hz, J$_{HH}$=3 Hz, 1H), 7.52 (dd, J$_{HF}$=8 Hz, J$_{HH}$=3 Hz, 1H), 3.01 (s, 3H)

LCMS m/z [M+H]$^-$ C$_8$H$_7$ClFNO$_4$S requires: 265.98. Found 265.09

Compound 127

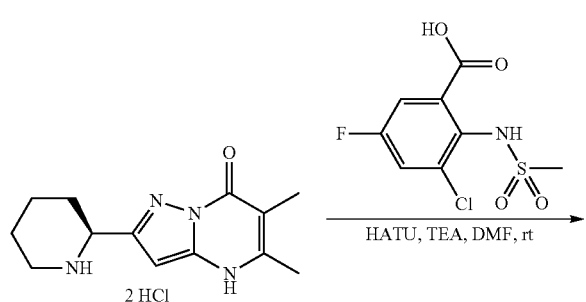

Following the procedure for the synthesis of compound 13, intermediate 110 (109 mg, 0.410 mmol) and intermediate 6 (102 mg, 0.318 mmol), compound 127 was synthesized as a white solid, trifluoroacetate salt, after lyophilization. (77 mg, 40%).

$^1$H-NMR (CDCl$_3$, 300 MHz): δ 12.1 (s, 1H) 9.35 (s, 1H), 7.7-7.2 (m, 2H), 6.17 (s, 1H), 5.95 (s, 1H), 4.27 (br s, 1H), 3.23 (m, 1H), 3.17 (s, 3H), 2.39 (m, 1H), 2.30 (s, 3H), 2.08 (m, 1H), 1.97 (s, 3H), 1.94 (m, 1H), 1.65-1.25 (m, 5H)

LCMS m/z [M+H]$^+$ C$_{21}$H$_{23}$ClFN$_5$O$_4$S requires: 496.11. Found 496.02

HPLC Tr (min), purity %: 5.64, 90%

Compound 128

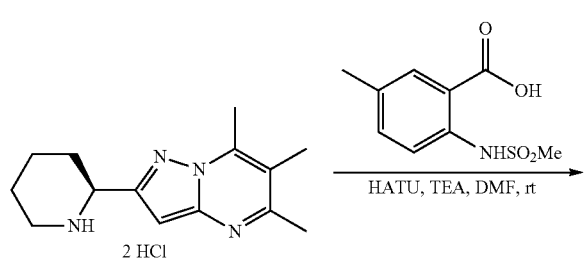

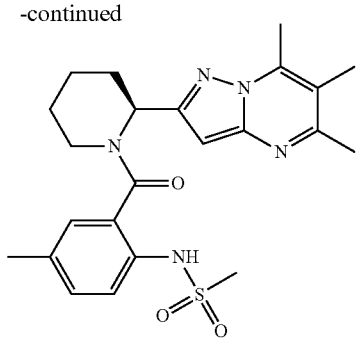

HATU (25.8 mg, 0.0678 mmol) was added to a solution of 5-methyl-2-(methylsulfonamido)benzoic acid (13.2 mg, 0.058 mmol) in 1.0 mL of anhydrous DMF at room temperature. After 45 min of stirring, Boc-deprotected intermediate 25 (12.2 mg, 0.044 mmol) was added followed immediately by triethylamine (0.020 mL, 0.150 mmol). Intermediate 25 was BOC-deprotected using the procedure cited in the preparation of intermediate 28. Reaction mixture stirred at room temperature overnight under argon. Mixture was then poured into 20 mL of H$_2$O and 10 mL of brine and extracted three times with 20 mL of ethyl acetate. The combined organic layers were washed with 60 mL of 1:1 water:brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 128 (12.8 mg, 54%) as a white solid, trifluoroacetate salt, after lyophilization.

$^1$H-NMR (DMSO, 300 MHz): δ 8.91 (s, 1H) 7.40-7.15 (m, 3H), 6.47 (d, 1H), 6.05 (s, 1H), 4.82 (m, 2H), 4.51 (m, 1H), 3.42 (m, 1H), 3.23 (m, 1H), 3.03 (s, 3H), 2.73 (s, 3H), 2.41 (m, 1H), 2.35 (s, 3H), 2.26 (s, 3H), 1.95 (m, 1H), 1.57 (m, 4H)

LCMS m/z [M+H]$^+$ C$_{23}$H$_{29}$N$_5$O$_3$S requires: 456.20. Found 456.47

HPLC Tr (min), purity %: 6.47, 98%.

Compound 129

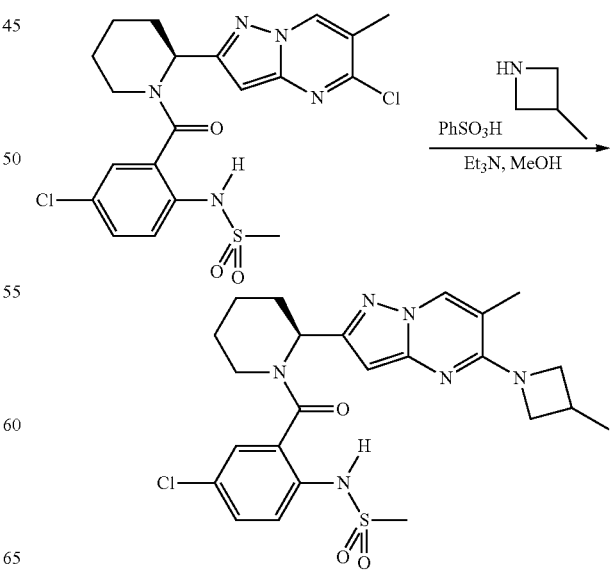

To a solution of intermediate 73 (15.0 mg, 0.03 mmol) in MeOH (400 μL) was added 3-methylazetidine benzenesulfonic acid salt (95.0 mg, 0.41 mmol) and triethylamine (112 μL, 0.82 mmol) at room temperature, and the reaction mixture was heated to 70° C. After 2 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 129 (18.3 mg, 93%) as a white solid trifluoroacetate salt.

$^1$H NMR (CD$_3$OD, 400 MHz): δ 8.81-8.56 (m, 1H), 7.75-7.60 (m, 1H), 7.55-7.37 (m, 2H), 6.16-6.05 (br s, 1H), 5.90 (s, 1H), 4.71-4.38 (m, 2H), 4.20-3.87 (m, 2H), 3.18-3.07 (m, 2H), 2.95 (br s, 3H), 2.43-2.33 (m, 1H), 2.27 (br s, 3H), 2.26-2.18 (m, 1H), 2.09-1.94 (m, 1H), 1.81-1.42 (m, 4H), 1.34 (br d, J=5.6 Hz, 3H).

LCMS (ESI) m/z 517.35 [M+H]$^+$, t$_R$=3.15 min.

HPLC t$_R$ (min), purity %: 4.53, 99%.

Intermediate 111

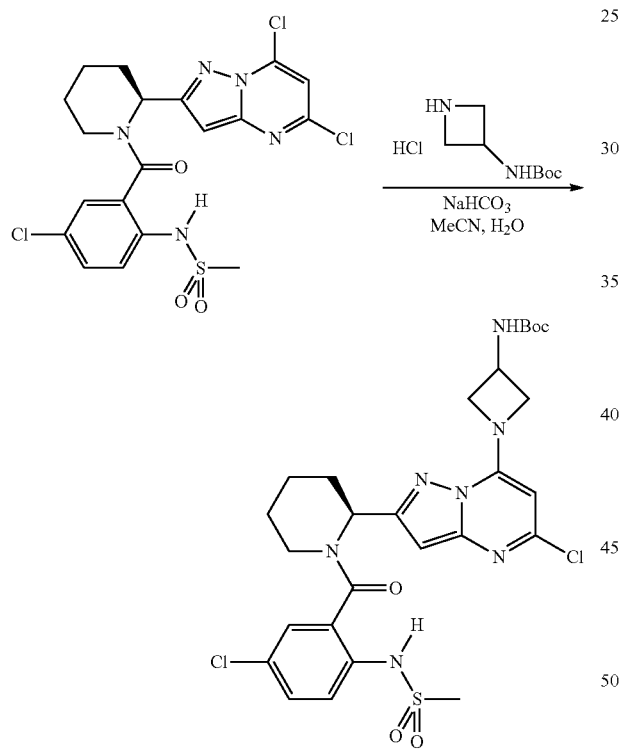

tert-butyl azetidin-3-ylcarbamate hydrochloride (62.3 mg, 0.30 mmol) and sodium bicarbonate (50.3 mg, 0.60 mmol) were added to a solution of intermediate 56 (150 mg, 0.30 mmol) in acetonitrile (0.85 mL) and water (0.85 mL) and the reaction mixture was stirred at room temperature. After 18 h, the reaction mixture was partitioned between ethyl acetate (50 mL) and water (50 mL), and the layers were separated. The organic layer was washed with saturated aqueous sodium bicarbonate solution (50 mL) and saturated sodium chloride solution (50 mL), was dried over Na$_2$SO$_4$, and was concentrated under reduced pressure. The crude residue was purified via SiO$_2$ column chromatography (12 g SiO$_2$ Combiflash HP Gold Column, 0-100% ethyl acetate/hexanes) to afford intermediate 111 (166.8 mg, 87%) as a light yellow solid.

LCMS (ESI) m/z 638.12 [M+H]$^+$, t$_R$=2.99 min.

HPLC t$_R$ (min), purity %: 5.61, 89%.

R$_f$=0.65 (75% EtOAc/hexanes).

Intermediate 112

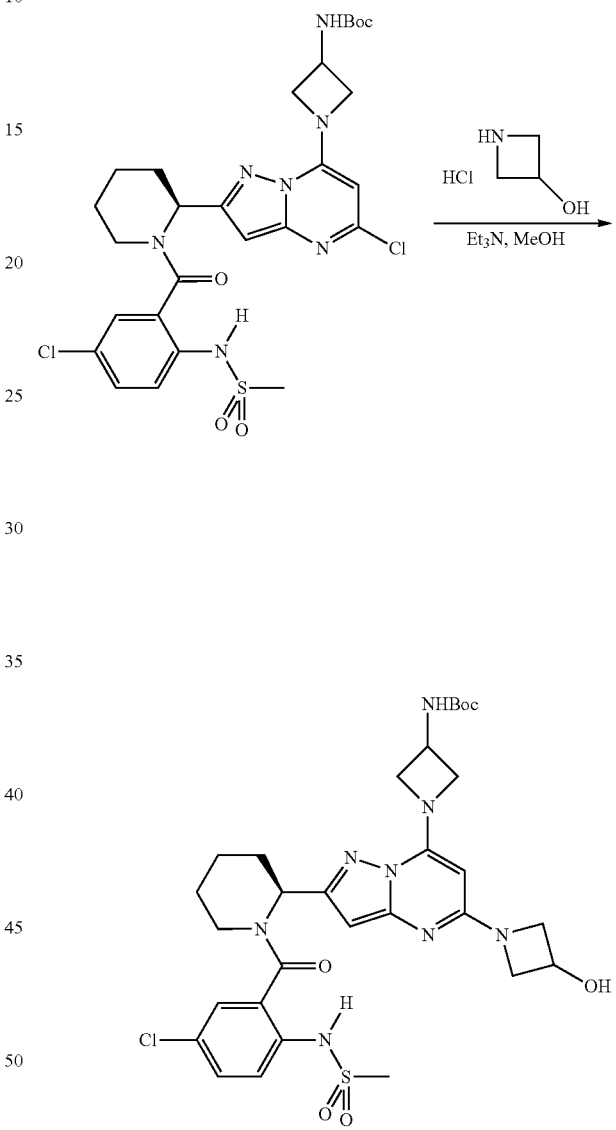

To a solution of intermediate 111 (25.0 mg, 0.05 mmol) in MeOH (1.00 mL) was added azetidin-3-ol hydrochloride (109.0 mg, 1.00 mmol) and triethylamine (279 μL, 2.00 mmol) at room temperature, and the reaction mixture was heated to 70° C. After 18 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford intermediate 112 (3.7 mg, 11%) as a white solid.

LCMS (ESI) m/z 675.22 [M+H]$^+$, t$_R$=2.10 min.

HPLC t$_R$ (min), purity %: 3.83, 99%.

R$_f$=0.15 (EtOAc).

341
Compound 130

342
Intermediate 113

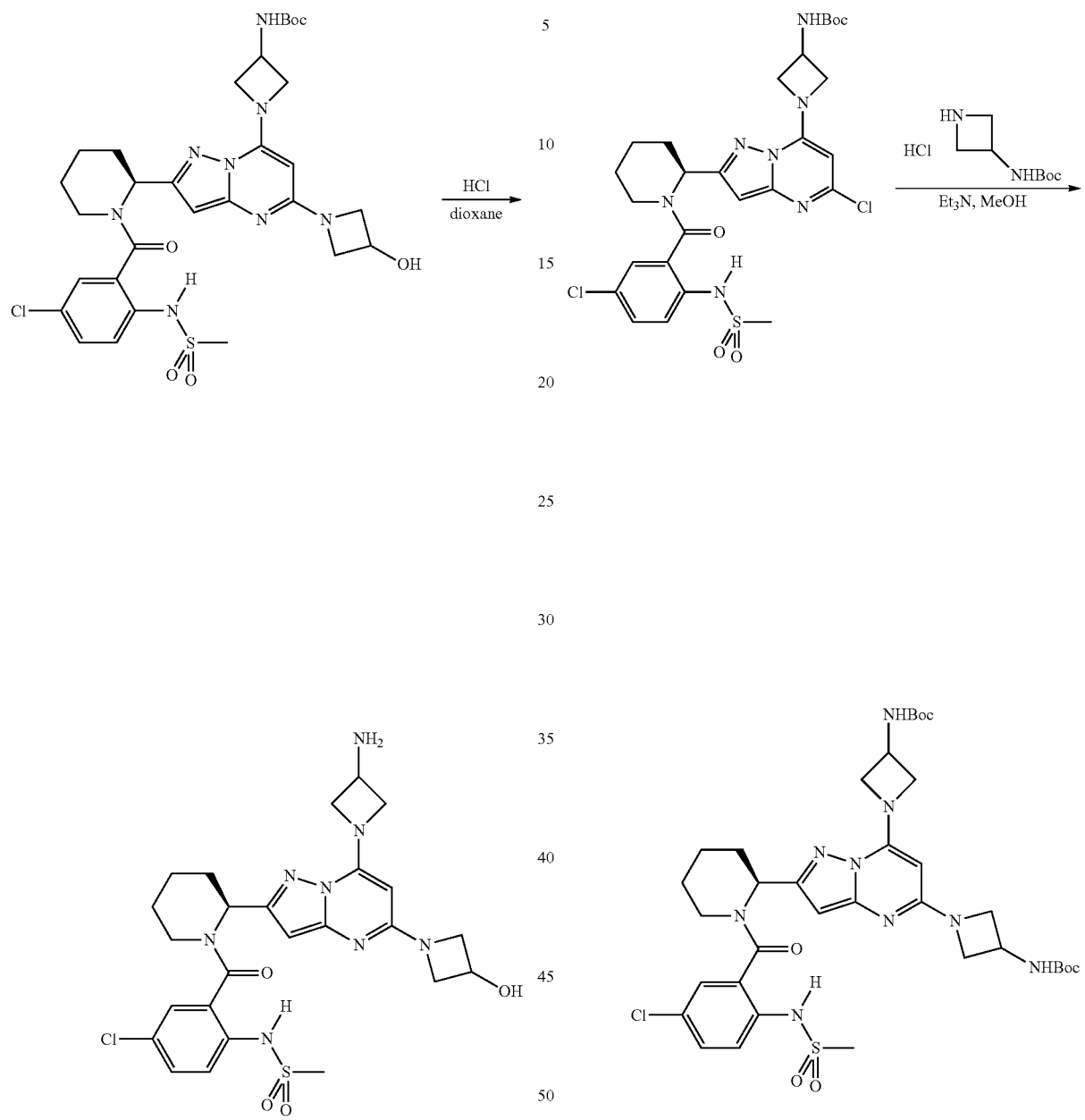

To a solution of intermediate 112 (3.7 mg, 5.5 μmol) in dioxane (0.50 mL) was added 4N HCl in dioxane solution (1.00 mL, 4.00 mmol) and the reaction mixture was stirred at room temperature. After 2 h, the reaction mixture was concentrated under reduced pressure to afford compound 130 (1.1 mg, 33%) as a white solid hydrochloric acid salt.

$^1$H NMR (CD$_3$OD, 400 MHz): δ 7.55-7.36 (m, 3H), 6.20 (br s, 1H), 6.09-5.91 (m, 2H), 4.57-4.48 (m, 1H), 4.21 (dd, J=5.7, 1.9 Hz, 4H), 4.09 (br d, J=6.0 Hz, 1H), 3.76-3.68 (m, 4H), 3.63-3.54 (m, 1H), 3.09 (s, 3H), 2.46-2.26 (m, 1H), 2.24-1.92 (m, 2H), 1.84-1.51 (m, 4H).

LCMS (ESI) m/z 575.17 [M+H]$^+$, t$_R$=1.63 min.

HPLC t$_R$ (min), purity %: 2.50, 95%.

R$_f$=0.45 (20% methanol/CH$_2$Cl$_2$).

To a solution of intermediate 111 (25.0 mg, 0.05 mmol) in MeOH (1.00 mL) was added tert-butyl azetidin-3-ylcarbamate hydrochloride (104.0 mg, 0.5 mmol) and triethylamine (139 μL, 1.00 mmol) at room temperature, and the reaction mixture was heated to 70° C. After 18 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford intermediate 113 (5.0 mg, 13%) as a white solid.

LCMS (ESI) m/z 774.31 [M+H]$^+$, t$_R$=2.43 min.

HPLC t$_R$ (min), purity %: 4.48, 99%.

R$_f$=0.56 (EtOAc).

343
Compound 131

344
Compound 132

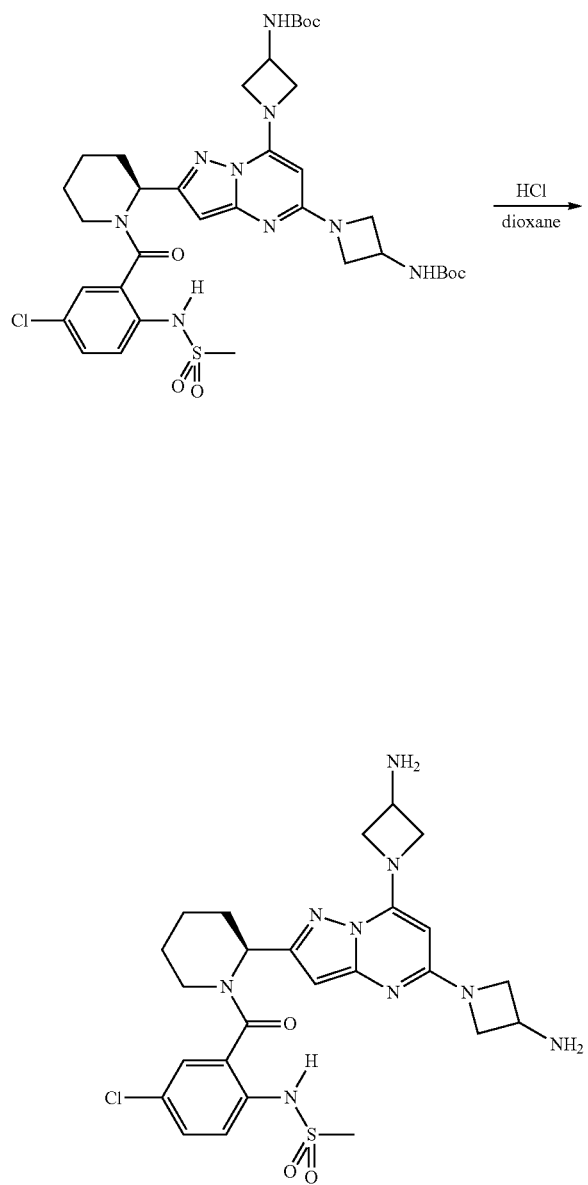

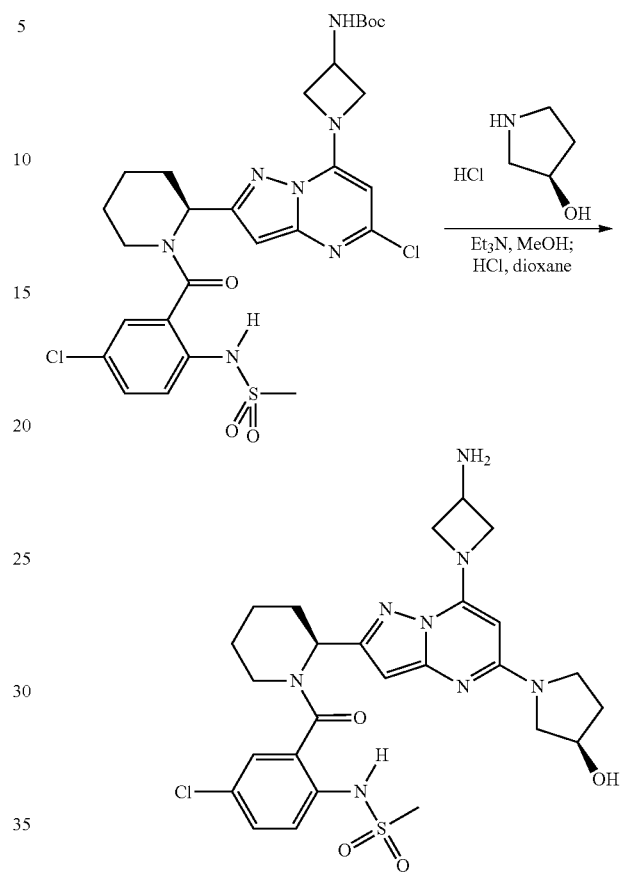

To a solution of intermediate 113 (5.0 mg, 6.5 µmol) in dioxane (0.50 mL) was added 4N HCl in dioxane solution (1.00 mL, 4 mmol) and the reaction mixture was stirred at room temperature. After 2 h, the reaction mixture was concentrated under reduced pressure to afford compound 131 (1.8 mg, 43%) as a white solid bis-hydrochloric acid salt.

$^1$H NMR (CD$_3$OD, 400 MHz): δ 7.56-7.31 (m, J=32.0 Hz, 3H), 6.25 (br s, 1H), 6.12-5.94 (m, 2H), 4.73-4.65 (m, 1H), 4.48-4.32 (m, 5H), 4.21 (dd, J=5.7, 1.9 Hz, 4H), 3.55-3.45 (m, 1H), 3.08 (s, 3H), 2.46-2.25 (m, 1H), 2.23-1.97 (m, 2H), 1.84-1.53 (m, 4H).

LCMS (ESI) m/z 574.20 [M+H]$^+$, t$_R$=1.53 min.

HPLC t$_R$ (min), purity %: 2.32, 95%.

R$_f$=0.05 (20% methanol/CH$_2$Cl$_2$).

To a solution of intermediate 111 (10.0 mg, 15.7 µmol) in MeOH (1.00 mL) was added (R)-pyrrolidin-3-ol hydrochloride (62.0 mg, 0.50 mmol) and triethylamine (139 µL, 1.00 mmol) at room temperature, and the reaction mixture was heated to 70° C. After 20 h, the reaction mixture was allowed to cool to room temperature and was concentrated under reduced pressure. 4N HCl in dioxane solution (1.00 mL, 4 mmol) was added to the crude residue and the reaction mixture was stirred at room temperature. After 20 h, the reaction mixture was concentrated under reduced pressure, and the crude residue was purified by preparatory HPLC (5-100% MeCN/H$_2$O, 0.1% trifluoroacetic acid modifier) to afford compound 132 (4.2 mg, 45%) as a white solid trifluoroacetate salt.

$^1$H NMR (CD$_3$OD, 400 MHz): δ 7.57-7.42 (m, 3H), 6.39-5.99 (m, 2H), 5.56 (s, 1H), 4.64 (s, 1H), 4.10-3.88 (m, 4H), 3.85-3.68 (m, 4H), 3.66-3.35 (m, 2H), 3.08 (s, 3H), 2.51-2.34 (m, 1H), 2.33-1.97 (m, 4H), 1.87-1.49 (m, 4H).

LCMS (ESI) m/z 589.18 [M+H]$^+$, t$_R$=1.61 min.

HPLC t$_R$ (min), purity %: 2.74, 95%.

R$_f$=0.50 (20% methanol/CH$_2$Cl$_2$).

Compound 133

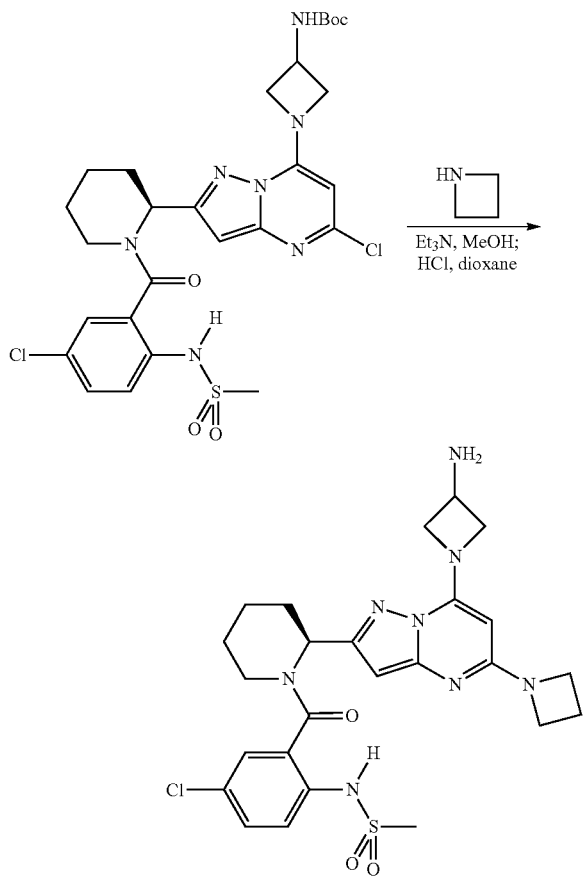

To a solution of intermediate 111 (48.0 mg, 64.0 µmol) in MeOH (1.00 mL) was added azetidine (86 µL, 1.3 mmol) and triethylamine (357 µL, 2.65 mmol) at room temperature, and the reaction mixture was heated to 70° C. After 18 h, the reaction mixture was allowed to cool to room temperature and was concentrated under reduced pressure. 4N HCl in dioxane solution (1.00 mL, 4 mmol) was added to the crude residue and the reaction mixture was stirred at room temperature. After 5 h, the reaction mixture was concentrated under reduced pressure, and the crude residue was purified by preparatory HPLC (5-100% MeCN/H$_2$O, 0.1% trifluoroacetic acid modifier) to afford compound 133 (19.2 mg, 54%) as a white solid trifluoroacetate salt.

$^1$H NMR (CD$_3$OD, 400 MHz): δ 7.61-7.31 (m, 3H), 6.38-5.98 (m, 2H), 5.71 (s, 1H), 4.80-4.50 (m, 1H), 4.08-3.80 (m, 5H), 3.72 (t, J=6.2 Hz, 2H), 3.59 (t, J=6.7 Hz, 2H), 3.50-3.30 (m, 1H), 3.08 (s, 3H), 2.43 (br d, J=12.3 Hz, 1H), 2.18 (quint, J=6.5 Hz, 2H), 2.13-2.00 (m, 2H), 1.82-1.50 (m, 4H).

LCMS (ESI) m/z 559.16 [M+H]$^+$, t$_R$=1.90 min.
HPLC t$_R$ (min), purity %: 3.07, 95%.
R$_f$=0.70 (10% methanol/CH$_2$Cl$_2$).

Compound 134

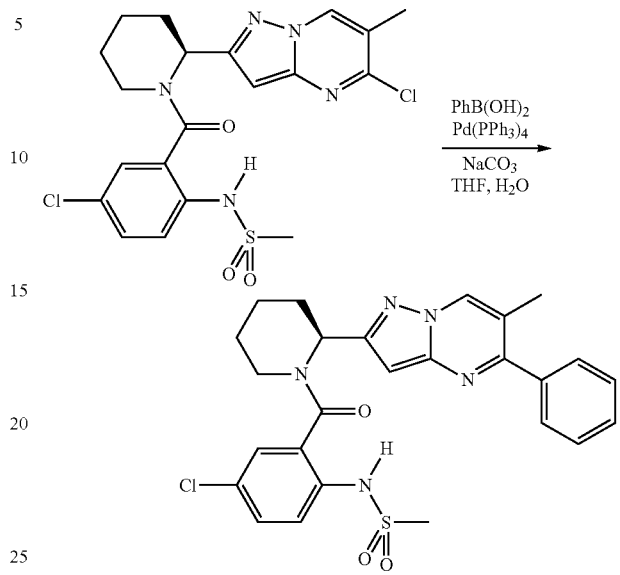

Tetrahydrofuran (620 µL) and water (62 µL) were added to intermediate 73 (30.0 mg, 62.0 µmol), phenylboronic acid (9.4 mg, 77.5 µmol), Pd(PPh$_3$)$_4$ (7.1 mg, 6.2 5 µmol), and sodium carbonate (32.9 mg, 310 µmol) at room temperature under an argon atmosphere, and the reaction mixture was heated to 60° C. After 3 h, the reaction mixture was allowed to cool to room temperature and was partitioned between ethyl acetate (10 mL) and water (10 mL). The phases were separated, and the organic layer was washed with saturated sodium chloride solution (10 mL), was dried over Na$_2$SO$_4$, and was concentrated under reduced pressure. The crude residue was purified by preparatory HPLC (5-100% MeCN/H$_2$O, 0.1% trifluoroacetic acid modifier) to afford compound 134 (13.5 mg, 42%) as a white solid.

$^1$H NMR (CDCl$_3$, 400 MHz): 9.19 (s, 1H), 9.15 (s, 1H), 7.72 (d, J=8.8 Hz, 1H), 7.63-7.52 (m, 2H), 7.53-7.45 (m, 2H), 7.41 (dd, J=8.8, 2.3 Hz, 1H), 7.36-7.30 (m, 1H), 6.32 (d, J=4.5 Hz, 1H), 4.56 (br t, J=13.8 Hz, 1H), 3.34 (d, J=12.7 Hz, 1H), 3.16 (app t, J=7.6 Hz, 1H), 2.95 (s, 3H), 2.46-2.28 (m, 1H), 2.36 (s, 3H), 2.14-1.92 (m, 1H), 1.90-1.70 (m, 2H), 1.69-1.40 (m, 2H).

LCMS (ESI) m/z 524.07 [M+H]$^+$, t$_R$=3.21 min.
HPLC t$_R$ (min), purity %: 5.75, 99%.
R$_f$=0.70 (EtOAc).

Intermediate 114

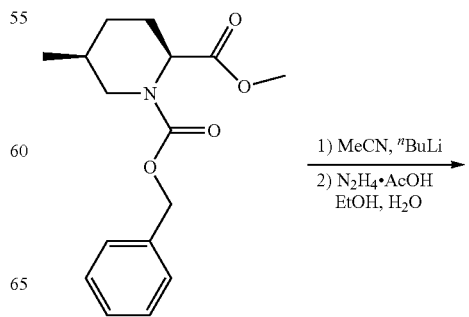

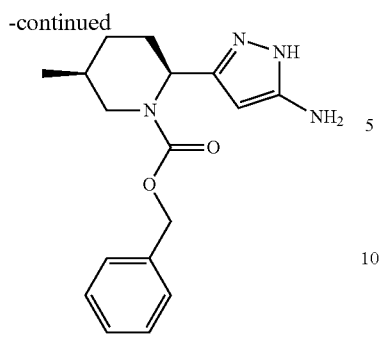

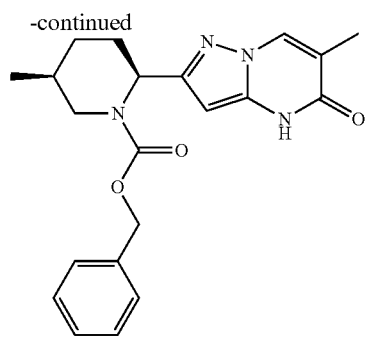

n-Butyl lithium (1.6 M in THF, 9.00 mL, 14.5 mmol) was added slowly via syringe to a solution of acetonitrile (1.41 mL, 27.0 mmol) in tetrahydrofuran (51 mL) at −78° C. under and argon atmosphere. After 30 min, a solution of (2S,5S)-1-benzyl 2-methyl 5-methylpiperidine-1,2-dicarboxylate (4.00 g, 13.7 mmol) in tetrahydrofuran (17 mL) was added slowly via cannula. After 1 h, a solution of acetic acid (2.35 mL, 41.1 mmol) in ethanol (5 mL) was added slowly and the reaction mixture was allowed to warm to room temperature. The reaction mixture was then partitioned between ethyl acetate (500 mL) and water (500 mL). The phases were separated, and the organic layer was washed with saturated sodium chloride solution (500 mL), was dried over $Na_2SO_4$, and was concentrated under reduced pressure. The residue was dissolved in ethanol (51 mL) and water (17 mL), and hydrazine acetate (1.64 g, 17.8 mmol) was added, and the resulting mixture was stirred at room temperature. After 15 h, the reaction mixture was partitioned between ethyl acetate (200 mL) and water (200 mL). The phases were separated, and the organic layer was washed with saturated sodium chloride solution (500 mL), was dried over $Na_2SO_4$, and was concentrated under reduced pressure. The crude residue was purified via $SiO_2$ column chromatography (80 g $SiO_2$ Combiflash HP Gold Column, 0-20% methanol/$CH_2Cl_2$) to afford intermediate 114 (2.95 g, 68%) as a light yellow foam.

LCMS (ESI) m/z 315.1 [M+H]$^+$, $t_R$=2.02 min.
HPLC $t_R$ (min), purity %: 3.33, 99%.

Intermediate 115

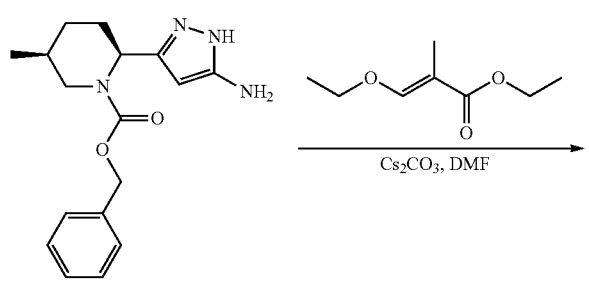

(E)-ethyl-3-ethoxy-2-methylacrylate (830 mg, 4.77 mmol) and $Cs_2CO_3$ (1.55 g, 4.77 mmol) were added to a solution of intermediate 114 (800 mg, 2.55 mmol) in DMF (15.9 mL) at room temperature and the reaction mixture was heated to 130° C. After 15 h, the reaction mixture was allowed to cool to room temperature and was concentrated under reduced pressure. The crude residue was diluted with ethyl acetate (250 mL) and was filtered. The resulting filtrate was concentrated under reduced pressure and the residue was purified via $SiO_2$ column chromatography (80 g $SiO_2$ Combiflash HP Gold Column, 0-100% ethyl acetate/hexanes) to afford intermediate 115 (230 mg, 24%) as a light yellow solid.

LCMS (ESI) m/z 381.1 [M+H]$^+$, $t_R$=2.39 min.
HPLC $t_R$ (min), purity %: 4.41, 99%.
$R_f$=0.45 (75% EtOAc/hexanes).

Intermediate 116

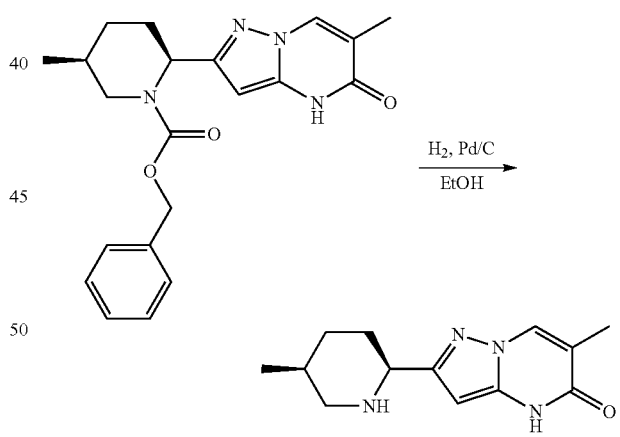

A slurry of 10% palladium on carbon (25 mg, 24.0 μmol) in ethanol (0.4 mL) was added to a solution of intermediate 115 (180 mg, 0.47 mmol) in ethanol (2.0 mL) under argon. A balloon containing hydrogen gas was applied and the reaction vessel was evacuated and refilled with a hydrogen gas atmosphere (3), and the reaction mixture was stirred vigorously at room temperature. After 7 h, the reaction mixture was filtered through celite and the filtrate was concentrated under reduced pressure to afford to afford intermediate 116 (116 mg, 99%) as a light yellow foam.

LCMS (ESI) m/z 247.15 [M+H]$^+$, $t_R$=0.28 min.

349

Intermediate 117

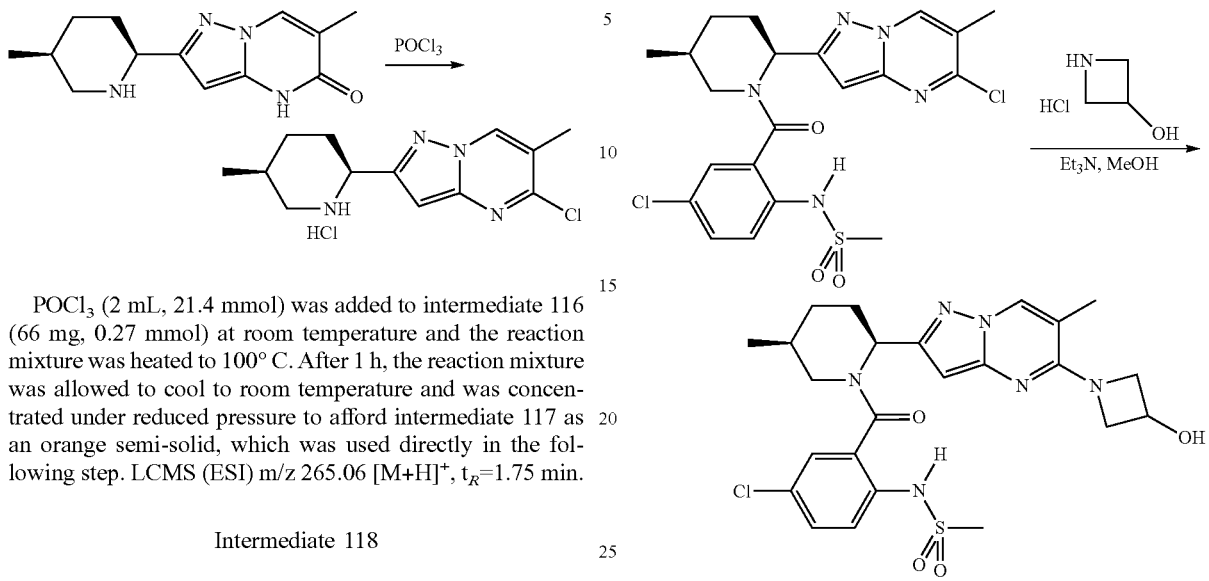

POCl$_3$ (2 mL, 21.4 mmol) was added to intermediate 116 (66 mg, 0.27 mmol) at room temperature and the reaction mixture was heated to 100° C. After 1 h, the reaction mixture was allowed to cool to room temperature and was concentrated under reduced pressure to afford intermediate 117 as an orange semi-solid, which was used directly in the following step. LCMS (ESI) m/z 265.06 [M+H]$^+$, t$_R$=1.75 min.

Intermediate 118

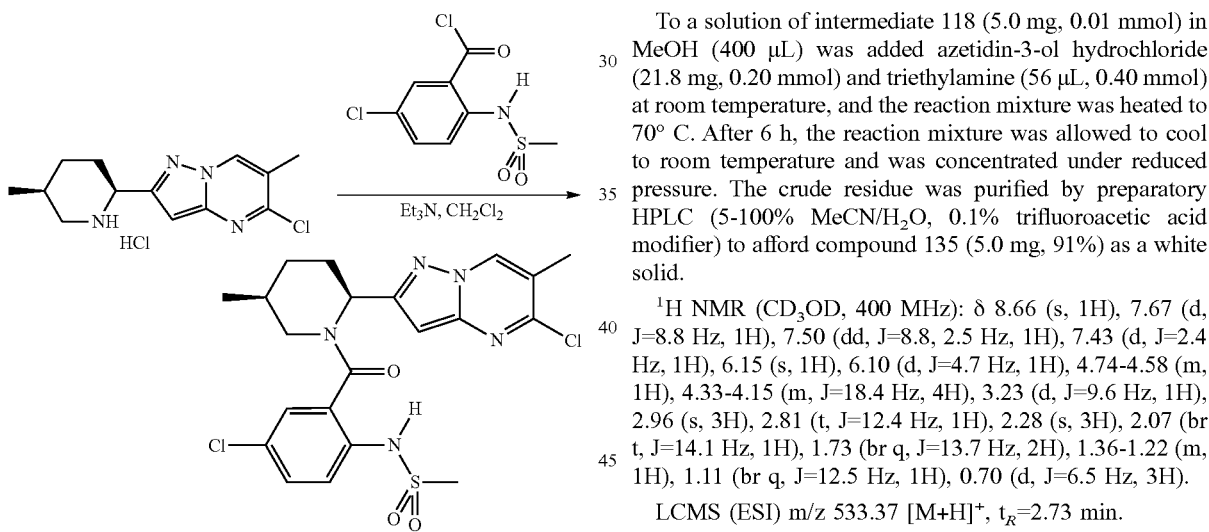

Crude intermediate 117 from the previous step was dissolved in dichloromethane (2.6 mL). Triethylamine (144 µl, 0.52 mmol) followed by (5-chloro-2-(methylsulfonamido) benzoyl chloride (138.8 mg, 0.52 mmol) were added and the reaction mixture was stirred at room temperature under and argon atmosphere. After 1 h, the reaction mixture was concentrated under reduced pressure and the residue was purified via SiO$_2$ column chromatography (12 g SiO$_2$ Combiflash HP Gold Column, 0-100% ethyl acetate/hexanes) to afford intermediate 118 (57.5 mg, 43% (2-steps)) as a white solid.

LCMS (ESI) m/z 496.27 [M+H]$^+$, t$_R$=3.20 min.
HPLC t$_R$ (min), purity %: 5.69, 90%.
R$_f$=0.55 (50% EtOAc/hexanes).

350

Compound 135

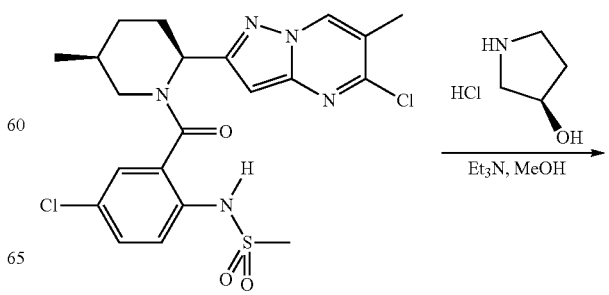

To a solution of intermediate 118 (5.0 mg, 0.01 mmol) in MeOH (400 µL) was added azetidin-3-ol hydrochloride (21.8 mg, 0.20 mmol) and triethylamine (56 µL, 0.40 mmol) at room temperature, and the reaction mixture was heated to 70° C. After 6 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 135 (5.0 mg, 91%) as a white solid.

$^1$H NMR (CD$_3$OD, 400 MHz): δ 8.66 (s, 1H), 7.67 (d, J=8.8 Hz, 1H), 7.50 (dd, J=8.8, 2.5 Hz, 1H), 7.43 (d, J=2.4 Hz, 1H), 6.15 (s, 1H), 6.10 (d, J=4.7 Hz, 1H), 4.74-4.58 (m, 1H), 4.33-4.15 (m, J=18.4 Hz, 4H), 3.23 (d, J=9.6 Hz, 1H), 2.96 (s, 3H), 2.81 (t, J=12.4 Hz, 1H), 2.28 (s, 3H), 2.07 (br t, J=14.1 Hz, 1H), 1.73 (br q, J=13.7 Hz, 2H), 1.36-1.22 (m, 1H), 1.11 (br q, J=12.5 Hz, 1H), 0.70 (d, J=6.5 Hz, 3H).

LCMS (ESI) m/z 533.37 [M+H]$^+$, t$_R$=2.73 min.
HPLC t$_R$ (min), purity %: 4.04, 99%.
R$_f$=0.45 (EtOAc).

Compound 136

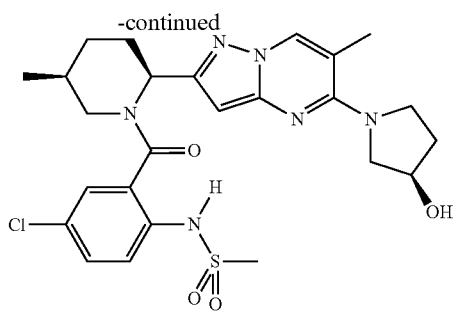

To a solution of intermediate 118 (10.0 mg, 0.02 mmol) in MeOH (400 µL) was added (R)-pyrrolidin-3-ol hydrochloride (44.0 mg, 0.40 mmol) and triethylamine (112 µL, 0.80 mmol) at room temperature, and the reaction mixture was heated to 70° C. After 6 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 136 (8.5 mg, 89%) as a white solid.

$^1$H NMR (CD$_3$OD, 400 MHz): δ 8.75 (s, 1H), 7.67 (d, J=8.1 Hz, 1H), 7.50 (dd, J=8.5, 2.0 Hz, 1H), 7.44 (d, J=2.1 Hz, 1H), 6.15, (s, 1H), 6.12 (d, J=5.0 Hz, 1H), 4.57 (br s, 1H), 4.11-3.91 (m, 3H), 3.81 (d, J=11.7 Hz, 1H), 3.23 (br d, J=14.4 Hz, 1H), 2.97 (s, 3H), 2.81 (t, J=12.2 Hz, 1H), 2.49 (s, 3H), 2.41 (d, J=13.7 Hz, 1H), 2.19-1.99 (m, 2H), 1.83-1.62 (m, 2H), 1.38-1.19 (m, 1H), 1.11 (br q, J=13.4 Hz, 1H), 0.71 (d, J=6.4 Hz, 3H).

LCMS (ESI) m/z 547.45 [M+H]$^+$, t$_R$=2.80 min.
HPLC t$_R$ (min), purity %: 4.06, 99%.
R$_f$=0.50 (EtOAc).

Compound 137

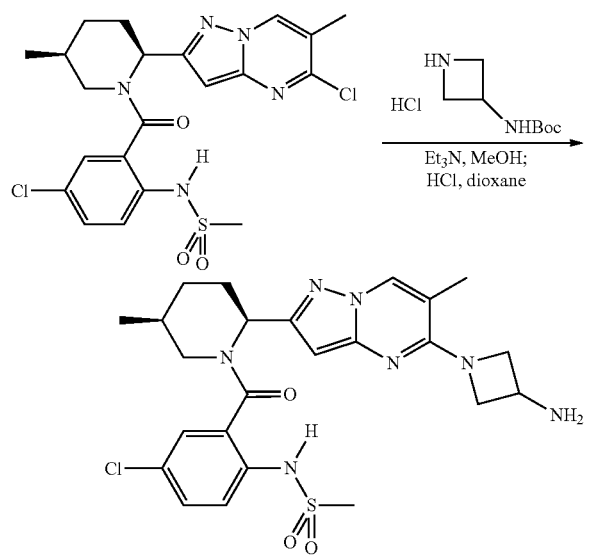

To a solution of intermediate 118 (10.0 mg, 0.02 mmol) in MeOH (400 µL) was added tert-butyl azetidin-3-ylcarbamate hydrochloride (20.3 mg, 0.10 mmol) and triethylamine (28.0 µL, 0.20 mmol) at room temperature, and the reaction mixture was heated to 70° C. After 2 h, the reaction mixture was allowed to cool to room temperature and was concentrated under reduced pressure. 4N HCl in dioxane solution (1.00 mL, 4 mmol) was added to the crude residue and the reaction mixture was stirred at room temperature. After 6 h, the reaction mixture was concentrated under reduced pressure, and the crude residue was purified by preparatory HPLC (5-100% MeCN/H$_2$O, 0.1% trifluoroacetic acid modifier) to afford compound 137 (8.9 mg, 68%) as a white solid trifluoroacetate salt.

$^1$H NMR (CD$_3$OD, 400 MHz): δ 8.77 (br s, 1H), 7.66 (d, J=8.4 Hz, 1H), 7.50 (dd, J=8.8, 2.4 Hz, 1H), 7.44 (d, J=2.4 Hz, 1H), 6.30 (s, 1H), 6.12 (d, J=4.2 Hz, 1H), 5.06-4.89 (m, 2H), 4.71 (br d, J=8.5 Hz, 2H), 4.38-4.27 (m, 1H), 3.28-3.23 (m, 1H), 2.98 (s, 3H), 2.81 (t, J=12.5 Hz, 1H), 2.33 (s, 3H), 2.14-2.01 (m, 1H), 1.82-1.63 (m, 2H), 1.38-1.28 (m, 1H), 1.10 (br q, J=13.3 Hz, 1H), 0.71 (d, J=6.3 Hz, 3H).

LCMS (ESI) m/z 532.43 [M+H]$^+$, t$_R$=1.95 min.
HPLC t$_R$ (min), purity %: 3.61, 99%.

Compound 138

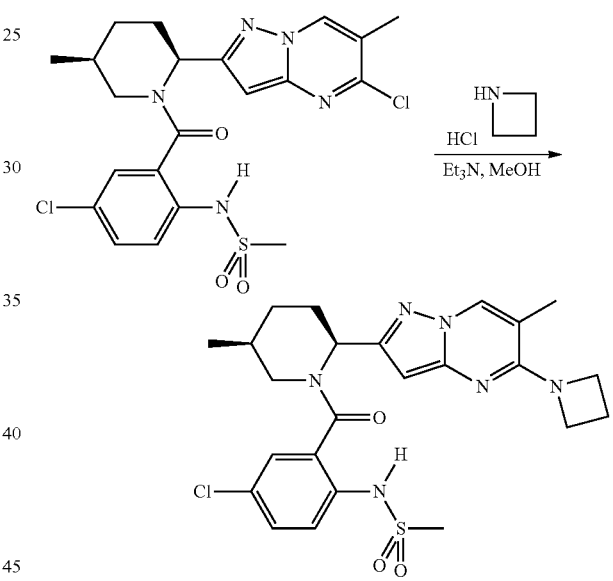

To a solution of intermediate 118 (10.0 mg, 0.02 mmol) in MeOH (400 µL) was added azetidine hydrochloride (37.0 mg, 0.40 mmol) and triethylamine (80.9 µL, 0.80 mmol) at room temperature, and the reaction mixture was heated to 70° C. After 3 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 138 (8.6 mg, 83%) as a white solid.

$^1$H NMR (CDCl$_3$, 400 MHz): δ 8.57 (s, 1H), 7.62 (d, J=8.8 Hz, 1H), 7.32 (dd, J=8.8, 2.5 Hz, 1H), 7.23 (d, J=2.5 Hz, 1H), 6.10 (d, J=4.4 Hz, 1H), 5.90 (s, 1H), 4.39-4.18 (m, 4H), 3.03 (d, J=12.8 Hz, 1H), 2.84 (s, 3H), 2.66 (t, J=12.4 Hz, 1H), 2.32 (quint, J=6.8 Hz, 2H), 2.15 (s, 3H), 1.99-1.81 (m, 1H), 1.74-1.44 (m, 2H), 1.28-0.98 (m, 2H), 0.61 (d, J=6.5 Hz, 3H)

LCMS (ESI) m/z 517.39 [M+H]$^+$, t$_R$=3.13 min.
HPLC t$_R$ (min), purity %: 4.49, 99%.
R$_f$=0.55 (EtOAc).

Compound 139

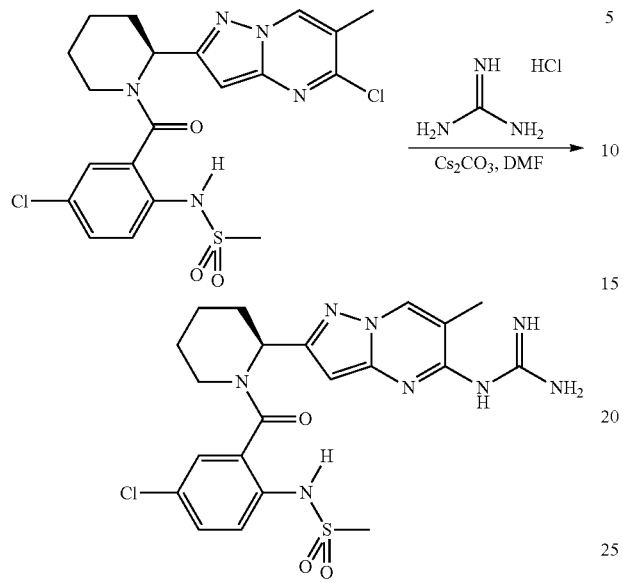

To a solution of intermediate 73 (30.0 mg, 0.06 mmol) in DMF (620 µL) was added guanidine hydrochloride (59.0 mg, 0.62 mmol) and Cs$_2$CO$_3$ (404 mg, 1.24 mmol) at room temperature, and the reaction mixture was heated to 70° C. After 8 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 139 (6.8 mg, 18%) as a white solid trifluoroacetic acid salt.

$^1$H NMR (CD$_3$OD, 400 MHz): δ 9.05 (s, 1H), 7.68 (d, J=8.4 Hz, 1H), 7.49 (d, J=8.8 Hz, 1H), 7.46 (s, 1H), 6.55 (s, 1H), 6.20 (d, J=2.6 Hz, 1H), 3.42-3.32 (m, 1H), 3.26-3.14 (m, 1H), 2.98 (s, 3H), 2.47 (d, J=13.6 Hz, 1H), 2.35 (s, 3H), 2.15-2.03 (m, 1H), 1.87-1.38 (m, 4H).

LCMS (ESI) m/z 505.33 [M+H]$^+$, t$_R$=1.97 min.
HPLC t$_R$ (min), purity %: 3.68, 99%.
R$_f$=0.62 (20% methanol/CH$_2$Cl$_2$).

Compound 140

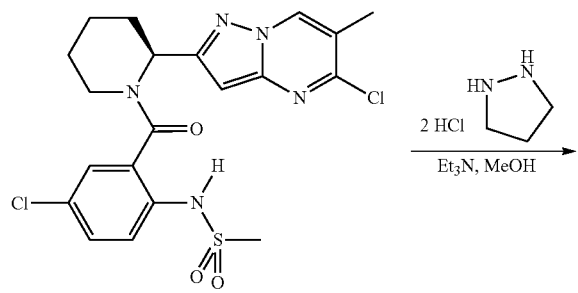

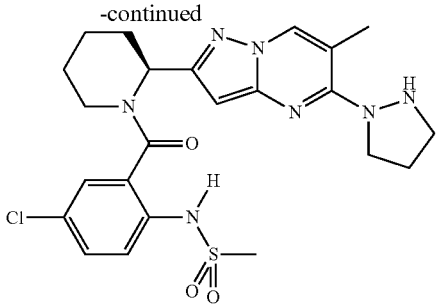

To a solution of intermediate 73 (50.0 mg, 0.10 mmol) in MeOH (1.00 mL) was added pyrazolidine dihydrochloride (150 mg, 1.04 mmol) and triethylamine (287 µL, 2.06 mmol) at room temperature, and the reaction mixture was heated to 70° C. After 1 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 140 (56.8 mg, 87%) as a white solid trifluoroacetic acid salt.

$^1$H NMR (CD$_3$OD, 400 MHz): δ 8.96 (s, 1H), 7.65 (d, J=5.0 Hz, 1H), 7.50 (d, J=5.0 Hz, 1H), 7.45 (s, 1H), 6.44 (br s, 1H), 6.17 (br s, 1H), 3.91 (t, J=4.5 Hz, 2H), 3.32 (t, J=4.2 Hz, 2H), 3.25-3.18 (m, 1H), 3.08-2.95 (m, 1H), 2.97 (s, 3H), 2.50-2.39 (m, 3H), 2.42 (s, 3H), 2.18-2.00 (m, 2H), 1.73 (d, J=7.7 Hz, 1H), 1.70-1.35 (m, 2H).

LCMS (ESI) m/z 518.38 [M+H]$^+$, t$_R$=2.64 min.
HPLC t$_R$ (min), purity %: 3.52, 97%.
R$_f$=0.60 (EtOAc).

Compound 141

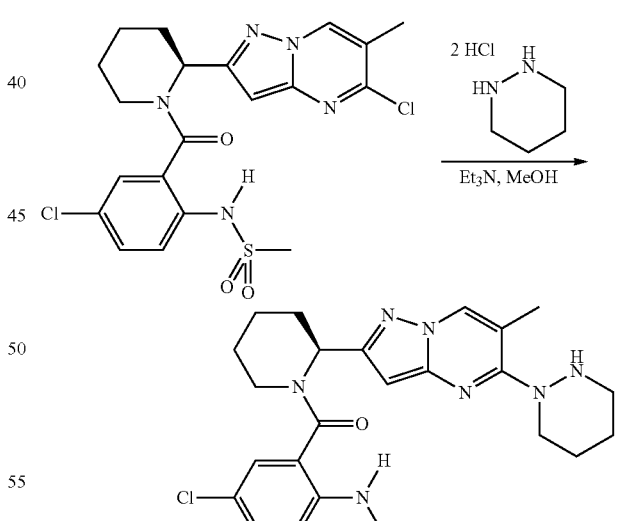

To a solution of intermediate 73 (50.0 mg, 0.10 mmol) in MeOH (1.00 mL) was added pyrazolidine dihydrochloride (164 mg, 1.03 mmol) and triethylamine (287 µL, 2.06 mmol) at room temperature, and the reaction mixture was heated to 70° C. After 1 h, the reaction mixture was allowed to cool to room temperature and was concentrated under reduced pressure. The crude residue was purified by preparatory HPLC (5-100% MeCN/H₂O, 0.1% trifluoroacetic acid modifier) to afford compound 141 (51.8 mg, 78%) as a white solid trifluoroacetic acid salt.

$^1$H NMR (CD₃OD, 400 MHz): δ 8.94 (s, 1H), 7.58 (d, J=4.7 Hz, 1H), 7.40 (d, J=4.7 Hz, 1H), 7.36 (s, 1H), 6.44 (br s, 1H), 6.10 (br s, 1H), 3.45-3.30 (m, 4H), 3.20-3.00 (m, 1H), 2.95-2.85 (m, 1H), 2.88 (s, 3H), 2.37 (d, J=8.5 Hz, 1H), 2.25 (s, 3H), 2.10-1.80 (m, 6H), 1.65 (d, J=7.7 Hz, 1H), 1.60-1.20 (m, 2H).

LCMS (ESI) m/z 532.38 [M+H]⁺, $t_R$=3.14 min.

HPLC $t_R$ (min), purity %: 3.74, 99%.

$R_f$=0.65 (EtOAc).

Intermediate 119

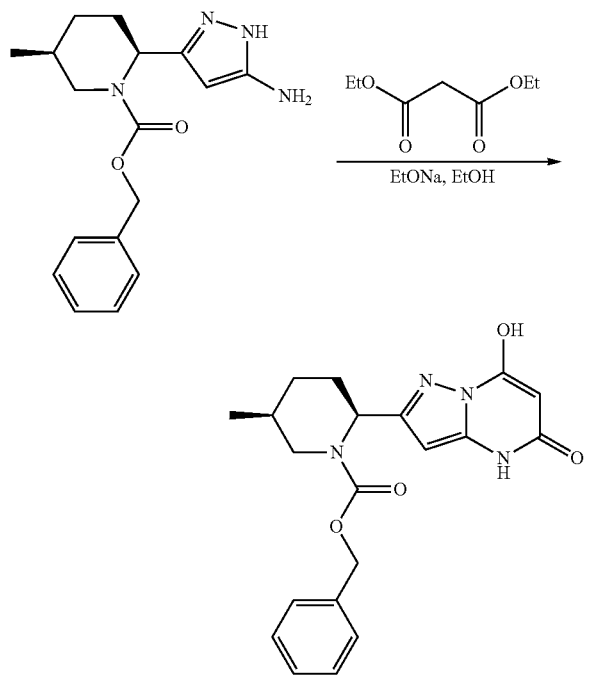

Diethyl malonate (729 μL, 6.36 mmol) and sodium ethoxide (432 mg, 6.36 mmol) were added to a solution of intermediate 114 (800 mg, 2.55 mmol) in ethanol (15.9 mL) at room temperature under an argon atmosphere, and the reaction mixture was heated to 70° C. After 7 h, the reaction mixture was allowed to cool to room temperature and was acidified to pH=3 with 1N aqueous hydrochloride acid solution. The resulting mixture was then partitioned between ethyl acetate (200 mL) and water (200 mL). The phases were separated, and the organic layer was washed with saturated sodium chloride solution (1500 mL), was dried over Na₂SO₄, and was concentrated under reduced pressure. The resulting filtrate was concentrated under reduced pressure and the residue was purified via SiO₂ column chromatography (40 g SiO₂ Combiflash HP Gold Column, 0-100% ethyl acetate/hexanes) to afford intermediate 119 (618 mg, 63%) as a light yellow solid.

LCMS (ESI) m/z 383.1 [M+H]⁺, $t_R$=2.40 min.

HPLC $t_R$ (min), purity %: 3.87, 99%.

Intermediate 120

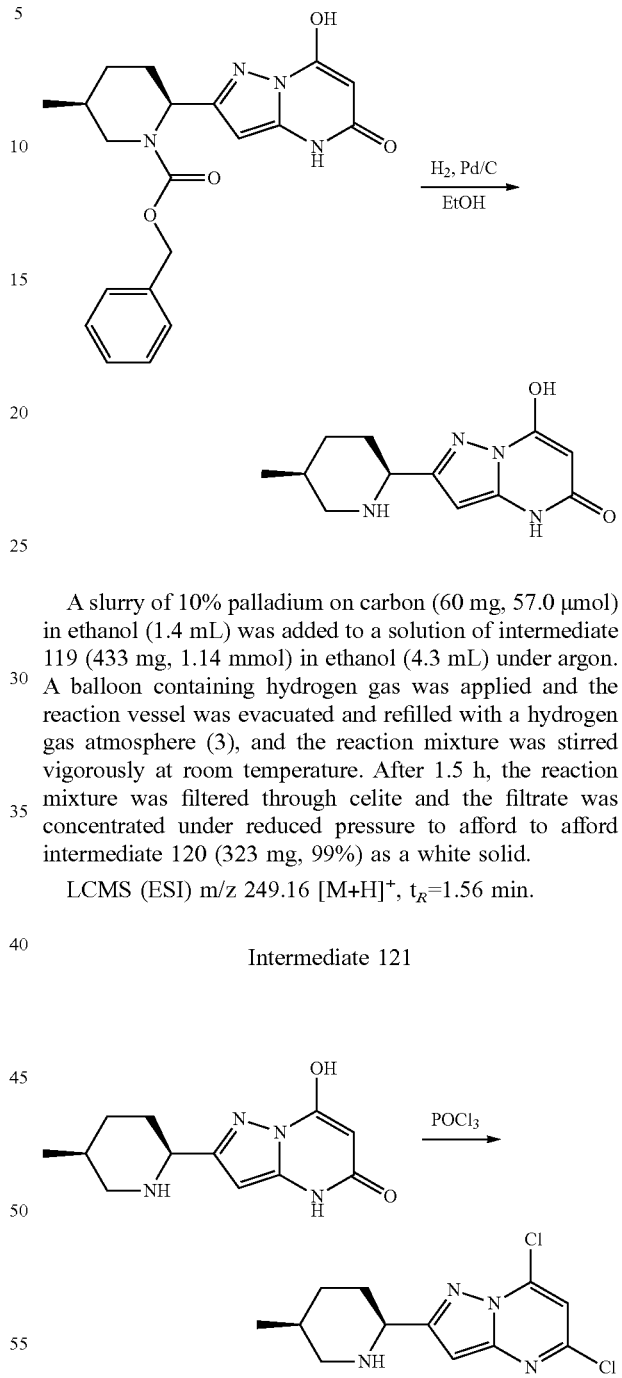

A slurry of 10% palladium on carbon (60 mg, 57.0 μmol) in ethanol (1.4 mL) was added to a solution of intermediate 119 (433 mg, 1.14 mmol) in ethanol (4.3 mL) under argon. A balloon containing hydrogen gas was applied and the reaction vessel was evacuated and refilled with a hydrogen gas atmosphere (3), and the reaction mixture was stirred vigorously at room temperature. After 1.5 h, the reaction mixture was filtered through celite and the filtrate was concentrated under reduced pressure to afford to afford intermediate 120 (323 mg, 99%) as a white solid.

LCMS (ESI) m/z 249.16 [M+H]⁺, $t_R$=1.56 min.

Intermediate 121

POCl₃ (2 mL, 10.7 mmol) was added to intermediate 120 (62.5 mg, 0.22 mmol) at room temperature and the reaction mixture was heated to 100° C. After 5 h, the reaction mixture was allowed to cool to room temperature and was concentrated under reduced pressure to afford intermediate 121 as an orange semi-solid, which was used directly in the following step.

LCMS (ESI) m/z 285.06 [M+H]⁺, $t_R$=1.75 min.

Intermediate 122

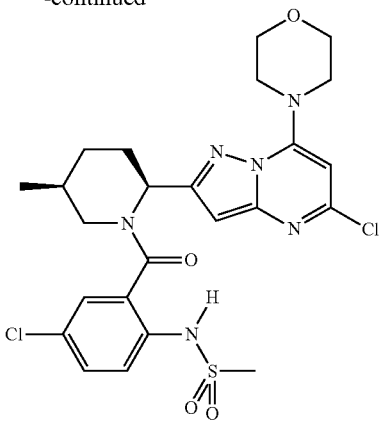

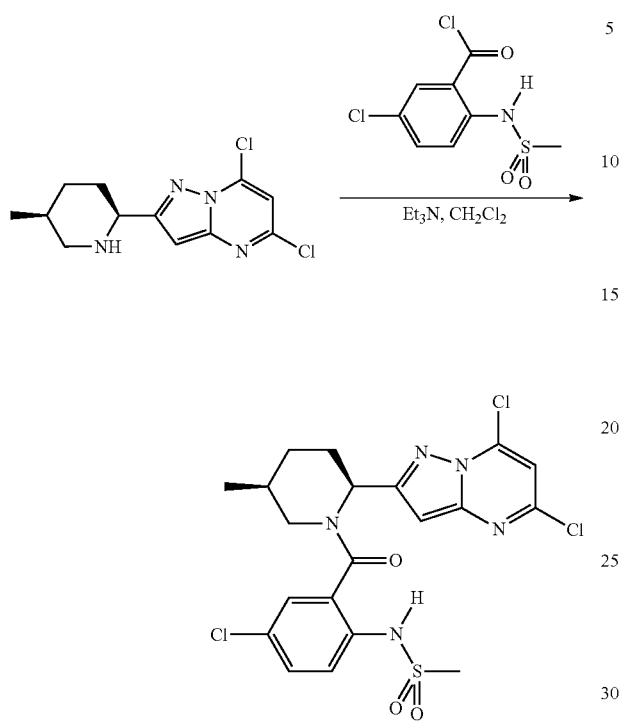

Crude intermediate 121 from the previous step was dissolved in dichloromethane (1 mL). Triethylamine (91 μl, 0.65 mmol) followed by (5-chloro-2-(methylsulfonamido) benzoyl chloride (58.0 mg, 0.22 mmol) were added and the reaction mixture was stirred at room temperature under and argon atmosphere. After 1 h, the reaction mixture was concentrated under reduced pressure was concentrated under reduced pressure to afford intermediate 122 as an orange semi-solid, which was used directly in the following step.

LCMS (ESI) m/z 516.23 [M+H]$^+$, t$_R$=3.06 min.

Intermediate 123

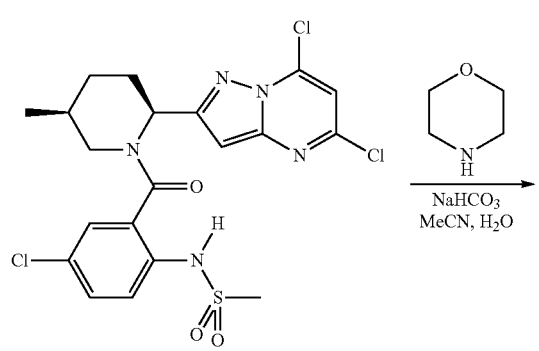

Crude intermediate 122 from the previous step was dissolved acetonitrile (0.5 mL) and water (0.5 mL). Morpholine (19 μL, 0.22 mmol) and sodium bicarbonate (36.5 mg, 0.43 mmol) were added and the reaction mixture was stirred at room temperature. After 1 h, the reaction mixture was partitioned between dichloromethane (20 mL) and water (20 mL), and the layers were separated. The organic layer was washed with saturated aqueous sodium bicarbonate solution (20 mL) and saturated sodium chloride solution (50 mL), was dried over Na$_2$SO$_4$, and was concentrated under reduced pressure. The crude residue was purified via SiO$_2$ column chromatography (12 g SiO$_2$ Combiflash HP Gold Column, 0-100% ethyl acetate/hexanes) to afford intermediate 123 (68.1 mg, 55% (3-steps) as a light orange solid.

LCMS (ESI) m/z 567.32 [M+H]$^+$, t$_R$=2.92 min.

Compound 142

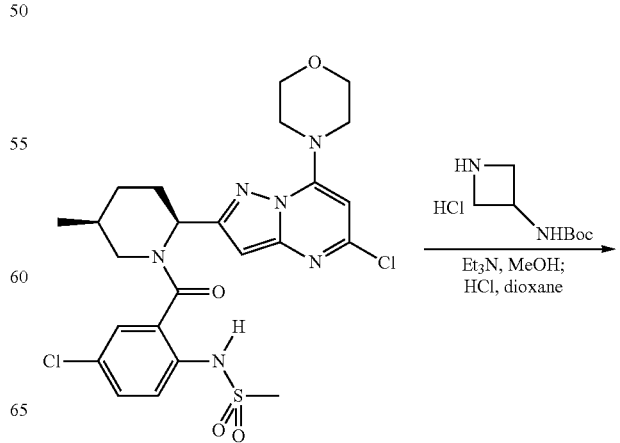

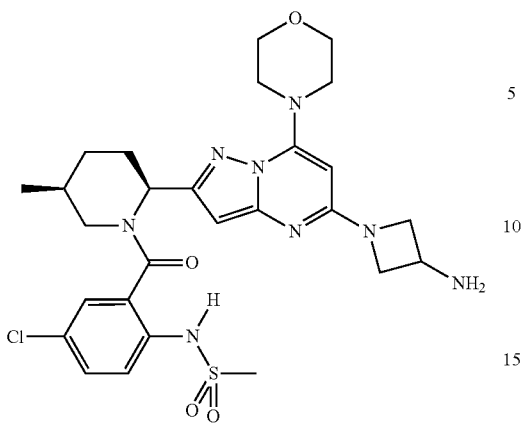

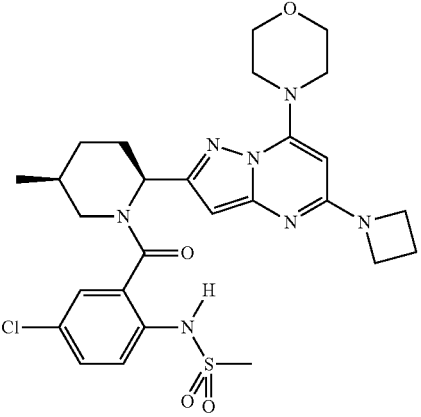

To a solution of intermediate 123 (20.0 mg, 35.0 µmol) in MeOH (700 µL) was added tert-butyl azetidin-3-ylcarbamate hydrochloride (73.7 mg, 0.35 mmol) and triethylamine (98.0 µL, 0.70 mmol) at room temperature, and the reaction mixture was heated to 70° C. After 2 h, the reaction mixture was allowed to cool to room temperature and was concentrated under reduced pressure. The residue was purified by preparatory HPLC (5-100% MeCN/H$_2$O, 0.1% trifluoroacetic acid modifier). 4N HCl in dioxane solution (1.00 mL, 4 mmol) was added and the reaction mixture was stirred at room temperature. After 4.5 h, the reaction mixture was concentrated under reduced pressure to afford compound 142 (9.5 mg, 43%) as a white solid hydrochloric acid salt.

$^1$H NMR (CD$_3$OD, 400 MHz): δ 7.58-7.33 (m, 3H), 6.30 (br s, 1H), 6.03 (d, J=4.8 Hz, 1H), 5.41 (br s, 1H), 4.55-4.32 (m, 5H), 4.11-3.85 (m, 8H), 3.04 (s, 3H), 2.84 (t, J=12.2 Hz, 1H), 2.41 (d, J=13.5 Hz, 1H), 2.22 (br s, 1H), 2.09 (t, J=12.5 Hz, 1H), 1.75 (d, J=11.6 Hz, 1H), 1.46-1.07 (m, 2H), 0.76 (d, J=6.3 Hz, 3H).

LCMS (ESI) m/z 603.40 [M+H]$^+$, t$_R$=1.89 min.
HPLC t$_R$ (min), purity %: 3.05, 93%.
R$_f$=0.50 (10% methanol/CH$_2$Cl$_2$).

To a solution of intermediate 123 (10.0 mg, 18 µmol) in MeOH (360 µL) was added azetidine hydrochloride (16.8 mg, 0.18 mmol) and triethylamine (50.0 µL, 0.36 mmol) at room temperature, and the reaction mixture was heated to 70° C. After 3 h, the reaction mixture was allowed to cool to room temperature and was concentrated under reduced pressure. The residue was purified by preparatory HPLC (5-100% MeCN/H$_2$O, 0.1% trifluoroacetic acid modifier) to afford compound 143 (5.1 mg, 40%) as a white solid trifluoroacetate salt.

$^1$H NMR (CD$_3$OD, 400 MHz): δ 7.58-7.31 (m, 3H), 6.22 (br s, 1H), 6.03 (br s, 1H), 5.26 (s, 1H), 4.37 (t, J=7.4 Hz, 1H), 4.02-3.80 (m, 8H), 3.04 (s, 3H), 2.85 (t, J=12.7 Hz, 1H), 2.56 (quint, J=7.7 Hz, 2H), 2.40 (d, J=14.2 Hz, 1H), 2.27-2.16 (m, 1H), 2.09 (br t, J=13.7 Hz, 1H), 1.75 (d, J=13.3 Hz, 1H), 1.38-1.23 (m, 1H), 1.22-1.09 (m, 1H), 036 (d, J=6.5 Hz, 1H).

LCMS (ESI) m/z 588.43 [M+H]$^+$, t$_R$=2.14 min.
HPLC t$_R$ (min), purity %: 3.67, 99%.
R$_f$=0.50 (EtOAc).

Compound 144

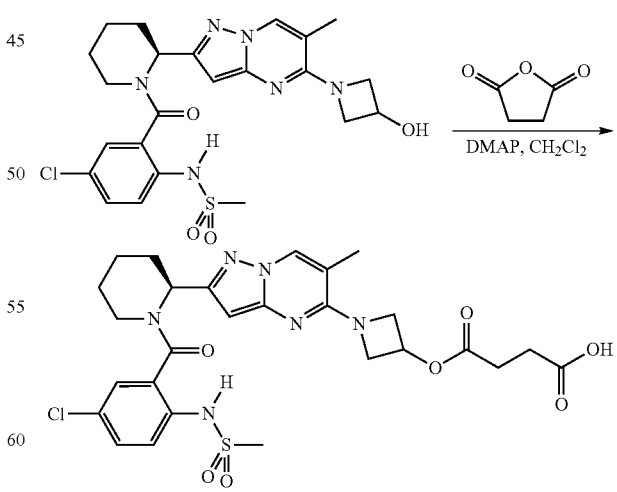

Compound 143

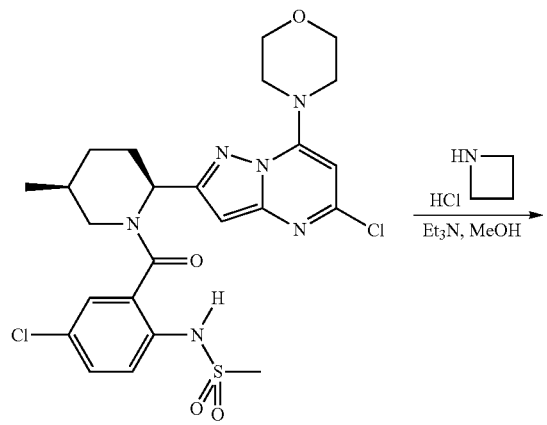

To a solution of compound 92 (50.0 mg, 0.10 mmol) in dichloromethane (500 µL) was added dihydrofuran-2,5-dione (10 mg, 0.10 mmol) and DMAP (1.2 mg, 0.01 mmol) at room temperature under an argon atmosphere. After 20 min, the reaction mixture was concentrated under reduced pressure. The residue was purified by preparatory HPLC (5-100% MeCN/H$_2$O, 0.1% trifluoroacetic acid modifier) to afford compound 144 (35.6 mg, 57%) as a white solid.

$^1$H NMR (CD$_3$OD, 400 MHz): δ 8.64 (s, 1H), 7.66 (d, J=8.8 Hz, 1H), 7.48 (d, J=8.8 Hz, 1H), 7.43 (s, 1H), 6.10 (br s, 2H), 5.31 (s, 1H), 4.76-1.59 (m, 2H), 4.34 (d, J=10.1 Hz, 2H), 3.27-3.04 (m, 1H), 3.00 (br s, 1H), 2.95 (s, 3H), 2.72-2.56 (m, 4H), 2.39 (d, J=14.1 Hz, 1H), 2.23 (s, 3H), 2.08-1.95 (m, 1H), 1.84-1.58 (m, 2H), 1.58-1.39 (m, 2H).

LCMS (ESI) m/z 619.37 [M+H]$^+$, t$_R$=2.77 min.
HPLC t$_R$ (min), purity %: 4.28, 99%.
R$_f$=0.50 (10% methanol/CH$_2$Cl$_2$).

Intermediate 124

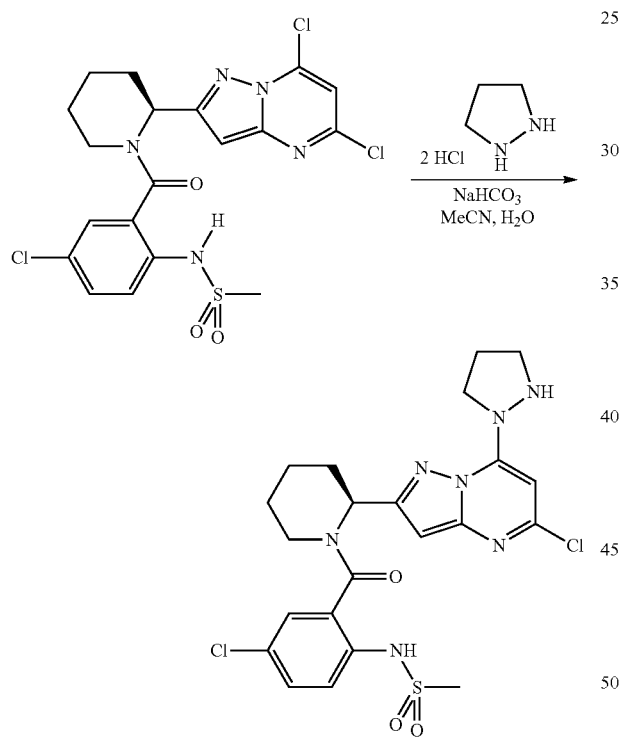

Pyrazolidine dihydro chloride (14.5 mg, 0.10 mmol) and sodium bicarbonate (16.8 mg, 0.20 mmol) were added to a solution of intermediate 56 (50 mg, 0.10 mmol) in acetonitrile (0.50 mL) and water (0.50 mL) and the reaction mixture was stirred at room temperature. After 3 h, the reaction mixture was purified by preparatory HPLC (5-100% MeCN/H$_2$O, 0.1% trifluoroacetic acid modifier) to afford intermediate 124 (37.4 mg, 57%) as a white solid trifluoroacetate salt.

LCMS (ESI) m/z 538.31 [M+H]$^+$, t$_R$=2.90 min.
HPLC t$_R$ (min), purity %: 4.74, 99%.
R$_f$=0.65 (EtOAc).

Compound 145

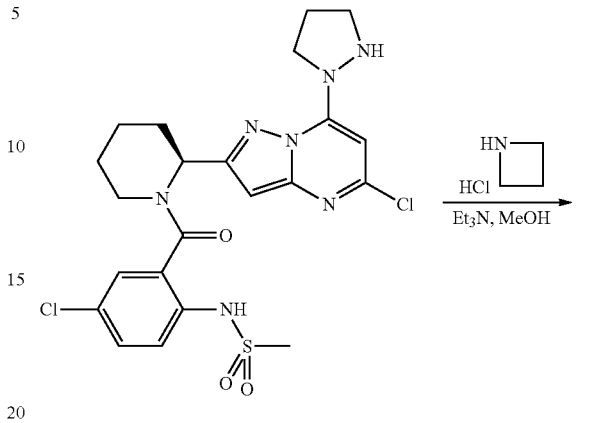

To a solution of intermediate 124 (37.0 mg, 0.07 mmol) in MeOH (1.4 mL) was added azetidine hydrochloride (64.0 mg, 0.70 mmol) and triethylamine (192 µL, 1.40 mmol) at room temperature, and the reaction mixture was heated to 70° C. After 14 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 145 (6.3 mg, 14%) as a white solid trifluoroacetate salt.

$^1$H NMR (CD$_3$OD, 400 MHz): δ 7.48 (br s, 2H), 7.37 (br s, 1H), 6.15 (br s, 1H), 6.02 (br s, 1H), 5.61 (s, 1H), 4.47-4.18 (m, 8H), 3.56-3.42 (m, 1H), 3.20 (t, J=14.1 Hz, 1H), 3.06 (s, 3H), 2.54 (quint, J=7.7 Hz, 2H), 2.46-2.32 (m, 1H), 2.24 (quint, J=6.8 Hz, 2H), 2.18-1.99 (m, 1H), 1.85-1.47 (m, 4H).

LCMS (ESI) m/z 559.42 [M+H]$^+$, t$_R$=2.06 min.
HPLC t$_R$ (min), purity %: 3.57, 99%.
R$_f$=0.60 (10% methanol/CH$_2$Cl$_2$).

Compound 146

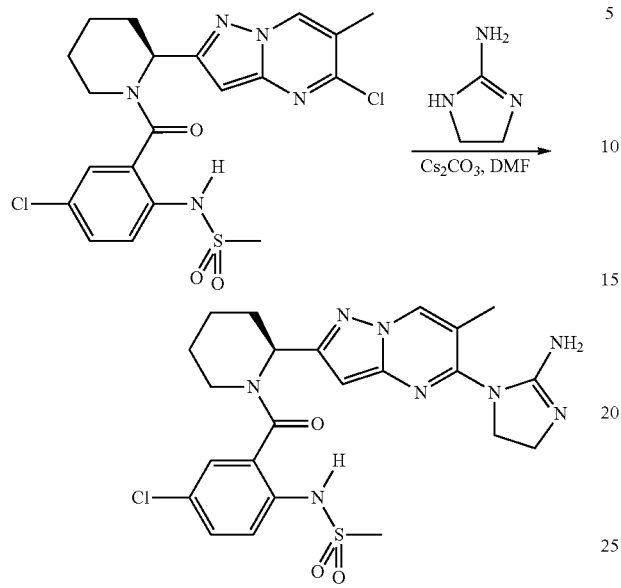

To a solution of intermediate 73 (50 mg, 0.10 mmol) in DMF (1.00 mL) was added 4,5-dihydro-1H-imidazol-2-amine (88 mg, 1.04 mmol) and $Cs_2CO_3$ (677 mg, 2.08 mmol) at room temperature, and the reaction mixture was heated to 70° C. After 4 h, the reaction mixture was allowed to cool to room temperature and was purified by preparatory HPLC (5-100% MeCN/$H_2O$, 0.1% trifluoroacetic acid modifier) to afford compound 146 (10.7 mg, 16%) as a white solid trifluoroacetic acid salt.

$^1$H NMR (CD$_3$OD, 400 MHz): δ 9.25 (br s, 1H), 7.68 (d, J=8.1 Hz, 1H), 7.50 (d, J=9.0 Hz, 1H), 7.48 (s, 1H), 6.71 (s, 1H), 6.24 (br s, 1H), 4.23 (t, J=8.5 Hz, 2H), 3.88 (t, J=8.4 Hz, 2H), 3.39 (d, J=12.8 Hz, 1H), 3.24-3.11 (m, 1H), 2.99 (s, 3H), 2.51 (d, J=14.3 Hz, 1H), 2.40 (s, 3H), 2.19-2.01 (m, 2H), 1.87-1.34 (m, 4H).

LCMS (ESI) m/z 531.40 [M+H]$^+$, $t_R$=1.90 min.

HPLC $t_R$ (min), purity %: 3.47, 91%.

Intermediate 125

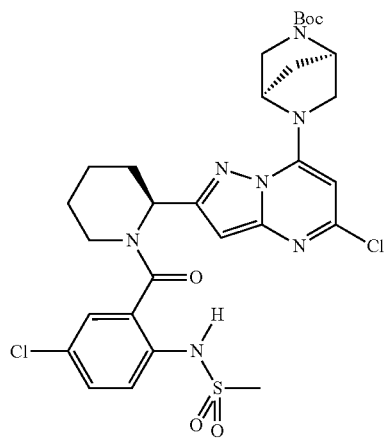

(1R,4R)-tert-butyl-2,5-diazabicyclo[2.2.1]heptane-2-carboxylate (50 mg, 0.10 mmol) and sodium bicarbonate (16.8 mg, 0.20 mmol) were added to a solution of intermediate 56 (50 mg, 0.10 mmol) in acetonitrile (0.50 mL) and water (0.50 mL) and the reaction mixture was stirred at room temperature. After 3.5 h, the reaction mixture was purified by preparatory HPLC (5-100% MeCN/$H_2O$, 0.1% trifluoroacetic acid modifier) to afford intermediate 125 (43.1 mg, 65%) as a white solid trifluoroacetate salt.

LCMS (ESI) m/z 664.37 [M+H]$^+$, $t_R$=3.05 min.

HPLC $t_R$ (min), purity %: 5.30, 99%.

Compound 147

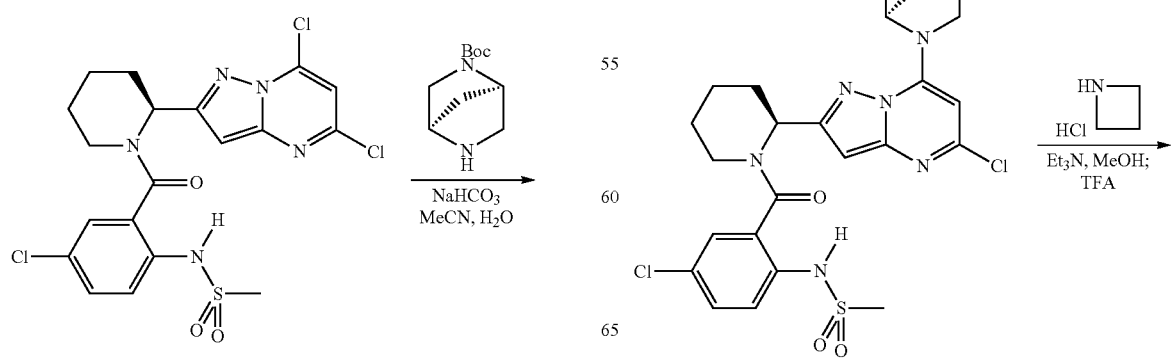

-continued

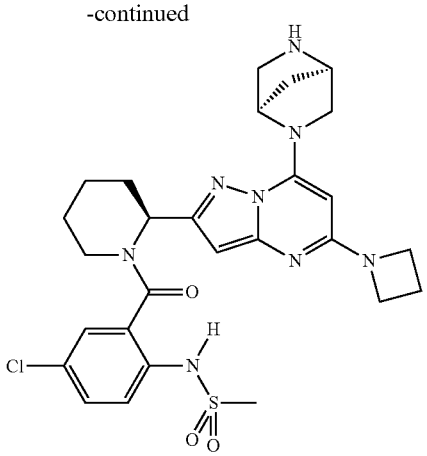

To a solution of intermediate 125 (43.1 mg, 65.0 µmol) in MeOH (1.00 mL) was added azetidine hydrochloride (60.0 mg, 0.65 mmol) and triethylamine (181 µL, 1.30 mmol) at room temperature, and the reaction mixture was heated to 70° C. After 11 h, the reaction mixture was allowed to cool to room temperature and was purified by preparatory HPLC (5-100% MeCN/H$_2$O, 0.1% trifluoroacetic acid modifier). Trifluoroacetic acid (1 mL) was added at room temperature. After 45 min, the resulting mixture was concentrated to afford compound 147 (18.6 mg, 41%) as a white solid trifluoroacetate salt.

$^1$H NMR (CD$_3$OD, 400 MHz): δ 7.48 (br s, 2H), 7.38 (br s, 1H), 6.21 (br s, 1H), 6.00 (br s, 2H), 5.03 (s, 1H), 4.64 (s, 1H), 4.34 (t, J=7.7 Hz, 4H), 4.27-4.00 (m, 2H), 3.69 (d, J=11.2 Hz, 1H), 3.50 (d, J=11.3 Hz, 2H), 3.08 (s, 3H), 2.61-2.51 (m, 2H), 2.40 (d, J=11.7 Hz, 2H), 2.21 (d, J=11.4 Hz, 2H), 2.16-1.98 (m, 1H), 1.84-1.52 (m, 4H).

LCMS (ESI) m/z 585.46 [M+H]$^+$, t$_R$=1.66 min.
HPLC t$_R$ (min), purity %: 2.59, 96%.

Compound 148

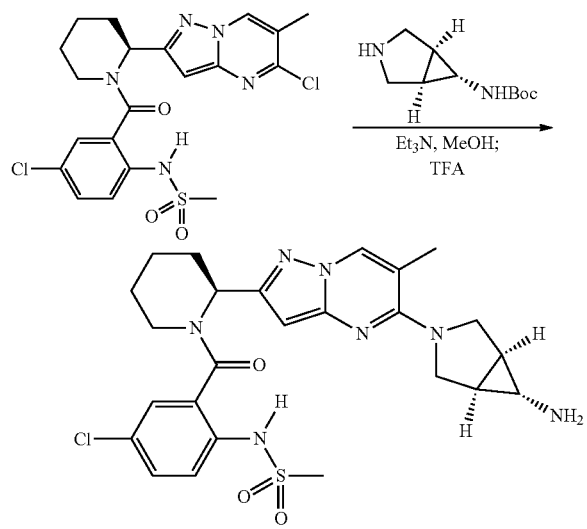

To a solution of intermediate 73 (24.3 mg, 50.0 µmol) in MeOH (250 µL) was added tert-butyl-(1R,5S,6S)-3-azabicyclo[3.1.0]hexan-6-ylcarbamate (10 mg, 50.0 µmol) and triethylamine (14 µL, 0.10 mmol) at room temperature, and the reaction mixture was heated to 70° C. After 6 h, the reaction mixture was allowed to cool to room temperature and was purified by preparatory HPLC (5-100% MeCN/H$_2$O, 0.1% trifluoroacetic acid modifier). Trifluoroacetic acid (1 mL) was added at room temperature. After 40 min, the resulting mixture was concentrated to afford compound 148 (26.9 mg, 82%) as a grey solid trifluoroacetate salt.

$^1$H NMR (CD$_3$OD, 400 MHz): δ 8.66 (br s, 1H), 7.65 (d, J=8.6 Hz, 1H), 7.47 (d, J=8.8 Hz, 1H), 7.41 (s, 1H), 6.11 (br s, 2H), 4.15 (d, J=11.0 Hz, 2H), 3.75 (d, J=10.5 Hz, 2H), 3.23-3.10 (m, 1H), 2.94 (s, 3H), 2.78-2.62 (m, 1H), 2.56 (s, 1H), 2.36 (s, 3H), 2.13 (s, 2H), 2.07-1.91 (m, 2H), 1.82-1.36 (m, 4H).

LCMS (ESI) m/z 546.40 [M+H]$^+$, t$_R$=1.94 min.
HPLC t$_R$ (min), purity %: 3.44, 97%.

Compound 149

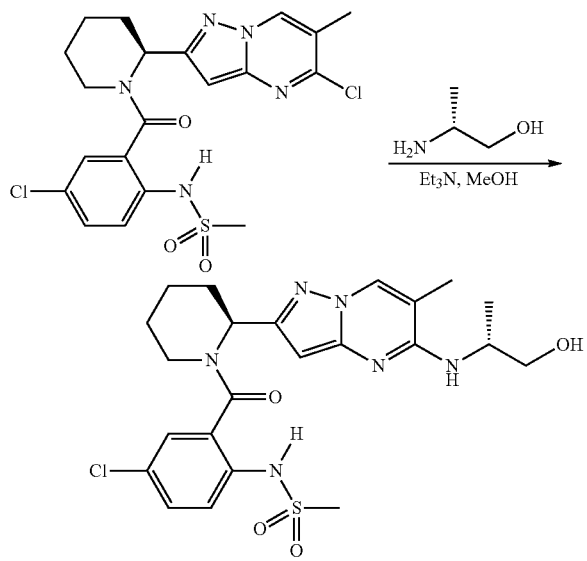

To a solution of intermediate 73 (30.0 mg, 62.0 µmol) in MeOH (1 mL) was added (R)-2-aminopropan-1-ol (48.0 µL, 0.62 mmol) and triethylamine (174 µL, 1.25 mmol) at room temperature, and the reaction mixture was heated to 70° C. After 11 h, the reaction mixture was allowed to cool to room temperature and was purified by preparatory HPLC (5-100% MeCN/H$_2$O, 0.1% trifluoroacetic acid modifier) to afford compound 149 (10.5 mg, 32%) as a white solid.

$^1$H NMR (CD$_3$OD, 400 MHz): δ 8.66 (s, 1H), 7.67 (d, J=8.7 Hz, 1H), 7.48 (d, J=8.3 Hz, 1H), 7.44 (s, 1H), 6.12 (br s, 2H), 4.37-4.23 (m, 1H), 3.67 (d, J=5.6 Hz, 2H), 3.25-3.15 (m, 1H), 2.95 (s, 3H), 2.40 (d, J=13.7 Hz, 1H), 2.16 (s, 3H), 2.08-1.95 (m, 2H), 1.84-1.40 (m, 4H), 1.31 (d, J=6.6 Hz, 3H).

LCMS (ESI) m/z 521.13 [M+H]$^+$, t$_R$=2.69 min.
HPLC t$_R$ (min), purity %: 3.93, 96%.
R$_f$=0.35 (EtOAc).

Compound 150

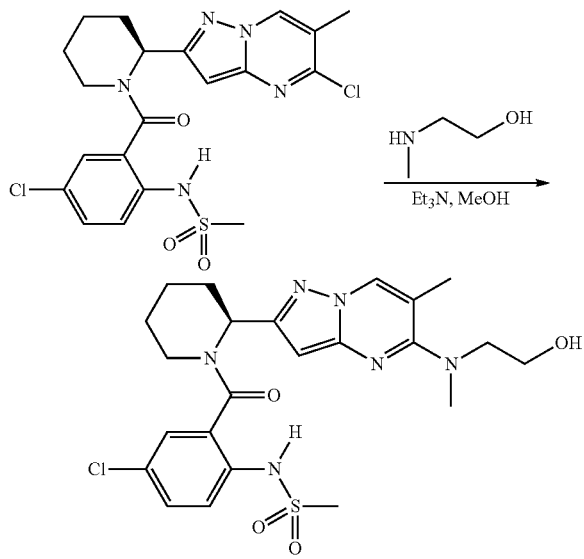

To a solution of intermediate 73 (30.0 mg, 62.0 µmol) in MeOH (1 mL) was added 2-(methylamino)ethanol (48.0 µL, 0.62 mmol) and triethylamine (174 µL, 1.25 mmol) at room temperature, and the reaction mixture was heated to 70° C. After 11 h, the reaction mixture was allowed to cool to room temperature and was purified by preparatory HPLC (5-100% MeCN/H$_2$O, 0.1% trifluoroacetic acid modifier) to afford compound 150 (15.1 mg, 48%) as a white solid.

$^1$H NMR (CD$_3$OD, 400 MHz): δ 8.75 (s, 1H), 7.67 (d, J=8.3 Hz, 1H), 7.48 (d, J=8.7 Hz, 1H), 7.44 (d, J=2.3 Hz, 1H), 6.45 (s, 1H), 6.14 (br d, J=3.9 Hz, 1H), 3.84 (br t, J=5.3 Hz, 2H), 3.67 (br t, J=5.4 Hz, 2H), 3.20 (s, 3H), 3.24-3.18 (m, 1H), 2.95 (s, 3H), 2.38 (s, 3H), 2.10-1.95 (m, 1H), 1.83-1.65 (m, 2H), 1.62-1.39 (m, 4H).

LCMS (ESI) m/z 521.15 [M+H]$^+$, t$_R$=2.75 min.
HPLC t$_R$ (min), purity %: 4.27, 87%.
R$_f$=0.40 (EtOAc).

Compound 151

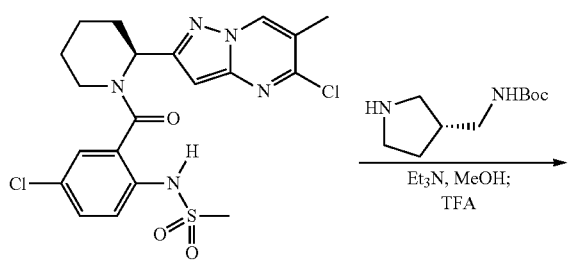

To a solution of intermediate 73 (30.0 mg, 62.0 µmol) in MeOH (1 mL) was added (R)-tert-butyl-pyrrolidin-3-ylmethylcarbamate (146 mg, 0.62 mmol) and triethylamine (174 µL, 1.25 mmol) at room temperature, and the reaction mixture was heated to 70° C. After 12 h, the reaction mixture was allowed to cool to room temperature and was purified by preparatory HPLC (5-100% MeCN/H$_2$O, 0.1% trifluoroacetic acid modifier). Trifluoroacetic acid (1 mL) was added at room temperature. After 30 min, the resulting mixture was concentrated to afford compound 151 (40.0 mg, 98%) as a light yellow solid trifluoroacetate salt.

$^1$H NMR (CD$_3$OD, 400 MHz): δ 8.67 (br s, 1H), 7.67 (d, J=8.5 Hz, 1H), 7.48 (d, J=8.9 Hz, 1H), 7.44 (d, J=2.3 Hz, 1H), 6.11 (br s, 2H), 4.05-3.75 (m, 3H), 3.57 (t, J=8.6 Hz, 1H), 3.26-3.15 (m, 1H), 3.14-3.05 (m, 3H), 2.95 (s, 3H), 2.68-2.51 (m, 1H), 2.40 (s, 3H), 2.31-2.19 (m, 1H), 2.11-1.96 (m, 2H), 1.90-1.36 (m, 5H).

LCMS (ESI) m/z 546.19 [M+H]$^+$, t$_R$=1.95 min.
HPLC t$_R$ (min), purity %: 3.39, 98%.

Intermediate 126

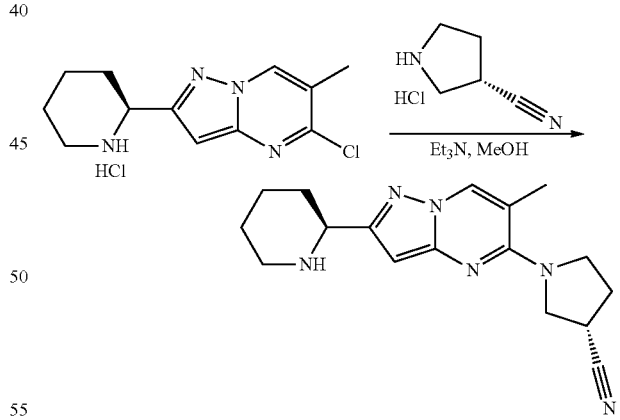

To a solution of intermediate 72 (100.0 mg, 0.35 mmol) in MeOH (1.74 mL) was added (S)-pyrrolidine-3-carbonitrile hydrochloride (459 mg, 3.48 mmol) and triethylamine (970 µL, 6.96 mmol) at room temperature, and the reaction mixture was heated to 70° C. After 2 h, the reaction mixture was allowed to cool to room temperature at which point a solid precipitate formed. The solids were collected by vacuum filtration to afford intermediate 126 (75 mg, 70%) as a grey solid.

LCMS (ESI) m/z 311.19 [M+H]$^+$, t$_R$=1.63 min.

Compound 152

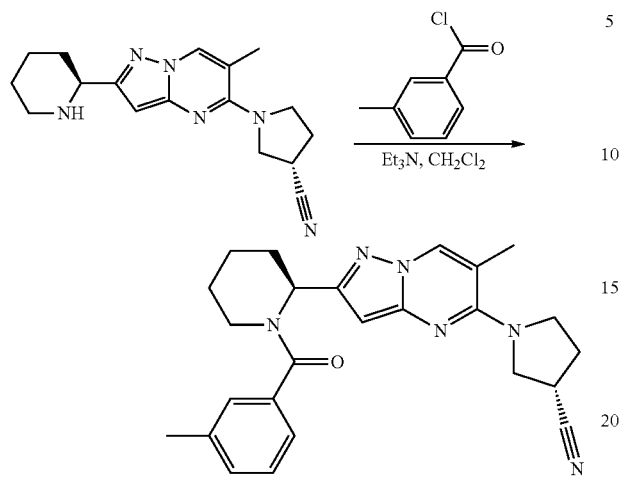

To a solution of intermediate 126 (45.0 mg, 0.15 mmol) in dichloromethane (725 μL) was added triethylamine (50 μl, 0.36 mmol) followed by 3-methylbenzoyl chloride (21 μL, 0.16 mmol) and the reaction mixture was stirred at room temperature under and argon atmosphere. After 15 min, the reaction mixture was concentrated under reduced pressure and was purified by preparatory HPLC (5-100% MeCN/H$_2$O, 0.1% trifluoroacetic acid modifier) to afford compound 152 (42.4 mg, 68%) as a white solid.

$^1$H NMR (CD$_3$OD, 400 MHz): δ 8.26 (s, 1H), 7.45-7.13 (m, 4H), 6.14-5.91 (m, 2H), 4.01 (dd, J=11.0, 7.0 Hz, 1H), 3.96-3.87 (m, 2H), 3.86-3.78 (m, 1H), 3.41 (quint, J=6.5 Hz, 1H), 3.20-2.96 (m, 1H), 2.58-2.21 (m, 9H), 2.01-1.80 (m, 2H), 1.79-1.46 (m, 4H).

LCMS (ESI) m/z 429.22 [M+H]$^+$, t$_R$=2.73 min.
HPLC t$_R$ (min), purity %: 4.32, 99%.
R$_f$=0.30 (EtOAc).

Compound 153

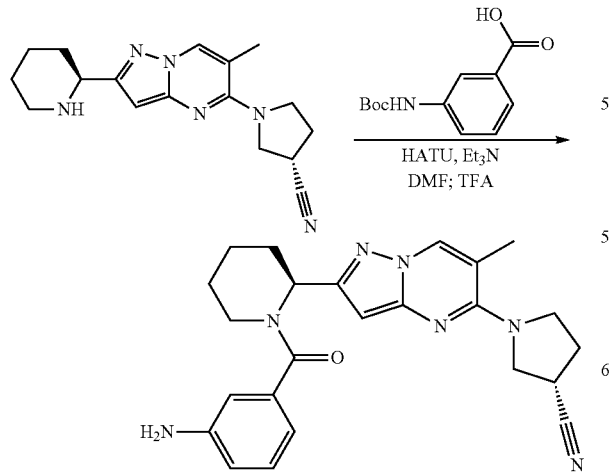

HATU (59.0 mg, 0.16 mmol) was added to a solution of 3-(tert-butoxycarbonylamino)benzoic acid (34 mg, 0.14 mmol) in DMF (645 μL), and the reaction mixture was stirred at room temperature. After 30 min, intermediate 126 (40 mg, 0.13 mmol) was added followed by the addition of triethylamine (45 μL, 0.32 mmol), and the reaction mixture was stirred at room temperature. After 19 h, the reaction mixture was purified via preparatory HPLC (5-100% MeCN/H$_2$O, 0.1% trifluoroacetic acid modifier). Trifluoroacetic acid (1 mL) was added at room temperature. After 30 min, the resulting mixture was concentrated to afford compound 153 (47.4 mg, 68%) as a tan solid trifluoroacetate salt.

$^1$H NMR (CD$_3$OD, 400 MHz): δ 8.28 (s, 1H), 7.67-7.36 (m, 4H), 6.18-5.94 (m, 2H), 4.03 (dd, J=10.9, 7.1 Hz, 1H), 3.98-3.88 (m, 2H), 3.88-3.79 (m, 1H), 3.43 (quint, J=6.5 Hz, 1H), 3.17-2.93 (m, 1H), 2.54-2.22 (m, 6H), 2.00-1.82 (m, 2H), 1.78-1.50 (m, 4H).

LCMS (ESI) m/z 430.19 [M+H]$^+$, t$_R$=2.35 min.
HPLC t$_R$ (min), purity %: 2.93, 98%.

Intermediate 127

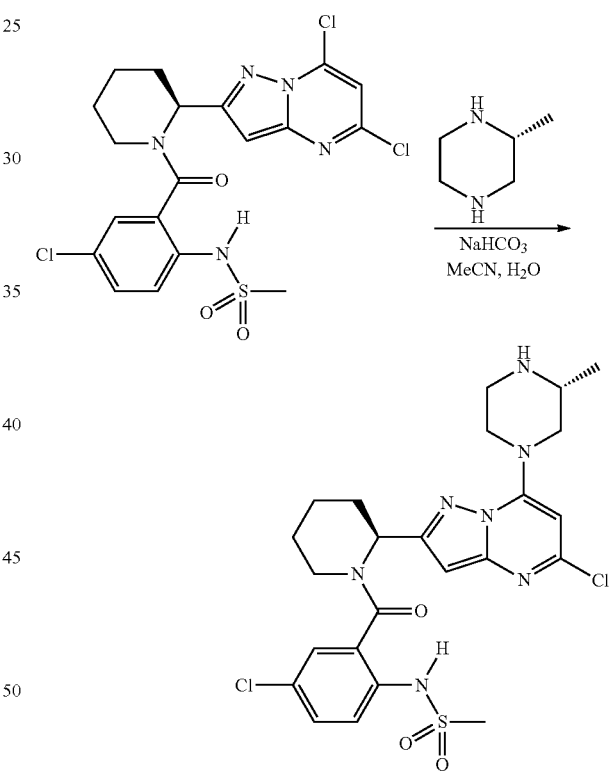

(R)-2-methylpiperazine (12 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 4 h, the reaction mixture was purified by preparatory HPLC (5-100% MeCN/H$_2$O, 0.1% trifluoroacetic acid modifier) to afford compound 127 (73.4 mg, 90%) as a white solid trifluoroacetate salt.

LCMS (ESI) m/z 566.13 [M+H]$^+$, t$_R$=1.90 min.

Compound 154

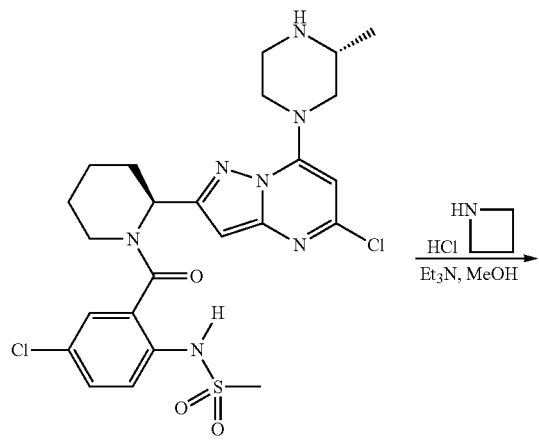

Intermediate 128

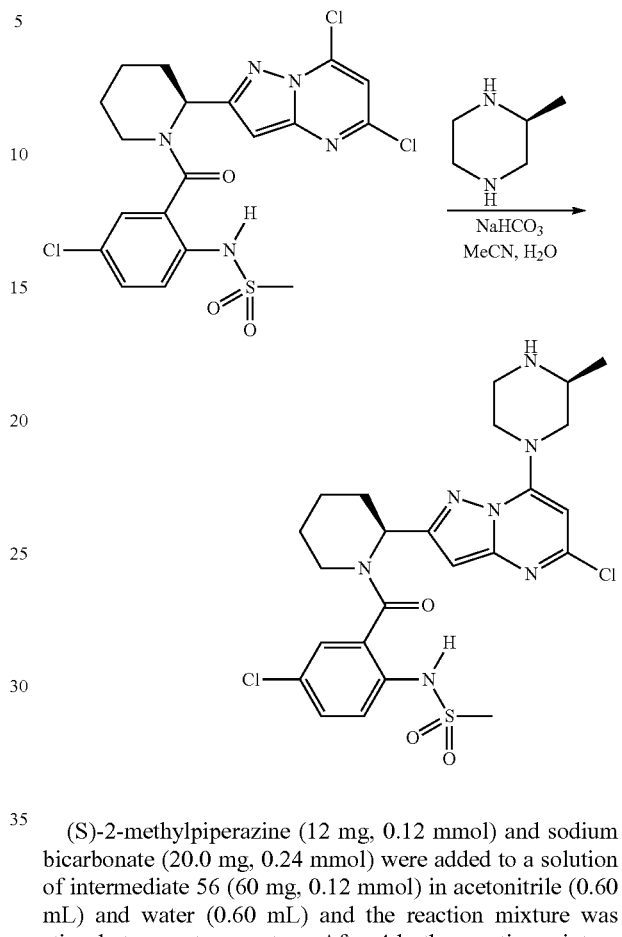

To a solution of intermediate 127 (73 mg, 0.11 mmol) in MeOH (1.20 mL) was added azetidine hydrochloride (112 mg, 1.20 mmol) and triethylamine (335 μL, 2.40 mmol) at room temperature, and the reaction mixture was heated to 70° C. After 6 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 154 (58.6 mg, 77%) as a white solid trifluoroacetate salt.

$^1$H NMR (CD$_3$OD, 400 MHz): δ 7.50 (br s, 2H), 7.41 (br s, 1H), 6.05 (br s, 1H), 5.44 (s, 1H), 4.69-4.47 (m, 2H), 4.35 (br t, J=7.3 Hz, 4H), 3.77-3.63 (m, 1H), 3.6-3.39 (m, 3H), 3.25-3.11 (m, 3H), 3.02 (s, 3H), 2.62-2.47 (m, 2H), 2.46-2.30 (m, 1H), 2.25-2.00 (m, 2H), 1.83-1.55 (m, 4H), 1.40 (d, J=5.9 Hz, 3H).

LCMS (ESI) m/z 587.15 [M+H]$^+$, t$_R$=1.86 min.
HPLC t$_R$ (min), purity %: 2.61, 94%.

(S)-2-methylpiperazine (12 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 4 h, the reaction mixture was purified by preparatory HPLC (5-100% MeCN/H$_2$O, 0.1% trifluoroacetic acid modifier) to afford compound 128 (51.0 mg, 63%) as a white solid trifluoroacetate salt.

LCMS (ESI) m/z 566.13 [M+H]$^+$, t$_R$=1.90 min.

Compound 155

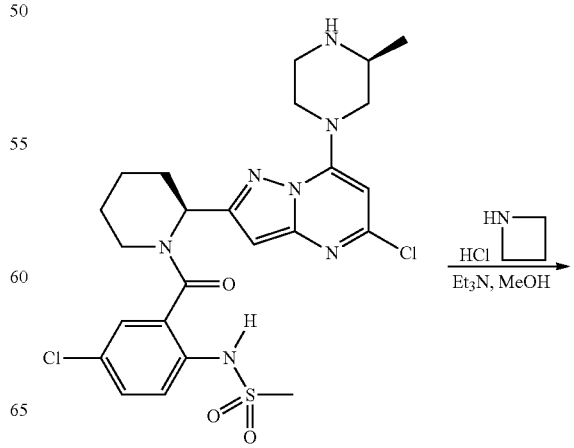

-continued

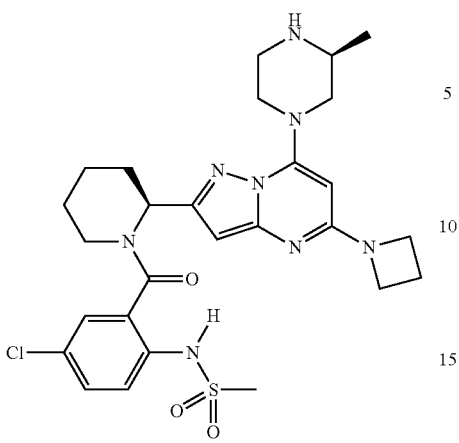

To a solution of intermediate 128 (51 mg, 75 µmol) in MeOH (1.20 mL) was added azetidine hydrochloride (112 mg, 1.20 mmol) and triethylamine (335 µL, 2.40 mmol) at room temperature, and the reaction mixture was heated to 70° C. After 7 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 155 (24.7 mg, 77%) as a white solid trifluoroacetate salt.

$^1$H NMR (CD$_3$OD, 400 MHz): δ 7.50 (br s, 2H), 7.42 (br s, 1H), 6.05 (br s, 1H), 5.44 (s, 1H), 5.12-4.77 (m, 1H), 4.69-4.42 (m, 1H), 4.33 (br t, J=7.3 Hz, 4H), 3.77-3.63 (m, 1H), 3.63-3.37 (m, 4H), 3.14-2.95 (m, 2H), 3.02 (s, 3H), 2.62-2.47 (m, 2H), 2.46-2.30 (m, 1H), 2.25-2.00 (m, 2H), 1.83-1.55 (m, 4H), 1.41 (br s, 3H).

LCMS (ESI) m/z 587.14 [M+H]$^+$, $t_R$=1.87 min.
HPLC $t_R$ (min), purity %: 2.60, 99%.

Intermediate 129

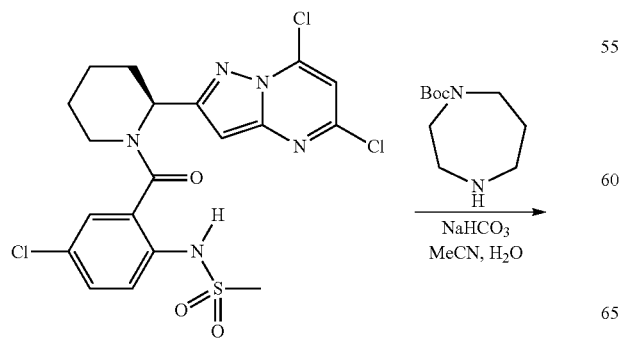

-continued

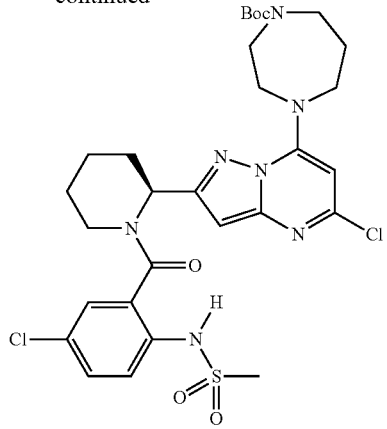

tert-butyl-1,4-diazepane-1-carboxylate (24 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 5 h, the reaction mixture was purified by preparatory HPLC (5-100% MeCN/H$_2$O, 0.1% trifluoroacetic acid modifier) to afford compound 129 (64.0 mg, 80%) as a white solid trifluoroacetate salt.

LCMS (ESI) m/z 666.14 [M+H]$^+$, $t_R$=3.06 min.

Compound 156

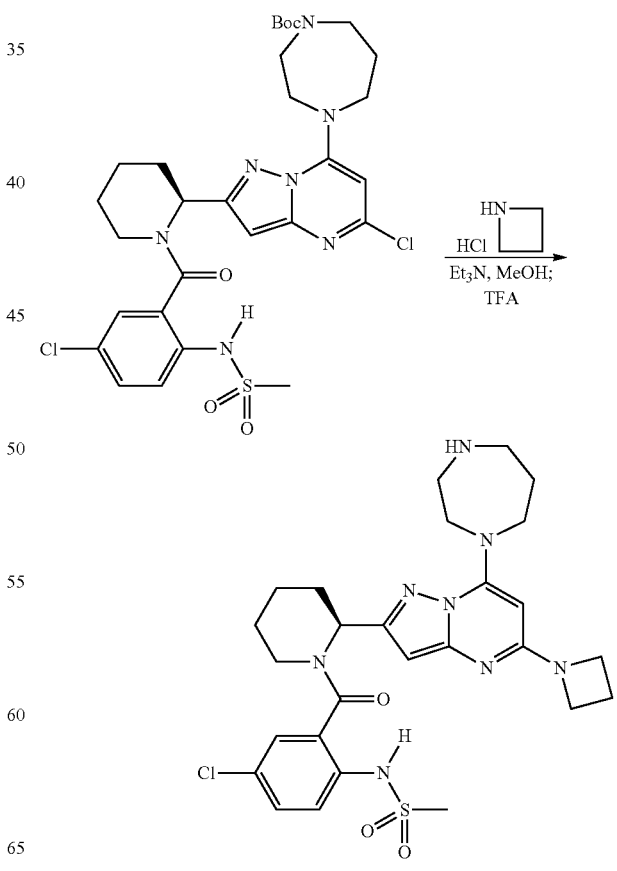

To a solution of intermediate 129 (64.0 mg, 0.10 mmol) in MeOH (1.20 mL) was added azetidine hydrochloride (112 mg, 1.20 mmol) and triethylamine (335 µL, 2.40 mmol) at room temperature, and the reaction mixture was heated to 70° C. After 7 h, the reaction mixture was allowed to cool to room temperature and was concentrated under reduced pressure. The crude residue was purified by preparatory HPLC (5-100% MeCN/H₂O, 0.1% trifluoroacetic acid modifier). Trifluoroacetic acid (1 mL) was added at room temperature. After 20 min, the resulting mixture was concentrated to afford compound 156 (17.2 mg, 24%) as a white solid trifluoroacetate salt.

$^1$H NMR (CD₃OD, 400 MHz): 7.58-7.43 (m, 2H), 7.38 (br s, 1H), 6.02 (br s, 1H), 5.16 (s, 1H), 4.42-4.25 (m, 6H), 3.85 (br s, 2H), 3.68 (br s, 2H), 3.49-3.41 (m, 2H), 3.19-3.01 (m, 1H), 3.07 (s, 3H), 2.57 (quint, J=7.7 Hz, 2H), 2.39 (quint, J=5.7 Hz, 2H), 2.26-2.04 (m, 3H), 1.86-1.53 (m, 4H).

LCMS (ESI) m/z 587.11 [M+H]⁺, t$_R$=1.63 min.

HPLC t$_R$ (min), purity %: 2.53, 98%.

Intermediate 130

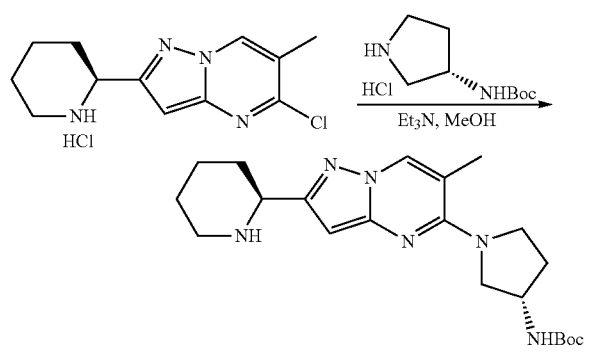

To a solution of intermediate 72 (100.0 mg, 0.35 mmol) in MeOH (1.74 mL) was added (S)-tert-butyl pyrrolidin-3-ylcarbamate (648 mg, 3.48 mmol) and triethylamine (970 µL, 6.96 mmol) at room temperature, and the reaction mixture was heated to 70° C. After 4 h, the reaction mixture was allowed to cool to room temperature and was concentrated under reduced pressure. The crude residue was purified by preparatory HPLC (5-100% MeCN/H₂O, 0.1% trifluoroacetic acid modifier) to afford intermediate 130 (169 mg, 95%) as an orange solid.

LCMS (PSI) m/z 401.23 [M+H]⁺, t$_R$=1.86 min.

Compound 157

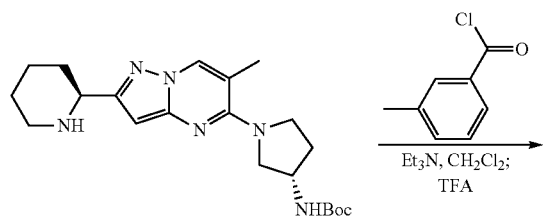

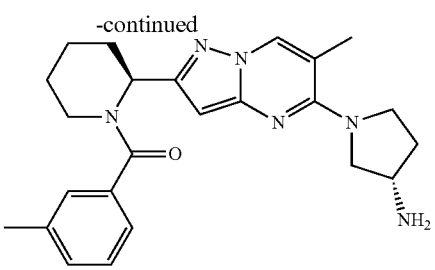

To a solution of intermediate 130 (20.0 mg, 0.05 mmol) in dichloromethane (500 µL) was added triethylamine (28 µl, 0.20 mmol) followed by 3-methylbenzoyl chloride (7 µL, 50 µmol) and the reaction mixture was stirred at room temperature under and argon atmosphere. After 2 h, the reaction mixture was concentrated under reduced pressure and the crude residue was purified via SiO₂ column chromatography (12 g SiO₂ Combiflash HP Gold Column, 0-100% ethyl acetate/hexanes). Trifluoroacetic acid (1 mL) was added at room temperature. After 20 min, the resulting mixture was concentrated to afford compound 157 (16.8 mg, 63%) as a grey solid trifluoroacetate salt.

$^1$H NMR (CD₃OD, 400 MHz): δ 8.29 (s, 1H), 7.44-7.17 (m, 4H), 6.06 (br s, 1H), 5.07 (br s, 1H), 4.57 (br s, 1H), 4.06-3.93 (m, 3H), 3.92-3.76 (m, 2H), 3.62 (br s, 1H), 3.13 (br s, 1H), 3.00 (br s, 1H), 2.53-2.23 (m, 6H), 2.21-2.07 (m, 1H), 2.02-1.80 (m, 1H), 1.56 (m, 4H).

LCMS (ESI) m/z 419.16 [M+H]⁺, t$_R$=1.89 min.

HPLC t$_R$ (min), purity %: 2.99, 97%.

R$_f$=0.20 (20% methanol/CH₂Cl₂).

Compound 158

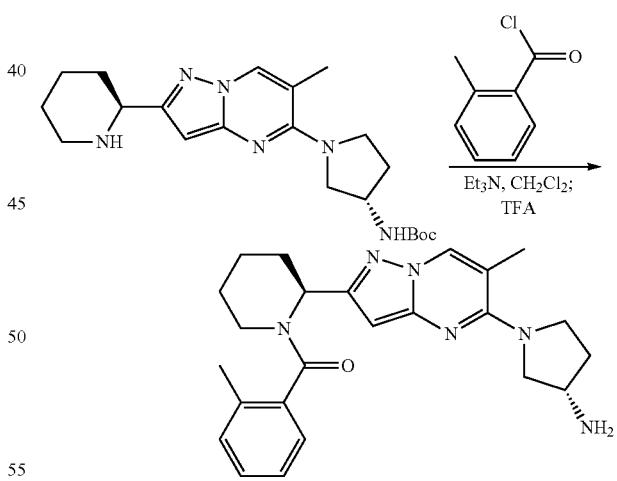

To a solution of intermediate 130 (20.0 mg, 0.05 mmol) in dichloromethane (500 µL) was added triethylamine (28 µl, 0.20 mmol) followed by 2-methylbenzoyl chloride (7 µL, 50 µmol) and the reaction mixture was stirred at room temperature under and argon atmosphere. After 2.5 h, the reaction mixture was concentrated under reduced pressure and the crude residue was purified via SiO₂ column chromatography (12 g SiO₂ Combiflash HP Gold Column, 0-100% ethyl acetate/hexanes). Trifluoroacetic acid (1 mL) was added at room temperature. After 20 min, the resulting mixture was concentrated to afford compound 158 (24.6 mg, 92%) as a grey solid trifluoroacetate salt.

$^1$H NMR (CD$_3$OD, 400 MHz): δ 8.29 (br s, 1H), 7.38-7.16 (m, 4H), 6.13 (br dd, J=11.2, 4.1 Hz, 1H), 4.67 (br t, J=15.5 Hz, 1H), 4.06-3.93 (m, 4H), 3.91-3.75 (m, 3H), 3.26-2.99 (m, 2H), 2.57-2.36 (m, 6H), 2.20-2.09 (m, 1H), 1.99-1.82 (m, 1H), 1.79-1.44 (m, 4H).

LCMS (ESI) m/z 419.17 [M+H]$^+$, t$_R$=1.86 min.

HPLC t$_R$ (min), purity %: 2.96, 98%.

R$_f$=0.20 (20% methanol/CH$_2$Cl$_2$).

Intermediate 131

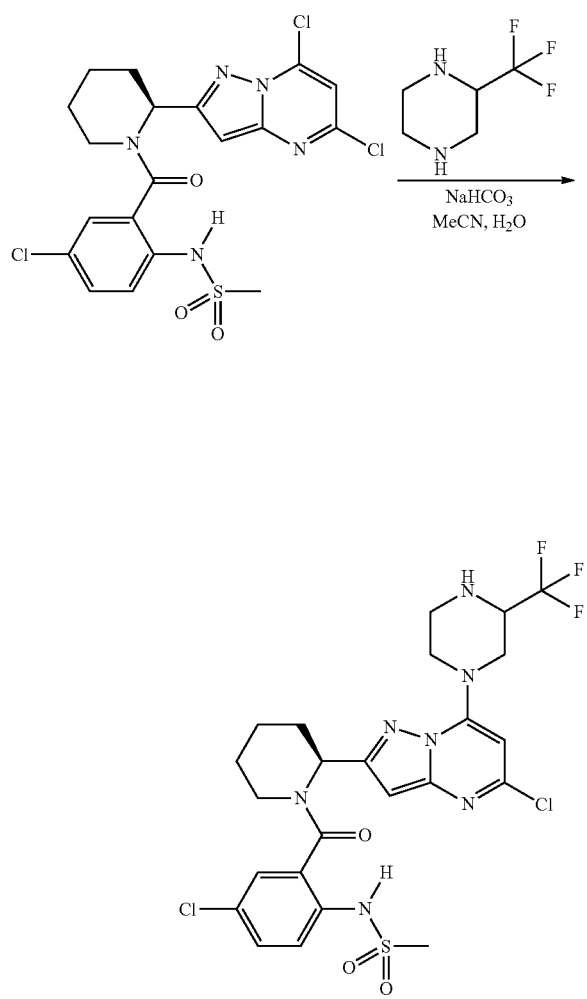

2-(trifluoromethyl)piperazine (18.5 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 20 h, the reaction mixture was purified by preparatory HPLC (5-100% MeCN/H$_2$O, 0.1% trifluoroacetic acid modifier) to afford intermediate 131 (31.1 mg, 35%) as a white solid trifluoroacetate salt.

LCMS (ESI) m/z 620.09 [M+H]$^+$, t$_R$=2.83 min.

Compound 159

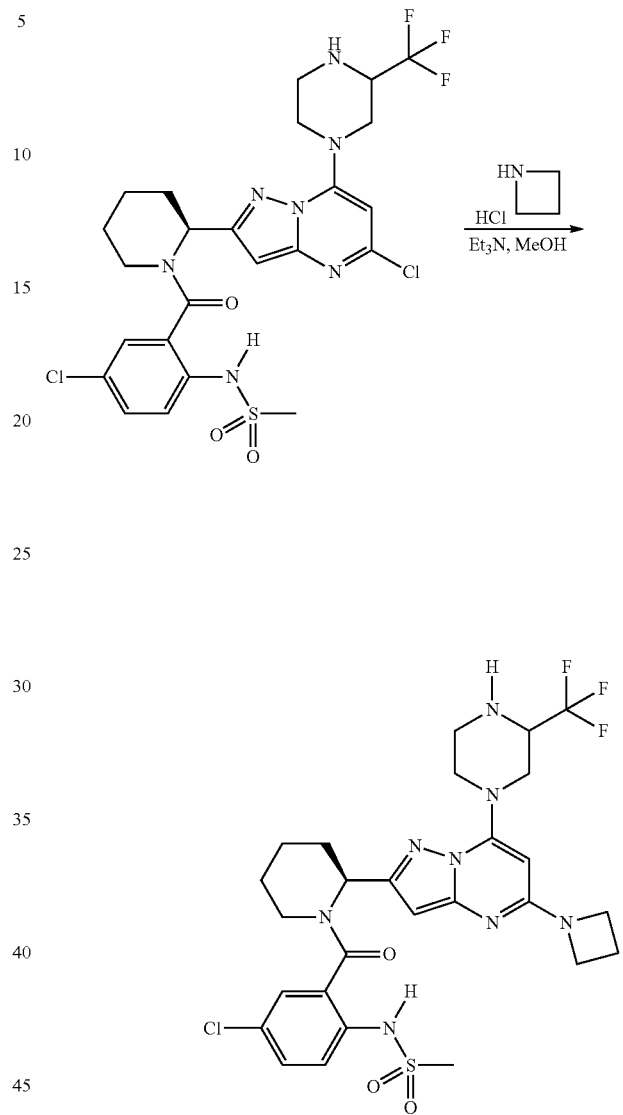

To a solution of intermediate 131 (31.1 mg, 50 μmol) in MeOH (1.00 mL) was added azetidine hydrochloride (23 mg, 0.25 mmol) and triethylamine (70 μL, 0.5 mmol) at room temperature, and the reaction mixture was heated to 70° C. After 20 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 159 (17.4 mg, 46%) as a white solid trifluoroacetate salt.

$^1$H NMR (CD$_3$OD, 400 MHz): δ 7.49 (br s, 2H), 7.40 (br s, 1H), 6.03 (br s, 1H), 5.36 (s, 1H), 5.02-4.89 (m, 1H), 4.65-4.46 (m, 2H), 4.35 (br t, J=7.5 Hz, 4H), 4.23-4.00 (m, 2H), 3.93-3.76 (m, 2H), 3.23-3.09 (m, 2H), 3.03 (br s, 3H), 2.55 (quint, J=7.9 Hz, 2H), 2.49-2.29 (m, 1H), 2.26-1.95 (m, 2H), 1.82-1.53 (m, 4H).

LCMS (ESI) m/z 641.12 [M+H]$^+$, t$_R$=2.44 min.

HPLC t$_R$ (min), purity %: 3.16, 98%.

Compound 160

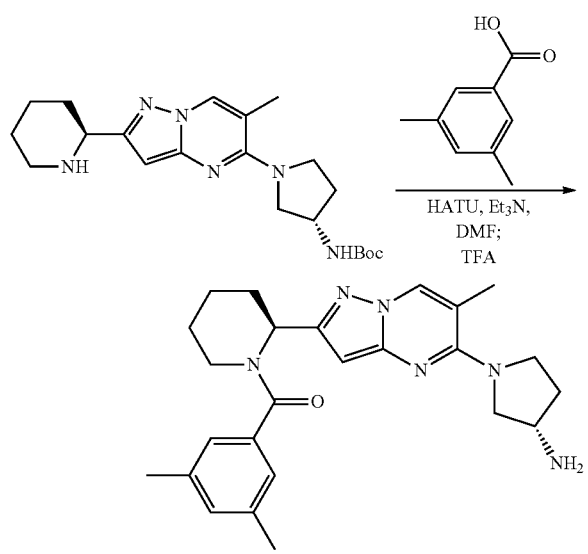

HATU (85.8 mg, 0.23 mmol) was added to a solution of 3,5-dimethylbenzoic acid (21.7 mg, 0.21 mmol) in DMF (1.00 mL), and the reaction mixture was stirred at room temperature. After 30 min, intermediate 130 (75 mg, 0.19 mmol) was added followed by the addition of triethylamine (39.3 µL, 0.28 mmol), and the reaction mixture was stirred at room temperature. After 17 h, the reaction mixture was purified via preparatory HPLC (5-100% MeCN/H$_2$O, 0.1% trifluoroacetic acid modifier). Trifluoroacetic acid (1 mL) was added at room temperature. After 30 min, the resulting mixture was concentrated to afford compound 160 (88.8 mg, 87%) as a white solid trifluoroacetate salt.

$^1$H NMR (CD$_3$OD, 400 MHz): δ 8.28 (s, 1H), 7.19-7.02 (m, 3H), 6.05 (br s, 1H), 5.07 (br s, 1H), 4.55 (br s, 1H), 4.06-3.91 (m, 3H), 3.91-3.78 (m, 2H), 3.68-3.55 (m, 1H), 3.25-3.09 (m, 1H), 3.07-2.91 (m, 1H), 2.41 (s, 3H), 2.38-2.21 (m, 6H), 2.20-2.09 (m, 1H), 2.00-1.81 (m, 1H), 1.78-1.48 (m, 4H).

LCMS (ESI) m/z 433.12 [M+H]$^+$, t$_R$=1.93 min.
HPLC t$_R$ (min), purity %: 3.20, 94%.

Compound 161

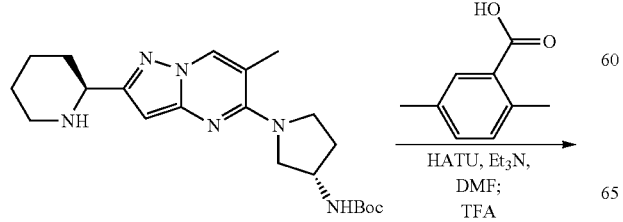

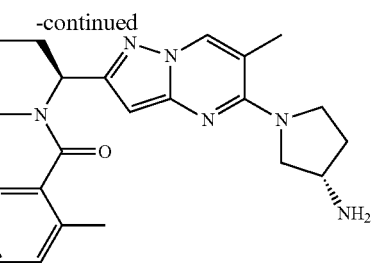

HATU (85.8 mg, 0.23 mmol) was added to a solution of 2,5-dimethylbenzoic acid (21.7 mg, 0.21 mmol) in DMF (1.00 mL), and the reaction mixture was stirred at room temperature. After 30 min, intermediate 130 (75 mg, 0.19 mmol) was added followed by the addition of triethylamine (39.3 µL, 0.28 mmol), and the reaction mixture was stirred at room temperature. After 17 h, the reaction mixture was purified via preparatory HPLC (5-100% MeCN/H$_2$O, 0.1% trifluoroacetic acid modifier). Trifluoroacetic acid (1 mL) was added at room temperature. After 30 min, the resulting mixture was concentrated to afford compound 161 (45 mg, 44%) as a white solid trifluoroacetate salt.

$^1$H NMR (CD$_3$OD, 400 MHz): δ 8.28 (s, 1H), 7.21-7.01 (m, 3H), 6.05 (br s, 1H), 5.13-4.97 (m, 1H), 4.65-4.45 (m, 1H), 3.98 (app q, J=8.5 Hz, 3H), 3.91-3.76 (m, 2H), 3.67-3.53 (m, 1H), 3.25-2.89 (m, 2H), 2.57-2.20 (m, 9H), 2.21-2.09 (m, 1H), 1.98-1.79 (m, 1H), 1.79-1.45 (m, 4H).

LCMS (ESI) m/z 433.14 [M+H]$^+$, t$_R$=1.90 min.
HPLC t$_R$ (min), purity %: 3.10, 98%.

Intermediate 132

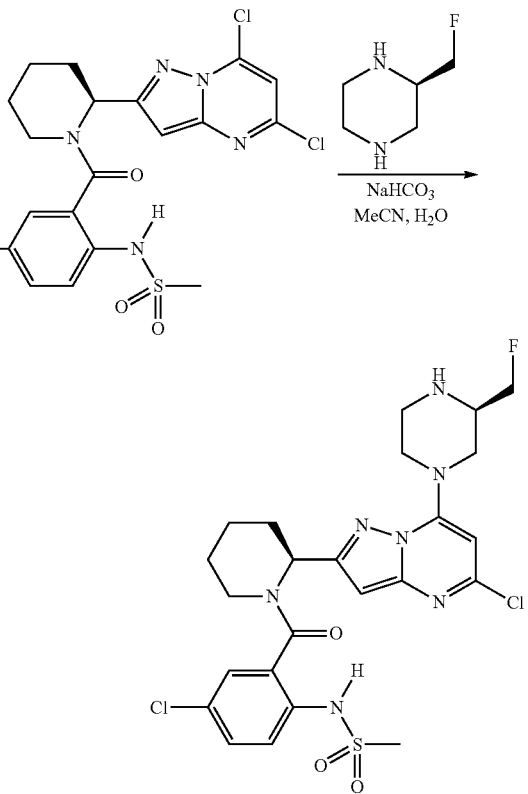

381

(R)-2-(fluoromethyl)piperazine (20.0 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 22 h, the reaction mixture was purified by preparatory HPLC (5-100% MeCN/H₂O, 0.1% trifluoroacetic acid modifier) to afford intermediate 132 (79.1 mg, 95%) as a white solid trifluoroacetate salt.

LCMS (ESI) m/z 584.05 [M+H]⁺, $t_R$=1.96 min.

Compound 162

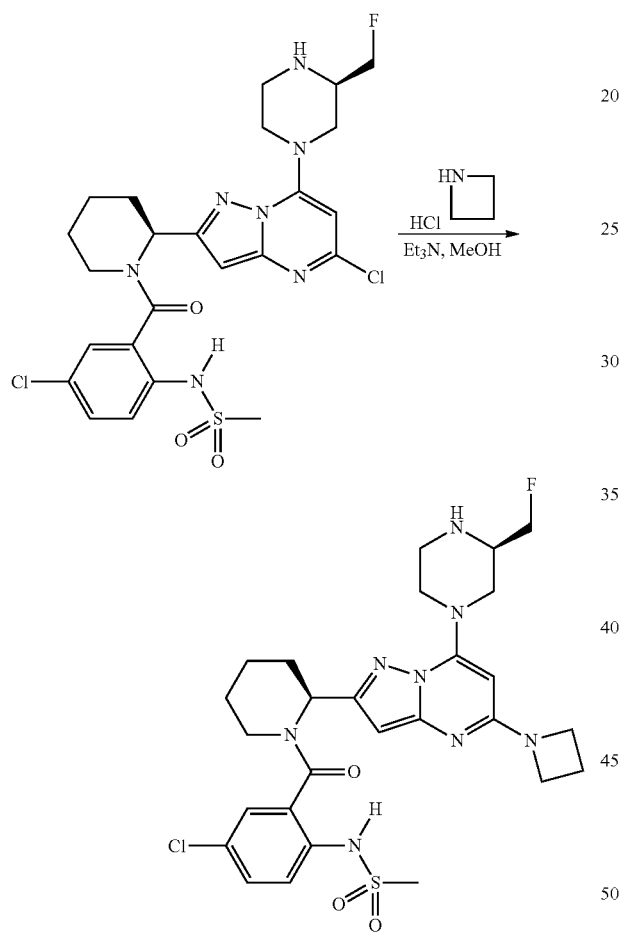

To a solution of intermediate 132 (79.1 mg, 0.11 mmol) in MeOH (1.00 mL) was added azetidine hydrochloride (71.1 mg, 0.76 mmol) and triethylamine (1.06 mL, 7.60 mmol) at room temperature, and the reaction mixture was heated to 70° C. After 17 h, the reaction mixture was allowed to cool to room temperature and was concentrated under reduced pressure. The crude residue was purified by preparatory HPLC (5-100% MeCN/H₂O, 0.1% trifluoroacetic acid modifier) to afford compound 162 (20.3 mg, 25%) as a white solid trifluoroacetate salt.

382

¹H NMR (CD₃OD, 400 MHz): δ 7.50 (br s, 2H), 7.43 (br s, 1H), 6.15-5.93 (m, 1H), 5.48 (s, 1H), 4.81-4.66 (m, 3H), 4.63-4.48 (m, 1H), 4.31 (br s, 4H), 4.04-3.85 (m, 1H), 3.69-3.36 (m, 7H), 3.00 (br s, 3H), 2.54 (quint, J=8.3 Hz, 2H), 2.45-2.27 (m, 1H), 2.24-2.04 (m, 1H), 1.85-1.46 (m, 4H).

LCMS (ESI) m/z 605.38 [M+H]⁺, $t_R$=1.88 min.

HPLC $t_R$ (min), purity %: 2.63, 97%.

Intermediate 133

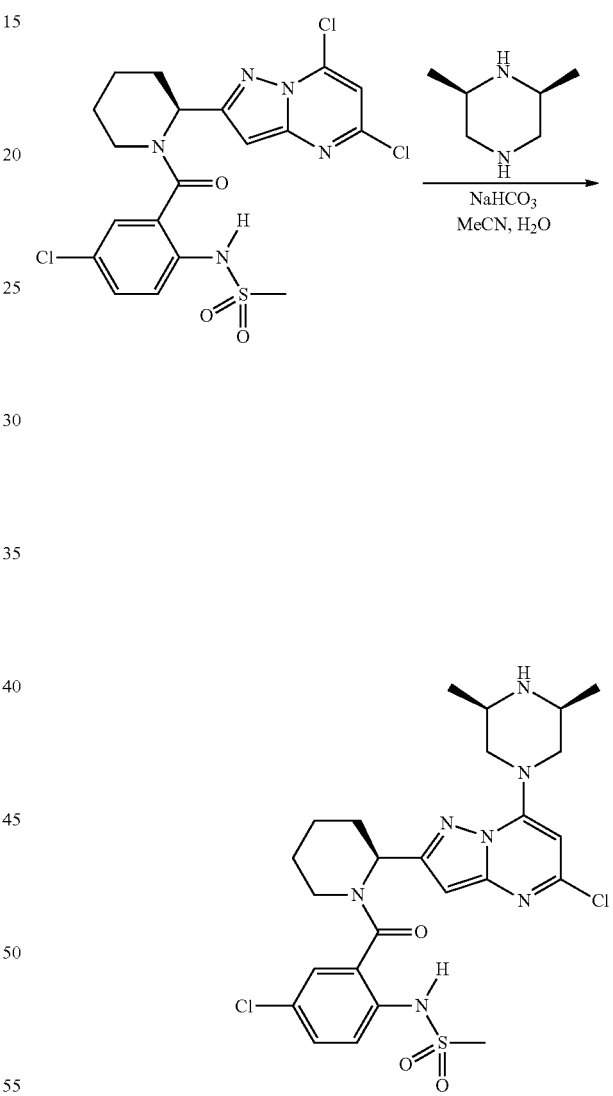

(2S,6R)-2,6-dimethylpiperazine (20.0 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 16 h, the reaction mixture was purified by preparatory HPLC (5-100% MeCN/H₂O, 0.1% trifluoroacetic acid modifier) to afford intermediate 133 (75.0 mg, 90%) as a white solid trifluoroacetate salt.

LCMS (ESI) m/z 580.35 [M+H]⁺, $t_R$=1.93 min.

Compound 163

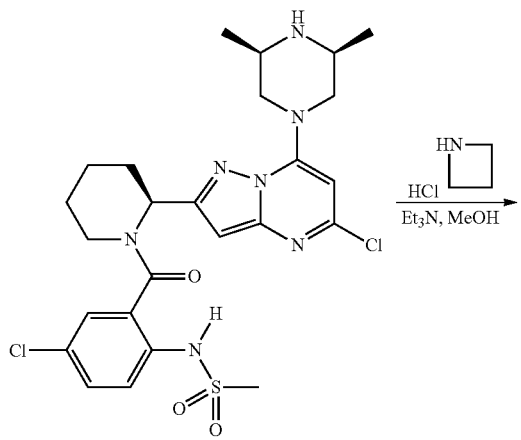

Compound 164

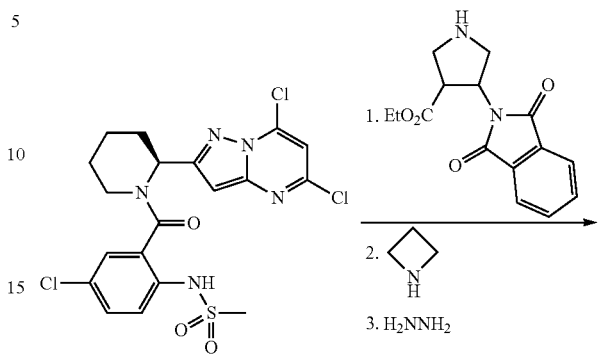

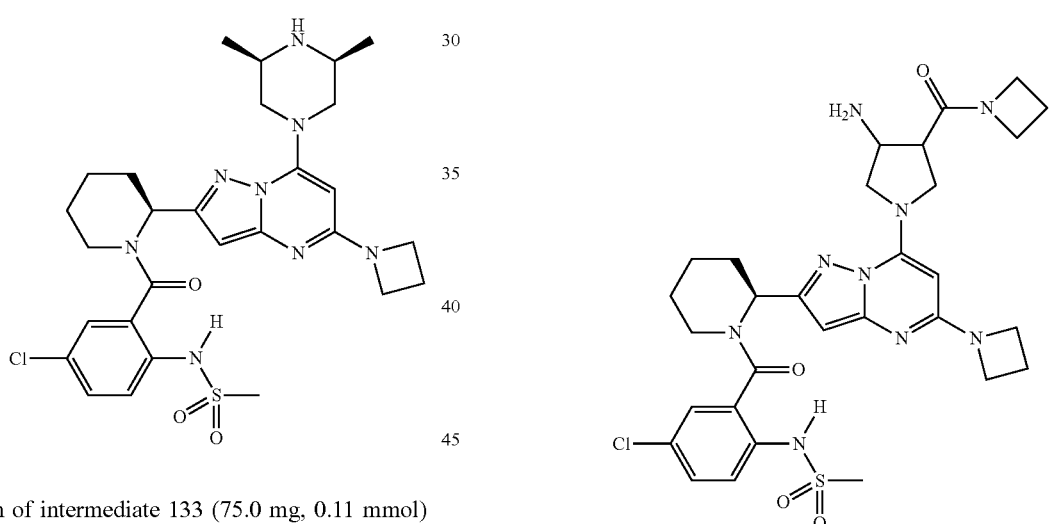

To a solution of intermediate 133 (75.0 mg, 0.11 mmol) in MeOH (1.00 mL) was added azetidine hydrochloride (71.1 mg, 0.76 mmol) and triethylamine (0.17 mL, 1.20 mmol) at room temperature, and the reaction mixture was heated to 70° C. After 16 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 163 (41.1 mg, 52%) as a white solid trifluoroacetate salt.

$^1$H NMR (CD$_3$OD, 400 MHz): δ 7.49 (br s, 2H), 7.41 (br s, 1H), 6.31-6.12 (m, 1H), 6.11-5.94 (m, 1H), 5.46 (s, 1H), 5.08-4.90 (m, 1H), 4.79-4.61 (m, 1H), 4.59-4.43 (m, 1H), 4.36 (br s, 4H), 3.79-3.61 (m, 2H), 3.24-2.91 (m, 6H), 2.56 (quint, J=5.6 Hz, 2H), 2.45-2.27 (m, 1H), 2.25-2.04 (m, 1H), 1.88-1.52 (m, 4H), 1.41 (br s, 6H).

LCMS (ESI) m/z 601.42 [M+H]$^+$, t$_R$=1.85 min.

HPLC t$_R$ (min), purity %: 2.69, 98%.

R$_f$=0.45 (10% methanol/CH$_2$Cl$_2$).

Dissolved intermediate 56 ((S)—N-(4-chloro-2-(2-(5,7-dichloropyrazolo[1,5-a]pyrimidin-2-yl)piperidine-1-carbonyl)phenyl)methanesulfonamide) (100 mg, in MeCN (1.5 mL). Added ethyl 4-(1,3-dioxoisoindolin-2-yl)pyrrolidine-3-carboxylate (114 mg) and NEt$_3$ to adjust the pH to >9. Stirred for 15 min at RT followed by the addition of azetidine (1 ml) and stirring at RT for 5 h. Volatiles were removed and the residue dissolved in THF (3 ml) and hydrazine (1 ml). The solution was heated to reflux for 2 h. Volatiles were removed and the product purified by preparative HPLC to give compound 164 (40 mg, 40% yield).

Ethyl 4-(1,3-dioxoisoindolin-2-yl)pyrrolidine-3-carboxylate was prepared according to WO2005/77918 A1.

LCMS (ESI) m/z 656.19 [M+H]$^+$, t$_R$=1.87 min.

Compound 165

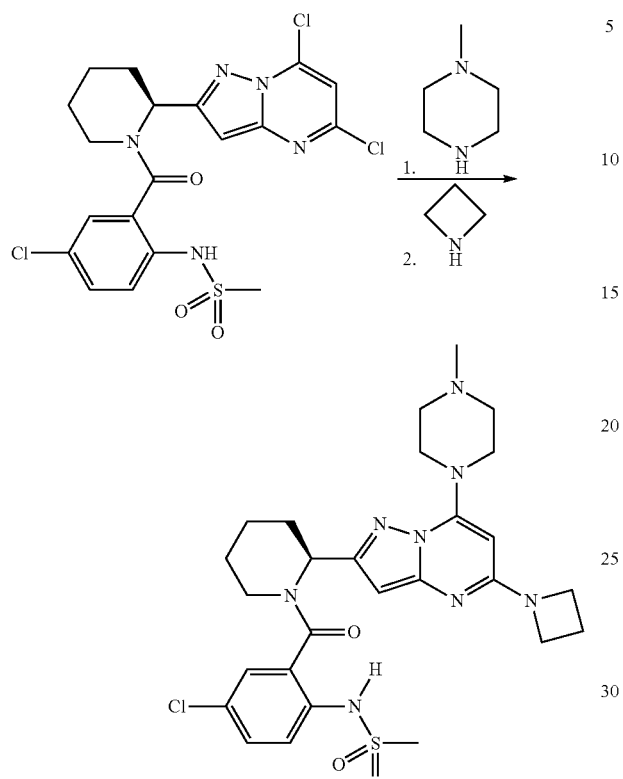

Dissolved intermediate 56 ((S)—N-(4-chloro-2-(2-(5,7-dichloropyrazolo[1,5-a]pyrimidin-2-yl)piperidine-1-carbonyl)phenyl)methanesulfonamide) (200 mg) in MeCN (1.5 mL). Added N-methylpiperazine (65 mg) and NEt₃ to adjust the pH to >9. Stirred for 15 min at RT followed by the addition of azetidine (1 ml) and stirring at RT for 5 h. Volatiles were removed and the product purified by preparative HPLC to give compound 165 (18.2 mg, ~20% yield).

LCMS (ESI) m/z 587.4 [M+H]⁺, $t_R$=1.6 min.

¹H-NMR (CD₃OD, 400 MHz): δ 7.76 (bs, 2H), 7.69 (bs, 1H), 6.03 (bs, 1H), 6.23 (bs, 1H), 6.16 (bs, 1H), 5.63 (s, 1H), 5.15 (bs, 1H), 4.36-4.31 (m, 4H), 3.84 (bs, 2H), 3.68 (bs, 2H), 3.29 (bs, 2H), 3.29 (bs, 2H), 3.13 (bs, 1H), 2.71-2.62 (m, 7H), 1.95 (bs, 2H), 1.80 (bs, 2H), 1.53 (bs, 2H).

Compound 166

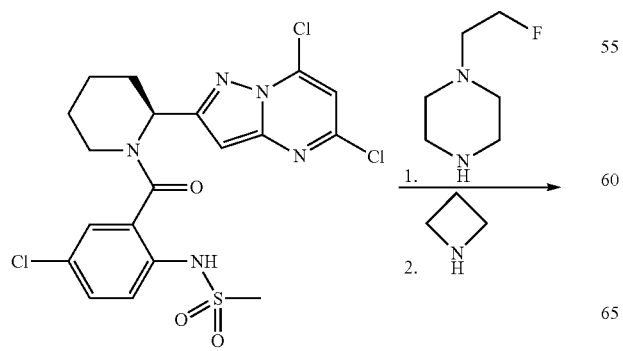

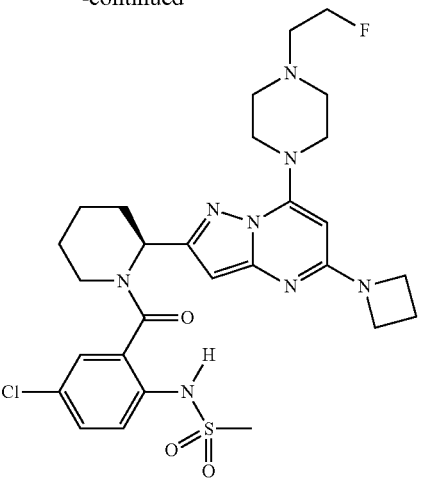

Dissolved intermediate 56 ((S)—N-(4-chloro-2-(2-(5,7-dichloropyrazolo[1,5-a]pyrimidin-2-yl)piperidine-1-carbonyl)phenyl)methanesulfonamide) (270 mg) in MeCN (1.5 mL). Added N-2-fluoroethyl-piperazine (92 mg) and NEt₃ to adjust the pH to >9. Stirred for 55 min at RT followed by the addition of azetidine (1 ml) and stirring at RT for 5 h. Volatiles were removed and the product purified by preparative HPLC to give compound 166 (41 mg, 12% yield).

LCMS (ESI) m/z 619.24 [M+H]⁺, $t_R$=1.83 min.

Compound 167

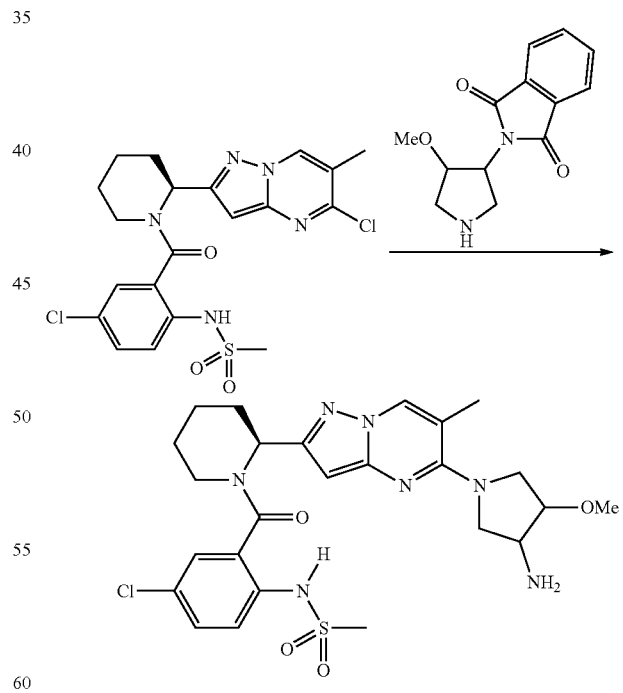

Dissolved intermediate 73 (150 mg) in MeCN (1.5 mL). Added ethyl 4-(1,3-dioxoisoindolin-2-yl)pyrrolidine-3-carboxylate (200 mg) and NEt₃ to adjust the pH to >9. Stirred for 1 h at 70 C. Volatiles were removed and the product purified by preparative HPLC to give phthalate protected intermediate (20 mg). Deprotection was accomplished by stirring in 0.2 M hydrazine in MeOH at RT for 4 h. Volatiles were removed and the product purified by preparative HPLC to give compound 167 (12.9 mg, 7%)

LCMS (ESI) m/z 562.2 [M+H]$^+$, $t_R$=2.18 min.

Intermediate 134

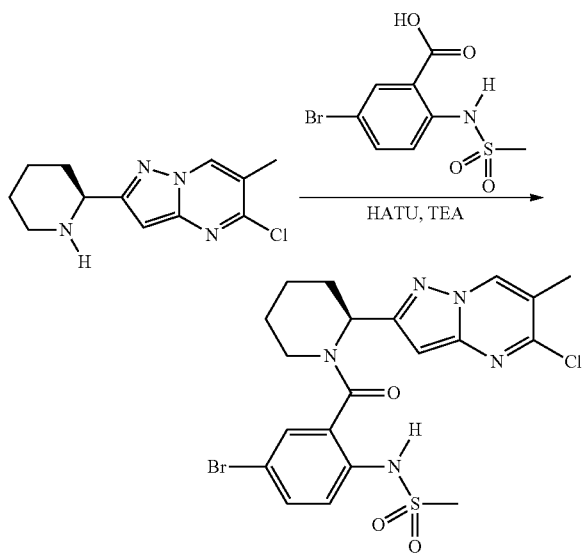

5-Bromo-2-(methylsulfonamido)benzoic acid (66 mg, 0.22 mmol) in DMF (1 mL) was treated with HATU (100 mg, 0.26 mmol) and stirred for 2 h. The solution was treated with intermediate 72 (50 mg, 0.17 mmol) and triethylamine (61 µL, 0.44 mmol) and stirred overnight. The solution was diluted with EtOAc (50 mL) and washed with H$_2$O (3 10 mL) and saturated NaCl (10 mL). The solution was dried (MgSO$_4$) and afford intermediate 134 which was used without further purification.

Compound 168

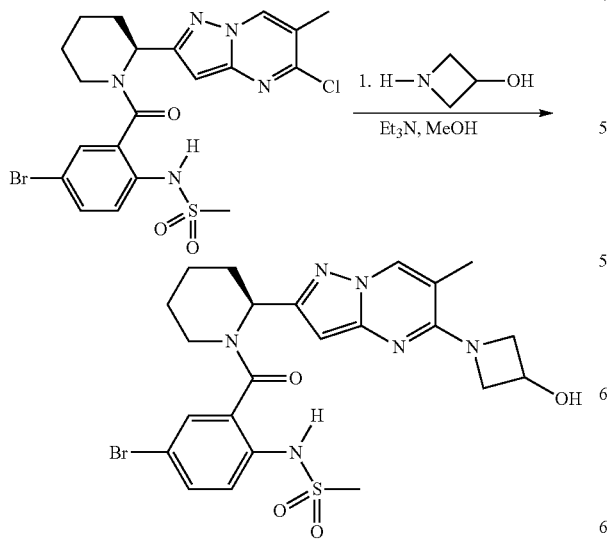

Intermediate 134 (50 mg, 0.17 mmol) in MeOH (2 mL) was treated with 3-hydroxy-azetidine (190 mg, 1.7 mmol) and triethylamine (485 µL, 3.5 mmol) and stirred at 70° C. for 18 h. The solution was concentrated and treated to preparatory RP-HPLC (5-100% MeCN/H$_2$O, 0.1% trifluoroacetic acid modifier) to afford compound 168 (20 mg, 98%) as a white solid:

$^1$H NMR (CD$_3$OD, 400 MHz): δ 8.66 (br s, 1H), 7.60 (m, 4H), 7.43 (t, J=8.8 Hz, 1H), 6.11 (br s, 1H), 4.61 (br s, 2H), 3.32 (m, 1H), 3.04 (br s, 3H), 2.39 (app d, J=12.8 Hz, 1H), 2.26 (s, 3H), 2.06 (m, 2H), 1.55 (m, 2H), 1.25 (m, 2H), 1.18 (m, 1H).

LC-MS (ESI) m/z 563 [M+H]$^+$, $t_R$=2.37 min.

HPLC $t_R$ (min): 3.86.

Compound 169

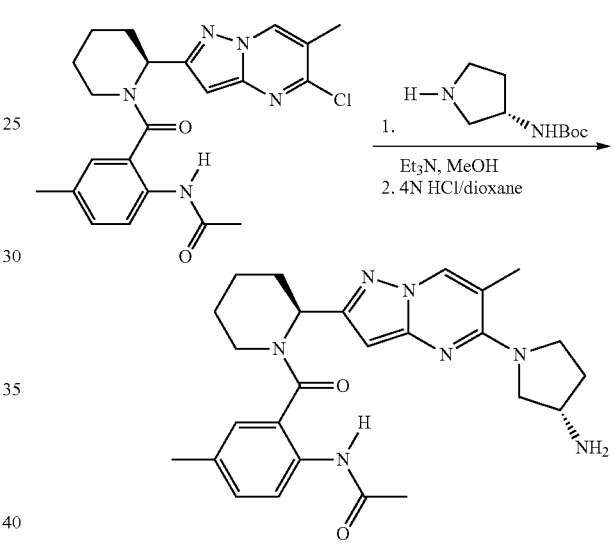

Intermediate 173 (6.5 g, 15.3 mmol) in MeOH (150 mL) was treated with 3-(S)-Boc-aminopyrrolidine (7.1 g, 38.2 mmol) and triethylamine (21 mL, 153 mmol) and stirred at 70° C. for 18 h. The solution was concentrated and suspended in EtOAc (200 mL). The solution was washed with H$_2$O (100 mL) and saturated NaCl solution (100 mL) and dried (MgSO$_4$). The concentrated solids (~500 mg) were suspended in DCM (1.75 mL), treated with 4 N HCl/dioxane (150 µL), and stirred for 10 min. The suspension was concentrated, resuspended in MeOH (2 mL), and treated to a 40 g SiO$_2$ Combiflash HP Gold column (0-100% NH$_4$OH/H$_2$O gradient) to afford compound 169 (400 mg, 97%) as a white solid:

$^1$H NMR (CD$_3$OD, 400 MHz): δ 8.28 (s, 1H), 7.45 (br m, 1H), 7.26 (br m, 1H), 7.22 (br m, 2H), 6.06 (s, 1H), 5.94 (s, 1H), 4.00 (m 3H), 3.85 (m, 2H), 3.31 (m, 1H), 3.30 (m, 1H), 3.01 (m, 1H), 2.42 (s, 3H), 2.20 (s, 3H), 2.12 (s, 3H), 1.93 (br m, 2H), 1.53 (br m, 3H), 1.42 (m, 2H).

LC-MS (ESI) m/z 476 [M+H]$^+$, $t_R$=1.66 min.

HPLC $t_R$: 2.99 min.

Compound 170

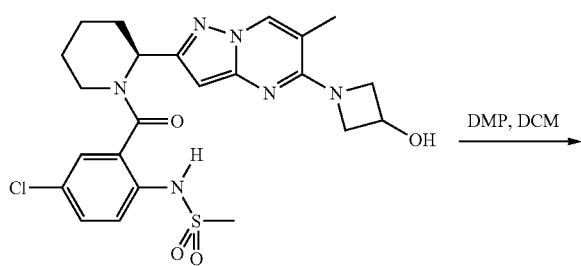

Compound 92 (50 mg, 0.1 mmol) in DCM (1 mL) was treated with Dess-Martin periodinane (123 mg, 0.29 mmol) and stirred for 3 h. The solution was concentrated and treated to preparatory RP-HPLC (5-100% MeCN/H$_2$O, 0.1% trifluoroacetic acid modifier) to afford compound 170 (10 mg, 20%) as a white solid.

$^1$H NMR (CD$_3$OD, 400 MHz): δ 8.59 (s, 1H), 8.23 (s, 1H), 7.55 (app d, J=7.7 Hz 1H), 7.18 (br d, J=7.6 Hz, 2H), 7.10 (s, 1H), 6.01 (br s, 1H), 4.35 (app d, J=7.6 Hz, 3H), 4.30 (app d, J=7.6 Hz, 3H), 3.19 (m, 1H), 2.90 (s, 3H), 2.15 (s, 3H), 1.95 (br s, 2H), 1.63 (br m, 3H), 1.45 (m, 2H).

LC-MS (ESI) m/z 518 [M+H]$^+$, t$_R$=2.88 min.
HPLC t$_R$: 4.78 min.

Compound 171

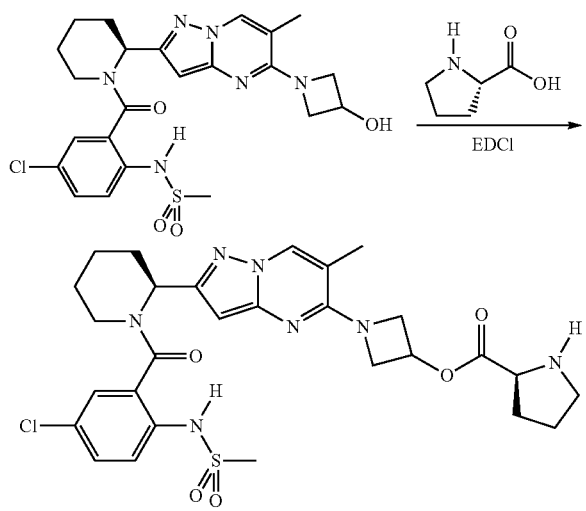

Compound 92 (25 mg, 0.05 mmol) in DCM (1 mL) was treated with (S)-proline (8 mg, 0.053 mmol), EDCI (20 mg, 0.11 mmol), and DMAP (3 mg, 0.025 mmol) and stirred for 3 h. The solution was concentrated and treated to preparatory RP-HPLC (5-100% MeCN/H$_2$O, 0.1% trifluoroacetic acid modifier) to afford compound 171 (20 mg, 66%) as a white solid:

$^1$H NMR (CD$_3$OD, 400 MHz): δ 8.61 (br s, 1H), 8.35 (br s, 1H), 7.65 (br s, 1H), 7.43 (br m, 3H), 6.05 (br m, 2H), 5.51 (br m, 2H), 4.75 (br m, 3H), 4.61 (br m, 2H), 4.37 (br m, 3H), 4.14 (br m, 2H), 3.43 (m, 3H), 2.98 (s, 3H), 2.45 (m, 2H), 2.25 (s, 3H), 2.16 (m, 2H), 2.05 (m, 2H), 1.76 (br s, 2H), 1.55 (br m, 3H), 1.23 (m, 2H).

LC-MS (ESI) m/z 617 [M+H]$^+$, t$_R$=1.82 min.
HPLC t$_R$: 3.61 min.

Compound 172

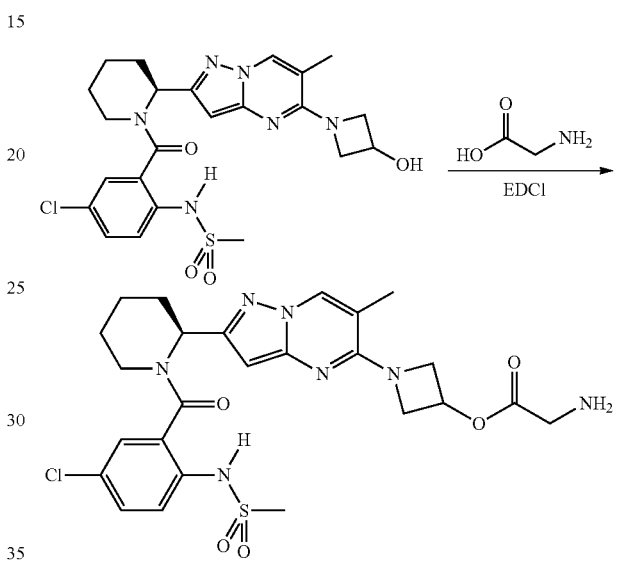

Compound 92 (50 mg, 0.10 mmol) in DCM (2 mL) was treated with glycine (8 mg, 0.11 mmol), EDCI (40 mg, 0.22 mmol), and DMAP (6 mg, 0.05 mmol) and stirred for 3 h. The solution was concentrated and treated to preparatory RP-HPLC (5-100% MeCN/H$_2$O, 0.1% trifluoroacetic acid modifier) to afford compound 172 (36 mg, 65%) as a white solid:

$^1$H NMR (CD$_3$OD, 400 MHz): δ 8.63 (br s, 1H), 8.38 (br s, 1H), 7.64 (m, 1H), 7.47 (m, 1H), 7.42 (s, 2H), 6.14 (, m, 2H), 5.45 (m, 1H), 4.70 (m, 2H), 4.32 (m, 2H), 3.94 (s, 3H), 3.23 (m, 1H), 2.99 (s, 2H), 2.22 (s, 3H), 2.01 (m, 1H), 1.70 (m, 2H), 1.54 (m, 2H).

LC-MS (ESI) m/z 577 [M+H]$^+$, t$_R$=1.84 min.
HPLC t$_R$: 3.47 min.

Compound 173

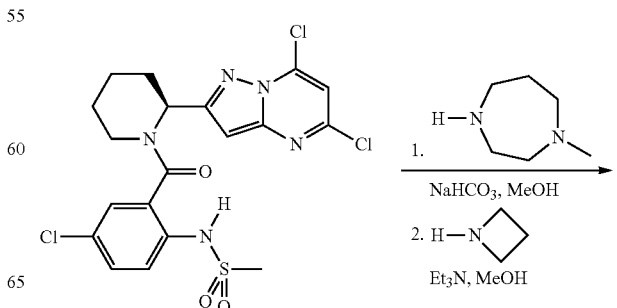

-continued

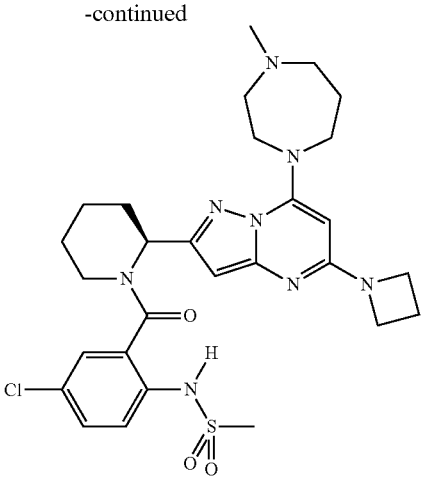

Intermediate 56 (105 mg, 0.21 mmol) in MeOH (2 mL) was treated with NaHCO$_3$ (175 mg, 2.1 mmol) and 1-methyl-1,4-diazepane (23 µL, 0.20 mmol) and stirred for 3 h. The solution was filtered and concentrated, then suspended in MeOH (2 mL) and treated with azetidine.HCl (100 mg, 1.0 mmol) and triethylamine (300 µL, 2.1 mmol). The solution is stirred at 70° C. for 18 h, then concentrated and treated to preparatory RP-HPLC (5-100% MeCN/H$_2$O, 0.1% trifluoroacetic acid modifier) to afford compound 173 (11 mg, 9%) as a white solid.

LC-MS (ESI) m/z 602 [M+H]$^+$, t$_R$=1.78 min.
HPLC t$_R$: 2.57 min.

Intermediate 135

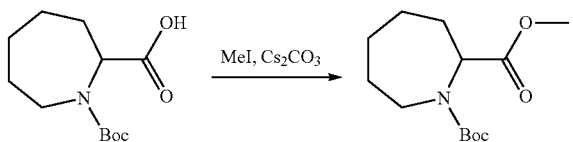 [SMILES: CC(C)(C)OC(=O)N1CCCCCC1C(=O)O ; COC(=O)C1CCCCCN1C(=O)OC(C)(C)C]

N-Boc-azepane-2-carboxylic acid (5.03 g, 20.7 mmol) in THF (40 mL) was treated with Cs$_2$CO$_3$ (7.08 g, 21.7 mmol) and MeI (2.16 mL, 34.6 mmol) and stirred for 18 h. The solution was concentrated then diluted with EtOAc (50 mL) and washed with H$_2$O (10 mL) and saturated NaCl (10 mL). The solution was dried (MgSO$_4$) and afford intermediate 135 which was used without further purification:

$^1$H NMR (CDCl$_3$, 400 MHz): δ 4.57 (m, 1H), 4.42 (m, 1H), 3.97 (m, 1H), 3.81 (m, 1H), 3.75 (s, 3H), 3.02 (m, 1H), 2.90 (m, 1H), 2.36 (m, 2H), 1.90 (m, 1H), 1.80 (m, 3H), 1.53 (s, 9H), 1.34 (m, 1H).

Intermediate 136

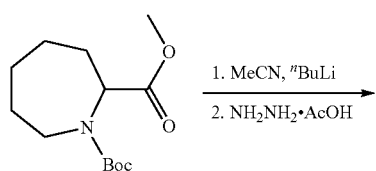

-continued

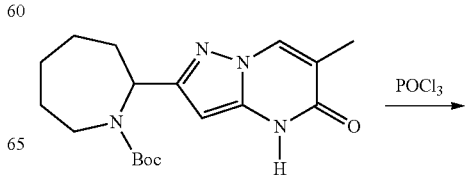

MeCN (2 mL, 38 mmol) in THF (30 mL) was cooled to −78° C. and treated with dropwise with $^n$BuLi (2.5 M, 8 mL, 20). The mixture was stirred for 30 min, and then treated dropwise with intermediate 135 (4.98 g, 19.4 mmol) in THF (30 mL) over 15 min. The mixture was stirred for 1 h, and then treated with AcOH (6 mL) in THF (30 mL). The mixture is concentrated then diluted with EtOAc (50 mL) and washed with H$_2$O (10 mL) and saturated NaCl (10 mL). The solution was dried (MgSO$_4$), concentrated, suspended in EtOH/H$_2$O (3:1, 60 mL) and treated with NH$_2$NH$_2$.AcOH (2.27 g, 24 mmol). The mixture was stirred overnight, concentrated, and then diluted with EtOAc (50 mL) and washed with H$_2$O (10 mL) and saturated NaCl (10 mL). The solution was dried (MgSO$_4$) and treated to a 80 g SiO$_2$ Combiflash HP Gold column (0-100% EtOAc-hexanes gradient) to afford intermediate 136 (3.5 g, 65%) as a white solid:

LC-MS (ESI) m/z 281 [M+H]$^+$, t$_R$=1.90 min.
HPLC t$_R$: 3.10 min.

Intermediate 137

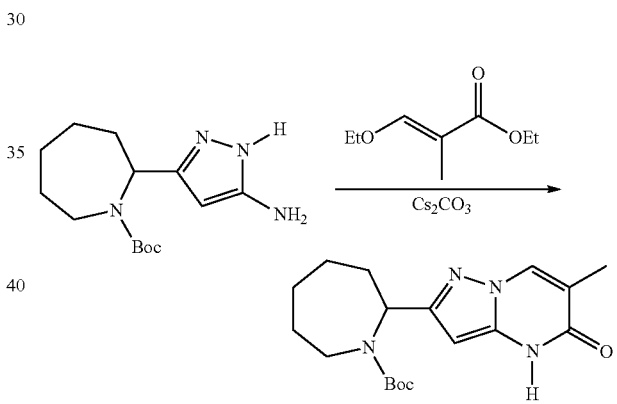

Intermediate 136 (1030 mg, 3.7 mmol) in DMF (12 mL) was treated with (E)-ethyl 3-ethoxy-2-methylacrylate (958 mg, 5.5 mmol) and Cs$_2$CO$_3$ (1.8 g, 5.5 mmol). in THF (30 mL) over 15 min. The mixture was heated at 130° C. and stirred for 18 h. The mixture was concentrated, filtered, and treated to a 80 g SiO$_2$ Combiflash HP Gold column (0-100% EtOAc-hexanes gradient) to afford intermediate 137 (525 mg, 41%) as a white solid:

LC-MS (ESI) m/z 347 [M+H]$^+$, t$_R$=2.30 min.
HPLC t$_R$: 4.12 min.

Intermediate 138

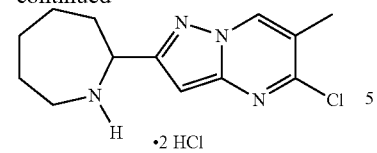

Intermediate 137 (550 mg, 1.6 mmol) in POCl₃ (6 mL) was heated at 100° C. and stirred for 3 h. The mixture was concentrated to afford intermediate 138 which was used without further purification.

Intermediate 139

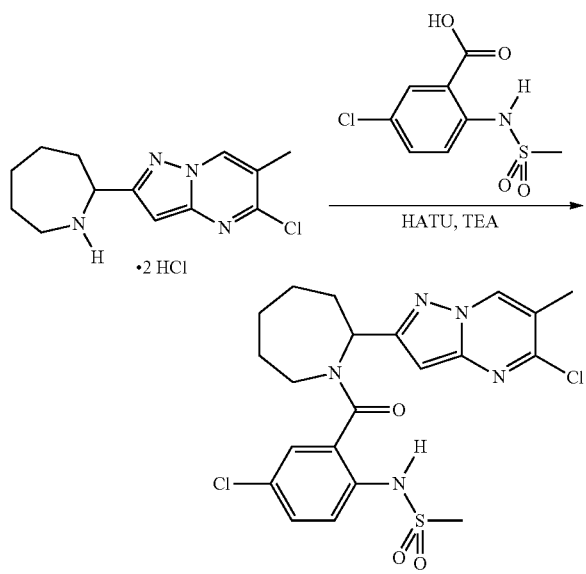

5-Chloro-2-(methylsulfonamido)benzoic acid (258 mg, 1.03 mmol) in DMF (4 mL) was treated with HATU (453 mg, 1.19 mmol) and stirred for 2 h. The solution was treated with intermediate 138 (239 mg, 0.80 mmol) and triethylamine (277 µL, 2.0 mmol) and stirred overnight. The solution was diluted with EtOAc (50 mL) and washed with H₂O (3 10 mL) and saturated NaCl (10 mL). The solution was dried (MgSO₄) and treated to a 24 g SiO₂ Combiflash HP Gold column (0-100% EtOAc-hexanes gradient) to afford intermediate 139 (120 mg, 30%) as a white solid.

Compound 174

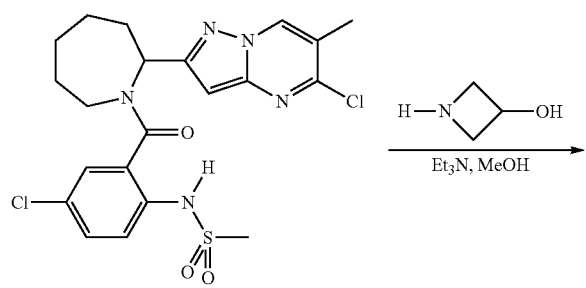

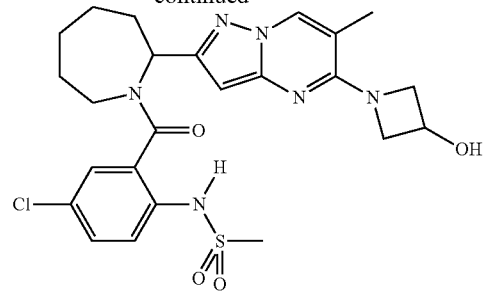

Intermediate 139 (25 mg, 0.05 mmol) in MeOH (1 mL) was treated with 3-hydroxy-azetidine (27 mg, 0.25 mmol) and triethylamine (70 µL, 0.50 mmol) stirred at 70° C. for 1 h. The solution was concentrated and treated to preparatory RP-HPLC (5-100% MeCN/H₂O, 0.1% trifluoroacetic acid modifier) to afford compound 174 (11 mg, 41%) as a white solid:

¹H NMR (CD₃OD, 400 MHz): δ 8.46 (app t, J=7.7 Hz, 1H), 8.13 (m, 1H), 7.53 (m, 2H), 7.44 (m, 1H), 7.23 (m, 1H), 5.55 (m, 1H), 3.85-4.75 (complex m, 6H), 3.10 (app t, J=16 Hz, 1H), 2.84 (app d, J=9.2 Hz, 1H), 2.29 (m, 1H), 2.16 (s, 3H), 1.80 (m, 3H), 1.26 (m, 2H).

LC-MS (ESI) m/z 534 [M+H]⁺, $t_R$=1.80 min.
HPLC $t_R$: 2.82 min.

Compound 175

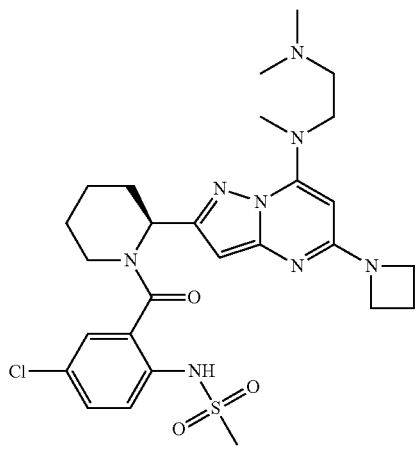 [SMILES: CN(C)CCN(C)c1cc(N2CCC2)nc2cc([C@@H]3CCCCN3C(=O)c3cc(Cl)ccc3NS(C)(=O)=O)nn12]

Used the same procedures as described for the preparation of compound 56. Isolated 175 as white powder (7.9 mg, 22%).

¹H NMR (400 MHz, CD₃OD): δ 7.55-7.38 (m, 3H), 6.35-6.02 (m, 1H), 5.18 (s, 1H), 4.45-4.25 (m, 6H), 3.67 (m, 2H), 3.26 (s, 3H), 3.20-2.95 (m, 11H), 2.57 (m, 2H), 2.35-2.10 (m, 2H), 1.85-1.65 (m, 4H).

LC/MS (m/z): 589.2 [M+H]⁺

Intermediate 140

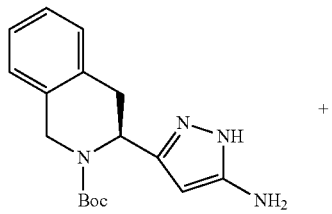

mixture was allowed to cool to room temperature. Added aqueous HCl to give pH of 3-4 and then concentrated under reduced pressure. Dissolved the resulting material with EtOAc and washed with saturated aqueous NaCl solution. Dried organic over anhydrous $Na_2SO_4$ and concentrated under reduced pressure. The crude residue was purified by preparatory HPLC (5-100% MeCN/$H_2O$, 0.1% trifluoroacetic acid modifier) to afford intermediate 140 (115 mg, 48%).

LC/MS (m/z): 397.0 $[M+H]^+$

Compound 176

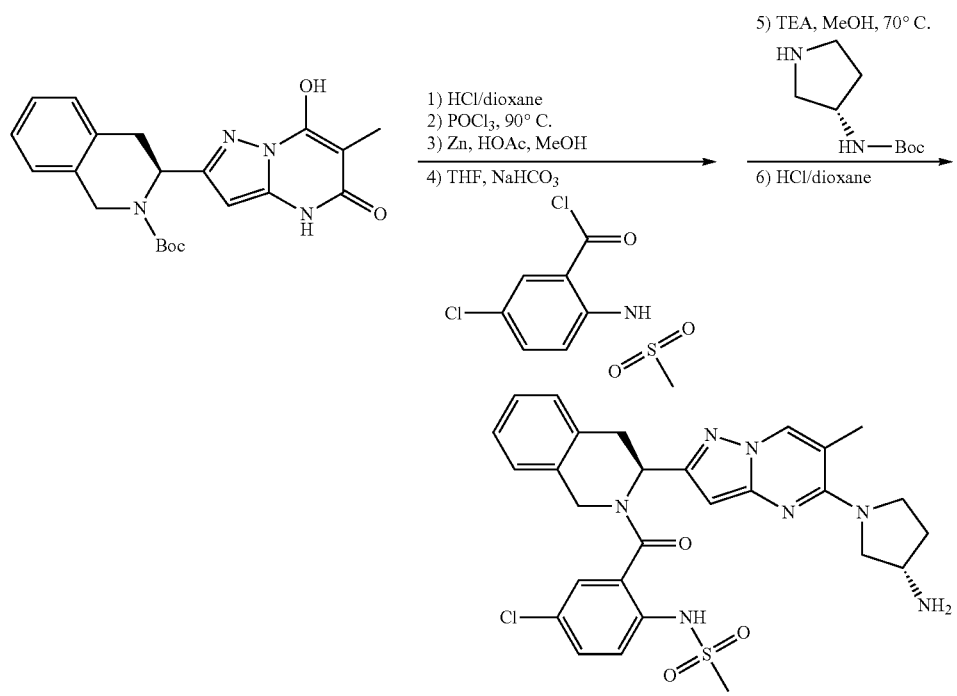

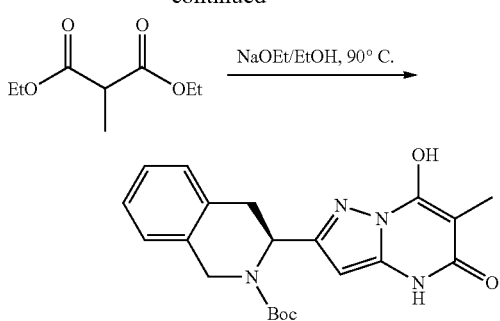

Dissolved intermediate 39 (191 mg, 0.608 mmol) in EtOH (10 mL). Added diethyl methyl malonate (207 uL, 1.22 mmol) and 21 wt % NaOEt in EtOH (454 μL, 1.217 mmol), and the reaction mixture was stirred at 90° C. for 4 h. Added more diethyl methyl malonate (207 uL, 1.22 mmol), and the reaction mixture was stirred at 90° C. for 16 h. The reaction Mixed intermediate 140 with 4N HCl in dioxane (3 mL) and stirred for 30 mins. Concentrated under reduced pressure to give solid. Mixed residue with $POCl_3$ (5 mL) and stirred at 80° C. for 16 h. Concentrated under reduced pressure. Dissolved residue in ACN and stirred in an ice bath. Added small amount of MeOH and stirred for 15 mins. Concentrated under reduced pressure. Dissolved residue in MeOH and stirred in an ice bath. Added Zinc powder (100 mg). Stirred for 30 mins. Added HOAc (50 uL) and stirred for 30 mins. Filtered off solid and washed with MeOH. Concentrated under reduced pressure. Dissolved in anhydrous THF and added $NaHCO_3$ solid. Added 5-chloro-2-(methylsulfonamido)benzoyl chloride (50 mg) and stirred for 2 h. Filtered and concentrated filtrate under reduced pressure. Purified with preparative HPLC. Dissolved material in MeOH (1 mL). Added (S)-3-(Boc-amino)pyrrolidine (60 mg) and TEA (100 uL). Stirred at 70° C. for 3 h. Concentrated under reduced pressure. Dissolved in EtOAc and washed with 5% aqueous citric acid solution. Dried organic over anhydrous $Na_2SO_4$ and concentrated under reduced pressure. Purified with preparative HPLC.

Dissolved material in 4N HCl in dioxane (2 mL) and stirred for 30 mins. Concentrated under reduced pressure and purified with preparative HPLC to afford compound 176 (1.3 mg, 0.6%).

$^1$H NMR (400 MHz, CD$_3$OD): δ 8.57-8.35 (m, 1H), 7.75-7.46 (m, 3H), 7.25-6.90 (m, 4H), 6.30 (m, 1H), 5.95-5.70 (m, 1H), 5.25-5.13 (m, 1H), 4.41-4.25 (m, 1H), 3.92-3.70 (m, 4H), 3.55-3.45 (m, 1H), 3.05-2.98 (m, 3H), 2.42-2.35 (m, 4H), 2.18-2.05 (m, 1H).

LC/MS (m/z): 580.3 [M+H]$^+$

Intermediate 141

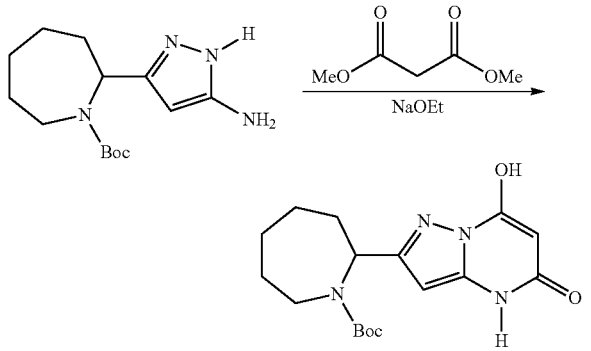

Intermediate 136 (1010 mg, 3.6 mmol) in EtOH (10 mL) was treated with dimethyl malonate (825 µL, 7.2 mmol) and NaOEt (21% in EtOH, 2.69 mL, 7.2 mmol). The solution was heated to 80° C. for 18 h then treated with AcOH (825 µL, 14.4 mmol). The solution was concentrated and diluted with EtOAc (100 mL). The solution was washed with washed with H$_2$O (10 mL) and saturated NaCl (10 mL). The solution was dried (MgSO$_4$) and treated to an 80 g SiO$_2$ Combiflash HP Gold column (0-100% EtOAc-hexanes gradient) to afford intermediate 141 (670 mg, 54%) as a white solid:

LC-MS (ESI) m/z 349 [M+H]$^+$, t$_R$=2.17 min.
HPLC t$_R$: 3.54 min.

Intermediate 142

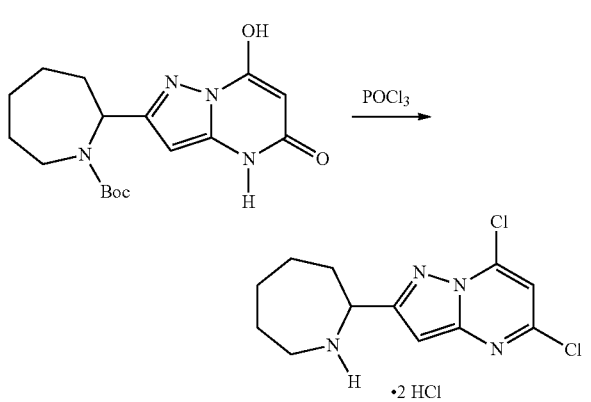

Intermediate 141 (550 mg, 1.6 mmol) was treated with POCl$_3$ (6 mL) and the solution was heated to 80° C. for 3 h.

The solution is concentrated to afford intermediate 142 as a black oil which was used without further purification.

Intermediate 143

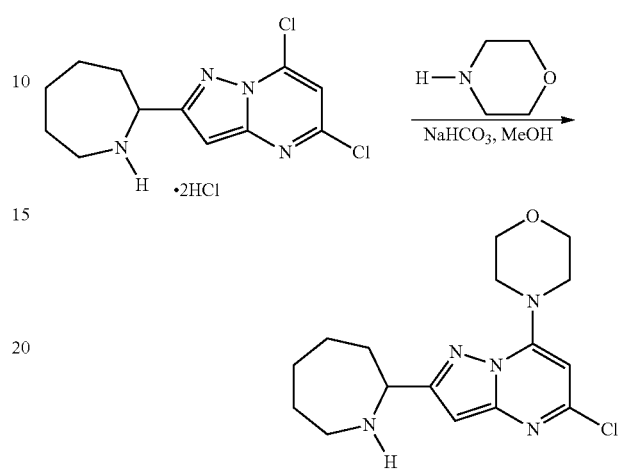

Intermediate 142 (246 mg, 0.69 mmol) in THF (20 mL) was treated with NaHCO$_3$ (1.44 g, 17.2 mmol) and morpholine (62 µL, 0.71 mmol). The solution was stirred for 18 h then filtered and concentrated. The mixture was treated to a 40 g SiO$_2$ Combiflash HP Gold column (0-100% EtOAc-hexanes gradient) to afford intermediate 143 as a white solid:

LC-MS (ESI) m/z 567 [M+H]$^+$, t$_R$=2.58 min.

Intermediate 144

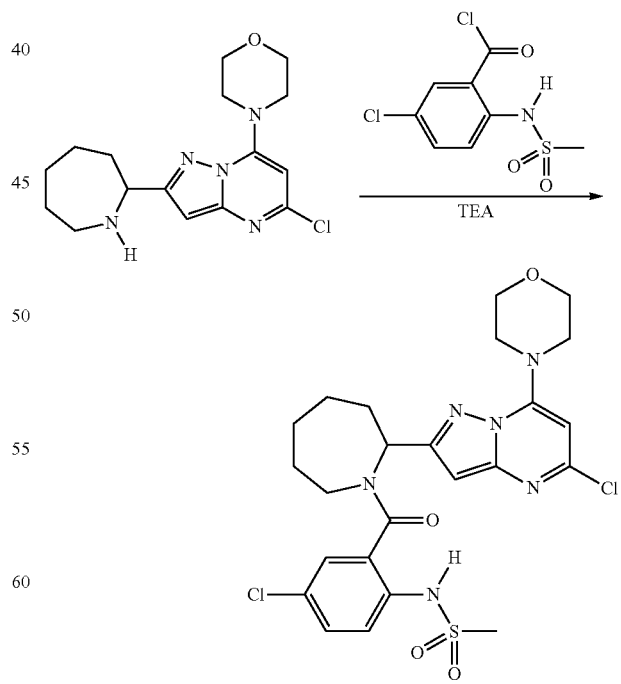

Intermediate 143 (231 mg, 0.69 mmol) in DCM (7 mL) was treated with TEA (201 µL, 1.44 mmol) and 5-chloro- 2-(methylsulfonamido)benzoyl chloride (193 mg, 0.72 mmol). The solution was stirred for 18 h and concentrated. The mixture was treated to a 40 g SiO$_2$ Combiflash HP Gold column (0-100% EtOAc-hexanes gradient) to afford intermediate 144 as a white solid:

LC-MS (ESI) m/z 567 [M+H]$^+$, t$_R$=2.58 min.

Compound 177

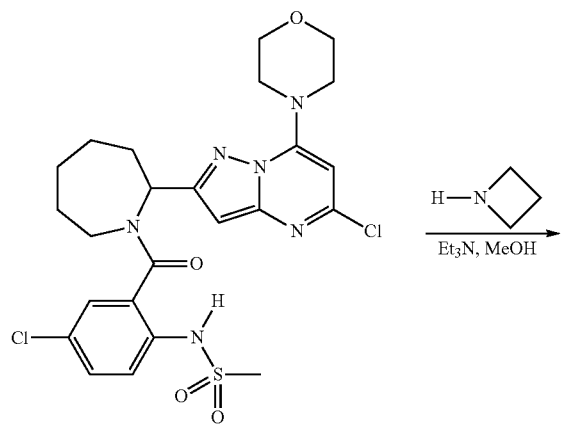

Intermediate 144 (33 mg, 0.06 mmol) in MeOH (1 mL) was treated with TEA (100 µL, 0.6 mmol) and azetidine.HCl (27 mg, 0.29 mmol). The solution was stirred at 70° C. for 18 h and concentrated. The mixture was treated to preparatory RP-HPLC (5-100% MeCN/H$_2$O, 0.1% trifluoroacetic acid modifier) to afford compound 177 (23 mg, 69%) as a white solid:

$^1$H NMR (CD$_3$OD, 400 MHz): δ 7.48 (d, J=8.4 Hz, 1H), 7.43 (m, 2H), 7.34 (s, 1H), 6.14 (s, 1H), 5.65 (m, 1H), 5.17 (app d, J=9.2 Hz, 1H), 4.67 (m, 1H), 4.28 (m, 7H), 3.87 (m, 2H), 3.81 (m, 6H), 3.60 (m, 2H), 3.40 (m, 2H), 3.17 (m, 1H), 3.13 (app t, J=12.4 Hz, 1H), 2.97 (s, 1H), 2.71 (s, 3H), 2.37 (br m, 5H), 1.34-1.94 (br m, 12H).

LC-MS (ESI) m/z 589 [M+H]$^+$, t$_R$=2.21 min.

HPLC t$_R$ (min): 3.61.

Compound 178

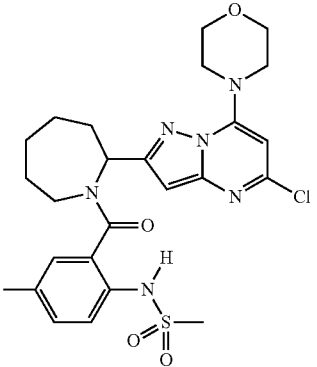

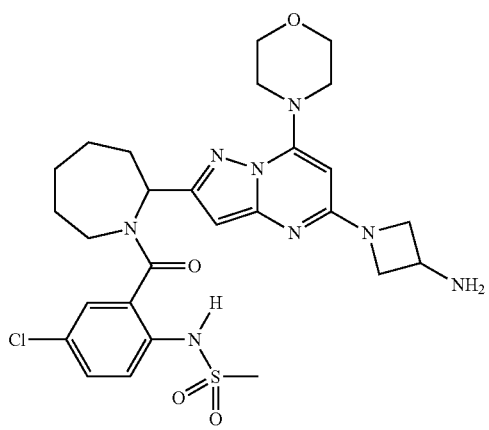

Intermediate 144 (50 mg, 0.09 mmol) in MeOH (1 mL) was treated with TEA (125 µL, 0.9 mmol) and BOC-azetidine.HCl (76 mg, 0.4 mmol). The solution was stirred at 70° C. for 2 h and concentrated. The solids are treated with 4 N HCl/dioxanes (2 mL) and stirred for 30 min. The mixture was concentrated and treated to preparatory RP-HPLC (5-100% MeCN/H$_2$O, 0.1% trifluoroacetic acid modifier) to afford compound 178 (21 mg, 40%) as a white solid:

$^1$H NMR (CD$_3$OD, 400 MHz): δ 7.53 (d, J=8.4 Hz, 1H), 7.50 (m, 2H), 7.41 (s, 1H), 7.12 (br s, 1H), 6.21 (s, 1H), 5.95 (s, 1H), 5.77 (m, 1H), 5.40 (app d, J=6.0 Hz, 1H), 4.80 (m, 1H), 4.60 (m, 4H), 4.45 (app d, J=13.6 Hz, 1H), 4.30 (m, 6H), 3.99 (m, 1H), 3.90 (m, 6H), 3.71 (m, 1H), 3.65 (m, 1H), 3.49 (m, 1H), 3.25 (app t, J=11.6 Hz, 1H), 3.03 (s, 1H), 2.74 (s, 3H), 2.50 (m, 1H), 2.40 (m, 1H), 1.43-1.98 (br m, 12H).

LC-MS (ESI) m/z 604 [M+H]$^+$, t$_R$=1.70 min.

HPLC t$_R$ (min): 3.08.

Intermediate 145

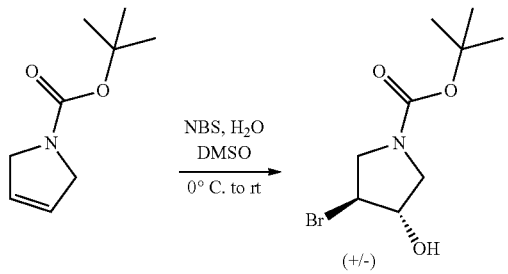

A solution of tert-butyl 2,5-dihydro-1H-pyrrole-1-carboxylate (955 mg, 5.64 mmol) in 7 mL of DMSO and 0.3 mL of water was cooled to 0° C. NBS (1.51 g, 8.44 mmol) was added slowly over eight minutes and then reaction mixture was warmed to room temperature. After four hours, mixture was poured into 100 mL of ice water and extracted with ethyl acetate (2×70 mL). Combined organics were washed with 100 mL of water and 100 mL of brine, then dried (MgSO$_4$), filtered, and concentrated under reduced pressure to yield intermediate 145 (1.48 g, 99%) as a yellow film, which was used in the next step without further purification.

$^1$H NMR (CDCl$_3$, 400 MHz): δ 4.46 (m, 1H), 4.15 (m, 1H), 4.02 (dd, J=5.2 Hz, 13 Hz), 3.81 (m, 2H), 3.40 (m, 1H), 1.46 (s, 9H)

Intermediate 146

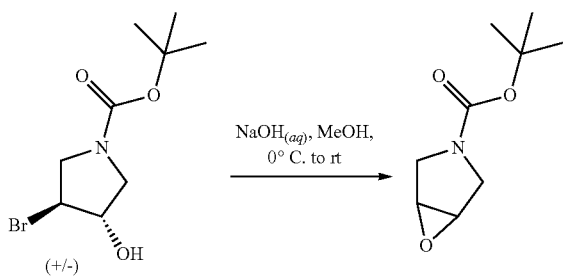

To a solution of intermediate 145 (467 mg, 1.75 mmol) in 7 mL of methanol at 0° C., was slowly added a 1.0 N aqueous solution of NaOH (2.4 mL, 2.4 mmol). Reaction mixture was warmed to room temperature and stirred overnight. Methanol was then concentrated under reduced pressure and 20 mL of water was added. Aqueous was extracted with ethyl acetate (3×25 mL) and combined organics were washed with 50 mL of brine, then dried (MgSO$_4$), filtered, and concentrated under reduced pressure to yield intermediate 146 (1.48 g, 99%) as a colorless oil, which was used in the next step without further purification.

$^1$H NMR (CDCl$_3$, 400 MHz): δ 3.80 (d, J=12.8 Hz, 1H), 3.73 (d, J=12.8 Hz), 3.65 (d, J=3.2 Hz, 2H), 3.31 (d, J=4.8 Hz, 1H), 3.28 (d, J=4.8 Hz, 1H), 1.43 (s, 9H)

Intermediate 147

A solution of diethylaluminum cyanide in toluene (1.0 M, 3.3 mL, 3.3 mmol) was added slowly to a solution of intermediate 146 (298 mg, 1.61 mmol) in 9 mL of toluene at room temperature. After stirring overnight, reaction mixture was quenched carefully (caution: exothermic) by slow addition of 1.0 N solution of NaOH$_{(aq)}$ and then diluted with 15 mL of water. Aqueous was extracted with ethyl acetate (2×60 mL) and combined organics were washed with water (2×60 mL) and 60 mL of brine, then dried (MgSO$_4$), filtered, and concentrated under reduced pressure to yield intermediate 147 (314 mg, 85%) as a light yellow oil, which was used in the next step without further purification.

$^1$H NMR (CDCl$_3$, 400 MHz): δ 4.63 (m, 1H), 3.80-3.61 (m, 3H), 3.36 (m, 1H), 3.05 (m, 1H), 2.64 (br s, 1H), 1.47 (s, 9H)

Compound 179

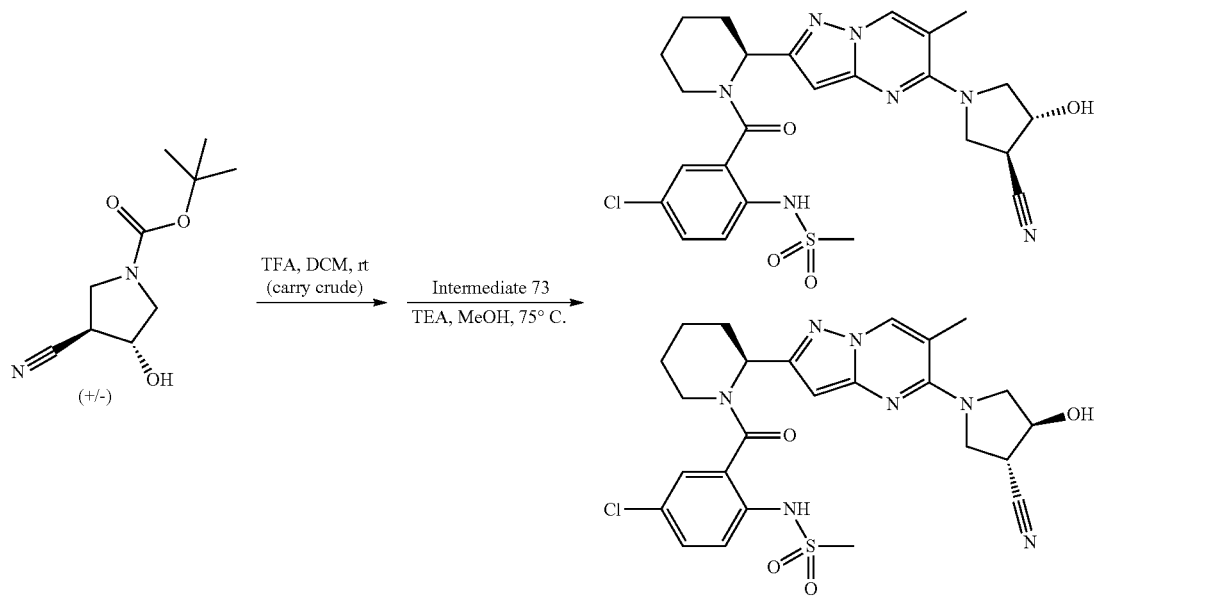

Trifluoroacetic acid (3.6 mL, 47.6 mmol) was added to a solution of tert-butyl 3-cyano-4-hydroxypyrrolidine-1-carboxylate (287 mg, 1.36 mmol) in 30 mL of dichloromethane. After stirring overnight, reaction mixture was concentrated under reduced pressure and dried in vacuo for 2 hours yielding a brown film. This was combined with intermediate 73 (320 mg, 0.664 mmol) and solids were taken up in 24 mL of anhydrous methanol. To this mixture was added triethylamine (0.28 mL, 2.01 mmol) and mixture was heated at 75° C. overnight. After cooling to room temperature, reaction mixture was concentrated under reduced pressure and purified by prep HPLC (15-100% Acetonitrile (with 0.1% trifluoroacetic acid) in water (with 0.1% trifluoroacetic acid)) to yield compound 179 (mixture of 2 trans isomers) (200 mg, 45%) as a white solid, trifluoroacetic acid salt, after lyophilization.

$^1$H-NMR (DMSO, 400 MHz): δ 9.22 (s, 1H) 8.53 (s, 1H), 7.50 (m, 2H), 7.41 (m, 1H), 6.15 (s, 1H), 5.94 (m, 2H), 4.51 (m, 1H), 3.98 (m, 3H), 3.86 (m, 1H), 3.52 (m, 1H), 3.22 (m, 2H), 3.05 (m, 1H), 3.03 (s, 3H), 2.31 (s, 3H), 1.89 (m, 1H), 1.68-1.22 (m, 4H).

LCMS m/z [M+H]$^+$ C$_{25}$H$_{28}$ClN$_7$O$_4$S requires: 558.16. Found 558.36

HPLC Tr (min), purity %: 6.54, 95%~1:1 mixture of diastereomers.

Compound 180

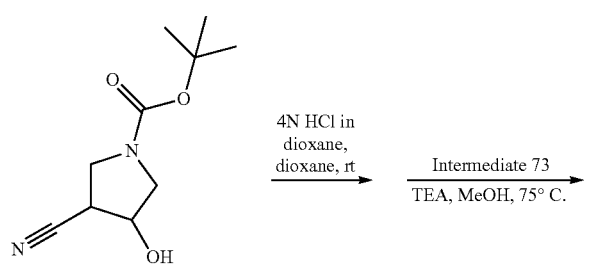

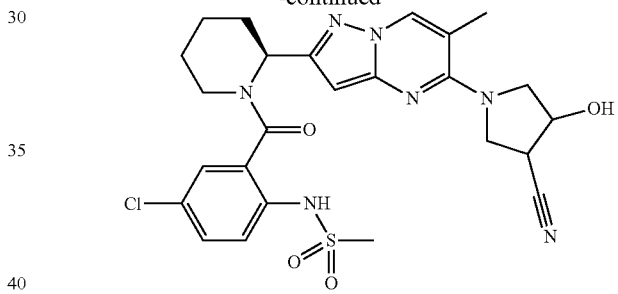

A dioxane solution of commercially available (+/−) cis and trans tert-butyl 3-cyano-4-hydroxypyrrolidine-1-carboxylate (129 mg, 0.87 mmol) and 4.2 mL of 4N HCl in dioxane was stirred for eighteen hours. After removal of the solvent by concentration under reduced pressure, resulting residue was treated with intermediate 73 (41.4 mg, 0.0858 mmol) and triethylamine (0.23 mL, 1.66 mmol) in accordance with the previous example of compound 179. Purification with prep HPLC (15-100% Acetonitrile (with 0.1% trifluoroacetic acid) in water (with 0.1% trifluoroacetic acid)) to yield compound 180 (mixture of isomers) (32 mg, 55%) as a white solid, trifluoroacetic acid salt, after lyophilization.

$^1$H-NMR (DMSO, 400 MHz): δ 9.22 (s, 1H) 8.53 (s, 1H), 7.52-7.41 (m, 3H), 6.15 (s, 1H), 5.96 (m, 1H), 4.49 (m, 1H), 3.98 (m, 2H), 3.86 (m, 2H), 3.49 (m, 3H), 3.20 (m, 1H), 3.08 (m, 1H), 3.03 (s, 3H), 2.36 (s, 3H), 1.86 (m, 1H), 1.77-1.25 (m, 4H).

LCMS m/z [M+H]$^+$ C$_{25}$H$_{28}$ClN$_7$O$_4$S requires: 558.16. Found 558.35

HPLC Tr (min), purity %: 6.45, 6.58, 99% as a mixture of four diastereomers.

Intermediate 148

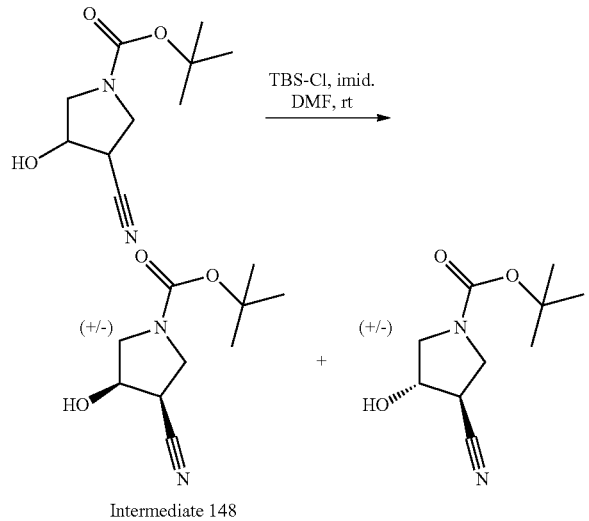

Intermediate 148

Tert-butyldimethylsilyl chloride (783 mg, 5.19 mmol) was added to a solution of (+/−) cis and trans tert-butyl 3-cyano-4-hydroxypyrrolidine-1-carboxylate (1.00 g, 4.72 mmol) and imidazole (390 mg, 5.73 mmol) in 5 mL of DMF at room temperature. After stirring overnight, TLC indicated near complete consumption of starting material. Reaction mixture was poured into 50 mL of 1:1 water/brine and extracted with ethyl acetate (3×40 mL). Combined organics were washed with 100 mL of water then 100 mL of brine, dried (Na2SO4), filtered and concentrated under reduced pressure. Residue was purified by silica gel column chromatography (0-40% ethyl acetate in hexanes) to yield the desired (+/−) cis-isomer intermediate 148 as a white solid (664 mg, 43%) and the (+/−) trans isomer as a clear oil side product (778 mg, 51%), (WO2006 066896 A2)

$^1$H-NMR of cis (+/−) isomer (CDCl$_3$, 400 MHz): δ 4.48 (m, 1H), 3.73 (m, 1H), 3.65 (m, 1H), 3.51-3.27 (m, 2H), 3.00 (m, 1H), 1.46 (s, 9H), 0.92 (s, 9H), 0.17 (s, 3H), 0.13 (s, 3H).

Intermediate 149

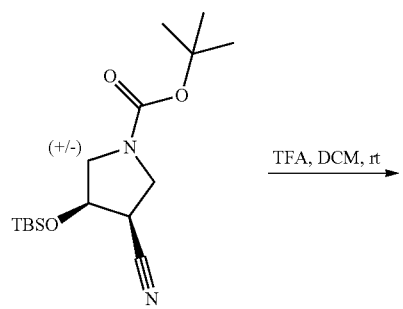

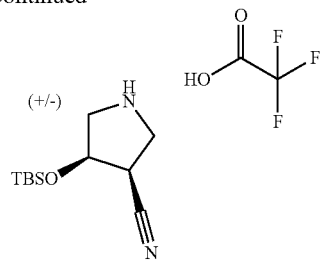

Trifluoroacetic acid (3.6 mL, 47.6 mmol) was added to a solution of intermediate 148 isomers (620 mg, 1.90 mmol) in 40 mL of dichloromethane. After stirring four hours, reaction mixture was concentrated under reduced pressure and dried in vacuo for 2 hours yielding intermediate 149 as a clear oil (mixture of isomers) (633 mg, 98%), which was used in the next step without further purification.

$^1$H-NMR (CDCl$_3$, 400 MHz): δ 9.65 (br s, 1H), 9.12 (br s, 1H), 4.72 (m, 1H), 3.83 (m, 1H), 3.69 (m, 1H), 3.47 (m, 1H), 3.37-3.31 (m, 2H), 0.93 (s, 9H), 0.22 (s, 3H), 0.17 (s, 3H).

Intermediate 150

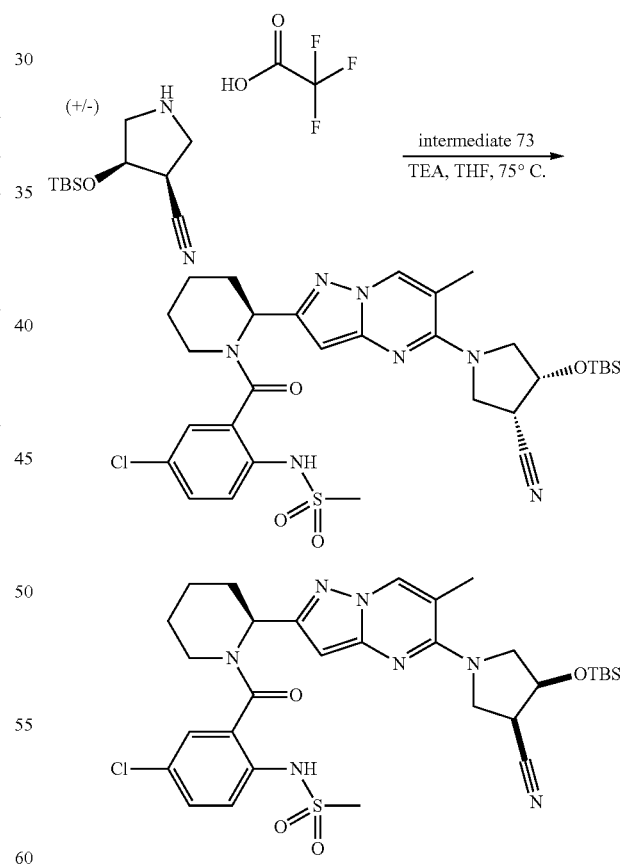

Following the procedure of compound 179, beginning with intermediate 149 (367 mg, 0.761 mmol) and intermediate 73 (620 mg, 1.82 mmol) in 24 mL of anhydrous THF, intermediate 150 was recovered after silica gel column chromatography (15-50% ethyl acetate in hexanes) as a white solid (289 mg, 57%, mixture of two isomers shown)

LCMS m/z [M+H]+ $C_{31}H_{42}ClN_7O_4SSi$ requires: 672.25. Found 672.46

Compound 181

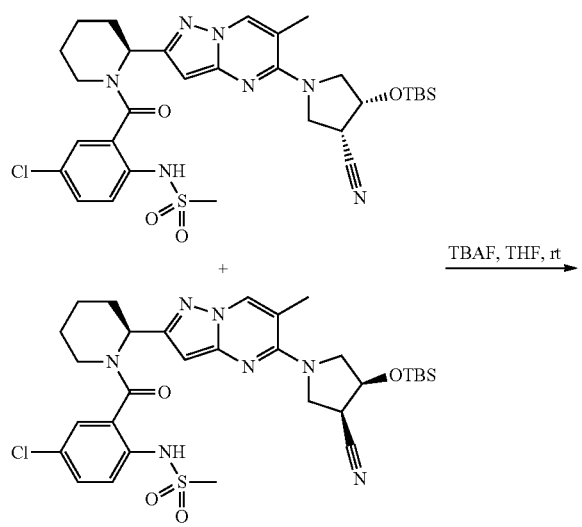

A solution TBAF in THF (1.0 M, 0.6 mL, 0.6 mmol) was added slowly to a solution of intermediate 150 (258 mg, 0.384 mmol) in 5 mL of THF at room temperature. After stirring overnight, reaction mixture was concentrated under reduced pressure and residue was purified by silica gel column chromatography (15-75% ethyl acetate in hexanes) to yield compound 181 as a white solid (+/− cis isomers shown) (98 mg, 46%)

$^1$H-NMR (DMSO, 400 MHz): δ 9.22 (s, 1H), 8.52 (m, 1H), 7.53-7.39 (m, 3H), 6.14 (s, 1H), 5.95 (m, 1H), 4.48 (m, 1H), 4.01 (m, 2H), 3.86 (m, 2H), 3.61-3.27 (m, 3H), 3.19 (m, 1H), 3.04 (m, 1H), 3.02 (s, 3H), 2.30 (s, 3H), 1.83 (m, 1H), 1.70-1.22 (m, 4H).

LCMS m/z [M+H]+ $C_{25}H_{28}ClN_7O_4S$ requires: 558.16. Found 558.35

HPLC Tr (min), purity %: 99% as a mixture of two diastereomers

Intermediate 151

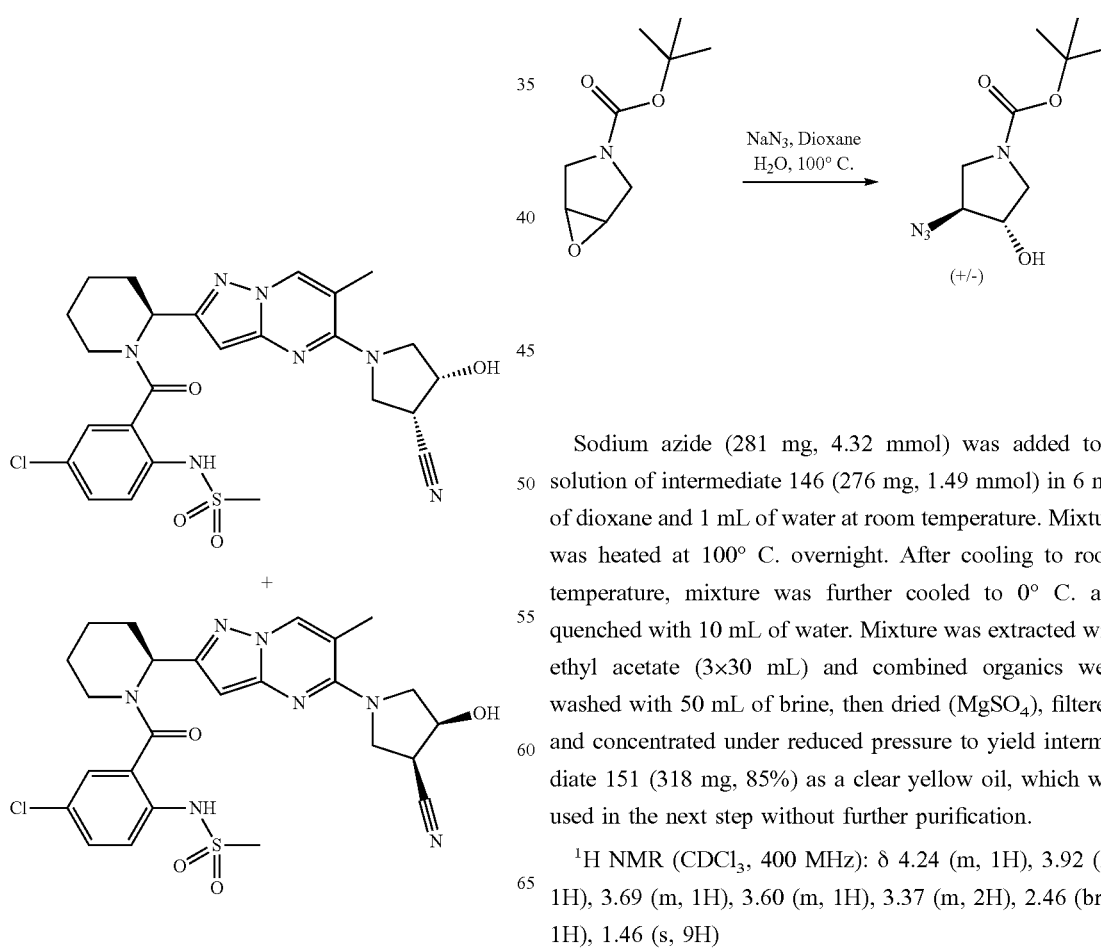

Sodium azide (281 mg, 4.32 mmol) was added to a solution of intermediate 146 (276 mg, 1.49 mmol) in 6 mL of dioxane and 1 mL of water at room temperature. Mixture was heated at 100° C. overnight. After cooling to room temperature, mixture was further cooled to 0° C. and quenched with 10 mL of water. Mixture was extracted with ethyl acetate (3×30 mL) and combined organics were washed with 50 mL of brine, then dried (MgSO$_4$), filtered, and concentrated under reduced pressure to yield intermediate 151 (318 mg, 85%) as a clear yellow oil, which was used in the next step without further purification.

$^1$H NMR (CDCl$_3$, 400 MHz): δ 4.24 (m, 1H), 3.92 (m, 1H), 3.69 (m, 1H), 3.60 (m, 1H), 3.37 (m, 2H), 2.46 (br s, 1H), 1.46 (s, 9H)

Compound 182

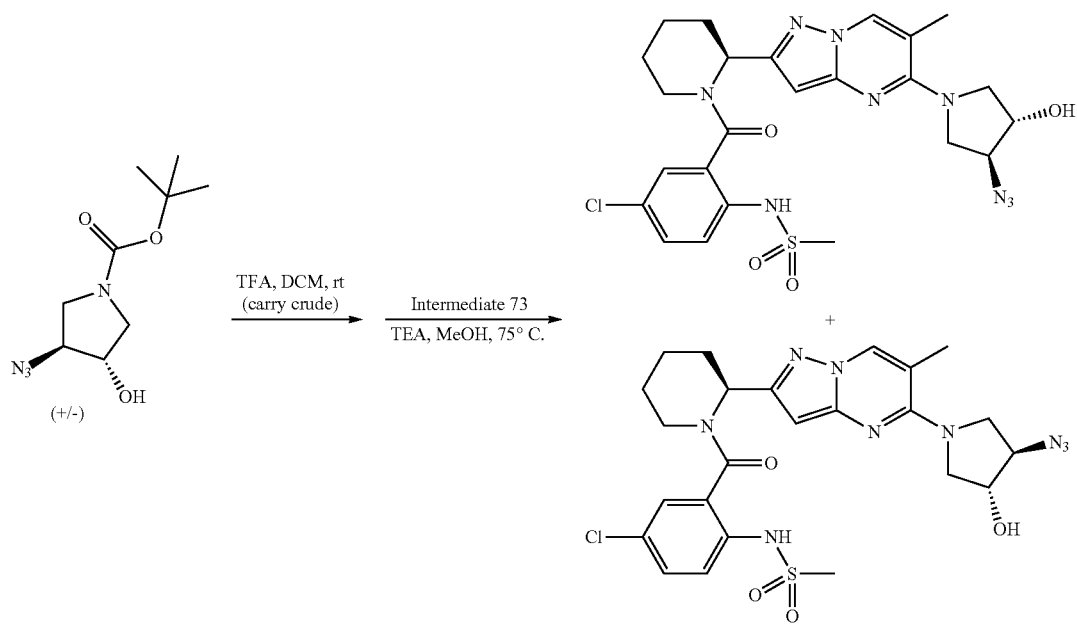 [SMILES: CC(C)(C)OC(=O)N1C[C@H](N=[N+]=[N-])[C@@H](O)C1 ; Cc1cn2nc([C@@H]3CCCCN3C(=O)c3cc(Cl)ccc3NS(C)(=O)=O)cc2nc1N1C[C@@H](O)[C@H](N=[N+]=[N-])C1 ; Cc1cn2nc([C@@H]3CCCCN3C(=O)c3cc(Cl)ccc3NS(C)(=O)=O)cc2nc1N1C[C@H](N=[N+]=[N-])[C@@H](O)C1]

Trifluoroacetic acid (3.3 mL, 42.7 mmol) was added to a solution of intermediate 151 (270 mg, 1.18 mmol) in 25 mL of dichloromethane. After stirring overnight, reaction mixture was concentrated under reduced pressure and dried in vacuo for 2 hours yielding a brown film. This was combined with intermediate 73 (230 mg, 0.477 mmol) and solids were taken up in 14 mL of anhydrous methanol. To this mixture was added triethylamine (0.33 mL, 2.36 mmol) and mixture was heated at 75° C. overnight. After cooling to room temperature, reaction mixture was concentrated under reduced pressure and purified by silica gel column chromatography (15-80% Ethyl Acetate in Hexanes) to yield compound 182 (222 mg, 82%) as a white solid and mixture of 2 trans isomers.

$^1$H-NMR (DMSO, 400 MHz): δ 9.23 (s, 1H) 8.50 (s, 1H), 7.54-7.30 (m, 3H), 6.12 (s, 1H), 5.95 (m, 1H), 5.63 (d, 1H), 4.17 (m, 1H), 4.09 (m, 1H), 4.00-3.83 (m, 2H), 3.60 (m, 1H), 3.51 (m, 1H), 3.21 (m, 1H), 3.08 (m, 1H), 3.04 (s, 3H), 2.32 (m, 1H), 2.31 (s, 3H), 1.86 (m, 1H), 1.55-1.15 (m, 4H).

LCMS m/z [M+H]$^+$ $C_{24}H_{28}ClN_9O_4S$ requires: 574.17. Found 574.45

HPLC Tr (min), purity %: 6.67, 99%, ~1:1 mixture of diastereomers.

Compound 183

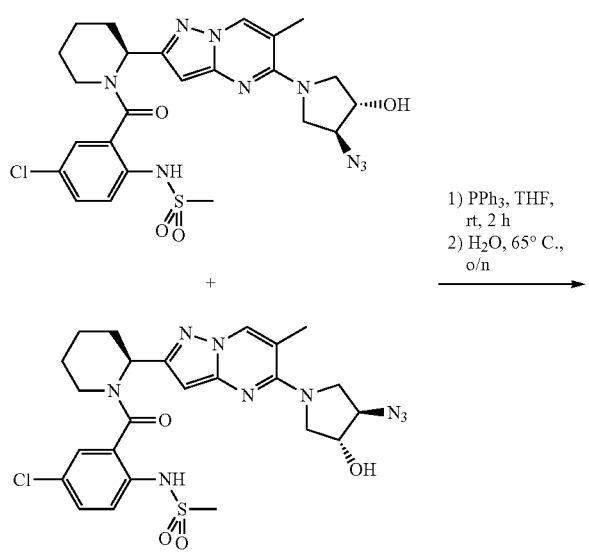

1) PPh$_3$, THF, rt, 2 h
2) H$_2$O, 65° C., o/n

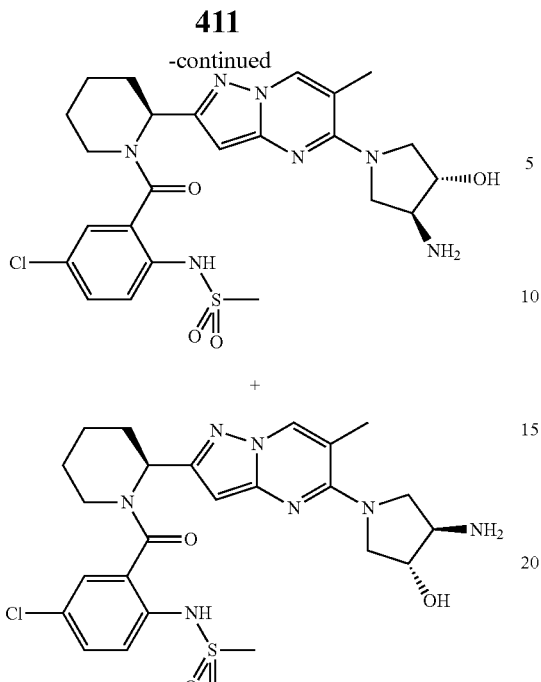

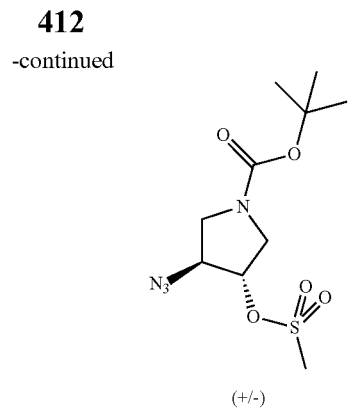

(+/-)

Methanesulfonyl chloride (0.08 mL, 1.04 mmol) was added to a solution of intermediate 151 (200 mg, 0.876 mmol) and triethylamine (0.16 mL, 1.14 mmol) in 8 mL of dichloromethane at 0° C. After warming to room temperature, reaction mixture was stirred overnight and then quenched with 15 mL of water. Mixture was separated and aqueous was extracted with ethyl acetate (3×25 mL). Combined organics were washed with 50 mL of water and brine, then dried (MgSO₄), filtered, and concentrated under reduced pressure to yield intermediate 152 (244 mg, 91%) as a brown oil, which was used in the next step without further purification.

$^1$H-NMR (CDCl$_3$, 400 MHz): δ 4.96 (m, 1H), 4.25 (m, 1H), 3.80-3.45 (m, 4H), 3.09 (s, 3H), 1.47 (s, 9H)

Intermediate 153

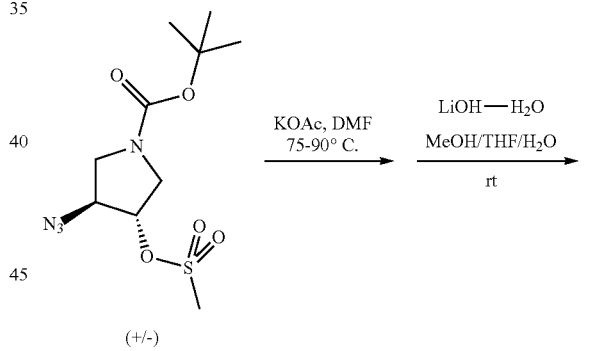

Triphenylphosphine (201 mg, 0.767 mmol) was added to a solution of compound 182 in 9 mL of THF at room temperature. After 2 hours, 0.5 mL of water was added and mixture was heated at 65° C. overnight. After cooling to room temperature, solvents were concentrated under reduced pressure and remaining residue was purified by prep HPLC (10-100% Acetonitrile (with 0.1% trifluoroacetic acid) in water (with 0.1% trifluoroacetic acid)) to yield compound 183 (mixture of trans isomers) as a white solid, trifluoroacetic acid salt (35 mg, 82%), after lyophilization.

$^1$H-NMR (DMSO, 400 MHz): δ 9.23 (s, 1H), 8.53 (s, 1H), 8.10 (s, 3H), 7.56-7.37 (m, 3H), 6.14 (s, 1H), 5.96 (m, 1H), 4.27 (m, 1H), 4.05 (m, 1H), 3.94 (m, 1H), 3.69-3.56 (m, 1H), 3.21 (m, 1H), 3.04-3.02 (m, 2H), 3.03 (s, 3H), 2.33 (s, 1H), 2.32 (s, 3H), 1.87 (m, 1H), 1.68-1.21 (m, 4H).

LCMS m/z [M+H]$^+$ C$_{24}$H$_{28}$ClN$_9$O$_4$S requires: 548.18. Found 548.16

HPLC Tr (min), purity %: 5.22, 99%, ~1:1 mixture of diastereomers.

Intermediate 152

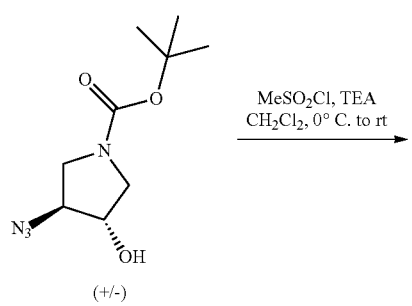

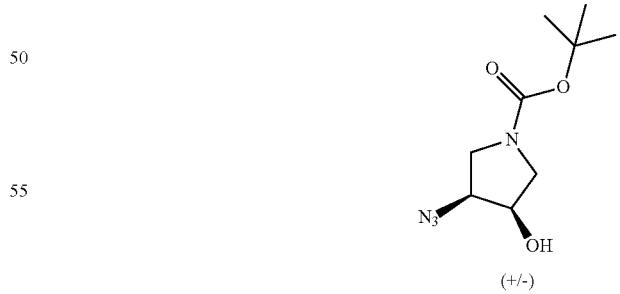

Potassium acetate (165 mg, 1.68 mmol) was added to a solution of intermediate 152 (240 mg, 0.784 mmol) in 6 mL of DMF at room temperature. Mixture was heated at 75° C. overnight. LC/MS analysis indicated ~20% displacement to azido acetate. Additional potassium acetate (920 mg) was added and mixture was heated at 90° C. overnight. Mixture was poured into 50 mL of 1:1 water/brine and aqueous was extracted with ethyl acetate (3×35 mL). Combined organics were washed with 50 mL of brine, then dried (MgSO₄), filtered, and concentrated under reduced pressure to yield a brown film. Film was dissolved in a 1:1:1 mixture of methanol/THF/water and LiOH—H₂O (80 mg, 1.91 mmol) was added at room temperature. After stirring eighteen hours, mixture was quenched with sat. $NH_4Cl_{(aq)}$ and extracted with ethyl acetate (3×20 mL). Combined organics were washed with 30 mL of water and brine, then dried (MgSO₄), filtered, and concentrated under reduced pressure to yield intermediate 153 (179 mg, 50%) as a brown oil in ~1:1 mixture with 152, which was used in the next step without further purification.

¹H-NMR (CDCl₃, 400 MHz): δ 4.35 (m, 1H), 4.02 (m, 1H), 3.55-3.33 (m, 4H), 2.13 (br s, 1H), 1.46 (s, 9H)

Compound 184

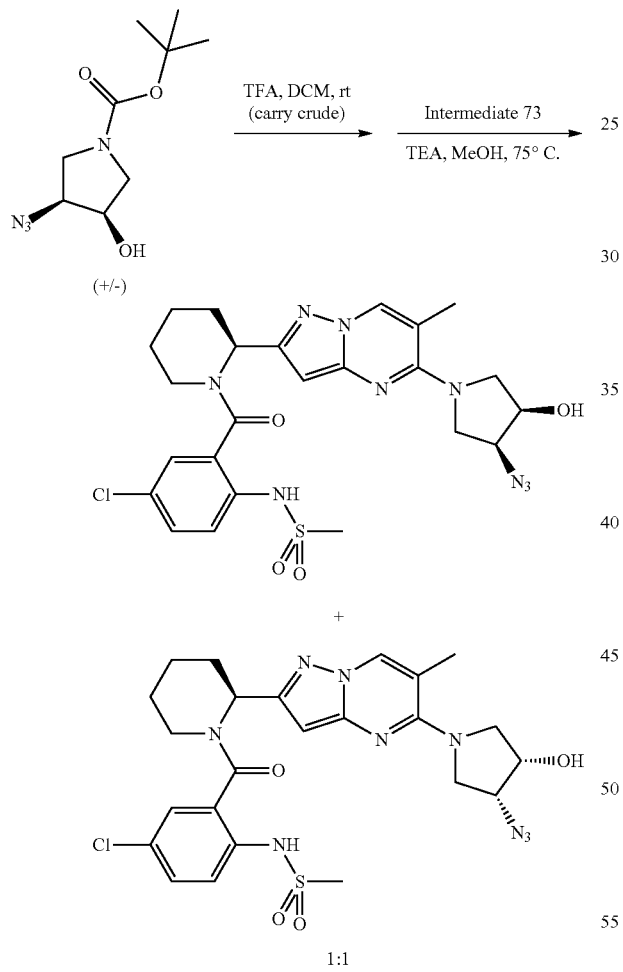

1:1

Following the procedure for the synthesis of compound 182, starting with intermediate 153 (166 mg, 0.727 mmol, 50% purity) then intermediate 73 (117 mg, 0.243 mmol) and triethylamine (0.3 mL, 2.17 mmol), compound 184 was recovered as a white solid (100 mg, 73%) after silica gel chromatography (20-70% ethyl acetate in hexanes).

¹H-NMR (DMSO, 400 MHz): δ 9.22 (s, 1H) 8.49 (s, 1H), 7.55-7.38 (m, 3H), 6.11 (s, 1H), 5.95 (m, 1H), 5.74 (d, 1H), 4.41 (m, 1H), 4.04 (m, 1H), 3.84 (m, 1H), 3.60 (m, 1H), 3.21 (m, 1H), 3.05 (m, 1H), 3.03 (s, 3H), 2.33 (s, 3H), 2.32 (m, 2H), 1.87 (m, 1H), 1.71-1.22 (m, 5H)

LCMS m/z [M+H]⁺ C₂₄H₂₈ClN₉O₄S requires: 574.17. Found 574.15

HPLC Tr (min), purity %: 6.57, 90%, ~1:1 mixture of diastereomers.

Compound 185

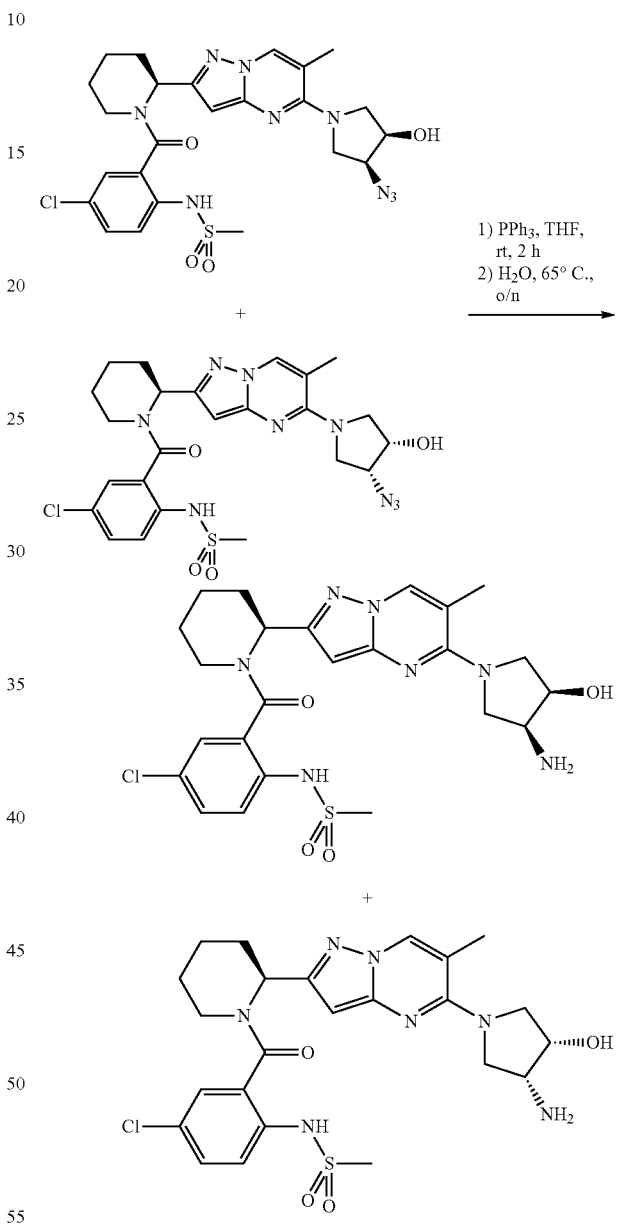

Following the procedure for the synthesis of compound 185, starting with compound 184 (90 mg, 0.157 mmol), compound 185 was synthesized as a white solid trifluoroacetic acid salt (73 mg, 70%) after lyophilization.

¹H-NMR (DMSO, 400 MHz): δ 9.23 (s, 1H) 8.52 (m, 1H), 8.17 (s, 3H), 7.54-7.35 (m, 3H), 6.13 (s, 1H), 5.94 (m, 1H), 4.39 (m, 1H), 3.96-3.80 (m, 2H), 3.79-3.61 (m, 3H), 3.21 (m, 1H), 3.04 (m, 1H), 3.03 (s, 3H), 2.35 (s, 3H), 1.87 (m, 1H), 1.72-1.22 (m, 4H).

LCMS m/z [M+H]⁺ C₂₄H₂₈ClN₉O₄S requires: 548.18. Found 548.15

HPLC Tr (min), purity %: 5.22, 99%, ~1:1 mixture of diastereomers.

Intermediate 154

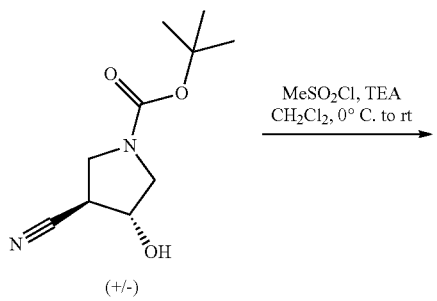

(+/-)

Following the synthesis of intermediate 152, beginning with intermediate 147 (175 mg, 0.829 mmol), intermediate 154 was synthesized as a yellow film (240 mg, 98%) and used in the next step without further purification $^1$H-NMR (CDCl$_3$, 400 MHz): δ 5.41 (m, 1H), 3.92 (m, 1H), 3.80 (m, 2H), 3.67 (m, 1H), 3.44 (m, 1H), 3.12 (s, 3H), 1.47 (s, 9H).

Intermediate 155

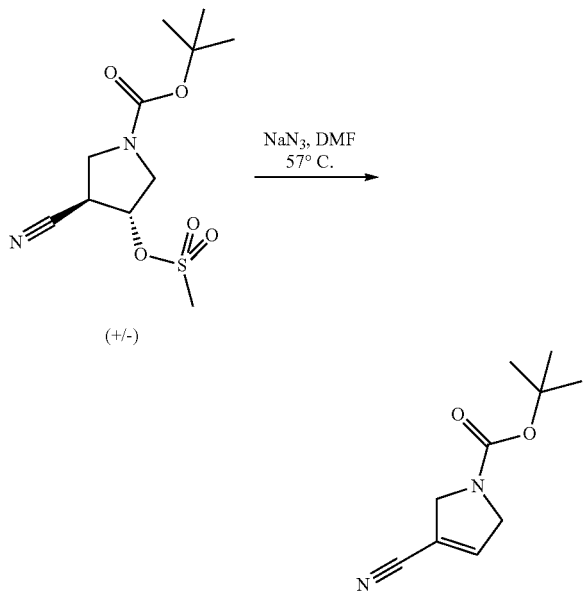

A mixture of intermediate 154 (300 mg, 1.03 mmol) and sodium azide (108 mg, 1.66 mmol) in 3 mL of DMF was heated at 57° C. overnight. After cooling to room temperature, reaction mixture was quenched with 30 mL of cold water and extracted with ethyl acetate (3×30 mL). Combined organics were washed with water (2×50 mL) and brine (1×500 mL), dried (MgSO$_4$), filtered and concentrated to yield intermediate 155 as a yellow creamy solid (190 mg, 95%) that was used in the next step without further purification.

$^1$H-NMR (CDCl$_3$, 400 MHz): δ 6.65 (m, 1H), 4.30 (m, 4H), 1.48 (s, 9H).

Intermediate 156

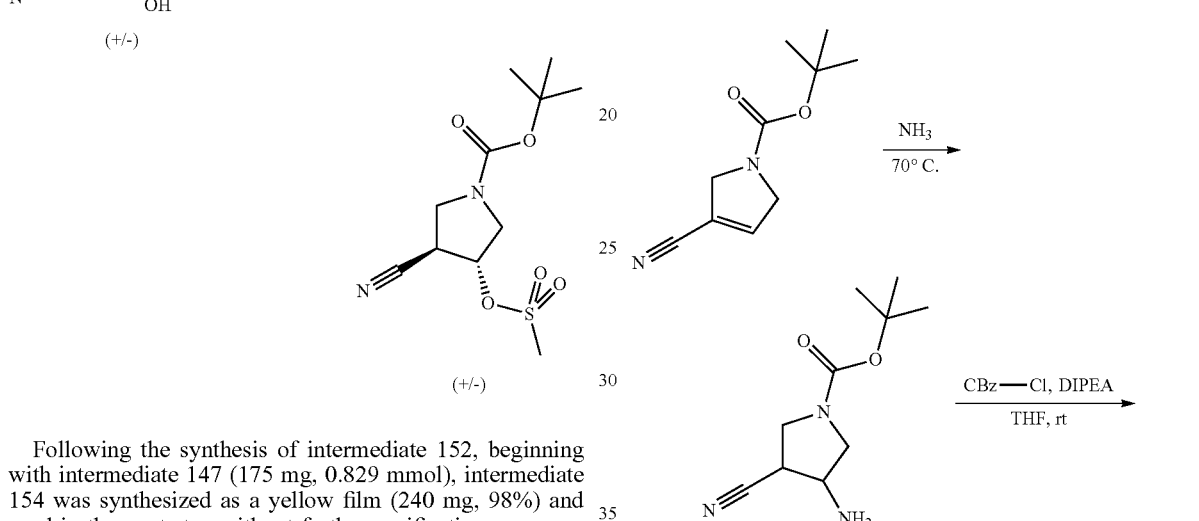

Liquid ammonia (5 mL) was added at −78° C. to intermediate 155 (119 mg, 0.611 mmol) in a bomb apparatus. Mixture was heated at 80° C. under pressure overnight. After cooling to room temperature, reaction mixture was indicated as complete by LC/MS. Mixture was evaporated and residue was dissolved in 6 mL of THF. Diisopropylethylamine (0.15 mL, 0.733 mmol) and CBz-chloride (0.100 mL, 0.68 mmol) were then added and mixture stirred at room temperature overnight. Solvents were then removed under reduced pressure and residue was dissolved in ethyl acetate and washed with water and brine. Organics were dried (MgSO$_4$), filtered and concentrated under reduced pressure. Residue was then purified by silica gel column chromatography (0-100% ethyl acetate in hexanes) to yield intermediate 156 as a clear film (158 mg, 73%) (mixture of isomers).

$^1$H-NMR (CDCl$_3$, 400 MHz): δ 7.41-7.28 (m, 5H), 5.21 (s, 1H), 5.11 (s, 2H), 4.71 (br s, 1H), 4.40 (m, 1H), 3.78-3.57 (m, 3H), 3.42-3.18 (m, 2H), 1.45 (s, 9H).

Intermediate 157

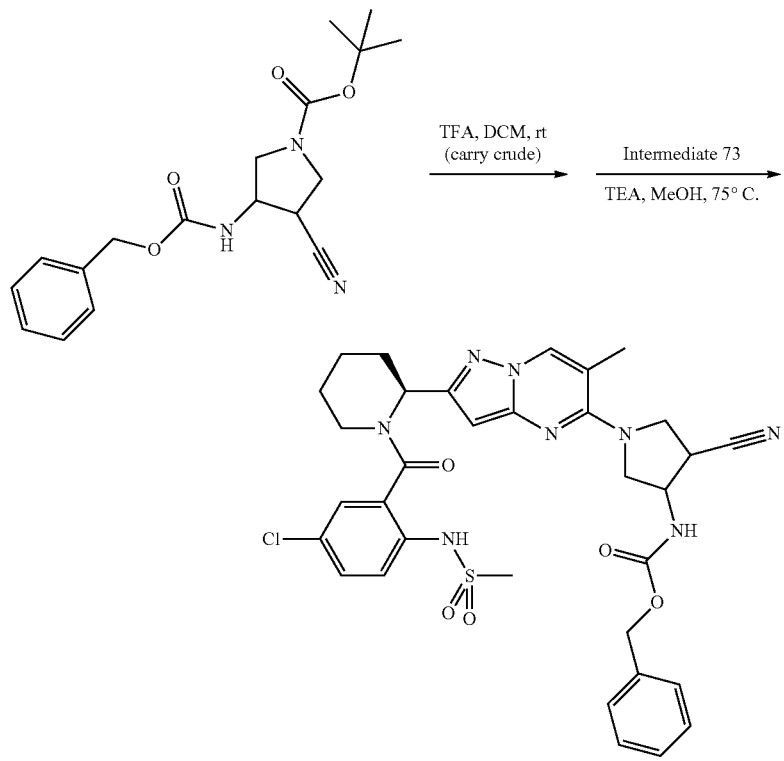

Following the synthesis of compound 182, beginning with intermediate 156 (100 mg, 0.289 mmol) then intermediate 73 (92 mg, 0.191 mmol) and triethylamine (0.081 mL, 0.578 mmol), intermediate 157 was recovered as a white film (25 mg, 19%) after silica gel chromatography (10-60% ethyl acetate in hexanes).

LCMS m/z [M+H]$^+$ C$_{33}$H$_{35}$ClN$_8$O$_5$S requires: 691.21. Found 691.15

Compound 186

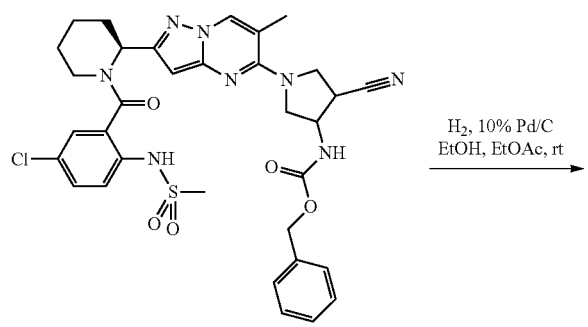

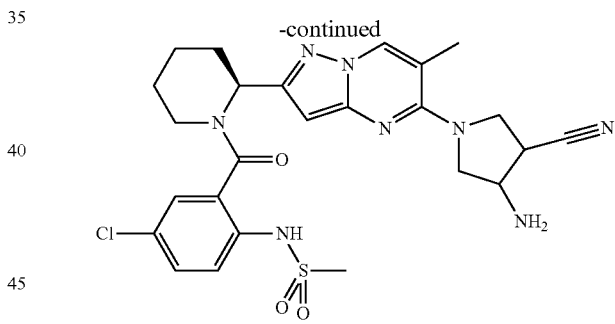

A mixture of intermediate 157 (25 mg, 0.036 mmol) and 10% palladium on carbon (5 mg, 0.0047 mmol) in 2 mL of ethanol and 0.9 mL of ethyl acetate was hydrogenated under an atmosphere of hydrogen for 3 hours. LC/MS indicated <3% conversion. Hydrogen was removed and mixture was concentrated under reduced pressure. Residue was taken up in 6 mL of 1:1 ethyl acetate/ethanol and fresh 10% palladium on carbon (76 mg, 0.071 mmol) was added. Mixture was hydrogenated under an atmosphere of hydrogen for 2 hours. Hydrogen was removed and mixture was filtered over celite, washing with ethanol. Filtrate was concentrated and remaining residue was purified by prep HPLC (15-100% Acetonitrile (with 0.1% trifluoroacetic acid) in water (with 0.1% trifluoroacetic acid)) to yield compound 186 as a white solid, trifluoroacetic acid salt (13 mg, 54%), after lyophilization.

$^1$H-NMR (DMSO, 400 MHz): δ 9.23 (s, 1H) 8.53 (s, 1H), 7.52 (m, 2H), 7.42 (m, 1H), 6.15 (s, 1H), 5.97 (s, 1H), 3.96 (m, 1H), 3.85 (m, 3H), 3.50 (m, 1H), 3.21 (m, 1H), 3.06 (m, 1H), 3.04 (s, 3H), 2.37 (s, 3H), 2.33 (m, 2H), 2.20 (m, 1H), 1.91 (m, 1H), 1.67-1.27 (m, 4H).

LCMS m/z [M+H]$^+$ C$_{25}$H$_{29}$ClN$_8$O$_3$S requires: 557.18. Found 557.07

HPLC Tr (min), purity 5.56, 99%:
Intermediate 158
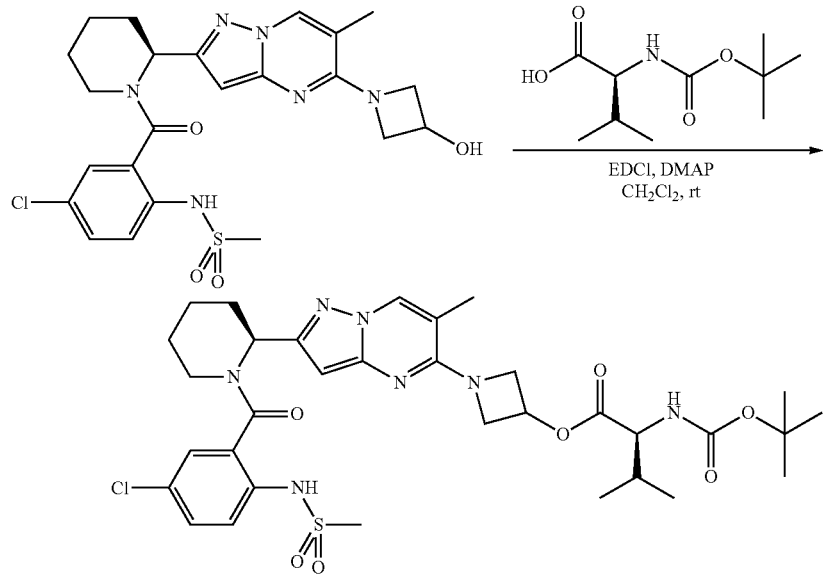
Compound 92 (306 mg, 0.590 mmol) and DMAP (44.1 mg, 0.361 mmol) were added to a solution of EDCI (235 mg, 1.23 mmol) and L-Valine (134 mg, 0.617 mmol) in 7 mL of dichloromethane at room temperature. After stirring overnight, reaction mixture was concentrated and submitted to silica gel chromatography to yield intermediate 158 (320 mg, 76%).
LCMS m/z [M+H]$^+$ $C_{33}H_{44}ClN_7O_7S$ requires: 718.27. Found 718.52
Compound 187
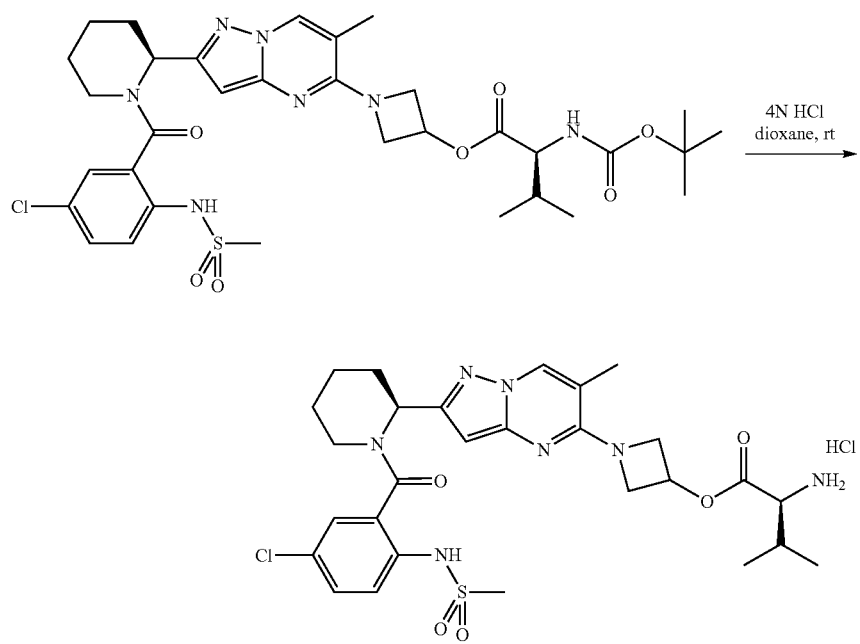 [SMILES: Cc1cn2nc([C@@H]3CCCCN3C(=O)c3cc(Cl)ccc3NS(C)(=O)=O)cc2nc1N1CC(OC(=O)[C@@H](NC(=O)OC(C)(C)C)C(C)C)C1 ; Cc1cn2nc([C@@H]3CCCCN3C(=O)c3cc(Cl)ccc3NS(C)(=O)=O)cc2nc1N1CC(OC(=O)[C@@H](N)C(C)C)C1 ; Cl]

A solution of hydrogen chloride (4N, 6 mL, 24 mmol) was added to a solution of intermediate 158 (315 mg, 0.439 mmol) in 28 mL of dioxane. After stirring overnight, reaction mixture was concentrated to yield compound 187 as a white solid HCl salt (259 mg, 90%)

$^1$H-NMR (DMSO, 400 MHz): δ 9.19 (s, 1H), 8.60 (s, 3H), 8.51 (s, 1H), 7.53-7.38 (m, 3H), 6.17 (s, 1H), 5.95 (m, 1H), 5.37 (m, 1H), 4.61 (m, 1H), 4.23 (m, 2H), 3.92 (m, 1H), 3.66 (m, 2H), 3.48 (m, 2H), 3.20 (m, 1H), 3.03 (s, 3H), 2.34 (m, 1H), 2.21 (m, 1H), 2.15 (s, 3H), 1.87 (m, 1H), 1.65-1.20 (m, 4H), 0.99 (m, 6H), 0.86 (m, 1H).

LCMS m/z [M+H]$^+$ $C_{28}H_{36}ClN_7O_5S$ requires: 618.22. Found 618.41

HPLC Tr (min), purity %: 5.74, 85%

Intermediate 159

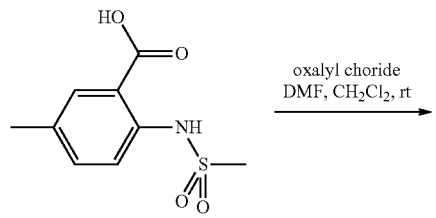

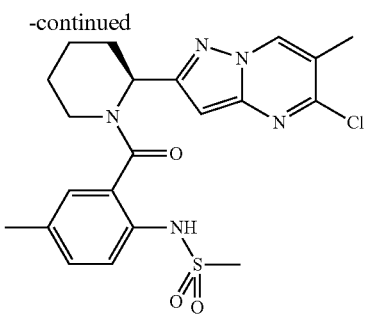

DMF (0.070 mL, 0.908 mmol) was added slowly to a suspension of 5-methyl-2-(methylsulfonamido)benzoic acid (1.01 g, 4.59 mmol) and oxalyl chloride (1.6 mL, 18.3 mmol) in 11 mL of anhydrous dichloromethane. After 3 hours, reaction mixture was concentrated and dried in-vacuo to yield intermediate 159 as a yellow solid (987 mg, 90%) which was used in the next step without further purification.

$^1$H-NMR (CDCl$_3$, 400 MHz): δ 10.2 (s, 1H), 7.92 (s, 1H), 7.64 (m, 1H), 7.39 (m, 1H), 3.03 (s, 3H), 2.35 (s, 3H).

Intermediate 160

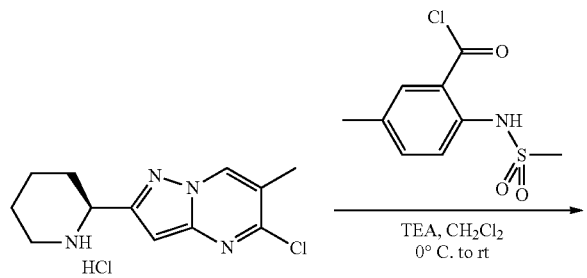

Triethylamine (0.58 mL, 4.16 mmol) was added slowly to a mixture of intermediate 159 (479 mg, 2.01 mmol) and intermediate 72 (573 mg, 2.00 mmol) in 10 mL of dichloromethane under argon at 0° C. After 3 hours, LC/MS indicated full conversion to desired product. Reaction mixture was concentrated and dried in-vacuo to yield intermediate 160 as a yellow solid (924 mg, 92%) that was used in the next steps without further purification.

LCMS m/z [M+H]$^+$ $C_{21}H_{24}ClN_5O_3S$ requires: 462.13. Found 462.32

Compound 188

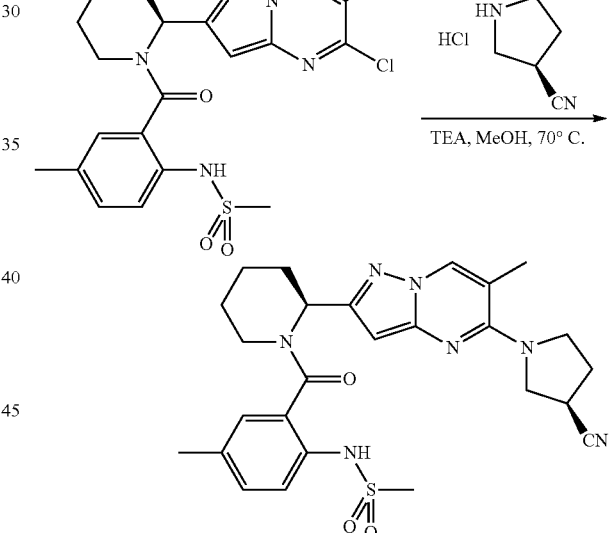

Triethylamine (0.367 mL, 2.65 mmol) was added to a mixture of intermediate 160 (70 mg, 0.152 mmol) and (R)-pyrrolidine-3-carbonitrile hydrochloride (175 mg, 1.32 mmol) in 8 mL of methanol at room temperature. After heating at 70° C. overnight, reaction mixture was cooled to room temperature and concentrated under reduced pressure. The remaining residue was purified by prep HPLC (15-100% Acetonitrile (with 0.1% trifluoroacetic acid) in water (with 0.1% trifluoroacetic acid)) to yield compound 188 as a white solid, trifluoroacetic acid salt (58.9 mg, 61%), after lyophilization.

$^1$H-NMR (DMSO, 400 MHz): δ 9.01 (s, 1H) 8.53 (s, 1H), 7.39 (m, 1H), 7.25 (m, 1H), 7.17 (s, 1H), 6.13 (s, 1H), 5.97 (m, 1H), 3.92 (m, 1H), 3.84-3.70 (m, 3H), 3.47 (m, 1H), 3.20 (m, 1H), 3.04 (m, 1H), 2.95 (s, 3H), 2.31 (s, 3H), 2.30-2.13 (m, 6H), 1.84 (m, 1H), 1.61 (m, 1H), 1.57-1.22 (m, 3H).

LCMS m/z [M+H]⁺ C₂₆H₃₁ClN₇O₃S requires: 522.22. Found 522.37

HPLC Tr (min), purity %: 6.77, 99%

Compound 189

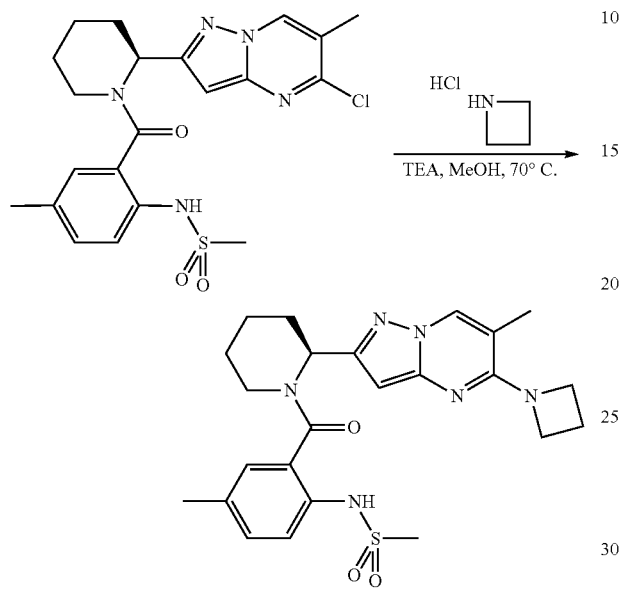

Following the procedure of compound 188, using intermediate 160 (75 mg, 0.163 mmol), compound 189 was recovered as a white solid, trifluoroacetic acid salt (61 mg, 63%) after lyophilization.

¹H-NMR (DMSO, 400 MHz): δ 9.03 (s, 1H), 8.46 (s, 1H), 7.42-7.15 (m, 3H), 6.05 (s, 1H), 5.95 (s, 1H), 4.21 (m, 3H), 3.43 (m, 1H), 3.22 (m, 1H), 3.02 (m, 1H), 2.95 (s, 3H), 2.32 (s, 3H), 2.28 (m, 2H), 2.20 (m, 1H), 2.14 (s, 3H), 1.85 (m, 1H), 1.69-1.21 (m, 4H).

LCMS m/z [M+H]⁺ C₂₄H₃₀ClN₆O₃S requires: 483.21. Found 483.45

HPLC Tr (min), purity %: 5.63, 97%

Intermediate 161

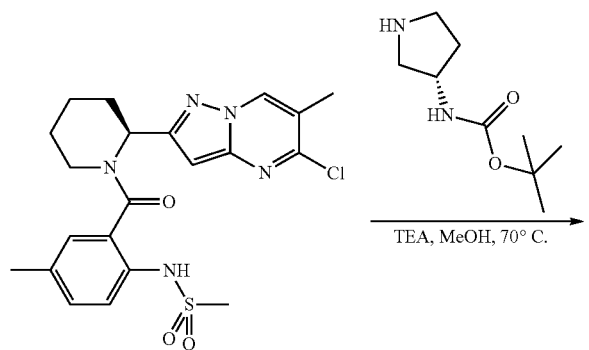

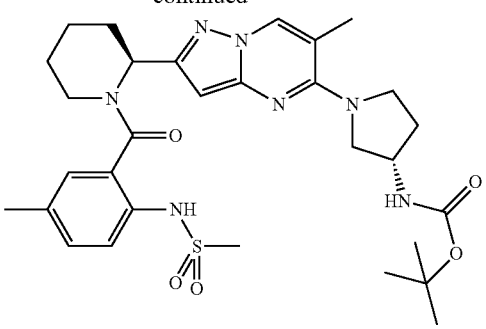

Following the procedure of compound 188, intermediate 161 was recovered as a white solid (81 mg, 82%) after silica gel column chromatography (10-60% Ethyl Acetate/Hexanes).

LCMS m/z [M+H]⁺ C₃₀H₄₁ClN₇O₅S requires: 612.29. Found 612.22

Compound 190

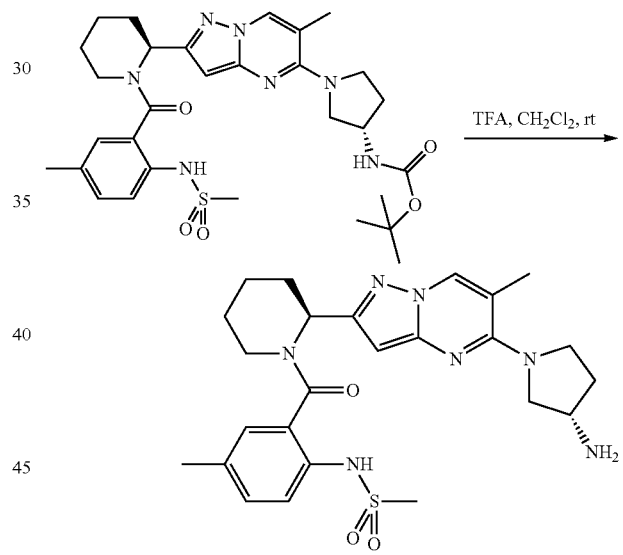

Trifluoroacetic acid (0.35 mL, 4.58 mmol) was added to a solution of intermediate 161 (79 mg, 0.129 mmol) in 5 mL of dichloromethane. After stirring overnight, reaction mixture was concentrated under reduced pressure and dried in-vacuo for 3 hours to yield compound 190 as an off white solid (76.6 mg, 95%), trifluoroacetic acid salt.

¹H-NMR (DMSO, 400 MHz): δ 9.02 (s, 1H) 8.53 (s, 1H), 8.01 (s, 3H), 7.39 (m, 1H), 7.25 (m, 1H), 7.19 (m, 1H), 6.11 (s, 1H), 5.97 (m, 1H), 3.85 (m, 4H), 3.24 (m, 1H), 3.03 (m, 1H), 2.95 (s, 3H), 2.33 (s, 3H), 2.32 (s, 3H), 2.29 (m, 3H), 2.05-1.81 (m, 2H), 1.67-1.22 (m, 4H).

LCMS m/z [M+H]⁺ C₂₅H₃₃ClN₇O₃S requires: 512.24. Found 512.20

HPLC Tr (min), purity %: 5.10, 99%

Intermediate 162

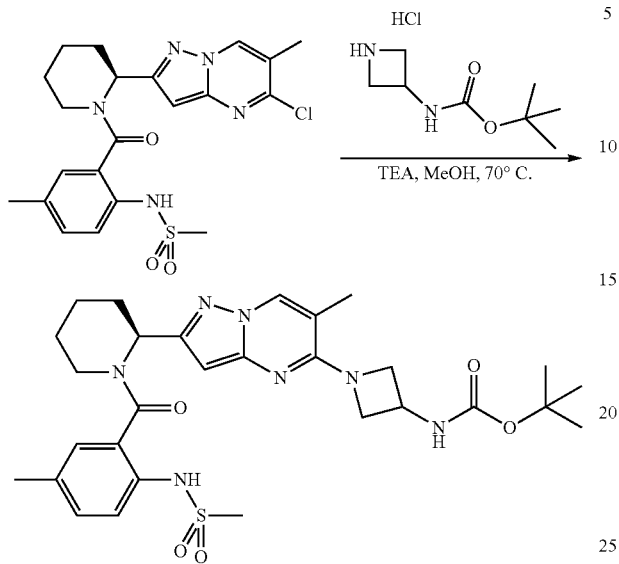

Following the procedure of compound 188, intermediate 162 was recovered as a white solid (92 mg, 98%) after silica gel column chromatography.

LCMS m/z [M+H]$^+$ $C_{29}H_{39}ClN_7O_5S$ requires: 598.27. Found 598.21

Compound 191

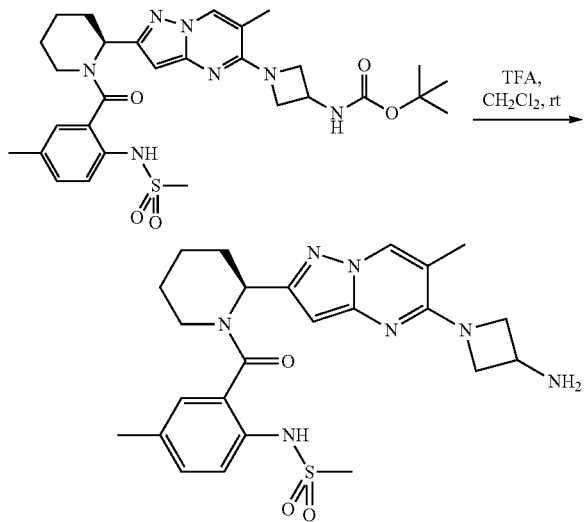

Following the procedure of compound 190, after three hours, compound 191 was recovered as an off-white solid (88 mg, 97%), trifluoroacetic acid salt.

$^1$H-NMR (DMSO, 400 MHz): δ 8.97 (s, 1H) 8.53 (s, 1H), 8.31 (s, 2H), 7.38 (m, 2H), 7.25 (m, 2H), 7.17 (s, 1H), 6.16 (s, 1H), 5.98 (m, 1H), 4.47 (m, 1H), 4.16 (m, 1H), 3.21 (m, 1H), 3.04 (m, 1H), 3.03 (s, 3H), 2.36 (m, 1H), 2.32 (s, 3H), 2.23 (m, 1H), 2.15 (s, 3H), 1.86 (m, 1H), 1.62-1.21 (m, 4H).

LCMS m/z [M+H]$^+$ $C_{24}H_{31}ClN_7O_3S$ requires: 498.22. Found 498.13

HPLC Tr (min), purity %: 5.03, 99%

Compound 192

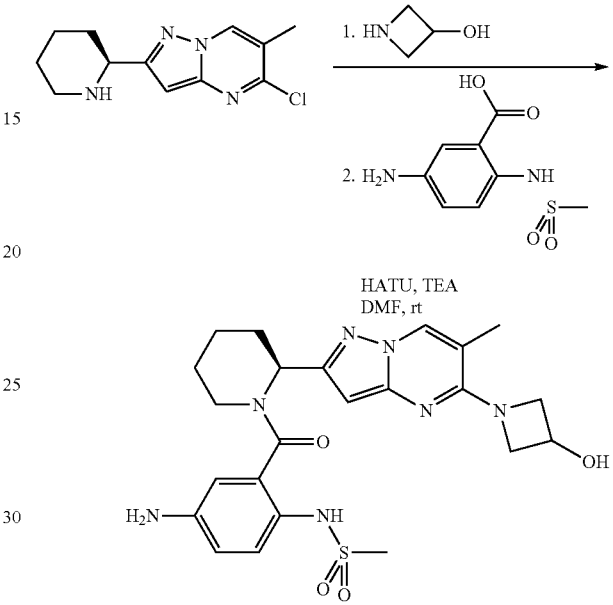

Triethylamine (10.0 mL, 76.6 mmol) was added to a mixture of azetidin-3-ol hydrochloride (4.2 g, 38.3 mmol) and intermediate 72 (1.1 g, 3.83 mmol) in 5 mL of anhydrous methanol at room temperature. Reaction mixture was heated to 70° C. for 2 hours, after which LC/MS indicated reaction was complete. Solvent was concentrated under reduced pressure and remaining residue was suspended in dichloromethane and filtered. Processed was repeated two times and filtrate was concentrated to yield a solid. Solid was taken up in a minimal amount of dichloromethane and stirred overnight. Resulting precipitate was filtered to isolate (S)-1-(6-methyl-2-(piperidin-2-yl)pyrazolo[1,5-a]pyrimidin-5-yl)azetidin-3-olas a pale solid (LCMS m/z [M+H]$^+$ $C_{15}H_{21}N_5O$ requires: 288.17. Found 288.20).

HATU (88 mg, 0.231 mmol) was added to a solution of 5-amino-2-(methylsulfonamido)benzoic acid (47 mg, 0.204 mmol) in 3 mL of DMF. After 2 hours, above intermediate (55 mg, 0.203 mmol) and triethylamine (0.060 mL, 0.433 mmol) were added sequentially and reaction mixture stirred at room temperature overnight. Mixture was then poured into 20 mL of H$_2$O and 10 mL brine and extracted three times with 30 mL of ethyl acetate. The combined organic layers were washed with 60 mL of 1:1 water:brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 192 (41 mg, 46%) as a white solid, trifluoroacetic acid salt, after lyophilization.

$^1$H-NMR (DMSO, 400 MHz): δ 8.84 (s, 1H) 8.44 (m, 1H), 7.24-7.11 (m, 2H), 6.82 (m, 1H), 6.74 (s, 2H), 6.08 (s, 1H), 5.93 (d, 1H), 4.77 (m, 1H), 4.50 (m, 1H), 4.39 (m, 2H), 3.94 (m, 2H), 3.21 (m, 1H), 3.02 (m, 1H), 2.89 (s, 3H), 2.33 (m, 1H), 2.13 (s, 3H), 1.82 (m, 1H), 1.65-1.11 (m, 4H).

LCMS m/z [M+H]$^+$ C$_{23}$H$_{29}$ClN$_7$O$_4$S requires: 500.20. Found 500.17

HPLC Tr (min), purity %: 4.09, 88%

Compound 193

LCMS m/z [M+H]$^+$ C$_{26}$H$_{34}$ClN$_8$O$_4$S requires: 555.24. Found 555.24

HPLC Tr (min), purity %: 4.30, 96%

Compound 194

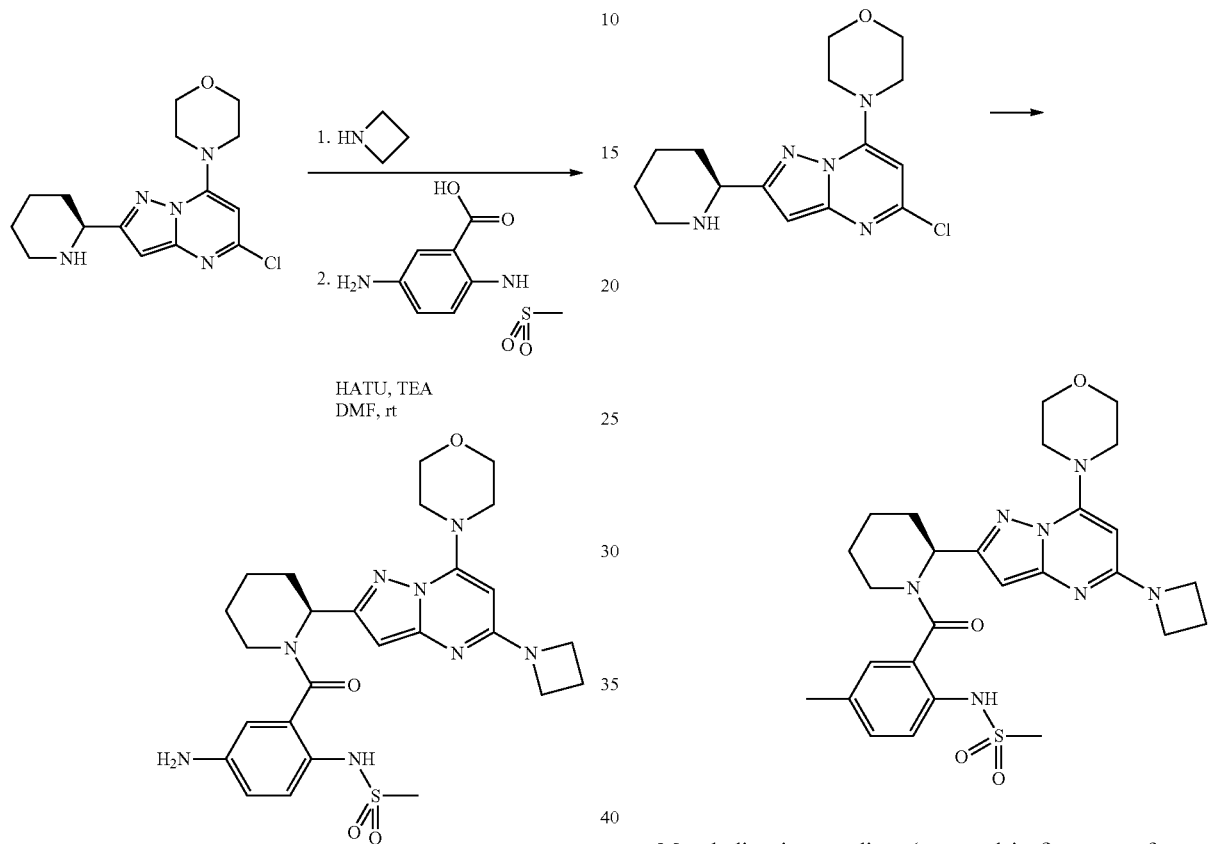

Morpholine intermediate (prepared in first step of morpholine intermediate 65 synthesis) (1.0 g, 3.11 mmol) was taken up in 15 mL of ethanol and placed in a sealed reaction tube. Azetidine (2.1 mL, 31.1 mmol) was added and tube was sealed and heated at 80° C. for two hours. Solvents were removed under reduced pressure and residue was purified by silica gel column chromatography (20-50% methanol in ethyl acetate) to yield (S)-4-(5-(azetidin-1-yl)-2-(piperidin-2-yl)pyrazolo[1,5-a]pyrimidin-7-yl)morpholine as a solid (850 mg, 80%).

LCMS m/z [M+H]$^+$ C$_{18}$H$_{26}$N$_6$O requires: 343.22. Found 343.30

Following the procedure of compound 192, using intermediate above ((S)-4-(5-(azetidin-1-yl)-2-(piperidin-2-yl)pyrazolo[1,5-a]pyrimidin-7-yl)morpholine), (50 mg, 0.146 mmol), compound 193 was recovered as an off-white solid (41 mg, 42%), trifluoroacetic acid salt.

$^1$H-NMR (DMSO, 400 MHz): δ 8.71 (s, 1H), 7.09 (m, 1H), 6.72 (m, 1H), 6.58 (m, 1H), 6.07 (s, 1H), 5.90 (m, 1H), 5.34 (s, 2H), 4.13 (m, 4H), 3.75 (m, 7H), 3.40 (m, 1H), 3.08 (m, 1H), 2.92 (s, 3H), 2.34 (m, 2H), 2.09 (m, 1H), 1.81 (m, 1H), 1.69-1.28 (m, 4H).

Morpholine intermediate (prepared in first step of morpholine intermediate 65 synthesis) (1.0 g, 3.11 mmol) was taken up in 15 mL of ethanol and placed in a sealed reaction tube. Azetidine (2.1 mL, 31.1 mmol) was added and tube was sealed and heated at 80° C. for two hours. Solvents were removed under reduced pressure and residue was purified by silica gel column chromatography (20-50% methanol in ethyl acetate) to yield (S)-4-(5-(azetidin-1-yl)-2-(piperidin-2-yl)pyrazolo[1,5-a]pyrimidin-7-yl)morpholine as a solid (850 mg, 80%).

LCMS m/z [M+H]$^+$ C$_{18}$H$_{26}$N$_6$O requires: 343.22. Found 343.30

Following the procedure of compound 192, using intermediate above (46 mg, 0.134 mmol), compound 194 was recovered as an off-white solid (45 mg, 50%), trifluoroacetic acid salt.

$^1$H-NMR (DMSO, 400 MHz): δ 9.02 (s, 1H), 7.29 (m, 2H), 7.09 (m, 1H), 6.10 (s, 1H), 5.92 (m, 1H), 5.35 (s, 1H), 4.17 (m, 4H), 3.77 (m, 6H), 3.37 (m, 1H), 3.12 (m, 1H), 2.99 (s, 3H), 2.37 (m, 2H), 2.32 (m, 3H), 2.18 (m, 1H), 1.89 (m, 1H), 1.65-1.32 (m, 4H).

LCMS m/z [M+H]$^+$ C$_{27}$H$_{35}$ClN$_7$O$_4$S requires: 554.24. Found 554.23

HPLC Tr (min), purity %: 5.34, 98%

Compound 195

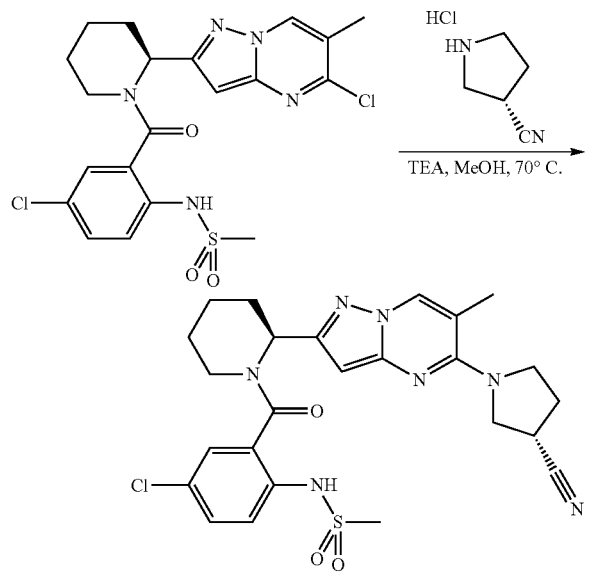

Following the procedure of compound 188, starting from intermediate 73, compound 195 was recovered as a tan solid, trifluoroacetic acid salt (31 mg, 67%) after washing the residue with water.

$^1$H-NMR (DMSO, 400 MHz): δ 9.22 (s, 1H), 8.53 (s, 1H), 7.55-7.27 (m, 3H) 6.15 (s, 1H), 5.96 (m, 1H), 3.93 (m, 1H), 3.85-3.71 (m, 3H), 3.49 (m, 1H), 3.21 (m, 1H), 3.05 (m, 1H), 3.03 (s, 3H), 2.34 (m, 1H), 2.32 (s, 3H), 2.17 (m, 1H), 1.87 (m, 1H), 1.66-1.20 (m, 5H).

LCMS m/z [M+H]$^+$ C$_{25}$H$_{28}$ClN$_7$O$_3$S requires: 542.17. Found 542.14

HPLC Tr (min), purity %: 7.16, 92%

Compound 196

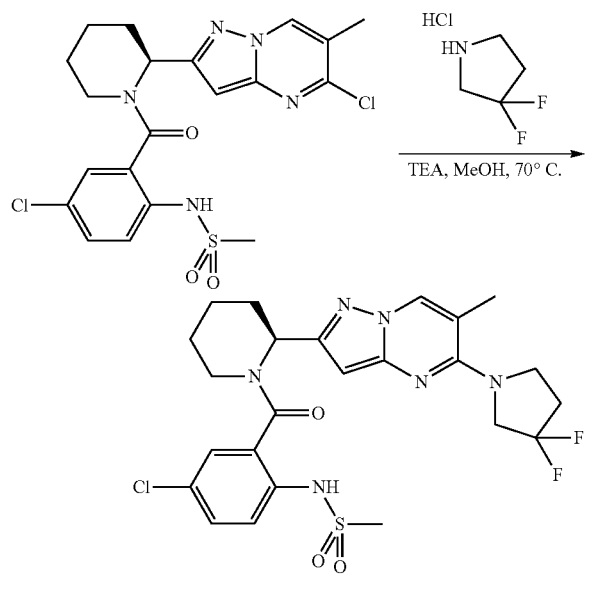

Following the procedure of compound 188, starting from intermediate 73 compound 196 was recovered as a white solid, trifluoroacetic acid salt (45 mg, 82%) after lyophilization.

$^1$H-NMR (DMSO, 400 MHz): δ 9.20 (s, 1H) 8.55 (s, 1H), 7.52-7.38 (m, 3H), 6.18 (s, 1H), 5.95 (d, 1H), 4.60 (m, 2H), 4.06 (m, 2H), 3.85 (m, 2H), 3.20 (m, 1H), 3.04 (s, 3H), 2.46-2.39 (m, 2H), 2.38 (s, 3H), 2.29 (m, 1H), 1.67-1.20 (m, 4H).

LCMS m/z [M+H]$^+$ C$_{24}$H$_{27}$ClF$_2$N$_6$O$_3$S requires: 553.15. Found 553.13

HPLC Tr (min), purity %: 7.96, 99%

Compound 197

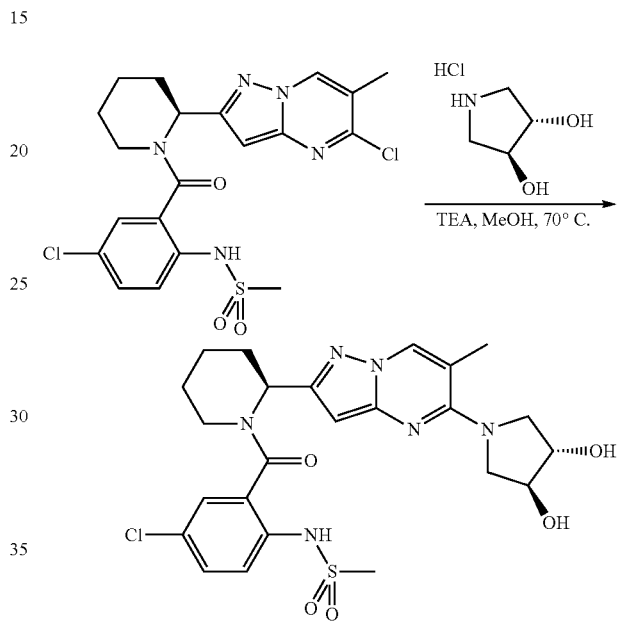

Following the procedure of compound 188, starting from intermediate 73, compound 197 was recovered as a white solid, trifluoroacetic acid salt (37.5 mg, 66%) after lyophilization.

$^1$H-NMR (DMSO, 400 MHz): δ 9.25 (s, 1H), 8.47 (s, 1H), 7.54-7.35 (m, 3H), 6.06 (s, 1H), 5.96 (m, 1H), 3.98 (m, 2H), 5.00 (br s, 1H), 3.86 (m, 2H), 3.49 (m, 2H), 3.19 (m, 1H), 3.08 (m, 1H), 3.04 (s, 3H), 2.35 (m, 1H), 2.32 (s, 3H), 1.85 (m, 1H), 1.66-1.27 (m, 4H).

LCMS m/z [M+H]$^+$ C$_{24}$H$_{29}$ClN$_6$O$_5$S requires: 549.16. Found 549.10

HPLC Tr (min), purity %: 5.30, 98%

Compound 198

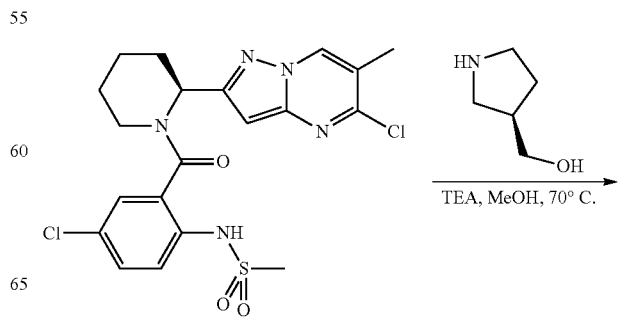

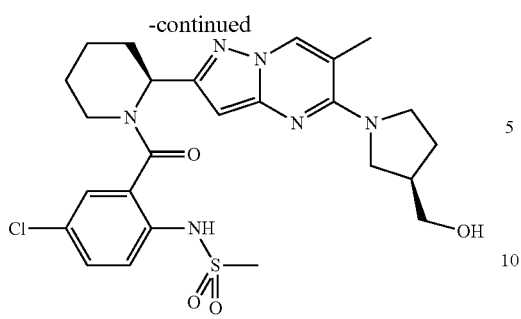

Following the procedure of compound 188, starting from intermediate 73, compound 198 was recovered as a white solid, trifluoroacetic acid salt (20.4 mg, 46%) after lyophilization.

$^1$H-NMR (DMSO, 400 MHz): δ 9.25 (s, 1H) 8.44 (s, 1H), 7.50 (m, 2H), 7.41 (m, 1H), 6.05 (s, 1H), 5.94 (m, 1H), 3.85-3.38 (m, 5H), 3.17 (m, 1H), 3.04 (m, 1H), 3.02 (s, 3H), 2.35 (m, 1H), 2.32 (s, 5H), 1.98-1.80 (m, 2H), 1.67-1.59 (m, 3H), 1.55-1.22 (m, 3H).

LCMS m/z [M+H]$^+$ C$_{25}$H$_{31}$ClN$_6$O$_4$S requires: 547.18. Found 547.17

HPLC Tr (min), purity %: 5.78, 92%

Compound 199

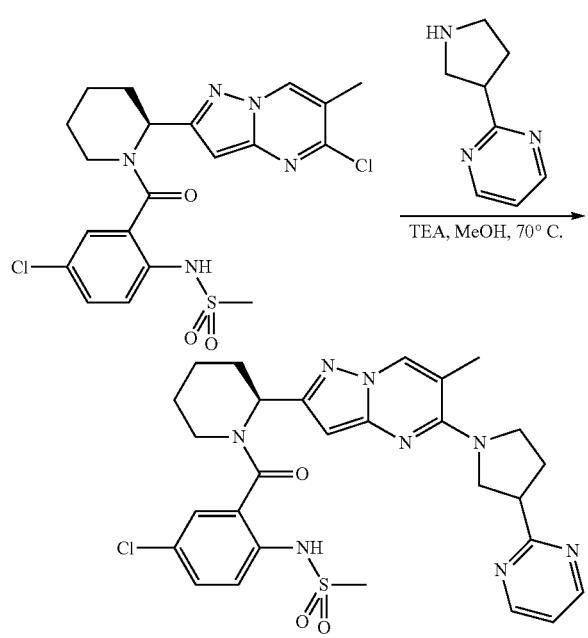

Following the procedure of compound 188, starting from intermediate 73, compound 199 was recovered as a white solid, trifluoroacetic acid salt (34 mg, 56%) after lyophilization.

$^1$H-NMR (DMSO, 400 MHz): δ 9.25 (s, 1H), 8.69 (m, 1H), 8.60 (m, 1H), 8.53 (m, 1H), 8.49 (m, 1H), 7.55-7.37 (m, 3H), 6.08 (s, 1H), 5.94 (m, 1H), 4.09 (m, 1H), 3.89-3.72 (m, 3H), 3.70 (m, 1H), 3.19 (m, 1H), 3.04 (m, 1H), 3.03 (s, 3H), 2.35-2.30 (m, 2H), 2.34 (s, 3H), 2.16 (m, 1H), 1.80 (m, 1H), 1.66-1.23 (m, 4H).

LCMS m/z [M+H]$^+$ C$_{28}$H$_{31}$ClN$_8$O$_3$S requires: 595.19. Found 595.20

HPLC Tr (min), purity %: 6.64, 99%

Compound 200

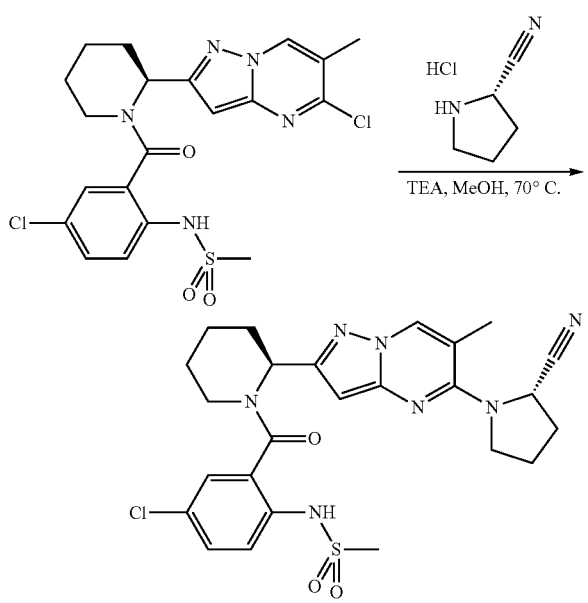

Following the procedure of compound 188, starting from intermediate 73, compound 200 was recovered as a yellow solid film, trifluoroacetic acid salt (11 mg, 13%) after lyophilization.

$^1$H-NMR (DMSO, 400 MHz): δ 9.23 (s, 1H) 8.53 (s, 1H), 7.52 (m, 2H), 7.42 (m, 1H), 6.15 (s, 1H), 5.97 (s, 1H), 3.96 (m, 1H), 3.85 (m, 3H), 3.50 (m, 1H), 3.21 (m, 1H), 3.06 (m, 1H), 3.04 (s, 3H), 2.37 (s, 3H), 2.33 (m, 2H), 2.20 (m, 1H), 1.91 (m, 1H), 1.67-1.27 (m, 4H).

LCMS [M+H]$^+$ C$_{25}$H$_{28}$ClN$_7$O$_3$S requires: 542.17. Found 542.11

HPLC Tr (min), purity %: 7.44, 97%

Intermediate 163

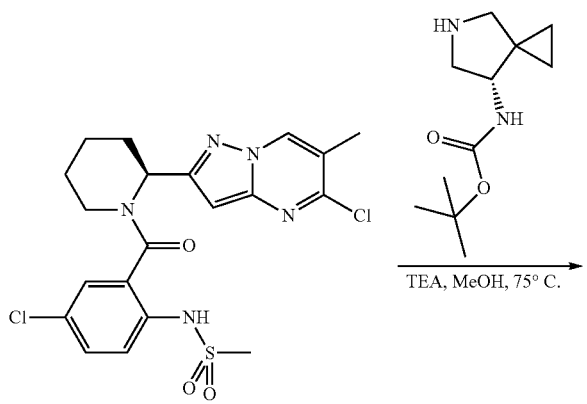

Intermediate 164

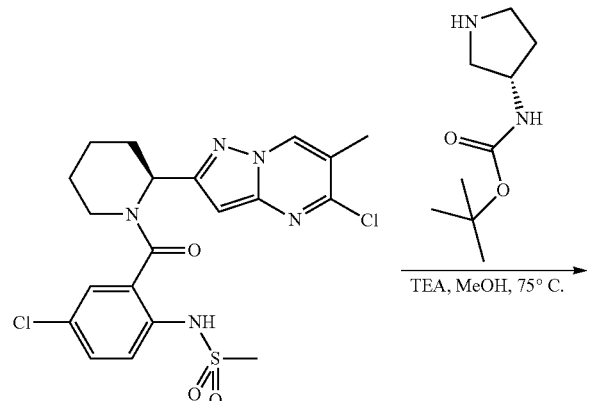

Following the procedure of compound 188, starting from intermediate 73, intermediate 163 was recovered as a white solid (79 mg, 89%) after silica gel chromatography (10-50% ethyl acetate in hexanes).

LCMS m/z [M+H]$^+$ C$_{31}$H$_{40}$ClN$_7$O$_5$S requires: 658.25. Found 658.22

Compound 201

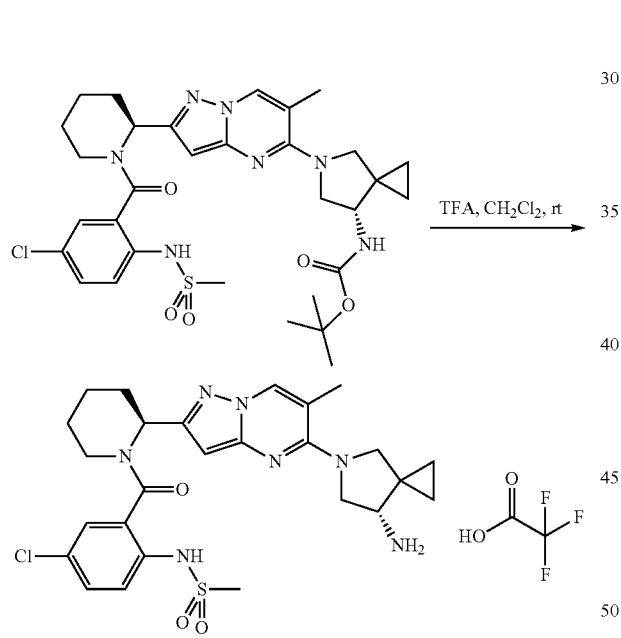

Following the procedure of compound 190, beginning with intermediate 163 (78 mg, 0.118 mmol), compound 201 was recovered as a white solid, trifluoroacetic acid salt (76 mg, 96%) after drying in-vacuo.

$^1$H-NMR (DMSO, 400 MHz): δ 9.24 (s, 1H) 8.51 (s, 1H), 8.09 (s, 3H), 7.53-7.37 (m, 3H), 6.12 (s, 1H), 5.94 (s, 1H), 4.14 (m, 1H), 4.01 (m, 1H), 3.91 (m, 1H), 3.42 (m, 2H), 3. 3.21 (m, 1H), 3.04 (m, 1H), 3.02 (s, 3H), 2.35 (m, 1H), 2.32 (s, 3H), 1.84 (m, 1H), 1.65-1.22 (m, 4H), 1.02 (m, 1H), 0.78 (m, 3H).

LCMS m/z [M+H]$^+$ C$_{26}$H$_{32}$ClN$_7$O$_3$S requires: 557.20. Found 557.15

HPLC Tr (min), purity %: 5.60, 99%

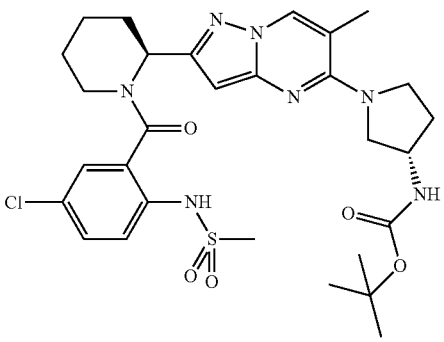

Following the procedure of compound 188, starting from intermediate 73, intermediate 164 was recovered as a white solid trifluoroacetic acid salt (79 mg, 89%) after prep HPLC (15-100% Acetonitrile (with 0.1% trifluoroacetic acid) in water (with 0.1% trifluoroacetic acid)).

LCMS m/z [M+H]$^+$ C$_{29}$H$_{38}$ClN$_7$O$_5$S requires: 632.23. Found 632.52

Compound 202

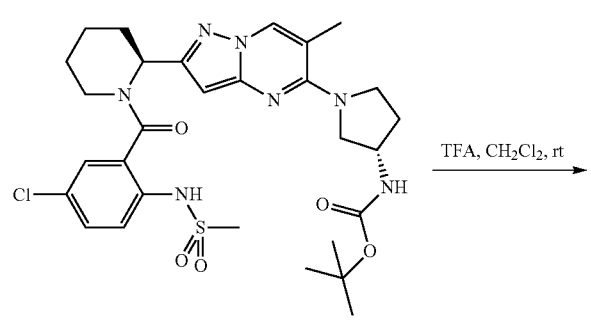

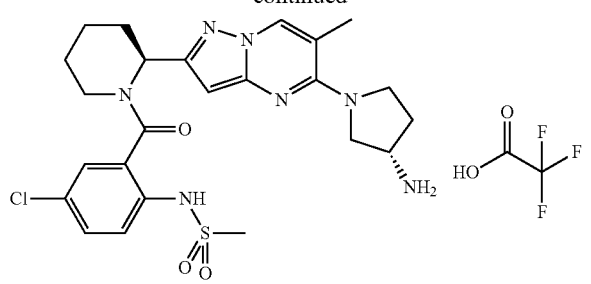

Following the procedure of compound 190, using intermediate 164, compound 202 was recovered as a white solid, trifluoroacetic acid salt (69 mg, 98%) after drying in-vacuo.

$^1$H-NMR (DMSO, 400 MHz): δ 9.24 (s, 1H) 8.52 (s, 1H), 8.08 (s, 3H), 7.55-7.38 (m, 3H), 6.13 (s, 1H), 5.95 (m, 1H), 3.90 (m, 2H), 3.81-3.60 (m, 2H), 3.21 (m, 1H), 3.04-3.00 (m, 1H), 3.03 (s, 3H), 2.39-2.13 (m, 2H), 2.33 (s, 3H), 2.08-1.80 (m, 2H), 1.69-1.21 (m, 5H).

LCMS m/z [M+H]$^+$ C$_{24}$H$_{30}$ClN$_7$O$_3$S requires: 532.18. Found 532.42

HPLC Tr (min), purity %: 5.28, 98%

Intermediate 165

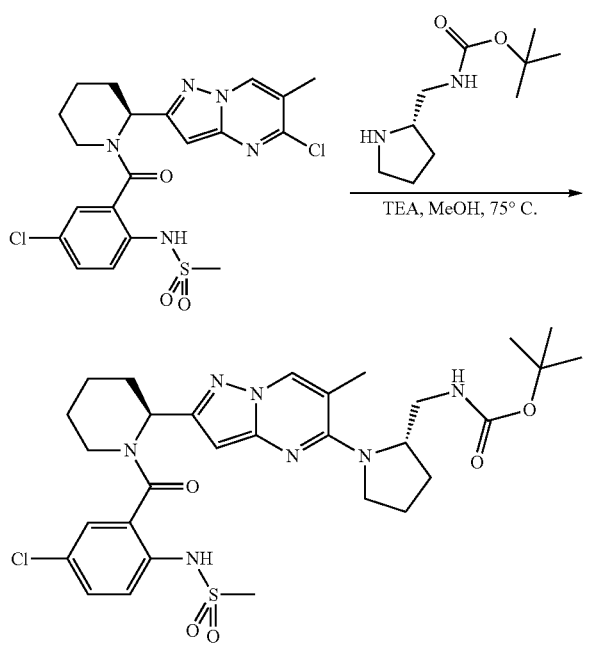

Following the procedure of compound 188, starting from intermediate 73, intermediate 165 was recovered as a white solid (75 mg, 82%) after silica gel chromatography (5-60% ethyl acetate in hexanes).

LCMS m/z [M+H]$^+$ C$_{30}$H$_{40}$ClN$_7$O$_5$S requires: 646.25. Found 646.17

Compound 203

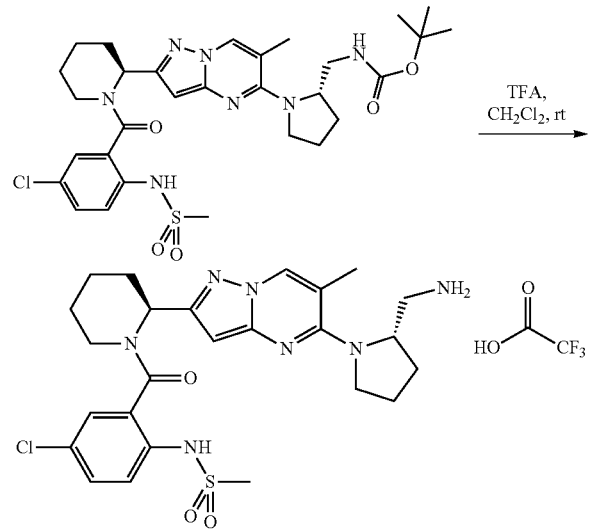

Following the procedure of compound 190, starting from intermediate 165, compound 203 was recovered as an off white solid, trifluoroacetic acid salt (72 mg, 97%) after drying in-vacuo.

$^1$H-NMR (DMSO, 400 MHz): δ 9.23 (s, 1H) 8.58 (s, 1H), 7.71 (s, 3H), 7.53-7.30 (m, 3H), 6.13 (s, 1H), 5.98 (d, 1H), 4.52 (m, 1H), 3.81-3.43 (m, 5H), 3.21 (m, 1H), 3.06 (m, 1H), 3.04 (s, 3H), 2.36 (m, 1H), 2.33 (s, 3H), 2.05-1.71 (m, 4H), 1.67-1.20 (m, 4H).

LCMS m/z [M+H]$^+$ C$_{25}$H$_{32}$ClN$_7$O$_3$S requires: 546.20. Found 546.10

HPLC Tr (min), purity %: 5.88, 99%

Compound 204

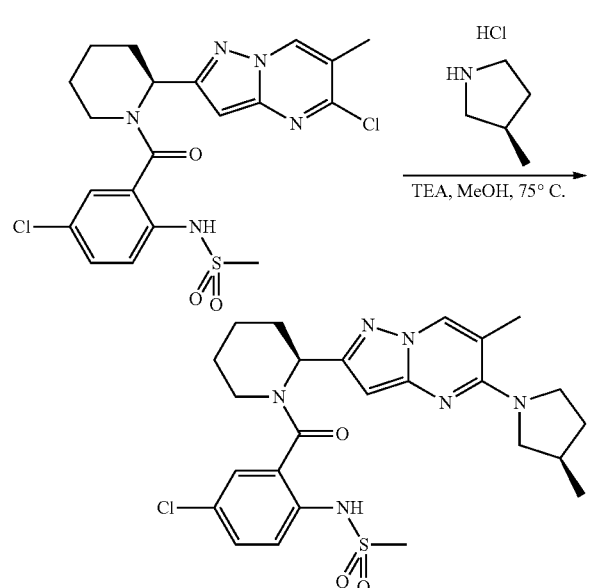

Following the procedure of compound 188, starting from intermediate 73, compound 204 was recovered as a white solid, trifluoroacetic acid salt (51 mg, 96%) after lyophilization.

$^1$H-NMR (DMSO, 400 MHz): δ 9.23 (s, 1H) 8.53 (s, 1H), 7.52 (m, 2H), 7.42 (m, 1H), 6.15 (s, 1H), 5.97 (s, 1H), 3.96 (m, 1H), 3.85 (m, 3H), 3.50 (m, 1H), 3.21 (m, 1H), 3.06 (m, 1H), 3.04 (s, 3H), 2.37 (s, 3H), 2.33 (m, 2H), 2.20 (m, 1H), 1.91 (m, 1H), 1.67-1.27 (m, 4H), 1.06 (s, 3H).

LCMS m/z [M+H]$^+$ C$_{25}$H$_{30}$ClN$_6$O$_3$S requires: 531.19. Found 531.14

HPLC Tr (min), purity %: 6.74, 98%

Compound 205

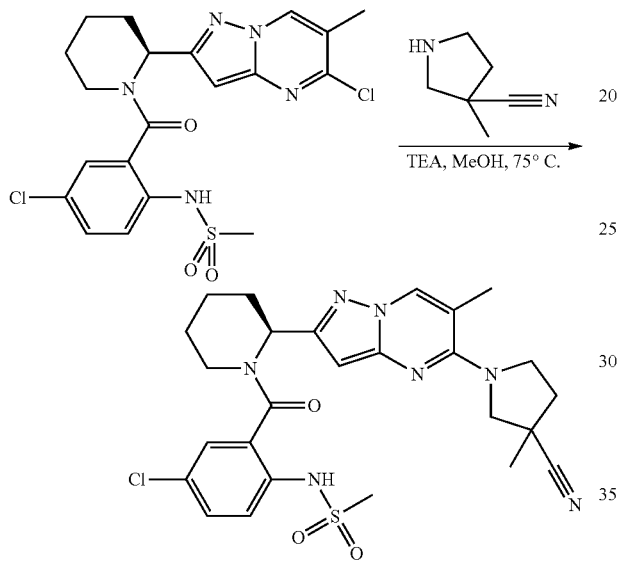

Following the procedure of compound 188, starting from intermediate 73, compound 205 was recovered as a white solid, trifluoroacetic acid salt (61 mg, 72%) after lyophilization.

$^1$H-NMR (DMSO, 400 MHz): δ 9.22 (s, 1H) 8.53 (d, 1H), 7.52-7.36 (m, 3H), 6.13 (s, 1H), 5.96 (m, 1H), 4.58 (m, 1H), 4.04 (m, 1H), 3.83 (m, 2H), 3.62 (m, 1H), 3.20 (m, 1H), 3.04 (m, 1H), 3.03 (s, 3H), 2.37 (m, 2H), 2.32 (s, 3H), 2.04 (m, 1H), 1.86 (m, 1H), 1.61 (m, 1H), 1.49 (s, 3H), 1.47 (m, 2H)

LCMS m/z [M+H]$^+$ C$_{26}$H$_{30}$ClN$_7$O$_3$S requires: 556.18. Found 556.45

HPLC Tr (min), purity %: 7.29, 99%

Compound 206

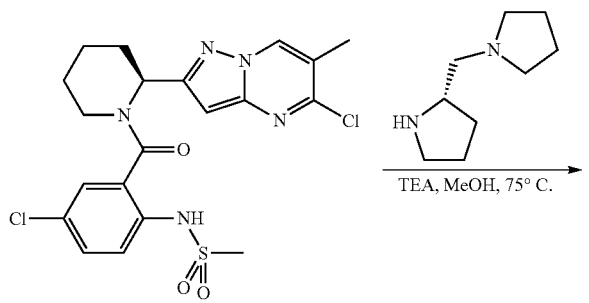

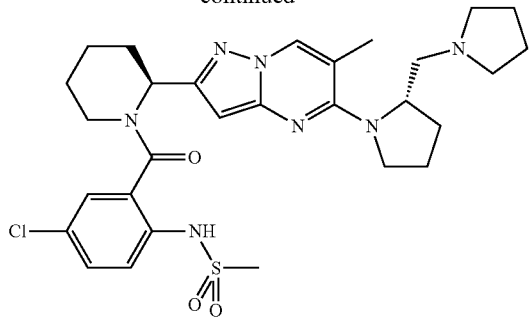

Following the procedure of compound 188, starting from intermediate 73, compound 206 was recovered as a white solid, trifluoroacetic acid salt (80 mg, 89%) after lyophilization.

$^1$H-NMR (DMSO, 400 MHz): δ 9.41 (s, 1H), 9.23 (s, 1H) 8.58 (s, 1H), 7.54-7.35 (m, 3H), 6.17 (s, 1H), 5.97 (m, 1H), 4.65 (m, 1H), 3.85-3.58 (m, 5H), 3.33 (m, 1H), 3.23 (m, 2H), 3.11 (m, 1H), 3.04 (s, 3H), 2.36 (m, 1H), 2.32 (s, 3H), 2.16 (m, 1H), 2.04-1.73 (m, 9H), 1.63 (m, 1H), 1.52-1.21 (m, 3H).

LCMS m/z [M+H]$^+$ C$_{29}$H$_{38}$ClN$_7$O$_3$S requires: 600.24. Found 600.16

HPLC Tr (min), purity %: 6.35, 98%

Compound 207

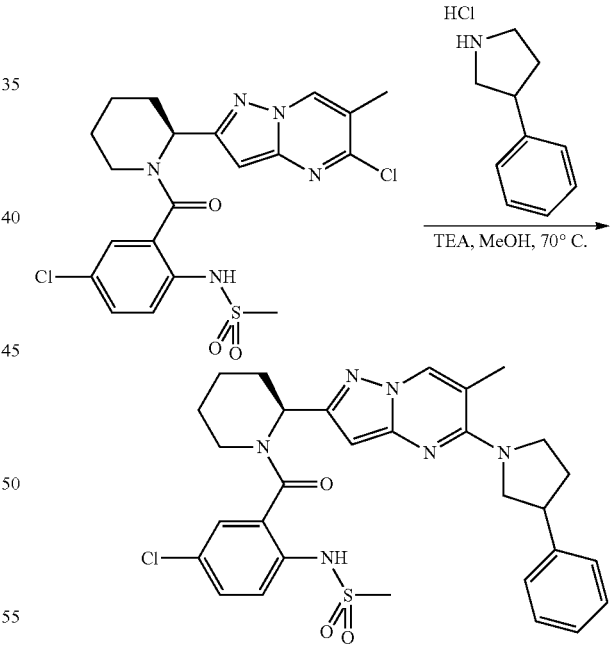

Following the procedure of compound 188, starting from intermediate 73, compound 207 was recovered as a white solid, trifluoroacetic acid salt (37 mg, 85%) after lyophilization.

$^1$H-NMR (DMSO, 400 MHz): δ 9.25 (s, 1H), 8.48 (d, 1H), 7.50 (m, 2H), 7.41 (m, 1H), 7.31 (m, 4H), 7.23 (m, 1H), 6.08 (s, 1H), 5.94 (m, 1H), 4.09 (m, 1H), 3.80 (m, 2H), 3.68 (m, 1H), 3.42 (m, 1H), 3.21 (m, 1H), 3.05 (m, 1H), 3.04 (s, 3H), 2.34 (s, 3H), 2.31 (m, 2H), 1.98-1.81 (m, 2H), 1.61 (m, 1H), 1.57-1.25 (m, 3H).

LCMS [M+H]⁺ C₃₀H₃₃ClN₆O₃S requires: 593.20. Found 593.37

HPLC Tr (min), purity %: 7.77, 99%

Compound 208

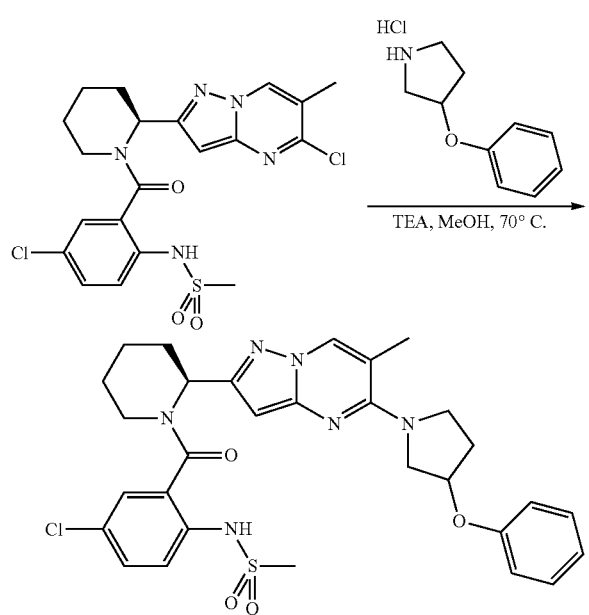

Following the procedure of compound 188, starting from intermediate 73, compound 208 was recovered as a white solid, trifluoroacetic acid salt (49 mg, 84%) after lyophilization.

¹H-NMR (DMSO, 400 MHz): δ 9.24 (s, 1H), 8.48 (d, 1H), 7.50 (m, 2H), 7.42 (m, 1H), 7.27 (m, 2H), 6.94 (m, 3H), 6.06 (s, 1H), 5.94 (m, 1H), 5.09 (m, 1H), 4.11-3.62 (m, 3H), 3.19 (m, 1H), 3.05 (m, 1H), 3.04 (s, 3H), 2.34 (s, 3H), 2.31 (m, 1H), 1.86 (m, 3H), 1.91 (m, 1H), 1.62-1.23 (m, 4H).

LCMS m/z [M+H]⁺ C₃₀H₃₃ClN₆O₄S requires: 609.20. Found 609.16

HPLC Tr (min), purity %: 7.99, 99%

Compound 209

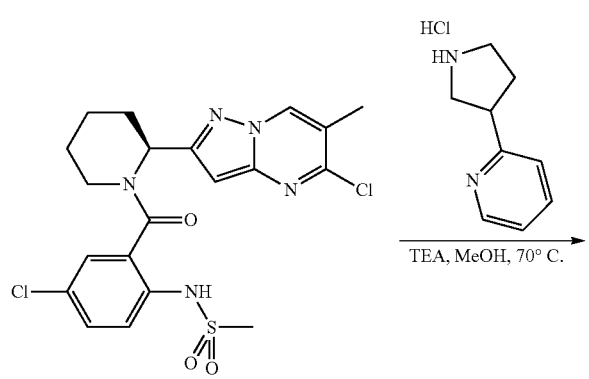

-continued

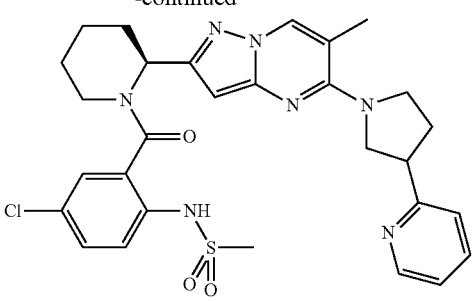

Following the procedure of compound 188, starting from intermediate 73, compound 209 was recovered as a white solid, trifluoroacetic acid salt (36 mg, 63%) after lyophilization.

¹H-NMR (DMSO, 400 MHz): δ 9.24 (s, 1H) 8.64 (d, 1H), 8.49 (d, 1H), 8.01 (m, 1H), 7.62 (m, 1H), 7.55-7.40 (m, 3H), 6.08 (s, 1H), 5.94 (m, 1H), 4.35 (m, 2H), 4.09 (m, 2H), 3.92-3.81 (m, 3H), 3.69 (m, 1H), 3.10 (m, 1H), 3.06 (m, 1H), 3.03 (s, 3H), 2.35 (m, 1H), 2.34 (s, 3H), 2.15 (m, 1H), 1.81 (m, 1H), 1.65-1.22 (m, 3H).

LCMS m/z [M+H]⁺ C₂₉H₃₂ClN₇O₃S requires: 594.20. Found 594.14

HPLC Tr (min), purity %: 5.86, 98%

Compound 210

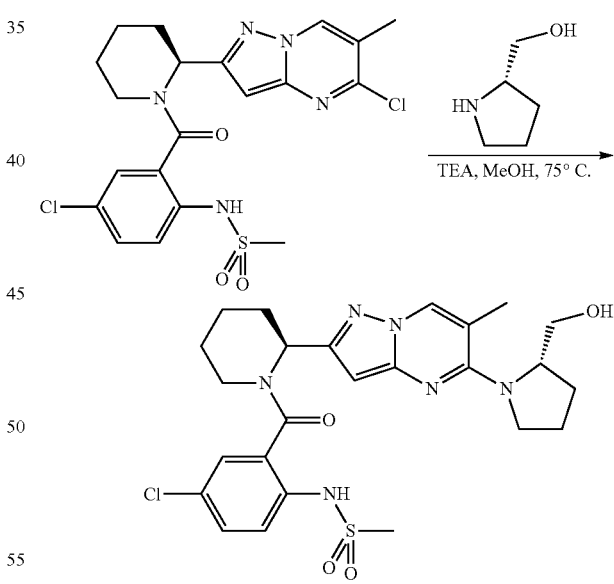

Following the procedure of compound 188, starting from intermediate 73, compound 210 was recovered as a white solid (67 mg, 86%) after silica gel column chromatography (15-90% ethyl acetate in hexanes).

¹H-NMR (DMSO, 400 MHz): δ 9.26 (s, 1H) 8.49 (s, 1H), 7.55-7.30 (m, 3H), 6.08 (s, 1H), 5.96 (s, 1H), 4.66 (m, 1H), 4.41 (m, 1H), 3.72 (m, 1H), 3.54 (m, 2H), 3.34 (m, 1H), 3.18 (m, 1H), 3.03 (s, 3H), 2.36 (m, 1H), 2.32 (s, 3H), 1.97-1.86 (m, 5H), 1.74 (m, 1H), 1.62-1.27 (m, 4H).

LCMS m/z [M+H]+ C25H31ClN6O4S requires: 547.18. Found 547.11

HPLC Tr (min), purity %: 6.22, 99%

Intermediate 166

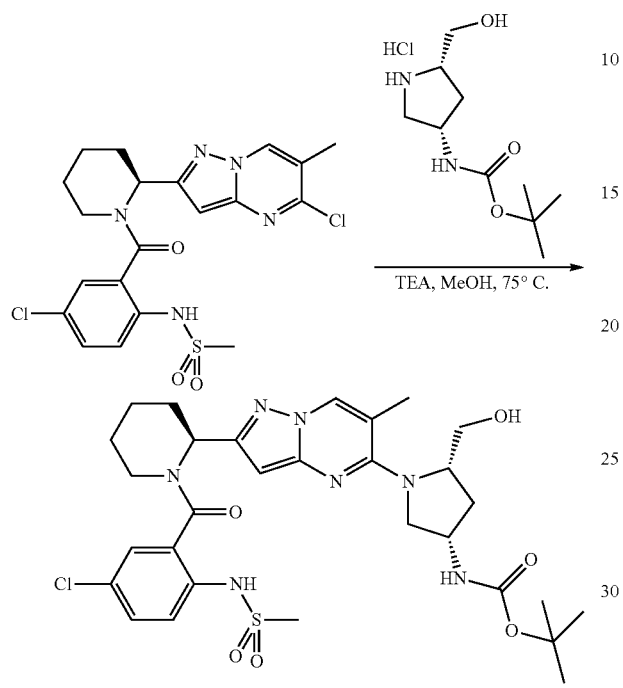

Following the procedure of compound 188, starting from intermediate 73, intermediate 166 was recovered as a white solid (87 mg, 81%) after silica gel chromatography (20-100% ethyl acetate/hexanes).

LCMS m/z [M+H]+ C30H40ClN7O6S requires: 662.24. Found 662.19

Compound 211

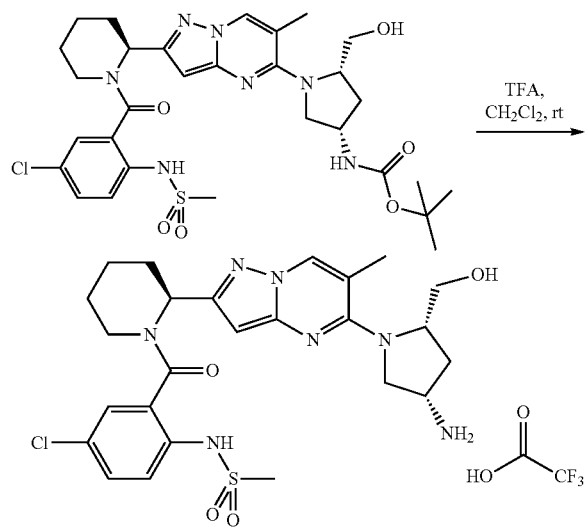

Following the procedure of compound 190, beginning with intermediate 166 (85 mg, 0.128 mmol), compound 211 was recovered as a pink solid, trifluoroacetic acid salt (48 mg, 55%) after drying in-vacuo.

¹H-NMR (DMSO, 400 MHz): δ 9.22 (s, 1H) 8.59 (s, 1H), 8.06 (s, 3H), 7.54-7.38 (m, 3H), 6.14 (s, 1H), 5.97 (m, 1H), 4.53 (m, 1H), 3.81 (m, 3H), 3.61 (m, 1H), 3.49 (m, 2H), 3.21 (m, 1H), 3.06 (m, 1H), 3.04 (s, 3H), 2.41-2.35 (m, 2H), 2.31 (s, 3H), 1.97-1.87 (m, 2H), 1.65-1.21 (m, 4H).

LCMS m/z [M+H]+ C25H32ClN7O4S requires: 562.19. Found 562.17

HPLC Tr (min), purity %: 5.38, 95%

Compound 212

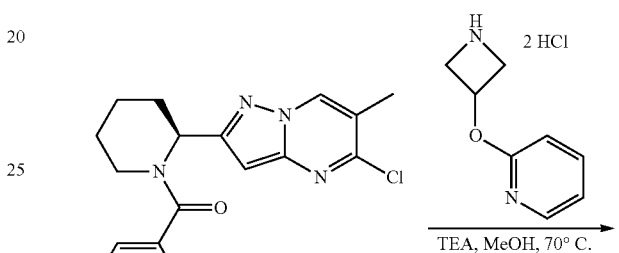

Following the procedure of compound 188, starting from intermediate 73, compound 212 was recovered as a white solid, trifluoroacetic acid salt (35 mg, 59%) after lyophilization.

¹H-NMR (DMSO, 400 MHz): δ 9.19 (s, 1H) 8.50 (d, 1H), 8.37 (d, 1H), 8.32 (d, 1H), 7.54-7.38 (m, 4H), 6.15 (s, 1H), 5.96 (m, 1H), 4.72 (m, 3H), 4.23 (m, 3H), 3.21 (m, 1H), 3.05 (m, 1H), 3.03 (s, 3H), 2.33 (m, 1H), 2.16 (s, 3H), 1.87 (m, 1H), 1.67-1.18 (m, 4H).

LCMS m/z C28H30ClN7O4S requires: 596.18. Found 596.14

HPLC Tr (min), purity %: 5.87, 99%

Compound 213

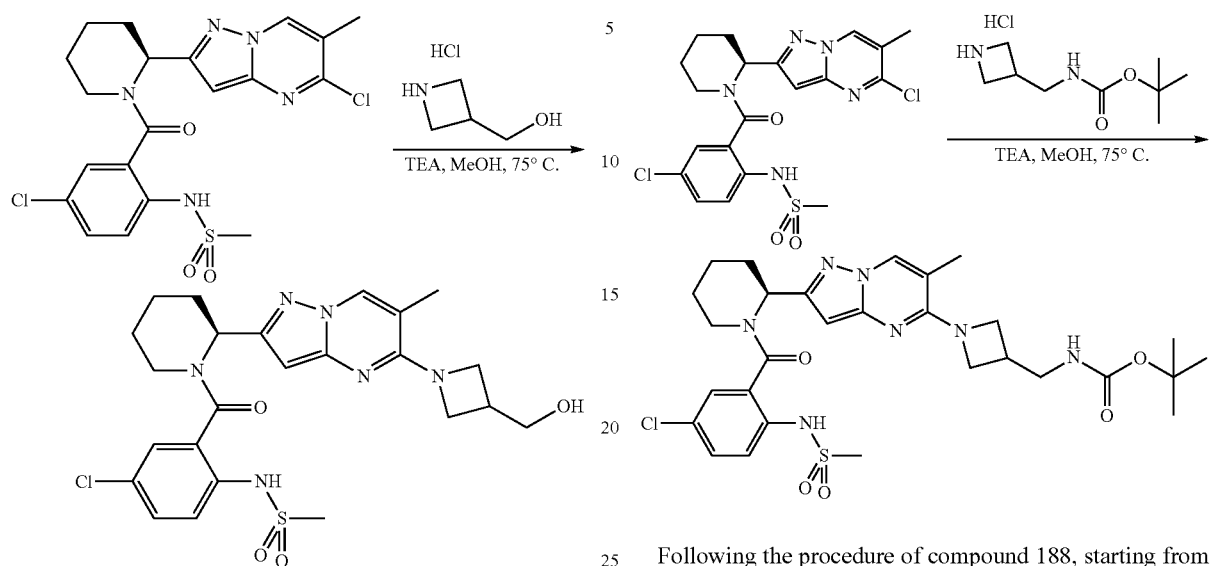

Following the procedure of compound 188, beginning with intermediate 73 (62 mg, 0.129 mmol), compound 213 was recovered as a white solid, trifluoroacetic acid salt (45 mg, 54%) after lyophilization.

$^1$H-NMR (DMSO, 400 MHz): δ 9.20 (s, 1H) 8.43 (s, 1H), 7.53-7.37 (m, 3H), 6.08 (s, 1H), 5.93 (m, 1H), 4.24 (m, 2H), 3.99 (m, 2H), 3.57 (m, 2H), 3.19 (m, 1H), 3.05 (m, 1H), 3.02 (s, 3H), 2.73 (m, 1H), 2.31 (m, 1H), 2.14 (s, 3H), 2.12 (m, 1H), 1.87 (m, 1H), 1.65-1.22 (m, 4H)

LCMS m/z [M+H]$^+$ C$_{24}$H$_{29}$ClN$_6$O$_4$S requires: 533.17. Found 533.14

HPLC Tr (min), purity %: 5.45, 99%

Intermediate 167

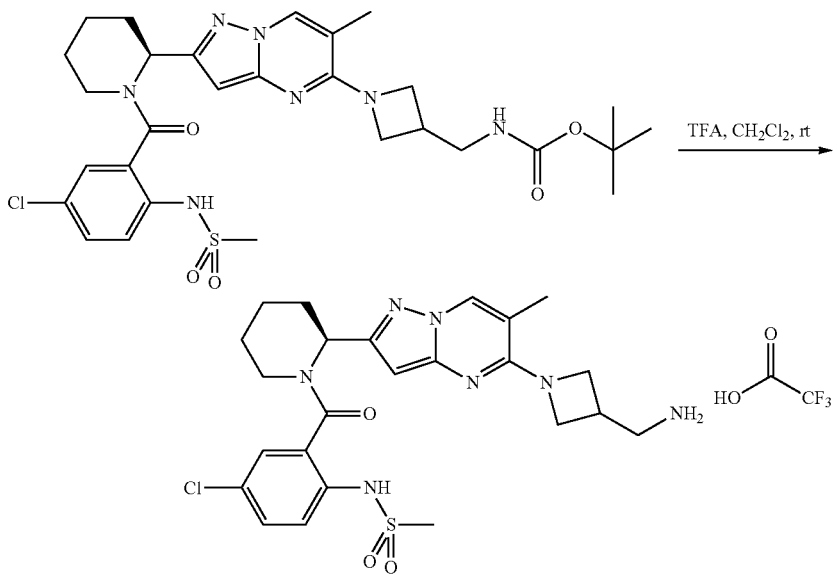

Following the procedure of compound 188, starting from intermediate 73, intermediate 167 was recovered as a white solid, (84 mg, 93%) after silica gel chromatography (10-90% ethyl acetate in hexanes).

LCMS m/z [M+H]$^+$ C$_{29}$H$_{38}$ClN$_7$O$_5$S requires: 632.23. Found 632.13

Compound 214

Following the procedure of compound 190, beginning with intermediate 167 (80 mg, 0.127 mmol), compound 214 was recovered as a white solid, trifluoroacetic acid salt (80 mg, 98%) after drying in-vacuo.

$^1$H-NMR (DMSO, 400 MHz): δ 9.21 (s, 1H) 8.46 (s, 1H), 7.80 (s, 3H), 7.52-7.31 (m, 3H), 6.11 (s, 1H), 5.95 (m, 1H), 4.93 (m, 2H), 4.30 (m, 2H), 4.02 (m, 2H), 3.20 (m, 1H), 3.11 (m, 2H), 3.03 (s, 3H), 2.88 (m, 1H), 2.32 (m, 1H), 2.14 (s, 3H), 1.86 (m, 1H), 1.71-1.22 (m, 4H).

445

LCMS m/z [M+H]+ C$_{24}$H$_{30}$ClN$_7$O$_3$S requires: 532.18. Found 532.09

HPLC Tr (min), purity %: 5.15, 99%

Compound 215

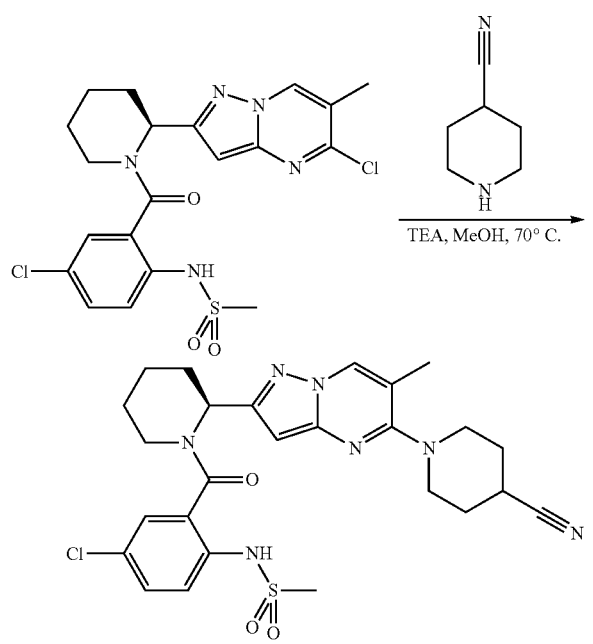

Following the procedure of compound 188, starting from intermediate 73, compound 215 was recovered as a white solid, trifluoroacetic acid salt (64 mg, 73%) after lyophilization.

$^1$H-NMR (DMSO, 400 MHz): δ 9.17 (s, 1H) 8.67 (s, 1H), 7.52-7.37 (m, 3H), 6.35 (s, 1H), 5.99 (m, 1H), 3.48 (m, 2H), 3.21-3.08 (m, 4H), 3.04 (s, 3H), 2.38 (m, 1H), 2.21 (s, 3H), 1.99 (m, 2H), 1.88 (m, 3H), 1.63-1.22 (m, 5H).

446

LCMS m/z [M+H]+ C$_{26}$H$_{30}$ClN$_7$O$_3$S requires: 556.18. Found 556.45

HPLC Tr (min), purity %: 7.60, 97%

Intermediate 168

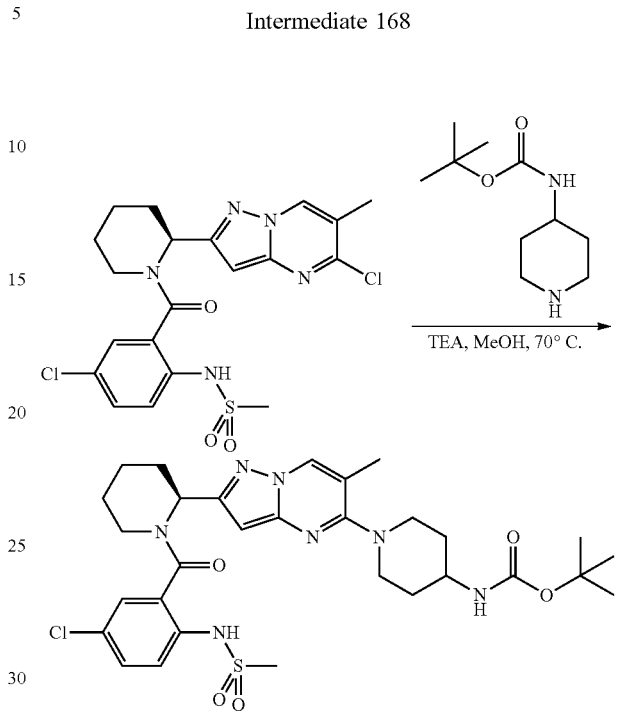

Following the procedure of compound 188, starting from intermediate 73, intermediate 168 was recovered as a white solid, trifluoroacetic acid salt (86 mg, 88%) after lyophilization.

LCMS m/z [M+H]+ C$_{30}$H$_{40}$ClN$_7$O$_5$S requires: 646.25. Found 646.46

Compound 216

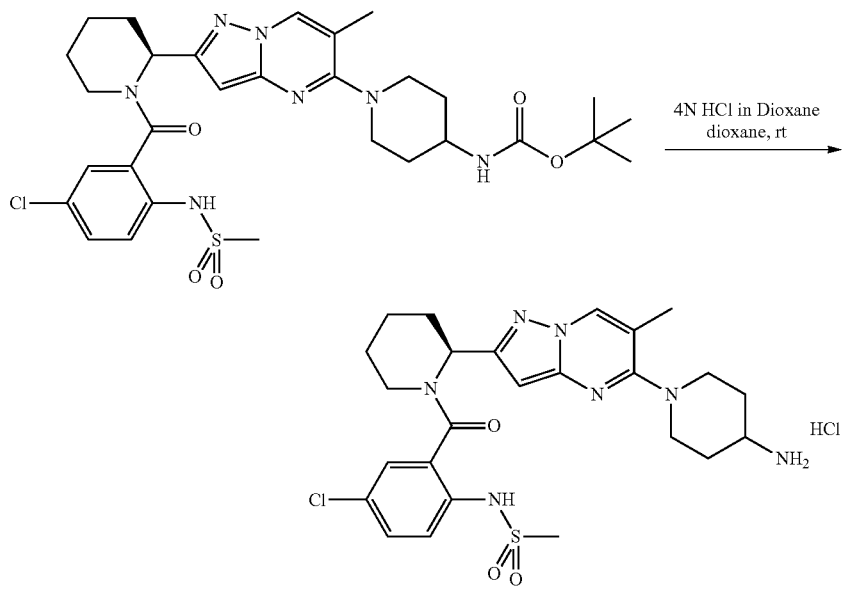

Following the procedure of compound 187, beginning with intermediate 168 (78 mg, 0.120 mmol), compound 216 was recovered as a white solid, hydrochloric acid salt (68 mg, 97%)

$^1$H-NMR (DMSO, 400 MHz): δ 9.18 (s, 1H) 8.67 (s, 1H), 8.25 (s, 3H), 7.55-7.38 (m, 3H), 6.32 (s, 1H), 5.98 (m, 1H), 3.79 (m, 2H), 3.65 (m, 0.5H), 3.46 (m, 0.5H), 3.22 (m, 2H), 3.04 (s, 3H), 2.89 (m, 2H), 2.36 (m, 1H), 2.21 (s, 3H), 2.01 (m, 2H), 1.88 (m, 1H), 1.75-1.27 (m, 6H).

LCMS m/z [M+H]$^+$ C$_{25}$H$_{32}$ClN$_7$O$_3$S requires: 546.20. Found 546.41

HPLC Tr (min), purity %: 5.50, 98%

Compound 217

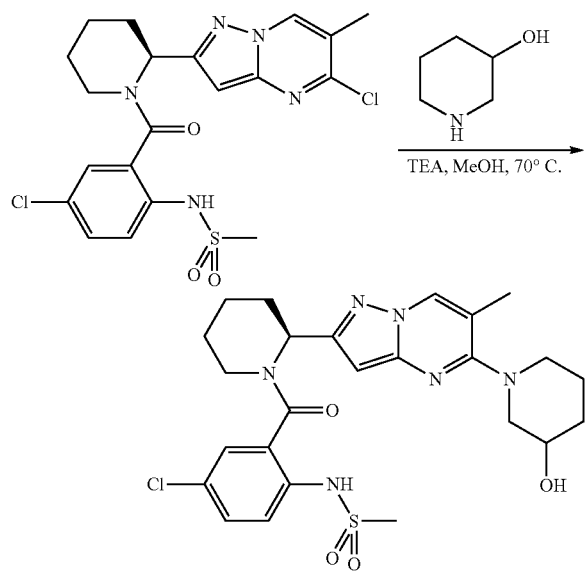

Following the procedure of compound 188, beginning with intermediate 73 (61.2 mg, 0.131 mmol), compound 217 was recovered as a white solid, trifluoroacetic acid salt (69 mg, 80%) after lyophilization.

$^1$H-NMR (DMSO, 400 MHz): δ 9.19 (s, 1H), 8.63 (s, 1H), 7.54-7.37 (m, 3H), 6.29 (s, 1H), 5.98 (m, 1H), 3.65 (m, 2H), 3.49 (m, 1H), 3.21 (m, 1H), 3.05 (m, 1H), 3.04 (s, 3H), 2.87 (m, 1H), 2.70 (m, 1H), 2.37 (m, 1H), 2.21 (s, 3H), 2.20 (m, 1H), 1.94-1.77 (m, 3H), 1.72-1.25 (m, 6H).

LCMS m/z [M+H]$^+$ C$_{25}$H$_{31}$ClN$_6$O$_4$S requires: 547.18. Found 547.40

HPLC Tr (min), purity %: 6.78, 99%

Compound 218

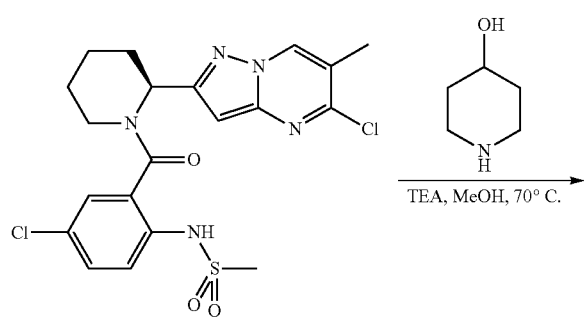

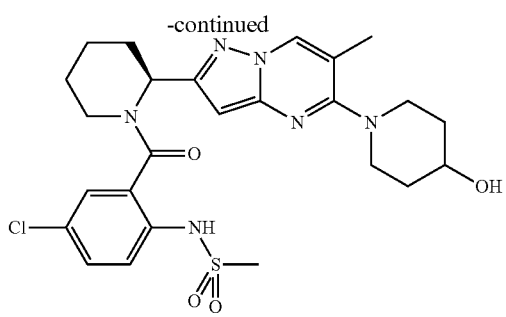

Following the procedure of compound 188, starting from intermediate 73, compound 218 was recovered as a white solid, trifluoroacetic acid salt (58 mg, 67%) after lyophilization.

$^1$H-NMR (DMSO, 400 MHz): δ 9.14 (s, 1H) 8.59 (s, 1H), 7.49-7.32 (m, 3H), 6.25 (s, 1H), 5.94 (m, 1H), 4.85 (br s, 1H), 3.64 (m, 1H), 3.52 (m, 2H), 3.16 (m, 1H), 2.99 (s, 3H), 2.97-2.85 (m, 2H), 2.37 (s, 3H), 2.31 (m, 1H), 2.16 (s, 3H), 1.79 (m, 3H), 1.62-1.18 (m, 4H).

LCMS m/z [M+H]$^+$ C$_{25}$H$_{31}$ClN$_6$O$_4$S requires: 547.18. Found 547.45

HPLC Tr (min), purity %: 6.53, 99%

Intermediate 169

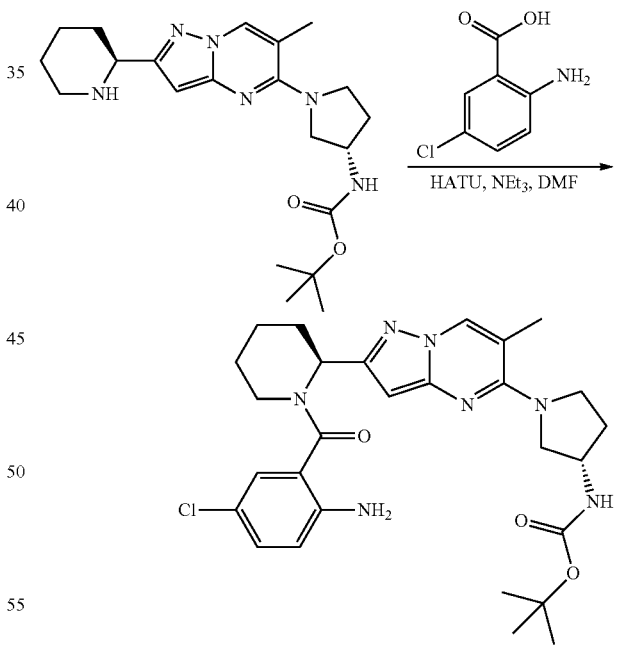

2-Amino-5-chlorobenzoic acid (82 mg, 0.48 mmol), HATU (228 mg, 0.6 mmol) were dissolved in anhydrous DMF (2 ml). After activation for 1 hour, to the above solution was added the intermediate 130 (120 mg, 0.3 mmol) and triethylamine (0.17 ml). The reaction was stirred under nitrogen for 2 hours. Solvents were removed by rotary evaporation. The residue was purified with silica gel column chromatography to provide intermediate 169. (Yield 134 mg, 81%).

LCMS m/z [M+H]$^+$ C$_{28}$H$_{36}$ClN$_7$O$_3$ requires: 554.26. Found 554.18

HPLC Tr (min), purity %: 2.00, 98%

Intermediate 170

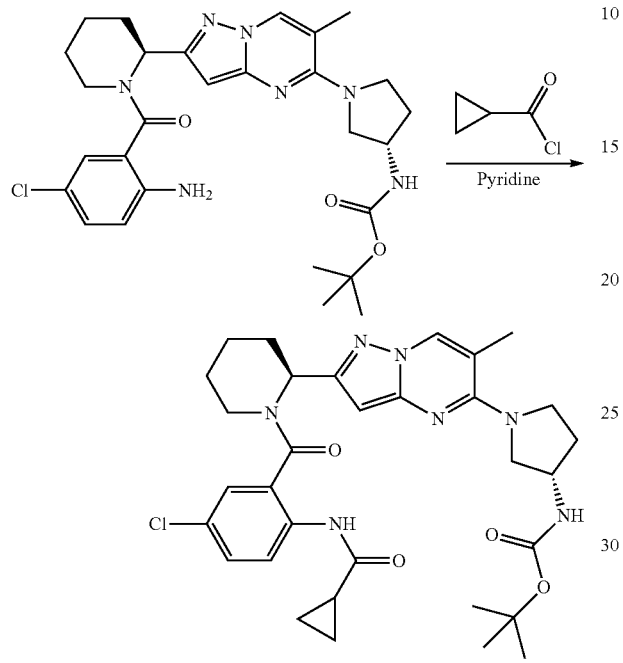

Intermediate 169 (40 mg, 0.072 mmol) was dissolved in pyridine (2 ml). Then cyclopropane carboxylic acid chloride (9.1 mg, 0.087 mmol) was added to the above solution. The reaction was stirred under nitrogen for 2 hours. Solvents were removed by rotary evaporation. The residue was purified with silica gel column chromatography to provide intermediate 170. (Yield 25 mg, 64%).

LCMS m/z [M+H]$^+$ C$_{32}$H$_{40}$ClN$_7$O$_4$ requires: 622.28. Found 622.06

HPLC Tr (min), purity %: 2.83, 98%

Compound 219

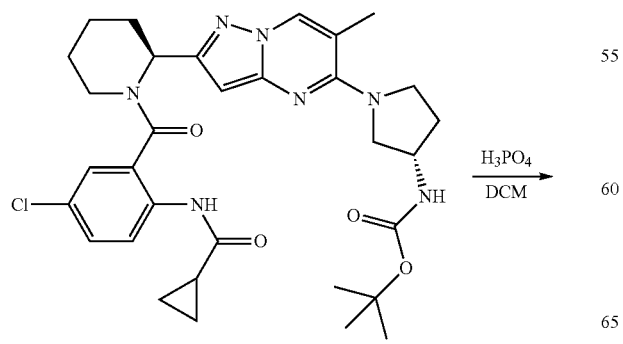

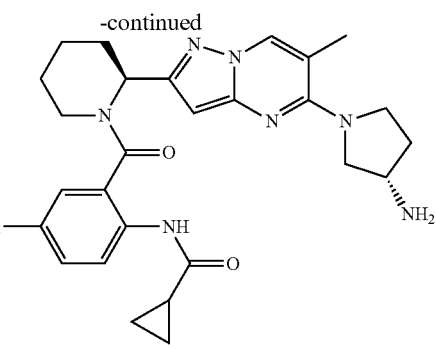

Intermediate 170 (25 mg, 0.04 mmol) was dissolved in DCM (0.2 ml). Then phosphoric acid (7.9 mg, 0.08 mmol) was added to the above solution. The reaction was stirred under nitrogen for 5 mins. Solvents were removed by rotary evaporation. The residue was purified with preparatory HPLC to provide compound 219. (Yield 6 mg, 24%).

$^1$H-NMR (CD$_3$OD, 400 MHz): δ 8.19 (s, 1H), 7.34 (bs, 2H), 5.93-5.82 (m, 2H), 5.39 (s, 1H), 3.91-3.89 (m, 4H), 3.80-3.69 (m, 3H), 2.36 (s, 3H), 2.06-1.84 (m, 4H), 1.73-1.48 (m, 5H), 0.88-0.80 (m, 4H).

LCMS m/z [M+H]$^+$ C$_{27}$H$_{32}$ClN$_7$O$_2$ requires: 522.23. Found 522.08

HPLC Tr (min), purity %: 2.02, 98%

Intermediate 171

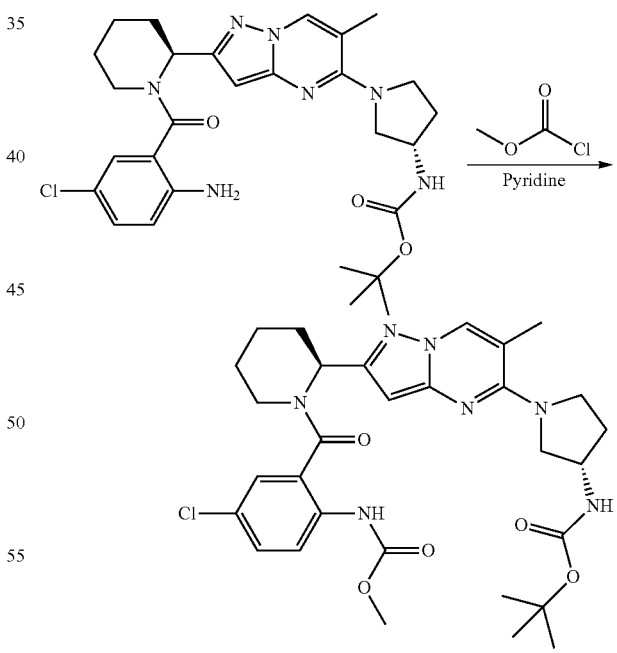

Intermediate 169 (40 mg, 0.072 mmol) was dissolved in pyridine (2 ml). Then methyl chloroformate (328 mg, 3.48 mmol) was added to the above solution. The reaction was stirred under nitrogen overnight. Solvents were removed by rotary evaporation. The residue was purified with silica gel column chromatography to provide intermediate 171. (Yield 31 mg, 79%).

LCMS m/z [M+H]⁺ C₃₀H₃₈ClN₇O₅ requires: 612.26. Found 612.08

HPLC Tr (min), purity %: 2.96, 98%

Compound 220

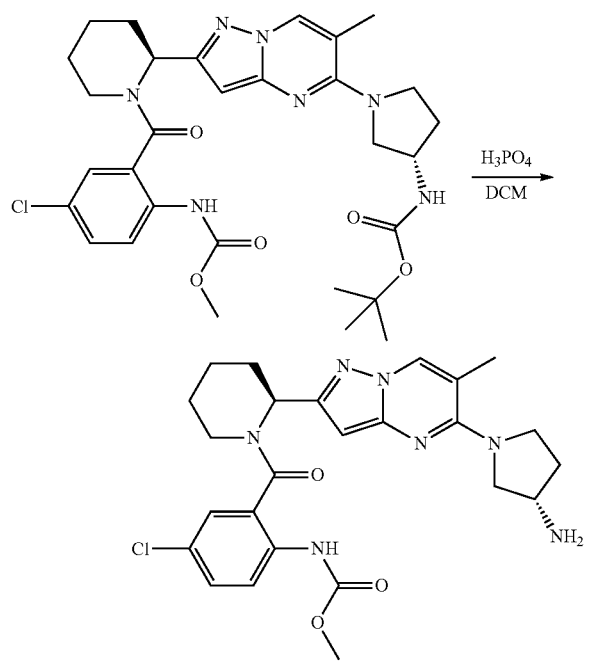

Intermediate 171 (30 mg, 0.05 mmol) was dissolved in DCM (0.2 ml). Then phosphoric acid (9.6 mg, 0.1 mmol) was added to the above solution. The reaction was stirred under nitrogen for 5 mins. Solvents were removed by rotary evaporation. The residue was purified with preparatory HPLC to provide compound 220. (Yield 16 mg, 53%).

¹H-NMR (CD₃OD, 400 MHz): δ 8.31-8.21 (m, 1H), 7.33-7.28 (m, 2H), 5.98-5.85 (m, 2H), 3.92-3.88 (m, 4H), 3.77-3.73 (m, 3H), 3.68 (s, 3H), 2.36 (s, 3H), 2.09-2.07 (m, 1H), 1.90 (bs, 1H), 1.64-1.44 (m, 5H).

LCMS m/z [M+H]⁺ C₂₅H₃₀ClN₇O₃ requires: 512.21. Found 512.14

HPLC Tr (min), purity %: 2.24, 98%

Intermediate 172

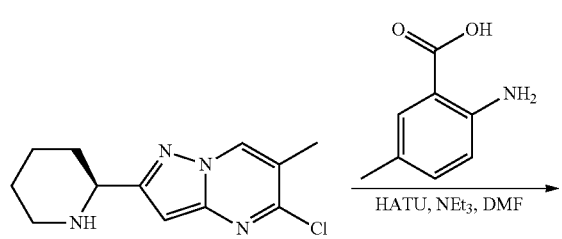

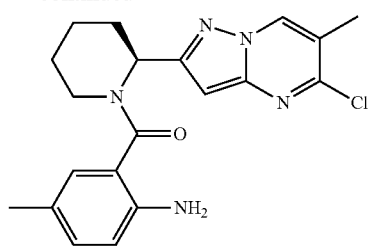

2-Amino-5-methylbenzoic acid (316 mg, 2.09 mmol), HATU (992 mg, 2.61 mmol) were dissolved in anhydrous DMF (2 ml). After activation for 1 hour, to the above solution was added intermediate 72 (500 mg, 1.74 mmol) and triethylamine (0.7 ml). The reaction was stirred under nitrogen for 2 hours. Solvents were removed by rotary evaporation. The residue was purified with silica gel column chromatography to provide intermediate 172. (Yield 320 mg, 42%).

LCMS m/z [M+H]⁺ C₂₀H₂₂ClN₅O requires: 384.15. Found 383.99

HPLC Tr (min), purity %: 2.00, 98%

Intermediate 173

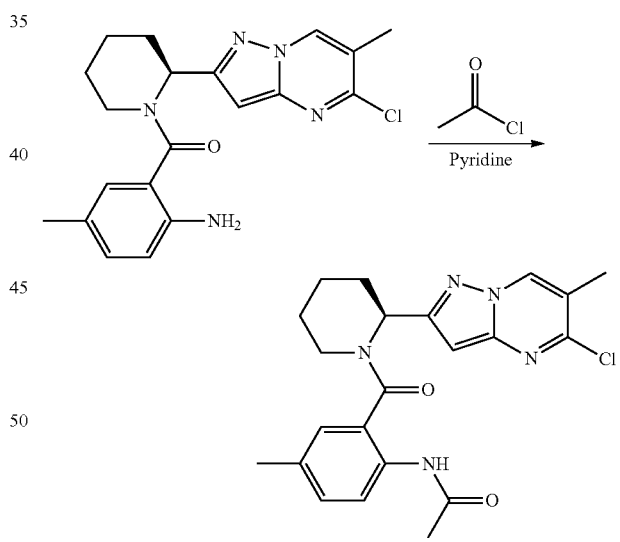

Intermediate 172 (320 mg, 0.84 mmol) was dissolved in pyridine (2 ml). Then acetyl chloride (78 mg, 1.0 mmol) was added to the above solution. The reaction was stirred under nitrogen for 30 mins. Solvents were removed by rotary evaporation. The residue was purified with silica gel column chromatography to provide intermediate 173. (Yield 305 mg, 86%).

LCMS m/z [M+H]⁺ C₂₂H₂₄ClN₅O₂ requires: 426.16. Found 425.89

HPLC Tr (min), purity %: 2.40, 98%

Compound 221

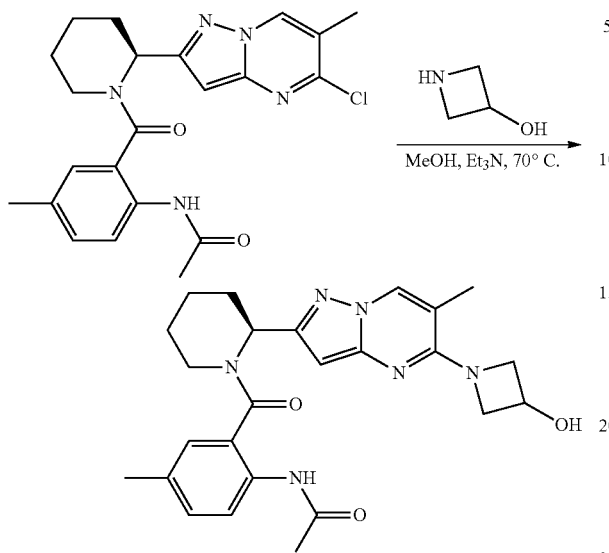

Intermediate 173 (35 mg, 0.09 mmol) was dissolved in MeOH (5 ml). Then 3-hydroxyazetidine HCl salt (100 mg, 0.9 mmol) and triethylamine (184 mg, 1.82 mmol) was added to the above solution. The reaction was heated at 70° C. for 1 h. Solvents were removed by rotary evaporation. The residue was purified with preparatory HPLC to provide compound 221. (Yield 23 mg, 65%).

$^1$H-NMR (CD$_3$OD, 400 MHz): δ 8.75-8.71 (m, 1H), 8.13-7.96 (m, 2H), 7.22-7.05 (m, 2H), 6.20-6.13 (m, 1H), 4.78-4.65 (m, 1H), 4.52-4.43 (m, 2H), 4.18-4.05 (m, 2H), 2.43-2.25 (m, 4H), 2.18 (s, 3H), 2.16 (s, 3H), 2.05 (s, 3H), 1.75-1.23 (m, 5H)

LCMS m/z [M+H]$^+$ C$_{25}$H$_{30}$ClN$_6$O$_3$ requires: 463.24. Found 463.03

HPLC Tr (min), purity %: 2.27, 98%

Intermediate 174

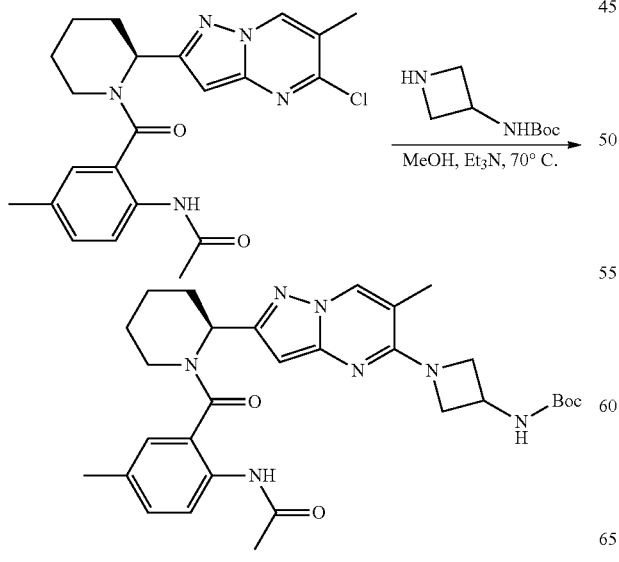

Intermediate 173 (30 mg, 0.06 mmol) was dissolved in MeOH (2 ml). Then 3-boc-aminoazetidine (11 mg, 0.18 mmol) and triethylamine (60 ul) was added to the above solution. The reaction was heated at 70° C. for 1 h. Solvents were removed by rotary evaporation. The residue was purified with preparatory HPLC to provide intermediate 174. (Yield 30 mg, 75%).

LCMS m/z [M+H]$^+$ C$_{30}$H$_{39}$N$_7$O$_4$ requires: 562.31. Found 562.16

HPLC Tr (min), purity %: 2.27, 98%

Compound 222

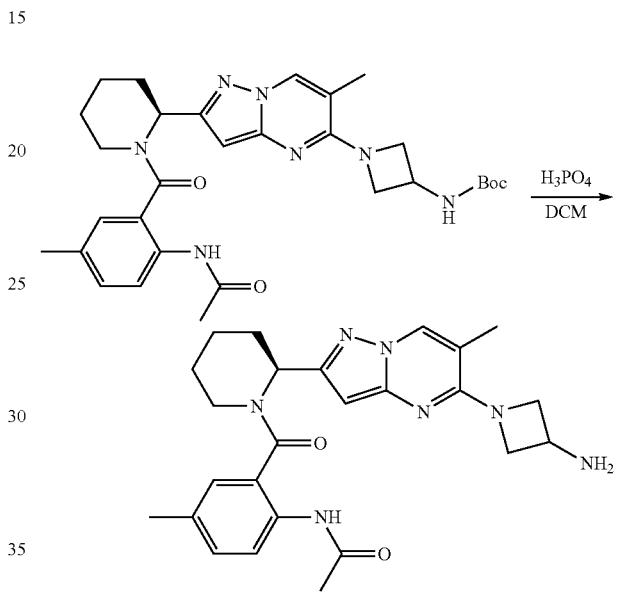

Intermediate 174 (10 mg, 0.018 mmol) was dissolved in DCM (0.2 ml). Then phosphoric acid (3.6 mg, 0.036 mmol) was added to the above solution. The reaction was stirred under nitrogen for 5 mins. Solvents were removed by rotary evaporation. The residue was purified with preparatory HPLC to provide compound 222. (Yield 3.5 mg, 43%).

$^1$H-NMR (CD$_3$OD, 400 MHz): δ 8.72 (bs, 1H), 7.30-7.25 (m, 3H), 6.03 (s, 1H), 4.63-4.32 (m, 3H), 3.55-3.42 (m, 1H), 3.22-3.13 (m, 1H), 2.39 (s, 3H), 2.34-1.92 (m, 4H), 2.17 (s, 3H), 2.14 (s, 3H), 1.73-1.56 (m, 5H)

LCMS m/z [M+H]$^+$ C$_{25}$H$_{31}$N$_7$O$_2$ requires: 462.25. Found 462.14

HPLC Tr (min), purity %: 2.24, 98%

Intermediate 175

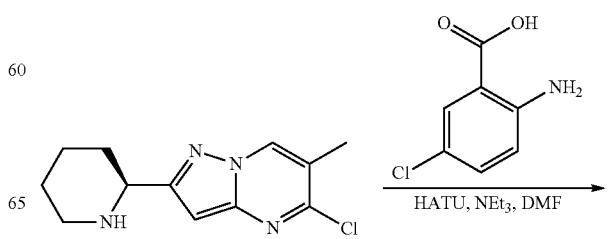

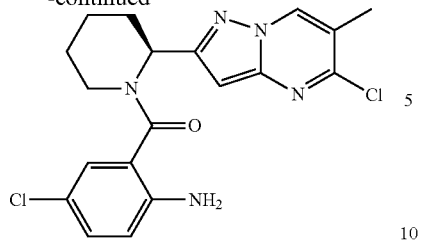

2-Amino-5-chlorobenzoic acid (343 mg, 2.0 mmol), HATU (1.22 g, 3.2 mmol) were dissolved in anhydrous DMF (5 ml). After activation for 1 hour, to the above solution was added intermediate 72 (400 mg, 1.6 mmol) and triethylamine (0.9 ml). The reaction was stirred under nitrogen for 2 hours. Solvents were removed by rotary evaporation. The residue was purified with silica gel column chromatography to provide intermediate 175. (Yield 320 mg, 42%).

LCMS m/z [M+H]$^+$ $C_{19}H_{19}Cl_2N_5O$ requires: 404.10. Found 403.99

HPLC Tr (min), purity %: 2.56, 98%

Intermediate 176

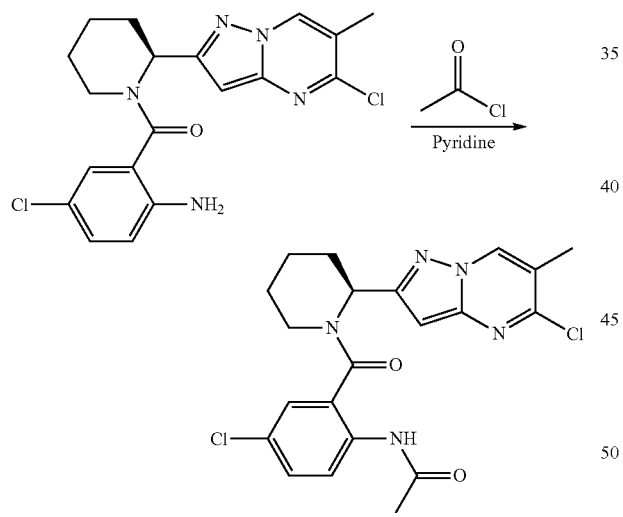

Intermediate 175 (30 mg, 0.07 mmol) was dissolved in pyridine (2 ml). Then acetyl chloride (8.7 mg, 0.11 mmol) was added to the above solution. The reaction was stirred under nitrogen for 30 mins. Solvents were removed by rotary evaporation. The residue was purified with silica gel column chromatography to provide intermediate 176. (Yield 25 mg, 76%).

LCMS m/z [M+H]$^+$ $C_{21}H_{21}Cl_2N_5O_2$ requires: 446.11. Found 445.84

HPLC Tr (min), purity %: 2.43, 98%

Compound 223

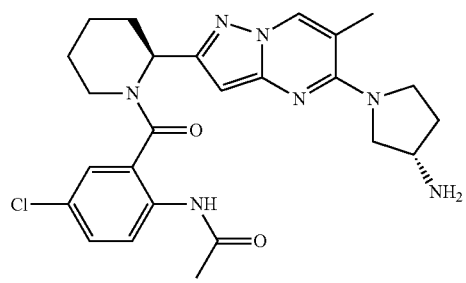 [SMILES: CC(=O)Nc1ccc(Cl)cc1C(=O)N1CCCC[C@H]1c1cc2nc(N3CC[C@H](N)C3)c(C)cn2n1]

The title compound was prepared in an analogous way as described for compound 222 but starting from intermediate 176 and using (S)-tert-butyl pyrrolidin-3-ylcarbamate.

$^1$H-NMR (CD$_3$OD, 400 MHz): δ 8.28 (bs, 2H), 7.48-7.45 (m, 2H), 6.05 (bs, 1H), 4.03-3.85 (m, 2H), 3.84-3.59 (m, 2H), 3.42-3.18 (m, 2H), 2.43 (s, 3H), 2.14 (s, 3H), 2.01-1.94 (m, 2H), 1.71-1.56 (m, 4H), 1.46-1.31 (m, 3H).

LCMS m/z [M+H]$^+$ $C_{25}H_{30}ClN_7O_2$ requires: 496.21. Found 496.08

HPLC Tr (min), purity %: 2.14, 98%

Compound 224

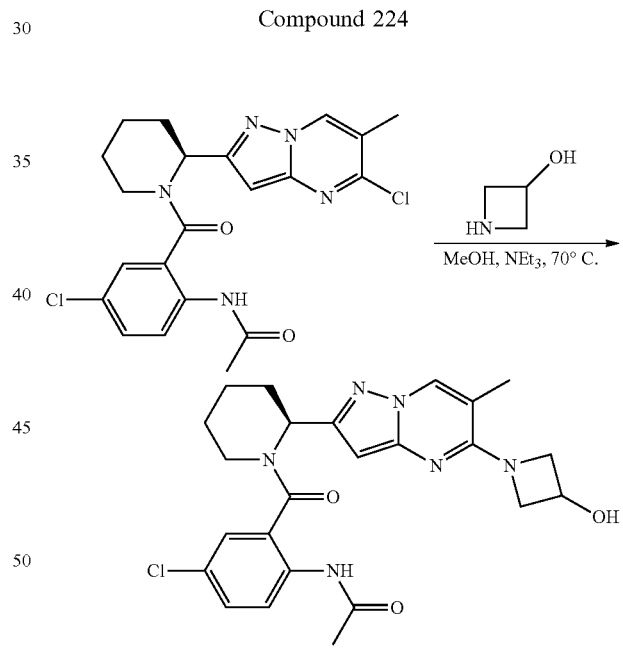

Intermediate 176 (25 mg, 0.06 mmol) was dissolved in MeOH (5 ml). Then 3-hydroxyazetidine HCl salt (12 mg, 0.11 mmol) and triethylamine (24 mg, 0.24 mmol) was added to the above solution. The reaction was heated at 70° C. for 1 h. Solvents were removed by rotary evaporation. The residue was purified with preparatory HPLC to provide compound 224. (Yield 23 mg, 85%).

$^1$H-NMR (CD$_3$OD, 400 MHz): δ 8.19 (s, 1H), 7.45-7.38 (m, 2H), 6.04-5.94 (m, 2H), 4.67-4.64 (m, 1H), 4.52 (t, J=7.2 Hz, 2H), 4.09 (dd, J=4.0, 9.6 Hz, 2H), 3.43-3.02 (m, 3H), 2.43-2.20 (m, 1H), 2.24 (s, 3H), 2.14 (s, 3H), 1.96 (bs, 3H), 1.55-1.54 (m, 4H)

LCMS m/z [M+H]+ C24H27ClN6O3 requires: 483.18. Found 483.05

HPLC Tr (min), purity %: 2.30, 98%

Intermediate 177

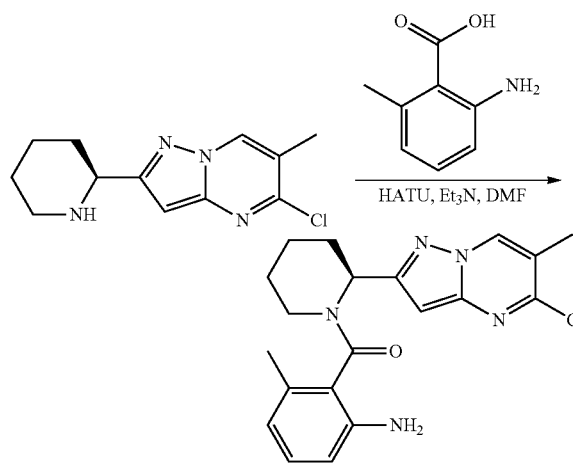

2-Amino-5-methylbenzoic acid (84 mg, 0.56 mmol), HATU (266 mg, 0.7 mmol) were dissolved in anhydrous DMF (5 ml). After activation for 1 hour, to the above solution was added intermediate 72 (100 mg, 0.35 mmol) and triethylamine (0.2 ml). The reaction was stirred under nitrogen for 2 hours. Solvents were removed by rotary evaporation. The residue was purified with silica gel column chromatography to provide intermediate 177. (Yield 42 mg, 36%).

LCMS m/z [M+H]+ C20H22ClN5O requires: 384.87. Found 384.80

HPLC Tr (min), purity %: 2.76, 98%

Intermediate 178

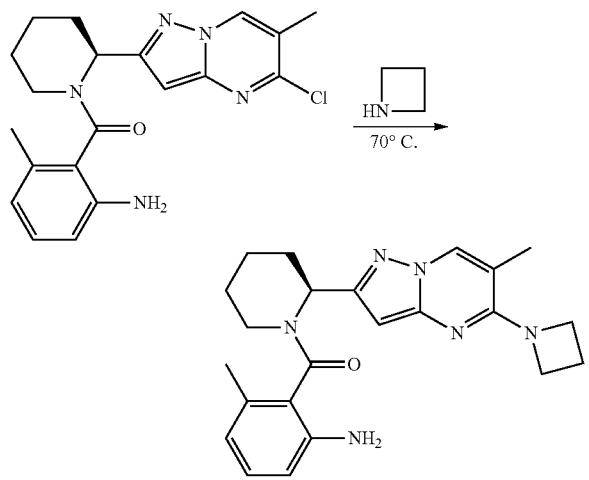

Intermediate 177 (42 mg, 0.11 mmol) was dissolved in azetidine (1 ml). The reaction was heated at 70° C. for 1 h. Solvents were removed by rotary evaporation. The residue was purified with preparatory HPLC to provide intermediate 178. (Yield 40 mg, 91%).

LCMS m/z [M+H]+ C23H28N6O requires: 405.23. Found 405.15

HPLC Tr (min), purity %: 2.40, 98%

Compound 225

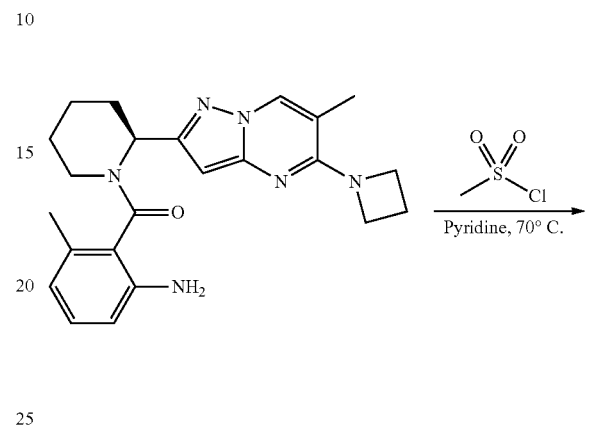

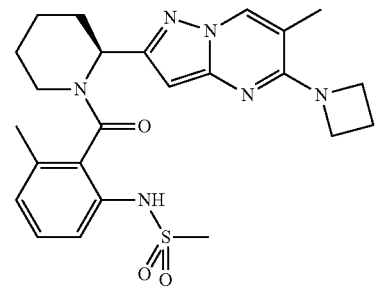

Intermediate 178 (30 mg, 0.07 mmol) was dissolved in pyridine (2 ml). Then methanesulfonyl chloride (171 mg, 1.5 mmol) was added to the above solution. The reaction was stirred under nitrogen for 30 mins. Solvents were removed by rotary evaporation. The residue was purified with silica gel column chromatography to provide compound 225. (Yield 11 mg, 32%).

$^1$H-NMR (CD$_3$OD, 400 MHz): δ 9.38 (s, 0.5H), 8.62 (s, 0.5H), 7.48 (d, J=7.2 Hz, 0.5H), 7.40-7.21 (m, 2H), 7.05 (d, J=7.2 Hz, 0.5H), 6.22 (d, J=4.0 Hz, 0.5H), 6.03 (s, 0.5H), 4.38-4.25 (m, 1H), 3.38-3.21 (m, 2H), 2.40-2.25 (m, 3H), 2.35 (s, 3H), 2.19 (s, 3H), 2.12-1.85 (m, 5H), 1.48-1.21 (m, 4H)

LCMS m/z [M+H]+ C24H30N6O3S requires: 483.21. Found 483.13

HPLC Tr (min), purity %: 2.79, 98%

Compound 226

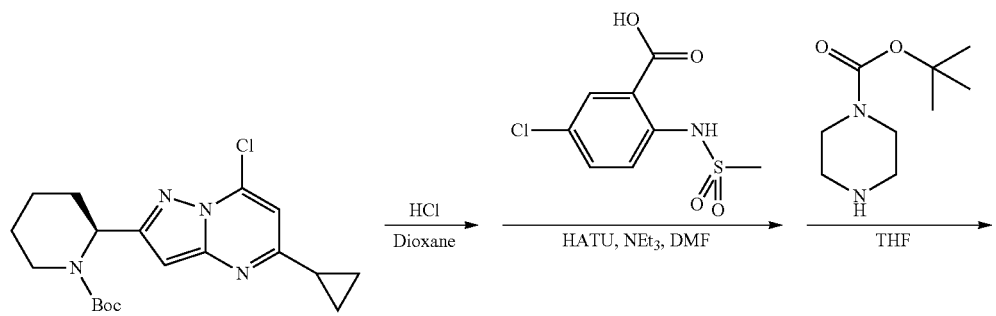

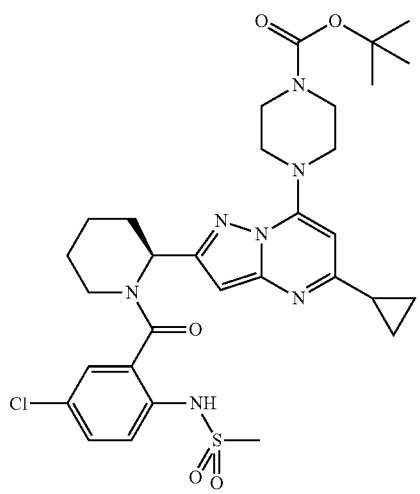

Intermediate 58 (80 mg, 0.21 mmol) was dissolved in dioxane (2 ml), and then HCl (0.1 ml) was added. The reaction mixture was stirred at RT for 30 mins. Solvents were removed by rotary evaporation and the residue was added to the DMF (3 ml) solution of 5-chloro-2-methanesulfonamidobenzoic acid (72 mg, 0.29 mmol), HATU (138 mg, 0.36 mmol). To the above reaction mixture was added triethylamine (0.1 ml). The reaction was stirred at RT for 1 h. The reaction was quenched with brine (5 ml) and extracted with EtOAc (20 ml). Organic solvent was evaporated and dissolved in THF (2 ml). Then 1-boc-piperazine (18 mg, 0.09 mmol) was added to the above solution. The reaction was stirred under nitrogen overnight. Solvents were removed by rotary evaporation. The residue was purified with preparative HPLC to provide compound 226. (Yield 32 mg, 23%).

$^1$H-NMR (CD$_3$OD, 400 MHz): δ 7.50 (bs, 1H), 7.28 (bs, 2H), 6.14 (bs, 1H), 5.95 (s, 1H), 3.60-3.41 (m, 7H), 2.98-2.85 (m, 3H), 2.22 (bs, 1H), 1.92-1.85 (m, 2H), 1.66-1.48 (m, 4H), 1.41 (s, 9H), 1.17 (s, 3H), 1.04-0.78 (m, 5H).

LCMS m/z [M+H]$^+$ C$_{31}$H$_{40}$ClN$_7$O$_5$S requires: 658.25. Found 658.15

HPLC Tr (min), purity %: 2.93, 98%

Intermediate 179

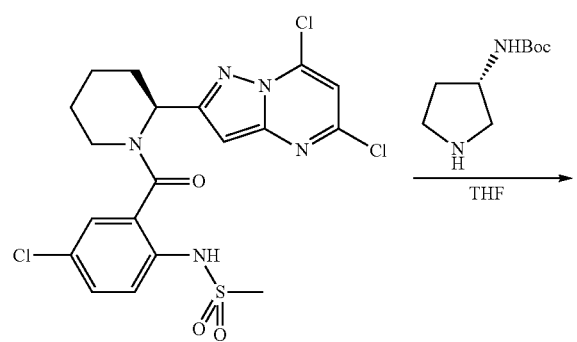

461
-continued

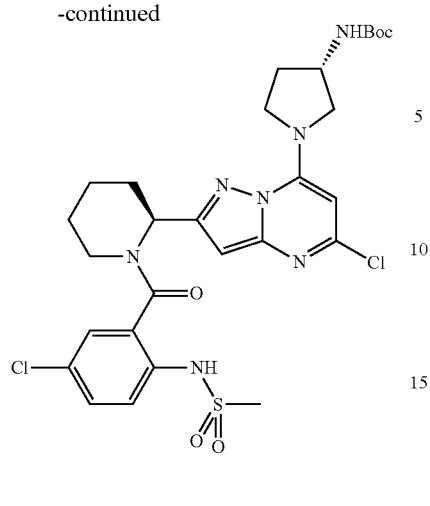

Intermediate 56 (30 mg, 0.06 mmol) was dissolved in THF (2 ml). Then (S)-3-(Boc-amino)pyrrolidine (12 mg, 0.06 mmol) was added to the above solution. The reaction was stirred under nitrogen for 1 h. Solvents were removed by rotary evaporation. The residue was purified with combi flash column to provide intermediate 179 (Yield 35 mg, 90%).

LCMS m/z [M+H]$^+$ C$_{28}$H$_{35}$Cl$_2$N$_7$O$_5$S requires: 652.18. Found 652.01

HPLC Tr (min), purity %: 2.90, 98%

Compound 227

462
-continued

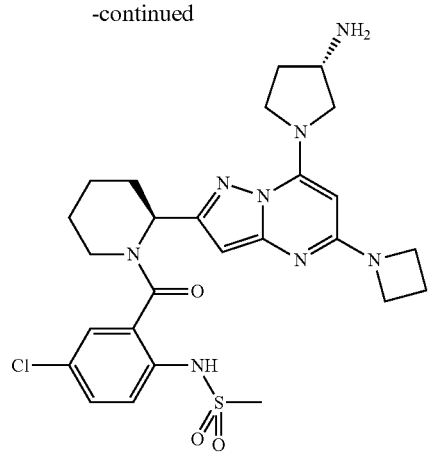

Intermediate 179 (25 mg, 0.04 mmol) was dissolved in THF (2 ml). Then azetidine (0.5 ml) was added to the above solution. The reaction was heated at 70° C. for 1 h. To the above solution was added HCl (0.5 ml), the reaction mixture was heated at 50° for 10 mins. The reaction was quenched with NaHCO$_3$ (5 ml) and extracted with EtOAc (20 ml). Organic solvents were removed by rotary evaporation. The residue was purified with preparatory HPLC to provide compound 227. (Yield 17 mg, 17%).

$^1$H-NMR (CD$_3$OD, 400 MHz): δ 7.39-7.37 (m, 1H), 7.25-7.21 (m, 2H), 6.89-6.88 (m, 1H), 4.13-6.05 (m, 1H), 4.80-3.88 (m, 5H), 3.58-3.31 (m, 2H), 2.77 (s, 3H), 2.41-2.26 (m, 2H), 2.24-2.20 (m, 2H), 1.88-1.68 (m, 4H), 1.68-1.48 (m, 6H).

LCMS m/z [M+H]$^+$ C$_{26}$H$_{33}$ClN$_8$O$_3$S requires: 573.21. Found 573.22

HPLC Tr (min), purity %: 2.10, 98%

Intermediate 180

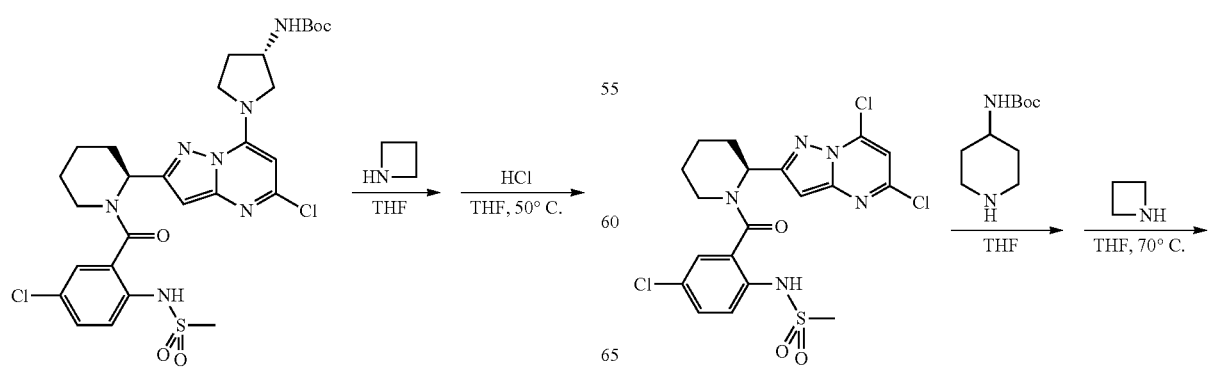

-continued

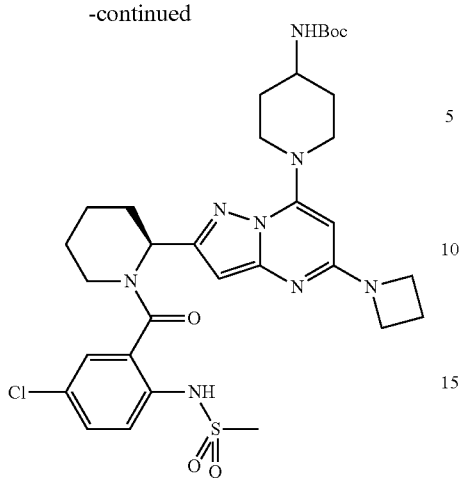

Intermediate 56 (30 mg, 0.06 mmol) was dissolved in THF (2 ml). Then 4-(N-Boc-amino)piperidine (12 mg, 0.06 mmol) was added to the above solution. The reaction was stirred under nitrogen for 1 h. To the reaction mixture was added azetidine (0.5 ml) and was stirred overnight at RT. Solvents were removed by rotary evaporation. The residue was purified with combi flash column to provide intermediate 180 (Yield 25 mg, 62%).

LCMS m/z [M+H]$^+$ C$_{32}$H$_{43}$ClN$_8$O$_5$S requires: 687.28. Found 687.17

HPLC Tr (min), purity %: 2.78, 98%

Compound 228

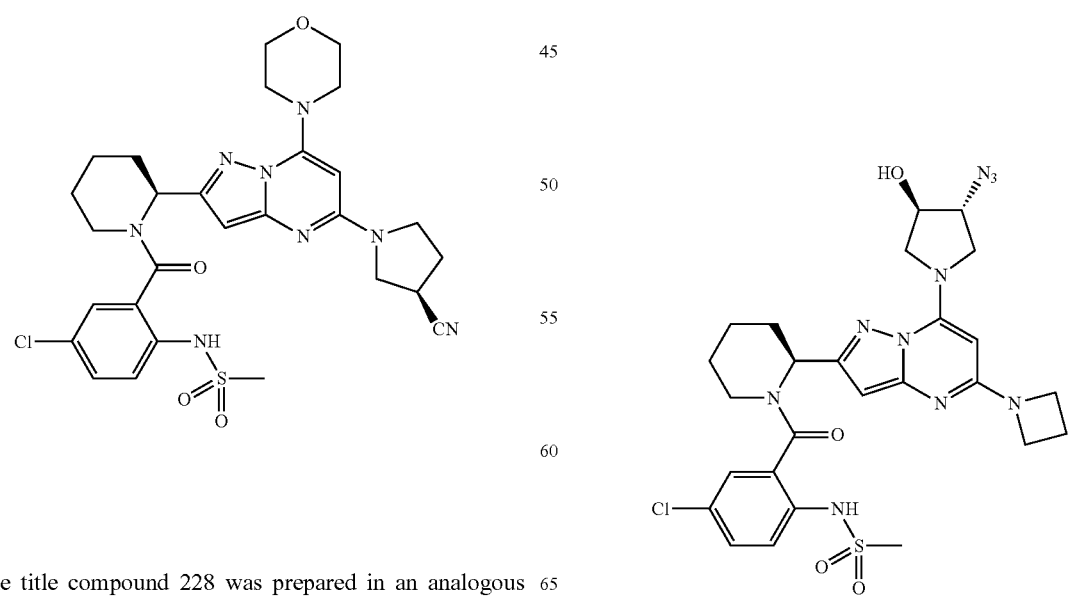

The title compound 228 was prepared in an analogous way as described for compound 224 starting from intermediate 66.

$^1$H-NMR (CD$_3$OD, 400 MHz): δ 7.55 (bs, 2H), 7.31-7.20 (m, 2H), 6.24-6.13 (m, 1H), 3.94-3.60 (m, 6H), 3.29-3.14 (m, 3H), 2.97-2.85 (m, 5H), 2.39 (s, 3H), 2.20 (bs, 2H), 1.93 (bs, 2H), 1.68-1.42 (m, 5H)

LCMS m/z [M+H]$^+$ C$_{28}$H$_{33}$ClN$_8$O$_4$S requires: 613.20. Found 613.18

HPLC Tr (min), purity %: 2.55, 98%

Compound 229

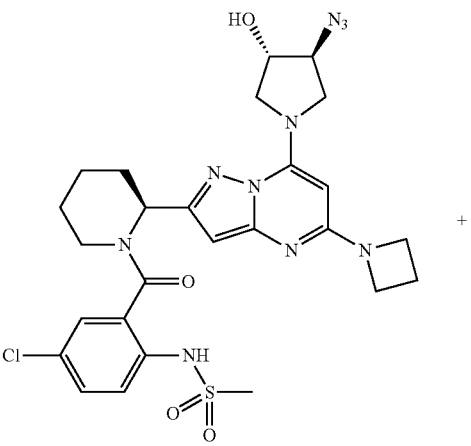

+

The title compound 229 was prepared in an analogous way as described for intermediate 180 starting from intermediate 56 and intermediate 147. Intermediate 147 is first BOC deprotected as described in the preparation of compound 179.

¹H-NMR (CD₃OD, 400 MHz): δ 7.85 (bs, 2H), 7.38-7.20 (m, 2H), 6.32-6.17 (m, 1H), 4.54-4.42 (m, 4H), 4.24-4.10 (m, 2H), 3.85-3.65 (m, 4H), 2.45 (s, 3H), 2.25 (bs, 2H), 1.98 (bs, 2H), 1.76-1.62 (m, 5H)

LCMS m/z [M+H]⁺ $C_{26}H_{31}ClN_{10}O_4S$ requires: 615.19. Found 615.10

HPLC Tr (min), purity %: 2.85, 98%

Compound 230

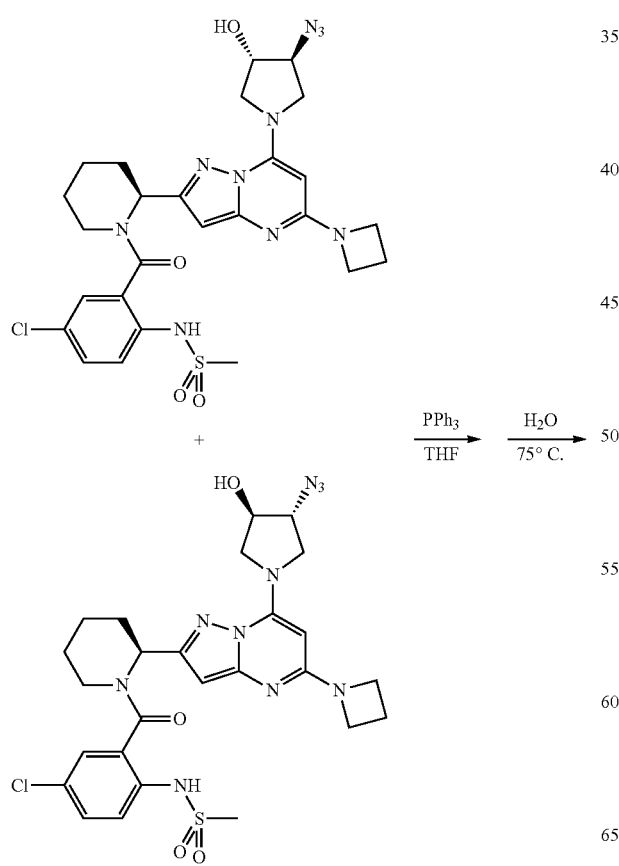

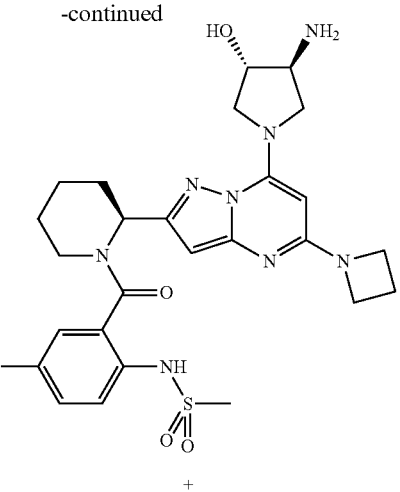

Compound 229 isomer mixture (35 mg, 0.057 mmol) was dissolved in THF (2 ml). Then to the above solution was added triphenyl phosphine (22 mg, 0.085 mmol), the reaction mixture was stirred at RT for 3 h. Then to the above solution was added water (1 ml) and heated at 75° overnight. The solvents were removed by rotary evaporation. The residue was purified with preparatory HPLC to provide compound 230 as a mixture of trans isomers. (Yield 18.0 mg, 54%).

¹H-NMR (CD₃OD, 400 MHz): δ 7.83 (bs, 2H), 7.35-7.22 (m, 2H), 6.41-6.24 (m, 1H), 4.35-4.32 (m, 4H), 4.21-4.11 (m, 2H), 3.80-3.62 (m, 4H), 2.48 (s, 3H), 2.21 (bs, 2H), 1.90 (bs, 2H), 1.74-1.60 (m, 5H)

LCMS m/z [M+H]⁺ $C_{26}H_{33}ClN_8O_4S$ requires: 589.20. Found 589.18

HPLC Tr (min), purity %: 2.07, 98%

Compound 231

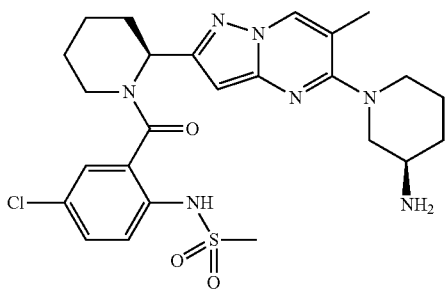 [SMILES: Cc1cn2nc([C@@H]3CCCCN3C(=O)c3cc(Cl)ccc3NS(C)(=O)=O)cc2nc1N1CCC[C@@H](N)C1]

The title compound 231 was prepared in an analogous way as described for compound 220 from intermediate 73 and commercially available (R)-tert-butyl piperidin-3-ylcarbamate.

$^1$H-NMR (CD$_3$OD, 400 MHz): δ 8.82 (bs, 1H), 7.65-7.42 (m, 3H), 6.25 (s, 1H), 6.21-6.13 (m, 1H), 3.82-3.78 (m, 1H), 3.56-3.43 (m, 3H), 3.28-2.95 (m, 2H), 2.92 (s, 3H), 2.35 (s, 3H), 2.18-1.95 (m, 3H), 1.83-1.62 (m, 5H), 1.38-1.15 (m, 4H)

LCMS m/z [M+H]$^+$ C$_{25}$H$_{32}$ClN$_7$O$_3$S requires: 546.20. Found 546.20

HPLC Tr (min), purity %: 2.41, 98%

Compound 232

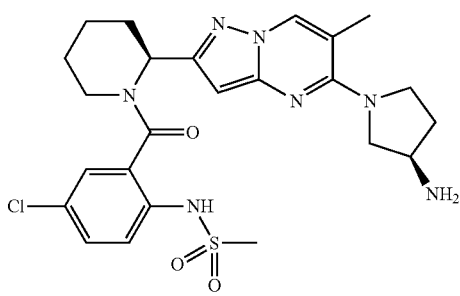

The title compound 232 was prepared in an analogous way as described for compound 231 starting from intermediate 73 and (R)-tert-butyl pyrrolidin-3-ylcarbamate.

$^1$H-NMR (CD$_3$OD, 400 MHz): d 8.62 (s, 1H) 8.52 (s, 1H), 7.65-7.40 (m, 4H), 6.13 (s, 1H), 6.05-5.95 (m, 1H), 3.95-3.86 (m, 2H), 3.81-3.60 (m, 2H), 3.58 (bs, 1H), 3.04-3.00 (m, 1H), 2.98 (s, 3H), 2.39-2.13 (m, 2H), 2.33 (s, 3H), 2.07-1.85 (m, 2H), 1.68-1.48 (m, 5H).

LCMS m/z [M+H]$^+$ C$_{24}$H$_{30}$ClN$_7$O$_3$S requires: 532.18. Found 532.18

HPLC Tr (min), purity %: 2.59, 98%

Compound 233

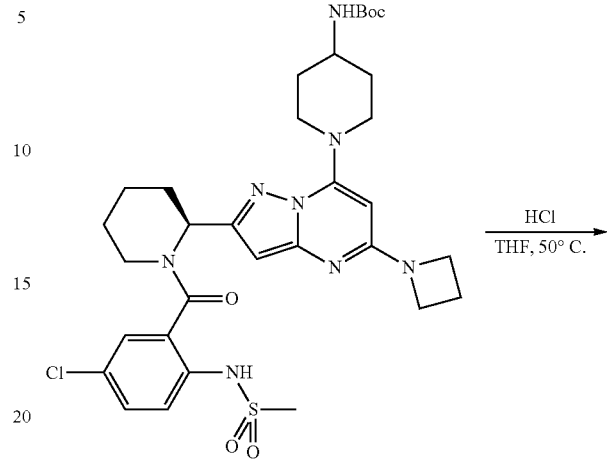

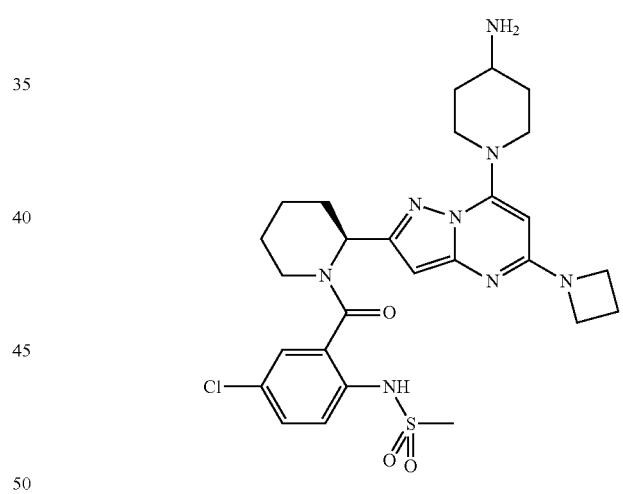

Intermediate 180 (10 mg, 0.015 mmol) was dissolved in THF (2 ml). Then to the above solution was added HCl (0.5 ml), the reaction mixture was heated at 50° for 10 mins. The reaction was quenched with NaHCO$_3$ (5 ml) and extracted with EtOAc (20 ml). Organic solvents were removed by rotary evaporation. The residue was purified with preparatory HPLC to provide compound 233. (Yield 8.0 mg, 94%).

$^1$H-NMR (CD$_3$OD, 400 MHz): δ 7.36-7.23 (m, 3H), 5.96-5.89 (m, 2H), 5.18 (s, 1H), 4.19 (d, J=10.8 Hz, 2H), 4.04-3.95 (m, 4H), 3.26-3.21 (m, 1H), 2.91-2.83 (m, 3H), 2.84 (s, 3H), 2.34-2.30 (m, 3H), 2.13 (bs, 1H), 1.97-1.91 (m, 3H), 1.60-1.38 (m, 6H).

LCMS m/z [M+H]$^+$ C$_{27}$H$_{35}$ClN$_8$O$_3$S requires: 587.22. Found 587.24

HPLC Tr (min), purity %: 2.07, 98%

469
Intermediate 181

470
Compound 234

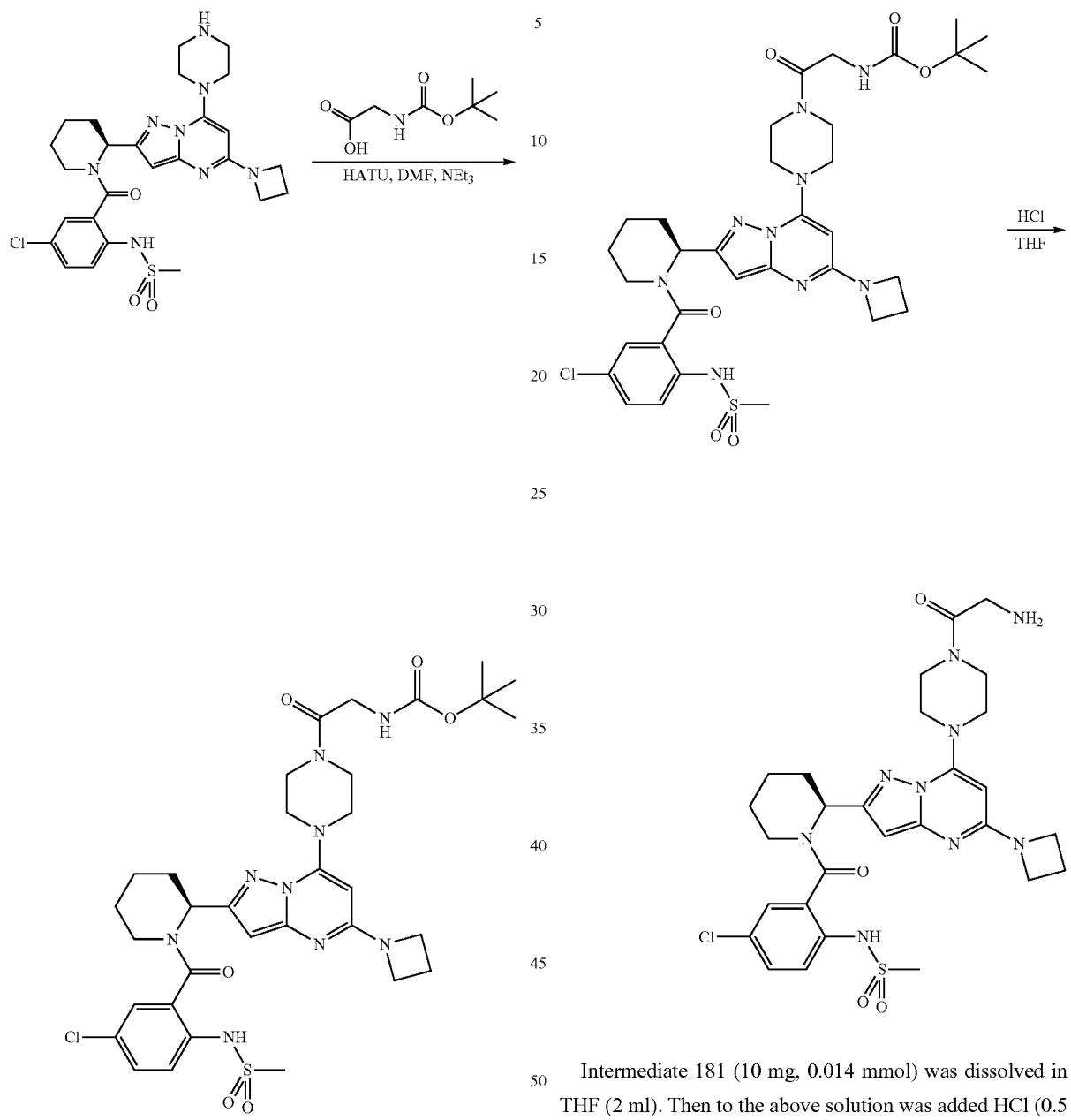

Boc-aminoacetic acid (15 mg, 0.08 mmol), HATU (38 mg, 0.1 mmol) were dissolved in anhydrous DMF (2 ml). After activation for 1 hour, to the above solution was added compound 45 (30 mg, 0.05 mmol) and triethylamine (0.1 ml). The reaction was stirred under nitrogen for 2 hours. Solvents were removed by rotary evaporation. The residue was purified with silica gel column chromatography to provide intermediate 181. (Yield 16 mg, 42%).

LCMS m/z [M+H]⁺ $C_{20}H_{22}ClN_5O$ requires: 729.29. Found 729.7

HPLC Tr (min), purity %: 2.86, 98%

Intermediate 181 (10 mg, 0.014 mmol) was dissolved in THF (2 ml). Then to the above solution was added HCl (0.5 ml), the reaction mixture was stirred at RT overnight. The reaction was quenched with NaHCO₃ (5 ml) and extracted with EtOAc (20 ml). Organic solvents were removed by rotary evaporation. The residue was purified with preparatory HPLC to provide compound 234. (Yield 7.7 mg, 90%).

¹H-NMR (CD₃OD, 400 MHz): δ 7.41-7.32 (m, 4H), 6.20-5.95 (m, 1H), 4.32 (t, J=6.4 Hz, 4H), 3.96-3.79 (m, 8H), 3.66 (bs, 2H), 2.96 (s, 3H), 2.48 (bs, 2H), 2.25-1.91 (m, 4H), 1.66-1.59 (m, 5H).

LCMS m/z [M+H]⁺ $C_{29}H_{37}ClN_8O_4S$ requires: 629.23 Found 629.18

HPLC Tr (min), purity %: 1.87, 98%

Compound 235

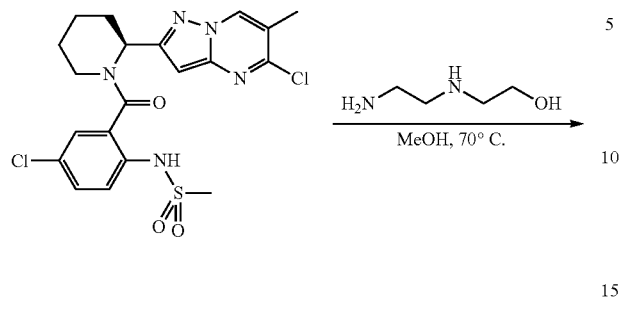

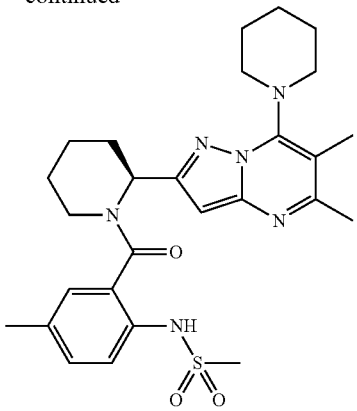

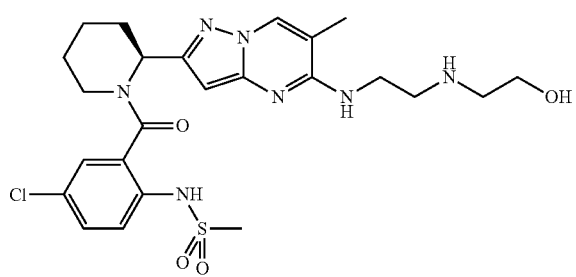

Intermediate 73 (50 mg, 0.1 mmol) was dissolved in MeOH (2 ml). Then 2-(2-aminoethylamino)ethanol (11 mg, 0.11 mmol) was added to the above solution. The reaction was heated at 70° C. overnight. Solvents were removed by rotary evaporation. The residue was purified with preparatory HPLC to provide compound 235. (Yield 37 mg, 64%).

$^1$H-NMR (CD$_3$OD, 400 MHz): δ 8.55-8.30 (m, 1H), 7.45-7.27 (m, 2H), 6.10-5.96 (m, 2H), 4.88-3.34 (m, 4H), 3.09-230 (m, 5H), 2.47-2.31 (m, 2H), 2.13 (s, 3H), 2.13-1.53 (m, 6H)

LCMS m/z [M+H]$^+$ C$_{24}$H$_{32}$ClN$_7$O$_4$S requires: 550.19. Found 550.15

HPLC Tr (min), purity %: 2.17, 98%

Compound 236

HATU (81 mg, 0.213 mmol) was added to a solution of 5-methyl-2-(methylsulfonamido)benzoic acid (42.3 mg, 0.184 mmol) in 4.5 mL of anhydrous DMF at room temperature. After 45 min of stirring, intermediate 81 (55 mg, 0.130 mmol) was added followed immediately by triethylamine (0.09 mL, 0.641 mmol). Reaction mixture stirred at room temperature overnight under argon. Mixture was then poured into 50 mL of H$_2$O and extracted three times with 50 mL of ethyl acetate. The combined organic layers were washed with 100 mL Brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 236 (67.2 mg, 81%) as a white solid, trifluoroacetate salt, after lyophilization.

$^1$H-NMR (DMSO, 400 MHz): δ 9.08 (s, 1H) 7.32-7.16 (m, 3H), 6.48 (s, 1H), 6.04 (s, 1H), 4.91-4.65 (m, 4H), 3.60 (s, 3H), 3.58 (m, 1H), 3.38 (m, 1H), 3.12 (m, 1H), 3.01 (s, 3H), 2.91 (m, 1H), 2.52 (m, 1H), 2.33 (m, 2H), 2.21 (s, 3H), 2.18 (m, 1H), 1.94 (m, 1H), 1.72 (s, 3H), 1.63-1.40 (m, 5H).

LCMS m/z [M+H]$^+$ C$_{27}$H$_{36}$N$_6$O$_3$S requires: 525.26. Found 525.41

HPLC Tr (min), purity %: 5.85, 99%

Compound 237

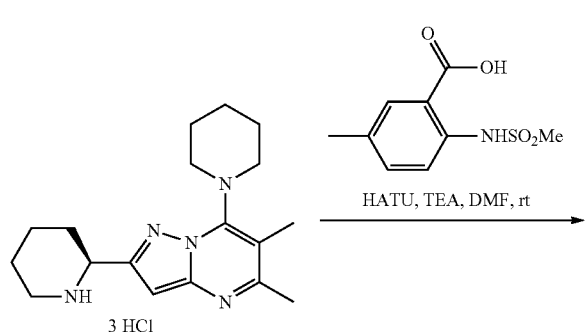

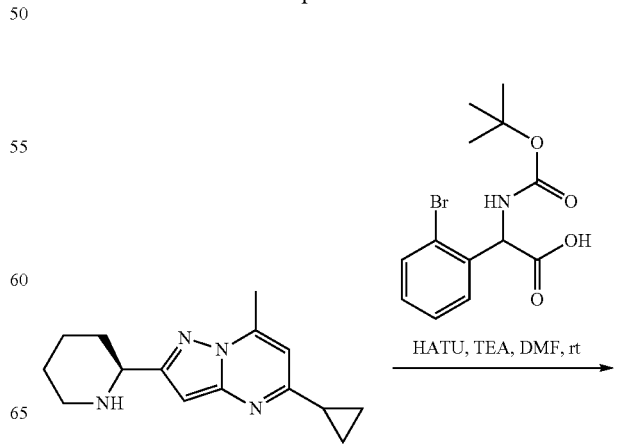

473

-continued

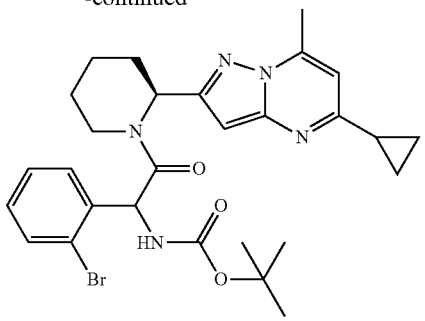

HATU (85.8 mg, 0.226 mmol) was added to a solution of 2-(2-bromophenyl)-2-(tert-butoxycarbonylamino)acetic acid (97.8 mg, 0.296 mmol) in 3.0 mL of anhydrous DMF at room temperature. After two hours of stirring, intermediate 31 (75 mg, 0.228 mmol) was added followed immediately by triethylamine (0.11 mL, 0.798 mmol). Reaction mixture stirred at room temperature overnight under argon. Mixture was then added directly to purification by prep HPLC (15-100% Acetonitrile (with 0.1% trifluoroacetic acid) in water (with 0.1% trifluoroacetic acid)) to yield compound 237 (73 mg, 47%) as a off white solid, trifluoroacetic acid salt, after lyophilization.

$^1$H-NMR (DMSO, 400 MHz): δ 7.61 (m, 1H), 7.37 (m, 2H), 7.25 (m, 1H), 6.87 (m, 1H), 4.37 (m, 1H), 3.66 (m, 1H), 3.13-2.99 (m, 1H), 2.64 (s, 3H), 2.58 (m, 2H), 2.40 (m, 1H), 2.09 (m, 1H), 1.77-1.42 (m, 3H), 1.38 (s, 9H), 1.12 (m, 3H), 1.00 (m, 4H).

LCMS m/z [M+H]$^+$ C$_{28}$H$_{34}$BrN$_5$O$_3$ requires: 568.8. Found 568.36

HPLC Tr (min), purity %: 7.95, 99% as mixture of two diastereomers.

Compound 238

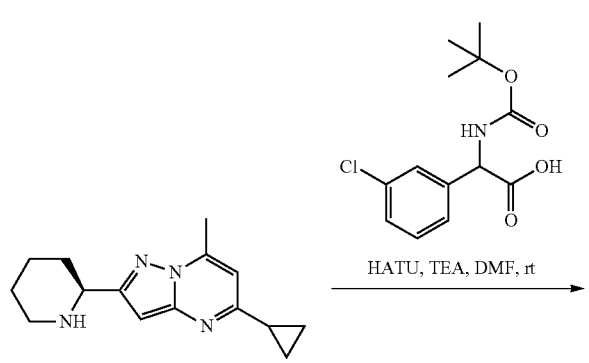

474

Following the procedure for compound 237, beginning with 2-(tert-butoxycarbonylamino)-2-(3-chlorophenyl)acetic acid (56.6 mg, 0.198 mmol), compound 238 was recovered as a tan solid (47 mg, 48%), trifluoroacetic acid salt after lyophilization.

$^1$H-NMR (DMSO, 400 MHz): δ 7.51-7.34 (m, 4H), 6.85 (m, 1H), 6.03 (m, 0.5H), 5.89 (m, 0.5H), 5.78-5.57 (m, 1H), 4.33 (m, 1H), 3.87 (m, 1H), 2.61 (m, 1H), 2.51 (s, 3H), 2.42-2.25 (m, 1H), 2.08 (m, 1H), 1.63-1.40 (m, 2H), 1.37 (s, 9H), 1.29-1.17 (m, 3H), 1.09-0.92 (m, 4H).

LCMS m/z [M+H]$^+$ C$_{28}$H$_{34}$ClN$_5$O$_3$ requires: 524.24. Found 524.40

HPLC Tr (min), purity %: 8.01, 8.07, 99% as mixture of two diastereomers.

Compound 239

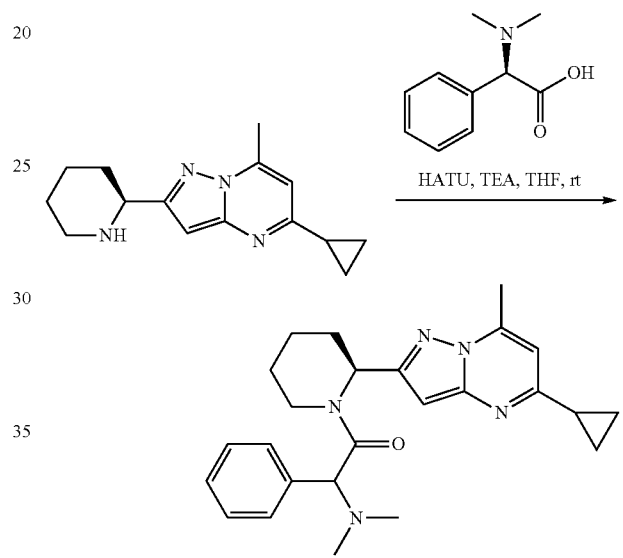

Following the procedure for compound 237, beginning with (R)-2-(dimethylamino)-2-phenylacetic acid (35 mg, 0.195 mmol) and THF as solvent, compound 239 was recovered as a white solid trifluoroacetic acid salt mixture of diastereomers (40 mg, 50%), after lyophilization.

$^1$H-NMR (DMSO, 400 MHz): δ 10.1 (s, 1H), 7.51-7.36 (m, 5H), 6.81 (m, 1H), 6.68 (m, 1H), 6.35 (m, 1H), 5.84 (m, 1H), 5.79-5.49 (m, 2H), 5.05 (m, 0.5H), 4.30 (m, 0.5H), 3.57 (m, 0.5H), 3.05 (m, 0.5H), 2.87 (m, 3H), 2.38 (s, 6H), 2.31-2.20 (m, 4H), 2.04 (m, 1H), 1.55-1.13 (m, 4H), 1.03-0.75 (m, 4H).

LCMS m/z [M+H]$^+$ C$_{25}$H$_{31}$N$_5$O requires: 418.25. Found 418.43

HPLC Tr (min), purity %: 5.49, 98% as mixture of two diastereomers.

Intermediate 182

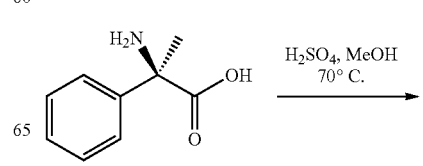

-continued

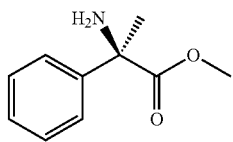

A solution of (R)-2-amino-2-phenylpropanoic acid (304 mg, 1.84 mmol) and 0.7 mL of concentrated $H_2SO_4$ in 6.5 mL of anhydrous methanol was heated overnight. After cooling to room temperature, methanol was concentrated under reduced pressure. Residue was taken up in 40 mL of water and added to a separatory funnel. Solid sodium carbonate was added slowly until gas evolution ceased (pH 9-10). Aqueous layer was extracted with ethyl acetate (3×50 mL). The combined organic layers were washed with 100 mL sat. $NaHCO_{3(aq)}$ and 100 mL of Brine, separated, dried ($MgSO_4$), filtered, and concentrated under reduced pressure to yield intermediate 182 (225 mg, 68%) as a oily residue that was used in the next step without further purification.

$^1$H-NMR (DMSO, 400 MHz): δ 7.44 (m, 2H), 7.30 (m, 2H), 7.22 (m, 1H), 3.58 (s, 3H), 2.36 (s, 2H), 1.50 (s, 3H)

Intermediate 183

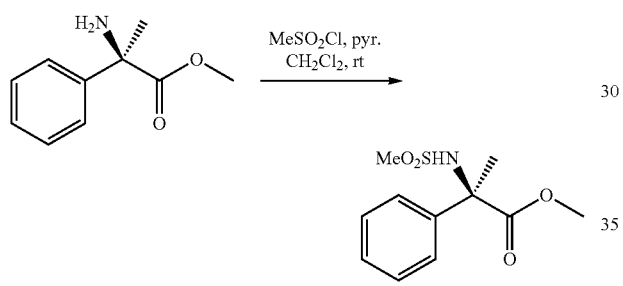

To a solution of intermediate 182 (225 mg, 1.25 mmol) and pyridine (0.30 mL, 3.75 mmol) in 4 mL of anhydrous $CH_2CL_2$, was added slowly methane sulfonylchloride (0.15 mL, 1.91 mmol). After stirring overnight, reaction mixture was quenched with 30 mL of 1N $HCl_{(aq)}$. Aqueous mixture was extracted with ethyl acetate (3×30 mL) and combined organic layers were washed with 1N $HCl_{(aq)}$ and then brine. Organics were dried ($MgSO_4$), filtered, and concentrated under reduced pressure to yield intermediate 183 (312 mg, 97%) as a yellow-green oily residue that was used in the next step without further purification.

LCMS m/z $C_{11}H_{15}NO_4S$ requires: 258.08. Found 258.31

Intermediate 184

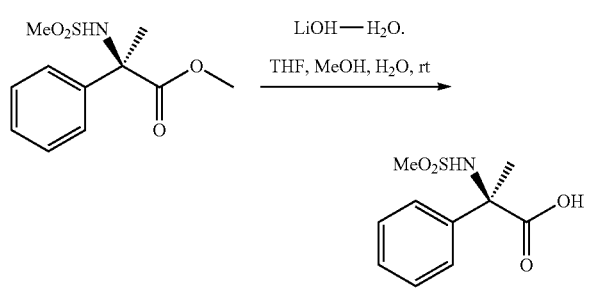

Lithium hydroxide monohydrate (507 mg, 12.1 mmol) was added to a solution of intermediate 183 (310 mg, 1.2 mmol) in 15 mL of 1:1:1 THF:MeOH:$H_2O$ at room temperature. Reaction mixture was stirred overnight and then was acidified with 40 mL of 1N $HCl_{(aq)}$ and extracted with ethyl acetate (3×50 mL). The combined organic layers were washed 100 mL of Brine, separated, dried ($MgSO_4$), filtered, and concentrated under reduced pressure to yield intermediate 184 as a oily residue (285 mg, 98%).

$^1$H-NMR (DMSO, 400 MHz): δ 13.1 (s, 1H), 7.50 (m, 2H), 7.39 (m, 2H), 7.31 (m, 1H), 2.80 (s, 3H), 1.86 (s, 3H).

Compound 240

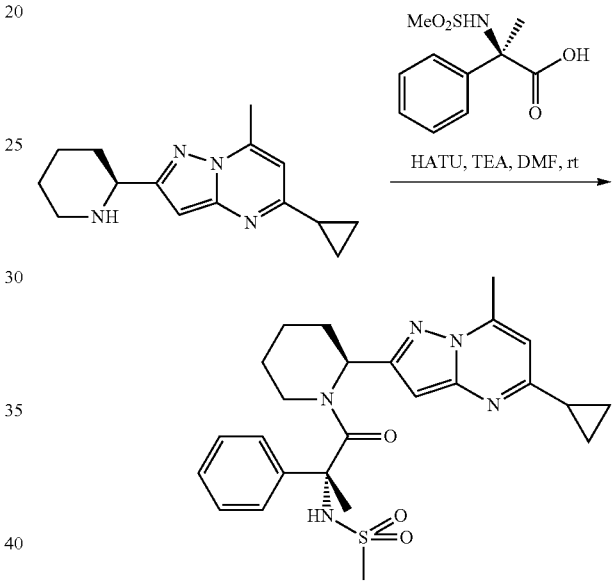

Following the procedure for compound 237, beginning with a DMF solution of 31 (0.1 M, 2 mL, 0.2 mmol), compound 240 was recovered as an off white solid (6.2 mg, 7%), trifluoroacetic acid salt after lyophilization.

LCMS m/z [M+H]$^+$ $C_{25}H_{31}N_5O_3S$ requires: 482.21. Found 482.41

HPLC Tr (min), purity %: 7.16, 87%.

Compound 241

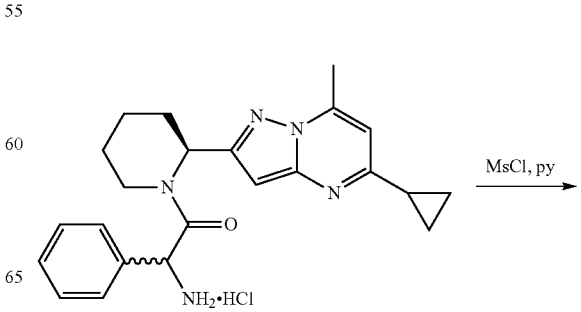

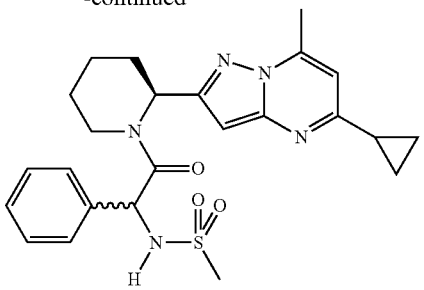

Compound 243 (37 mg, 0.10 mmol) in pyridine (1.5 mL) was treated with methanesulfonyl chloride (200 μL, 2.2 mmol) and stirred for 18 h. The mixture was treated to preparatory RP-HPLC (5-100% MeCN/H$_2$O, 0.1% trifluoroacetic acid modifier) to afford compound 241 (35 mg, 80%) as a white solid:

$^1$H NMR (CD$_3$OD, 400 MHz, data for both isomers): δ 7.53 (m, 1H), 7.44 (m, 5H), 6.75 (s, 1H), 6.66 (s, 1H), 6.44 (s, 1H), 5.65 (br s, 1H), 5.63 (s, 1H), 5.22 (br s, 1H), 4.54 (m 1H), 3.89 (m, 1H), 3.78 (m, 1H), 2.98 (m, 1H), 2.83 (s, 3H), 2.80 (s, 3H), 2.73 (s, 3H), 2.61 (s, 3H), 2.42 (m, 1H), 1.56 (m, 4H), 1.35 (m, 1H), 1.15 (m, 6H).

LC-MS (ESI) m/z 468 [M+H]$^+$, t$_R$=2.54 min.

HPLC t$_R$ (isomer A): 4.52 mm; t$_R$ (isomer B): 4.58 min

Compound 242

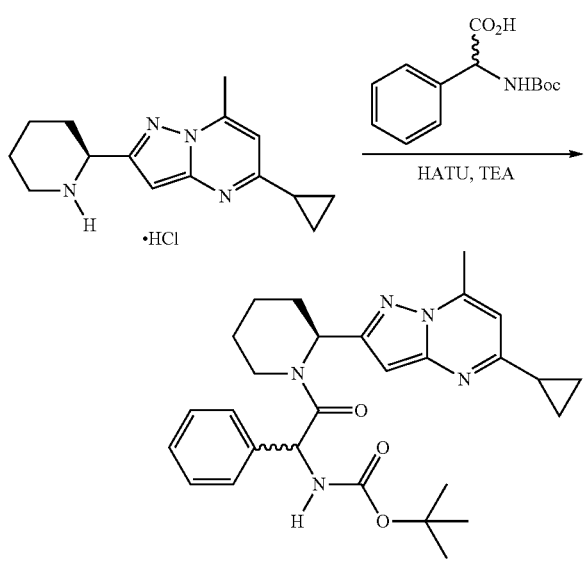

N-Boc-DL-phenylglycine (49 mg, 0.20 mmol) and HATU (86 mg, 0.23 mmol) in DMF (5 mL) were stirred for 1 h. Intermediate 31 (38 mg, 0.15 mmol) and triethylamine (52 μL, 0.38 mmol) were added and the solution was stirred for 18 h. The solution was diluted with EtOAc (50 mL) and washed with saturated NaHCO$_3$ (20 mL) and dried (MgSO$_4$). The mixture was treated to a 12 g SiO$_2$ Combi-flash HP Gold column (0-100% EtOAc-hexanes gradient) to afford Compound 242 (57 mg, 78%) as a white solid:

LC-MS (ESI) m/z 490 [M+H]$^+$, t$_R$=2.88 min.

HPLC t$_R$ (isomer A): 5.37 min; t$_R$ (isomer B): 5.45 min.

Compound 243

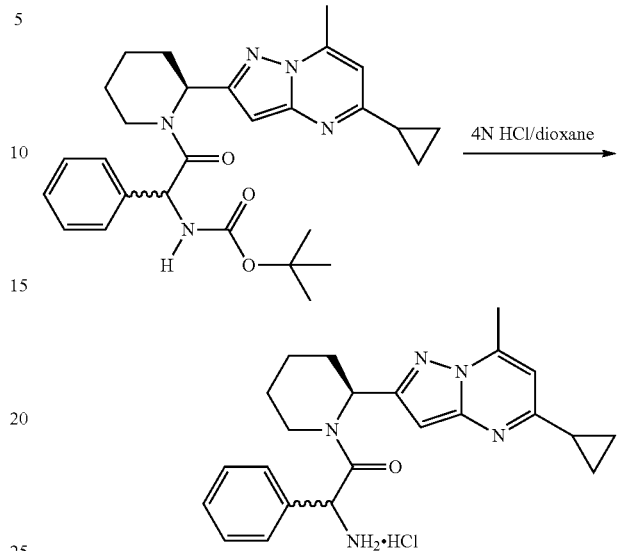

Compound 242 (53 mg, 0.11 mmol) was treated with 4 N HCl/dioxane (3 mL) and stirred for 18 h to afford compound 243 (42 mg, >99%) as a white solid:

LC-MS (ESI) m/z 390 [M+H]$^+$, t$_R$=1.71 min.

HPLC t$_R$ 3.33 min (isomers unresolved).

Compound 244

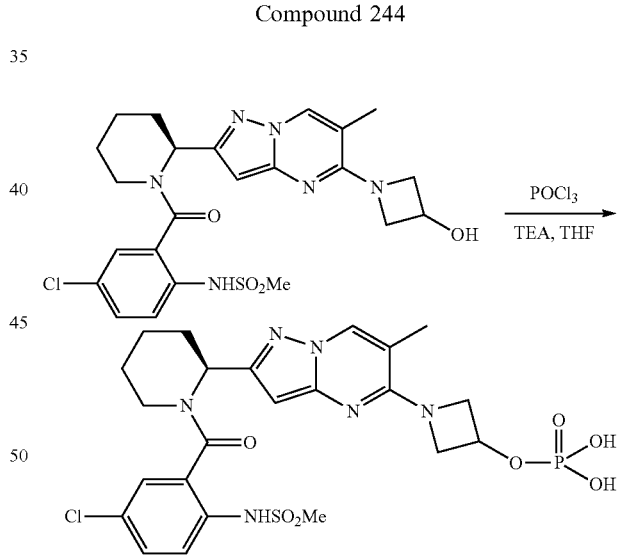

To a solution of compound 92 (300 mg, 0.578 mmol) in THF at 0° C. was added POCl3 (500 mg, 3.27 mmol) and TEA (410 mg, 4.06 mmol). The reaction mixture was stirred at 0° C. for 0.5 h, and quenched with triethylammonium bicarbonate buffer (1M). The mixture was concentrated and purified by HPLC to give the compound 244 (370 mg, contained about 1 eq of TFA, 90%).

$^1$H NMR (400 MHz, CDCl3): δ 9.05 (brs), 8.72 (s), 8.53 (s), 7.62 (d, J=8 Hz), 7.36 (d, J=8 Hz), 7.3 (s), 7.26 (s), 6.27 (s), 6.09 (s), 5.23 (brs), 5.06 (brs), 4.81 (brs), 3.33 (m), 3.13 (m), 3.03 (s), 2.91 (s), 2.28 (s), 1.98 (m), 1.71 (m), 1.54 (m), 1.31 (m). $^{31}$P NMR (400 MHz, CDCl$_3$): δ−2.198.

MS=519.2 (M-phosphate) (627.2, when quenched with MeOH to give the methyl ester, MS=627.2 (M+1), 625.2 (M−1)), tR=2.93 min (3.17 min for SM).

Compound 245

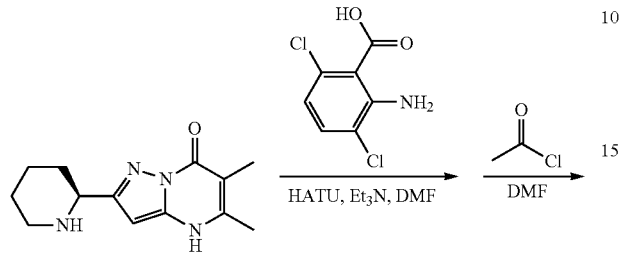

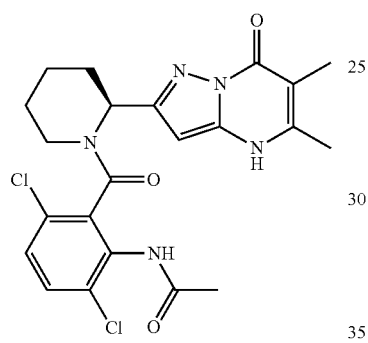

Intermediate 6 (50 mg, 0.156 mmol), HATU (76 mg, 0.203 mmol), 2-amino-3,6-dichlorobenzoic acid (39 mg, 0.187 mmol) and triethylamine (0.1 mL) were dissolved in anhydrous DMF (1 ml). After 1 hour, MP-Carbonate resin (100 mg) was added to the above solution and the reaction vial was put on a shaker overnight. The reaction mixture was then filtered and acetyl chloride (14.6 mg, 0.187 mmol) was added. The reaction was stirred for 10 mins. The reaction mixture was filtered and purified by prep HPLC to provide compound 245. (Yield 34 mg, 35%).

LCMS m/z [M+H]$^+$ C$_{22}$H$_{23}$Cl$_2$N$_5$O$_3$ requires: 476.12. Found 476.15

HPLC Tr (min), purity %: 2.19, 98%

Compound 246

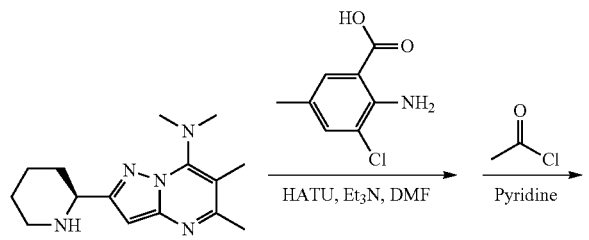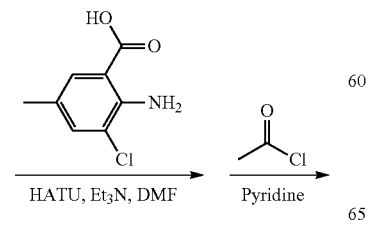

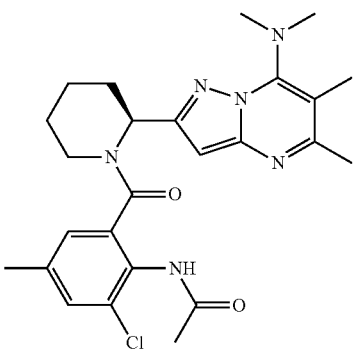

2-amino-5-methyl-3-chlorobenzoic acid (20 mg, 0.069 mmol), HATU (53 mg, 0.087 mmol) were dissolved in anhydrous DMF (2 ml). After activation for 1 hour, to the above solution was added intermediate 82 (bis-HCl salt, 32 mg, 0.058 mmol) and triethylamine (0.1 ml). The reaction was stirred under nitrogen for 2 hours. Solvents were removed by rotary evaporation. The residue was dissolved in pyridine (1 ml). To the above solution was added acetyl chloride (5.4 mg, 0.070 mmol). The reaction was stirred at RT for 4 h. Solvents were removed by rotary evaporation and the residue was purified with silica gel column chromatography to provide compound 246. (Yield 18 mg, 51%).

LCMS m/z [M+H]$^+$ C$_{25}$H$_{31}$ClN$_6$O$_2$ requires: 483.22. Found 483.14

HPLC Tr (min), purity %: 2.93, 98%

Compound 247

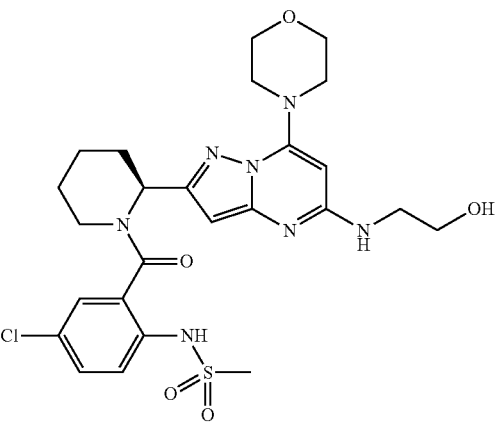 [SMILES: CS(=O)(=O)Nc1ccc(Cl)cc1C(=O)N1CCCC[C@H]1c1cc2nc(NCCO)cc(N3CCOCC3)n2n1]

The title compound 247 was prepared in an analogous way as described for compound 67 from intermediate 56.

LCMS m/z [M+H]$^+$ C$_{25}$H$_{32}$ClN$_7$O$_5$S requires: 578.19. Found 578.24

HPLC Tr (min), purity %: 2.24, 98%

481

Compound 248

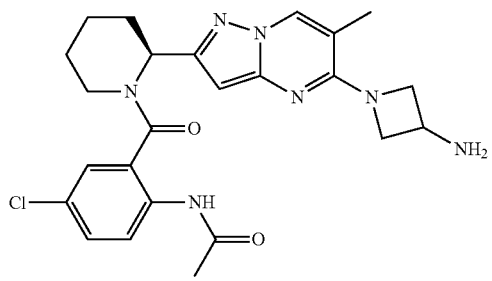 [SMILES: CC(=O)Nc1ccc(Cl)cc1C(=O)N1CCCC[C@H]1c1cc2nc(N3CC(N)C3)c(C)cn2n1]

The title compound 248 was prepared in an analogous way as described for compound 227 from intermediate 176.

LCMS m/z [M+H]+ C$_{24}$H$_{28}$ClN$_7$O$_2$ requires: 482.20. Found 482.24

HPLC Tr (min), purity %: 2.35, 98%

Compound 249

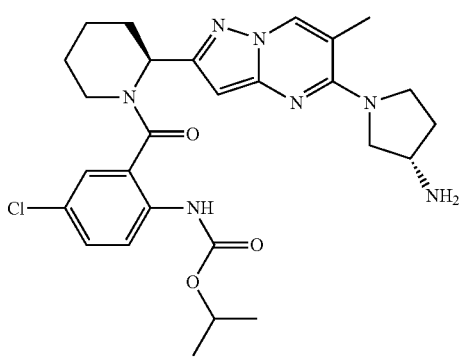 [SMILES: Cc1cn2nc([C@@H]3CCCCN3C(=O)c3cc(Cl)ccc3NC(=O)OC(C)C)cc2nc1N1CC[C@H](N)C1]

The title compound 249 was prepared in an analogous way as described for compound 220 starting from intermediate 171.

LCMS m/z [M+H]+ C$_{27}$H$_{34}$ClN$_7$O$_3$ requires: 540.24. Found 540.31

HPLC Tr (min), purity %: 2.68, 98%

482

Intermediate 185

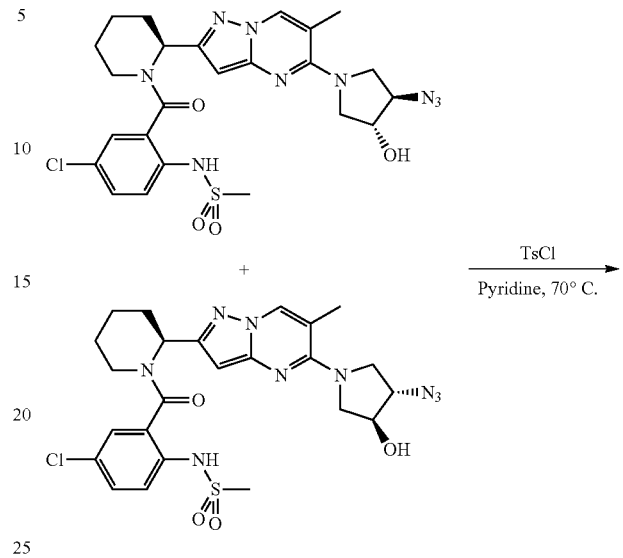

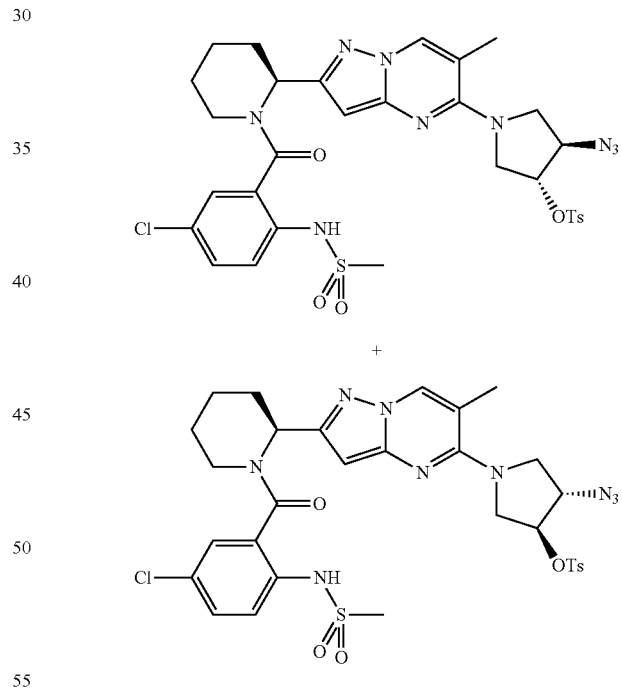

Compound 182 (64 mg, 0.11 mmol) was dissolved in pyridine (2 ml). Then tosyl chloride (690 mg, 3.6 mmol) was added to the above solution. The reaction was heated at 70° C. overnight. Solvents were removed by rotary evaporation. The residue was purified with combi flash column to provide intermediate 185 as a mixture of isomers (Yield 30 mg, 37%).

LCMS m/z [M+H]+ C$_{31}$H$_{34}$ClN$_9$O$_6$S$_2$ requires: 728.18. Found 728.13

HPLC Tr (min), purity %: 2.88, 98%

Intermediate 186

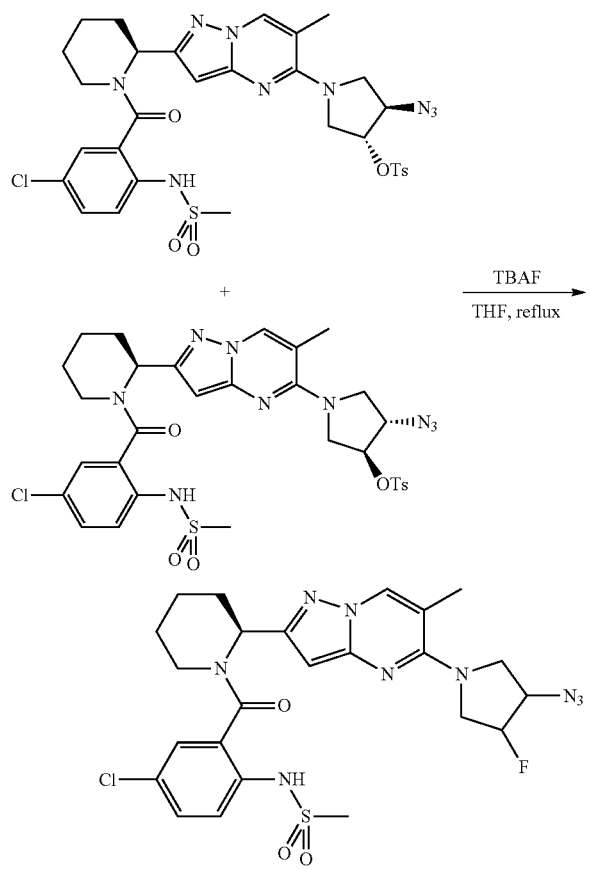

Intermediate 185 (30 mg, 0.04 mmol) was dissolved in THF (2 ml). Then 1.0 M TBAF in THF (0.25 ml) was added to the above solution. The reaction was heated refluxed overnight. The reaction was diluted with EtOAc (20 ml) and washed with brine (10 ml). organic solvents were removed by rotary evaporation. The residue was purified with combi flash column to provide intermediate 186. (Yield 5 mg, 21%).

LCMS m/z [M+H]$^+$ C$_{24}$H$_{27}$ClFN$_9$O$_3$S$_2$ requires: 576.16. Found 576.13

HPLC Tr (min), purity %: 2.85, 98%

Compound 250

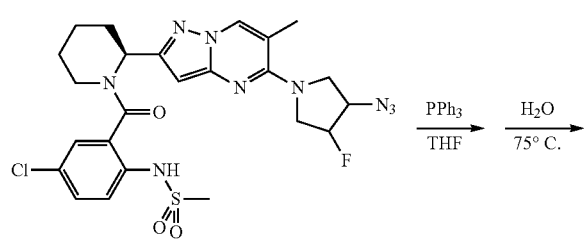

-continued

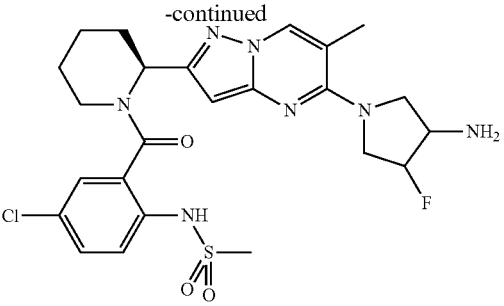

Intermediate 186 (5 mg, 0.009 mmol) was dissolved in THF (2 ml). Then triphenyl phosphine (3.4 mg, 0.013 mmol) was added to the above solution. The reaction was stirred at RT overnight. Then H$_2$O (1 ml) was added the above solution and heated at 75° overnight. Solvents were removed by rotary evaporation. The residue was purified with prep HPLC to provide compound 250. (Yield 1 mg, 21%).

LCMS m/z [M+H]$^+$ C$_{24}$H$_{29}$ClFN$_7$O$_3$S$_2$ requires: 550.17. Found 550.26

HPLC Tr (min), purity %: 2.52, 98%

(±)-cis Intermediate 187

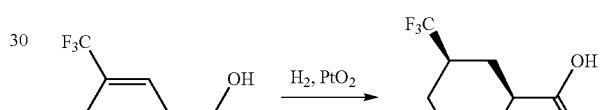

4-Trifluoromethylpicolinic acid (4.5 g, 23.5 mmol) in EtOH/H$_2$O (1:1, 80 mL) was treated with PtO$_2$ (2 g) and placed under H$_2$ (60 psi). The mixture was shaken for 72 h then filtered over Celite. The Celite was washed with H$_2$O (3 10 mL) and EtOH (3 10 mL). The solution was concentrated to afford (±)-intermediate 187 (4.6 g) which was used without further purification.

$^1$H NMR (CD$_3$OD, 400 MHz): δ 3.50 (m, 3H), 3.05 (t, J=13.5 Hz, 1H), 2.68 (m, 1H), 2.53 (d, J=13.8 Hz, 1H), 2.07 (d, J=18.8 Hz), 1.75 (m, 2H).

$^{19}$F NMR (CD$_3$OD, 377 MHz): δ−76.1.

(±)-cis Intermediate 188

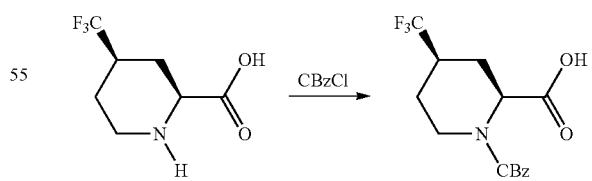

(±)-Intermediate 187 (4.6 g, 23.5 mmol) in 1,4-dioxane (250 mL) was treated with 1 N NaOH (70 mL) and CbzCl (5.0 mL, 35.3 mmol). The solution was stirred for 18 h then concentrated and suspended in EtOAc (100 mL). The solution was acidified with 1 N HCl then dried (MgSO$_4$) to afford (±)-Intermediate 188 which was used without further purification.

(±)-cis Intermediate 189

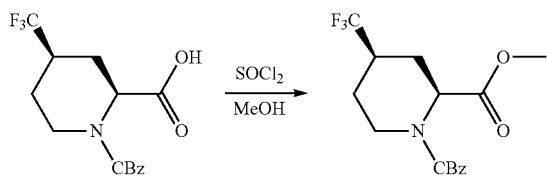

(±)-Intermediate 188 (7.8 g, 23.5 mmol) in MeOH (100 mL) was treated with SOCl₂ (4.3 mL, 58.8 mmol) at 0° C. and stirred for 18 h with warming to room temperature. The solution was concentrated then treated to a 120 g SiO₂ Combiflash HP Gold column (0-100% EtOAc-hexanes gradient) to afford (±)-Intermediate 189 (6.1 g, 75% over 3 steps) as a white solid:

$^1$H NMR (CDCl₃, 400 MHz): δ 7.35 (m 5H), 5.15 (m, 2H), 4.47 (t, J=8.8 Hz, 1H), 3.70 (s, 3H), 3.52 (br m, 1H), 2.37 (m, 1H), 2.28 (m, 4H), 1.90 (m, 1H), 1.77 (m, 1H).

$^{19}$F NMR (CD₃OD, 377 MHz): δ −72.4.

LC-MS (ESI) m/z 346 [M+H]$^+$, $t_R$=2.53 min.

(±)-cis/(±)-trans Intermediate 190

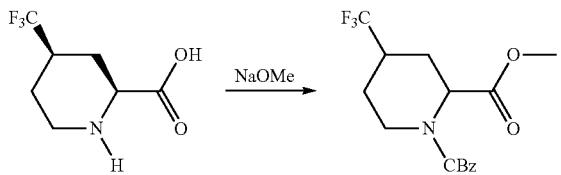

(±)-Intermediate 189 (6.1 g, 17.6 mmol) in MeOH (100 mL) was treated with NaOMe (400 µL) and stirred for 4 days. The solution was diluted with EtOAc (50 mL) and washed with 1 N HCl (2 50 mL) and saturated NaCl (50 mL). The solution was dried (MgSO₄) and then treated to a 120 g SiO₂ Combiflash HP Gold column (0-50% EtOAc-hexanes gradient) to afford a (±)-cis/(±)-trans mixture of Intermediate 190 (5.2 g, 85%) as a white solid.

(±)-Intermediate 191

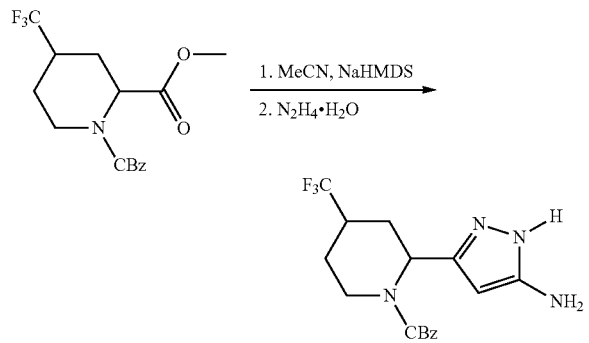

MeCN (2.4 mL, 45 mmol) in THF (20 mL) was cooled to −78° C. and treated dropwise with NaHMDS (1.0 M in THF, 30 mL, 30 mmol) over 30 min. The solution was warmed to −45° C. and stirred for 30 min. The mixture was cooled to −78° C. and (±)-cis/(±)-trans Intermediate 190 (5.2 g, 15 mmol) in THF (20 mL) was added dropwise over 30 min. The solution was warmed to −45° C. and stirred for 3 h. The solution is treated with AcOH (5.1 mL, 90 mmol) in THF (20 mL) and warmed. The solution is diluted with EtOAc (100 mL) and washed with saturated NaCl (2 50 mL). The solution is dried (MgSO₄) and concentrated. The solid is dissolved in EtOH (50 mL) and treated with N₂H₄.HOAc (1.66 g, 18 mmol) and heated at 100° C. for 18 h. The solution is concentrated and treated to a 120 g SiO₂ Combiflash HP Gold column (0-100% EtOAc-hexanes gradient) to afford faster eluting (±)-isomer A (2.8 g, 51%) as a white solid and slower eluting (±)-isomer B (0.96 g, 17%) as a white solid (data for (±)-isomer A):

LC-MS (ESI) m/z 369 [M+H]$^+$, $t_R$=2.22 min.

HPLC $t_R$ (min): 4.07.

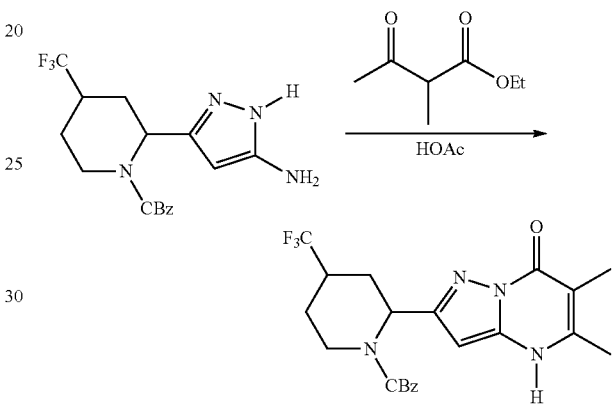

(±)-Isomer A from the above separation (2.8 g, 7.6 mmol) in EtOH (70 mL) was treated with ethyl 2-methylacetoacetate (3.3 mL, 23 mmol) and HOAc (4.4 mL, 76 mmol) stirred at 80° C. for 18 h. The solution was concentrated and treated to a 120 g SiO₂ Combiflash HP Gold column (0-100% EtOAc-hexanes gradient) to afford (±)-intermediate 191 (2.7 g, 80%) as a white solid:

LC-MS (ESI) m/z 449 [M+H]$^+$, $t_R$=2.34 min.

HPLC $t_R$ (min): 4.76.

(±)-Intermediate 192

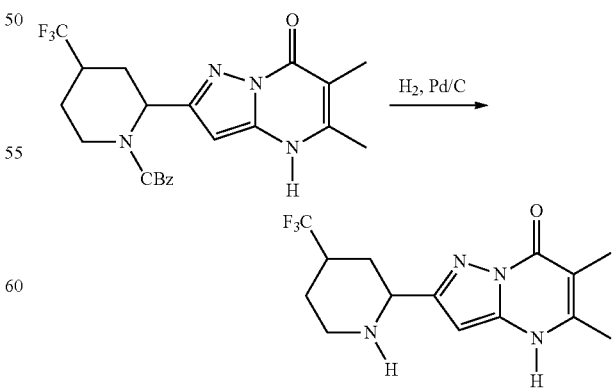

(±)-Intermediate 191 (390 mg, 0.87 mmol) in EtOH (10 mL) was treated with 10% Pd/C (40 mg) and placed under a H₂ atmosphere. The mixture is stirred for 18 h then filtered and concentrated to afford (±)-Intermediate 192 as a white solid which was used without further purification:
LC-MS (ESI) m/z 315 [M+H]⁺, $t_R$=1.29 min.
HPLC $t_R$ (min): 2.73.

(±)-Compound 251

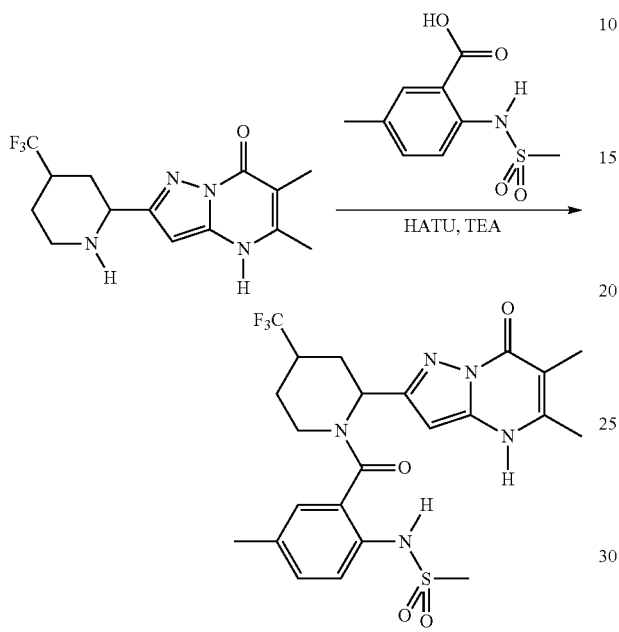

5-Methyl-2-(methylsulfonamido)benzoic acid (90 mg, 0.37 mmol) in DMF (1.5 mL) was treated with HATU (165 mg, 0.43 mmol) and stirred for 2 h. The solution was treated with intermediate 192 (91 mg, 0.29 mmol) in DMF (1.5 mL) and N-methylmorpholine (125 µL, 0.87 mmol) and stirred for 18 h. The solution was concentrated and treated to preparatory RP-HPLC (5-100% MeCN/H₂O, 0.1% trifluoroacetic acid modifier) to afford (±)-Compound 251 (14 mg, 9%) as a white solid:
¹H NMR (CD₃OD, 400 MHz): δ 7.30 (m, 3H), 6.25 (m, 1H), 6.13 (br m, 1H), 3.63 (m, 1H), 3.43 (m, 1H), 3.06 (s, 3H), 2.70 (m, 1H), 3.65 (m, 1H), 2.38 (s, 6H), 2.25 (br s, 1H), 2.09 (s, 3H), 2.01 (m, 1H), 1.75 (m, 2H).
¹⁹F NMR (CD₃OD, 377 MHz): δ−76.
LC-MS (ESI) m/z 524 [M−H]⁺, $t_R$=2.01 min.
HPLC $t_R$: 4.17 min.

Intermediate 193

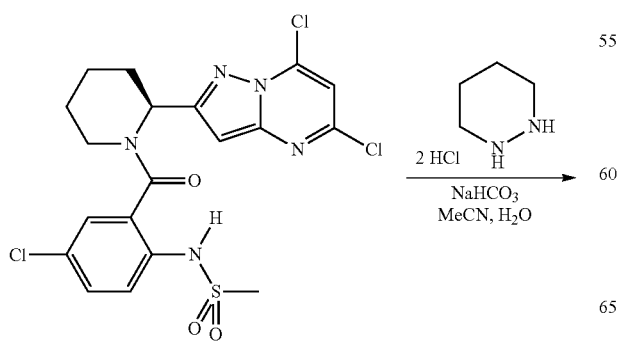

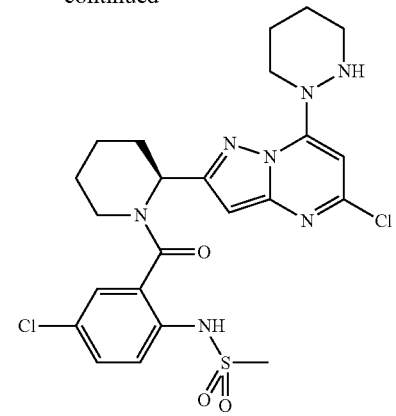

Hexahydropyridazine dihydrochloride (15.9 mg, 0.10 mmol) and sodium bicarbonate (16.8 mg, 0.20 mmol) were added to a solution of intermediate 56 (50 mg, 0.10 mmol) in acetonitrile (0.50 mL) and water (0.50 mL) and the reaction mixture was stirred at room temperature. After 2 h, the reaction mixture was purified by preparatory HPLC (5-100% MeCN/H₂O, 0.1% trifluoroacetic acid modifier) to afford intermediate 193 (52 mg, 78%) as a white solid trifluoroacetate salt.
LCMS (ESI) m/z 552.40 [M+H]⁺, $t_R$=2.99 min.
HPLC $t_R$ (min), purity %: 4.93, 99%.
$R_f$=0.68 (EtOAc).

Compound 252

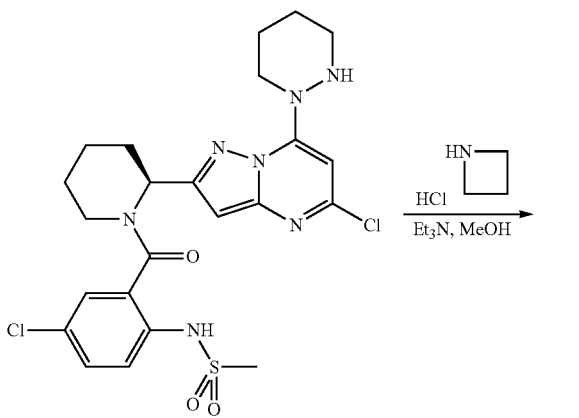

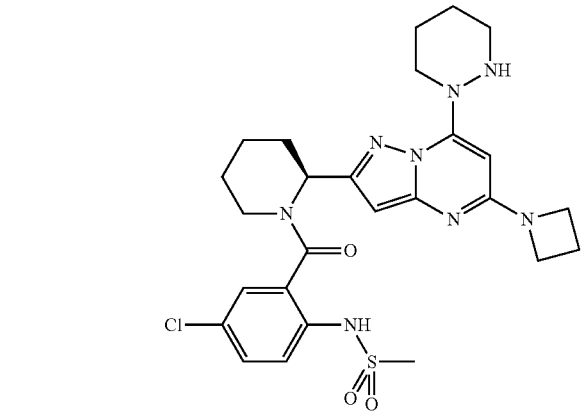

489

To a solution of intermediate 193 (52.0 mg, 0.09 mmol) in MeOH (1.90 mL) was added azetidine hydrochloride (88.0 mg, 0.94 mmol) and triethylamine (262 μL, 1.88 mmol) at room temperature, and the reaction mixture was heated to 70° C. After 25 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 252 (12.0 mg, 18%) as a white solid trifluoroacetate salt.

$^1$H NMR (CD$_3$OD, 400 MHz): δ 7.48 (br s, 2H), 7.35 (br s, 1H), 6.18 (br s, 1H), 6.03 (br s, 1H), 5.76 (s, 1H), 4.74 (br s, 2H), 4.30 (t, J=7.7 Hz, 4H), 3.48 (br s, 1H), 3.26-3.18 (m, 1H), 3.14-2.99 (m, 5H), 2.54 (quint, J=7.7 Hz, 2H), 2.45-2.28 (m, 1H), 2.28-1.98 (m, 2H), 1.97-1.85 (m, 2H), 1.82-1.49 (m, 5H).

LCMS (ESI) m/z 574.46 [M+H]$^+$, t$_R$=2.18 min.

HPLC t$_R$ (min), purity %: 3.80, 99%.

R$_f$=0.50 (10% methanol/CH$_2$Cl$_2$).

Intermediate 194

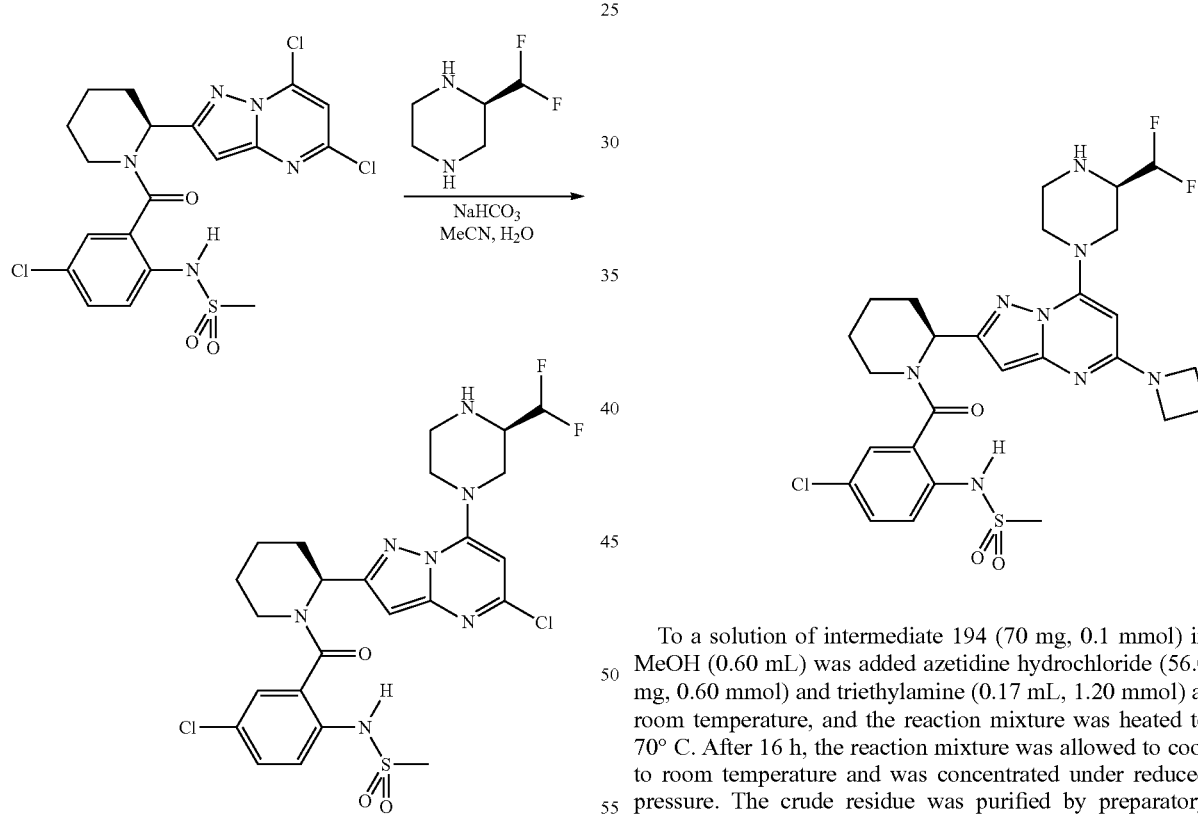

(R)-2-(difluoromethyl)piperazine (see WO2004/112793 A1 for synthesis, 19.0 mg, 0.12 mmol) and sodium bicarbonate (20.0 mg, 0.24 mmol) were added to a solution of intermediate 56 (60 mg, 0.12 mmol) in acetonitrile (0.60 mL) and water (0.60 mL) and the reaction mixture was stirred at room temperature. After 17 h, the reaction mixture was purified by preparatory HPLC (5-100% MeCN/H$_2$O, 0.1% trifluoroacetic acid modifier) to afford intermediate 194 (70.0 mg, 82%) as a white solid trifluoroacetate salt.

LCMS (ESI) m/z 602.28 [M+H]$^+$, t$_R$=2.41 min.

490

Compound 253

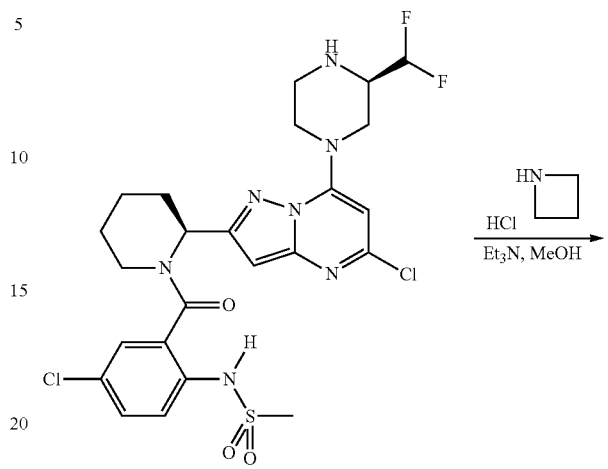

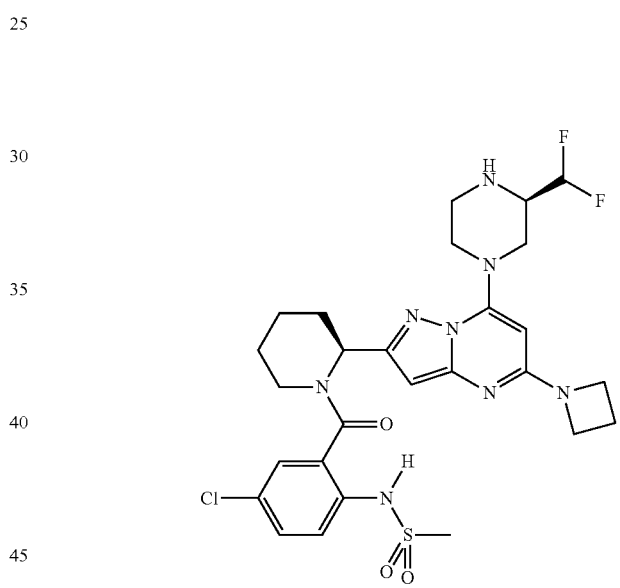

To a solution of intermediate 194 (70 mg, 0.1 mmol) in MeOH (0.60 mL) was added azetidine hydrochloride (56.0 mg, 0.60 mmol) and triethylamine (0.17 mL, 1.20 mmol) at room temperature, and the reaction mixture was heated to 70° C. After 16 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 253 (18.5 mg, 26%) as a white solid trifluoroacetate salt.

$^1$H NMR (CD$_3$OD, 400 MHz): δ 7.49 (br s, 2H), 7.42 (br s, 1H), 6.48-6.25 (m, 1H), 6.22-5.92 (m, 1H), 5.50 (s, 1H), 4.62-4.40 (m, 2H), 4.35 (br s, 4H), 4.22-4.04 (m, 1H), 3.69-3.34 (m, 7H), 3.01 (s, 3H), 2.56 (quint, J=6.5 Hz, 2H), 2.46-2.05 (m, 2H), 1.85-1.50 (m, 4H).

LCMS (ESI) m/z 623.36 [M+H]$^+$, t$_R$=2.05 min.

HPLC t$_R$ (min), purity %: 2.73, 99%.

R$_f$=0.55 (10% methanol/CH$_2$Cl$_2$).

Compound 254

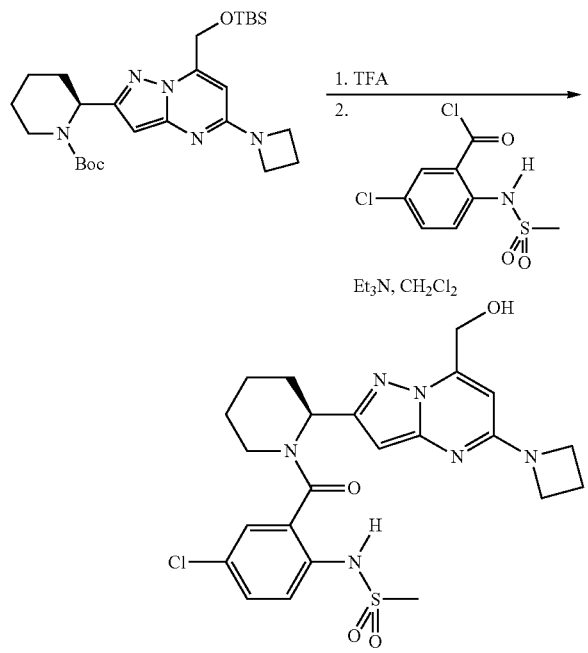

Trifluoromethanesulfonic acid (4 mL) was added to intermediate 197 (340 mg, 0.67 mmol) at room temperature. After 2 h, the resulting mixture was concentrated under reduced pressure. The resulting residue was dissolved into dichloromethane (5.65 mL) and triethylamine (330 µl, 2.37 mmol) followed by 5-chloro-2-(methylsulfonamido)benzoyl chloride (303 mg, 1.13 mmol) were added. The reaction mixture was stirred at room temperature under and argon atmosphere for 6 h, at which point the reaction mixture was directly purified via SiO$_2$ column chromatography (40 g SiO$_2$ Combiflash HP Gold Column, 0-100% ethyl acetate/hexanes) to afford compound 254 (171 mg, 49%) as a light yellow solid.

$^1$H NMR (CD$_3$OD, 400 MHz): δ 7.63-7.33 (m, 3H), 6.22 (s, 1H), 6.15-5.90 (m, 1H), 5.48 (s, 1H), 5.08 (br d, J=13.2 Hz, 1H), 4.95 (d, J=17.2 Hz, 1H), 4.19 (t, J=7.5 Hz, 4H), 3.45 (br s, 1H), 2.98 (s, 3H), 2.44 (quint, J=7.5 Hz, 2H), 2.37-2.15 (m, 2H), 2.09-1.96 (m, 1H), 1.80-1.49 (m, 4H).

LCMS (ESI) m/z 519.36 [M+H]$^+$, t$_R$=2.51 min.
HPLC t$_R$ (min), purity %: 3.16, 99%.
R$_f$=0.50 (EtOAc).

Compound 255

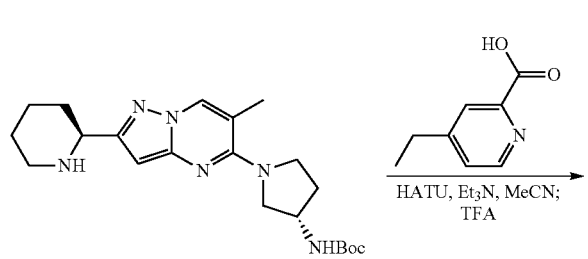

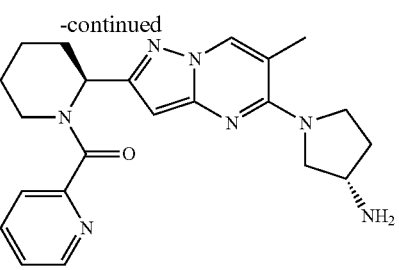

HATU (19.0 mg, 50.0 µmol) was added to a solution of 4-ethylpicolinic acid (9.4 mg, 50 µmol) in acetonitrile (250 µL), and the reaction mixture was stirred at room temperature. After 30 min, intermediate 130 (20.0 mg, 50.0 µmol) was added followed by the addition of triethylamine (10 µL, 75 µmol), and the reaction mixture was stirred at room temperature. After 18 h, the reaction mixture was concentrated under reduced pressure and trifluoroacetic acid (250 µL) was added at room temperature. After 30 min, the resulting mixture was concentrated under reduced pressure, and the crude residue was purified by preparatory HPLC (5-100% MeCN/H$_2$O, 0.1% trifluoroacetic acid modifier) to afford compound 255 (22 mg, 81%) as a tan solid trifluoroacetate salt.

LCMS (ESI) m/z 409.38 [M+H]$^+$, t$_R$=1.68 min.
HPLC t$_R$ (min), purity %: 2.27, 94%.
R$_f$=0.10 (20% methanol/CH$_2$Cl$_2$).

Intermediate 195

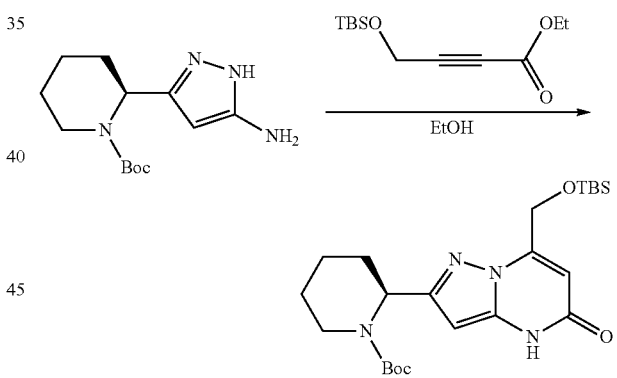

Ethyl 4-(tert-butyldimethylsilyloxy)but-2-ynoate (Koppisch, A. T.; Blagg, B. S. J.; Poulter, C. D. Org. Lett. 2000, 2, 215-217, 500 mg, 2.19 mmol) was added to a solution of intermediate 4 (549 mg, 1.82 mmol) in ethanol (9.10 mL) at room temperature under an argon atmosphere, and the reaction mixture was heated to 80° C. After 20 h, the reaction mixture was allowed to cool to room temperature and was partitioned between ethyl acetate (100 mL) and water (100 mL). The phases were separated, and the organic layer was washed with saturated sodium chloride solution (100 mL), was dried over Na$_2$SO$_4$, and was concentrated under reduced pressure. The resulting residue was purified via SiO$_2$ column chromatography (24 g SiO$_2$ Combiflash HP Gold Column, 0-100% ethyl acetate/hexanes) to afford intermediate 195 (520 mg, 62%) as a light yellow oil.

LCMS (ESI) m/z 463.33 [M+H]$^+$, t$_R$=2.76 min.
R$_f$=0.20 (50% EtOAc/hexanes).

Intermediate 196

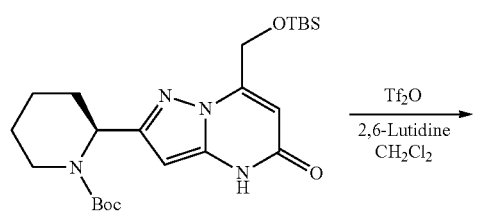

Trifluoromethanesulfonic anhydride (228 µL, 1.36 mmol) was added slowly to a solution of intermediate 195 (522 mg, 1.13 mmol) and 2,6-lutidine (262 µL, 2.26 mmol) in dichloromethane (5.65 mL) at −78° C. under an argon atmosphere. After 10 min, the reaction mixture was allowed to warm to room temperature. After 1 h, the reaction mixture was partitioned between ethyl acetate (100 mL) and saturated aqueous sodium bicarbonate solution (100 mL). The phases were separated, and the organic layer was washed with saturated sodium chloride solution (100 mL), was dried over $Na_2SO_4$, and was concentrated under reduced pressure to afford intermediate 196 (680 mg, >100%) as a light yellow oil.

LCMS (ESI) m/z 595.41 [M+H]$^+$, $t_R$=3.50 min.
$R_f$=0.55 (25% EtOAc/hexanes).

Intermediate 197

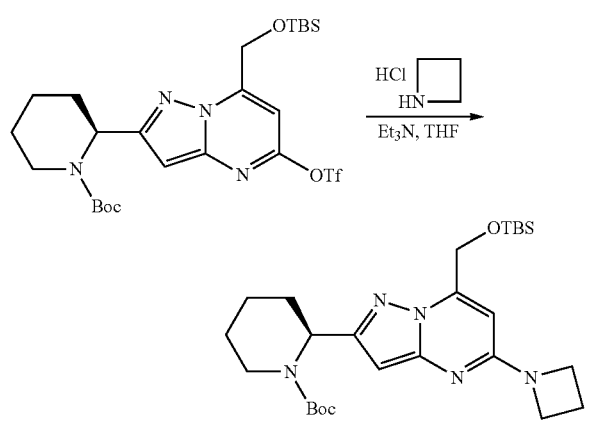

To a solution of intermediate 196 (680 mg, 1.36 mmol) in tetrahydrofuran (5.65 mL) was added azetidine hydrochloride (528 mg, 5.65 mmol) and triethylamine (1.57 mL, 11.3 mmol) at room temperature, and the reaction mixture was heated to 70° C. After 2.5 h, the reaction mixture was allowed to cool to room temperature and was partitioned between ethyl acetate (100 mL) and saturated aqueous sodium bicarbonate solution (100 mL). The phases were separated, and the organic layer was washed with saturated sodium chloride solution (100 mL), was dried over $Na_2SO_4$, and was concentrated under reduced pressure. The crude residue was purified via $SiO_2$ column chromatography (24 g $SiO_2$ Combiflash HP Gold Column, 0-100% ethyl acetate/hexanes) to afford intermediate 197 (340 mg, 60%) as a light yellow oil.

LCMS (ESI) m/z 502.5 [M+H]$^+$, $t_R$=3.47 min.

Compound 256

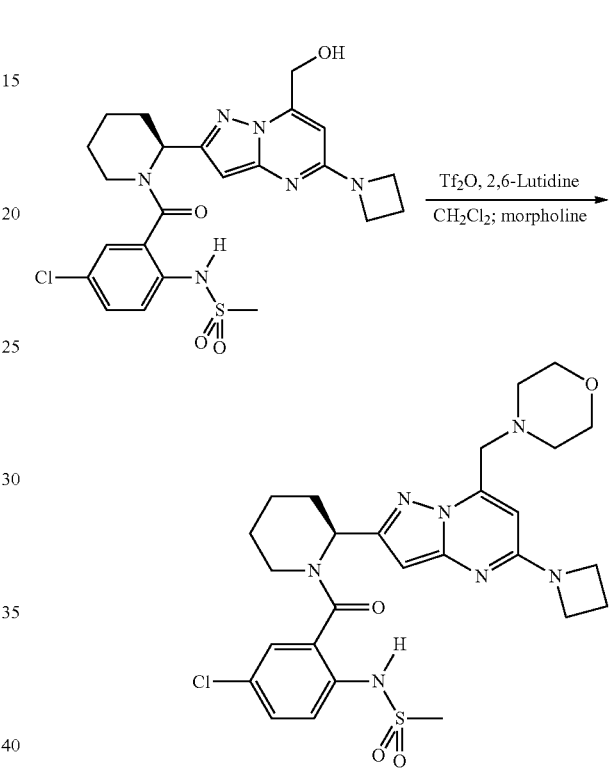

Trifluoromethanesulfonic anhydride (18 µL, 0.11 mmol) was added slowly to a solution of compound 254 (56 mg, 0.11 mmol) and 2,6-lutidine (25 µL, 0.22 mmol) in dichloromethane (0.54 mL) at −78° C. under an argon atmosphere. After 30 min, morpholine (94 µL, 1.10 mmol) was added and the reaction was allowed to warm to room temperature. After 2.5 h, the reaction mixture was concentrated under reduced pressure and the crude residue was purified via $SiO_2$ column chromatography (40 g $SiO_2$ Combiflash HP Gold Column, 0-100% ethyl acetate/hexanes) to afford compound 256 (17.5 mg, 28%) as a white solid.

$^1$H NMR (CD$_3$CN, 400 MHz): δ 7.87 (br s, 1H), 7.65-7.38 (m, 3H), 6.22 (s, 1H), 5.96 (br s, 1H), 4.13 (t, J=7.5 Hz, 4H), 4.06-3.90 (m, 2H), 3.70 (br s, 4H), 3.55-3.35 (m, 1H), 2.94 (br s, 3H), 2.64 (br s, 4H), 2.39 (quint, J=7.5 Hz, 2H), 2.32-2.08 (m, 2H), 2.01-1.89 (m, 1H), 1.76-1.45 (m, 4H).

LCMS (ESI) m/z 588.35 [M+H]$^+$, $t_R$=2.08 min.
HPLC $t_R$ (min), purity %: 3.12, 99%.
$R_f$=0.20 (EtOAc).

Compound 257

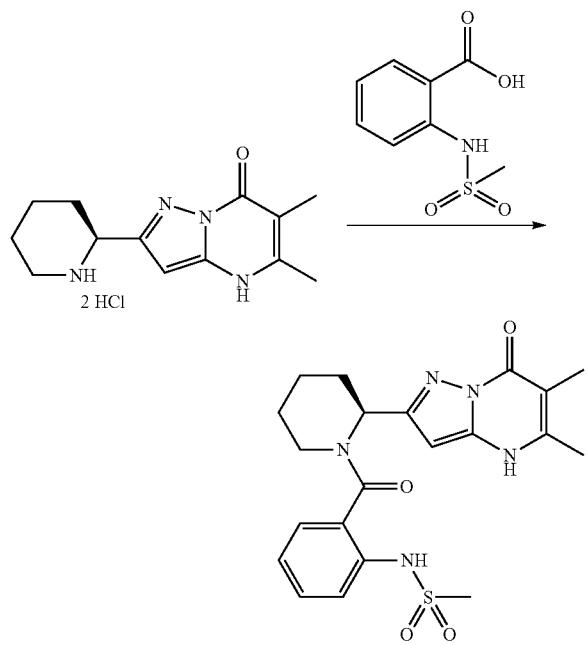

Intermediate 6 (50 mg) was suspended in DMF (2 ml). Two drops of bis(trimethylsilyl)acetamide was added and a clear solution was obtained. A solution of the acid sulphonamide (90 mg) and HATU (152 mg) in DMF (2 ml) was added and the pH adjusted to >9 with Et₃N. This solution was stirred for 2 h, volatiles removed and purified by preparatory HPLC (5-100% MeCN/H$_2$O, 0.1% trifluoroacetic acid modifier) to afford compound 257 (22 mg, 81%) as a colorless solid trifluoroacetate salt.

$^1$H-NMR (CDCl$_3$, 300 MHz): δ 9.0 (s, br, 1H), 7.67-21 (m, 5H), 6.1 (s, 0.5H), 5.75 (s, 0.5H), 3.4-3.2 (3H), 2.2 (s, 3H), 2.05-1.2 (m, 12H).

LCMS m/z [M+H]$^+$ C$_{21}$H$_{25}$N$_5$O$_4$S requires: 443.16. Found 444.04

HPLC tR (min), purity %: 2.198, 99%.

(±)-cis/(±)-trans Intermediate 198

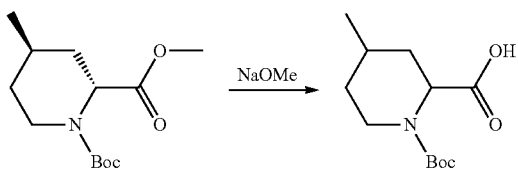 [SMILES: COC(=O)[C@H]1C[C@H](C)CCN1C(=O)OC(C)(C)C ; CC1CCN(C(=O)OC(C)(C)C)C(C(=O)O)C1 ; "NaOMe"]

The starting material (J&W PharmLab LLC, 9.0 g, 37 mmol) in MeOH (40 mL) was treated with NaOMe (10 mL, 44 mmol) and stirred for 4 days. The solution was concentrated and to afford (±)-cis/(±)-trans intermediate 198 which was used without further purification.

(±)-cis/(±)-trans Intermediate 199

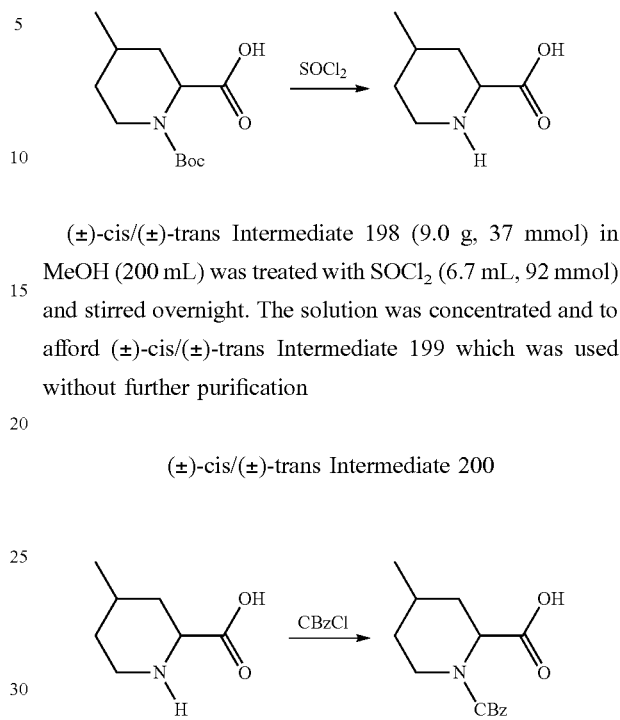

(±)-cis/(±)-trans Intermediate 198 (9.0 g, 37 mmol) in MeOH (200 mL) was treated with SOCl$_2$ (6.7 mL, 92 mmol) and stirred overnight. The solution was concentrated and to afford (±)-cis/(±)-trans Intermediate 199 which was used without further purification

(±)-cis/(±)-trans Intermediate 200

(±)-cis/(±)-trans Intermediate 199 (2.9 g, 18 mmol) in dioxane (50 mL) was treated with 1 N NaOH (55 mL, 55 mmol) and CbzCl (3.9 mL, 28 mmol) and stirred overnight. The solution is concentrated and treated to a 120 g SiO$_2$ Combiflash HP Gold column (0-100% EtOAc-hexanes gradient) to afford (±)-cis/(±)-trans Intermediate 200 (3.6 g, 65%) as a white solid:

LC-MS (ESI) m/z 278 [M+H]$^+$, t$_R$=2.27 min.

(±)-cis/(±)-trans Intermediate 201

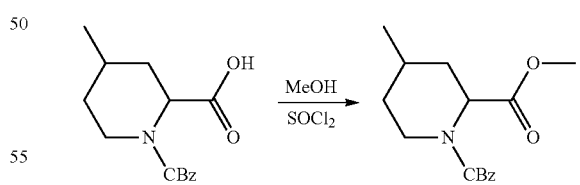

(±)-cis/(±)-trans Intermediate 200 (3.6 g, 13 mmol) in MeOH (50 mL) was treated with SOCl$_2$ (2.4 mL, 33 mmol) and stirred overnight. The solution is concentrated and treated to a 120 g SiO$_2$ Combiflash HP Gold column (0-100% EtOAc-hexanes gradient) to afford (±)-cis/(±)-trans Intermediate 201 (3.1 g, 83%) as a white solid:

$^1$H NMR (CDCl$_3$, 400 MHz): δ 7.38 (m, 5H), 5.15 (m, 2H), 4.51 (m, 1H), 3.69 (br s, 3H), 3.45 (m, 1H), 2.05 (m, 2H), 1.97 (m, 4H), 1.89 (m, 1H), 1.38 (m, 1H), 0.95 (m, 3H).

(±)-cis/(±)-trans Intermediate 202

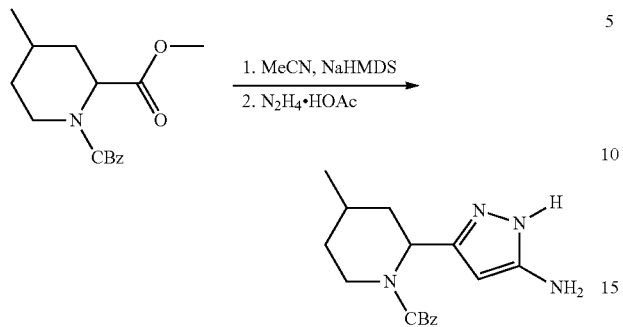

MeCN (1.7 mL, 32 mmol) in THF (13 mL) was cooled to −78° C. and treated dropwise with NaHMDS (1.0 M in THF, 22 mL, 22 mmol) over 30 min. The solution was warmed to −45° C. and stirred for 30 min. The mixture was cooled to −78° C. and (±)-cis/(±)-trans Intermediate 201 (3.1 g, 11 mmol) in THF (12 mL) was added dropwise over 30 min. The solution was warmed to −45° C. and stirred for 3 h. The solution is treated with AcOH (3.8 mL, 66 mmol) in THF (20 mL) and warmed. The solution is diluted with EtOAc (100 mL) and washed with saturated NaCl (2 50 mL). The solution is dried (MgSO₄) and concentrated. The solid is dissolved in EtOH (20 mL) and treated with N₂H₄—HOAc (1.2 g, 13 mmol) and heated at 100° C. for overnight. The solution is concentrated and treated to a 120 g SiO₂ Combiflash HP Gold column (0-100% EtOAc-hexanes gradient) to afford (±)-cis/(±)-trans Intermediate 202 (3.4 g, >99%) as a white solid:

LC-MS (ESI) m/z 315 [M+H]⁺, $t_R$=1.93 min.

(±)-cis/(±)-trans Intermediate 203

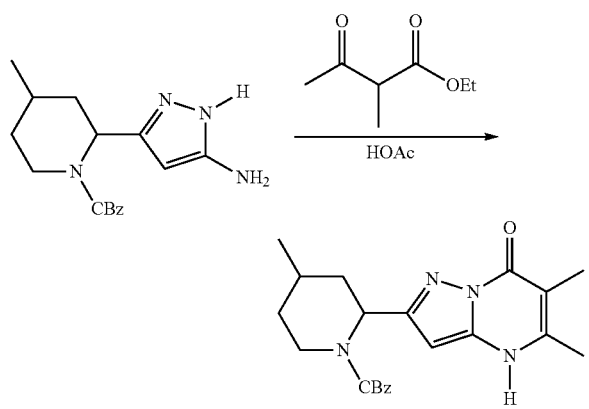

(±)-cis/(±)-trans Intermediate 202 (3.4 g, 11 mmol) in EtOH (25 mL) was treated with ethyl 2-methylacetoacetate (4.7 mL, 33 mmol) and HOAc (6.2 mL, 108 mmol) stirred at 80° C. overnight. The solution was concentrated and treated to a 120 g SiO₂ Combiflash HP Gold column (0-100% EtOAc-hexanes gradient) to (±)-cis/(±)-trans Intermediate 203 (1.5 g, 36%) as a white solid:

LC-MS (ESI) m/z 395 [M+H]⁺, $t_R$=2.29 min.
HPLC $t_R$ (min): 4.50.

General Procedure for Compounds 258-412

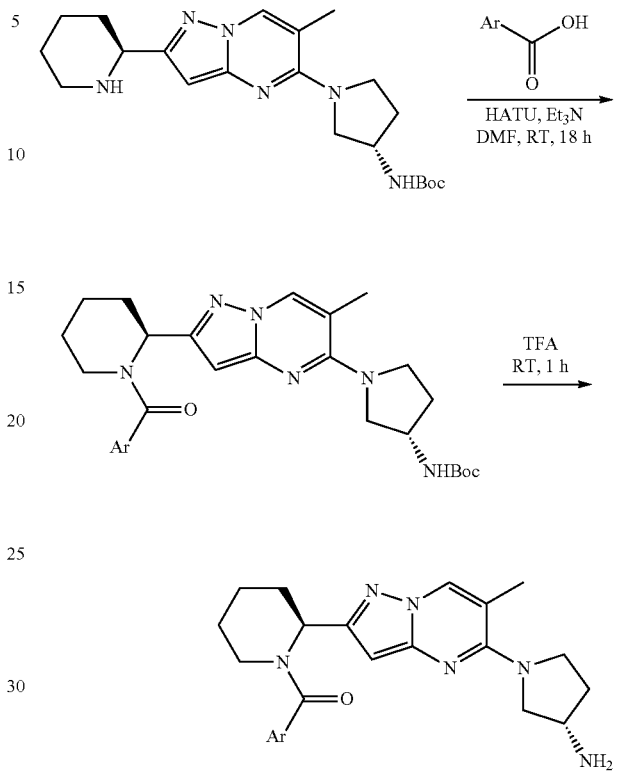

Intermediate 130 (20.0 mg, 0.05 mmol), a representative carboxylic acid (0.10 mmol), and HATU (21.0 mg, 0.06 mmol) were charged to a 2-mL reaction vial. Dimethylformamide (250 µL) and triethylamine (50.0 µL, 0.35 mmol) were added sequentially. After stirring at room temperature for 18 h, the reaction vial was transferred to Genevac and heated at 40° C. for 2 h to remove most of solvent. Then, a solution of 1 N NaOH (500 µL) was added and the mixture was sonicated for 1 minute. Then, it was centrifuged and the resulting supernatant was drained. The remaining solid in the reaction vial was washed with H₂O (1 mL×6), and dried in Genevac at 40° C. for 2 h. Trifluoroacetic acid (100 µL) and dichloromethane (100 µL) were added to the crude product and the reaction mixture was stirred at room temperature for 1 h. Then, the reaction vial was transferred to Genevac and heated at 40° C. for 2 h to remove solvent and most of trifluoroacetic acid. The resulting crude product was diluted with MeOH:EtOAc (1:4, 1 mL) and loaded into the BCX column. Then, it was washed with MeOH:EtOAc (1:4, 3×3 mL) to remove all non-basic by-products. The product was collected by eluting with 2N NH₃ in MeOH:EtOAc (1:3, 3 mL), and concentrated under reduced pressure to afford the target compound in the table below.

| Compound | Structure | MW calc | MW measured |
|---|---|---|---|
| 258 | 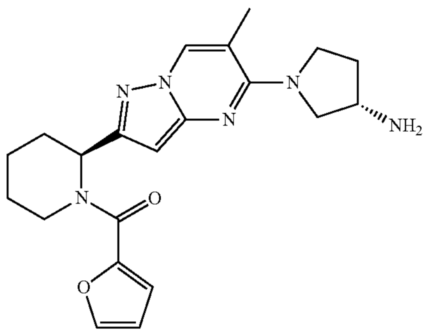 [SMILES: Cc1cn2nc([C@@H]3CCCCN3C(=O)c3ccco3)cc2nc1N1CC[C@H](N)C1] | 394.479 | 395.2 |
| 259 | 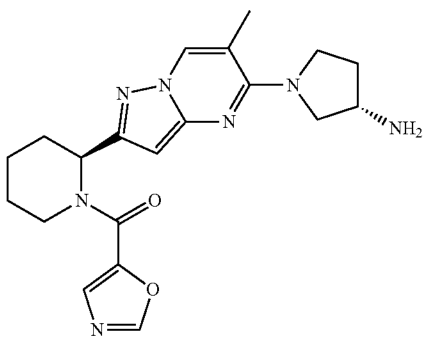 [SMILES: Cc1cn2nc([C@@H]3CCCCN3C(=O)c3cnco3)cc2nc1N1CC[C@H](N)C1] | 395.467 | 396.3 |
| 260 | 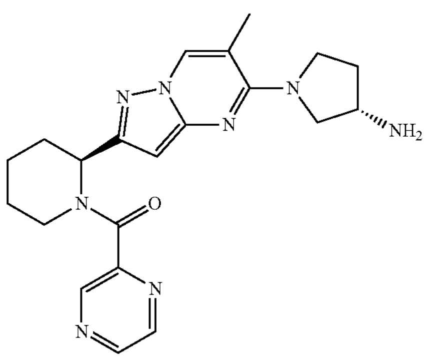 [SMILES: Cc1cn2nc([C@@H]3CCCCN3C(=O)c3cnccn3)cc2nc1N1CC[C@H](N)C1] | 406.494 | 407.4 |
| 261 | 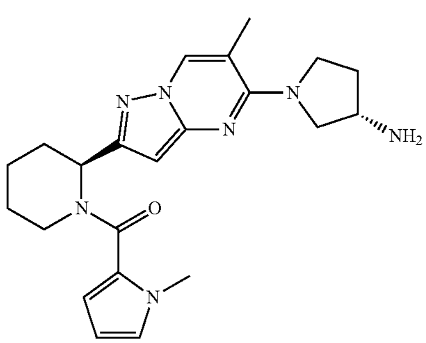 [SMILES: Cc1cn2nc([C@@H]3CCCCN3C(=O)c3cccn3C)cc2nc1N1CC[C@H](N)C1] | 407.522 | 408.4 |

-continued

| Compound | Structure | MW calc | MW measured |
|---|---|---|---|
| 262 | 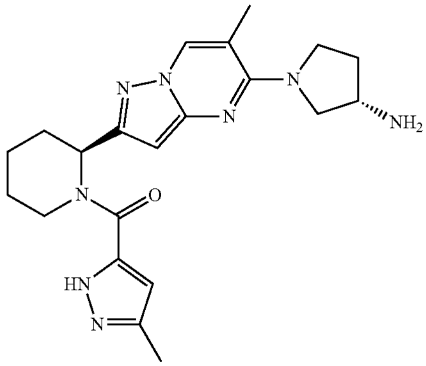 [SMILES: Cc1cc(C(=O)N2CCCC[C@H]2c2cc3nc(N4CC[C@H](N)C4)c(C)cn3n2)[nH]n1] | 408.51 | 409.4 |
| 263 | 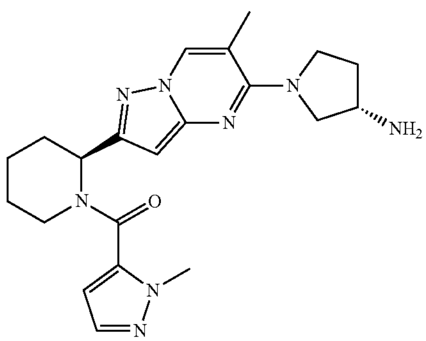 [SMILES: Cc1cn2nc([C@@H]3CCCCN3C(=O)c3ccnn3C)cc2nc1N1CC[C@H](N)C1] | 408.51 | 409.4 |
| 264 | 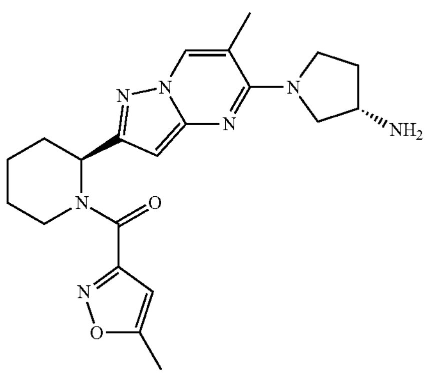 [SMILES: Cc1cc(C(=O)N2CCCC[C@H]2c2cc3nc(N4CC[C@H](N)C4)c(C)cn3n2)no1] | 409.494 | 410.4 |
| 265 | 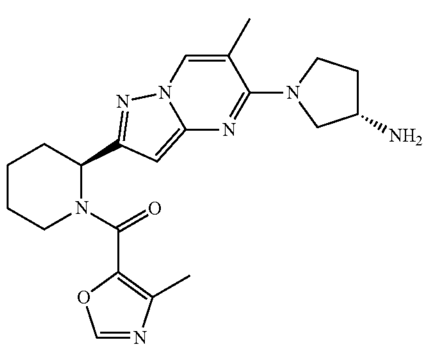 [SMILES: Cc1cn2nc([C@@H]3CCCCN3C(=O)c3ocnc3C)cc2nc1N1CC[C@H](N)C1] | 409.494 | 410.3 |

-continued

| Compound | Structure | MW calc | MW measured |
|---|---|---|---|
| 266 | 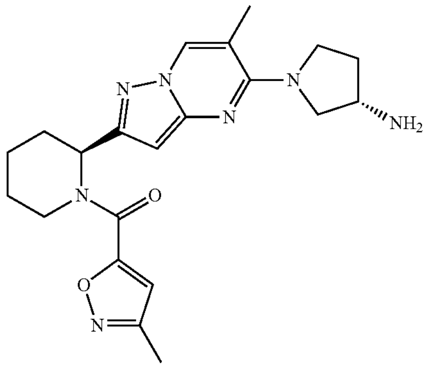 [SMILES: Cc1cc(C(=O)N2CCCC[C@H]2c2cc3nc(N4CC[C@H](N)C4)c(C)cn3n2)on1] | 409.494 | 410.3 |
| 267 | 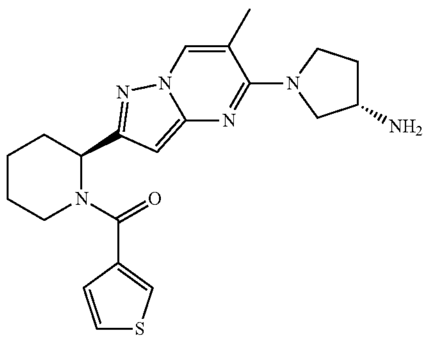 [SMILES: Cc1cn2nc([C@@H]3CCCCN3C(=O)c3ccsc3)cc2nc1N1CC[C@H](N)C1] | 410.544 | 411.3 |
| 268 | 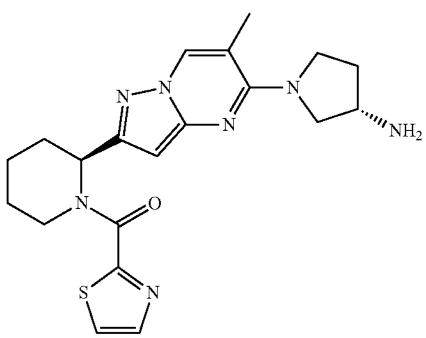 [SMILES: Cc1cn2nc([C@@H]3CCCCN3C(=O)c3nccs3)cc2nc1N1CC[C@H](N)C1] | 411.532 | 412.3 |
| 269 | 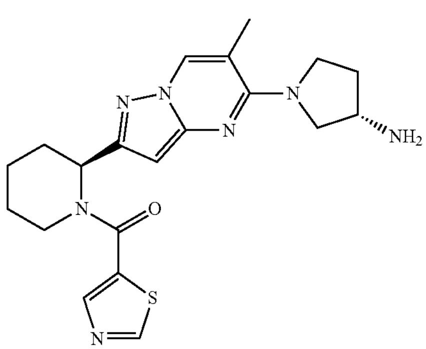 [SMILES: Cc1cn2nc([C@@H]3CCCCN3C(=O)c3cncs3)cc2nc1N1CC[C@H](N)C1] | 411.532 | 412.3 |

-continued

| Compound | Structure | MW calc | MW measured |
|---|---|---|---|
| 270 | 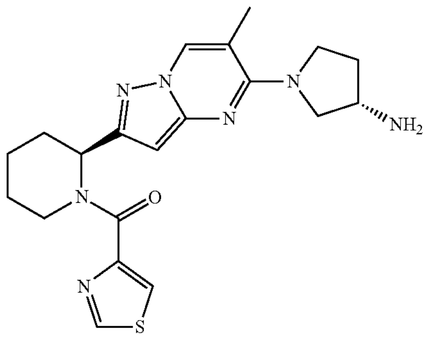 | 411.532 | 412.3 |
| 271 | 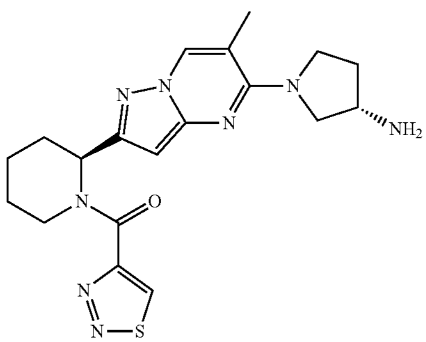 [SMILES: Cc1cn2nc([C@@H]3CCCCN3C(=O)c3csnn3)cc2nc1N1CC[C@H](N)C1] | 412.52 | 413.3 |
| 272 | 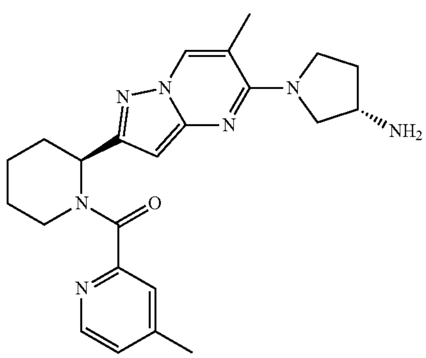 [SMILES: Cc1ccnc(C(=O)N2CCCC[C@H]2c2cc3nc(N4CC[C@H](N)C4)c(C)cn3n2)c1] | 419.533 | 420.4 |
| 273 | 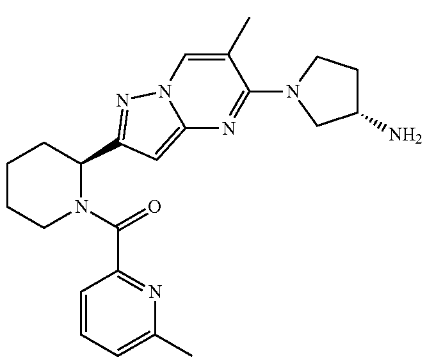 [SMILES: Cc1cccc(C(=O)N2CCCC[C@H]2c2cc3nc(N4CC[C@H](N)C4)c(C)cn3n2)n1] | 419.533 | 420.4 |

-continued
| Compound | Structure | MW calc | MW measured |
|---|---|---|---|
| 274 | 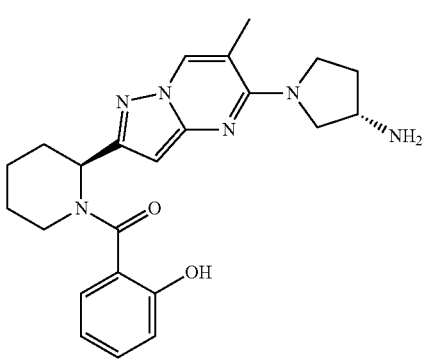 [SMILES: Cc1cn2nc([C@@H]3CCCCN3C(=O)c3ccccc3O)cc2nc1N1CC[C@H](N)C1] | 420.517 | 421.4 |
| 275 | 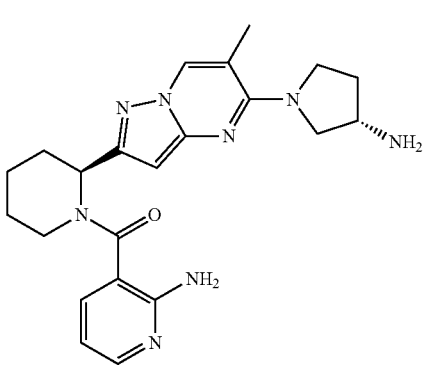 [SMILES: Cc1cn2nc([C@@H]3CCCCN3C(=O)c3cccnc3N)cc2nc1N1CC[C@H](N)C1] | 420.521 | 421.4 |
| 276 | 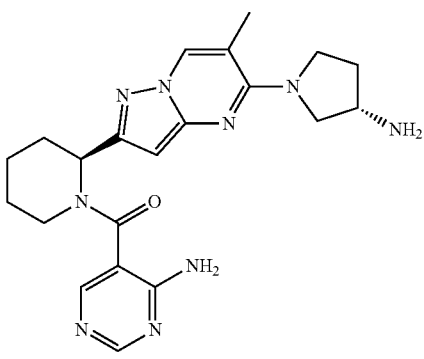 [SMILES: Cc1cn2nc([C@@H]3CCCCN3C(=O)c3cncnc3N)cc2nc1N1CC[C@H](N)C1] | 421.509 | 422.4 |
| 277 | 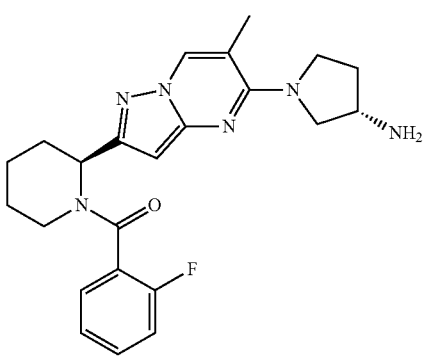 | 422.508 | 423.4 |

-continued

| Compound | Structure | MW calc | MW measured |
|---|---|---|---|
| 278 | 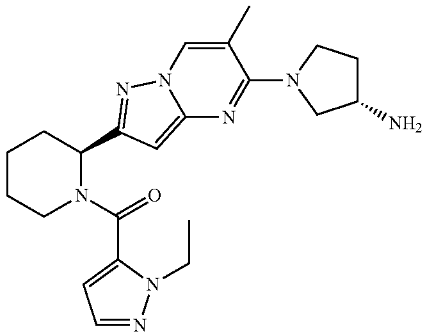 [SMILES: CCn1nccc1C(=O)N1CCCC[C@H]1c1cc2nc(N3CC[C@H](N)C3)c(C)cn2n1] | 422.537 | 423.6 |
| 279 | 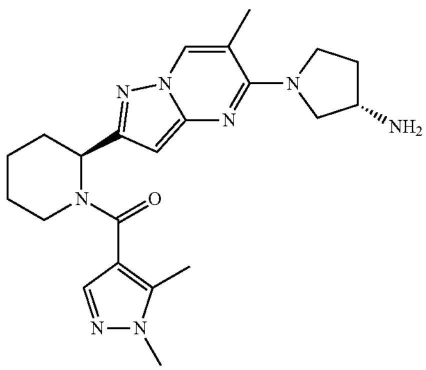 [SMILES: Cc1cn2nc([C@@H]3CCCCN3C(=O)c3cnn(C)c3C)cc2nc1N1CC[C@H](N)C1] | 422.537 | 423.4 |
| 280 | 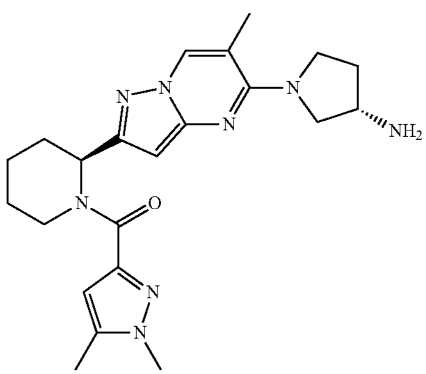 [SMILES: Cc1cn2nc([C@@H]3CCCCN3C(=O)c3cc(C)n(C)n3)cc2nc1N1CC[C@H](N)C1] | 422.537 | 423.4 |
| 281 | 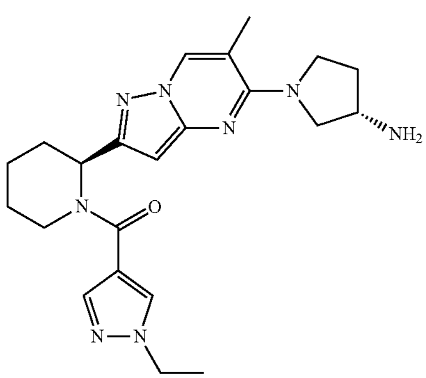 [SMILES: CCn1cc(C(=O)N2CCCC[C@H]2c2cc3nc(N4CC[C@H](N)C4)c(C)cn3n2)cn1] | 422.537 | 423.4 |

-continued
| Compound | Structure | MW calc | MW measured |
|---|---|---|---|
| 282 | 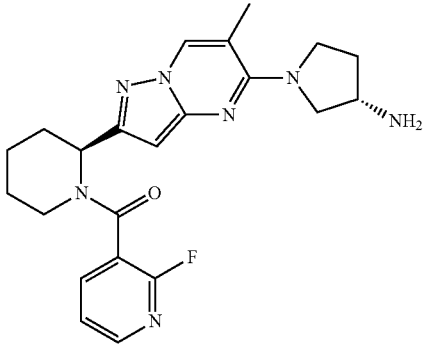 [SMILES: Cc1cn2nc([C@@H]3CCCCN3C(=O)c3cccnc3F)cc2nc1N1CC[C@H](N)C1] | 423.496 | 424.3 |
| 283 | 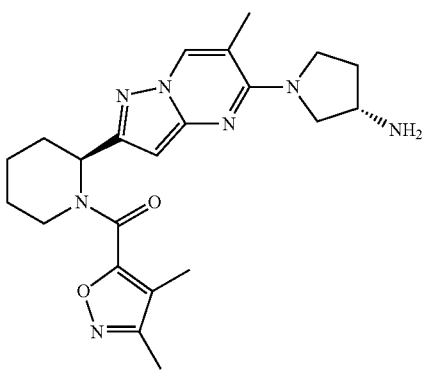 [SMILES: Cc1cn2nc([C@@H]3CCCCN3C(=O)c3onc(C)c3C)cc2nc1N1CC[C@H](N)C1] | 423.521 | 424.4 |
| 284 | 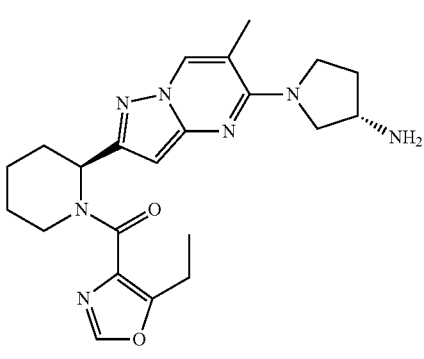 [SMILES: CCc1ocnc1C(=O)N1CCCC[C@H]1c1cc2nc(N3CC[C@H](N)C3)c(C)cn2n1] | 423.521 | 424.4 |
| 285 | 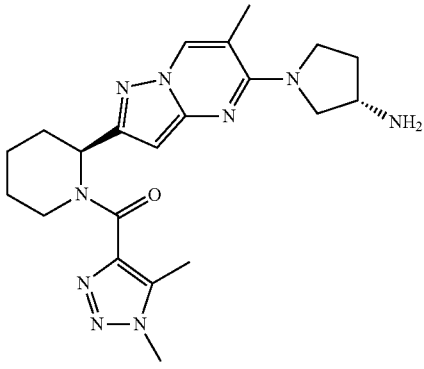 [SMILES: Cc1cn2nc([C@@H]3CCCCN3C(=O)c3nnn(C)c3C)cc2nc1N1CC[C@H](N)C1] | 423.525 | 424.4 |

| Compound | Structure | MW calc | MW measured |
|---|---|---|---|
| 286 | 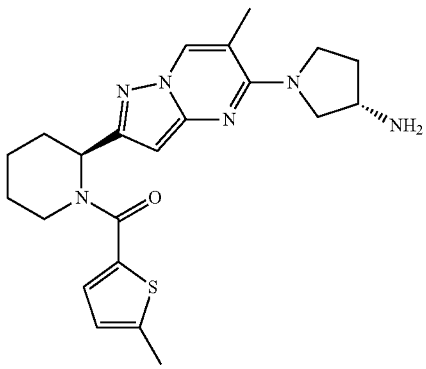 [SMILES: Cc1ccc(C(=O)N2CCCC[C@H]2c2cc3nc(N4CC[C@H](N)C4)c(C)cn3n2)s1] | 424.571 | 425.3 |
| 287 | 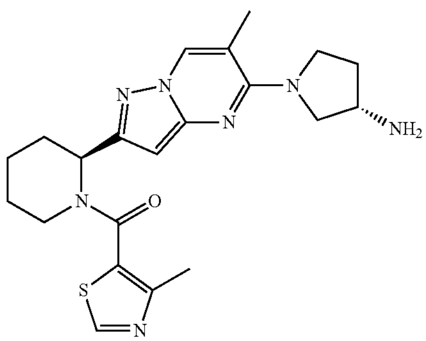 [SMILES: Cc1cn2nc([C@@H]3CCCCN3C(=O)c3scnc3C)cc2nc1N1CC[C@H](N)C1] | 425.559 | 426.3 |
| 288 | 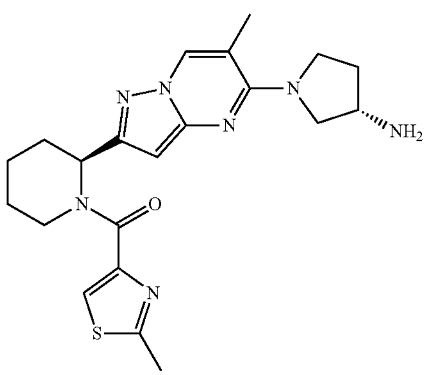 [SMILES: Cc1nc(C(=O)N2CCCC[C@H]2c2cc3nc(N4CC[C@H](N)C4)c(C)cn3n2)cs1] | 425.559 | 426.3 |
| 289 | 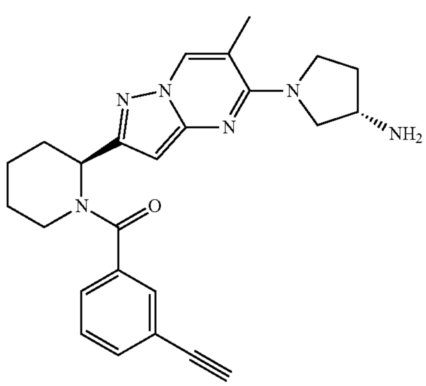 [SMILES: C#Cc1cccc(C(=O)N2CCCC[C@H]2c2cc3nc(N4CC[C@H](N)C4)c(C)cn3n2)c1] | 428.54 | 429.4 |

-continued

| Compound | Structure | MW calc | MW measured |
|---|---|---|---|
| 290 | 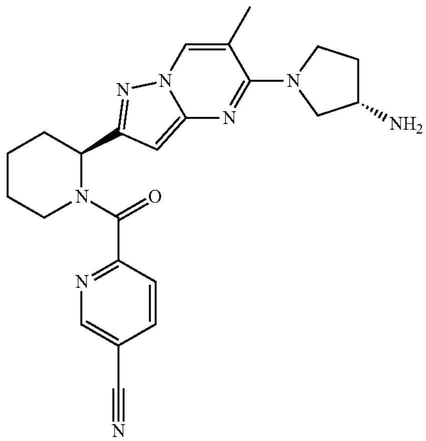 [SMILES: Cc1cn2nc([C@@H]3CCCCN3C(=O)c3ccc(C#N)cn3)cc2nc1N1CC[C@H](N)C1] | 430.516 | 431.4 |
| 291 | 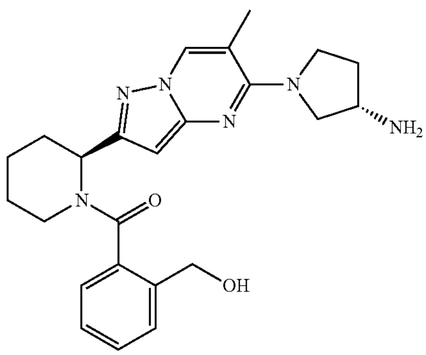 [SMILES: Cc1cn2nc([C@@H]3CCCCN3C(=O)c3ccccc3CO)cc2nc1N1CC[C@H](N)C1] | 434.544 | 419.4 |
| 292 | 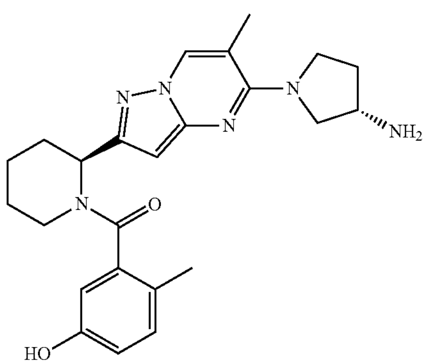 [SMILES: Cc1ccc(O)cc1C(=O)N1CCCC[C@H]1c1cc2nc(N3CC[C@H](N)C3)c(C)cn2n1] | 434.544 | 435.4 |
| 293 | 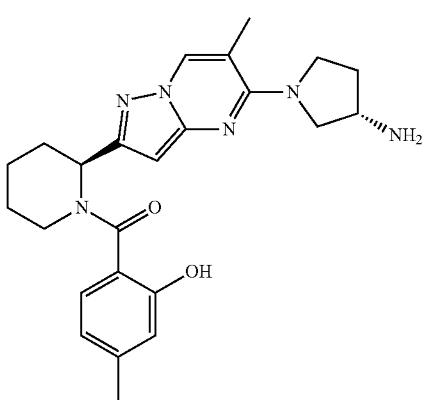 [SMILES: Cc1ccc(C(=O)N2CCCC[C@H]2c2cc3nc(N4CC[C@H](N)C4)c(C)cn3n2)c(O)c1] | 434.544 | 435.4 |

-continued

| Compound | Structure | MW calc | MW measured |
|---|---|---|---|
| 294 | 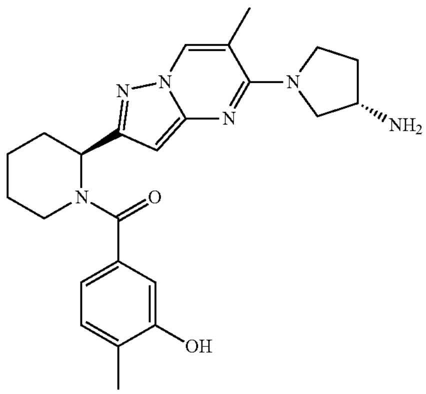 [SMILES: Cc1ccc(C(=O)N2CCCC[C@H]2c2cc3nc(N4CC[C@H](N)C4)c(C)cn3n2)cc1O] | 434.544 | 435.4 |
| 295 | 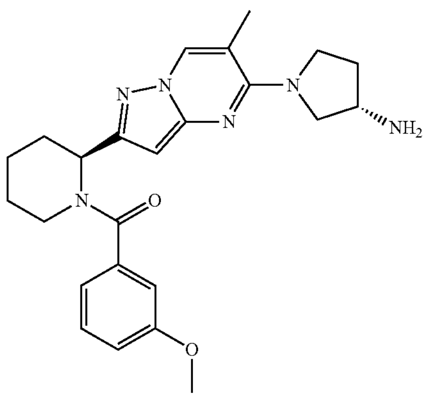 [SMILES: COc1cccc(C(=O)N2CCCC[C@H]2c2cc3nc(N4CC[C@H](N)C4)c(C)cn3n2)c1] | 434.544 | 435.4 |
| 296 | 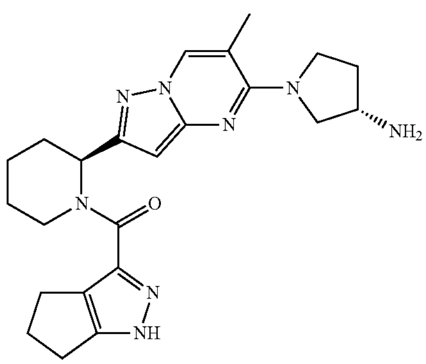 [SMILES: Cc1cn2nc([C@@H]3CCCCN3C(=O)c3n[nH]c4c3CCC4)cc2nc1N1CC[C@H](N)C1] | 434.548 | 435.4 |
| 297 | 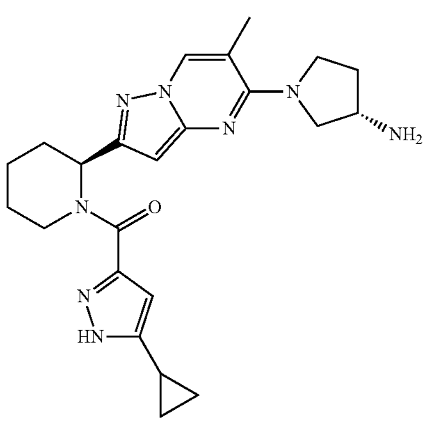 [SMILES: Cc1cn2nc([C@@H]3CCCCN3C(=O)c3cc(C4CC4)[nH]n3)cc2nc1N1CC[C@H](N)C1] | 434.548 | 435.4 |

-continued

| Compound | Structure | MW calc | MW measured |
|---|---|---|---|
| 298 | 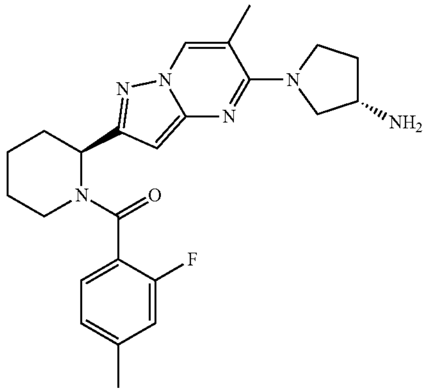 [SMILES: Cc1ccc(C(=O)N2CCCC[C@H]2c2cc3nc(N4CC[C@H](N)C4)c(C)cn3n2)c(F)c1] | 436.535 | 437.4 |
| 299 | 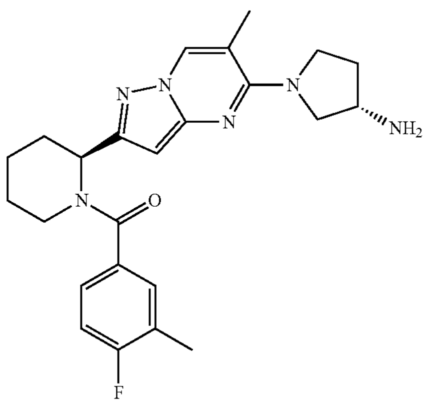 [SMILES: Cc1cc(C(=O)N2CCCC[C@H]2c2cc3nc(N4CC[C@H](N)C4)c(C)cn3n2)ccc1F] | 436.535 | 437.4 |
| 300 | 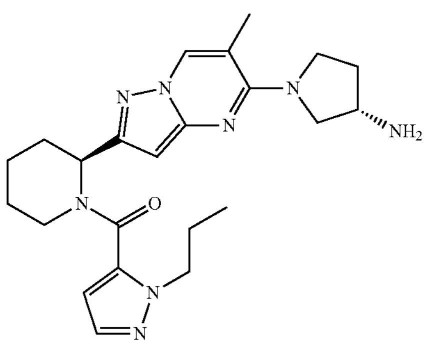 [SMILES: CCCn1nccc1C(=O)N1CCCC[C@H]1c1cc2nc(N3CC[C@H](N)C3)c(C)cn2n1] | 436.564 | 437.4 |
| 301 | 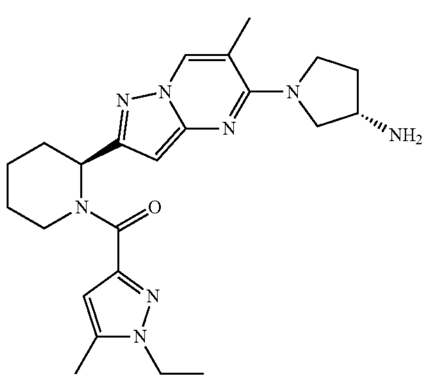 [SMILES: CCn1nc(C(=O)N2CCCC[C@H]2c2cc3nc(N4CC[C@H](N)C4)c(C)cn3n2)cc1C] | 436.564 | 437.4 |

-continued

| Compound | Structure | MW calc | MW measured |
|---|---|---|---|
| 302 | 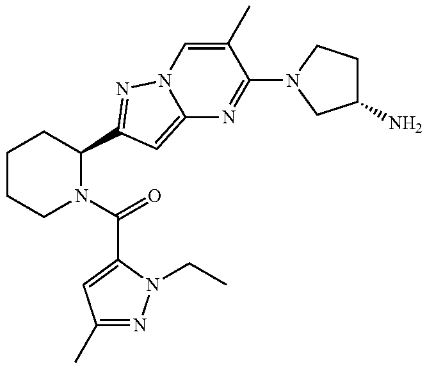 [SMILES: CCn1nc(C)cc1C(=O)N1CCCC[C@H]1c1cc2nc(N3CC[C@H](N)C3)c(C)cn2n1] | 436.564 | 437.4 |
| 303 | 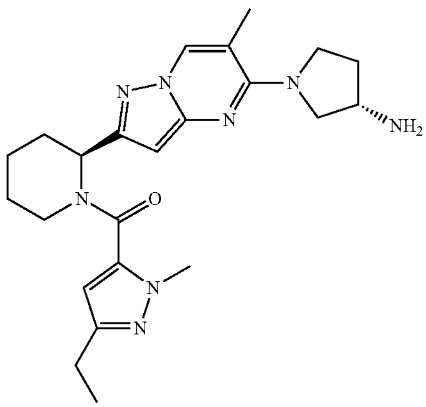 | 436.564 | 437.4 |
| 304 | 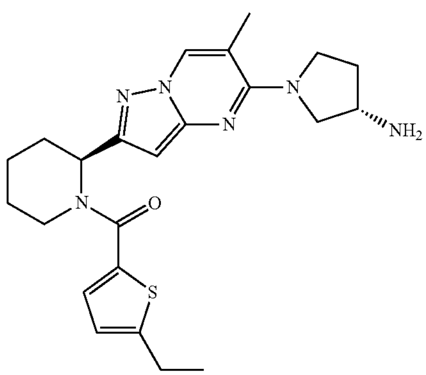 [SMILES: CCc1ccc(C(=O)N2CCCC[C@H]2c2cc3nc(N4CC[C@H](N)C4)c(C)cn3n2)s1] | 438.598 | 439.3 |
| 305 | 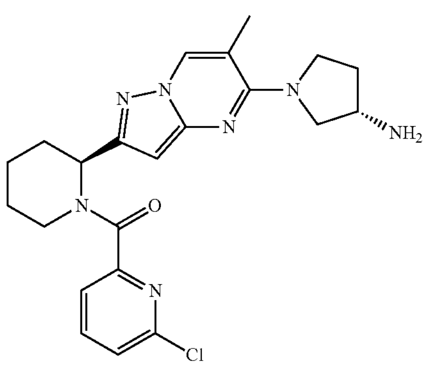 [SMILES: Cc1cn2nc([C@@H]3CCCCN3C(=O)c3cccc(Cl)n3)cc2nc1N1CC[C@H](N)C1] | 439.951 | 440.3 |

-continued
| Compound | Structure | MW calc | MW measured |
|---|---|---|---|
| 306 | 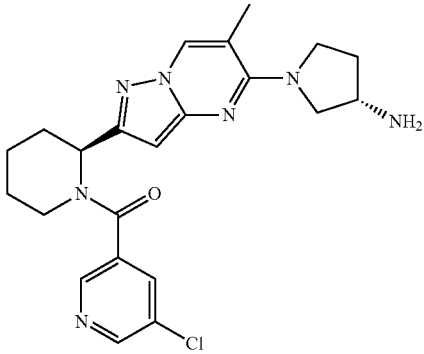 [SMILES: Cc1cn2nc([C@@H]3CCCCN3C(=O)c3cncc(Cl)c3)cc2nc1N1CC[C@H](N)C1] | 439.951 | 440.3 |
| 307 | 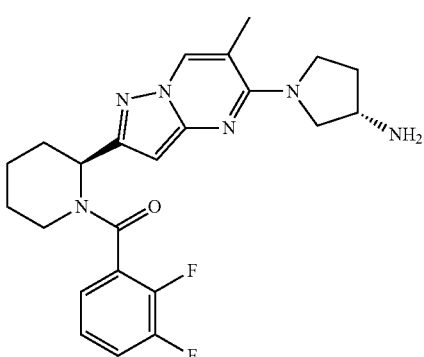 | 440.498 | 441.4 |
| 308 | 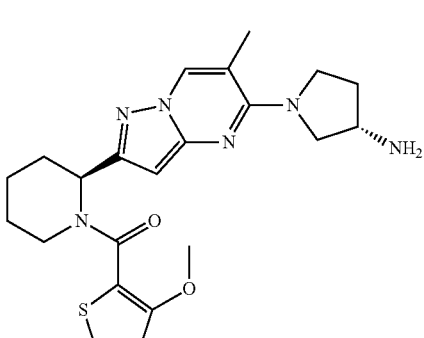 | 440.57 | 441.3 |
| 309 | 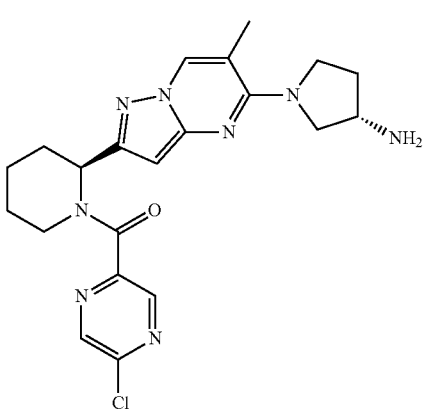 [SMILES: Cc1cn2nc([C@@H]3CCCCN3C(=O)c3cnc(Cl)cn3)cc2nc1N1CC[C@H](N)C1] | 440.939 | 441.3 |

| Compound | Structure | MW calc | MW measured |
|---|---|---|---|
| 310 | 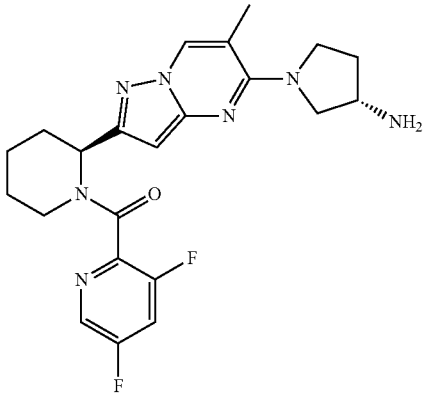 [SMILES: Cc1cn2nc([C@@H]3CCCCN3C(=O)c3ncc(F)cc3F)cc2nc1N1CC[C@H](N)C1] | 441.486 | 442.3 |
| 311 | 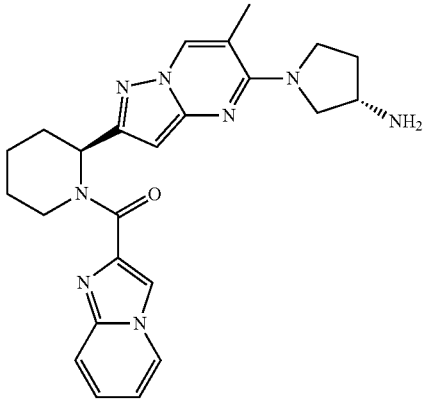 [SMILES: Cc1cn2nc([C@@H]3CCCCN3C(=O)c3cn4ccccc4n3)cc2nc1N1CC[C@H](N)C1] | 444.543 | 445.4 |
| 312 | 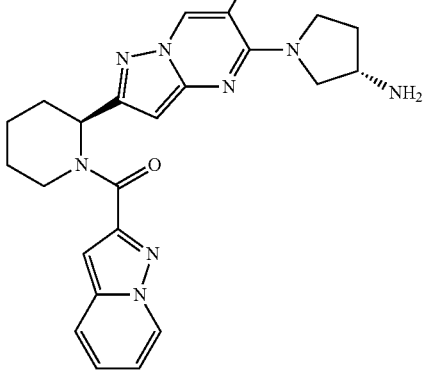 | 444.543 | 445.4 |

-continued

| Compound | Structure | MW calc | MW measured |
|---|---|---|---|
| 313 | 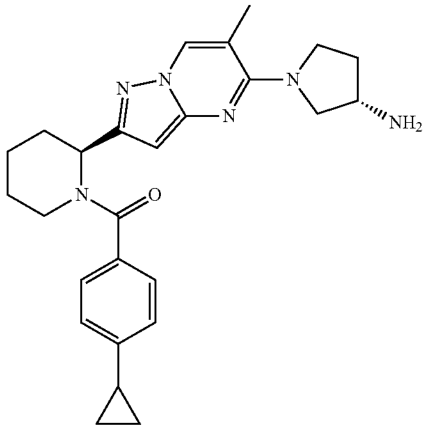 [SMILES: Cc1cn2nc([C@@H]3CCCCN3C(=O)c3ccc(C4CC4)cc3)cc2nc1N1CC[C@H](N)C1] | 444.583 | 445.4 |
| 314 | 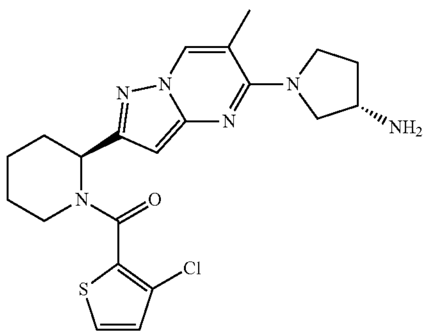 [SMILES: Cc1cn2nc([C@@H]3CCCCN3C(=O)c3sccc3Cl)cc2nc1N1CC[C@H](N)C1] | 444.989 | 445.3 |
| 315 | 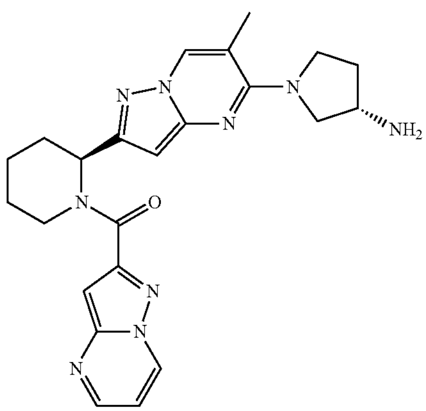 [SMILES: Cc1cn2nc([C@@H]3CCCCN3C(=O)c3cc4ncccn4n3)cc2nc1N1CC[C@H](N)C1] | 445.531 | 446.4 |
| 316 | 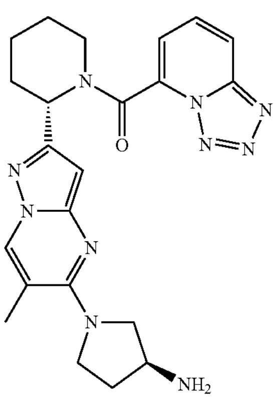 [SMILES: Cc1cn2nc([C@@H]3CCCCN3C(=O)c3cccc4nnnn34)cc2nc1N1CC[C@H](N)C1] | 446.519 | 447.4 |

| Compound | Structure | MW calc | MW measured |
|---|---|---|---|
| 317 | 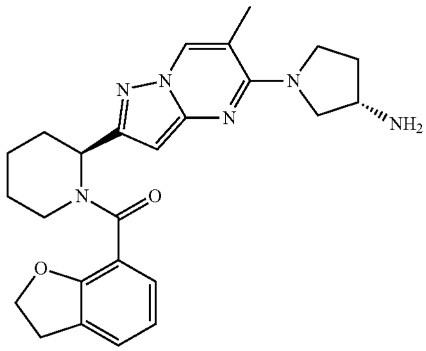 [SMILES: Cc1cn2nc([C@@H]3CCCCN3C(=O)c3cccc4c3OCC4)cc2nc1N1CC[C@H](N)C1] | 446.555 | 447.4 |
| 318 | 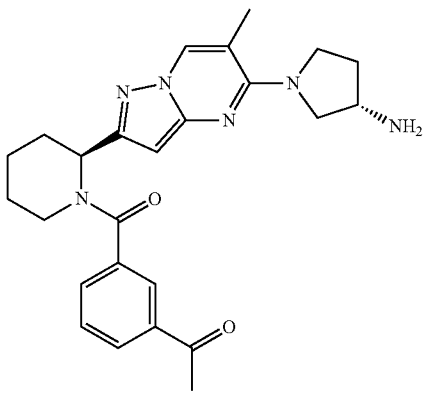 [SMILES: CC(=O)c1cccc(C(=O)N2CCCC[C@H]2c2cc3nc(N4CC[C@H](N)C4)c(C)cn3n2)c1] | 446.555 | 447.4 |
| 319 | 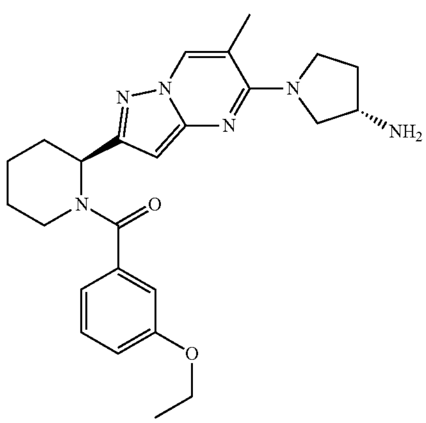 [SMILES: CCOc1cccc(C(=O)N2CCCC[C@H]2c2cc3nc(N4CC[C@H](N)C4)c(C)cn3n2)c1] | 448.571 | 449.4 |
| 320 | 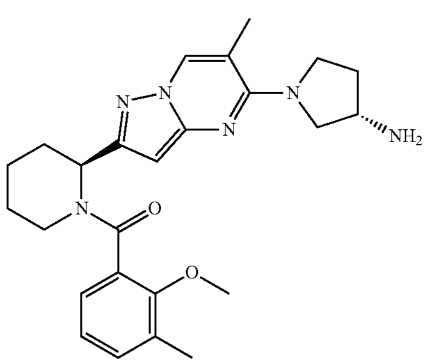 [SMILES: COc1c(C)cccc1C(=O)N1CCCC[C@H]1c1cc2nc(N3CC[C@H](N)C3)c(C)cn2n1] | 448.571 | 449.4 |

-continued

| Compound | Structure | MW calc | MW measured |
|---|---|---|---|
| 321 | 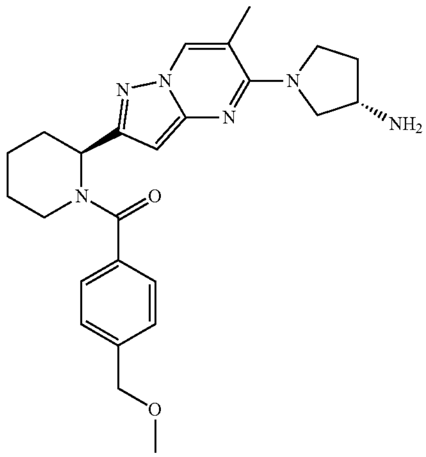 [SMILES: COCc1ccc(C(=O)N2CCCC[C@H]2c2cc3nc(N4CC[C@H](N)C4)c(C)cn3n2)cc1] | 448.571 | 449.4 |
| 322 | 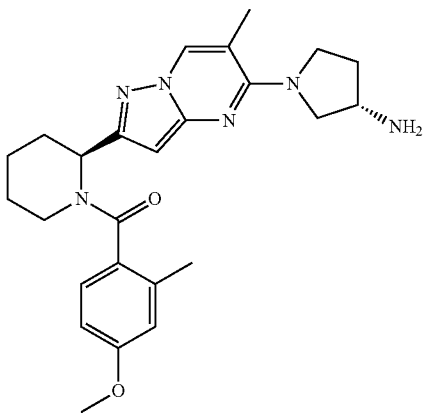 [SMILES: COc1ccc(C(=O)N2CCCC[C@H]2c2cc3nc(N4CC[C@H](N)C4)c(C)cn3n2)c(C)c1] | 448.571 | 449.4 |
| 323 | 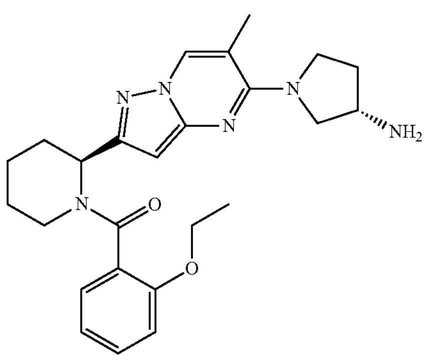 [SMILES: CCOc1ccccc1C(=O)N1CCCC[C@H]1c1cc2nc(N3CC[C@H](N)C3)c(C)cn2n1] | 448.571 | 449.4 |
| 324 | 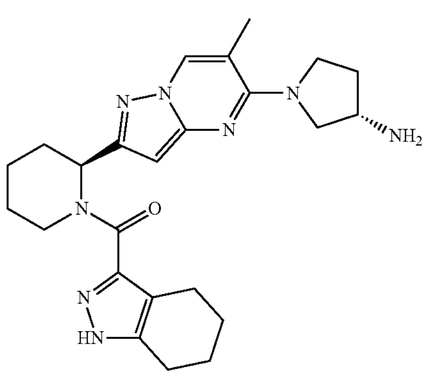 [SMILES: Cc1cn2nc([C@@H]3CCCCN3C(=O)c3n[nH]c4c3CCCC4)cc2nc1N1CC[C@H](N)C1] | 448.575 | 449.4 |

-continued
| Compound | Structure | MW calc | MW measured |
|---|---|---|---|
| 325 | 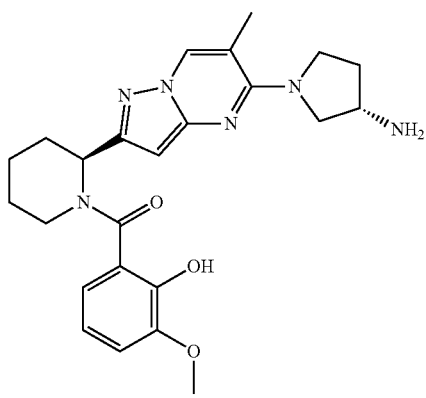 | 450.543 | 451.4 |
| 326 | 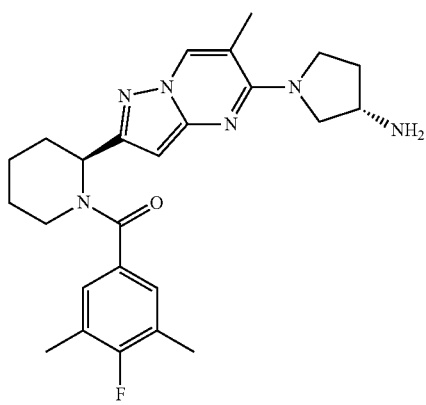 [SMILES: Cc1cn2nc([C@@H]3CCCCN3C(=O)c3cc(C)c(F)c(C)c3)cc2nc1N1CC[C@H](N)C1] | 450.562 | 451.4 |
| 327 | 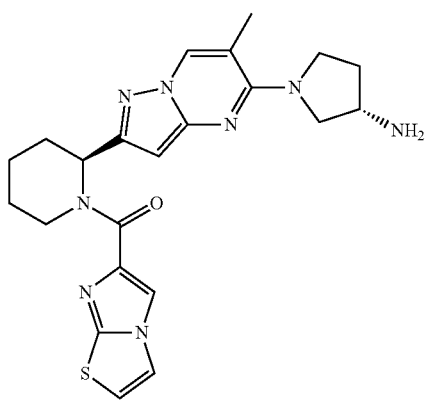 [SMILES: Cc1cn2nc([C@@H]3CCCCN3C(=O)c3cn4ccsc4n3)cc2nc1N1CC[C@H](N)C1] | 450.569 | 451.4 |

-continued

| Compound | Structure | MW calc | MW measured |
|---|---|---|---|
| 328 | 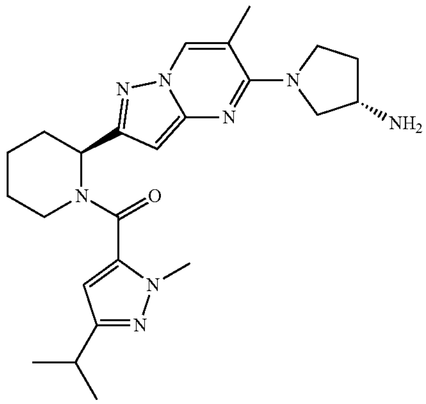 [SMILES: Cc1cn2nc([C@@H]3CCCCN3C(=O)c3cc(C(C)C)nn3C)cc2nc1N1CC[C@H](N)C1] | 450.591 | 451.4 |
| 329 | 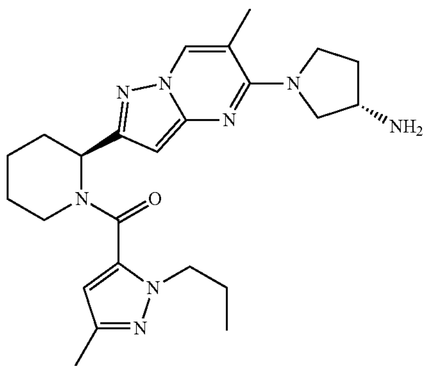 [SMILES: CCCn1nc(C)cc1C(=O)N1CCCC[C@H]1c1cc2nc(N3CC[C@H](N)C3)c(C)cn2n1] | 450.591 | 451.4 |
| 330 | 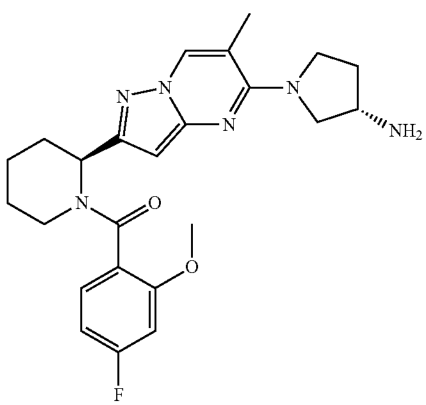 [SMILES: COc1cc(F)ccc1C(=O)N1CCCC[C@H]1c1cc2nc(N3CC[C@H](N)C3)c(C)cn2n1] | 452.534 | 453.4 |
| 331 | 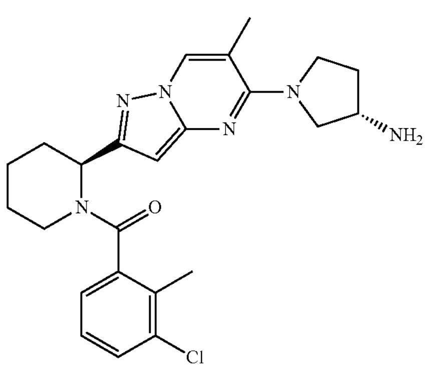 [SMILES: Cc1cn2nc([C@@H]3CCCCN3C(=O)c3cccc(Cl)c3C)cc2nc1N1CC[C@H](N)C1] | 452.99 | 453.4 |

-continued

| Compound | Structure | MW calc | MW measured |
|---|---|---|---|
| 332 | 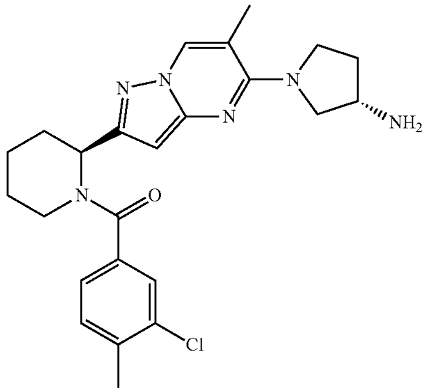 [SMILES: Cc1ccc(C(=O)N2CCCC[C@H]2c2cc3nc(N4CC[C@H](N)C4)c(C)cn3n2)cc1Cl] | 452.99 | 453.4 |
| 333 | 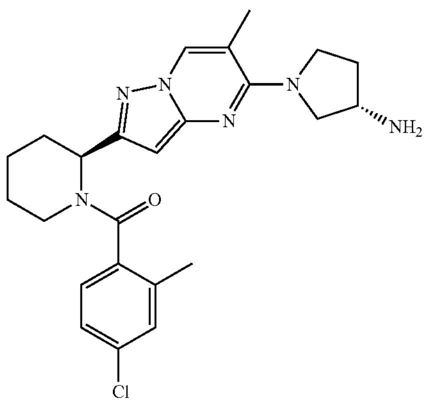 [SMILES: Cc1cc(Cl)ccc1C(=O)N1CCCC[C@H]1c1cc2nc(N3CC[C@H](N)C3)c(C)cn2n1] | 452.99 | 453.4 |
| 334 | 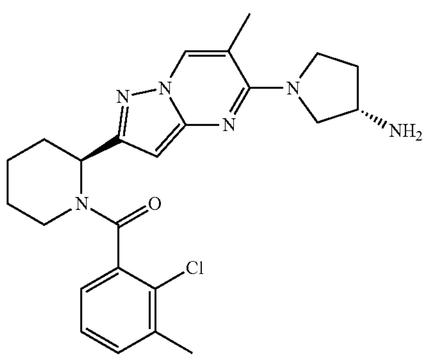 [SMILES: Cc1cn2nc([C@@H]3CCCCN3C(=O)c3cccc(C)c3Cl)cc2nc1N1CC[C@H](N)C1] | 452.99 | 453.4 |
| 335 | 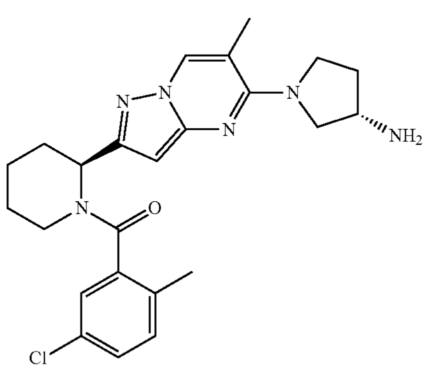 [SMILES: Cc1ccc(Cl)cc1C(=O)N1CCCC[C@H]1c1cc2nc(N3CC[C@H](N)C3)c(C)cn2n1] | 452.99 | 453.4 |

| Compound | Structure | MW calc | MW measured |
|---|---|---|---|
| 336 | 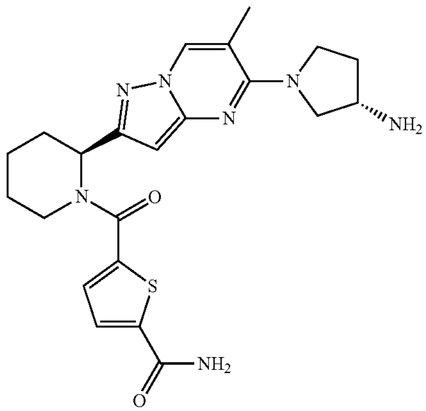 [SMILES: Cc1cn2nc([C@@H]3CCCCN3C(=O)c3ccc(C(N)=O)s3)cc2nc1N1CC[C@H](N)C1] | 453.569 | 454.4 |
| 337 | 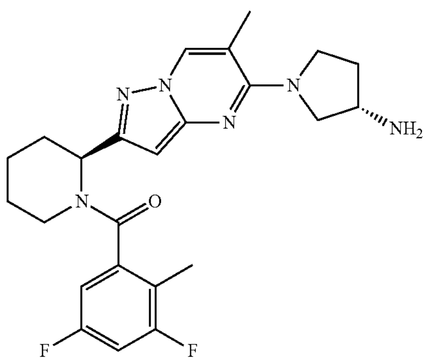 [SMILES: Cc1cn2nc([C@@H]3CCCCN3C(=O)c3cc(F)cc(F)c3C)cc2nc1N1CC[C@H](N)C1] | 454.525 | 455.4 |
| 338 | 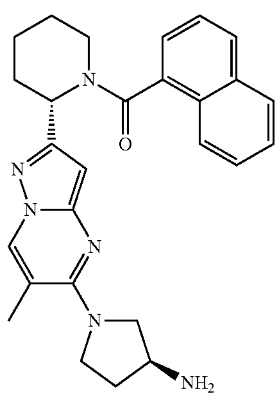 [SMILES: Cc1cn2nc([C@@H]3CCCCN3C(=O)c3cccc4ccccc34)cc2nc1N1CC[C@H](N)C1] | 454.578 | 455.4 |
| 339 | 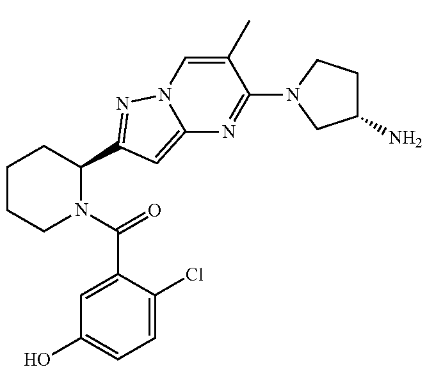 [SMILES: Cc1cn2nc([C@@H]3CCCCN3C(=O)c3cc(O)ccc3Cl)cc2nc1N1CC[C@H](N)C1] | 454.962 | 455.3 |

-continued

| Compound | Structure | MW calc | MW measured |
|---|---|---|---|
| 340 | 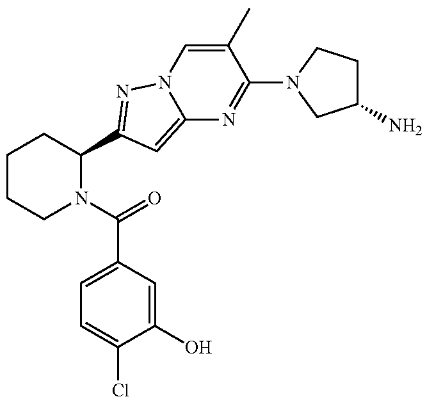 [SMILES: Cc1cn2nc([C@@H]3CCCCN3C(=O)c3ccc(Cl)c(O)c3)cc2nc1N1CC[C@H](N)C1] | 454.962 | 455.3 |
| 341 | 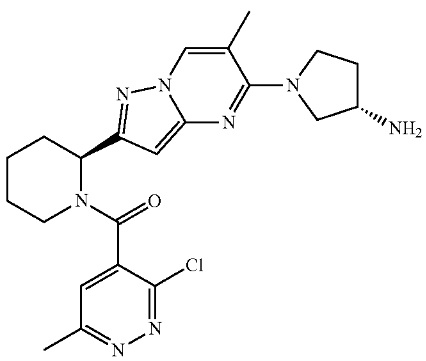 [SMILES: Cc1cc(C(=O)N2CCCC[C@H]2c2cc3nc(N4CC[C@H](N)C4)c(C)cn3n2)c(Cl)nn1] | 454.966 | 455.3 |
| 342 | 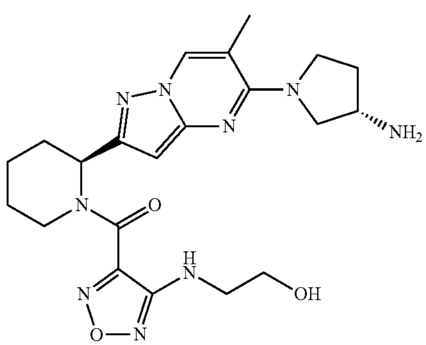 [SMILES: Cc1cn2nc([C@@H]3CCCCN3C(=O)c3nonc3NCCO)cc2nc1N1CC[C@H](N)C1] | 455.523 | 456.4 |
| 343 | 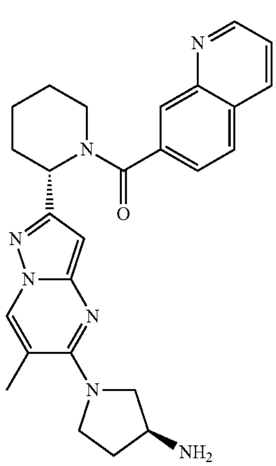 [SMILES: Cc1cn2nc([C@@H]3CCCCN3C(=O)c3ccc4cccnc4c3)cc2nc1N1CC[C@H](N)C1] | 455.566 | 456.4 |

-continued

| Compound | Structure | MW calc | MW measured |
|---|---|---|---|
| 344 | 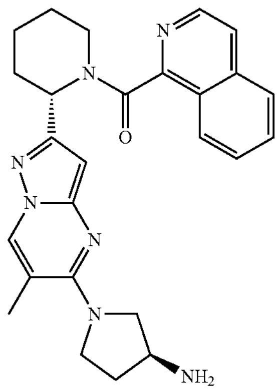 [SMILES: Cc1cn2nc([C@@H]3CCCCN3C(=O)c3nccc4ccccc34)cc2nc1N1CC[C@H](N)C1] | 455.566 | 456.4 |
| 345 | 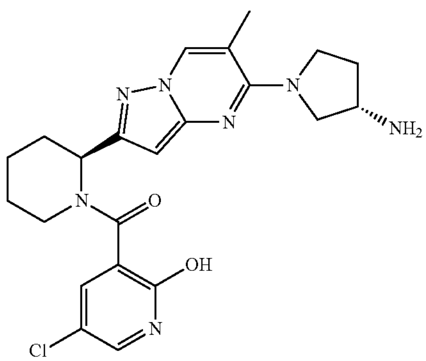 [SMILES: Cc1cn2nc([C@@H]3CCCCN3C(=O)c3cc(Cl)cnc3O)cc2nc1N1CC[C@H](N)C1] | 455.95 | 456.3 |
| 346 | 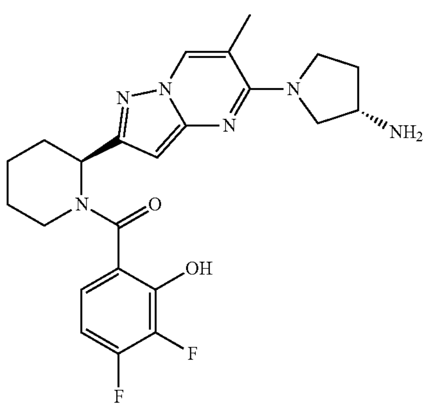 [SMILES: Cc1cn2nc([C@@H]3CCCCN3C(=O)c3ccc(F)c(F)c3O)cc2nc1N1CC[C@H](N)C1] | 456.497 | 457.3 |
| 347 | 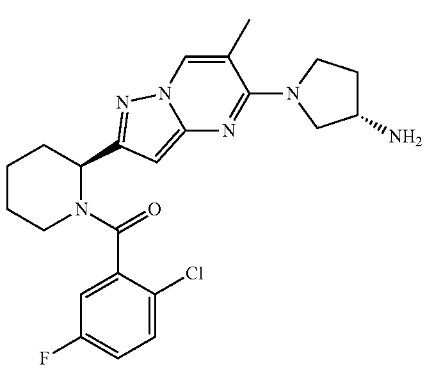 [SMILES: Cc1cn2nc([C@@H]3CCCCN3C(=O)c3cc(F)ccc3Cl)cc2nc1N1CC[C@H](N)C1] | 456.953 | 457.3 |

-continued
| Compound | Structure | MW calc | MW measured |
|---|---|---|---|
| 348 | 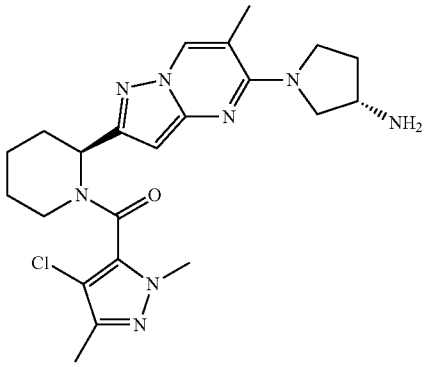 [SMILES: Cc1cn2nc([C@@H]3CCCCN3C(=O)c3c(Cl)c(C)nn3C)cc2nc1N1CC[C@H](N)C1] | 456.982 | 457.4 |
| 349 | 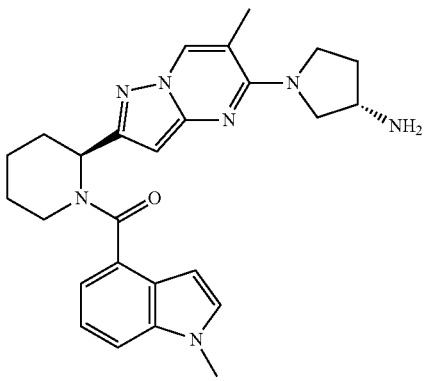 [SMILES: Cc1cn2nc([C@@H]3CCCCN3C(=O)c3cccc4c3ccn4C)cc2nc1N1CC[C@H](N)C1] | 457.582 | 458.4 |
| 350 | 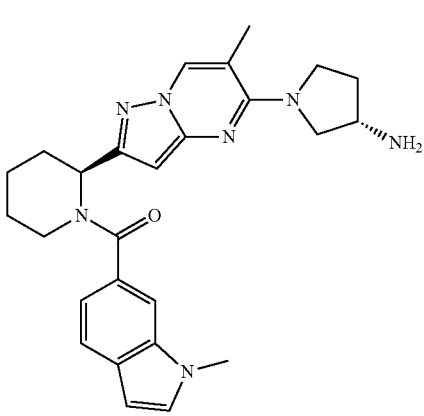 [SMILES: Cc1cn2nc([C@@H]3CCCCN3C(=O)c3ccc4ccn(C)c4c3)cc2nc1N1CC[C@H](N)C1] | 457.582 | 458.5 |
| 351 | 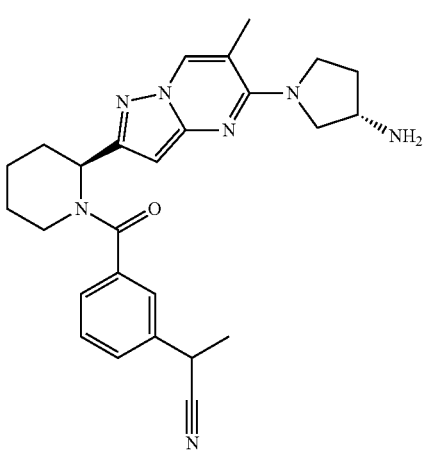 [SMILES: Cc1cn2nc([C@@H]3CCCCN3C(=O)c3cccc(C(C)C#N)c3)cc2nc1N1CC[C@H](N)C1] | 457.582 | 458.4 |

-continued
| Compound | Structure | MW calc | MW measured |
|---|---|---|---|
| 352 | 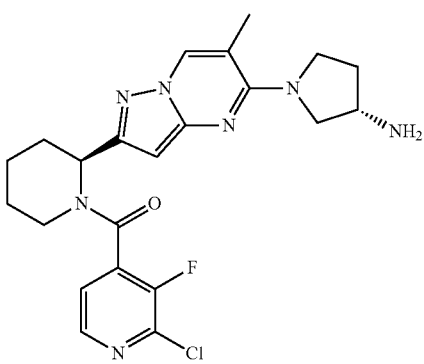 [SMILES: Cc1cn2nc([C@@H]3CCCCN3C(=O)c3ccnc(Cl)c3F)cc2nc1N1CC[C@H](N)C1] | 457.941 | 458.3 |
| 353 | 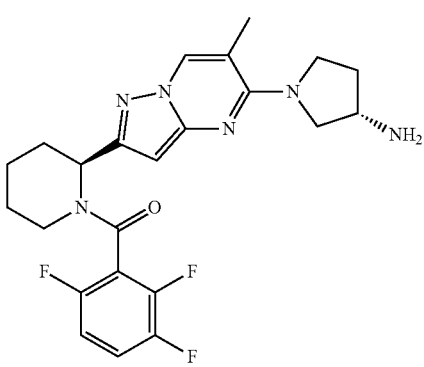 [SMILES: Cc1cn2nc([C@@H]3CCCCN3C(=O)c3c(F)ccc(F)c3F)cc2nc1N1CC[C@H](N)C1] | 458.488 | 459.4 |
| 354 | 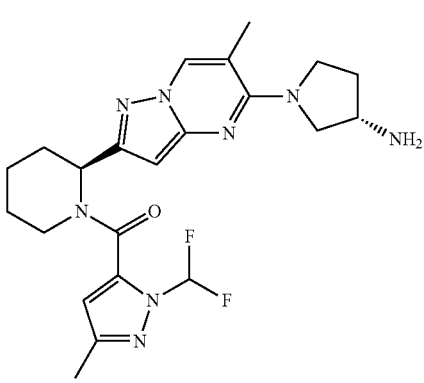 [SMILES: Cc1cc(C(=O)N2CCCC[C@H]2c2cc3nc(N4CC[C@H](N)C4)c(C)cn3n2)n(C(F)F)n1] | 458.517 | 459.4 |
| 355 | 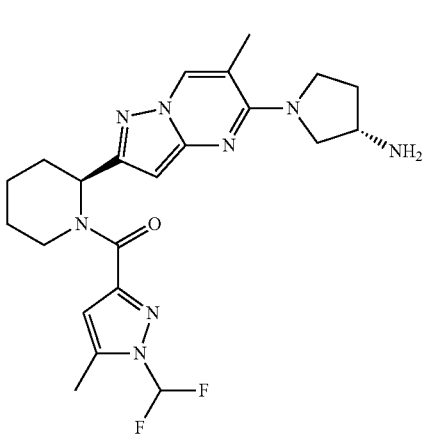 [SMILES: Cc1cn2nc([C@@H]3CCCCN3C(=O)c3cc(C)n(C(F)F)n3)cc2nc1N1CC[C@H](N)C1] | 458.517 | 459.4 |

-continued

| Compound | Structure | MW calc | MW measured |
|---|---|---|---|
| 356 | 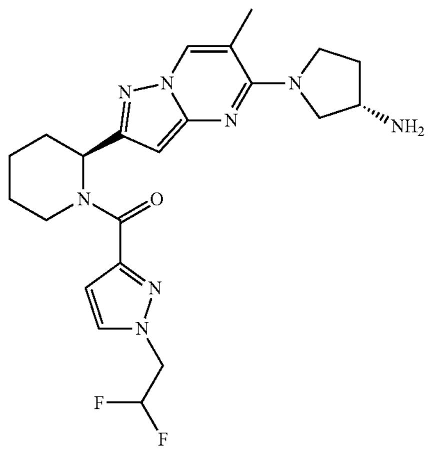 [SMILES: Cc1cn2nc([C@@H]3CCCCN3C(=O)c3ccn(CC(F)F)n3)cc2nc1N1CC[C@H](N)C1] | 458.517 | 459.4 |
| 357 | 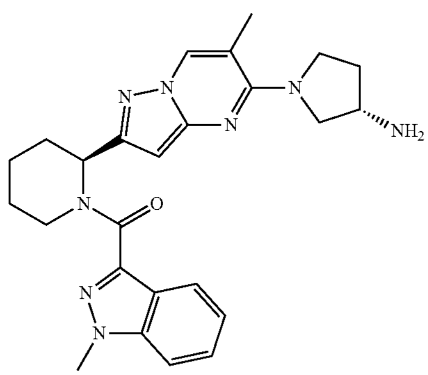 [SMILES: Cc1cn2nc([C@@H]3CCCCN3C(=O)c3nn(C)c4ccccc34)cc2nc1N1CC[C@H](N)C1] | 458.57 | 4594 |
| 358 | 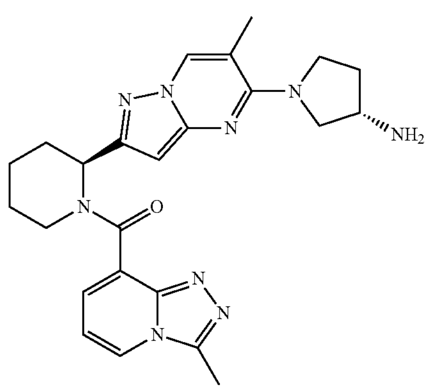 [SMILES: Cc1cn2nc([C@@H]3CCCCN3C(=O)c3cccn4c(C)nnc34)cc2nc1N1CC[C@H](N)C1] | 459.558 | 460.3 |

-continued
| Compound | Structure | MW calc | MW measured |
|---|---|---|---|
| 359 | 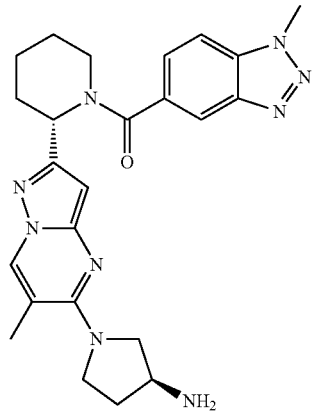 [SMILES: Cc1cn2nc([C@@H]3CCCCN3C(=O)c3ccc4c(c3)nnn4C)cc2nc1N1CC[C@H](N)C1] | 459.558 | 460.4 |
| 360 | 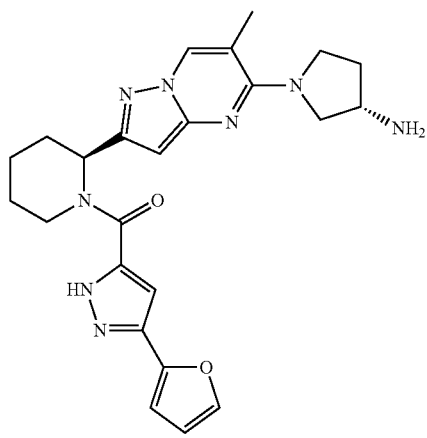 | 460.542 | 461.4 |
| 361 | 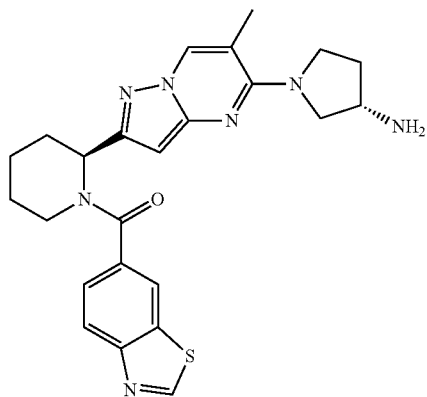 [SMILES: Cc1cn2nc([C@@H]3CCCCN3C(=O)c3ccc4ncsc4c3)cc2nc1N1CC[C@H](N)C1] | 461.592 | 462.3 |

-continued
| Compound | Structure | MW calc | MW measured |
|---|---|---|---|
| 362 | 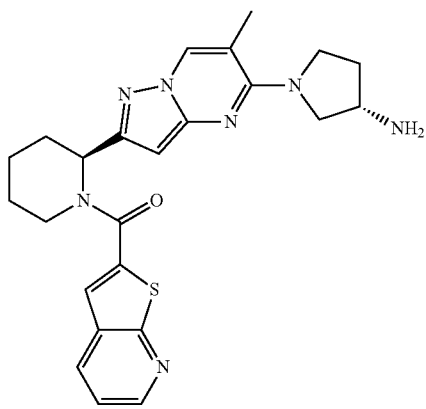 [SMILES: Cc1cn2nc([C@@H]3CCCCN3C(=O)c3cc4cccnc4s3)cc2nc1N1CC[C@H](N)C1] | 461.592 | 462.4 |
| 363 | 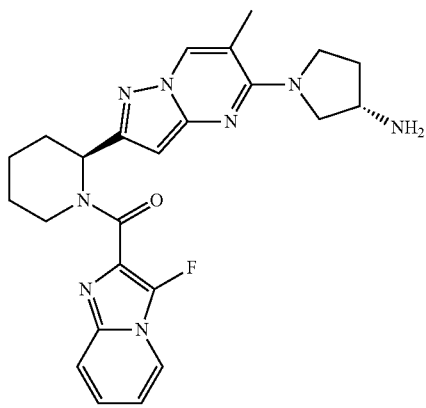 [SMILES: Cc1cn2nc([C@@H]3CCCCN3C(=O)c3nc4ccccn4c3F)cc2nc1N1CC[C@H](N)C1] | 462.533 | 463.4 |
| 364 | 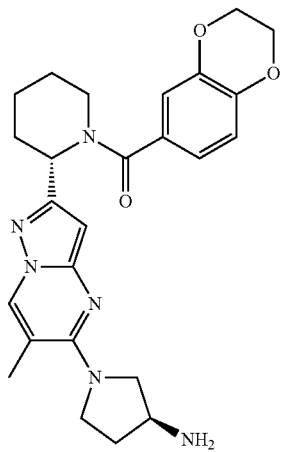 [SMILES: Cc1cn2nc([C@@H]3CCCCN3C(=O)c3ccc4c(c3)OCCO4)cc2nc1N1CC[C@H](N)C1] | 462.554 | 463.4 |

-continued
| Compound | Structure | MW calc | MW measured |
|---|---|---|---|
| 365 | 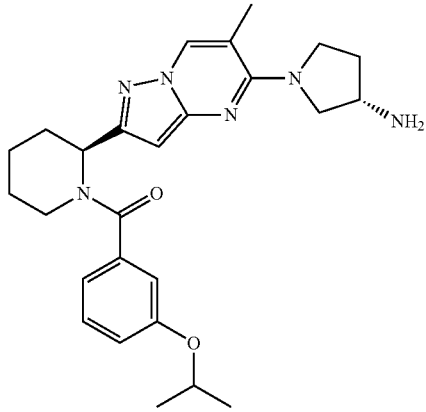 [SMILES: Cc1cn2nc([C@@H]3CCCCN3C(=O)c3cccc(OC(C)C)c3)cc2nc1N1CC[C@H](N)C1] | 462.598 | 463.4 |
| 366 | 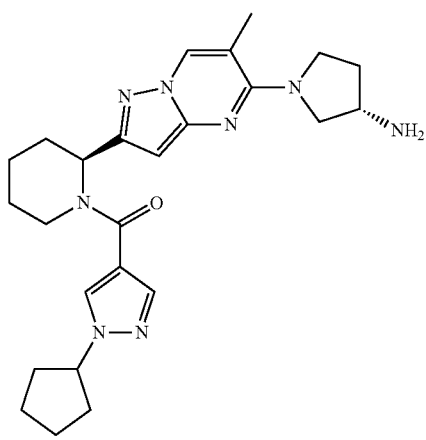 [SMILES: Cc1cn2nc([C@@H]3CCCCN3C(=O)c3cnn(C4CCCC4)c3)cc2nc1N1CC[C@H](N)C1] | 462.602 | 463.4 |
| 367 | 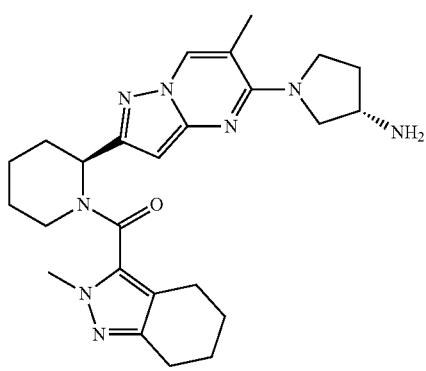 [SMILES: Cc1cn2nc([C@@H]3CCCCN3C(=O)c3c4c(nn3C)CCCC4)cc2nc1N1CC[C@H](N)C1] | 462.602 | 463.4 |

| Compound | Structure | MW calc | MW measured |
|---|---|---|---|
| 368 | 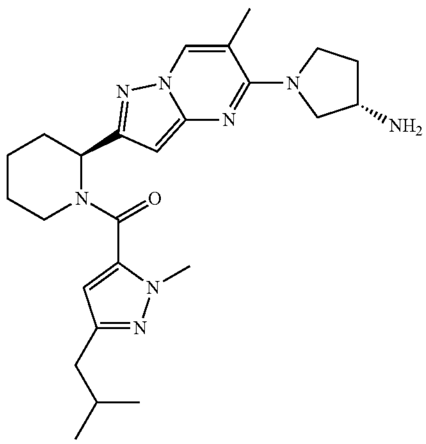 [SMILES: Cc1cn2nc([C@@H]3CCCCN3C(=O)c3cc(CC(C)C)nn3C)cc2nc1N1CC[C@H](N)C1] | 464.618 | 465.5 |
| 369 | 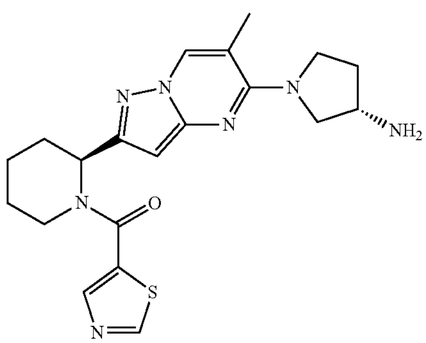 | 464.636 | 465.4 |
| 370 | 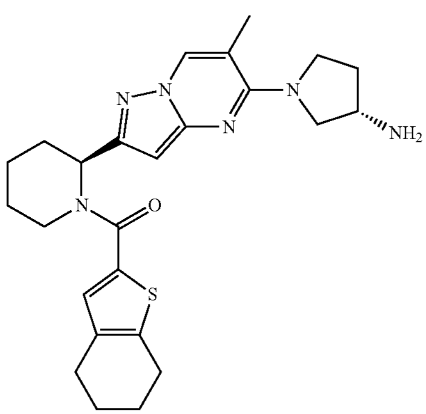 [SMILES: Cc1cn2nc([C@@H]3CCCCN3C(=O)c3cc4c(s3)CCCC4)cc2nc1N1CC[C@H](N)C1] | 464.636 | 465.4 |

-continued

| Compound | Structure | MW calc | MW measured |
|---|---|---|---|
| 371 | 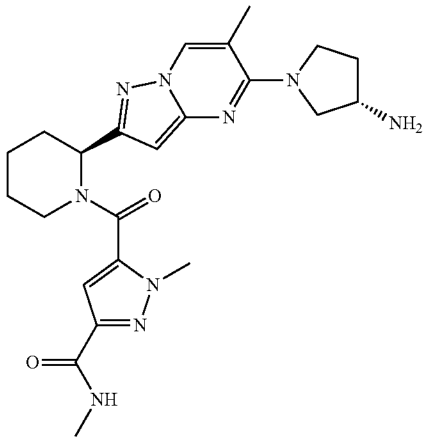 [SMILES: CNC(=O)c1cc(C(=O)N2CCCC[C@H]2c2cc3nc(N4CC[C@H](N)C4)c(C)cn3n2)n(C)n1] | 465.562 | 466.4 |
| 372 | 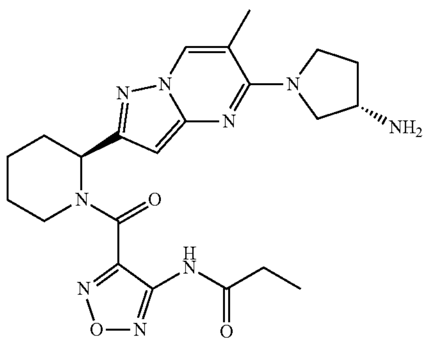 [SMILES: CCC(=O)Nc1nonc1C(=O)N1CCCC[C@H]1c1cc2nc(N3CC[C@H](N)C3)c(C)cn2n1] | 467.534 | 468.4 |
| 373 | 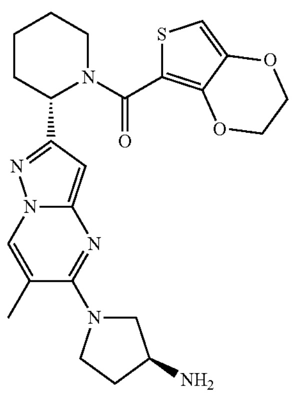 [SMILES: Cc1cn2nc([C@@H]3CCCCN3C(=O)c3scc4c3OCCO4)cc2nc1N1CC[C@H](N)C1] | 468.58 | 469.4 |
| 374 | 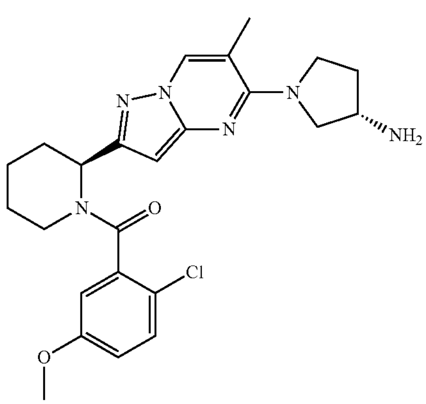 [SMILES: COc1ccc(Cl)c(C(=O)N2CCCC[C@H]2c2cc3nc(N4CC[C@H](N)C4)c(C)cn3n2)c1] | 468.989 | 469.4 |

-continued

| Compound | Structure | MW calc | MW measured |
|---|---|---|---|
| 375 | 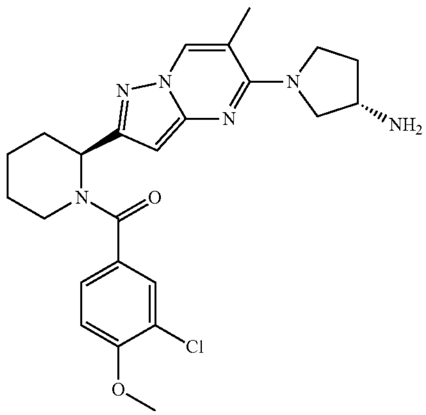 [SMILES: COc1ccc(C(=O)N2CCCC[C@H]2c2cc3nc(N4CC[C@H](N)C4)c(C)cn3n2)cc1Cl] | 468.989 | 469.4 |
| 376 | 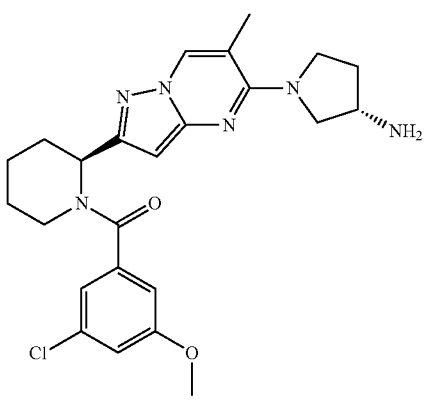 [SMILES: COc1cc(Cl)cc(C(=O)N2CCCC[C@H]2c2cc3nc(N4CC[C@H](N)C4)c(C)cn3n2)c1] | 468.989 | 469.4 |
| 377 | 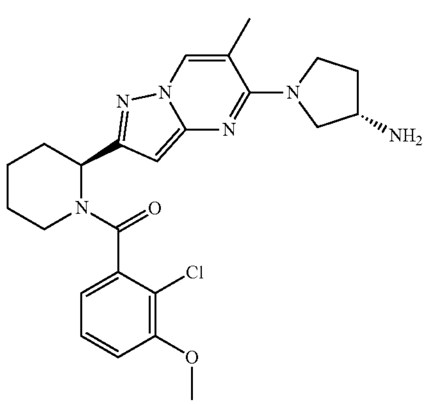 [SMILES: COc1cccc(C(=O)N2CCCC[C@H]2c2cc3nc(N4CC[C@H](N)C4)c(C)cn3n2)c1Cl] | 468.989 | 469.4 |

-continued
| Compound | Structure | MW calc | MW measured |
|---|---|---|---|
| 378 | 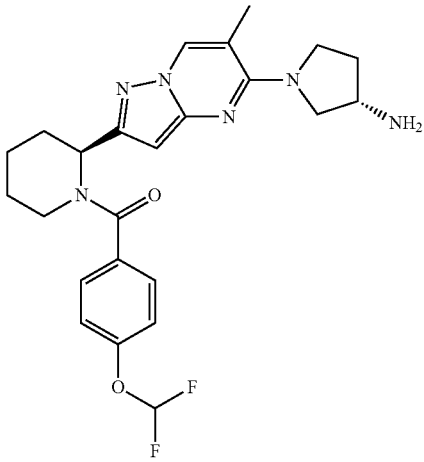 [SMILES: Cc1cn2nc([C@@H]3CCCCN3C(=O)c3ccc(OC(F)F)cc3)cc2nc1N1CC[C@H](N)C1] | 470.524 | 471.4 |
| 379 | 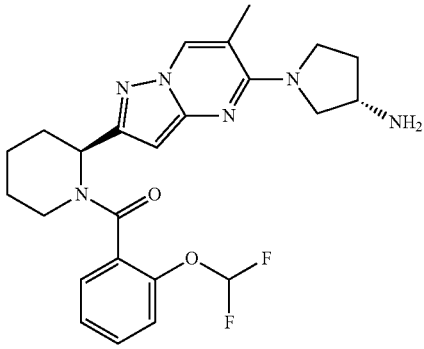 [SMILES: Cc1cn2nc([C@@H]3CCCCN3C(=O)c3ccccc3OC(F)F)cc2nc1N1CC[C@H](N)C1] | 470.524 | 471.4 |
| 380 | 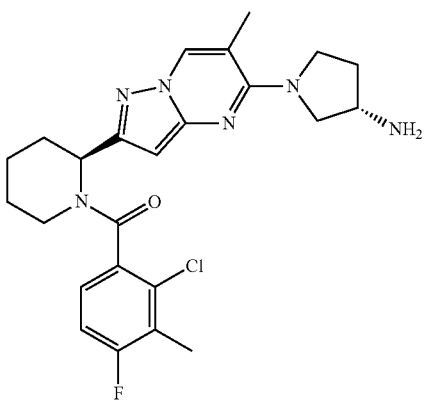 [SMILES: Cc1cn2nc([C@@H]3CCCCN3C(=O)c3ccc(F)c(C)c3Cl)cc2nc1N1CC[C@H](N)C1] | 470.98 | 471.4 |
| 381 | 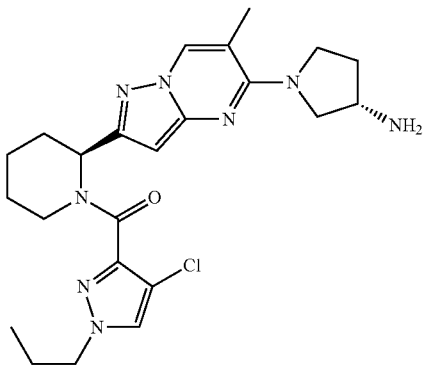 [SMILES: CCCn1cc(Cl)c(C(=O)N2CCCC[C@H]2c2cc3nc(N4CC[C@H](N)C4)c(C)cn3n2)n1] | 471.009 | 471.4 |

-continued
| Compound | Structure | MW calc | MW measured |
|---|---|---|---|
| 382 | 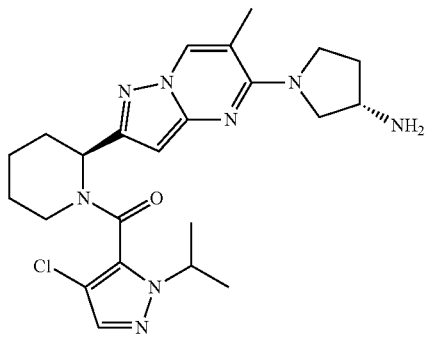 [SMILES: Cc1cn2nc([C@@H]3CCCCN3C(=O)c3c(Cl)cnn3C(C)C)cc2nc1N1CC[C@H](N)C1] | 471.009 | 471.4 |
| 383 | 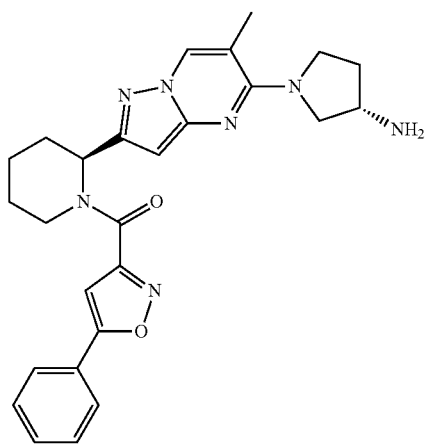 [SMILES: Cc1cn2nc([C@@H]3CCCCN3C(=O)c3cc(-c4ccccc4)on3)cc2nc1N1CC[C@H](N)C1] | 471.565 | 472.4 |
| 384 | 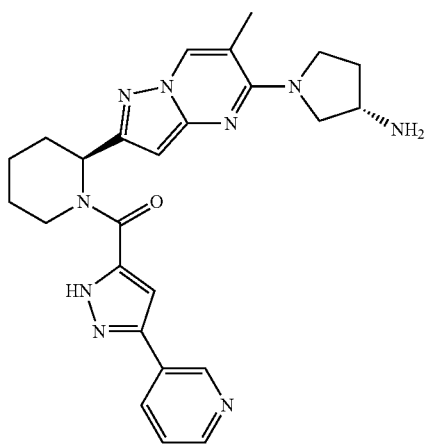 [SMILES: Cc1cn2nc([C@@H]3CCCCN3C(=O)c3cc(-c4cccnc4)n[nH]3)cc2nc1N1CC[C@H](N)C1] | 471.569 | 472.4 |

| Compound | Structure | MW calc | MW measured |
|---|---|---|---|
| 385 | 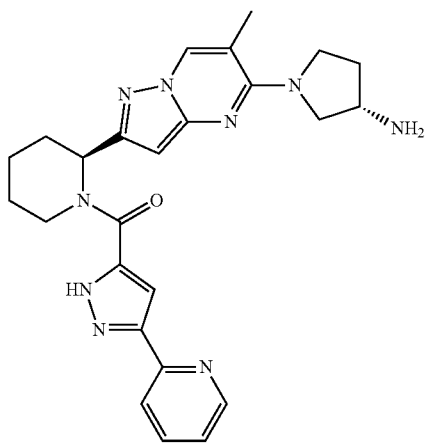 [SMILES: Cc1cn2nc([C@@H]3CCCCN3C(=O)c3cc(-c4ccccn4)n[nH]3)cc2nc1N1CC[C@H](N)C1] | 471.569 | 472.5 |
| 386 | 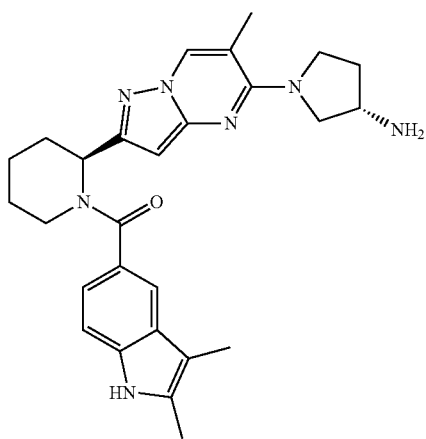 [SMILES: Cc1cn2nc([C@@H]3CCCCN3C(=O)c3ccc4[nH]c(C)c(C)c4c3)cc2nc1N1CC[C@H](N)C1] | 471.609 | 472.5 |
| 387 | 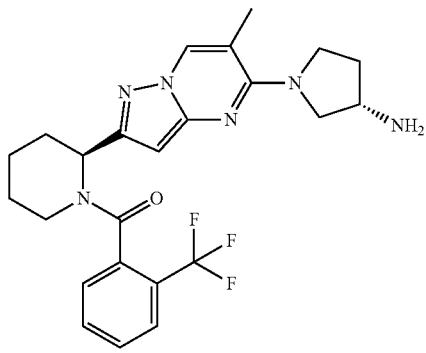 [SMILES: Cc1cn2nc([C@@H]3CCCCN3C(=O)c3ccccc3C(F)(F)F)cc2nc1N1CC[C@H](N)C1] | 472.515 | 473.4 |

-continued
| Compound | Structure | MW calc | MW measured |
|---|---|---|---|
| 388 | 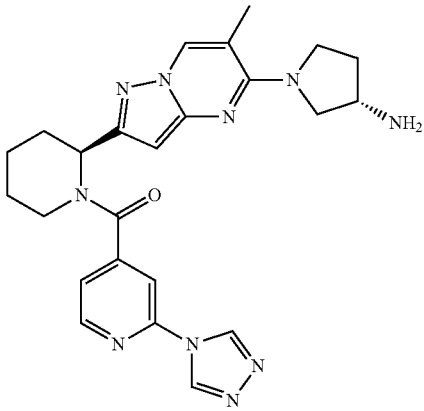 [SMILES: Cc1cn2nc([C@@H]3CCCCN3C(=O)c3ccnc(-n4cnnc4)c3)cc2nc1N1CC[C@H](N)C1] | 472.557 | 473.4 |
| 389 | 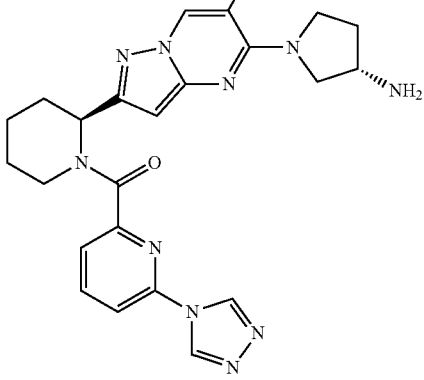 | 472.557 | 473.4 |
| 390 | 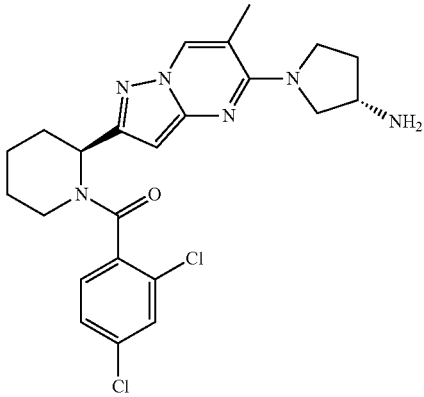 [SMILES: Cc1cn2nc([C@@H]3CCCCN3C(=O)c3ccc(Cl)cc3Cl)cc2nc1N1CC[C@H](N)C1] | 473.408 | 473.2 |
| 391 | 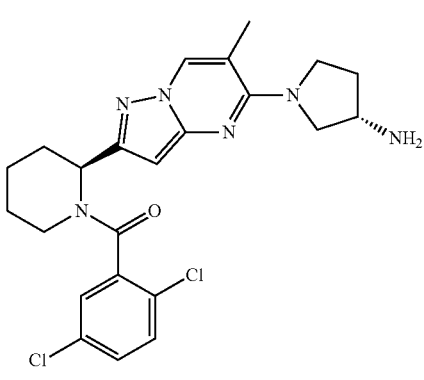 [SMILES: Cc1cn2nc([C@@H]3CCCCN3C(=O)c3cc(Cl)ccc3Cl)cc2nc1N1CC[C@H](N)C1] | 473.408 | 473.3 |

-continued
| Compound | Structure | MW calc | MW measured |
|---|---|---|---|
| 392 | 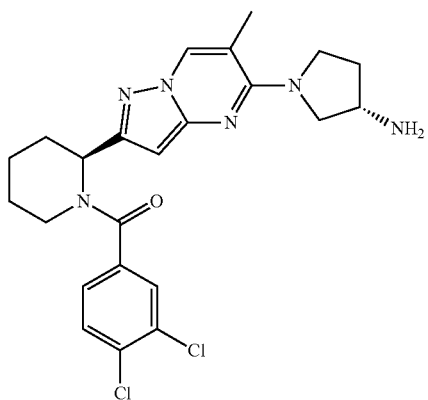 [SMILES: Cc1cn2nc([C@@H]3CCCCN3C(=O)c3ccc(Cl)c(Cl)c3)cc2nc1N1CC[C@H](N)C1] | 473.408 | 473.3 |
| 393 | 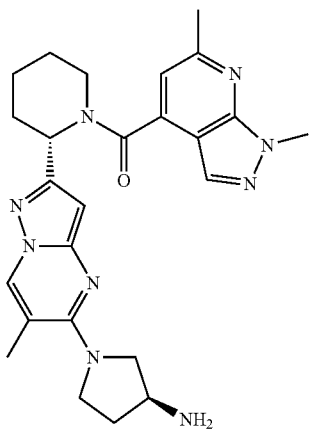 [SMILES: Cc1cc(C(=O)N2CCCC[C@H]2c2cc3nc(N4CC[C@H](N)C4)c(C)cn3n2)c2cnn(C)c2n1] | 473.585 | 474.4 |
| 394 | 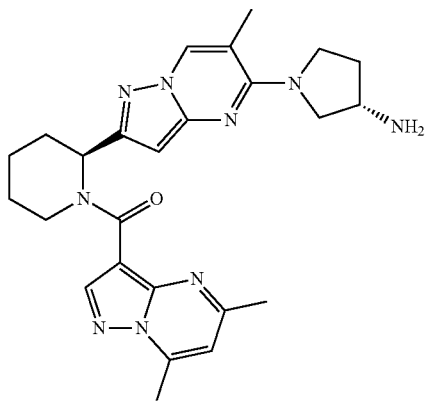 [SMILES: Cc1cc(C)n2ncc(C(=O)N3CCCC[C@H]3c3cc4nc(N5CC[C@H](N)C5)c(C)cn4n3)c2n1] | 473.585 | 474.4 |

-continued
| Compound | Structure | MW calc | MW measured |
|---|---|---|---|
| 395 | 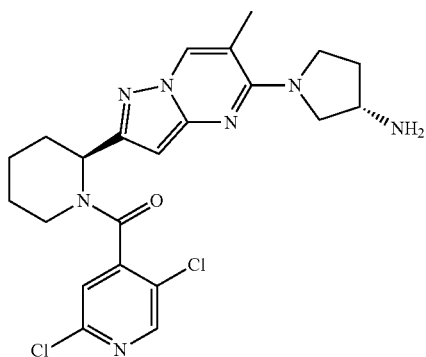 [SMILES: Cc1cn2nc([C@@H]3CCCCN3C(=O)c3cc(Cl)ncc3Cl)cc2nc1N1CC[C@H](N)C1] | 474.396 | 474.3 |
| 396 | 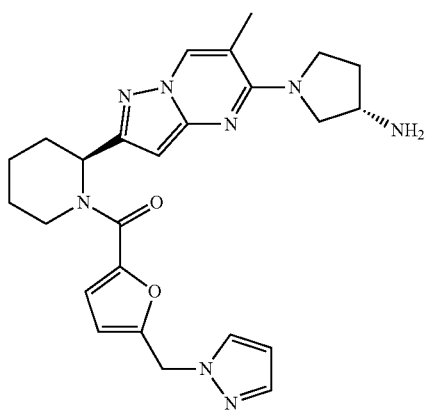 [SMILES: Cc1cn2nc([C@@H]3CCCCN3C(=O)c3ccc(Cn4cccn4)o3)cc2nc1N1CC[C@H](N)C1] | 474.569 | 475.4 |
| 397 | 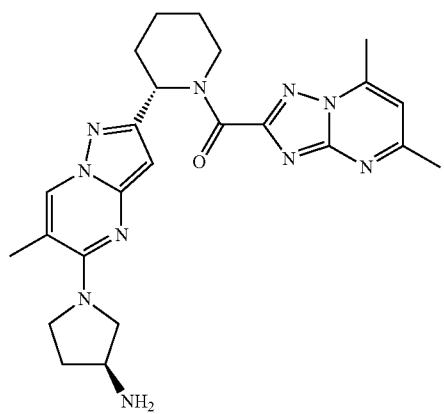 | 474.573 | 475.4 |

-continued

| Compound | Structure | MW calc | MW measured |
|---|---|---|---|
| 398 | 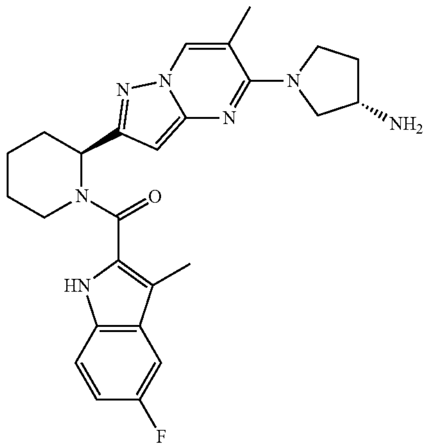 [SMILES: Cc1cn2nc([C@@H]3CCCCN3C(=O)c3[nH]c4ccc(F)cc4c3C)cc2nc1N1CC[C@H](N)C1] | 475.572 | 476.4 |
| 399 | 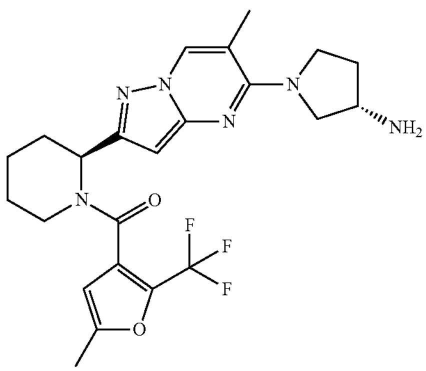 [SMILES: Cc1cc(C(=O)N2CCCC[C@H]2c2cc3nc(N4CC[C@H](N)C4)c(C)cn3n2)c(C(F)(F)F)o1] | 476.503 | 477.4 |
| 400 | 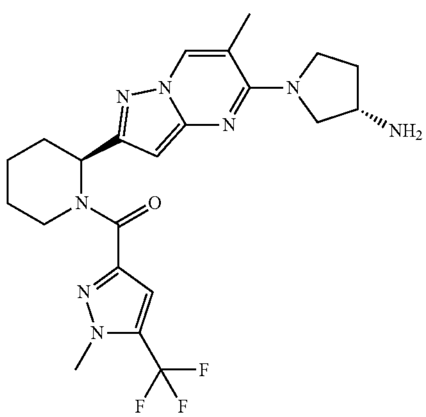 [SMILES: Cc1cn2nc([C@@H]3CCCCN3C(=O)c3cc(C(F)(F)F)n(C)n3)cc2nc1N1CC[C@H](N)C1] | 476.507 | 477.5 |
| 401 | 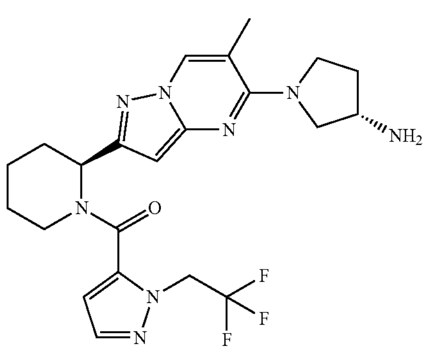 [SMILES: Cc1cn2nc([C@@H]3CCCCN3C(=O)c3ccnn3CC(F)(F)F)cc2nc1N1CC[C@H](N)C1] | 476.507 | 477.4 |

-continued
| Compound | Structure | MW calc | MW measured |
|---|---|---|---|
| 402 | 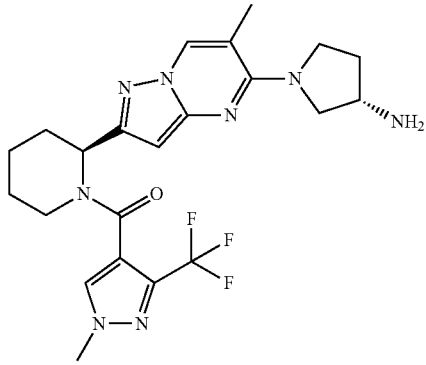 [SMILES: Cc1cn2nc([C@@H]3CCCCN3C(=O)c3cn(C)nc3C(F)(F)F)cc2nc1N1CC[C@H](N)C1] | 476.507 | 477.5 |
| 403 | 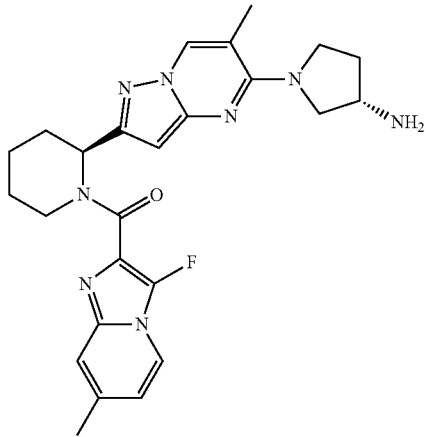 [SMILES: Cc1ccn2c(F)c(C(=O)N3CCCC[C@H]3c3cc4nc(N5CC[C@H](N)C5)c(C)cn4n3)nc2c1] | 476.56 | 477.4 |
| 404 | 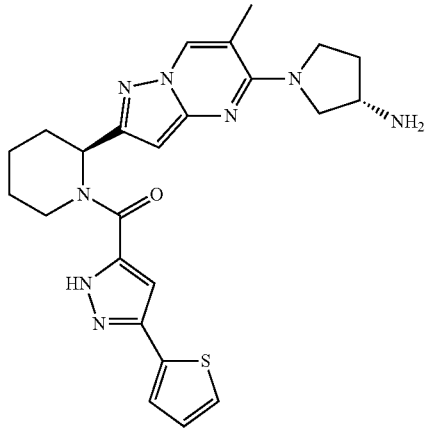 | 476.607 | 477.3 |

| Compound | Structure | MW calc | MW measured |
|---|---|---|---|
| 405 | 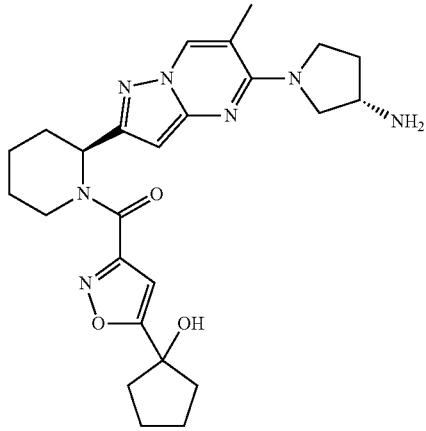 [SMILES: Cc1cn2nc([C@@H]3CCCCN3C(=O)c3cc(C4(O)CCCC4)on3)cc2nc1N1CC[C@H](N)C1] | 479.585 | 480.4 |
| 406 | 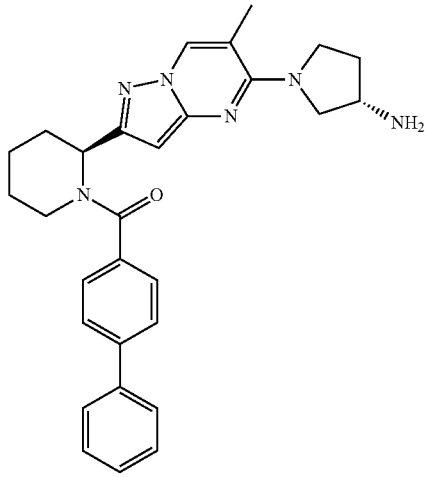 [SMILES: Cc1cn2nc([C@@H]3CCCCN3C(=O)c3ccc(-c4ccccc4)cc3)cc2nc1N1CC[C@H](N)C1] | 480.616 | 481.4 |
| 407 | 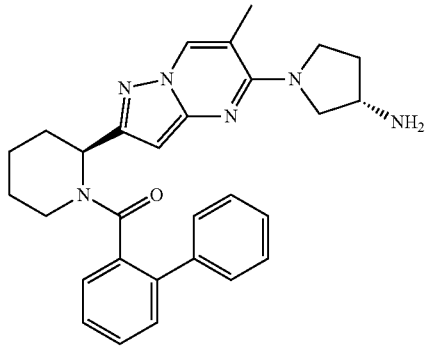 [SMILES: Cc1cn2nc([C@@H]3CCCCN3C(=O)c3ccccc3-c3ccccc3)cc2nc1N1CC[C@H](N)C1] | 480.616 | 481.5 |

-continued
| Compound | Structure | MW calc | MW measured |
|---|---|---|---|
| 408 | 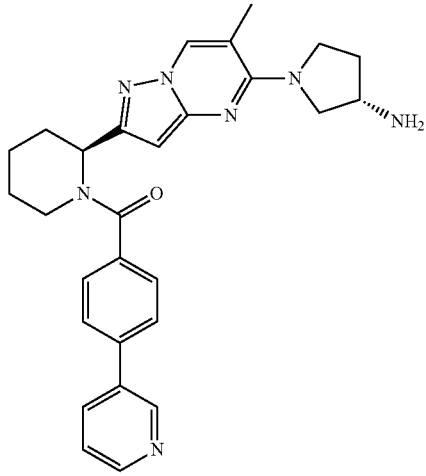 [SMILES: Cc1cn2nc([C@@H]3CCCCN3C(=O)c3ccc(-c4cccnc4)cc3)cc2nc1N1CC[C@H](N)C1] | 481.604 | 482.4 |
| 409 | 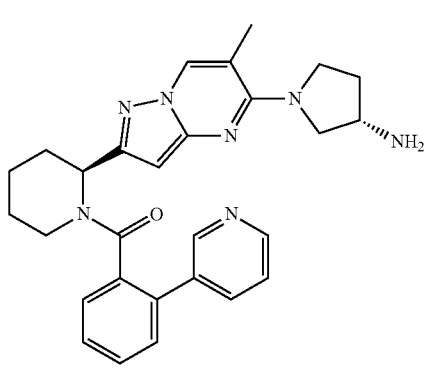 [SMILES: Cc1cn2nc([C@@H]3CCCCN3C(=O)c3ccccc3-c3cccnc3)cc2nc1N1CC[C@H](N)C1] | 481.604 | 482.4 |
| 410 | 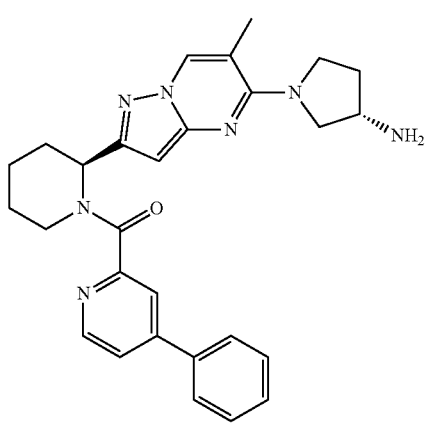 [SMILES: Cc1cn2nc([C@@H]3CCCCN3C(=O)c3cc(-c4ccccc4)ccn3)cc2nc1N1CC[C@H](N)C1] | 481.604 | 482.4 |

| Compound | Structure | MW calc | MW measured |
|---|---|---|---|
| 411 | 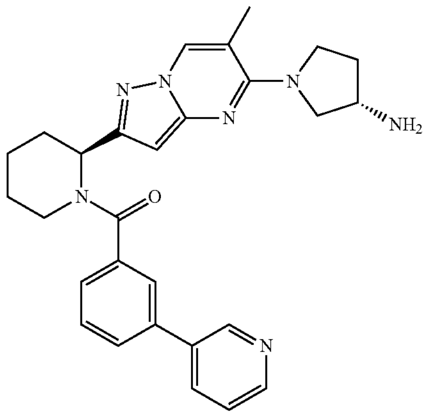 [SMILES: Cc1cn2nc([C@@H]3CCCCN3C(=O)c3cccc(-c4cccnc4)c3)cc2nc1N1CC[C@H](N)C1] | 481.604 | 482.4 |
| 412 | 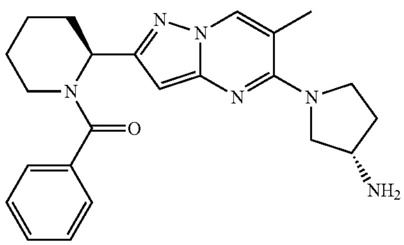 [SMILES: Cc1cn2nc([C@@H]3CCCCN3C(=O)c3ccccc3)cc2nc1N1CC[C@H](N)C1] | 404.5 | 405.4 |

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound of the invention after application of the composition can be observed by any method including direct and indirect methods of detecting such activity. Quantitative, qualitative, and semi-quantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Respiratory Syncytial Virus (RSV) Antiviral Activity and Cytotoxicity Assays

Anti-RSV Activity

Antiviral activity against RSV was determined using an in vitro cytoprotection assay in Hep2 cells. In this assay, compounds inhibiting the virus replication exhibit cytoprotective effect against the virus-induced cell killing were quantified using a cell viability reagent. The method used was similar to methods previously described in published literature (Chapman et al., *Antimicrob Agents Chemother.* 2007, 51(9):3346-53.)

Hep2 cells were obtained from ATCC (Manassas, VI) and maintained in MEM media supplemented with 10% fetal bovine serum and penicillin/streptomycin. Cells were passaged twice a week and kept at subconfluent stage. Commercial stock of RSV strain A2 (Advanced Biotechnologies, Columbia, Md.) was titered before compound testing to determine the appropriate dilution of the virus stock that generated desirable cytopathic effect in Hep2 cells.

For antiviral tests, Hep2 cells were seeded into 96-well plates 24 hours before the assay at a density of 3,000 cells/well. On a separate 96 well plate, compounds to be tested were serially diluted in cell culture media. Eight concentrations in 3-fold serial dilution increments were prepared for each tested compound and 100 uL/well of each dilution was transferred in duplicate onto plates with seeded Hep2 cells. Subsequently, appropriate dilution of virus stock previously determined by titration was prepared in cell culture media and 100 uL/well was added to test plates containing cells and serially diluted compounds. Each plate included three wells of infected untreated cells and three wells of uninfected cells that served as 0% and 100% virus inhibition control, respectively. Following the infection with RSV, testing plates were incubated for 4 days in a tissue culture incubator. After the incubation, RSV-induced cytopathic effect was determined using a Cell TiterGlo reagent (Promega, Madison, Wis.) followed by a luminescence read-out. The percentage inhibition was calculated for each tested concentration relative to the 0% and 100% inhibition controls and the EC50 value for each compound was determined by non-linear regression as a concentration inhibiting the RSV-induced cytopathic effect by 50%. Ribavirin (purchased from Sigma, St. Louis, Mo.) was used as a positive control for antiviral activity.

Compounds were also tested for antiviral activity against RSV in Hep2 cells using a 384 well format. Compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 μL of media (Mediatech Inc. MEM supplemented with Glutamine, 10% FBS and Pen/Strep). DMSO and a suitable positive control compound, such as 80 μM GS-329467 or 10 μM 427346 was used for the 100% and 0% cell killing controls, respectively.

Hep2 cells ($1.0 \times 10^5$ cells/ml) were prepared as above in batch to at least 40 mls excess of the number of sample plates (8 mls cell mix per plate) and infected with vendor supplied (ABI) RSV strain A2 to arrive at an MOI of 1:1000 (virus:cell #) or 1:3000 (vol virus: cell vol). Immediately after addition of virus, the RSV infected Hep2 cell suspension was added to each stamped 384-well plate at 20 μl per well using a uFlow dispenser, giving a final volume of 40 μL/well, each with 2000 infected cells. The plates were then incubated for 5 days at 37° C. and 5% $CO_2$. Following incubation, the plates were equilibrated to room temperature in a biosafety cabinet hood for 1.5 hrs and 40 μL of Cell-Titer Glo viability reagent (Promega) was added to each well via uFlow. Following al 0-20 minute incubation, the plates were read using an EnVision or Victor Luminescence plate reader (Perkin-Elmer). The data was then uploaded and analyzed on the Bioinformatics portal under the RSV Cell Infectivity and 8-plate EC50-Hep2-384 or 8-plate EC50-Hep2-Envision protocols.

Multiple point data generated in the assay was analysed using Pipeline Pilot (Accelrys, Inc., Version 7.0) to generate a dose response curve based on least squares fit to a 4-parameter curve. The generated formula for the curve was then used to calculate the % inhibition at a given concentration. The % inhibition reported in the table was then adjusted based on the normalization of the bottom and top of the curve % inhibition values to 0% and 100% respectively.

Representative activity for the compounds of Formula I-IX against RSV-induced cytopathic effects are shown in the Table below wherein A=$EC_{50}$ of 0.1-100 nM, B=$EC_{50}$ of 101-1000 nM, and C=$EC_{50}$ of 1001-10,000 nM.

| Compound # | % inh @ 1 uM | % inh @ 0.5 uM | EC50/nM |
|---|---|---|---|
| 1 | 34 | 70 | B |
| 2 | 46 | 36 | B |
| 3 | 70 | 40 | B |
| 4 | 99 | 66 | B |
| 5 | 79 | 66 | B |
| 6 | 99 | 96 | A |
| 7 | 98 | 93 | A |
| 8 | 94 | 81 | B |
| 9 | 63 | 49 | B |
| 10 | 99 | 94 | A |
| 11 | 99 | 98 | A |
| 12 | 90 | 64 | B |
| 13 | 97 | 91 | A |
| 14 | 98 | 96 | A |
| 15 | 42 | 30 | B |

-continued

| Compound # | % inh @ 1 uM | % inh @ 0.5 uM | EC50/nM |
|---|---|---|---|
| 16 | 97 | 89 | A |
| 17 | 97 | 75 | B |
| 18 | 89 | 94 | B |
| 19 | 84 | 67 | B |
| 20 | 53 | 7 | C |
| 21 | 10 | 4 | C |
| 22 | 99 | 95 | A |
| 23 | 100 | 94 | A |
| 24 | 25 | 11 | C |
| 25 | 96 | 92 | A |
| 26 | 99 | 95 | A |
| 27 | 63 | 35 | B |
| 28 | 95 | 73 | B |
| 29 | 100 | 100 | A |
| 30 |  | 99 | B |
| 31 | 99 | 65 | A |
| 32 |  | 99 | A |
| 33 |  | 98 | A |
| 34 |  | 91 | A |
| 35 |  | 96 | A |
| 36 |  | 90 | A |
| 37 |  | 100 | A |
| 38 |  | 3 | >10000 |
| 39 |  | 100 | A |
| 40 |  | 100 | A |
| 41 |  | 95 | A |
| 42 |  | 100 | A |
| 43 |  | 100 | A |
| 44 |  | 100 | A |
| 45 |  | 100 | A |
| 46 |  | 100 | A |
| 47 |  | 100 | A |
| 48 |  | 99 | A |
| 49 |  | 98 | A |
| 50 |  | 100 | A |
| 51 |  | 98 | A |
| 52 |  | 100 | A |
| 53 |  | 98 | A |
| 54 |  | 100 | A |
| 55 |  | 100 | A |
| 56 |  | 100 | A |
| 57 |  | 100 | A |
| 58 |  | 99 | A |
| 59 |  | 100 | A |
| 60 |  | 100 | A |
| 61 |  | 100 | A |
| 62 |  | 100 | A |
| 63 |  | 98 | A |
| 64 |  | 98 | A |
| 65 |  | 100 | A |
| 66 |  | 99 | A |
| 67 |  | 100 | A |
| 68 |  | 100 | A |
| 69 |  | 100 | A |
| 70 |  | 99 | A |
| 71 |  | 95 | A |
| 72 |  | 98 | A |
| 73 |  | 99 | A |
| 74 |  | 100 | A |
| 75 |  | 100 | A |
| 76 |  | 100 | A |
| 77 |  | 100 | A |
| 78 |  | 98 | A |
| 79 |  | 100 | A |
| 80 |  | 100 | A |
| 81 |  | 100 | A |
| 82 |  | 100 | A |
| 83 |  | 98 | A |
| 84 |  | 100 | A |
| 85 |  | 100 | A |
| 86 |  | 99 | A |
| 87 |  | 84 | B |
| 88 |  | 98 | A |
| 89 |  | 100 | A |
| 90 |  | 99 | A |
| 91 |  | 100 | A |
| 92 |  | 100 | A |

| Compound # | % inh @ 1 uM | % inh @ 0.5 uM | EC50/nM |
|---|---|---|---|
| 93 | | 100 | A |
| 94 | | 100 | A |
| 95 | | 100 | A |
| 96 | | 97 | A |
| 97 | | 100 | A |
| 98 | | 98 | A |
| 99 | | 99 | A |
| 100 | | 96 | A |
| 101 | | 100 | A |
| 102 | | 98 | A |
| 103 | | 98 | A |
| 104 | | 100 | A |
| 105 | | 100 | A |
| 106 | | 100 | A |
| 107 | | 100 | A |
| 108 | | 100 | A |
| 109 | | 100 | A |
| 110 | | 100 | A |
| 111 | | 95 | A |
| 112 | | 97 | A |
| 113 | | 100 | A |
| 114 | | 100 | A |
| 115 | | 100 | A |
| 116 | | 98 | A |
| 117 | | 99 | A |
| 118 | | 99 | A |
| 119 | | 98 | A |
| 120 | | 100 | A |
| 121 | | 97 | A |
| 122 | | 99 | A |
| 123 | | 99 | A |
| 124 | | 100 | A |
| 125 | | 100 | A |
| 126 | | 100 | A |
| 127 | | 99 | A |
| 128 | | 98 | A |
| 129 | | 100 | A |
| 130 | | 100 | A |
| 131 | | 100 | A |
| 132 | | 97 | A |
| 133 | | 96 | A |
| 134 | | 98 | A |
| 135 | | 100 | A |
| 136 | | 100 | A |
| 137 | | 100 | A |
| 138 | | 100 | A |
| 139 | | 99 | A |
| 140 | | 100 | A |
| 141 | | 95 | A |
| 142 | | 100 | A |
| 143 | | 100 | A |
| 144 | | 99 | A |
| 145 | | 99 | A |
| 146 | | 99 | A |
| 147 | | 98 | A |
| 148 | | 100 | A |
| 149 | | 98 | A |
| 150 | | 97 | A |
| 151 | | 99 | A |
| 152 | | 100 | A |
| 153 | | 100 | A |
| 154 | | 100 | A |
| 155 | | 100 | A |
| 156 | | 100 | A |
| 157 | | 100 | A |
| 158 | | 100 | A |
| 159 | | 100 | A |
| 160 | | 100 | A |
| 161 | | 100 | A |
| 162 | | 100 | A |
| 163 | | 100 | A |
| 164 | | 100 | A |
| 165 | | 100 | A |
| 166 | | 100 | A |
| 167 | | 100 | A |
| 168 | | 100 | A |
| 169 | | 100 | A |
| 170 | | 100 | A |
| 171 | | 100 | A |
| 172 | | 100 | A |
| 173 | | 100 | A |
| 174 | | 100 | A |
| 175 | | 100 | A |
| 176 | | 100 | A |
| 177 | | 99 | A |
| 178 | | 100 | A |
| 179 | | 100 | A |
| 180 | | 100 | A |
| 181 | | 100 | A |
| 182 | | 87 | A |
| 183 | | 100 | A |
| 184 | | 100 | A |
| 185 | | 100 | A |
| 186 | | 100 | A |
| 187 | | 100 | A |
| 188 | | 100 | A |
| 189 | | 100 | A |
| 190 | | 100 | A |
| 191 | | 100 | A |
| 192 | | 100 | A |
| 193 | | 100 | A |
| 194 | | 100 | A |
| 195 | | 100 | A |
| 196 | | 100 | A |
| 197 | | 100 | A |
| 198 | | 95 | A |
| 199 | | 89 | A |
| 200 | | 95 | A |
| 201 | | 64 | B |
| 202 | | 100 | A |
| 203 | | 86 | B |
| 204 | | 98 | A |
| 205 | | 91 | A |
| 206 | | 99 | A |
| 207 | | 96 | A |
| 208 | | 95 | A |
| 209 | | 88 | B |
| 210 | | 81 | B |
| 211 | | 100 | A |
| 212 | | 88 | B |
| 213 | | 99 | A |
| 214 | | 100 | A |
| 215 | | 99 | A |
| 216 | | 100 | A |
| 217 | | 89 | B |
| 218 | | 72 | B |
| 219 | | 100 | A |
| 220 | | 100 | A |
| 221 | | 100 | A |
| 222 | | 100 | A |
| 223 | | 100 | A |
| 224 | | 100 | A |
| 225 | | 100 | A |
| 226 | | 100 | A |
| 227 | | 100 | A |
| 228 | | 100 | A |
| 229 | | 100 | A |
| 230 | | 100 | A |
| 231 | | 98 | A |
| 232 | | 100 | A |
| 233 | | 100 | A |
| 234 | | 100 | A |
| 235 | | 99 | A |
| 236 | | 98 | A |
| 237 | | 99 | A |
| 238 | | 100 | B |
| 239 | | 36 | B |
| 240 | | 71 | B |
| 241 | | 99 | A |
| 242 | | 72 | B |
| 243 | | 95 | B |
| 244 | | 88 | A |
| 245 | | 92 | A |
| 246 | | 98 | A |

| Compound # | % inh @ 1 uM | % inh @ 0.5 uM | EC50/nM |
|---|---|---|---|
| 247 | | 94 | A |
| 248 | | 100 | A |
| 249 | | 86 | A |
| 250 | | 90 | A |
| 251 | | 73 | B |
| 252 | | 92 | A |
| 253 | | 88 | A |
| 254 | | 90 | A |
| 255 | | 96 | A |
| 256 | | 87 | A |
| 257 | | 93 | A |
| 258 | | 100.0 | A |
| 259 | | 28.0 | C |
| 260 | | 99.0 | A |
| 261 | | 81.0 | B |
| 262 | | 100.0 | A |
| 263 | | 99.0 | A |
| 264 | | 53.0 | B |
| 265 | | 100.0 | A |
| 266 | | 100.0 | A |
| 267 | | 99.0 | A |
| 268 | | 76.0 | B |
| 269 | | 90.0 | A |
| 270 | | 82.0 | B |
| 271 | | 97.0 | A |
| 272 | | 100.0 | A |
| 273 | | 100.0 | A |
| 274 | | 100.0 | A |
| 275 | | 100.0 | A |
| 276 | | 90.0 | B |
| 277 | | 98.0 | A |
| 278 | | 99.0 | A |
| 279 | | 63.0 | B |
| 280 | | 60.0 | B |
| 281 | | 37.0 | B |
| 282 | | 100.0 | A |
| 283 | | 99.8 | A |
| 284 | | 97.8 | A |
| 285 | | 100.0 | A |
| 286 | | 100.0 | A |
| 287 | | n.d. | C |
| 288 | | 100.0 | A |
| 289 | | 100.0 | A |
| 290 | | 993.0 | A |
| 291 | | 88.0 | A |
| 292 | | 59.0 | B |
| 293 | | 64.0 | B |
| 294 | | 14.0 | C |
| 295 | | 97.0 | A |
| 296 | | 49.0 | B |
| 297 | | 95.0 | A |
| 298 | | 21.0 | B |
| 299 | | n.d. | n.d. |
| 300 | | 99.0 | A |
| 301 | | 100.0 | A |
| 302 | | 100.0 | A |
| 303 | | 100.0 | A |
| 304 | | 100.0 | A |
| 305 | | 100.0 | A |
| 306 | | 100.0 | A |
| 307 | | 100.0 | A |
| 308 | | 100.0 | A |
| 309 | | 100.0 | A |
| 310 | | 100.0 | A |
| 311 | | 100.0 | A |
| 312 | | 100.0 | A |
| 313 | | 100.0 | A |
| 314 | | 100.0 | A |
| 315 | | 100.0 | A |
| 316 | | 100.0 | A |
| 317 | | 100.0 | A |
| 318 | | 100.0 | A |
| 319 | | 100.0 | A |
| 320 | | 100.0 | A |
| 321 | | 100.0 | A |
| 322 | | 100.0 | A |
| 323 | | 100.0 | A |
| 324 | | n.d. | n.d. |
| 325 | | 98.0 | A |
| 326 | | 100.0 | A |
| 327 | | 100.0 | A |
| 328 | | 99.0 | A |
| 329 | | 98.0 | A |
| 330 | | 68.0 | B |
| 331 | | 99.0 | A |
| 332 | | 100.0 | A |
| 333 | | 99.0 | A |
| 334 | | 100.0 | A |
| 335 | | 99.0 | A |
| 336 | | 78.0 | B |
| 337 | | n.d. | n.d. |
| 338 | | 72.0 | B |
| 339 | | 99.0 | A |
| 340 | | 100.0 | A |
| 341 | | 75.0 | A |
| 342 | | 79.0 | B |
| 343 | | 60.0 | B |
| 344 | | 100.0 | A |
| 345 | | 100.0 | A |
| 346 | | 100.0 | A |
| 347 | | 100.0 | A |
| 348 | | 99.0 | A |
| 349 | | 100.0 | A |
| 350 | | 83.6 | B |
| 351 | | 100.0 | A |
| 352 | | 100.0 | A |
| 353 | | 100.0 | A |
| 354 | | 87.0 | B |
| 355 | | 96.0 | A |
| 356 | | 100.0 | A |
| 357 | | 82.0 | B |
| 358 | | 100.0 | A |
| 359 | | 100.0 | A |
| 360 | | 66.0 | B |
| 361 | | 88.0 | A |
| 362 | | 100.0 | A |
| 363 | | 99.0 | A |
| 364 | | 99.0 | A |
| 365 | | 100.0 | A |
| 366 | | 100.0 | A |
| 367 | | 94.0 | A |
| 368 | | 58.0 | B |
| 369 | | 91.0 | A |
| 370 | | 99.0 | A |
| 371 | | 100.0 | A |
| 372 | | 38.0 | B |
| 373 | | 99.0 | A |
| 374 | | 100.0 | A |
| 375 | | 99.0 | A |
| 376 | | 100.0 | A |
| 377 | | 99.0 | A |
| 378 | | 48.0 | B |
| 379 | | 100.0 | A |
| 380 | | 80.0 | B |
| 381 | | 100.0 | A |
| 382 | | 99.0 | A |
| 383 | | 99.0 | A |
| 384 | | 48.0 | B |
| 385 | | n.d. | n.d. |
| 386 | | 97.0 | A |
| 387 | | 77.0 | B |
| 388 | | 100.0 | A |
| 389 | | 98.0 | A |
| 390 | | 86.0 | B |
| 391 | | 99.0 | A |
| 392 | | 95.0 | A |
| 393 | | 99.0 | A |
| 394 | | 100.0 | A |
| 395 | | 100.0 | A |
| 396 | | 99.0 | A |
| 397 | | 3.0 | C |
| 398 | | 99.0 | A |
| 399 | | 100.0 | A |
| 400 | | 100.0 | A |

| Compound # | % inh @ 1 uM | % inh @ 0.5 uM | EC50/nM |
|---|---|---|---|
| 401 | | 100.0 | A |
| 402 | | 99.0 | A |
| 403 | | 100.0 | A |
| 404 | | 100.0 | A |
| 405 | | 99.0 | A |
| 406 | | 98.0 | A |
| 407 | | 92.0 | A |
| 408 | | 59.0 | B |
| 409 | | 99.0 | A |
| 410 | | n.d. | C |
| 411 | | 95.0 | B |
| 412 | | 100.0 | A |

(n.d. not determined)

Cytotoxicity

Cytotoxicity of tested compounds was determined in uninfected Hep2 cells in parallel with the antiviral activity using the cell viability reagent in a similar fashion as described before for other cell types (Cihlar et al., *Antimicrob Agents Chemother.* 2008, 52(2):655-65.). The same protocol as for the determination of antiviral activity was used for the measurement of compound cytotoxicity except that the cells were not infected with RSV. Instead, fresh cell culture media (100 uL/well) without the virus was added to tested plates with cells and prediluted compounds. Cells were then incubated for 4 days followed by a cell viability test using CellTiter Glo reagent and a luminescence readout. Untreated cell and cells treated with 50 ug/mL puromycin (Sigma, St. Louis, Mo.) were used as 100% and 0% cell viability control, respectively. The percent of cell viability was calculated for each tested compound concentration relative to the 0% and 100% controls and the CC50 value was determined by non-linear regression as a compound concentration reducing the cell viability by 50%.

To test for compound cytotoxicity in Hep2 cells using a 384 well format, compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 μL of media (Mediatech Inc. MEM supplemented with Glutamine, 10% FBS and Pen/Strep). 50 μg/mL puromycin and DMSO were used for the 100% and 0% cytotoxicity controls, respectively.

Hep2 cells ($1.0 \times 10^5$ cells/ml) were added to each stamped plate at 20 ul per well to give a total of 2000 cells/well and a final volume of 40 μL/well. Usually, the cells were batch prediluted to $1.0 \times 10^5$ cells/mL in excess of the number of sample plates and added at 20 ul per well into each assay plate using a uFlow dispenser. The plates were then incubated for 4 days at 37° C. and 5% $CO_2$. Following incubation, the plates were equilibrated to room temperature in a biosafety cabinet hood for 1.5 hrs and 40 μL of Cell-Titer Glo viability reagent (Promega) was added to each well via uFlow. Following a 10-20 minute incubation, the plates were read using an EnVision or Victor Luminescence plate reader (Perkin-Elmer). The data was then uploaded and analyzed on the Bioinformatics portal (Pipeline Pilot) under the Cytotoxicity assay using the 8-plate CC50-Hep2 or 8-plate CC50-Hep2 Envision protocols.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A compound of formula:

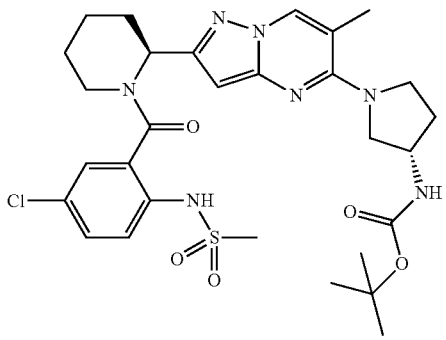 [SMILES: Cc1cn2nc([C@@H]3CCCCN3C(=O)c3cc(Cl)ccc3NS(C)(=O)=O)cc2nc1N1CC[C@H](NC(=O)OC(C)(C)C)C1]

or a pharmaceutically acceptable salt thereof.

2. A process of making the compound of claim 1 or a pharmaceutically acceptable salt thereof, comprising reacting a compound of formula:

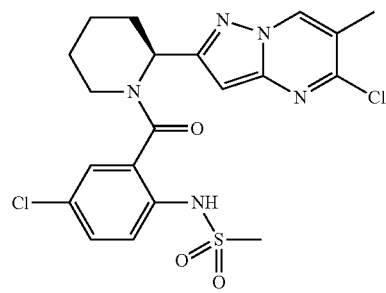 [SMILES: Cc1cn2nc([C@@H]3CCCCN3C(=O)c3cc(Cl)ccc3NS(C)(=O)=O)cc2nc1Cl]

with a compound of formula:

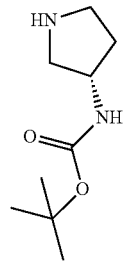

to form the compound of claim 1 or a pharmaceutically acceptable salt thereof.

3. The process of claim 2, wherein the reacting step is performed in a solvent comprising triethylamine and methanol.

4. The process of claim 2, comprising heating the reaction to about 75° C.

5. The process of claim 2, wherein the pharmaceutically acceptable salt is trifluoroacetic acid salt.

6. A process of making a compound of formula:

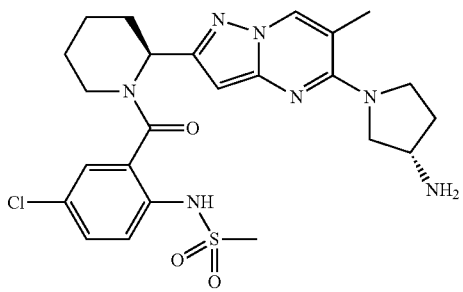 [SMILES: Cc1cn2nc([C@@H]3CCCCN3C(=O)c3cc(Cl)ccc3NS(C)(=O)=O)cc2nc1N1CC[C@H](N)C1]

or a pharmaceutically acceptable salt thereof, comprising contacting the compound of claim 1 with an acid to form the compound of formula:

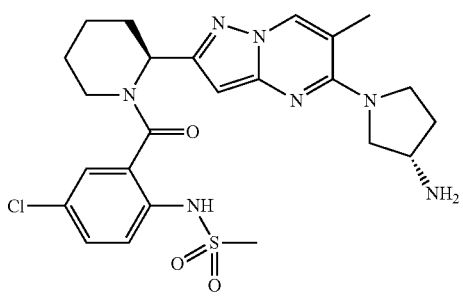 [SMILES: Cc1cn2nc([C@@H]3CCCCN3C(=O)c3cc(Cl)ccc3NS(C)(=O)=O)cc2nc1N1CC[C@H](N)C1]

or a pharmaceutically acceptable salt thereof.

7. The process of claim 6 wherein the pharmaceutically acceptable salt is trifluoroacetic acid salt.

8. The process of claim 6 wherein the contacting step is performed in a solvent comprising trifluoroacetic acid and dichloromethane.

9. The process of claim 6 wherein the contacting step comprises stirring overnight.

10. A compound of formula:

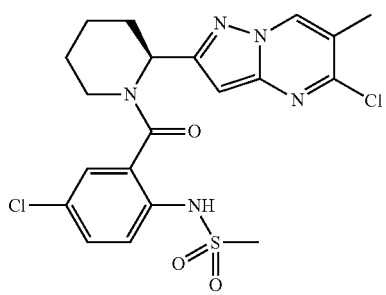 [SMILES: Cc1cn2nc([C@@H]3CCCCN3C(=O)c3cc(Cl)ccc3NS(C)(=O)=O)cc2nc1Cl]

or a pharmaceutically acceptable salt thereof.

11. A process of making the compound of claim 10 or a pharmaceutically acceptable salt thereof, comprising contacting a compound of formula:

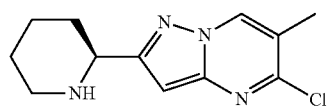 [SMILES: Cc1cn2nc([C@@H]3CCCCN3)cc2nc1Cl]

with an acid of formula:

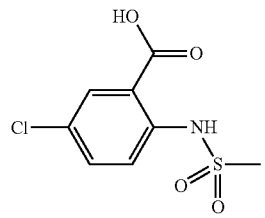

to form the compound of claim 10 or a pharmaceutically acceptable salt thereof.

12. The process of claim 11 wherein the contacting step is performed in a solution, the solution comprising a solvent and a reagent.

13. The process of claim 11 wherein the contacting step is performed in a solution, the solution comprising dimethylformamide and a reagent of formula:

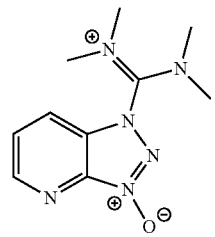

14. The process of claim 11 wherein the contacting step further comprises contacting the compound of formula:

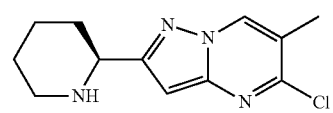

with an acid of formula:

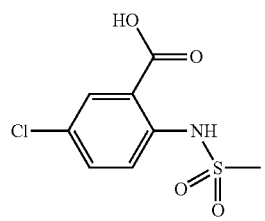

and with triethylamine.

15. A compound of formula:

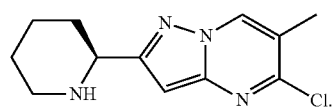

16. A process of making the compound of claim 15 comprising reacting a compound of formula:

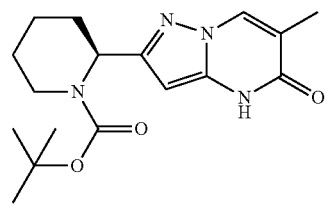 [SMILES: Cc1cn2nc([C@@H]3CCCCN3C(=O)OC(C)(C)C)cc2[nH]c1=O]
with phosphorus oxychloride to form the compound of claim 15.
17. The process of claim 16 wherein the reacting step is heated to 100° C.